US008986958B2

(12) United States Patent
Raymond

(10) Patent No.: US 8,986,958 B2
(45) Date of Patent: Mar. 24, 2015

(54) METHODS FOR GENERATING TARGET SPECIFIC PROBES FOR SOLUTION BASED CAPTURE

(75) Inventor: Christopher Raymond, Seattle, WA (US)

(73) Assignee: Life Technologies Corporation, Carlsbad, CA (US)

( * ) Notice: Subject to any disclaimer, the term of this patent is extended or adjusted under 35 U.S.C. 154(b) by 634 days.

(21) Appl. No.: 13/260,906

(22) PCT Filed: Mar. 30, 2010

(86) PCT No.: PCT/US2010/029276
§ 371 (c)(1),
(2), (4) Date: Jan. 25, 2012

(87) PCT Pub. No.: WO2010/117817
PCT Pub. Date: Oct. 14, 2010

(65) Prior Publication Data
US 2012/0115744 A1    May 10, 2012

Related U.S. Application Data

(60) Provisional application No. 61/164,859, filed on Mar. 30, 2009.

(51) Int. Cl.
*C12P 19/34* (2006.01)
*C12Q 1/68* (2006.01)

(52) U.S. Cl.
CPC .................................. *C12Q 1/6811* (2013.01)
USPC ...................................................... 435/91.2

(58) Field of Classification Search
USPC ................................................ 435/91.2, 6.1
See application file for complete search history.

(56) References Cited

U.S. PATENT DOCUMENTS

| | | | |
|---|---|---|---|
| 4,710,465 | A | 12/1987 | Weissman et al. |
| 4,868,105 | A | 9/1989 | Urdea et al. |
| 5,118,604 | A | 6/1992 | Weissman et al. |
| 5,968,786 | A | 10/1999 | Dunn et al. |
| 6,428,957 | B1 | 8/2002 | Delenstarr |
| 6,815,167 | B2 | 11/2004 | Crothers et al. |
| 7,211,390 | B2 | 5/2007 | Rothberg |
| 2001/0049125 | A1* | 12/2001 | Stemmer et al. .............. 435/91.1 |
| 2007/0059692 | A1 | 3/2007 | Gao et al. |
| 2007/0172873 | A1* | 7/2007 | Brenner et al. ................... 435/6 |
| 2010/0029498 | A1 | 2/2010 | Gnirke et al. |

FOREIGN PATENT DOCUMENTS

| | | |
|---|---|---|
| WO | WO-98/44151 | 10/1998 |
| WO | WO-2010/117817 | 10/2010 |
| WO | WO-2010/117817 A3 | 10/2010 |

OTHER PUBLICATIONS

Albert, Thomas J. et al., "Direct selection of human genomic loci by microarray hybridization", *Nature Methods*, vol. 4, No. 11, 2007, 903-905.
Dahl, F. et al., "Multigene amplification and massively parallel sequencing for cancer mutation discovery", *Proceedings of the national academy of sciences of the USA*, 104, May 29, 2007, 9387-9392 pgs.
Gao, Xiaolian et al., "In Situ Synthesis of Oligonucleotide Microarrays", *Biopolymers*, vol. 73, 2004, 579-596.
Hodges, Emily et al., "Genome-wide in situ exon capture for selective resequencing", *Nature Genetics*, vol. 39, No. 12, Dec. 2007, 1522-1527.
Lage, J et al., "Whole Genome Analysis of Genetic alterations in Small DNA Samples Using Hyperbranched Strand Displacement Amplification and Array-CGH", *Genome Research*, 13, 2003, pp. 294-307.
Lipshutz, et al., "High density synthetic oligonucleotide arrays", *Nature Genomics*; vol. 21, 1999, 20-24.
Okou, David T. et al., "Microarray-based genomic selection for high-throughput resequencing", *Nature Methods*, vol. 4, No. 11, 2007, 907-909.
PCT/US2010/029276, International Preliminary Report on Patentability mailed on Oct. 13, 2011, 6 pgs.
PCT/US2010/029276, International Search Report mailed Jan. 28, 2011, 9 pgs.
Zhou, X. et al., "Microfluidic PicoArray synthesis of oligonucleotides and simultaneous assembling of multiple DNA sequences", *Nucleic Acids Research*, vol. 32, No. 18, Oct. 2004, 5409-5417.

* cited by examiner

*Primary Examiner* — Cynthia B Wilder

(57) ABSTRACT

Provided herein are compositions and kits for single-stranded nucleic acid probes, and methods for making the single-stranded nucleic acid probes, where the single-stranded nucleic acid probes comprise a probe region having a predetermined sequence which is flanked by a 5' region having a first restriction enzyme recognition sequence and flanked by a 3' region having a second restriction enzyme recognition sequence, and a region which hybridizes to a capture nucleic acid molecule. The single-stranded nucleic acid probes are useful for solution-based capture methods.

28 Claims, 9 Drawing Sheets

STEP F
Psi1 DIGEST

STEP G
LAMBDA EXONUCLEASE DIGESTION

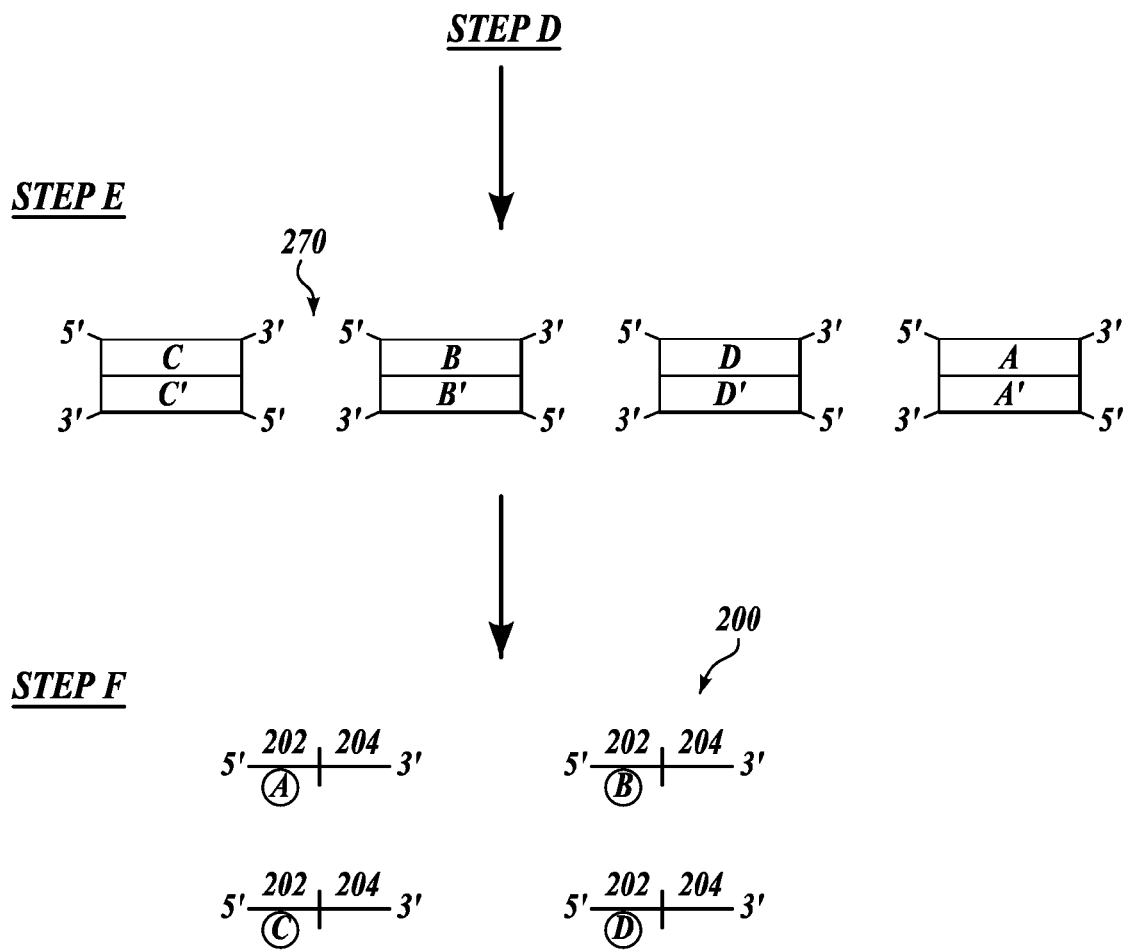

METHODS FOR GENERATING TARGET SPECIFIC PROBES FOR SOLUTION BASED CAPTURE

This application claims the filing date benefit of U.S. Provisional Application No. 61/164,859, filed on Mar. 30, 2009. The contents of each foregoing patent applications are incorporated by reference in their entirety.

Throughout this application various publications are referenced. The disclosures of these publications in their entireties are hereby incorporated by reference into this application in order to more fully describe the state of the art to which this invention pertains.

FIELD

The present invention relates generally to the field of genomic analysis, and more particularly, to methods and kits for making libraries of single-stranded nucleic acid probes comprising predetermined sequences.

BACKGROUND

The ability to sequence deoxyribonucleic acid (DNA) accurately and rapidly is revolutionizing biology and medicine. The pharmacogenomics challenge is to comprehensively identify the genes and functional polymorphisms associated with the variability in drug response. Screens for numerous genetic markers performed for populations large enough to yield statistically significant data are needed before associations can be made between a given genotype and a particular disease.

The study of complex genomes, and in particular, the search for the genetic basis of disease in humans, requires genotyping on a massive scale, which is demanding in terms of cost, time, and labor. Such costly demands are even greater when the methodology employed involves serial analysis of individual DNA samples, i.e., separate reactions for individual samples. Resequencing of polymorphic areas in the genome that are linked to disease development will contribute greatly to the understanding of diseases, such as cancer, and therapeutic development. Oligonucleotide libraries are the cornerstone of sequence-based gene resequencing and digital profiling strategies. To realize the full commercial potential of various high-throughput sequencing platforms, the cost of generating oligonucleotide libraries must be reduced by a substantial amount. Thus, there is a need for cost-effective methods for preparing populations of high quality oligonucleotide probes with sufficient yield for use in high throughput sequencing platforms and solution based capture methods.

SUMMARY

Provided herein are methods for generating a population of single-stranded nucleic acid probes, each probe comprising a predetermined nucleotide sequence, the method comprising: (a) providing a starting population of linear double-stranded nucleic acid precursor molecules each precursor molecule having (i) a probe region having the predetermined sequence which is flanked at a 5' and a 3' end by a first and a second restriction enzyme recognition sequence for generating ligation substrates and for ligating a plurality of the double-stranded nucleic acid precursor molecules into head-to-tail concatemers (ii) the 5' flanking region including the first restriction enzyme recognition sequence and (iii) the 3' flanking region including the second restriction enzyme recognition sequence; (b) contacting the 5' and 3' flanking regions of the linear double-stranded nucleic acid precursor molecules with the first and second restriction enzymes to cleave the first and second restriction enzyme recognition sequences so as to generate the ligation substrates; (c) ligating the ligation substrates together so as to generate a plurality of random head-to-tail concatemers; (d) amplifying the plurality of head-to-tail concatemers; (e) contacting the amplified head-to-tail concatemers with the first and second restriction enzymes so as to release a plurality double-stranded monomer linear precursor molecules; and (f) selectively removing one strand of the double-stranded monomer linear precursor molecules so as to generate a population of single-stranded nucleic acid probes, each probe comprising the predetermined nucleotide sequence.

In one embodiment, the single-stranded nucleic acid probes further comprise a region which hybridizes to a capture nucleic acid molecule.

In yet another embodiment, the selectively removing one strand from the double-stranded monomer linear precursor molecules comprises: (a) contacting the released precursor molecules of step (e) above with alkaline phosphatase; (b) contacting the released precursor molecules of step (e) above with a third restriction enzyme which cleaves the third restriction enzyme recognition sequence; and (c) contacting the released precursor molecules of step (e) above with an exonuclease so as to selectively degrade the one strand of the double-stranded monomer linear precursor molecules.

In one embodiment, the exonuclease is lambda exonuclease.

In another embodiment, the members of the starting population of the linear double-stranded nucleic acid precursor molecules each comprise the same nucleotide sequence in the 5' flanking region or each comprise the same nucleotide sequence in the 3' flanking region.

In another embodiment, the 3' flanking region further comprises a third restriction enzyme recognition sequence.

In another embodiment, the members of the starting population of the linear double-stranded nucleic acid precursor molecules each comprise the same predetermined sequences or different predetermined sequences.

In another embodiment, the ligation substrates of step (b) comprise overhanging nucleic acid ends capable of annealing together.

In another embodiment, the first or second restriction enzyme recognition sequence is cleaved by a type II restriction enzyme.

In another embodiment, the first or second restriction enzyme recognition sequence is cleaved by a Bsm1 enzyme.

In another embodiment, each predetermined nucleotide sequence in the population of linear double-stranded nucleic acid precursor molecules comprise a nucleotide sequence which is at least 95% identical to at least a portion of a sense or anti-sense strand of a target nucleic acid sequence.

In another embodiment, the predetermined sequence hybridizes to one target sequence or hybridizes to different target sequences.

In another embodiment, the predetermined sequences in the population of linear double-stranded nucleic acid precursor molecules hybridize to at least 10 different exon nucleotide sequences.

In another embodiment, the predetermined sequences in the population of linear double-stranded nucleic acid precursor molecules hybridize to at least 1000 different exon nucleotide sequences.

In another embodiment, the predetermined sequences hybridize to the target sequence at an interval of at least every 35 bases across the target sequence.

In another embodiment, the predetermined sequences hybridize to the target sequence of interest at an interval of one base across the target sequence.

In another embodiment, the probe region comprises 20-200 nucleotides.

In another embodiment, the predetermined nucleotide sequence comprises 10-50 nucleotides.

In another embodiment, the region of the single-stranded nucleic acid probe which hybridizes to the capture nucleic acid molecule comprises 10-50 nucleotides.

In another embodiment, the amplifying according to step (d) comprises isothermal amplification.

In another embodiment, the amplifying according to step (d) comprises random amplification primers.

In another embodiment, the random amplification primers each comprise a random 7-mer oligonucleotide and two additional nitroindole residues at the 5' end.

In another embodiment, the random amplification primers each comprise a random 7-mer oligonucleotide and a phosphorothioate linkage to the 3' end.

In another embodiment, the capture nucleic acid molecule further comprises a protein binding partner.

In another embodiment, the protein binding partner is biotin.

In another embodiment, each single-stranded nucleic acid probe comprises (i) the predetermined nucleotide sequence having a nucleotide sequence which is at least 95% identical to at least a portion of a sense or an anti-sense strand of a target nucleic acid sequence and (ii) a region which hybridizes to a capture nucleic acid molecule.

Provided herein are also a population of single-stranded nucleic acid probes generated by the disclosed methods.

Provided herein are also methods, wherein the starting population of linear double-stranded nucleic acid precursor molecules is generated by steps comprising: (a) providing a population of a first single-stranded nucleic acid molecule comprising the 5' flanking region, the probe region which comprises the predetermined sequence, and the capture sequence; (b) providing a population of a second single-stranded nucleic acid molecules comprising the sequence which is complementary to the capture sequence, and the 3' flanking region; (c) annealing the first and second populations of the single-stranded nucleic acid molecules to form a nucleic acid duplex having overhanging 5' ends; and (d) conducting a polymerase-dependent strand extension reaction on the overhanging 5' ends so as to generate the population of double-stranded nucleic acid precursor molecules.

Provided herein are also, methods for enriching a target nucleic acid sequence of interest from a nucleic acid library, comprising: (a) contacting the population of single-stranded nucleic acid probes of the method above with the nucleic acid library having at least one target nucleic acid sequence of interest to form a mixture having unhybridized nucleic acid sequences and duplexes, each duplex having the single-stranded nucleic acid probe hybridized to the target nucleic acid sequence of interest; (b) contacting the duplexes with a population of capture nucleic acid molecules to form complexes having the single-stranded nucleic acid probe hybridized to the target nucleic acid sequence of interest and hybridized to the capture nucleic acid molecule; (c) separating the complex from the mixture; and (d) eluting the target nucleic acid sequence of interest from the complex.

DETAILED DESCRIPTION

Figure 1A:
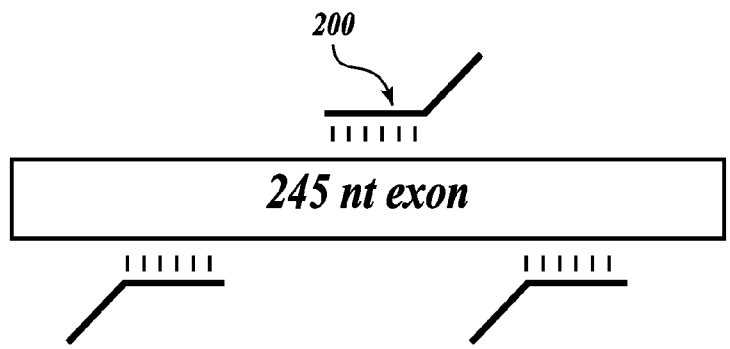
FIG. 1A illustrates a population of target capture probes (200) for solution-based capture, designed to provide low density coverage of a target exon (10), as described in Example 1.

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is explicitly or implicitly set forth herein that is contrary to or otherwise inconsistent with any definition set forth in the patents, patent applications, published applications, and other publications that are herein incorporated by reference, the definition and/or description set forth herein prevails over the definition that is incorporated by reference.

The practice of the present disclosure will employ, unless otherwise indicated, conventional techniques of molecular biology, microbiology and recombinant DNA techniques, which are within the skill of the art. Such techniques are explained fully in the literature. See, for example, Sambrook, J., and Russell, D. W., 2001, Molecular Cloning: A Laboratory Manual, Third Edition; Ausubel, F. M., et al., eds., 2002, Short Protocols in Molecular Biology, Fifth Edition.

As used herein, the terms "comprising" (and any form or variant of comprising, such as "comprise" and "comprises"), "having" (and any form or variant of having, such as "have" and "has"), "including" (and any form or variant of including, such as "includes" and "include"), or "containing" (and any form or variant of containing, such as "contains" and "contain"), are inclusive or open-ended and do not exclude additional, unrecited additives, components, integers, elements or method steps.

As used herein, the terms "a," "an," and "the" and similar referents used herein are to be construed to cover both the singular and the plural unless their usage in context indicates otherwise. Accordingly, the use of the word "a" or "an" when used in the claims or specification, including when used in conjunction with the term "comprising", may mean "one," but it is also consistent with the meaning of "one or more," "at least one," and "one or more than one."

As used herein, the term "nucleic acid molecule" and its variants encompasses both deoxyribonucleotides and ribonucleotides and refers to a polymeric form of nucleotides including two or more nucleotide monomers. The nucleotides can be naturally occurring, artificial, and/or modified nucleotides.

As used herein, an "isolated nucleic acid" and its variants is a nucleic acid molecule that exists in a physical form that is non-identical to any nucleic acid molecule of identical sequence as found in nature; "isolated" does not require, although it does not prohibit, that the nucleic acid so described has itself been physically removed from its native environment. For example, a nucleic acid can be said to be "isolated" when it includes nucleotides and/or internucleoside bonds not found in nature. When, instead, composed of natural nucleosides in phosphodiester linkage, a nucleic acid can be said to be "isolated" when it exists at a purity not found in nature, where purity can be adjudged with respect to the presence of nucleic acids of other sequences, with respect to the presence of proteins, with respect to the presence of lipids, or with respect to the presence of any other component of a biological cell, or when the nucleic acid lacks a sequence that flanks an otherwise identical sequence in an organism's genome, or when the nucleic acid possesses a sequence not identically present in nature. As so defined, "isolated nucleic acid" includes nucleic acids integrated into a host cell chromosome at a heterologous site, recombinant fusions of a native fragment to a heterologous sequence, recombinant vectors present as episomes, or as integrated into a host cell chromosome.

As used herein, "subject" and its variants refers to an organism or to a cell sample, tissue sample, or organ sample derived therefrom, including, for example, cultured cell lines, biopsy, blood sample, or fluid sample containing a cell. For example, an organism may be an animal, including but not limited to, an animal such as a cow, a pig, a mouse, a rat, a chicken, a cat, a dog, etc., and is usually a mammal, such as a human.

As used herein, the term "specifically bind" and its variants refers to two components (e.g., target-specific binding region and target) that are bound (e.g., hybridized, annealed, complexed) to one another sufficiently that the intended capture and enrichment steps can be conducted. As used herein, the term "specific" refers to the selective binding of two components (e.g., target-specific binding region and target) and not generally to other components unintended for binding to the subject components.

As used herein, the term "high stringency hybridization conditions" and its variants means any condition in which hybridization will occur when there is at least 95%, preferably about 97% to 100% nucleotide complementarity (identity) between the nucleic acid sequences of the nucleic acid molecule and its binding partner. However, depending upon the desired purpose, the hybridization conditions may be "medium stringency hybridization," which can be selected that require less complementarity, such as from about 50% to about 90% (e.g., 60%, 70%, 80%, 85%). The comparison of sequences and determination of percent identity between two sequences can be accomplished using a mathematical algorithm of Karlin and Altschul (Proc. Natl. Acad. Sci. USA 87:2264-2268 (1990)), modified as in Karlin and Altschul (Proc. Natl. Acad. Sci. USA 90:5873-5877 (1993)). Such an algorithm is incorporated into the NBLAST and XBLAST programs of Altschul et al. (J. Mol. Biol. 215:403-410 (1990)).

As used herein, the term "complementary" and its variants refers to nucleic acid sequences that are capable of base-pairing according to the standard Watson-Crick complementary rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA.

As used herein, the term "target" and its variants refers to a nucleic acid molecule or polynucleotide whose presence and/or amount and/or sequence is desired to be determined and which has an affinity for a given target capture probe. Examples of targets include regions of genomic DNA, PCR amplified products derived from RNA or DNA, DNA derived from RNA or DNA, ESTs, cDNA, and mutations, variants or modifications thereof.

As used herein, the term "predetermined nucleic acid sequence" and its variants means that the nucleic acid sequence of a nucleic acid probe is known and was chosen before synthesis of the nucleic acid molecule in accordance with the invention disclosed herein.

As used herein, the term "essentially identical" and its variants as applied to synthesized and/or amplified nucleic acid molecules refers to nucleic acid molecules that are designed to have identical nucleic acid sequences, but that may occasionally contain minor sequence variations in comparison to a desired sequence due to base changes introduced during the nucleic acid molecule synthesis process, amplification process, or due to other processes in the method. As used herein, essentially identical nucleic acid molecules are at least 95% identical to the desired sequence, such as at least 96%, such as at least 97%, such as at least 98%, such as at least 99% identical, or absolutely identical, to the desired sequence.

As used herein, the term "resequencing" and its variants refers to a technique that determines the sequence of a genome of an organism using a reference sequence that has already been determined. It should be understood that resequencing may be performed on both the entire genome/transcriptome of an organism or a portion of the genome/transcriptome large enough to include the genetic change of the organism as a result of selection. Resequencing may be carried out using various sequencing methods, such as any sequencing platform amenable to producing DNA sequencing reads that can be aligned back to a reference genome, and is typically based on highly parallel technologies such as, for example, dideoxy "Sanger" sequencing, pyrosequencing on beads (e.g., as described in U.S. Pat. No. 7,211,390, assigned to 454 Life Sciences Corporation, Branford, Conn.), ligation based sequencing on beads (e.g., Applied Biosystems Inc,/Invitrogen), sequencing on glass slides (e.g., Illumina Genome Analyzer System, based on technology described in WO 98/44151 (Mayer, P., and Farinelli, L.), microarrays, or fluorescently labeled micro-beads.

As used herein, the term "target nucleotide" and its variants refers to a nucleic acid molecule or polynucleotide in a starting population of nucleic acid molecules having a target sequence whose presence and/or amount and/or nucleotide sequence is desired to be determined and which has an affinity for a given target capture probe.

As used herein, the term "target sequence" and its variants refers generally to a nucleic acid sequence on a single strand of nucleic acid. The target sequence may be a portion of a gene, a regulatory sequence, genomic DNA, cDNA, RNA including mRNA and rRNA, or others. The target sequence may be a target sequence from a sample, or a secondary target such as a product of an amplification reaction.

As used herein, the term "processing" and its variants refers generally to a manipulation of a precursor nucleic acid substrate into a processed form of the substrate, such as by cleavage with a restriction endonuclease, modification and/or amplification with DNA polymerases, manipulation of DNA termini (e.g., by adding terminal 5' phosphates with a polynucleotide kinase or removing 5' terminal phosphates with a suitable phosphatase), degradation of unwanted DNA strands with exonuclease, and the like.

As used herein, the term "head to tail concatemer" and its variants refers to at least two or more monomeric structures each having a first end and a second end, such as double-stranded nucleic acid molecules, covalently joined in the configuration of the second end of the first monomer joined to the first end of the second monomer.

Other objects, features and advantages of the disclosed compositions, methods, systems and kits will become apparent from the following detailed description. It should be understood, however, that the detailed description and the specific examples, while indicating specific embodiments, are given by way of illustration only, since various changes and modifications within the spirit and scope of the inventions provided herein will become apparent to those skilled in the art from this detailed description.

Provided herein are compositions, systems, methods and kits for generating a population of single-stranded nucleic acid probes, each probe comprising a predetermined nucleic acid sequence. The methods of the invention are useful in any situation in which it is desirable to make populations of single-stranded nucleic acid molecules (hundreds to thousands, to tens of thousands, to hundreds of thousands, to millions of oligonucleotides), wherein each nucleic acid molecule has a predetermined nucleic acid sequence. For example, the methods may be used to generate a high quantity of a complex population (e.g., library) of single-stranded nucleic acid probes, while maintaining a uniform representation of the individual nucleic acid probes within the population. The applications for pools of oligonucleotides include, but are not limited to, using the oligonucleotides to generate primers for PCR amplification, primers for multiplexing PCR and transcription, probes for SNP (single nucleotide polymorphism) detection, and libraries of nucleic acid probes for genomic analysis, RNA expression analysis, including siRNA and shRNA expression analysis. In some embodiments, the methods according to this aspect of the invention are used to generate a library of target specific probes for solution based capture methods, as described in Examples 1-3 herein.

The methods according to this aspect of the invention comprise (a) providing a starting population of double-stranded nucleic acid precursor molecules, wherein each precursor molecule in the starting population comprises a probe region comprising a predetermined sequence that is flanked on the 5' end by a 5' flanking region comprising a first processing site and is flanked on the 3' end by a 3' flanking region comprising a second processing site, wherein the first and second processing sites are selected to generate ligation substrates for ligation of a plurality of the double-stranded nucleic acid precursor molecules into head-to-tail concatemers; (b) processing the 5' and 3' flanking regions of the double-stranded nucleic acid precursor molecules to generate ligation substrates; (c) ligating the ligation substrates together to generate head-to-tail concatemers; (d) amplifying the head-to-tail concatemers; (e) processing the amplified head-to-tail concatemers to release double-stranded monomer precursor molecules; and (f) selectively removing the complement strand of the double-stranded monomer precursor molecules to generate a population of single-stranded nucleic acid probes each probe a predetermined nucleic acid sequence.

In one embodiment of the method, a population of target specific capture probes (e.g., a library of capture probes) is generated that may be used in solution based capture methods for enriching a population of DNA molecules for one or more target sequences of interest, such as for resequencing analysis. In accordance with this embodiment, each single-stranded capture probe oligonucleotide in the population of capture probes comprises (i) a target-specific binding region consisting of a nucleic acid sequence that is at least 95% identical to at least a portion of the sense or antisense strand of a target nucleic acid sequence of interest, and (ii) a region for binding to a capture reagent. The methods according to this embodiment of the invention can be used to create populations of single-stranded capture nucleic acid molecules (i.e., capture probes). A population of capture probes is also referred to as a "library" of capture probes. The capture probes generated using the methods described herein may be used for solution based capture to enrich for targets of interest.

Figure 1B:
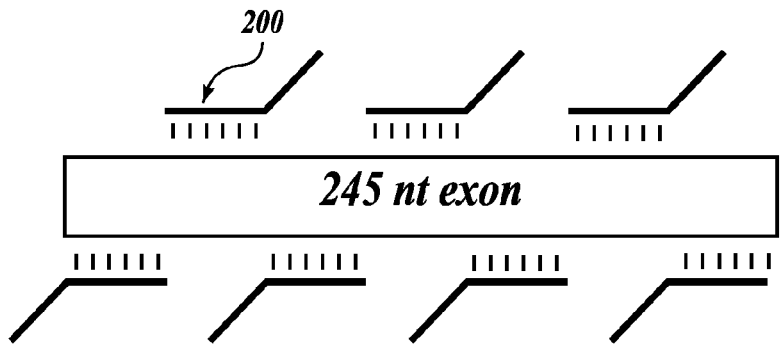
FIG. 1B illustrates a population of target capture probes (200) for solution-based capture, designed to provide high density coverage of a target exon (10), as described in Example 1.
Figure 1C:
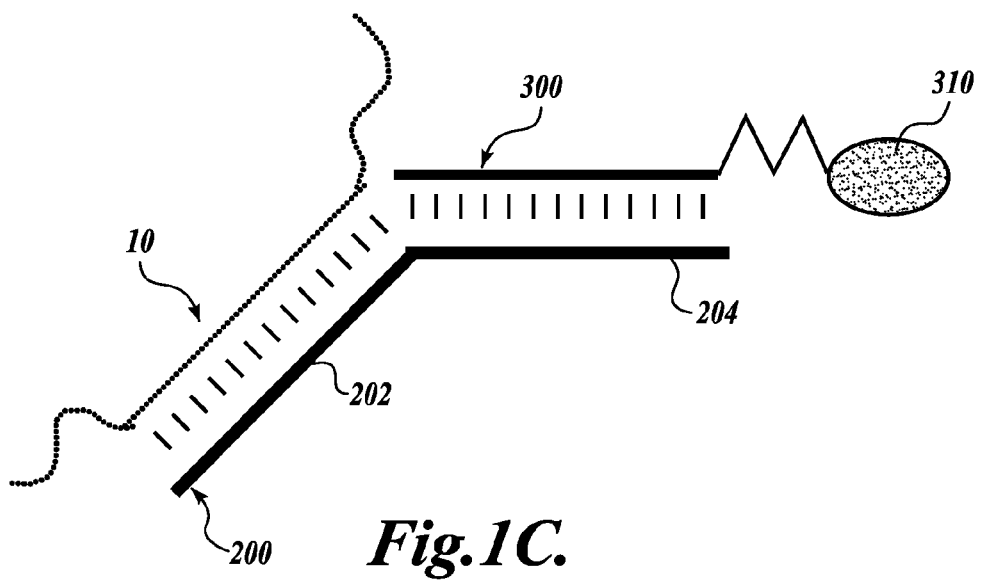
FIG. 1C is a schematic diagram of a representative target capture probe (200) comprising a target-specific binding region (202) bound to a nucleic acid target (10), and a region for binding to a capture reagent (204) bound to a universal adaptor oligonucleotide (300) comprising a moiety (310) that binds to a capture reagent.

FIG. 1C illustrates a representative capture probe 200 comprising a target-specific binding region 202 and a region 204 for binding to a capture reagent 300. In the embodiment shown in FIG. 1C, the capture reagent 300 is a universal adaptor oligonucleotide comprising a moiety 310 that binds to a capture reagent. The capture probes 200 generated using the methods of the present invention may be used to enrich a library for target nucleic acid regions of interest in a method referred to as solution based capture.

Figure 2:
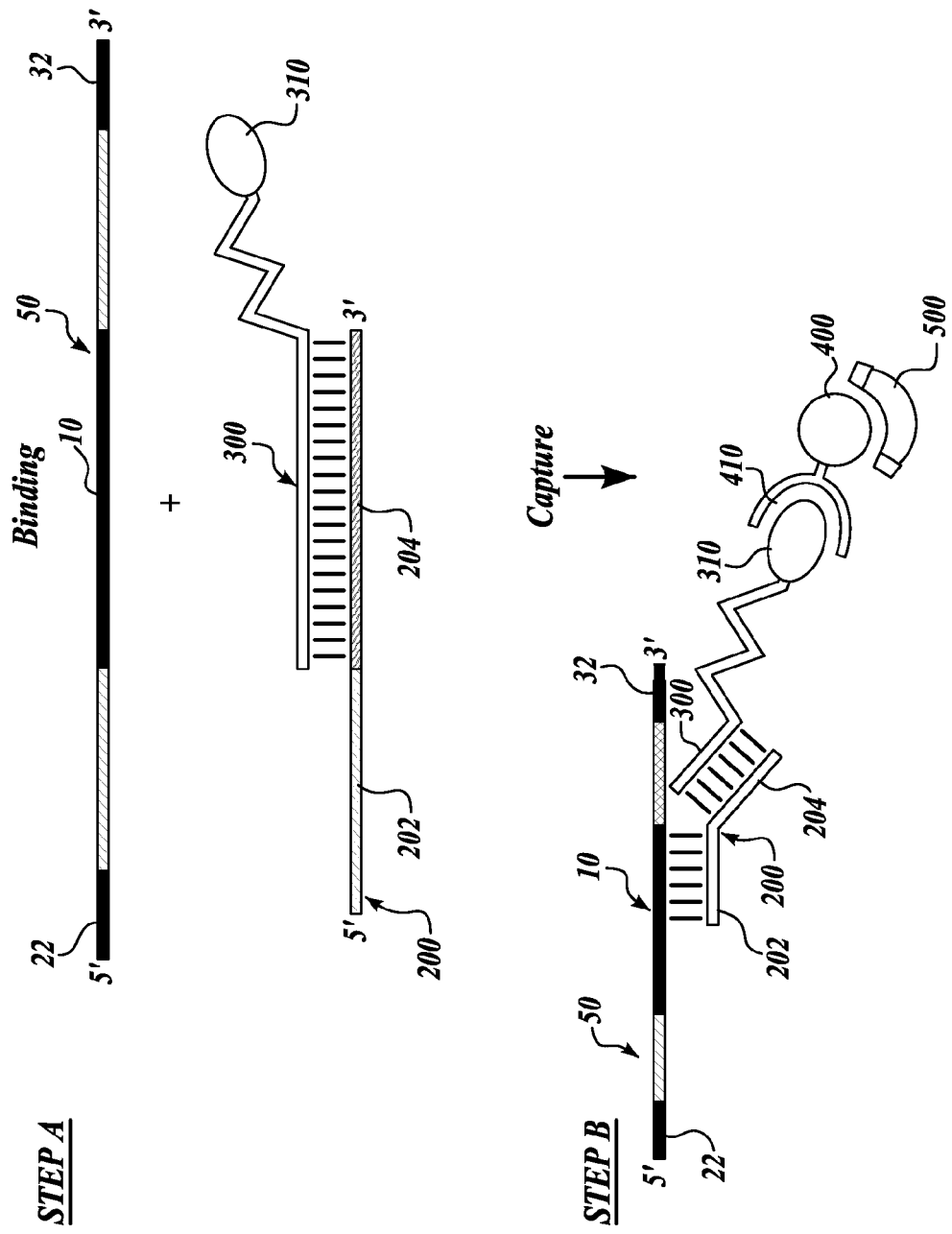
FIG. 2 illustrates a method of enriching a population of DNA molecules for target regions of interest using capture probes (200) generated in accordance with an embodiment of the present invention.

A representative method of solution based capture is illustrated in FIG. 2. The capture probes 200 (the capture probe 200 is representative of a population of capture probes) illustrated in FIG. 2 comprise a target-sequence specific binding region 202 and a capture reagent binding region 204 that hybridizes to a universal adaptor oligonucleotide 300 comprising a moiety 310 that binds to a capture reagent 400. As shown in FIG. 2 at step A, in one embodiment, solution based capture comprises contacting a library of DNA molecules 50 comprising a subpopulation of nucleic acid target insert sequences of interest 10 flanked by a first primer binding region 22 and a second primer binding region 32. The plurality of nucleic acid insert regions in the library include one or more target sequences 10, and can include enough different nucleic acid sequences to cover (i.e., represent) part or all of a source nucleic acid including, without limitation, the genome of an organism, a genomic locus, a cDNA library, a whole transcriptome of an organism, the exome of an organism and the like. As used herein the term "exome" refers to protein coding regions, promoters, known ncRNAs (non-coding RNAs) and UTRs, altogether comprising about 2% of the human genome.

As shown in FIG. 2 at step B, the target-specific binding region 202 of the target capture probe 200 binds to a substantially complementary target nucleic acid sequence 10, shown as an insert region 10 of a nucleic acid molecule 50 in a library of nucleic acid molecules. The universal adaptor oligonucleotide 300 is present at an equal concentration as the capture probes 200, and hybridizes to the capture reagent binding region 204. The moiety 310 (e.g., biotin) attached to the universal oligo adaptor 300 is then contacted with a capture reagent 400 (e.g., a magnetic bead) having a binding region 410 (e.g., streptavidin coating) and the complex is pulled out of solution with a sorting device 500 (e.g., a magnet) that binds to the capture reagent 400.

Any library of DNA molecules comprising a subpopulation of nucleic acid target insert sequences of interest may be enriched using the solution based capture methods described herein. In some embodiments, the library of DNA molecules comprises a plurality of distinct insert sequences flanked by a first primer binding region and a second primer binding region within a larger population of nucleic acid insert sequences flanked by the first primer binding region and the second primer binding region may be enriched for target sequences using the capture probes 200 generated using the methods disclosed herein. For example, a library of DNA molecules comprising a subpopulation of nucleic acid target insert sequences of interest flanked by a first primer binding region and a second primer binding region within a larger population of nucleic acid insert sequences flanked by the first primer binding region and the second primer binding region may be enriched using the capture probes generated using the methods of the invention. In some embodiments, the library of DNA molecules further comprises at least one anchor probe binding site, such as a flow cell binding site for binding to a flow cell sequencing platform, such as an Illumina Genome Analyzer for sequence analysis.

The use of solution-based capture to enrich a library allows for the efficient creation of resequencing samples (sequence-ready libraries) that are largely composed of target sequences, as demonstrated in Example 2.

The Design of the Target Capture Probe 200

The general design of the target capture probe 200 is described as follows. As shown in FIG. 1C, the target capture probe 200 comprises a target sequence-specific binding region 202 and a capture reagent region 204 for binding to a capture reagent 300.

The length of a target capture probe 200 is typically in the range of from 20 nucleotides to about 200 nucleotides, such as from about 20 nucleotides to about 150 nucleotides, such as from about 30 nucleotides to about 100 nucleotides, or such as from about 40 nucleotides to about 80 nucleotides.

The target-specific binding region 202 of the target capture probe 200 is typically from about 10 to about 150 nucleotides in length (e.g., 35 nucleotides, 50 nucleotides, 100 nucleotides) and is chosen to specifically hybridize to a target sequence of interest. In one embodiment, the target capture probe is about 60 to 80 nucleotides in length, comprising a target-specific binding region of about 20 to 40 nucleotides in length, such as about 35 nucleotides in length.

The target specific binding region 202 comprises a sequence that is substantially complementary (i.e., at least 95% identical, at least 96% identical, at least 97% identical, at least 98% identical, at least 99% identical, or 100% identical) to the target sequence of interest. Described in another way, for a target specific binding region 202 having a sequence with a length of from 10 to 100 nucleotides that is at least 95% complementary or at least 95% identical to a target sequence of interest, a region 202 that is from 20 nt to 35 nt in length may contain 1 mismatch, a region 202 that is from 40 nt to 50 nt in length may contain up to 2 mismatches, a region 202 that is from 60 nt to 70 nt may contain up to 3 mismatches, a region 202 that is from 80 nt to 90 nt may contain up to 4 mismatches, and a region 202 having a length of 100 nt may contain up to 5 mismatches with the target sequence.

In one embodiment, the method is used to generate a plurality of capture probes 200 each comprise a target-specific binding region 202 consisting of a sequence with a length of 35 nucleotides, that is at least 95% complementary, or at least 95% identical to a target sequence of interest (i.e., up to 1 mismatch with the target sequence).

The capture oligonucleotides may be designed to bind to a target region at selected positions spaced across the target region at various intervals. The capture oligo design and target selection process may also take into account genomic features of the target region such as genetic variation, G:C content, predicted oligo Tm, and the like. One of skill in the art can use art-recognized methods to determine the features of a target binding region that will hybridize to the target with minimal non-specific hybridization. For example, one of skill can determine experimentally the features such as length, base composition, and degree of complementarity that will enable a nucleic acid molecule (e.g., the target-specific binding region of a target capture probe) to specifically hybridize to another nucleic acid molecule (e.g., the nucleic acid target) under conditions of selected stringency, while minimizing non-specific hybridization to other substances or molecules. For example, for an exon target of interest, a target gene sequence is retrieved from a public database such as GenBank, and the sequence is searched for stretches of from 25 to 150 bp with a complementary sequence having a GC content in the range of 45% to 55%. The identified sequence may also be scanned to ensure the absence of potential secondary structure and may also be searched against a public database (e.g., a BLAST search) to ensure a lack of complementarity to other genes, as described in Example 3.

In some embodiments of the method, a set of capture probes (e.g., a library) is designed to specifically bind to target sequences across a genomic location, such as across a chromosomal region, and the capture probes are contacted with nucleic acid molecules from a total genomic library, or a whole-transcriptome library in order to analyze the whole transcriptome across the chosen genomic locus. In some embodiments of the method, a set of capture probes is designed to specifically bind to a plurality of target regions, such as the exons of a single gene, or multiple genes, such as at least 5 genes, at least 10 genes, at least 20 genes, at least 50 genes, at least 75 genes, at least 200 genes, at least 1000 genes, at least 10,000 genes, or more, as described in Examples 1-3. For example, as demonstrated in Example 3 herein, the methods according to this aspect of the invention were used to generate a set of capture probes comprising 1,148,286 distinct target-specific 35mer regions that were designed to capture all the exons from a total of 25,341 annotated genes from a sample containing nucleic acid sequences derived from a human.

In some embodiments of the method, a set of capture probes is designed to specifically bind to a genomic locus known to be associated with a clinical outcome or disease, or disease risk.

In some embodiments, the methods of the invention are used to capture and sequence a modified or mutated target, such as to determine the presence of a particular single nucleotide polymorphism (SNP), or deletion, addition, or other modification. In accordance with such embodiments, the set of target capture probes are typically designed such that there is a very dense array of capture probes that are closely spaced together such that a single target sequence, which may contain a mutation, will be bound by multiple capture probes that overlap the target sequence. For example, capture probes may be designed that cover every base of a target region, on one or both strands, (e.g., head to tail), or that are spaced at intervals of every 2, 3, 4, 5, 10, 15, 20, 40, 50, 90, 100, or more bases across a sequence region.

As another example, the selection of the target capture probes over a target region of interest is based on the size of the target region. For example, for a target region of less than 100 nucleotides in length, capture probes (either sense, antisense, or both) are typically designed to hybridize to target sequences spaced apart by from 0 to 100 nucleotides, such as every 45 nucleotides, or every 35 nucleotides. As another example, for a target region greater than 200 nucleotides, capture probes (either sense, antisense, or both) are typically designed to hybridize to target sequences spaced apart by from 0 to 200 nucleotides, such as at 45 to 65 nucleotide intervals, or at higher density coverage such as every 35 nucleotide intervals. In one embodiment, for a target region greater than 200 nucleotides (e.g., a 200,000-nucleotide target region), a set of sense and antisense capture probes are designed that are each about 35 nucleotides in length and are spaced about 45 nucleotides apart across the target region (alternating sense/antisense) in order to saturate the region (e.g., "tile" across the region of interest).

In one embodiment, a library of target specific probes are designed to bind to a desired target with high density coverage, such that at least one capture probe binds to at least every 35 nucleotide region of the target sequence. In one embodiment, a library of target specific probes are designed to bind to every nucleotide of the target, with alternating binding regions on the sense and antisense strands of the target sequence.

Referring now to FIG. 1C, in one embodiment, the target capture probes 200 each comprise a capture reagent binding region 204 that hybridizes to a universal adaptor oligonucleotide 300 comprising a moiety 310 that binds to a capture reagent 400. The capture reagent binding region 204 of the target capture probe 200 is typically from about 10 to about 50 nucleotides in length (e.g., 10 nucleotides, 15 nucleotides, 20 nucleotides, 35 nucleotides) and is chosen to specifically hybridize to a universal adaptor oligonucleotide comprising a moiety 310 that binds to a capture reagent. In one embodiment, the target capture probe is about 60 to 80 nucleotides in length, comprising a capture reagent binding region of about 10 to 40 nucleotides in length, such as about 35 nucleotides in length.

In operation, as shown in FIG. 2, the target-specific binding region 202 of the target capture probes bind to a complementary or substantially complementary nucleic acid sequence contained in a nucleic acid target 10 (i.e., an insert of a nucleic acid molecule in a library, or a genomic region of nucleic acids isolated from a sample). A universal adaptor oligonucleotide 300 is present at an equal concentration as the capture probes 200, and hybridizes to the capture reagent binding region 204. The moiety 310 (e.g., biotin) attached to the universal adaptor oligonucleotide 300 is then contacted with a capture reagent 400 (e.g., a magnetic bead) having a binding region 410 (e.g., streptavidin coating) and the complex is pulled out of solution with a sorting device 500 (e.g., a magnet) that binds to the capture reagent 400.

Figure 3:
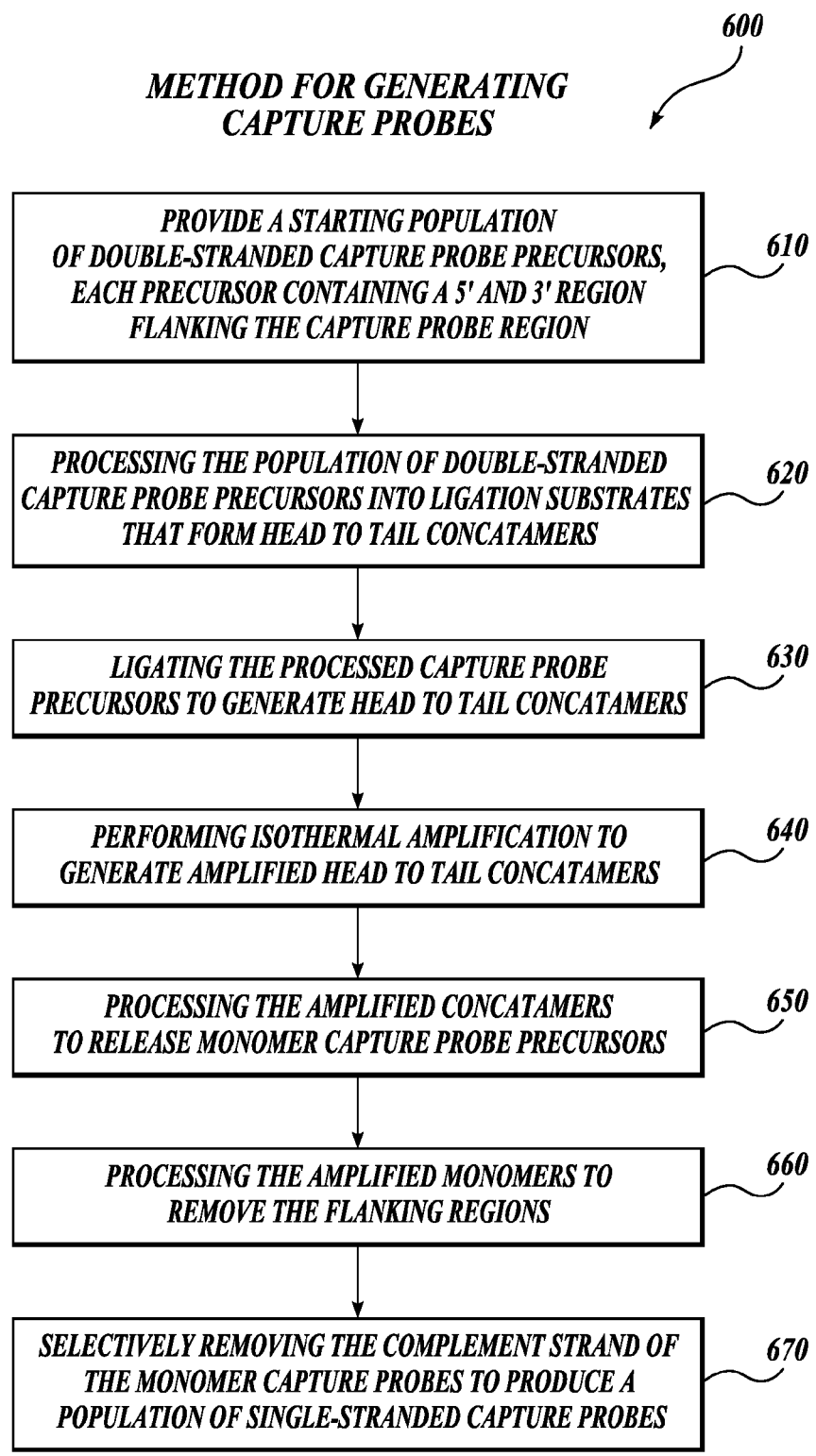
FIG. 3 is a flow chart of the steps of a method for generating a population of capture probes in accordance with various embodiments of the present invention.
Figure 4:
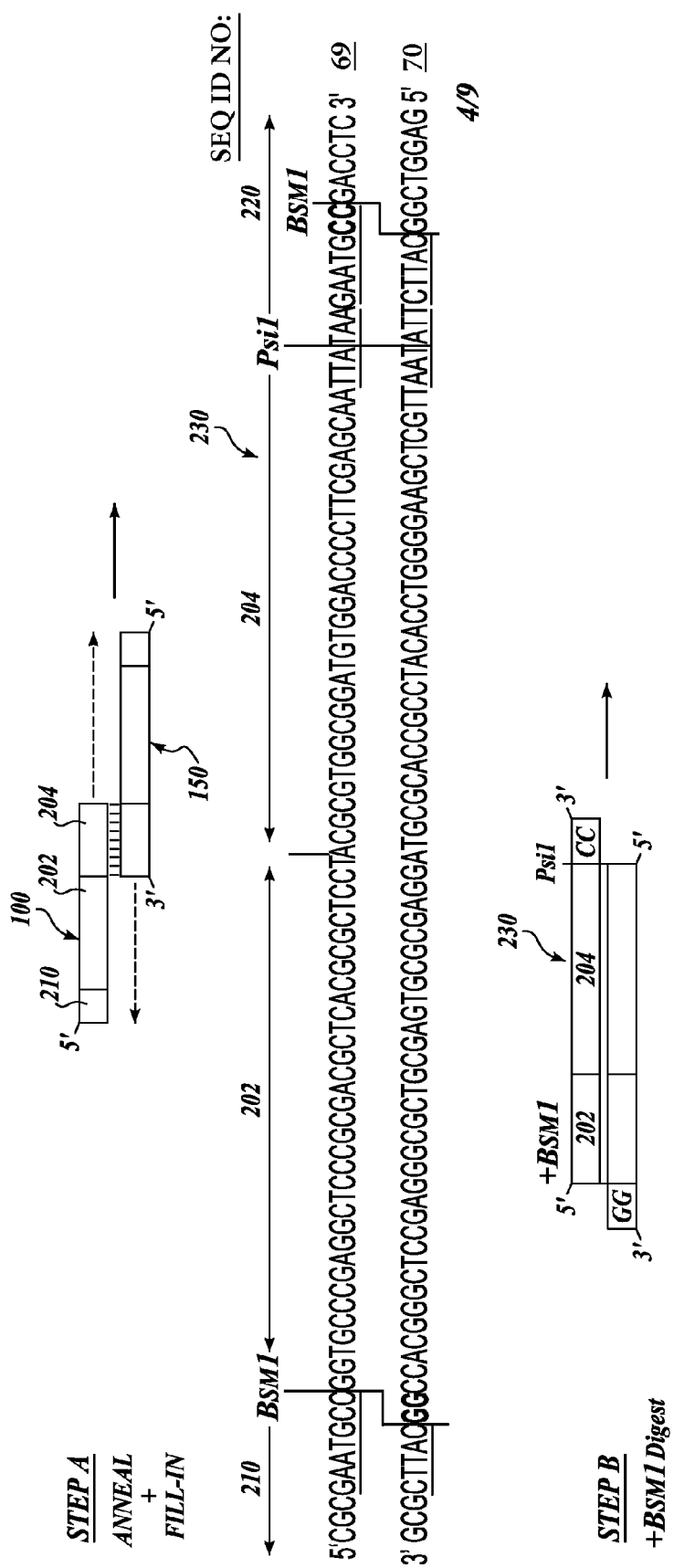
FIG. 4 (SEQ ID NOS: 69 and 70) illustrates a method of generating a population of single-stranded capture probes (200) in accordance with an embodiment of the present invention.
Figure 4:
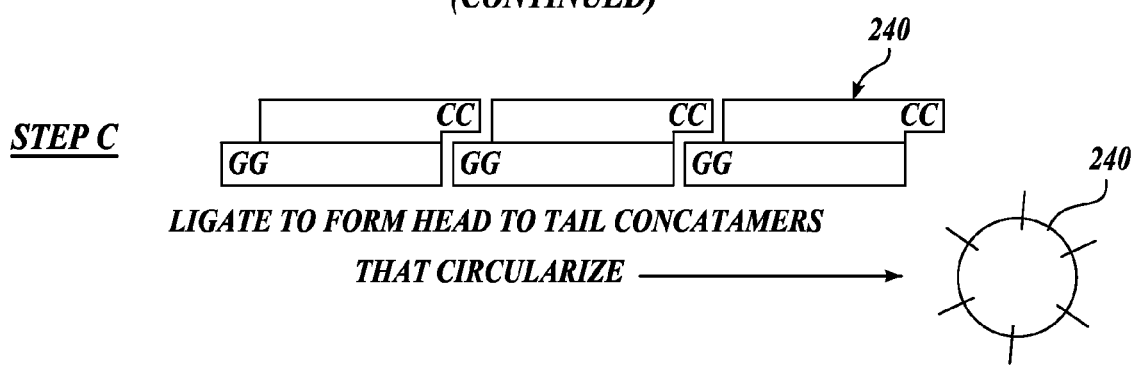
Figure 4:
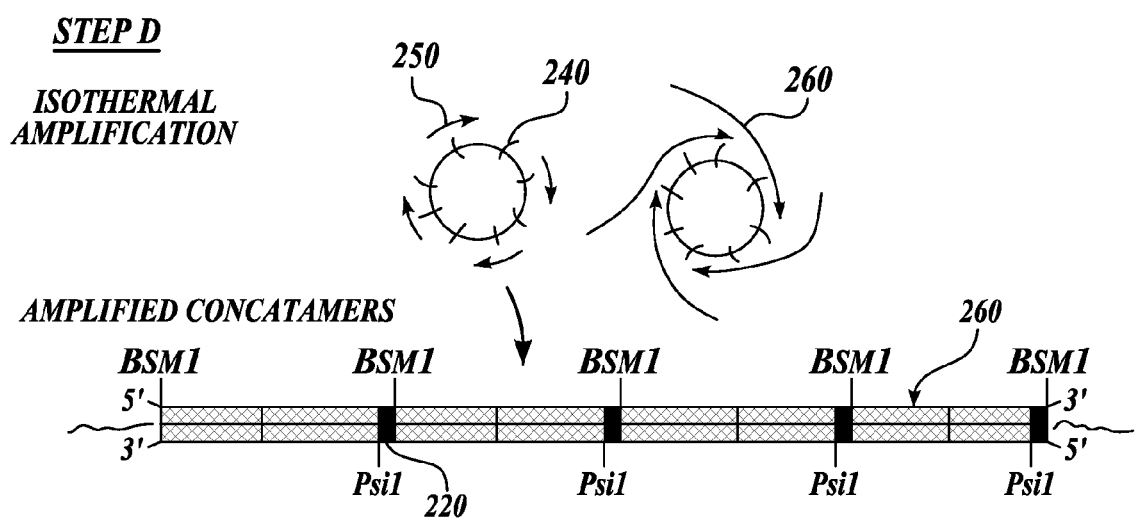
Figure 4:
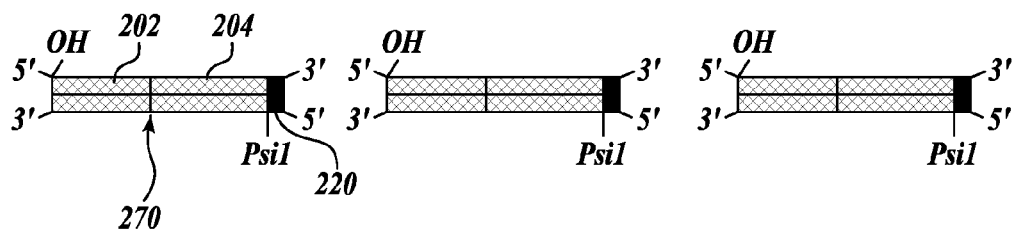
Figure 4:
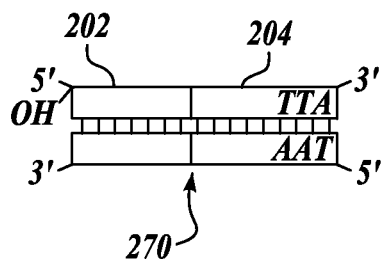
Figure 4:
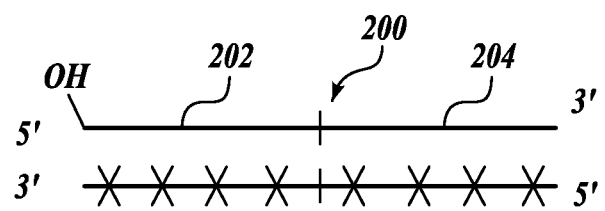

As shown in FIG. 3, the method 600 of generating a population of target-specific capture probes in accordance with one embodiment of the invention, includes the step 610 of providing a starting population of double-stranded capture probe precursors, each precursor comprising a capture probe region 200 (comprising a target-sequence specific binding region 202 and a capture reagent binding region 204), flanked by a 5' flanking region 210 and a 3' flanking region 220. The 5' flanking region 210 comprises a first processing site and the 3' flanking region 220 comprises a second processing site, wherein the first and second processing sites are selected to generate ligation substrates capable of ligation into head-to-tail concatemers. An exemplary double-stranded capture probe precursor 230 is illustrated in FIG. 4 at step A. As shown in FIG. 4 at step A, the exemplary double-stranded capture probe precursor 230 comprises a capture probe region 200 flanked on the 5' end by flanking region 210 comprising a first processing site (e.g., a first Bsm1 site) and is flanked on the 3' end by flanking region 220 comprising a second processing site (e.g., a second Bsm1 site). In some embodiments, the 3' flanking region 220 further comprises a third processing site (e.g., a Psi1 site or a HindIII site) selected to precisely cleave off the 3' flanking region.

The 5' flanking region 210 is typically from about 4 to about 30 nucleotides in length, such as from about 5 to about 15 nucleotides in length, or from about 5 to 10 nucleotides in length. The nucleotide sequence of the 5' flanking region 210 is chosen to provide a first processing site, such as a first restriction enzyme recognition site, such as a type II restriction endonuclease (e.g., Bsm1), to generate the desired nucleotide overhang at the first end of the double-stranded precursor molecule for ligation in a head to tail configuration, and for precise cleavage of the 5' flanking region 210 from the capture probe 200 region.

The 3' flanking region 220 is typically from about 4 to about 30 nucleotides in length, such as from about 5 to about 25 nucleotides in length, or from about 10 to 20 nucleotides in length. The nucleotide sequence of the 3' flanking region 220 is chosen to provide a second processing site, such as a second restriction enzyme recognition site (e.g., Bsm1), to generate the desired nucleotide overhang at the second end of the double-stranded molecule for ligation. In some embodiments, the 3' flanking region 220 further comprises an additional processing site (e.g., a third restriction enzyme recognition site, such as Psi1 or HindIII) for precise cleavage of the 3' flanking region 220 from the capture probe 200 region.

As illustrated in FIG. 4, step B, the population of double-stranded capture probe precursors 230 are processed into ligation substrates that form head-to-tail concatemers upon ligation with one another. Accordingly, the first processing site in the 5' flanking region and the second processing site in the 3' region are chosen such that upon digestion of the first and second processing sites in the double-stranded precursor 230, nucleotide overhangs are left on each end of the double-stranded precursor that can only ligate with one another in a head to tail configuration (e.g., a "CC" overhang on the first end of the molecule and a "GG" overhang on the second end of the molecule, as illustrated in FIG. 4, step C).

It will be understood by one of skill in the art that Bsm1 is a non-limiting example of a type II restriction endonuclease that recognizes an asymmetric sequence and cleaves outside of that asymmetric sequence to yield the desired nucleotide overhangs at the first end and the second end of the double-stranded precursor molecule for ligation in a head to tail configuration. For example, dozens of type II restriction endonuclease enzymes are commercially available and known to those of skill in the art (see, e.g., New England Biolabs catalogue and REBASE web site) from which one of skill in the art could design a first processing site in the 5' flanking region and a second processing site in the 3' flanking region to provide ligation substrates that could only ligate in a head to tail configuration.

The double-stranded capture probe precursor 230 for use in various embodiments of the methods of the invention may be generated using a variety of methods. In one embodiment, the double-stranded capture probe precursor 230 is generated by synthesizing pairs of single-stranded complementary sense and antisense oligonucleotides comprising the full length sequence of the capture probe precursor 230 and annealing the strands together to form the double-stranded capture probe precursor. In another embodiment, a ligation ready, double-stranded capture probe precursor 230 having from one to four nucleotide overhangs on each end, is generated by annealing a pair of synthesized complementary strands together to produce the desired nucleotide overhang that will result in head-to-tail concatemers upon ligation.

In another embodiment, as shown in FIG. 4, step A, and demonstrated in Example 1, a population of double-stranded precursor molecules 230 is generated by first synthesizing a population of single-stranded oligonucleotide precursors 100 comprising a 5' flanking region 210, a target-specific binding region 202, and a portion of the capture reagent binding region 204 (e.g., at least 10 to 20 nucleotides) and annealing the synthesized population of oligos 100 with a common reverse primer oligonucleotide 150 to form the double-stranded capture probe precursor molecules 230. As illustrated in FIG. 4, the common reverse primer oligo 150 is designed to hybridize to the region 204 for binding to a capture reagent on the synthesized oligos 100, and includes the complement of the remaining portion of the region 204, as well as the complement of the 3' flanking region 220. An advantage to the second strand fill in reaction with the reverse primer oligo 150 is the ability to change the 3' flanking region through the use of a reverse primer oligo 150 with different sequences in order to incorporate different restriction enzyme sites or other desired sequences in the 3' flanking region 220 of the double-stranded capture probe precursor molecule 230. For example, other sequences that could be included in the 3' flanking region 220 include primer binding sites, protein binding sites (e.g., for binding a prokaryotic polymerase such as T7 RNA polymerase), modified nucleotides for purification (e.g., biotinylated residues), or methylated 5-methylated 5-methyl-cytosine residues for resistance to bisulphate conversion.

Referring again to FIG. 3, at step 620, the population of double-stranded capture probe precursors 230 are processed into ligation substrates that form head-to-tail concatemers upon ligation with one another, as illustrated in FIG. 4, step B. One of skill in the art can use art-recognized methods to determine the sequence of a 5' flanking region 210 and a 3' flanking region 220 that will provide suitable processing sites, such as restriction endonuclease recognition sites, for generating a first overhang of from 1 to 12 nucleotides on the first end and a second overhang of from 1 to 12 nucleotides on the second end of the double-stranded capture probe precursor 230. In a non-limiting example, as described in Example 1, the double-stranded capture probe precursors 230 are designed to include a 5' flanking region 210 comprising a first restriction enzyme site for Bsm1, in order to create a two nucleotide "GG" overhang at the first end of the precursor 230 molecule, and a 3' flanking region 220 comprising a second restriction enzyme site for Bsm1, in order to create a two nucleotide "CC" overhang at the second end of the precursor 230 after digestion with Bsm1 to facilitate ligation into head-to-tail concatemers, as illustrated in FIG. 4, step B.

At step 630, the processed capture probe precursors are ligated to generate head-to-tail concatemers 240, as illustrated in FIG. 4, step C. As illustrated in FIG. 4, step C, it is noted that the ligation reaction naturally drives towards the formation of circularized templates due to the fact that in very dilute solutions of free ends, the probability of self-ligation (circularization) becomes higher than the probability of finding a separate free end.

At step 640, the head-to-tail concatemers 240 are amplified using any suitable amplification method, such as PCR amplification, in vitro transcription, Klenow, or isothermal amplification.

In one embodiment, the amplification of the head-to-tail concatemers 240 is carried out using isothermal amplification with either *Bacillus subtilis* phage phi29 polymerase (hereafter referred to as "phi29" polymerase) or *Bacillus stearothermophilus* (Bst) DNA polymerase large fragment, 5'→3' exo⁻ (hereafter referred to as "Bst DNA polymerase"). Isothermal amplification is based on random priming of denatured DNA, followed by strand-displacement synthesis at constant temperature, wherein multiple primers are extended over tens of kilobases, as described in Lage et al., Genome Res 13:294-307 (2003), incorporated herein by reference. The single-stranded DNA generated by strand displacement is targeted by new random priming events, and these new strands are elongated in the opposite direction, resulting in a hyperbranched network of amplified head-to-tail concatemers, as shown in FIG. 4, step D.

In one embodiment, as illustrated in FIG. 4, step D, a random primer 250 is used for amplification using the strand displacement polymerase technology found in the TEMPLIPHI isothermal amplification kit (phi29) (GE Life Sciences, Piscataway N.J.). In one embodiment, the random primer 250 comprises a random 7-mer amplification primer with an additional two nitroindole residues at the 5' end and a phosphorothioate linkage at the 3' end: 5'[nitroindole]2-[N] 6-(phosphothioate)-N (SEQ ID NO:77), as described by Lage et al., Genome Res 13:294-307 (2003).

At step 650, the amplified head-to-tail concatemers are processed to release monomer double-stranded capture probe precursors. In one embodiment, as shown in FIG. 4, step E, the concatemers are processed by restriction enzyme cleavage using a type II restriction enzyme that recognizes a site present in the 5' and 3' flanking regions, such as Bsm1.

At step 660, the amplified monomer double-stranded precursor molecules are processed to remove the 5' and/or 3' flanking regions. In one embodiment, as shown in FIG. 4, step E and step F, the 5' flanking region is precisely removed by digestion with Bsm1 and the 3' flanking region is precisely removed by digestion with either Psi1 or HindIII.

At step 670, the monomer double-stranded precursor molecules are further processed to selectively remove the complementary strand of the capture probe to produce a population of single-stranded target specific capture probes 200.

In one embodiment, as shown in FIG. 4, at step E, the Bsm1 digested monomers are treated with alkaline phosphatase to remove the 5' terminal phosphates. At step F, the precise 3' ends of capture probes are then liberated by digestion with either PsiI or HindIII, which each leaves 5' terminal phosphates on the complementary strands. At step G, single-strand capture probe 200 libraries containing only the target specific region 202 and the capture reagent binding region 204 are generated by digesting the double-stranded monomer capture probe precursors with an enzyme, such as Lambda exonuclease, that specifically degrades dsDNA by attacking at 5' phosphate sites and selectively digests away the non-capture complementary strand, thereby converting the dsDNA into ssDNA suitable for use as capture probes.

Alternatively, the non-capture complementary strand may be removed by first adding exonuclease resistant adaptors to the capture probe strand and degrading away the non-capture complementary strand with any suitable double-strand DNA specific exonuclease, such as Exonuclease III. In another example, the capture strand may be selectively amplified by adding an amplification primer binding site in the 5' flanking region 210 of the capture probe precursor 230, and selectively amplifying the plurality of amplified capture probe monomers 270 with an amplification primer that binds to the amplification primer binding site.

Figure 5:
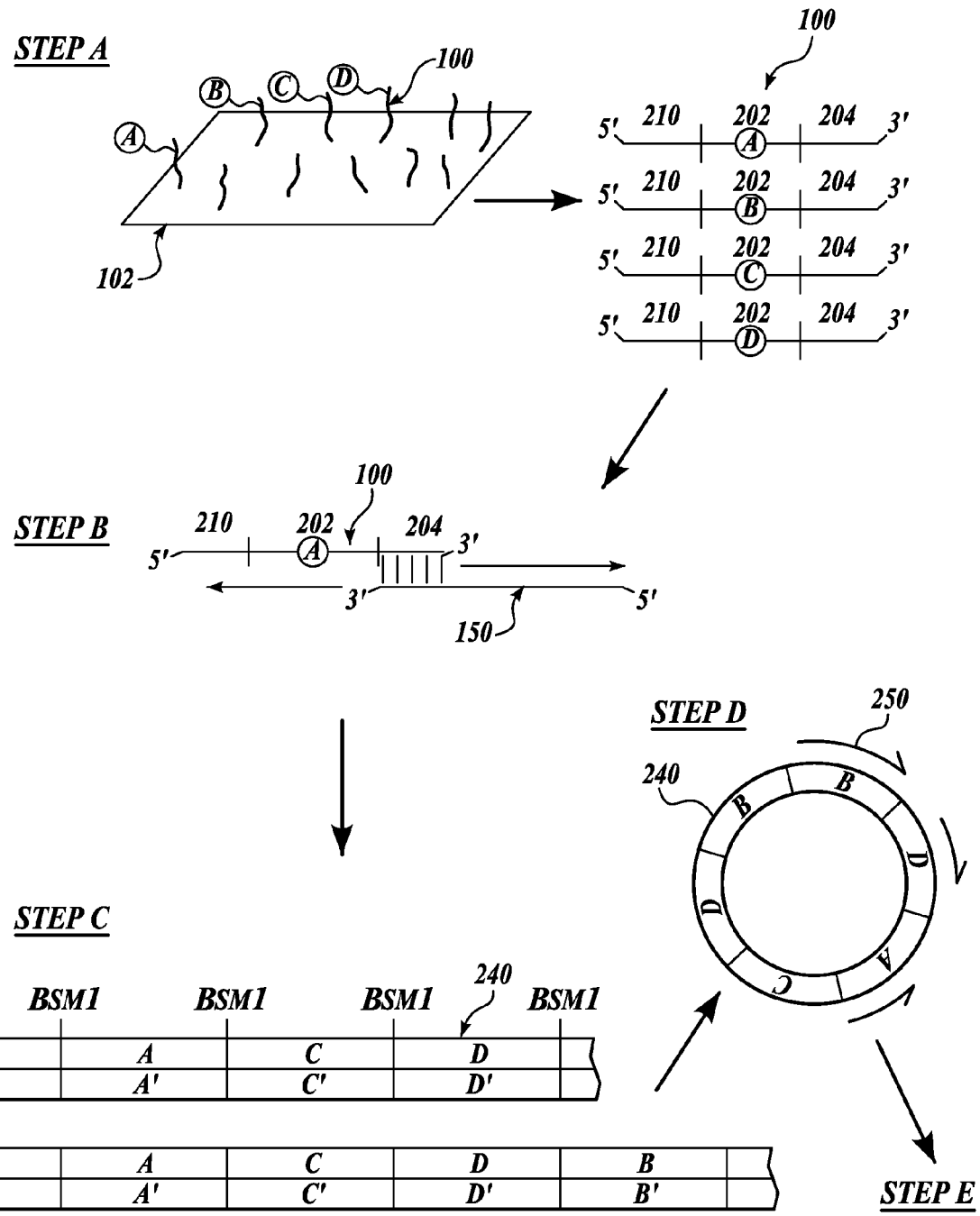
FIG. 5 illustrates more detail of the method illustrated in FIG. 4.

FIG. 5 illustrates further details of the method illustrated in FIG. 4, with regard to a library of single-stranded nucleic acid probes having distinct predetermined sequences A, B, C, and D, such as target-specific capture probes. It will be understood that the method of generating the library comprising probes A, B, C and D is representative for generating a library comprising at least 1,000, such as at least 5,000, such as at least 10,000, such as at least 50,000, such as at least 100,000, such as at least 1,000,000 or more single-stranded nucleic acid probes having predetermined nucleic acid sequences, such as target-specific capture probes. As shown in FIG. 5, step A, a library of single-stranded precursor molecules 100 is synthesized on a substrate 102, the synthesized population comprising a 5' flanking region 210, a target specific binding region 202 and a portion of the capture reagent binding region 204, wherein each of the target specific binding regions comprises a nucleic acid sequence selected to bind to target sequence A, B, C, or D.

The synthesized library of single-stranded precursor molecules 100 is then cleaved off the substrate 102, annealed to a common reverse primer 150 and extended with Klenow, to generate a library of double-stranded capture probe precursor molecules 230 (best illustrated in FIG. 4). Accordingly, the library of double-stranded nucleic acid precursor molecules 230 comprises a 5' flanking region 210 that is essentially identical to every other 5' flanking region in the library, a 3' flanking region 220 that is essentially identical to every other 3' flanking region in the library, and a probe region 200 comprising a nucleic acid sequence 202 that is different from a least a portion of the nucleic acid sequence 202 present in every other probe region 200.

Referring again to FIG. 5, at step C, the 5' and 3' regions of the double-stranded capture probe precursor molecules 230 are then processed to generate ligation substrates and ligated to form head-to-tail concatemers 240 as described with reference to FIG. 4. As illustrated in FIG. 5, step C, the head-to-tail concatemers 240 each comprise a plurality of ligated monomer capture probe regions (A, B, C, D) that are randomly ligated together. At step D, the circularized concatemers 240 are amplified via isothermal amplification with random primers 250, resulting in a plurality of amplified concatemers 260 (best shown in FIG. 4), which are then processed (e.g., with Bsm1) at Step E to generate a library of amplified capture probe monomers 270, which are further processed to remove the non-capture complementary strands, as described with reference to FIG. 4, into a library of single-stranded capture probes 200 comprising a plurality of different target specific binding regions 202 (e.g., that specifically bind to targets A, B, C, and D).

In some embodiments of the methods described herein, a library of capture probe precursors in the form of head-to-tail concatemers, with reference to FIG. 4, step C (e.g., the ligation mixture), or amplified head-to-tail concatemers, with reference to FIG. 4, step D (e.g., the amplified reaction) may be stored at −20° C. for a period of time from several hours up to 6 months or longer, for use as a template in a subsequent amplification reaction, in order to generate additional yields of the capture probe library 200, thus avoiding the need for repeated oligonucleotide synthesis of a particular library of capture probes.

The population of single-stranded capture probes 200 can be used in solution based capture methods as described herein. As demonstrated in Example 2, and shown in FIG. 6, it has been determined that the single-stranded capture probes generated from amplified head-to-tail concatemers, in accordance with the methods of the invention, work at least as well for solution based capture methods as a population of corresponding capture probes that were generated by direct oligonucleotide synthesis. Therefore, it is demonstrated that the methods are useful for generating a library of uniformly amplified single-stranded capture probes from a starting population of double-stranded capture probe precursor molecules.

Figure 6:
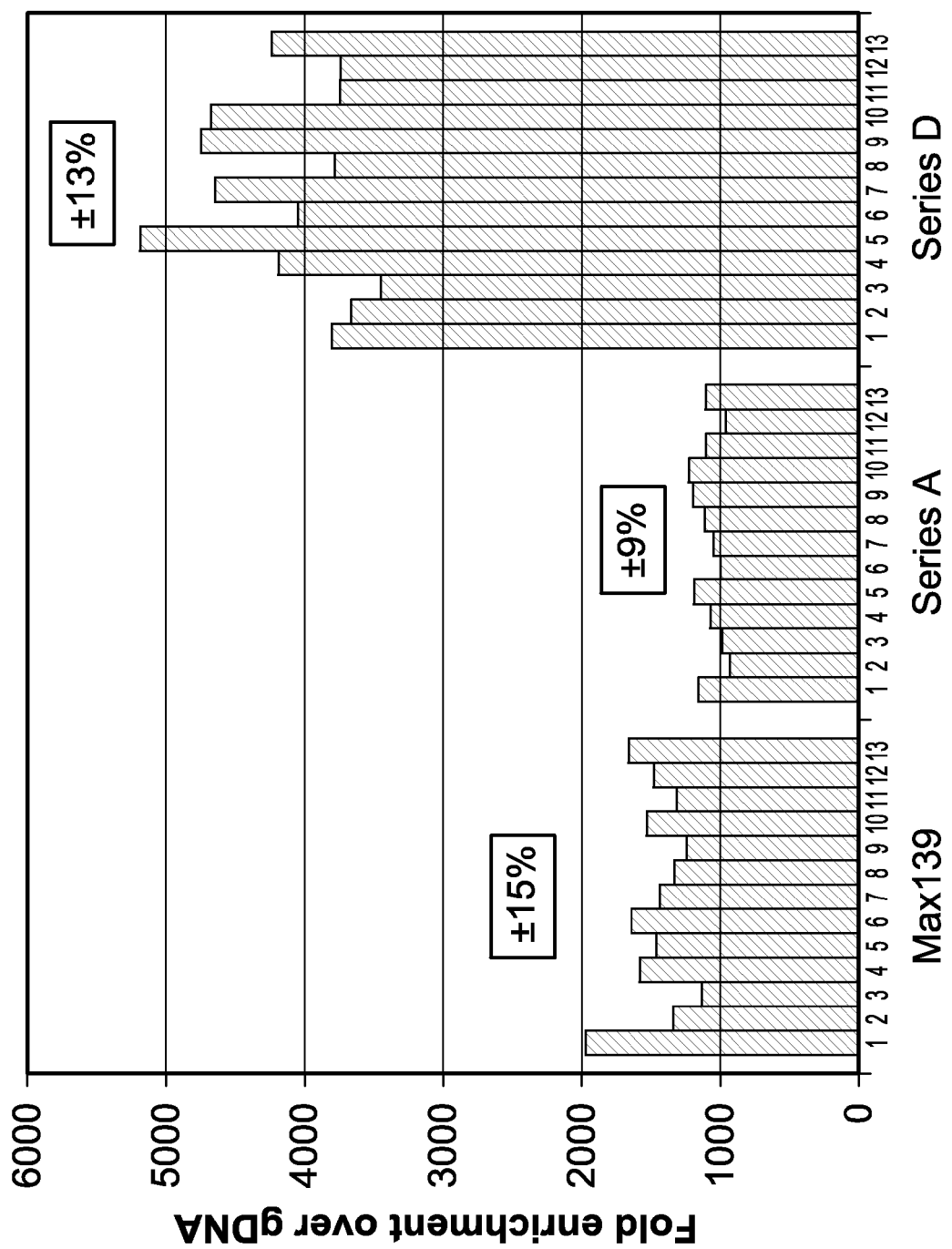
FIG. 6 graphically illustrates the fold enrichment obtained using capture probes generated in accordance with the methods of the present invention, as described in Example 2.

The level of representation of expected nucleic acid sequences in a library generated according to the methods of the invention typically has a variation of less than about 30% (such as a variation of less than about 20%). The level of representation of expected nucleic acid sequence in the final single stranded capture probe library 200 may be assessed using various methods. For example, as described in Example 2, a capture probe library 200 may be used for solution-based capture of a set of targets (e.g., the 13 exons of the AKT gene), and the standard deviation of the exon to exon capture efficiency, expressed as a percentage of the fold-enrichment can be determined, as shown in FIG. 6, thereby providing an indirect measure of the representation of the expected nucleic acid sequences in the capture probe library 200. As another example, quantitative PCR assays may be carried out for representative target sequences at an early step in the method shown in FIG. 4, such as after initial synthesis of the single-stranded precursor nucleic acid molecules 100, or after formation of the double-stranded precursor molecules 230, and compared to quantitative PCR results obtained from the final population of single-stranded capture probes 200 to verify uniform representation of the target sequence. As another example, a test sample that is representative of the final population of single-stranded capture probes 200 can be labeled and hybridized to a substrate comprising a population of nucleic acid molecules comprising the set of predetermined sequences expected to be present in the final population of single-stranded capture probes 200, and the representation of the expected nucleic acids in the test sample is evaluated by analyzing the resulting hybridization pattern.

Oligonucleotide Synthesis

DNA synthesis of the various oligonucleotides of the invention (e.g., single-stranded nucleic acid molecules having predetermined sequences, capture probe precursors and universal adaptor oligonucleotides) can be carried out by any art-recognized chemistry, including phosphodiester, phosphotriester, phosphate triester, or N-phosphonate and phosphoramidite chemistries (see, e.g., Froehler et al., Nucleic Acid Res. 14:5399-5407, 1986; McBride et al., Tetrahedron Lett. 24:246-248, 1983). Methods of oligonucleotide synthesis are well known in the art and generally involve coupling an activated phosphorous derivative on the 3' hydroxyl group of a nucleotide with the 5' hydroxyl group of the nucleic acid molecule (see, e.g., Gait, Oligonucleotide Synthesis: A Practical Approach, IRL Press, 1984).

A population of nucleic acid molecules can be synthesized on a substrate by any art-recognized means including, for example, photolithography (see, Lipshutz et al., Nat. Genet. 21(1 Suppl):20-24, 1999) and piezoelectric printing (see, Blanchard et al., Biosensors and Bioelectronics 11:687-690, 1996). In some embodiments, nucleic acid molecules are synthesized in a defined pattern on a solid substrate to form a high-density microarray. Techniques are known for producing arrays containing thousands of oligonucleotides comprising defined sequences at defined locations on a substrate (see, e.g., Pease et al., Proc. Nat'l. Acad. Sci. 91:5022-5026, 1994; Lockhart et al., Nature Biotechnol. 14:1675-80, 1996; and Lipshutz et al., Nat. Genet. 21 (1 Suppl):20-4, 1999).

In some embodiments, populations of nucleic acid molecules are synthesized on a substrate, to form a high density microarray, by means of an ink jet printing device for oligonucleotide synthesis, such as described by Blanchard in U.S. Pat. No. 6,028,189; Blanchard et al., Biosensors and Bioelectrics 11:687-690 (1996); Blanchard, Synthetic DNA Arrays in Genetic Engineering, Vol. 20, J. K. Setlow, Ed. Plenum Press, New York at pages 111-123; and U.S. Pat. No. 6,028,189 issued to Blanchard. The nucleic acid sequences in such microarrays are typically synthesized in arrays, for example, on a glass slide, by serially depositing individual nucleotide bases in "microdroplets" of a high surface tension solvent such as propylene carbonate. The microdroplets have small volumes (e.g., 100 picoliters (pL) or less, or 50 pL or less) and are separated from each other on the microarray (e.g., by hydrophobic domains) to form surface tension wells which define the areas containing the array elements (i.e., the different populations of nucleic acid molecules). Microarrays manufactured by this ink-jet method are typically of high density, typically having a density of at least about 2,000 different nucleic acid molecules per 1 cm$^2$. The nucleic acid molecules may be covalently attached directly to the substrate, or to a linker attached to the substrate at either the 3' or 5' end of the polynucleotide. Exemplary chain lengths of the synthesized nucleic acid molecules suitable for use in the present methods are in the range of about 20 to about 100 nucleotides in length, such as 50 to 100, 60 to 100, 70 to 100, 80 to 100, or 90 to 100 nucleotides in length. In some embodiments, the nucleic acid molecules are in the range of 80 to 100 nucleotides in length.

Exemplary ink jet printing devices suitable for oligonucleotide synthesis in the practice of the present invention contain microfabricated ink-jet pumps, or nozzles, which are used to deliver specified volumes of synthesis reagents to an array of surface tension wells (see, Kyser et al., J. Appl. Photographic Eng. 7:73-79, 1981).

In some embodiments, a population of nucleic acid molecules is synthesized to form a high-density microarray. A DNA microarray, or chip, is an array of nucleic acid molecules, such as synthetic oligonucleotides, disposed in a defined pattern onto defined areas of a solid support (see, Schena, BioEssays 18:427, 1996). The arrays are preferably reproducible, allowing multiple copies of a given array to be produced and easily compared with each other. Microarrays are typically made from materials that are stable under nucleic acid molecule hybridization conditions. In some embodiments, the nucleic acid molecules on the array are single-stranded DNA sequences. Exemplary microarrays and methods for their manufacture and use are set forth in T. R. Hughes et al., Nature Biotechnology 19:342-347, April 2001, which publication is incorporated herein by reference.

In some embodiments, the methods of the invention utilizes oligonucleotides that are synthesized on a multiplex parallel DNA synthesis system based on an integrated microfluidic microarray platform for parallel production of oligonucleotides, wherein the DNA synthesis system utilizes photogenerated acid chemistry, parallel microfluidics and a programmable digital light controlled synthesizer, as described in U.S. Patent Pub. No. 2007/0059692, Gao et al., Biopolymers 73:579-596 (2004), and Zhou et al., Nucleic Acids Research 32(18):5409-5417 (2004), each of which is incorporated herein by reference.

In some embodiments, the methods of the invention utilize synthesized oligonucleotides that are cleaved off a substrate, such as a microarray. The synthesized nucleic acid molecules can be harvested from the substrate by any useful means. In some embodiments, the portion of the nucleic acid molecule that is directly attached to the substrate, or attached to a linker that is attached to the substrate, is attached to the substrate or linker by an ester bond which is susceptible to hydrolysis by exposure to a hydrolyzing agent, such as hydroxide ions, for example, an aqueous solution of sodium hydroxide or ammonium hydroxide. The entire substrate can be treated with a hydrolyzing agent, or alternatively, a hydrolyzing agent can be applied to a portion of the substrate. For example, a silane linker can be cleaved by exposure of the silica surface to ammonium hydroxide, yielding various silicate salts and releasing the nucleic acid molecules with the silane linker into solution. In some embodiments, ammonium hydroxide can be applied to the portion of a substrate that is covalently attached to the nucleic acid molecules, thereby releasing the nucleic acid molecules into the solution (see, Scott and McLean, Innovations and Perspectives in Solid Phase Synthesis, 3$^{rd}$ International Symposium, 1994, Mayflower Worldwide, pp. 115-124).

In another aspect, the present invention provides a method for enriching a library for target nucleic acid regions of interest. The methods according to this aspect of the invention comprise: (a) amplifying a plurality of head-to-tail concatemers formed from ligating a population of double-stranded nucleic acid precursor molecules, wherein each double-stranded precursor molecule in the starting population comprises a target capture probe region comprising (i) a target-specific binding region comprising a nucleic acid sequence that is at least 95% identical to at least a portion of the sense or antisense strand of a target nucleic acid sequence of interest and (ii) a region for binding to a capture reagent; wherein the target capture region is flanked on the 5' end by a 5' flanking region comprising a first processing site and is flanked on the 3' end by a 3' flanking region comprising a second processing site; (b) processing the amplified head-to-tail concatemers to release double-stranded monomer precursor molecules; (c) selectively removing the complement strand of the double-stranded monomer precursor molecules to generate a population of single-stranded capture probes, each capture probe comprising (i) a target-specific binding region comprising a nucleic acid sequence that is at least 95% identical to at least a portion of the sense or antisense strand of a target nucleic acid sequence of interest and (ii) a region for binding to a capture reagent; (d) contacting the population of single-stranded capture probes with a library comprising at least one target nucleic acid sequence of interest under conditions that allow binding between the capture probes and the at least one nucleic acid target region of interest, to form a mixture comprising a plurality of complexes between target regions of interest and capture probes; (e) contacting the mixture of step (d) with a capture reagent and separating the capture reagent bound complex from the mixture; and (f) eluting the target regions of interest from the capture reagent bound complex.

The steps (a) to (c) may be carried out as previously herein described. The steps (d) to (f) of enriching a library for target sequences with the population of single-stranded capture probes may be carried out as illustrated in FIG. 2. As shown in FIG. 2A, solution-based capture is carried out by first annealing the library of single-stranded capture probes 200, each capture probe comprising a target specific region 202 that hybridizes to a target sequence contained in a library insert, with a library of nucleic acid molecules 50 comprising nucleic acid target insert sequences of interest 10 flanked by a first primer binding region 22 on one end and a second primer binding region 32 on the other end. As further shown in FIG. 2, step A, in one embodiment, the library of nucleic acid molecules 50 is annealed with a combination of a library of single-stranded capture probes 200 each comprising a region 204 that hybridizes to a universal adaptor oligo 300 and an equimolar amount of universal adaptor oligos 300 comprising a moiety 310 for binding to a capture reagent 400.

The annealing step is typically carried out by mixing a molar excess of capture probes (or capture probes plus universal adaptor oligos) with the library in a high salt solution comprising from 100 mM to 2 M NaCl (osmolarity=200 to 4000 molar). An exemplary high salt solution for annealing is 10 mM Tris pH 7.6, 0.1 mM EDTA, 1 M NaCl (osmolarity=2000 molar). The nucleic acid molecules in the mixture are then denatured (i.e., by heating to 94 degrees) and allowed to cool to room temperature. In one embodiment, the annealing step is carried out in a high salt solution comprising from 100 mM to 2 M NaCl with the addition of 0.1% triton X100 (or Tween or NP40) nonionic detergent.

An amount of capture reagent 400 is added to the annealed mixture sufficient to generate a plurality of complexes each containing a nucleic acid molecule, a capture probe (or a capture probe and a universal adaptor oligo), and a capture reagent. This step is carried out in a high salt solution comprising from 100 mM to 2 M NaCl (osmolarity=200 to 4000 molar). An exemplary high salt solution for anneal is 10 mM Tris pH 7.6, 0.1 mM EDTA, 1 M NaCl (osmolarity=2000 molar). The mixture is incubated at room temperature with mixing for about 15 minutes.

The complexes formed are then isolated or separated from solution with a sorting device 500 (e.g., a magnet) that pulls or sorts the capture reagent 400 out of solution.

The sorted complexes bound to the capture reagent 400 are washed with a low salt wash buffer (less than 10 mM NaCl, and more preferably no NaCl) to remove non-target nucleic acids. An exemplary low salt wash buffer is 10 mM Tris pH 7.6, 0.1 mM EDTA (osmolarity=10 millimolar). In some embodiments, the low salt wash optionally contains from 15% to 30% formamide, such as 25% formamide (osmolarity=6.3 molar). For each wash step, the capture reagent 400 bound to the complexes (e.g., magnetic beads) are resuspended in the low salt wash buffer and rocked for 5 minutes, then sorted again with the sorting device (magnet). The wash step may be repeated 2 to 4 times.

The nucleic acid molecules containing the target sequences are then eluted from the complexes bound to the capture reagent as follows. The washed complexes bound to the capture reagent 400 are resuspended in water, or in a low salt buffer (i.e., osmolarity less than 100 millimolar), heated to 94° C. for 30 seconds, the capture reagent (e.g., magnetic beads) is pulled out using a sorting device (e.g., magnet), and the supernatant (eluate) containing the target nucleic acid molecules is collected.

The eluate may optionally be amplified in a PCR reaction with a first PCR primer that binds to the first primer binding site 22 in the first linker and a second PCR primer that binds to the second primer binding site 32 in the second linker, producing an enriched library which can be optionally sequenced.

In another aspect, the present invention provides kits for generating a population of single-stranded nucleic acid molecules from a population of precursor double-stranded molecules. The kits according to this aspect of the invention are useful for carrying out various embodiments of the methods of the invention described herein. The kits in accordance with this aspect of the invention comprise (a) a plurality of random 7-mer oligonucleotide primers, (b) at least one of phi29 polymerase or Bst DNA polymerase large fragment 5'-3' exo-; and (c) a lambda exonuclease enzyme. In some embodiments of the kit, the plurality of random 7-mer oligonucleotide primers each comprise an additional two nitroindole residues at the 5' end and a phosphorothioate linkage at the 3' end (SEQ ID NO:77). In some embodiments, the kit may further comprise at least one of the following: an alkaline phosphatase enzyme, at least one type II restriction enzyme, a DNA ligase, and a DNA polymerase enzyme (Klenow).

In an embodiment of the kit comprising phi29 polymerase, the kit may optionally further comprise one or more of the following reagents: (i) a phi29 concentrated stock reaction buffer comprising at least one of the following: Tris-HCL (e.g., at 50 mM for 10× buffer), $(NH_4)_2SO_4$ (e.g., at 10 mM for 10× buffer), $MgCl_2$ (e.g., 10 mM for 10× buffer) and dithiothreitol (e.g., 4 mM for 10× buffer); (ii) a concentrated stock of dNTPs (e.g. from 100 μM to 10 mM dNTPs); and (iii) a reducing agent, such as dithiothreitol. In further embodiments, the kit may optionally comprise at least one or more of the following; a common reverse primer oligo 150 designed to hybridize to the region 204 for binding to the synthesized oligos 100, Klenow enzyme, at least one Type II Restriction Enzyme, ligase, and alkaline phosphatase.

The following examples merely illustrate the best mode now contemplated for practicing the invention, but should not be construed to limit the invention.

EXAMPLES

All of the compositions and methods disclosed and claimed herein can be made and executed without undue experimentation in light of the present disclosure. In some cases, the compositions and methods of this invention have been described in terms of embodiments, however these embodiments are in no way intended to limit the scope of the claims, and it will be apparent to those of skill in the art that variations may be applied to the compositions and/or methods and in the steps or in the sequence of steps of the methods described herein without departing from the concept, spirit and scope of the invention. More specifically, it will be apparent that certain components which are both chemically and physiologically related may be substituted for the components described herein while the same or similar results would be achieved. All such similar substitutes and modifications apparent to those skilled in the art are deemed to be within the spirit, scope and concept of the invention as defined by the appended claims.

Example 1

This Example demonstrates a method for uniformly amplifying a library of target capture probes specific for the AKT gene designed for solution based capture of the 13 exons of the AKT gene.
Rationale:
Several recent studies describe the complete resequencing of human genomes (Wang et al., Nature 456:60 (2008); Bentley et al., Nature 456:53 (2008); Ley et al., Nature 456:66 (2008)). One in particular describes the full genome sequence of a tumor and normal adjacent tissue (Ley et al. (2008)). Remarkably, the authors distill their analysis of the complete human genome to ten mutated genes, highlighting the point that a small percentage of human genome sequence variations, including the protein coding regions and some surrounding flanking sequences, is interpretable. At the opposite end of the spectrum, candidate gene resequencing strives to test phenotype to genotype hypotheses by seeking sequence variation in specific genes that are thought to influence traits. The caveat is that the selection of candidate genes can be somewhat arbitrary. The ideal solution is one in which the interpretable regions, referred to as the "exome" of the genome, can be selectively resequenced. As used herein, the term "exome" refers to the collection of genomic segments that include protein coding regions, exons, promoters, known ncRNAs (non-coding RNAs) and UTRs, altogether comprising about 2% of the human genome. Interestingly, if the exome could be captured from a sample, then the sequencing data from a single flow cell from a highly parallel sequencing technology (e.g., a single Illumina GAII flow cell) would be adequate to address all of the diploid variation present in the exomic fraction of that sample.

Solution-based capture of the human exome would require ~2 million oligonucleotides. Even with state-of-the-art, high-throughput oligo synthesis stations, the cost of each capture oligo is $7 and therefore the cost of synthesizing an exome solution based capture library would be approximately $14 million. An alternative—synthesized oligonucleotide libraries cleaved from microarrays, also initially appears to be an untenable solution due to the high cost involved to obtain sufficient yields of material. Each microarray typically produces about 50,000 individual oligonucleotide sequences that are high-quality, cleavable oligos in picomole quantities (e.g., commercially available from Agilent, Santa Clara, Calif.). Thus, the cost of synthesizing a library of exome capture oligonucleotide probes from microarrays (requiring ~40 arrays at an estimated cost of $400,000) is substantially reduced relative to conventional oligonucleotide synthesis, however, the yield of material produced by microarray synthesis is sufficient for only four solution based capture experiments. Moreover, the use of high density probe coverage (i.e., more than 4 probes per exon, or at least one capture probe per 35 nt), as shown in FIG. 1B, is preferable for solution based capture in comparison to low density probe coverage (i.e., less than 3 probes per exon, or less than one capture probe per 35 nt), as shown in FIG. 1A. The use of high density probe coverage is preferred in order to ensure that desired targets are enriched, thereby reducing the depth of re-sequencing required of the enriched material. However, such high density probe coverage calls for a greater number of capture oligonucleotides, which significantly inflates the overall expense of technologies that utilize solution based capture methods. Therefore, a need exists to provide a cost-effective method for generating high quality custom oligonucleotide libraries with sufficient yield for applications such as solution based capture.

This Example demonstrates a method for uniformly amplifying a library of synthesized capture oligonucleotides for use in solution based capture methods.

Design of Capture Probe Oligonucleotide Precursors for Amplification and Processing into a Library of Capture Probes:

As shown in FIG. 1C, capture probes 200 may be used to capture nucleic acid molecules comprising target sequences 10 from a mixture of target and non-target nucleic acid molecules. As shown in FIG. 1C, capture probes 200 comprise a target-specific binding region 202 and a region 204 for binding to a capture reagent 300. In the embodiment shown in FIG. 1C, the capture reagent 300 is a universal adaptor oligonucleotide comprising a moiety 310 that binds to a capture reagent, thereby resulting in a tri-molecular solution based capture complex.

Design of Capture Probe Precursor Oligonucleotides:

FIG. 4 at Step A illustrates the general structure of a double-stranded capture probe precursor 230 prior to processing into a single-stranded capture probe 200. The double-stranded capture probe precursor was designed to ensure that the ligation of a plurality of double-stranded capture oligonucleotide probe precursors 230 would result in head-to-tail concatemers 240, as illustrated at Step C, which were then used as templates for amplification, as illustrated at Step D, followed by cleavage into monomers and alkaline phosphatase, as illustrated at Step E, followed by selective degradation of the complementary strand of the capture probe precursor, as shown at Step G, thereby generating a single-stranded capture probe 200 comprising a target-specific binding region 202 and a region 204 for binding to a capture reagent 300, without the 5' flanking region 210 and the 3' flanking region 220.

As shown in FIG. 4, Step A, the general structure of the double-stranded capture probe precursor 230 includes a 5' flanking region 210 comprising a first restriction enzyme site for creating a first nucleotide overhang for ligation (e.g., Bsm1); a capture probe region 200 comprising a target specific hybridizing region 202 and a universal capture oligo hybridizing region 204, and a 3' flanking region 220 comprising a second restriction enzyme site (e.g., Bsm1) for creating a second nucleotide overhang for ligation, and further comprising a third restriction enzyme site (e.g., Psi or HindIII), for precisely cleaving off the 3' flanking region.

Design of the Target-Specific Region 202 of the Capture Probe 200:

In this Example, a 64 oligonucleotide library was synthesized for high density solution based capture of the 13 exon AKT1 gene (NM_005163). As illustrated in FIG. 1B, a library of oligonucleotide capture probes were designed such that each target AKT1 exon had at least 4 or more probes (high density), and the capture probes alternated in strand orientation and were perfectly head to tail with no spaces in between, each having the sequence identical to the corresponding exon sequences 1-13 from the AKT1 gene. The target specific binding regions 202 of the capture probes in the AKT1 capture probe library had a length of 35 nt, as shown below in TABLE 1.

Design of the Region 204 for Binding to a Capture Reagent 300:

The AKT1 capture probes 200 in the library were designed such that each final processed single-stranded capture probe had a 34 nucleotide common region 204 for binding to the universal oligo adaptor capture reagent 300.

As shown in FIG. 4, Step A, in order to further reduce costs of oligonucleotide synthesis, in this Example, the initial population of synthesized oligos 100 included the 5' flanking region 210, the target specific binding regions 202, and only a portion (15 nt of the 34 nt region) of the common region 204 for binding to a capture reagent 300. As shown in FIG. 4, Step A, the 15 nt of the region 204 (5' ACGCGTGGCGGATGT 3' (SEQ ID NO:1)) binds to a region of the reverse primer 150 that was used to anneal and fill-in the library synthesized oligos 100, thereby resulting in the double-stranded capture probe precursors 230.

Design of the 5' Flanking Region 210 of the Capture Probe Precursor 230:

The double-stranded AKT1 capture probe precursors 230 were designed to include a 5' flanking region 210 comprising a first restriction enzyme site for Bsm1, in order to create a two nucleotide "GG" overhang at the first end of the precursor molecules 230 after digestion with Bsm1 to facilitate ligation into head-to-tail concatemers.

The 5' flanking region 210 of the capture probe precursors in this Example had the following sequence: 5' CGCGAATGCC 3' (SEQ ID NO:2) to provide a first Bsm1 site.

Design of the 3' Flanking Region 220 of the Capture Probe Precursor 230:

The double-stranded AKT1 capture probe precursors 230 were designed to include a 3' flanking region 220 comprising a second restriction enzyme site for Bsm1, in order to create a two nucleotide "CC" overhang at the second end of the precursor 230 molecule after digestion with Bsm1 to facilitate ligation into head-to-tail concatemers.

The 3' flanking region was designed to also include a third restriction enzyme recognition sequence to precisely cleave off the 3' flanking region after amplification, and also leave 5' terminal phosphates on the complementary strands (e.g., Psi1 or HindIII).

Using the general design principles described above, several series of oligonucleotides were synthesized as follows:

"A" Series: a control set of 64 AKT capture probes that were directly synthesized (not amplified) having a total length of 69 nucleotides.

"B" Series: a set of 64 AKT capture probe precursor oligonucleotides for amplification, but which did not impose the head to tail ligation characteristics (later abandoned, as discussed below in the results section).

"C" Series: a set of 64 AKT capture probe precursor oligonucleotides for amplification, having a total length of 79 nucleotides (34 nt 204 region that binds to the reverse primer 150, with the same 5' flanking region 210 and target specific region 202 as D series). Note: this series was more expensive to synthesize because they required 0.2 micromolar synthesis, due to the longer size.

"D" Series: a set of 64 AKT capture probe precursor oligonucleotides for amplification, having a total length of 60 nucleotides, including a 15 nt 204 region that binds to the reverse primer 150, with a 10 nucleotide 5' flanking region 210 and a 35 nucleotide target-specific region 202. Note: this series was much less expensive because it was synthesized on a 50 nmole scale, due to shorter size, which was then extended with the reverse primer and Klenow fill-in reaction.

As described above, the C and D series oligos were designed such that after the fill-in reaction with the common reverse primer 150, a pair of asymmetric Bsm1 sites were created on the double-stranded precursor molecule 230, such that following digestion with Bsm1, a two nucleotide "CC" overhang is present on the top strand of each double-stranded oligonucleotide and a two nucleotide "GG" overhang is present on the bottom strand of each double-stranded oligonucleotide, thus creating a situation in which only head-to-tail ligation events are allowed. Moreover, ligation recreates the Bsm1 site for downstream processing after amplification. As described in detail below, the Bsm1 digested amplification products were then treated with Antarctic phosphatase to dephosphorylate the 5' end of the capture strand while leaving an exposed 5' phosphate on the complement strand to allow for degradation by treatment with lambda exonuclease, to generate the desired single-stranded capture probes.

For the "D" Series oligos each capture probe precursor 100 was synthesized as shown below in TABLE 1, with the 5' regions 210 and the 3' regions 220 underlined.

TABLE 1

| | | | The D Series probes for AKT (NM_005163) | |
|---|---|---|---|---|
| Exon | Distance from exon 5' edge | Strand | Probe Sequence | SEQ ID NO: |
| 1 | -35 | - | CGCGAATGCCGGTGCCCGAGGCTCCCGCGACGCTCACGCGCTCCTACG CGTGGCGGATGT | 3 |
| 1 | 0 | + | CGCGAATGCCATGAGCGACGTGGCTATTGTGAAGGAGGGTTGGCTACG CGTGGCGGATGT | 4 |
| 1 | 35 | - | CGCGAATGCCCCAGCCCTGGCAGCGGGTACTAACCTCGTTTGTGCACG CGTGGCGGATGT | 5 |
| 1 | 70 | + | CGCGAATGCCGCCTGGGGAGGGAGAGATGGGGGTAGTAGCCCCAGACG CGTGGCGGATGT | 6 |
| 2 | -35 | - | CGCGAATGCCCTACAGACGTGCGGGTGGTGAGAGCCACGCACACTACG CGTGGCGGATGT | 7 |
| 2 | 0 | + | CGCGAATGCCGGGAGTACATCAAGACCTGGCGGCCACGCTACTTCACG CGTGGCGGATGT | 8 |
| 2 | 35 | - | CGCGAATGCCTTGTAGCCAATGAAGGTGCCATCATTCTTGAGGAGACG CGTGGCGGATGT | 9 |
| 2 | 70 | + | CGCGAATGCCGGAGCGGCCGCAGGATGTGGACCAACGTGAGGCTCACG CGTGGCGGATGT | 10 |
| 2 | 105 | - | CGCGAATGCCGGGATACTTACGCGCCACAGAGAAGTTGTTGAGGGACG CGTGGCGGATGT | 11 |
| 2 | 140 | + | CGCGAATGCCCTTGGCCTCTCGGGATTCAGATTTGGGGGGTTGGCACG CGTGGCGGATGT | 12 |
| 3 | -35 | - | CGCGAATGCCCTGCGGGCAGGCAGAGCCTCTGTCTGCGTGCATCCACG CGTGGCGGATGT | 13 |
| 3 | 0 | + | CGCGAATGCCAGTGCCAGCTGATGAAGACGGAGCGGCCCCGGCCCACG CGTGGCGGATGT | 14 |
| 3 | 35 | - | CGCGAATGCCGTGGTCCACTGCAGGCAGCGGATGATGAAGGTGTTACG CGTGGCGGATGT | 15 |

TABLE 1-continued

The D Series probes for AKT (NM_005163)

| Exon | Distance from exon 5' edge | Strand | Probe Sequence | SEQ ID NO: |
|---|---|---|---|---|
| 3 | 70 | + | CGCGAATGCCTGTCATCGAACGCACCTTCCATGTGGAGACTCCTGACGCGTGGCGGATGT | 16 |
| 3 | 105 | − | CGCGAATGCCCCTGGCCTGGCCGCCACAGCCCACGTACCGCTCCTACGCGTGGCGGATGT | 17 |
| 4 | −35 | − | CGCGAATGCCCTGCAGGAGGTCAGGTGAGGCTGCAGGCCTGTACCACGCGTGGCGGATGT | 18 |
| 4 | 0 | + | CGCGAATGCCGGAGGAGTGGACAACCGCCATCCAGACTGTGGCTGACGCGTGGCGGATGT | 19 |
| 4 | 35 | − | CGCGAATGCCGTCCATCTCCTCCTCCTCCTGCTTCTTGAGGCCGTACGCGTGGCGGATGT | 20 |
| 4 | 70 | + | CGCGAATGCCTTCCGGTCGGGCTCACCCAGTGACAACTCAGGGGCACGCGTGGCGGATGT | 21 |
| 4 | 105 | − | CGCGAATGCCGCTTGGGCTTGGCCAGGGACACCTCCATCTCTTCAACGCGTGGCGGATGT | 22 |
| 4 | 140 | + | CGCGAATGCCACCGCGTGGTGAGGCCTGTCCCCACTTCTGCCTGTACGCGTGGCGGATGT | 23 |
| 5 | −35 | − | CGCGAATGCCCTATGGGCAGGCACCAGGGTCAGCAAGCGGCGCTGACGCGTGGCGGATGT | 24 |
| 5 | 0 | + | CGCGAATGCCACCATGAACGAGTTTGAGTACCTGAAGCTGCTGGGACGCGTGGCGGATGT | 25 |
| 5 | 35 | − | CGCGAATGCCCCTTCACCAGGATCACCTTGCCGAAAGTGCCCTTGACGCGTGGCGGATGT | 26 |
| 5 | 70 | + | CGCGAATGCCAGAAGGCCACAGGCCGCTACTACGCCATGAAGATCACGCGTGGCGGATGT | 27 |
| 5 | 105 | − | CGCGAATGCCGGCCCCACCTTGGCCACGATGACTTCCTTCTTGAGACGCGTGGCGGATGT | 28 |
| 6 | −35 | − | CGCGAATGCCCTGTAAAGCAGGGCTGGGTGAGCTGCCACCCCGCAACGCGTGGCGGATGT | 29 |
| 6 | 0 | + | CGCGAATGCCGACGAGGTGGCCCACACACTCACCGAGAACCGCGTACGCGTGGCGGATGT | 30 |
| 6 | 35 | − | CGCGAATGCCTCACTGTGAGGAAGGGGTGCCTGGAGTTCTGCAGGACGCGTGGCGGATGT | 31 |
| 6 | 70 | + | CGCGAATGCCGTGGGAGCCCAGATGGGGCTGAAGGGCTGGGGCCAACGCGTGGCGGATGT | 32 |
| 7 | −35 | − | CGCGAATGCCCTGCAAGGAAGGGGAGCTGGAACTGCGGCCCCACAACGCGTGGCGGATGT | 33 |
| 7 | 0 | + | CGCGAATGCCGCCCTGAAGTACTCTTTCCAGACCCACGACCGCCTACGCGTGGCGGATGT | 34 |
| 7 | 35 | − | CGCGAATGCCCCTCGCCCCCGTTGGCGTACTCCATGACAAAGCAGACGCGTGGCGGATGT | 35 |
| 7 | 70 | + | CGCGAATGCCTAGGGGCTGGGGCTGCGGGGATGGACTTCGCGGCACGCGTGGCGGATGT | 36 |
| 8 | −35 | − | CGCGAATGCCCTGCGGGAGGCGCAACCTGAGGCACAGCCGTGGCTACGCGTGGCGGATGT | 37 |
| 8 | 0 | + | CGCGAATGCCCTGTTCTTCCACCTGTCCCGGGAGCGTGTGTTCTCACGCGTGGCGGATGT | 38 |
| 8 | 35 | − | CGCGAATGCCCAATCTCAGCGCCATAGAAGCGGGCCCGGTCCTCGACGCGTGGCGGATGT | 39 |

TABLE 1-continued

The D Series probes for AKT (NM_005163)

| Exon | Distance from exon 5' edge | Strand | Probe Sequence | SEQ ID NO: |
|---|---|---|---|---|
| 8 | 70 | + | CGCGAATGCCTGTCAGCCCTGGACTACCTGCACTCGGAGAAGAACACGCGTGGCGGATGT | 40 |
| 8 | 105 | - | CGCGAATGCCGCCCGCCAGCGCACCTTGAGGTCCCGGTACACCACACGCGTGGCGGATGT | 41 |
| 9 | -35 | - | CGCGAATGCCCTAGGGGAAAGGTGGCCTCAGGTCAGTGCCGCCAGACGCGTGGCGGATGT | 42 |
| 9 | 0 | + | CGCGAATGCCCTGGAGAACCTCATGCTGGACAAGGACGGGCACATACGCGTGGCGGATGT | 43 |
| 9 | 35 | - | CGCGAATGCCTCCCCTCCTTGCACAGCCCGAAGTCTGTGATCTTAACGCGTGGCGGATGT | 44 |
| 9 | 70 | + | CGCGAATGCCTCAAGGACGGTGCCACCATGAAGACCTTTTGCGGCACGCGTGGCGGATGT | 45 |
| 9 | 105 | - | CGCGAATGCCGGGGCGCACACCTCGGGGGCCAGGTACTCAGGTGTACGCGTGGCGGATGT | 46 |
| 10 | -35 | - | CGCGAATGCCCTGCACGGGTGGCAGATGGGCAGGACTCGGCATCAACGCGTGGCGGATGT | 47 |
| 10 | 0 | + | CGCGAATGCCGTGCTGGAGGACAATGACTACGGCCGTGCAGTGGAACGCGTGGCGGATGT | 48 |
| 10 | 35 | - | CGCGAATGCCTCATCTCGTACATGACCACGCCCAGCCCCCACCAGACGCGTGGCGGATGT | 49 |
| 10 | 70 | + | CGCGAATGCCTGTGCGGTCGCCTGCCCTTCTACAACCAGGACCATACGCGTGGCGGATGT | 50 |
| 10 | 105 | - | CGCGAATGCCATCTCCTCCATGAGGATGAGCTCAAAAAGCTTCTCACGCGTGGCGGATGT | 51 |
| 10 | 140 | + | CGCGAATGCCCCGCTTCCCGCGCACGCTTGGTCCCGAGGCCAAGTACGCGTGGCGGATGT | 52 |
| 10 | 175 | - | CGCGAATGCCCTTGGGGTCCTTCTTGAGCAGCCCTGAAAGCAAGGACGCGTGGCGGATGT | 53 |
| 10 | 210 | + | CGCGAATGCCCAGAGGTGAGGGCCGCCCATCCCAGCTACAGGCTAACGCGTGGCGGATGT | 54 |
| 11 | -35 | - | CGCGAATGCCCTGCAGGCAGGAAACAAGGCCACAGTGTCGGTACCACGCGTGGCGGATGT | 55 |
| 11 | 0 | + | CGCGAATGCCGCTTGGCGGGGCTCCGAGGACGCCAAGGAGATCAACGCGTGGCGGATGT | 56 |
| 11 | 35 | - | CGCGAATGCCCTGCCACACGATACCGGCAAAGAAGCGATGCTGCAACGCGTGGCGGATGT | 57 |
| 11 | 70 | + | CGCGAATGCCCACGTGTACGAGAAGAAGGTGCGGCTGCTCCCCGCACGCGTGGCGGATGT | 58 |
| 12 | -35 | - | CGCGAATGCCCTGCAGAGGTGGGCAGACGGGACAGTCATGAGCTTACGCGTGGCGGATGT | 59 |
| 12 | 0 | + | CGCGAATGCCCTCAGCCCACCCTTCAAGCCCCAGGTCACGTCGGAACGCGTGGCGGATGT | 60 |
| 12 | 35 | - | CGCGAATGCCCCGTGAACTCCTCATCAAAATACCTGGTGTCAGTCACGCGTGGCGGATGT | 61 |
| 12 | 70 | + | CGCGAATGCCCCCAGATGATCACCATCACACCACCTGACCAAGGTACGCGTGGCGGATGT | 62 |
| 13 | -35 | - | CGCGAATGCCCTGTGGGTGTAGACAGCTCAGACCCCGGTGCCCCAACGCGTGGCGGATGT | 63 |

TABLE 1-continued

The D Series probes for AKT (NM_005163)

| Exon | Distance from exon 5' edge | Strand | Probe Sequence | SEQ ID NO: |
|---|---|---|---|---|
| 13 | 0 | + | CGCGAATGCCATGACAGCATGGAGTGTGTGGACAGCGAGCGCAGGACG CGTGGCGGATGT | 64 |
| 13 | 35 | - | CGCGAATGCCCCGCTGGCCGAGTAGGAGAACTGGGGGAAGTGGGGACG CGTGGCGGATGT | 65 |
| 13 | 70 | + | CGCGAATGCCCACGGCCTGAGGCGGCGGTGGACTGCGCTGGACGAACG CGTGGCGGATGT | 66 |

Oligo Synthesis: For this experiment, the initial population of oligonucleotides 100 were synthesized individually in solution by Operon (Huntsville, Ala.). In the future, the oligonucleotides will be synthesized on an array then cleaved. For example, synthesized and cleaved oligonucleotides are commercially available (e.g., available from LC Sciences, Houston, Tex., Agilent also manufactures "Sure-print" oligo arrays, cleaves the oligos and delivers pmol quantities of single-strand reagent).

Annealing and Fill-in to Generate Double-Stranded Capture Probe Precursors:

As shown in FIG. 4, Step A, the population of synthesized single-stranded oligonucleotide precursors 100 (free from substrate) were annealed with a common reverse primer oligonucleotide 150 and filled in with Klenow to form double-stranded capture probe precursor molecules 230 as shown in FIG. 4, Step A. The common reverse primer oligo 150 was designed to hybridize to the region 204 for binding to a capture reagent on the synthesized oligos 100, and includes the complement to the remaining portion of the region 204, as well as the complement to the 3' flanking region 220. An advantage to the second strand fill in reaction with the reverse primer oligo 150 is the ability to change the 3' flanking region 220 through the use of a reverse primer oligo 150 with different sequences in order to incorporate different restriction enzyme sites or other desired sequences in the 3' flanking region 220 of the double-stranded capture probe precursor molecule 230.

Design of the Second Strand Reverse Oligonucleotide 150:

The following reverse primer oligonucleotides 150 were used in this Example:

```
Reverse primer #1: (Psi 1, Bsm1 3' end)
                                       (SEQ ID NO: 67)
5' GAGGTCGGCATTCTTATAATTGCTCGAAGGGGTCCACATC
CGCCACGCGT 3';

Reverse primer #2: (HindIII, Bsm1 3' end)
                                       (SEQ ID NO: 68)
5'GAGGTCGGCATTCAAGCTTAATTGCTCGAAGGGGTCCACA
TCCGCCACGCGT 3'
```

Preparation of Oligo Pools and Annealing:

As shown in FIG. 4A, each oligonucleotide 100 in the pool of synthesized oligonucleotides (e.g., pool D, SEQ ID NO:3-66) was annealed to a common reverse primer 150 (SEQ ID NO:67 or SEQ ID NO:68) and filled-in with Klenow to generate a double-stranded oligonucleotide precursor 230 as follows:

Pooling of Oligonucleotides:

Each A, B, C, and D series oligos were resuspended to 100 μM, then each of the oligos in the A, B, C, and D series were pooled separately, to create an A series pool, a B series pool, a C series pool, and a D series pool at 100 μM, each pool containing a mixture of 64 different oligonucleotides. The DNA concentration of the oligo pool (100 μm of 70 to 80mer=2 μg/μl) was confirmed by agarose gel electrophoresis by diluting the pool 50-fold to 40 ng/μl, and loading 2.5 μl and 5 μl.

The common reverse primer 150 (#2: SEQ ID NO:68) for second strand synthesis was resuspended to 100 μM.

Annealing:

The following reagents were combined to give a 1 μM solution in each primer (40 ng/μl combined):

10 μl of 100 μM primer pool C or D (SEQ ID NO:3 to SEQ ID NO:66)
10 μl of 100 μM reverse primer #2 (SEQ ID NO:68)
100 μl New England Biolabs Buffer #4
880 μl H$_2$0
1000 μl total A 100 μl aliquot of the above mixture was heated to 95° C., then cooled down as shown below to room temperature:

95° C., 2 minutes
80° C., 1 minute
75° C., 1 minute
70° C., 1 minute
65° C., 1 minute
60° C., 1 minute
55° C., 1 minute
Room temperature, hold.

A 2.5 μl and 5.0 μl aliquot of the annealed mixture was checked on an agarose gel.

Fill-in Reaction:

The annealed mixture was then treated with Klenow to fill in both strands, thus generating a population of blunt ended, double-stranded precursor molecules 230 as shown in FIG. 4, Step B, each having a target-specific region 202 and a common sequence region 204 for binding to a capture reagent. It will be understood by those of skill in the art that the double-stranded precursor oligo structure 230 may also be generated by synthesis of the top and bottom strands, followed by annealing of the single strands into a double-stranded structure having the desired "GG" nucleotide overhang on the first end and the desired "CC" nucleotide overhang on the second end of the molecule to facilitate head to tail concatemerization upon ligation.

Second strand synthesis of each of the annealed oligo mixtures "C" and "D" were carried out as follows:

100 μl annealed primer mixture, described above
1 μl 10 mM dNTPs
2 μl Klenow (3' to 5' exo-) 5000 units/ml (M0212S), New England Biolabs, MA Incubated at 37° C. for 30 minutes, 75° C. for 20 minutes. A 3 µl or 6 µl aliquot of each pool was checked on an agarose gel.

Exemplary double-stranded capture probe precursors 230 are provided below based on the "D" series oligo for exon 1 (−35) (SEQ ID NO:3), provided in Table 1:

The top strand of the filled-in double stranded product (SEQ ID NO:3 annealed to Reverse primer #1 SEQ ID NO:67) is:

(SEQ ID NO: 69)
5'<u>CGCGAATGCC</u>GGTGCCCGAGGCTCCCGCGACGCTCACGCGCTCCT<u>AC
GCGTGGCGGA</u>TGTGGACCCCTTCGAGCAATTATAAGAATGCCGACC
TC 3'
(3' flanking region: PsiI/Bsm1)

The bottom strand of the filled-in double-stranded product (SEQ ID NO:3 annealed to Reverse Primer #1 SEQ ID NO:67) is:

(SEQ ID NO: 70)
5'GAGGTCGGCATTCTTATAATTGCTCGAAGGGGTCCACATCCGCCACG
CGTAGGAGCGCGTGAGCGTCGCGGGAGCCTCGGGCACCGGCATTCG
CG-3'
(3' flanking region: PsiI/Bsm1)

The top strand of the filled-in double-stranded product (SEQ ID NO:3 annealed to Reverse Primer #2 SEQ ID NO:68) is:

(SEQ ID NO: 71)
5'<u>CGCGAATGCC</u>GGTGCCCGAGGCTCCCGCGACGCTCACGCGCTCCT<u>AC
GCGTGGCGGA</u>TGTGGACCCCTTCGAGCAATTAAGCTTGAATGCCGACC
TC-3'
(3' flanking region: HindIII/Bsm1)

The bottom strand of the filled-in double stranded product shown is:

(SEQ ID NO: 72)
5'GAGGTCGGCATTCAAGCTTAATTGCTCGAAGGGGTCCACATCCGCCA
CGCGT<u>AGGAGCGCGTGAGCGTCGCGGGAGCCTCGGGCACCGGCATTCG
CG</u>-3'
(3' flanking region: HindIII/Bsm1)

Digestion with Bsm1 to Generate Ligation Substrates:

As shown in FIG. 4, Step B, the filled-in double-stranded capture probe precursors 230 were then digested with Bsm1 to generate ligation substrates as follows:

2 µl of Bsm1 (10,000 units/ml, R0134S, New England Biolabs) was added to each of the 100 µl heat inactivated fill-in reactions and incubated at 65° C. for 1 hour. 3 µl and 6 µl of each pool was checked on an agarose gel. The Bsm1 digests were then purified over a QIAQUICK column (Qiagen), eluted and quantified by nanodrop.

Resulting exemplary double-stranded oligonucleotide structures after Bsm1 digestion, as illustrated in FIG. 4, Step B:

The top strand of the Bsm1 digested double-stranded oligo (SEQ ID NO:69/SEQ ID NO:70) is:

(SEQ ID NO: 73)
5'GGTGCCCGAGGCTCCCGCGACGCTCACGCGCTCCT<u>ACGCGTGGCGGA</u>
TGTGGACCCCTTCGAGCAATTATAAGAATGCC 3'
(3' flanking region: PsiI)

The bottom strand of the Bsm1 digested double-stranded oligo (SEQ ID NO:69/SEQ ID NO:70) is:

(SEQ ID NO: 74)
5'CATTCTTATAATTGCTCGAAGGGGTCCACATCCGCCACGCGT<u>AGGAG
CGCGTGAGCGTCGCGGGAGCCTCGGGCACCGG</u>3'
(3' flanking region: PsiI).

The top strand of the Bsm1 digested double-stranded oligo (SEQ ID NO:71/SEQ ID NO:72) is:

(SEQ ID NO: 75)
5'GGTGCCCGAGGCTCCCGCGACGCTCACGCGCTCCT<u>ACGCGTGGCGGA</u>
TGTGGACCCCTTCGAGCAATTAAGCTTGAATGCC 3'
(3' flanking region: HindIII)

The bottom strand of the Bsm1 digested double-stranded oligo (SEQ ID NO:71/SEQ ID NO:72) is:

(SEQ ID NO: 76)
5'CATTCAAGCTTAATTGCTCGAAGGGGTCCACATCCGCCACGCGT<u>AGG
AGCGCGTGAGCGTCGCGGGAGCCTCGGGCACCGG</u>3'
(3' flanking region: HindIII)

Ligation of Bsm1 Digested Precursors to Form Head-to-Tail Concatemers:

As shown in FIG. 4, Step C, the Bsm-1 digested products 230 were then used as ligation substrates to generate a series of head-to-tail concatemers 240 for use as amplification templates.

Ligation was carried out as follows:

The following reagents were combined for each pool "C" and "D":

50 µl 2× quick ligase buffer (New England Biolabs)
11 µl of 48 ng/µl Bsm1 digested pool C or D
34 µl H$_2$O
5 µl ligase (New England Biolabs)
100 µl total Incubated at room temperature for ≥10 minutes. A no DNA control (no template) was also prepared.

As illustrated in FIG. 4, Step C, it is noted that the ligation reaction naturally drives towards the formation of circularized templates due to the fact that in very dilute solutions of free ends, the probability of self-ligation (circularization) becomes higher than the probability of finding a separate free end.

Amplification of Head-to-Tail Concatemers:

As shown in FIG. 4, Step D, circularized concatenated DNA was then amplified by greater than 1000 fold (i.e., 10,000 fold to 20,000 fold) to form amplified concatemers 260 by using a random amplification primer 250 with the strand displacement polymerase technology found in the TEMPLIPHI isothermal amplification kit (GE Life Sciences, Piscataway, N.J.).

The random amplification primer 250 used in this Example was a random 7-mer amplification primer with an additional two nitroindole residues at the 5' end and a phosphorothioate linkage at the 3' end: 5'[nitroindole]2-[N]6-(phosphothioate)-N (SEQ ID NO:77, wherein the "N" at positions 1-7 may be A, G, C or T), as described by Lage et al., Genome Res 13:294-307 (2003), incorporated herein by reference.
Isothermal Amplification:

Four reaction mixtures of "C" pool and "D" pool ligations were prepared as follows, along with 2 reaction mixtures of a "no template" control:

25 µl of 100 µM amplification primer [5-nitroindole]2-[N] 6-(phosphothioate)-N (SEQ ID NO:77)

10 µl ligated template "C" or "D" pool (or no template control)

5 µl 10× phi29 buffer (New England Biolabs)

10 µl H₂0

50 µl total

The above reagents were mixed and incubated at 95° C. for 3 minutes, then cooled to room temperature, then 50 µl of the following enzyme premix was added:

Enzyme Premix:

25 µl of 100 µM amplification primer (SEQ ID NO:77)

10 µl H₂0

5 µl 10× phi29 buffer (NEB)

4 µl 10 mM dNTPs

2 µl 100 mM DTT

2 µl 10 mg/ml BSA (NEB)

2.5 µl phi29 polymerase (NEB)

50 µl total volume of enzyme premix

The 50 µl annealed mixture was combined with the 50 µl enzyme premix, then incubated at 30° C. for 12 hours. The polymerase was inactivated by incubation at 65° C. for 10 minutes, then cooled to 4° C. The mixture was briefly centrifuged to pellet the protein and the supernatant was transferred to a fresh tube.

The isothermal amplification reactions were then ethanol precipitated by combining the four "C" reactions and the four "D" reactions (separately), then adding 600 µl TEzero, split into two tubes of 500 µl each, then adding 120 µl 3M NaOAc at pH 5.2 to each tube, then 1200 µl ethanol. The reactions were centrifuged for 10 minutes at 12K RPM and the pellets were resuspended in 880 µl TEzero. The amount of DNA recovered was quantitated. The yield was determined to be 65 to 79 ng/µl for all four tubes, therefore, each 100 µl isothermal amplification reaction produced 28.5 to 30 µg of DNA, which was an unexpectedly high yield. It is noted that the isothermal amplification reaction carried out with 50 µM of the random amplification primer [5-nitroindole]2-[N]6-(phosphothioate)-N (SEQ ID NO:77) in combination with 400 nM dNTPs and DTT as described above provided reaction conditions that yielded a significantly higher amount of amplification product than was obtained from an amplification reaction with the same templates using the reagents from a commercially available kit (GE Healthcare Life Sciences).

It is noted that an initial attempt was made to simply ligate dsDNA blunt-end oligonucleotide probes together followed by amplification (Series "B" pool). However, it was determined that this initial approach was not suitable for uniformly amplifying a population of probes for solution-based capture because the oligonucleotides were ligated in random head to tail, head to head and tail to tail orientation. In the head to head and tail to tail orientations some common tail sequences hybridized together, thereby creating a snap-back stem in ssDNA. These ssDNA stem regions were poisonous to polymerases, resulting in under-representation of amplified products.

Digestion of Amplified Concatenated Strands into Monomer Double-Stranded Capture Probe Precursors:

As shown in FIG. 4, Step E, the amplified concatenated strands 260 were then cleaved into monomer double-stranded capture precursors 270 with Bsm1 and 5' terminal phosphates were removed with Antarctic Phosphatase, as follows:

Digestion with Bsm1 after Isothermal Amplification:

55 µg from each amplification reaction was digested with 20 µl Bsm1 in a total volume of 1 ml in 1×NEB Buffer #4 buffer at 65° C. for two hours. After the two hour digestion, an aliquot of each digest was checked on an agarose gel. The majority of the "C" and "D" digested pool showed the expected 90 bp product, with a small amount of 130 bp product.

Phosphatase Treatment:

110 µl 10× Antarctic Phosphatase buffer (NEB) was added to the Bsm1 digested pool C and D. 50 µl Antarctic phosphatase was added (NEB), and incubated for one hour at 37° C. then 65° C. for 15 minutes. An aliquot of 10 µl was taken out of each sample, then the samples were ethanol precipitated.

After ethanol precipitation, each sample was split into four tubes of 250 µl each to which was added: 250 µl TEzero, 120 µl of 3M NaOAc pH5.2, 2 µl glycol and mixed. 1200 µl ethanol was added per tube, mixed, precipitated and centrifuged at 12K RPM, 10 minutes.

Digestion With Psi1 or HindIII to Liberate the Precise 3' Ends of the Capture Probes:

As shown in FIG. 4, Step F, monomeric capture precursors and the precise 3' ends of capture probes were then liberated by digestion with Psi1 or HindIII, which also leaves 5' terminal phosphates on the complementary strands.

After the phosphatase treatment as described above, the pellets were then resuspended in 960 µl of 1×NEB #4 buffer and 40 µl Psi1, then digested for 2 hours at 37° C. The digests were then ethanol precipitated.

Selective Removal of the Complementary Strand of the Monomer Capture Probe Precursors to Produce a Population of Single-Stranded Capture Probes for Solution Based Capture:

As shown in FIG. 4, Step G, a population of single-strand capture probes 200 (i.e., a library), each probe 200 containing a distinct target specific region 202 and a common capture reagent binding region 204, were generated by digesting the double-stranded monomer capture probe precursors 270 with Lambda exonuclease. Lambda exonuclease specifically degrades dsDNA by attacking at 5' phosphate sites and selectively digests away the non-capture complementary strand, thereby converting the dsDNA into ssDNA suitable for use as capture probes.

Lambda Exonuclease Digestion:

An enzyme titration was first run with lambda exonuclease starting at a concentration of 1 µl/10 µl and diluted down in 2-fold steps. Each reaction contained 10 µg substrate (digested with Bsm1, alkaline phosphatase and Psi1) in 100 µl and were digested at 37° C. for 10 minutes, 75° C. for 10 minutes, then cooled to 4° C. The reactions were run on an agarose gel and the conditions of 10 µg substrate in 100 µl with 5 µl exonuclease for 10 minutes at 37° C. was used for subsequent digestions of the pool C and pool D substrate.

Scaled Up Reaction:

For capture series "C", 90 µl of 89 ng/µl dsDNA precursor was digested with 5 µl lambda exonuclease in 100 µl 1× lambda exonuclease buffer (NEB).

For capture series "D", 100 µl of 208 ng/µl dsDNA precursor was digested with 5 µl lambda exonuclease in 200 µl 1× lambda exonuclease buffer (NEB).

The following is an exemplary structure of a final single-stranded capture probe 200 resulting from the capture probe precursor SEQ ID NO:69/70 or SEQ ID NO:71/72 after processing with lambda exonuclease:

(SEQ ID NO: 78)
5'GGTGCCCGAGGCTCCCGCGACGCTCACGCGCTCCT<u>ACGCGTGGCGGA</u>

<u>TGTGGACCCCTTCGAGCAATTA</u>3'  3'

The capture probe SEQ ID NO:78 comprises a 5' region 202 that hybridizes to the −35 exon 1 of the AKT gene, and a 3' region 204 (underlined) that hybridizes to a universal biotinylated oligonucleotide 300.

The universal capture hybridizing region 204 of capture probe SEQ ID NO:78 is:

(SEQ ID NO: 80)
5' ACGCGTGGCGGATGTGGACCCCTTCGAGCAATTA 3'

Discussion:

The isothermal amplification method described in this Example converted 2.5 ng (0.1 μmol) of starting material into 50 μg (2000 μmol) of raw, unprocessed double-stranded material, which is a 20,000-fold level of amplification. In comparison, the Agilent custom library array platform provides 250 ng (10 μmol) of cleaved oligonucleotide. Processing of the double-stranded DNA precursor capture probe 230 to single stranded capture probes 200 resulted in approximately 15 μg (1200 μmol) of single-stranded capture probe 200, which is a 60% yield from the starting amplified unprocessed double-stranded material 230. In addition to high yield of amplified products, the use of concatemers 240 as templates for amplification provides an equal distribution of amplified monomer products 270, resulting in an equal distribution of processed capture probes 200. The lambda exonuclease digested material (ssDNA) 200 was successfully used as a capture probe library for solution based capture of the AKT exons 1-13, as described in Example 2.

Example 2

This Example describes solution-based capture using a pool of capture probes 200 generated as described in Example 1, each capture probe 200 comprising a target specific region 202 specific for binding to one of the 13 exons of AKT (NM_005163) and a common region 204 that hybridizes to a universal biotinylated adaptor oligo 300.

Rationale:

As shown in FIG. 2, target gene enrichment of a genomic library may be achieved by indirect capture using a pool of chimeric capture ssDNA probes 200 with a first region 202 that hybridizes to a target nucleic acid sequence 10 and a second region 204 that hybridizes to a universal biotinylated oligo 300, mixing the chimeric oligo 200, the universal biotinylated oligo 300 and the sample containing the target nucleic acid sequence 10 under hybridizing conditions to form a tri-molecular complex (i.e., 10/200/300), and using magnetic beads 400 coated with streptavidin 410 to bind to the biotinylated region 310 of the universal oligo 300 and pull out the target sequences 10 bound in the complex to the chimeric capture probes 200, using a magnet 500.

While indirect capture is described in this Example, it will be understood by those of skill in the art that solution based capture may also be accomplished through the use of ssDNA probes 200 are directly labeled. For example, the probes 200 could be directly labeled by adding a biotin, deoxygenin, fluorescein, and the like (through the use of commercially available kits), followed by the use of antibody coated beads for purification.

Methods:

ssDNA capture probes were generated as described in Example 1. For capture series "C" and "D," the concentration of capture probe after the lambda exonuclease digestion was approximately 40 ng/μl to 50 ng/μl.

The following universal 5' biotinylated oligo (capture reagent 300) was used in this Example:

(SEQ ID NO: 81)
5' [BioTEG] TAATTGCTCGAAGGGGTCCACATCCGCCACGCGT 3'

As described in Example 1, a library of 64 ssDNA chimeric capture oligos 200 were generated that each target one of the 13 exons of AKT1 that each have a first 5' region 202 with the identical sequence to the oligos shown above in TABLE 1, and a second 3' region 204 consisting of the following additional sequence that hybridizes to the universal biotinylated oligo 300:

(SEQ ID NO: 80)
5' ACGCGTGGCGGATGTGGACCCCTTCGAGCAATTA 3'.

Capture Mixture:

A master mix was prepared by combining 62.5 μl of 80 ng/μl of a genomic DNA library containing an average insert size of 100 bp flanked by a first and second primer binding site, 10 μl of 1 μM universal biotinylated oligo (SEQ ID NO:81), 125 μl 2× binding buffer (20 mM Tris pH 7.6, 0.2 mM EDTA, 2M NaCl).

The master mix was then combined (separately) with the following:

10 μl of 1 μM Maxwell 139 AKT1 set, a set of 28 directly synthesized capture oligonucleotides specific for AKT exons 1-13 (low density coverage).

10 μl of 1 μM "A" series high density AKT1 control set (64 oligo pool) that was directly synthesized (not amplified). Each capture probe was synthesized to contain only the target specific portion 202 and the universal oligo hybridizing portion 204, without the flanking sequences. For example, the probe for AKT exon 1 (−35) was identical to the final processed amplified probe for AKT exon 1 (−35) (SEQ ID NO:78).

10 μl of processed "C" Series Capture probes (in duplicate): a set of 64 AKT capture probes generated using the amplification method described in Example 1.

10 μl of processed "D" Series Capture probes: a set of 64 AKT capture probes generated using the amplification method described in Example 1.

20 μl of processed "D" Series Capture probes, as described for Sample #4 above.

Each reaction was brought to a total volume of 250 μl, mixed, and annealed as follows:

95° C. for 5 minutes
80° C. for 15 minutes
75° C. for 15 minutes
70° C. for 15 minutes
65° C. for 15 minutes
60° C. for 15 minutes
55° C. for 15 minutes
Room Temperature.

Capture Reagents:

Washed streptavidin-coated magnetic beads were prepared by combining 66 μl beads (MyOne streptavidin-coated beads, InVitrogen) 500 μl 2× binding buffer and 440 μl water.

Capture:

Each of the annealed 250 μl mixtures were combined with 10 μl of washed beads in a total volume of 1 ml (10 mM Tris, pH 7.6, 0.1 mM EDTA, 1 M NaCl, 0.1% Triton X100) and incubated with mixing for 15 minutes. The beads were then washed four times, 5 minutes each, with 1 ml of TEzero wash buffer (10 mM Tris pH 7.6, 0.1 mM EDTA) containing 25% formamide.

Elution:

The DNA bound to the beads was eluted with two 25 µl aliquots of water by incubation at 95° C. for 1 minute, pulling over the beads, and removing the eluate, for a total eluate volume of 50 µl Amplification of Eluate:

PCR Reaction Mixture (Each Sample Performed in Duplicate)

10 µl template (eluate from enriched fragment library)

30 µl H$_2$O

20 µl 5×PCR buffer (supplied by manufacturer with the EXPAND$^{plus}$® kit, Roche)

10 µl 25 mM MgCl$_2$

```
10 µl Forward PCR primer
(5'-AATGATACGGCGACCACCGA-3' (SEQ ID NO: 82))

10 µl Reverse PCR primer
(5'-CAAGCAGAAGACGGCATACG-3' (SEQ ID NO: 83))
```

5 µl 10 mM dNTPs

5 µl DMSO

1 µl Expand$^{PLUS}$® polymerase (Roche)

100 µl total volume

PCR Cycling Conditions:

1 Cycle:

95° C. for 2 minutes

10 Cycles:

95° C. for 30 sec

60° C. for 30 sec

72° C. for 1 minute

10 Cycles:

95° C. for 30 sec

60° C. for 30 sec

72° C. for 1 minute plus 10 sec/cycle

1 Cycle:

72° C. for 5 minutes

4° C. hold

The PCR products were purified over a QIAQUICK column, quantified and diluted to 1 ng/µl for subsequent quantitative PCR (qPCR) (Taqman) analysis.

Quantitative PCR Analysis:

The PCR products generated as described above (1 ng/µl), no template control and genomic DNA control (10 ng/µl) were used as templates in Taqman assays directed against coding exons 1-13 of AKT1. Negative controls ANKHD, PIK3CA and TP53 were also included in this assay, which should not be captured as target sequences with the AKT specific probe pools.

Results:

The results of the qPCR analysis were analyzed in two ways. First, the fold-enrichment for each solution-based capture over genomic DNA was calculated, as shown in TABLE 2.

TABLE 2

Fold Enrichment relative to genomic DNA of solution-based capture using various capture probe pools

| Targeted AKT exon | Maxwell 139 (10 µl) | Series A (10 µl) | Series C (set #1) (10 µl) | Series C (set #2) (10 µl) | Series D (10 µl) | Series D (20 µl) |
|---|---|---|---|---|---|---|
| exon 1 | 1970 | 1158 | 3471 | 3376 | 3802 | 6370 |
| exon 2 | 1338 | 931 | 2790 | 2895 | 3662 | 6450 |
| exon 3 | 1131 | 989 | 2480 | 2568 | 3452 | 6044 |
| exon 4 | 1579 | 1072 | 2508 | 2507 | 4189 | 7122 |
| exon 5 | 1460 | 1189 | 3408 | 3840 | 5184 | 8878 |
| exon 6 | 1641 | 1002 | 3083 | 3461 | 4048 | 5586 |
| exon 7 | 1435 | 1048 | 3578 | 3660 | 4642 | 6167 |
| exon 8 | 1331 | 1112 | 2408 | 2212 | 3780 | 7418 |
| exon 9 | 1242 | 1194 | 3495 | 3817 | 4746 | 8526 |
| exon 10 | 1528 | 1227 | 3146 | 3176 | 4675 | 9464 |
| exon 11 | 1314 | 1103 | 2592 | 2638 | 3741 | 6904 |
| exon 12 | 1478 | 960 | 1964 | 2511 | 3739 | 6862 |
| exon 13 | 1662 | 1107 | 754 | 648 | 4236 | 6504 |
| ANKHD | 1 | 1 | 1 | 0 | 0 | 1 |
| PIK3CA | 0 | 0 | 0 | 0 | 0 | 0 |
| TP53 | 0 | 1 | 1 | 0 | 0 | 1 |

Second, the standard deviation of the exon-to-exon capture efficiency was calculated as a percent of the overall fold-enrichment, as shown below in TABLE 3. This latter number provides a measure of the uniformity of each capture reaction.

TABLE 3

Standard deviation of the exon-to-exon capture efficiency

| | Max 139 (10 µl) | Series A (10 µl) | Series C (set #1) (10 µl) | Series C (set #2) (10 µl) | Series D (10 µl) | Series D (20 µl) |
|---|---|---|---|---|---|---|
| Average fold enrichment for AKT exons 1-13 | 1470 | 1084 | 2745 | 2870 | 4146 | 7100 |
| standard deviation of exon-to-exon capture efficiency | 216 | 94 | 782 | 863 | 523 | 1175 |
| Percent deviation, expressed as a percentage of the fold-enrichment | 15% | 9% | 28% | 30% | 13% | 17% |

FIG. 6 graphically illustrates the fold of enrichment of the target AKT exons 1 to 13 (shown on the x-axis) relative to genomic DNA of solution-based capture using 100 of each of the following probe pools: the "Maxwell 139" capture probe pool (low density, directly synthesized oligonucleotides), the "Series A" capture probe pool (high density, directly synthesized oligonucleotides) and the "Series D" capture probe pool (high density, generated via amplification of head-to-tail concatemers). As shown in FIG. 6, the fold enrichment using the Series D capture probe pool was at least as good as the fold enrichment using the Series A capture probe pool.

Discussion:

The "A" series oligos were directly synthesized 69 mers (non-amplified) containing the identical sequence as the probe sequences generated after processing amplified sequences. The "C" series oligos were initially synthesized as 79mers, annealed to a reverse primer, filled-in, digested with Bsm1, ligated into concatemers, amplified, digested back to monomers, and lambda-exo treated to generate ssDNA probes. The "D" series oligos were initially synthesized as 60mers (less overlap with reverse primer than the "C" series), annealed to a reverse primer, filled-in, digested with Bsm1, ligated into concatemers, amplified, digested back to monomers and lambda-exo treated to generate ssDNA probes. It is important to note that the "D" series oligos are the least expensive to generate due to the fact that they can be made on a 50 nmole synthesis scale due to their smaller size. As described above in Example 1, the amplification of the capture probe pool "C" or "D" was observed to be in the range of 10,000 to 20,000 fold amplification, thereby facilitating the cost-effective use of solution based capture for target enrichment in a variety of applications.

It is noted that the absolute magnitude of the fold-enrichment shown in TABLE 2 may be exaggerated because the critical stoichiometry between the capture oligonucleotides and the common, biotinylated adaptor capture reagent oligonucleotide was not optimized in this experiment. However, the key metric is that the standard deviation of exon-to-exon capture efficiency, expressed as a percentage of the fold-enrichment, as shown in TABLE 3 and FIG. 6, was essentially identical for the synthetically generated capture probes (Series A=9%) versus the capture probes generated using the amplification methods described in Example 1 (Series D=13%).

Agarose gel analysis of the capture probes generated by the amplification methods described herein showed that they formed bimolecular complexes during solution based capture that were indistinguishable from the biomolecular complexes formed with directly synthesized capture probes. Importantly, as demonstrated in TABLES 2 and 3 and FIG. 6, the solution based capture of the 13 exons of the AKT gene with the capture reagent generated by amplification worked at least as well as control reactions performed with directly synthesized capture probes. This conclusion is based on the metrics of fold-enrichment and on the standard deviation of exon-to-exon enrichment as a percentage of the overall fold-enrichment.

Therefore, this Example demonstrates that the capture probes generated from amplified head-tail concatemers may be successfully used for solution based capture, and provide an advantage in targeted resequencing by reducing the cost of resequencing while increasing the feasibility of profiling applications that are dependent on complex oligonucleotide libraries.

Example 3

This Example describes a method for designing and uniformly amplifying a library of target capture probes designed to capture the entire collection of exons that include protein coding regions from a human genomic DNA library.
Rationale:

As described in Examples 1 and 2, a method for uniformly amplifying a library of synthesized capture oligonucleotides for use in solution based capture methods can be applied to capture all the exons of a gene, such as AKT. This Example demonstrates that the methods described herein can be applied on a very large scale, in order to generate a library of capture probes that capture the entire collection of genomic segments that include all protein coding regions from a human genomic library.
Methods:
Design of Capture Probe Oligonucleotide Precursors for Amplification and Processing into a Library of Capture Probes:

As shown in FIG. 4, step A, the general structure of the double-stranded capture probe precursor includes a 5' flanking region 210 comprising a first restriction enzyme site for creating a first nucleotide overhang for ligation (e.g., Bsm1), a capture probe region 200 comprising a target specific hybridizing region 202 and a universal capture oligo hybridizing region 204, and a 3' flanking region 220 comprising a second restriction enzyme site (e.g., Bsm1) for creating a second nucleotide overhang for ligation, and further comprising a third restriction enzyme site (e.g., Psi1 or HindIII), for precisely cleaving off the 3' flanking region.
Design of the Target-Specific Region 202 of the Capture Probe 200:

In this Example, a capture probe library 200 comprising 1,148,286 distinct target-specific regions 202 was generated for high density solution based capture of the entire collection of genomic segments that include protein coding regions (exons) for 25,341 annotated human genes.

The overall design principles for designing a capture probe library 200 comprising target-specific regions 202 for capture of all the exons of 25,341 human genes were as follows. Each target-specific region 202 was 35 nucleotides in length. The target-specific region was designed such that each target exon had at least 4 or more probes (high density), and the capture probes alternated in strand orientation and were oriented in a head to tail arrangement, with oligo probes alternating with respect to hybridizing to the coding or non-coding strand of the target exon.

In this Example, the term "candidate oligonucleotide" refers to a 35mer nucleotide sequence that was analyzed for potential use as target-specific region in a capture probe, to determine whether the candidate oligonucleotide sequence met the desired criteria, as described below. The 35mer nucleotide sequences that met all of the design criteria outlined herein were chosen as the set of target-specific regions 202 and were synthesized on a microarray along with flanking sequences to generate an oligonucleotide library having 1,148,286 distinct target-specific regions.
Step 1: Obtain Input Sequence:

In order to design the target-specific sequences of the library of capture probes, the genes and transcripts of interest were first identified. In this Example, the entire list of human high quality mRNA transcripts provided in the publicly accessible NCBI database "RefSeq NM transcripts" was selected as input sequence, which was a total of 25,341 human annotated mRNA transcripts. The protein coding exons in the 25,341 input human mRNA transcripts were then identified using the publicly accessible "UCSC Genome Browser" database. The UCSC Genome Browser is developed and maintained by the Genome Bioinformatics Group, a cross-departmental team within the Center for Biomolecular Science and Engineering at the University of California Santa Cruz. Once the protein coding exons were identified, the genomic sequences of interest plus 100 nucleotides of adjacent intronic sequences on either side of the exons were extracted. Overlapping regions were then identified and removed from the list of sequences by using genomic coordinates. For overlapping regions that were identified, the sequence that was retained was based on the 5' most and 3' most genomic coordinates between all the pairs of exons in the overlapping region.
Step 2: Upfront Sequence Classification:

The list of sequences generated as described in Step 1 was then searched using the software program "repeatmasker" to identify, but not mask, the repeat and low complexity elements.

Step 3: Determination of Uniqueness Score of Candidate Oligonucleotide Probe Sequences:

The uniqueness of all 35mer sequences in the sequenced human genome relative to the human genome was determined as follows. First, the "UCSC Genome Browser" database was used to extract every 35mer sequence from the sequenced human genome. Second, the software algorithm "Burrows-Wheeler Alignment" (hereinafter referred to as "BWA") was used to align (i.e., blast) these 35mer sequences against the entire sequenced human genome. BWA is a fast light-weighted tool that aligns short sequences to a sequence database, such as the human reference genome. For each 35mer candidate oligo sequence, BWA returned an alignment score that measures the confidence in the identified location, as described in Li, H., et al., *Genome Res.* 18(11):1851-8 (2008), incorporated herein by reference. The alignment score provided by BWA is a $-\log 10$ p-value, ranging from 37 (unique in the genome) to 0 (multiple perfect matches). Intermediate values reflect alignments that are similar but not 100% (e.g., with one nucleotide mismatch).

Step 4: Final Selection of the Target-Specific Regions 202 for Synthesis to Generate a Library of Capture Probes 200 for Total Exon Capture of the Human Genome:

The final selection of the 1,148,286 distinct target-specific regions for synthesis in order to generate a library of capture probes 200 that hybridizes to all the exons of 25,341 annotated genes was carried out as follows.

For each target exon at least 140 nucleotides or longer, analysis for candidate oligos began at the 5' edge of the exon. For target exons 140 nucleotides or shorter, the analysis began in the 5' intron such that the candidate oligos were equally spaced at the exon center.

From the starting position, each candidate oligo location was then "jittered" by shifting the region of analysis by +/−4 nucleotides as follows. The nucleotide sequence of the candidate oligo closest to the desired location was first examined, and the examination of candidate oligos was carried out by shifting the region of analysis in the order: +1, −1, +2, −2, +3, −3, +4, −4. The +/−4 nucleotide range was chosen because a wider range (more "jitter") may allow oligo dimers to form with adjacent oligos, which would be undesirable.

The best candidate oligos from each "jittered" position were then selected based on the following criteria. First, the BWA alignment score (uniqueness) of the candidate 35mer capture oligo sequences was maximized relative to the entire genome (wherein 37=unique and 0=multiple perfect matches). Second, among the candidate 35mer capture oligo sequences with the same BWA alignment score, the number of repeat/low-complexity nucleotides contained in the 35mer sequence was minimized.

The nucleic acid sequences of the 1,148,286 distinct target-specific 35mer regions were output as a text file to an oligonucleotide synthesis platform and synthesized.

In this Example, the target-specific regions were flanked by a 3' flanking region (SEQ ID NO:1) for annealing to a common reverse primer for second strand synthesis, and by a 5' flanking region (SEQ ID NO:2) which provides at least one processing site for ligation and amplification, resulting in a structure corresponding to the single-stranded capture probe precursor 100 as illustrated in FIG. 4, Step A, and described in Example 1. The processing of the library of capture probe precursors 100 to double-stranded precursors 230, processing of the 5' and 3' flanking regions to generate ligation substrates, ligation into head-to-tail concatemers, amplification and processing of the amplified head-to-tail concatemers to form monomers, and selective removal of the non-capture complement strand of the monomers to form a library of single-stranded capture probes, is carried out as described in Example 1.

TABLE 4 below provides the sequence information and scores from the selection criteria described above for a representative, randomly chosen subset of 2170 capture probe precursors from the total library of 1,148,286 capture probe precursors that were synthesized.

In particular, TABLE 4 provides the following information: Column 1: gene name; Column 2: Genbank transcript reference number; Column 3: target exon number; Column 4: the chromosome of the target exon; Column 5: the gene strand; Column 6: the distance of the capture probe from the 5' edge of the target exon; Column 7: the strand of the capture probe; Column 8: the number of repeat nucleotides; Column 9: the BWA alignment score (wherein 37=unique and 0=multiple perfect matches); Column 10: the number of hits from the BWA alignment (1=unique); Column 11: the number of hits from BWA mismatch (0=no mismatch; 1=mismatch); Column 12: the sequence of the single-stranded precursors, each including the common 5' flanking region (SEQ ID NO:2) and common 3' flanking region (SEQ ID NO:1); and Column 13: the SEQ ID NO: from SEQ ID NO:84 to SEQ ID NO:2253.

As shown in TABLE 4, Column 9, a score of "1" for the "number of hits from the BWA analysis corresponds to a uniqueness score of a perfect 37, in which capture oligo sequence only recognizes the intended target.

TABLE 4

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| KSR2 | NM_173598 | 15 | 12 | - | -35 | + | 0 | 37 | 1 | 0 | CGCGAATGCCCCTCTGTGTAACAGGCTGTTCTCTTCTCTCTAGACGCGTGGCGATGT | 84 |
| KSR2 | NM_173598 | 15 | 12 | - | 0 | - | 0 | 37 | 1 | 0 | CGCGAATGCCGATCTGCGGGGACCAGCGTGGCACTGACAGTGTGTACGCCGTGGCGATGT | 85 |
| KSR2 | NM_173598 | 15 | 12 | - | 35 | + | 0 | 37 | 1 | 0 | CGCGAATGCCCCTCGAGAGATCTCGGCAACTCCATCAAGCACAGACGCCGTGGCGATGT | 86 |
| KSR2 | NM_173598 | 15 | 12 | - | 70 | - | 0 | 37 | 1 | 0 | CGCGAATGCCAAGTAGGCACCAGTGCACACAGGAATCCAGCCTACACGCGTGGCGATGT | 87 |
| CHAF1A | NM_005483 | 13 | 19 | + | 0 | + | 0 | 37 | 1 | 0 | CGCGAATGCCTCCTGGCCCAGCTGCTGCCGCTCCTGCACGGCAATACGCGTGGCGATGT | 88 |
| CHAF1A | NM_005483 | 13 | 19 | + | 35 | - | 0 | 37 | 1 | 0 | CGCGAATGCCTGGAACTCCCGATGATGACCTTGCTCCCGTTCACACGCGTGGCGATGT | 89 |
| CHAF1A | NM_005483 | 13 | 19 | + | 70 | + | 0 | 37 | 1 | 0 | CGCGAATGCCGAGCACTGCGCCCGGGGACTGCTCAGCAACCACAACGCGTGGCGATGT | 90 |
| CHAF1A | NM_005483 | 13 | 19 | + | 105 | - | 0 | 37 | 1 | 0 | CGCGAATGCCAGGTAGGTGGTGGAGGGGCTCCGCGGGCTGCCGGACGCGTGGCGATGT | 91 |
| CHAF1A | NM_005483 | 13 | 19 | + | 140 | + | 0 | 37 | 1 | 0 | CGCGAATGCCACCCCCACCCCAGCGAGGATGCCGCCATCCCACGCGTGGCGATGT | 92 |
| CHAF1A | NM_005483 | 13 | 19 | + | 175 | - | 0 | 37 | 1 | 0 | CGCGAATGCCTCTGGAAATGAGCCGCTTGAGCCGGACTTAGAGACGCGTGGCGATGT | 93 |
| CHAF1A | NM_005483 | 13 | 19 | + | 210 | + | 0 | 37 | 1 | 0 | CGCGAATGCCACTCAGTGTATGAGAAGCGGCCTGACTTCAGGATGACGCGTGGCGATGT | 94 |
| CHAF1A | NM_005483 | 13 | 19 | + | 245 | - | 0 | 37 | 1 | 0 | CGCGAATGCCAAGCTCTGTAGCACCTGCGGGTGCACGTACCAACGCGTGGCGATGT | 95 |
| CHAF1A | NM_005483 | 13 | 19 | + | 280 | + | 0 | 37 | 1 | 0 | CGCGAATGCCCCAGCAGGAGCACCTGCCCGTGCCGTGCCAGTGGAACGCGTGGCGATGT | 96 |
| CHAF1A | NM_005483 | 13 | 19 | + | 315 | - | 0 | 37 | 1 | 0 | CGCGAATGCCCTCTTTGGGGCCGAGGGCACCGATGTCACATAGCACGCGTGGCGATGT | 97 |
| CHAF1A | NM_005483 | 13 | 19 | + | 350 | + | 0 | 37 | 1 | 0 | CGCGAATGCCGACAGTGCAGCGTCCCCTCCACGGGGCCCAGCCAACGCGTGGCGATGT | 98 |
| CHAF1A | NM_005483 | 13 | 19 | + | 385 | - | 0 | 37 | 1 | 0 | CGCGAATGCCCCCGCTGACTTCCTCTTCAGCGAGATGGAATGCCCACGCGTGGCGATGT | 99 |
| CHAF1A | NM_005483 | 13 | 19 | + | 420 | + | 0 | 37 | 1 | 0 | CGCGAATGCCCAGCATGTCATCACCCATTCATGAAGAAGGCCACGCGTGGCGATGT | 100 |
| CHAF1A | NM_005483 | 13 | 19 | + | 455 | - | 0 | 37 | 1 | 0 | CGCGAATGCCCACCTGCCCACCCCCACCTCACCTGGCCGTGCGTGCTACGCGTGGCGATGT | 101 |
| RBBP8 | NM_002894 | 15 | 18 | + | 0 | + | 0 | 37 | 1 | 0 | CGCGAATGCCATGAAGATACGCGTGGCGATGTTAGCTTGGAAGATACCTCTTCATGTGTTGTC | 102 |
| RBBP8 | NM_002894 | 15 | 18 | + | 35 | - | 0 | 37 | 1 | 0 | CGCGAATGCCGATTCATACTCTTCATGTGTTGTCCGATCAAACATACGCGTGGCGATGT | 103 |
| RBBP8 | NM_002894 | 15 | 18 | + | 70 | + | 0 | 37 | 1 | 0 | CGCGAATGCCCTGTTTGCAGACAGTTTCTCCCAAGCAGCAGATGACGCGTGGCGATGT | 104 |
| RBBP8 | NM_002894 | 15 | 18 | + | 105 | - | 0 | 37 | 1 | 0 | CGCGAATGCCTAGTTTTTTGTGCAGTAGACAATTCCTCCTTACGCCGTGGCGATGT | 105 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| RBBP8 | NM_002894 | 15 | 18 | + | 140 | + | 0 | 37 | 1 | 0 | CGCGAATGCCCACAGTAAGATTTTTCTGTTTA ATTATGCTTCACGCGTGGCGATGT | 106 |
| RBBP8 | NM_002894 | 17 | 18 | + | -22 | + | 0 | 37 | 1 | 0 | CGCGAATGCCATTTAATTCATTTTTCCCCAGAG AGACTAGCTTGACGCGTGGCGATGT | 107 |
| RBBP8 | NM_002894 | 17 | 18 | + | 13 | − | 0 | 37 | 1 | 0 | CGCGAATGCCTTTTTCCGAACCACCTCAATATGA GGAAAATTTTGACGCGTGGCGATGT | 108 |
| RBBP8 | NM_002894 | 17 | 18 | + | 48 | + | 0 | 37 | 1 | 0 | CGCGAATGCCAGAGGAGGAAGAAGAAACTGCTT GGGCACACGTGTAACGCGTGGCGATGT | 109 |
| RBBP8 | NM_002894 | 17 | 18 | + | 83 | − | 0 | 37 | 1 | 0 | CGCGAATGCCAGTATCTACATTAGTACTTACAA TTTCACATTCCTACGCGTGGCGATGT | 110 |
| PDGFRA | NM_006206 | 8 | 4 | + | -12 | + | 0 | 37 | 1 | 0 | CGCGAATGCCTTTTTTAAAAGTATCGAAGCA AATTAAAGCTGAACGCGTGGCGATGT | 111 |
| PDGFRA | NM_006206 | 8 | 4 | + | 23 | − | 0 | 37 | 1 | 0 | CGCGAATGCCAGTATAATGGCCACTGTCTTCTTC CTTAGCACGGAACGCGTGGCGATGT | 112 |
| PDGFRA | NM_006206 | 8 | 4 | + | 58 | + | 0 | 37 | 1 | 0 | CGCGAATGCCATTGTAGCTCAAAATGAAGATGC TGTGAAGAGCTAACGCGTGGCGATGT | 113 |
| PDGFRA | NM_006206 | 8 | 4 | + | 93 | − | 0 | 37 | 1 | 0 | CGCGAATGCCCCCTTTACATACCTTGAGTTAACA GTTCAAAAGTAACGCGTGGCGATGT | 114 |
| RB1 | NM_000321 | 17 | 13 | + | 0 | + | 0 | 37 | 1 | 0 | CGCGAATGCCGAAGTACATCTCAGAATCTTGAT TCTGAACAGATACGCGTGGCGATGT | 115 |
| RB1 | NM_000321 | 17 | 13 | + | 35 | − | 0 | 37 | 1 | 0 | CGCGAATGCCAAATTAAGCACATTCAGAATCCA TGGGAAAGACAAACGCGTGGCGATGT | 116 |
| RB1 | NM_000321 | 17 | 13 | + | 70 | + | 0 | 37 | 1 | 0 | CGCGAATGCCAAAAGCCTTTGATTTTTACAAAG TGATCGAAAGTTACGCGTGGCGATGT | 117 |
| RB1 | NM_000321 | 17 | 13 | + | 105 | − | 0 | 37 | 1 | 0 | CGCGAATGCCCATTTCTCTTGTCAAGTTGCCTTC TGCTTTGATAAACGCGTGGCGATGT | 118 |
| RB1 | NM_000321 | 17 | 13 | + | 140 | + | 0 | 37 | 1 | 0 | CGCGAATGCCATAAACATTTAGAACATGTGA ACATCGAATCATACGCGTGGCGATGT | 119 |
| RB1 | NM_000321 | 17 | 13 | + | 175 | − | 0 | 37 | 1 | 0 | CGCGAATGCCTTTAGCTACTTACTGAGAGCCAT GCAAGGGATTCCACGCGTGGCGATGT | 120 |
| EPHA3 | NM_182644 | 7 | 3 | + | 0 | + | 0 | 37 | 1 | 0 | CGCGAATGCCAGGAACAAGAAACAAGTTATAC CATTCTGAGGGCACGCGTGGCGATGT | 121 |
| EPHA3 | NM_182644 | 7 | 3 | + | 35 | − | 0 | 37 | 1 | 0 | CGCGAATGCCGCTTGAGGCTACTGATGTAACA TTTGTGCCTCTTACGCGTGGCGATGT | 122 |
| EPHA3 | NM_182644 | 7 | 3 | + | 70 | + | 0 | 37 | 1 | 0 | CGCGAATGCCCTGACACTATATACGTATTCCAA ATCCGAGCCCGAACGCGTGGCGATGT | 123 |
| EPHA3 | NM_182644 | 7 | 3 | + | 105 | − | 0 | 37 | 1 | 0 | CGCGAATGCCAACTTGCGCTGTTGTCCCATAT CCAGCGGCTGTACGCGTGGCGATGT | 124 |
| EPHA3 | NM_182644 | 7 | 3 | + | 140 | + | 0 | 37 | 1 | 0 | CGCGAATGCCTGAGTTTGAAACTAGTCCAGACT GTATGTATTATTACGCGTGGCGATGT | 125 |
| EPHA3 | NM_182644 | 7 | 3 | + | 175 | − | 0 | 37 | 1 | 0 | CGCGAATGCCGCAAGATCCCTGCCCCCCTCT AGACTGCATTGAACGCGTGGCGATGT | 126 |
| RET | NM_020630 | 2 | 10 | + | 0 | + | 0 | 37 | 1 | 0 | CGCGAATGCCTGGCATTGGGCCTCTACTTCTGA GGGATGCTTACACGCGTGGCGATGT | 127 |
| RET | NM_020630 | 2 | 10 | + | 35 | − | 0 | 37 | 1 | 0 | CGCGAATGCCGTGCCCTGCCTGGTCCACATA CAGCTTCTCCCAACGCGTGGCGATGT | 128 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit mismatch | # BWA Sequence with add-ons | SEQ ID NO: |
|---|---|---|---|---|---|---|---|---|---|---|---|
| RET | NM_020630 | 2 | 10 | + | 70 | + | 0 | 37 | 1 | 0 | CGCGAATGCCGCCCTTGCTGTACGTCCATGCCCT GCGGGACGCCCACGCGTGGCGATGT | 129 |
| RET | NM_020630 | 2 | 10 | + | 105 | − | 0 | 37 | 1 | 0 | CGCGAATGCCATGCTGCCCAGGCGGAAGCTGG GCACCTCCTCAGACGCGTGGCGATGT | 130 |
| RET | NM_020630 | 2 | 10 | + | 140 | + | 0 | 37 | 1 | 0 | CGCGAATGCCCTCTACGGCACGTACCGCACACG GCTGCATGAGAACGCCGTGGCGATGT | 131 |
| RET | NM_020630 | 2 | 10 | + | 175 | − | 0 | 37 | 1 | 0 | CGCGAATGCCGGAGGCCGGTGTCCTCCTGGATG CAGATCCAGTTGACGCGTGGCGATGT | 132 |
| RET | NM_020630 | 2 | 10 | + | 210 | + | 0 | 37 | 1 | 0 | CGCGAATGCCTCTACCTTAACCGAGCCTGGAC CATAGCTCCTGACGCGTGGCGATGT | 133 |
| RET | NM_020630 | 2 | 10 | + | 245 | − | 0 | 37 | 1 | 0 | CGCGAATGCCGGGGCGGCTCCCTTACTGCGAC ACTGAGCTCTCACGCGTGGCGATGT | 134 |
| PIK3CA | NM_006218 | 10 | 3 | + | −8 | + | 0 | 0 | 2 | 0 | CGCGAATGCCTTTACAGAGTAACAGACTAGCT AGAGACAATGAAACGCGTGGCGATGT | 135 |
| PIK3CA | NM_006218 | 10 | 3 | + | 27 | − | 0 | 0 | 2 | 0 | CGCGAATGCCATTGCTTTGAGCTGTTCTTTGTCA TTTCCCTTAAACGCGTGGCGATGT | 136 |
| PIK3CA | NM_006218 | 10 | 3 | + | 62 | + | 0 | 23 | 1 | 1 | CGCGAATGCCTTCTACACGAGATCCTCTCTGA AATCACTGAGACGCGTGGCGATGT | 137 |
| PIK3CA | NM_006218 | 10 | 3 | + | 97 | − | 0 | 37 | 1 | 0 | CGCGAATGCCCACTTACCTGTGACTCCATAGAA AATCTTTCTCCTACGCGTGGCGATGT | 138 |
| PDGFRA | NM_006206 | 11 | 4 | + | −22 | + | 0 | 37 | 1 | 0 | CGCGAATGCCGCTCTCTCTCTTGTCACGTAGCC CTGCGTTCGAACGCGTGGCGATGT | 139 |
| PDGFRA | NM_006206 | 11 | 4 | + | 13 | − | 0 | 37 | 1 | 0 | CGCGAATGCCCCAACAGCACCAGGACTGCAGCA GCCACCGTGAGTACGCGTGGCGATGT | 140 |
| PDGFRA | NM_006206 | 11 | 4 | + | 48 | + | 0 | 37 | 1 | 0 | CGCGAATGCCTGATTGTGATCATCTCACTTATTG TCCTGGTTGTCACGCGTGGCGATGT | 141 |
| PDGFRA | NM_006206 | 11 | 4 | + | 83 | − | 0 | 37 | 1 | 0 | CGCGAATGCCTAGTTTTATGAGAAAATATCTAC CTGTTTCCAAATACGCGTGGCGATGT | 142 |
| NFKB1 | NM_003998 | 4 | 4 | + | −50 | + | 0 | 37 | 1 | 0 | CGCGAATGCCGAGAAGCCTCACAGTTTCTTTTG GTTTCTGTTTGTACGCGTGGCGATGT | 143 |
| NFKB1 | NM_003998 | 4 | 4 | + | −15 | − | 0 | 37 | 1 | 0 | CGCGAATGCCTTGAAGGTATGGCCATCTGCTA AAAACAAAAACAACGCGTGGCGATGT | 144 |
| NFKB1 | NM_003998 | 4 | 4 | + | 20 | + | 0 | 37 | 1 | 0 | CGCGAATGCCATATTAGAGCAACCTAAACAGGT AAGATTAAGGGACGCGTGGCGATGT | 145 |
| NFKB1 | NM_003998 | 4 | 4 | + | 55 | − | 0 | 37 | 1 | 0 | CGCGAATGCCTATTAGACACTGGAATCTAACAT TTAAAGTCCACACGCGTGGCGATGT | 146 |
| EPHA4 | NM_004438 | 9 | 2 | − | −13 | + | 0 | 37 | 1 | 0 | CGCGAATGCCGTTTATCACTCAGGTGTAAGAAC ATATGTGACCACGCGTGGCGATGT | 147 |
| EPHA4 | NM_004438 | 9 | 2 | − | 22 | − | 0 | 37 | 1 | 0 | CGCGAATGCCCTGCCACTGCTTGGTTGGGATCTT CGTACGTAAAGACGCGTGGCGATGT | 148 |
| EPHA4 | NM_004438 | 9 | 2 | − | 57 | + | 0 | 37 | 1 | 0 | CGCGAATGCCAGTTTGCCAAAGAAATTGACGCA TCCTGCATTAAGACGCGTGGCGATGT | 149 |
| EPHA4 | NM_004438 | 9 | 2 | − | 92 | − | 0 | 37 | 1 | 0 | CGCGAATGCCCTTCAGACACTTACCAACTCCTAT AACTTTTTCAATACGCGTGGCGATGT | 150 |
| PALB2 | NM_024675 | 4 | 16 | − | −12 | + | 0 | 37 | 1 | 0 | CGCGAATGCCTTTTAATTACAGAGGCAAAGAAA ACCAATTTTGAACGCGTGGCGATGT | 151 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| PALB2 | NM_024675 | 4 | 16 | - | 23 | - | 0 | 37 | 1 | 0 | CGCGAATGCCCTCAGCAAAAGTTAGTATAGTCTCCTCAGGGGCAACGCTGGCGATGT | 152 |
| PALB2 | NM_024675 | 4 | 16 | - | 58 | + | 0 | 37 | 1 | 0 | CGCGAATGCCGTCCAAGGATGCAAGAAGCTCTGCTTGGTACTACACGCGTGGCGATGT | 153 |
| PALB2 | NM_024675 | 4 | 16 | - | 89 | - | 11 | 37 | 1 | 0 | CGCGAATGCCAGCTTACCAAATAACAATGTTGTTCATAATAGTAGACGCCTGGCGATGT | 154 |
| EPHA3 | NM_005233 | 3 | 3 | + | 0 | + | 0 | 37 | 1 | 0 | CGCGAATGCCTGGAAGAGATCAGTGGTGTGATGAACATTACACACGCGTGGCGATGT | 155 |
| EPHA3 | NM_005233 | 3 | 3 | + | 35 | - | 0 | 37 | 1 | 0 | CGCGAATGCCCATGACATTGCACACCTGGTAAGTCCTGATGGGTACGCCTGGCGATGT | 156 |
| EPHA3 | NM_005233 | 3 | 3 | + | 70 | + | 0 | 37 | 1 | 0 | CGCGAATGCCACCACAGTCAAAACAATTGGCTGAGAACAAACTGGACGCGTGGCGATGT | 157 |
| EPHA3 | NM_005233 | 3 | 3 | + | 105 | - | 0 | 37 | 1 | 0 | CGCGAATGCCTCCACATAAATCTTCTGAGCTGAGTTCCTGGGACACGCGTGGCGATGT | 158 |
| EPHA3 | NM_005233 | 3 | 3 | + | 140 | + | 0 | 37 | 1 | 0 | CGCGAATGCCGTCAAGTTCACTCTACAGACTGCAATAGCATTCACGCGTGGCGATGT | 159 |
| EPHA3 | NM_005233 | 3 | 3 | + | 175 | - | 0 | 37 | 1 | 0 | CGCGAATGCCGTTGAATGTCTCCTTGCAAGTTCCTAAAACCAATGACGCGTGGCGATGT | 160 |
| EPHA3 | NM_005233 | 3 | 3 | + | 210 | + | 0 | 37 | 1 | 0 | CGCGAATGCCCTGTACTACATGGAGTCTGATGATGATCATGGGGATACGCGTGGCGATGT | 161 |
| EPHA3 | NM_005233 | 3 | 3 | + | 245 | - | 0 | 37 | 1 | 0 | CGCGAATGCCTGTCAATCTTTGTAAACTGATGCTCTCGAAATTTCACGCGTGGCGATGT | 162 |
| EPHA3 | NM_005233 | 3 | 3 | + | 280 | + | 0 | 37 | 1 | 0 | CGCGAATGCCCCATTGCAGCTGATGAAAGTTTCACTCAAATGGATACGCCGTGGCGATGT | 163 |
| EPHA3 | NM_005233 | 3 | 3 | + | 315 | - | 0 | 37 | 1 | 0 | CGCGAATGCCATTCAGTGTTGAGCTTCAGAATACGGTCCCCAAGACGCCGTGGCGATGT | 164 |
| EPHA3 | NM_005233 | 3 | 3 | + | 350 | + | 0 | 37 | 1 | 0 | CGCGAATGCCTAGAGAGTAGGTCCTGTCAACAAGAAGGGATTTTACGCCTGGCGATGT | 165 |
| EPHA3 | NM_005233 | 3 | 3 | + | 385 | - | 0 | 37 | 1 | 0 | CGCGAATGCCGGCAACACAAGCACCAACATCTTGAAATGCCAAATACGCCTGGCGATGT | 166 |
| EPHA3 | NM_005233 | 3 | 3 | + | 420 | + | 0 | 37 | 1 | 0 | CGCGAATGCCTTGGTGTCTGTGAGAGTATACTTCAAAAAGTGCCCACGCGTGGCGATGT | 167 |
| EPHA3 | NM_005233 | 3 | 3 | + | 455 | - | 0 | 37 | 1 | 0 | CGCGAATGCCTGTCTGGAAACATAGCCAGATTCTTCACTGTAAATACGCCTGGCGATGT | 168 |
| EPHA3 | NM_005233 | 3 | 3 | + | 490 | + | 0 | 37 | 1 | 0 | CGCGAATGCCCGTACCCATGGACTCCCAGTCCCTGGTGAGGTTACGCCTGGCGATGT | 169 |
| EPHA3 | NM_005233 | 3 | 3 | + | 525 | - | 0 | 37 | 1 | 0 | CGCGAATGCCTCTTCTCCTTAGAATTGTTGACACAAGACCCTCTACGCCGTGGCGATGT | 170 |
| EPHA3 | NM_005233 | 3 | 3 | + | 560 | + | 0 | 37 | 1 | 0 | CGCGAATGCCTCCTCCAAGGATGTACTGCAGTACAGAAGGCGAATACGCCTGGCGATGT | 171 |
| EPHA3 | NM_005233 | 3 | 3 | + | 595 | - | 0 | 37 | 1 | 0 | CGCGAATGCCAGCATTGCAGGAACACACTTGCCAATGGGTACAAGCCACCGCGTGGCGATGT | 172 |
| EPHA3 | NM_005233 | 3 | 3 | + | 630 | + | 0 | 37 | 1 | 0 | CGCGAATGCCGGCTATGGAAGAAAGAGTTTATGTGCCAAGGTAAACGCGTGGCGATGT | 173 |
| KSR2 | NM_173598 | 13 | 12 | - | -32 | + | 6 | 37 | 1 | 0 | CGCGAATGCCTATCCATCTTTCTCTCTTTATCTTTCTCAGTTACGCGTGGCGATGT | 174 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| KSR2 | NM_173598 | 13 | 12 | - | -1 | - | 0 | 37 | 1 | 0 | CGCGAATGCCGGCTTCTTTGGTGCATTTGTTGTG GCACTTTAACCACGCGTGGCGGATGT | 175 |
| KSR2 | NM_173598 | 13 | 12 | - | 34 | - | 0 | 37 | 1 | 0 | CGCGAATGCCCCACCCTGTCATCTTCTGATCATC CACCGAGGAGGACGCGTGGCGGATGT | 176 |
| KSR2 | NM_173598 | 13 | 12 | - | 69 | - | 0 | 37 | 1 | 0 | CGCGAATGCCCCCTGCCCCTAGGGCAGTAAGT GTTAAATAGTTAACGCGTGGCGGATGT | 177 |
| NTRK3 | NM_001012338 | 2 | 15 | - | 0 | + | 0 | 37 | 1 | 0 | CGCGAATGCCGTGGAGGACACACCATGCTCCC CATTCGCTGGATACGCGTGGCGGATGT | 178 |
| NTRK3 | NM_001012338 | 2 | 15 | - | 35 | - | 0 | 37 | 1 | 0 | CGCGAATGCCTAGTGGACTTCCGTACATGATG CTTTCAGGAGGCACGCGTGGCGGATGT | 179 |
| NTRK3 | NM_001012338 | 2 | 15 | - | 70 | + | 0 | 37 | 1 | 0 | CGCGAATGCCCAGAGAGTGATGTATGGAGCTTC GGGGTGATCCTCACGCGTGGCGGATGT | 180 |
| NTRK3 | NM_001012338 | 2 | 15 | - | 105 | - | 0 | 37 | 1 | 0 | CGCGAATGCCAACCATGCTGCTTTCCATAGGT GAAGATCTCCAACGCGTGGCGGATGT | 181 |
| NTRK3 | NM_001012338 | 2 | 15 | - | 140 | + | 0 | 37 | 1 | 0 | CGCGAATGCCCCAACTCTCAAACACGGAGGTAA AAAGGGGTGCACGCGTGGCGGATGT | 182 |
| RPS6KA1 | NM_002953 | 4 | 1 | + | -29 | + | 0 | 37 | 1 | 0 | CGCGAATGCCCTGCCCTGCCCACTGTCAGGCCGGTGAC CTCAGGTCTTCACGCGTGGCGGATGT | 183 |
| RPS6KA1 | NM_002953 | 4 | 1 | + | 6 | - | 0 | 37 | 1 | 0 | CGCGAATGCCTGCCCAGACGCGTGGCGGATGT TTTCCGACCAGACGCGTGGCGGATGT | 184 |
| RPS6KA1 | NM_002953 | 4 | 1 | + | 41 | + | 0 | 37 | 1 | 0 | CGCGAATGCCCCTGTATGCTATGAAGGTGCTGA AGAAGGCAACGCACGCGTGGCGGATGT | 185 |
| RPS6KA1 | NM_002953 | 4 | 1 | + | 76 | - | 0 | 37 | 1 | 0 | CGCGAATGCCGTTCGCACAGGAGGTGTCCCC ACTCACCTTTCAACGCGTGGCGGATGT | 186 |
| PKN1 | NM_002741 | 7 | 19 | + | 0 | + | 0 | 37 | 1 | 0 | CGCGAATGCCGAGGGCCTGAGGTACGAGTGGTG GGCTGCAGAGACACGCGTGGCGGATGT | 187 |
| PKN1 | NM_002741 | 7 | 19 | + | 35 | - | 0 | 37 | 1 | 0 | CGCGAATGCCGAGGGGTAGGGTTCCACGGAT GGTCTCTGGGAGACGCGTGGCGGATGT | 188 |
| PKN1 | NM_002741 | 7 | 19 | + | 70 | + | 0 | 37 | 1 | 0 | CGCGAATGCCAATGGGGGACCTGGGACCCCAG ACAGCCGCCCCACGCGTGGCGGATGT | 189 |
| PKN1 | NM_002741 | 7 | 19 | + | 105 | - | 0 | 37 | 1 | 0 | CGCGAATGCCGTCTGTAAAGGCCCCGGGCTGGGC GGCTCAGGAAGGACGCGTGGCGGATGT | 190 |
| PKN1 | NM_002741 | 7 | 19 | + | 140 | + | 0 | 37 | 1 | 0 | CGCGAATGCCCGAAGCGGAAGCTCAGTGGCCG GAGCAGCCTCAAACGCGTGGCGGATGT | 191 |
| PKN1 | NM_002741 | 7 | 19 | + | 175 | - | 0 | 37 | 1 | 0 | CGCGAATGCCACGATGCCCACTCACTGTGTTC TCGGCTTCTGCTACGCGTGGCGGATGT | 192 |
| KSR2 | NM_173598 | 16 | 12 | - | 0 | + | 0 | 37 | 1 | 0 | CGCGAATGCCAGCCAAGAAGAAGAGCAAACCC TTGAACCTTCAAGAACGCGTGGCGGATGT | 193 |
| KSR2 | NM_173598 | 16 | 12 | - | 35 | - | 0 | 37 | 1 | 0 | CGCGAATGCCGGGATGTTTCTGCAGCTGCCTA CGCTGCTGTGGAACGCGTGGCGGATGT | 194 |
| KSR2 | NM_173598 | 16 | 12 | - | 70 | + | 0 | 37 | 1 | 0 | CGCGAATGCCTCTCAGCAGCGCTCCCCGCTGCT GTCCAGCGCTCACGCGTGGCGGATGT | 195 |
| KSR2 | NM_173598 | 16 | 12 | - | 105 | - | 0 | 37 | 1 | 0 | CGCGAATGCCCGAAAAGTGCGTGTCCCACAAAG AAGGAGCGGAGGACGCGTGGCGGATGT | 196 |
| KSR2 | NM_173598 | 16 | 12 | - | 140 | + | 0 | 37 | 1 | 0 | CGCGAATGCCTGCCTTCCACCCCTCCTGTTCACA CTGAGGCCAACACGCGTGGCGGATGT | 197 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| KSR2 | NM_173598 | 16 | 12 | - | 175 | - | 0 | 37 | 1 | 0 | CGCGAATGCCAGTGCAGCCCGGCAGGTGACTTACTTGCAGAGAAACGCTGGCGATGT | 198 |
| CHAF1A | NM_005483 | 4 | 19 | + | -42 | + | 0 | 37 | 1 | 0 | CGCGAATGCCTGAAATAACCCTGTTTAAAGATAAACGTCTTCTGACGCGTGGCGATGT | 199 |
| CHAF1A | NM_005483 | 4 | 19 | + | -7 | - | 0 | 37 | 1 | 0 | CGCGAATGCCTAGAGCCTTTGACGAATTTCTTAGTTATCTGAAAACGCTGGCGATGT | 200 |
| CHAF1A | NM_005483 | 4 | 19 | + | 28 | + | 0 | 37 | 1 | 0 | CGCGAATGCCCAGAGAAGAACAAGCTCAGACTGCAAAGAGTAAGACGCGTGGCGATGT | 201 |
| CHAF1A | NM_005483 | 4 | 19 | + | 63 | - | 0 | 37 | 1 | 0 | CGCGAATGCCGCACAGCAGGTTAATTTTCTATTTCAGGGAAAATGACGCGTGGCGATGT | 202 |
| RBBP8 | NM_002894 | 2 | 18 | + | -16 | + | 0 | 37 | 1 | 0 | CGCGAATGCCGAGCATATTAAGCAAGATGAACATCTCGGGAAGCAACGCGTGGCGATGT | 203 |
| RBBP8 | NM_002894 | 2 | 18 | + | 19 | - | 0 | 37 | 1 | 0 | CGCGAATGCCACTAGATGTATCTGCAGAGTTAGGGCTTCCACAGCACGCGTGGCGATGT | 204 |
| RBBP8 | NM_002894 | 2 | 18 | + | 54 | + | 0 | 37 | 1 | 0 | CGCGAATGCCGACTTTAAGGACCTTTGGACAAAACTAAAGAATGACGCGTGGCGATGT | 205 |
| RBBP8 | NM_002894 | 2 | 18 | + | 89 | - | 0 | 37 | 1 | 0 | CGCGAATGCCAAGAAAAGATTTTACCTTGTACTTCTCTATCATGAACGCGTGGCGATGT | 206 |
| CENTG1 | NM_001222772 | 19 | 12 | - | 0 | + | 0 | 37 | 1 | 0 | CGCGAATGCCATTGAGCCGGGCGCGGGCGCGCTTCAGCGCCGACACGCGTGGCGATGT | 207 |
| CENTG1 | NM_001222772 | 19 | 12 | - | 35 | - | 27 | 37 | 1 | 0 | CGCGAATGCCGCTTAACCAGGGTCAGCGAGATGAGGTAGGTCGTTACGCCTGGCGATGT | 208 |
| CENTG1 | NM_001222772 | 19 | 12 | - | 66 | + | 23 | 37 | 1 | 0 | CGCGAATGCCAAGCTCGAGTCGTGCCTCCGCGCCCCTTCTCCACGCGTGGCGATGT | 209 |
| CENTG1 | NM_001222772 | 19 | 12 | - | 109 | - | 0 | 37 | 1 | 0 | CGCGAATGCCCCTCGGAGCCTCTGGCACCGGCGGCGCCGCCGGGACGCGTGGCGATGT | 210 |
| CENTG1 | NM_001222772 | 19 | 12 | - | 140 | + | 0 | 37 | 1 | 0 | CGCGAATGCCCGAGACTGGGATCCTGCAGCCCCGAGGCGCGACGCGTGGCGATGT | 211 |
| CENTG1 | NM_001222772 | 19 | 12 | - | 175 | - | 0 | 37 | 1 | 0 | CGCGAATGCCGAAGAGACGTTCGTGCCGCTTCTTGCCCGGCTCCTACGCGTGGCGATGT | 212 |
| CENTG1 | NM_001222772 | 19 | 12 | - | 210 | + | 0 | 37 | 1 | 0 | CGCGAATGCCCACCGGCAGGATGCGCTGTGGATCAGCACGAGCAGACGCGTGGCGATGT | 213 |
| CENTG1 | NM_001222772 | 19 | 12 | - | 245 | - | 0 | 37 | 1 | 0 | CGCGAATGCCACAGGGCTGGGGCTCCGCGCCCCCGTGCCCGACGCGTGGCGATGT | 214 |
| CENTG1 | NM_001222772 | 19 | 12 | - | 280 | + | 0 | 37 | 1 | 0 | CGCGAATGCCCCCGGCTCCGGCCAGTCCGGCCCGCCCAGTCTCCACGCGTGGCGATGT | 215 |
| CENTG1 | NM_001222772 | 19 | 12 | - | 315 | - | 0 | 37 | 1 | 0 | CGCGAATGCCCCAGAGGAGGAGGCGGCGGCCGGGAGGCGGACGCCGTGGCGATGT | 216 |
| CENTG1 | NM_001222772 | 19 | 12 | - | 350 | + | 0 | 37 | 1 | 0 | CGCGAATGCCCCTCCGGAGACCCCGCTCTCCGGGGGACTGAGCCACGCGTGGCGATGT | 217 |
| CENTG1 | NM_001222772 | 19 | 12 | - | 385 | - | 0 | 37 | 1 | 0 | CGCGAATGCCGGAGGAGGTGGGGCGCCCCCAGGCTTGGGGTCGACGCGTGGCGATGT | 218 |
| CENTG1 | NM_001222772 | 19 | 12 | - | 420 | + | 0 | 37 | 1 | 0 | CGCGAATGCCGGCCCCCTGCTCAGCAGCCCGAGCTGGGCGGACGCGTGGCGATGT | 219 |
| CENTG1 | NM_001222772 | 19 | 12 | - | 455 | - | 0 | 37 | 1 | 0 | CGCGAATGCCCGCCCCCCGGCCTTCGGGCTCCGGGACGCGGTGGCGATGT | 220 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| CENTG1 | NM_001222772 | 19 | 12 | - | 490 | + | 0 | 37 | 1 | 0 | CGCGAATGCCCTGGCTCATCCTCTCCGCACCCTG GCACCGGCAGCACGCGTGGCGATGT | 221 |
| CENTG1 | NM_001222772 | 19 | 12 | - | 525 | - | 0 | 37 | 1 | 0 | CGCGAATGCCGGAGCCGGCGGAGGAGGCGCCA CCTTGAGCCTCCGACGCCGTGGCGATGT | 222 |
| CENTG1 | NM_001222772 | 19 | 12 | - | 560 | + | 0 | 37 | 1 | 0 | CGCGAATGCCAAGCTTGCAAGACCGTGACCA CGAGTGAGCCAAGCCGTGGCGATGT | 223 |
| CENTG1 | NM_001222772 | 19 | 12 | - | 595 | - | 0 | 37 | 1 | 0 | CGCGAATGCCCAGGCGGCTACCCGGCCCTTGC CCCCGCCGGCTTACGCGTGGCGATGT | 224 |
| CENTG1 | NM_001222772 | 19 | 12 | - | 630 | + | 0 | 37 | 1 | 0 | CGCGAATGCCTCATGGCCCGAAAGCGAGGGCAA GCCCAGGGTCAAACGCGTGGCGATGT | 225 |
| CENTG1 | NM_001222772 | 19 | 12 | - | 665 | - | 0 | 37 | 1 | 0 | CGCGAATGCCCCGAAGCTCCAGTCCCGCGCTG CTCTTTGACCCCACGCGTGGCGGATGT | 226 |
| CENTG1 | NM_001222772 | 19 | 12 | - | 700 | + | 25 | 37 | 1 | 0 | CGCGAATGCCTCTGCCCGCCACCCGCC GCCGCCGGGGAACGCGTGGCGATGT | 227 |
| CENTG1 | NM_001222772 | 19 | 12 | - | 735 | - | 0 | 37 | 1 | 0 | CGCGAATGCCCCGACCCCACCAGAGGTCGAAGC TGTAGAGCCCCCACGCGTGGCGATGT | 228 |
| CENTG1 | NM_001222772 | 19 | 12 | - | 770 | + | 0 | 37 | 1 | 0 | CGCGAATGCCGGCTGGGCGTGGAGCCCGAGGG AAGTTGTCCCCTCACGCGTGGCGGATGT | 229 |
| CENTG1 | NM_001222772 | 19 | 12 | - | 805 | - | 0 | 37 | 1 | 0 | CGCGAATGCCGTCACTGTTGTCCAAGGTCTTACT CTTGCCTTTCCACGCGTGGCGGATGT | 230 |
| CENTG1 | NM_001222772 | 19 | 12 | - | 840 | + | 0 | 37 | 1 | 0 | CGCGAATGCCTTGCATCCGGGACCGCCTGCCGG CTCTCCTCCTCCACGCCTGGCGGATGT | 231 |
| CENTG1 | NM_001222772 | 19 | 12 | - | 875 | - | 0 | 37 | 1 | 0 | CGCGAATGCCCAGTGGCTGGACTCGGAGTTGGT GGGAGGGTTAGACGCCGTGGCGATGT | 232 |
| CENTG1 | NM_001222772 | 19 | 12 | - | 910 | + | 0 | 37 | 1 | 0 | CGCGAATGCCCTGTCACCGCTGCTTCCGCGCAG CCCCCGGGCTACGCGTGGCGGATGT | 233 |
| CENTG1 | NM_001222772 | 19 | 12 | - | 945 | - | 0 | 37 | 1 | 0 | CGCGAATGCCCCCGGACTGAGGCTCCAGAGT GATTGGAGGTGCACGCGTGGCGGATGT | 234 |
| CENTG1 | NM_001222772 | 19 | 12 | - | 980 | + | 0 | 37 | 1 | 0 | CGCGAATGCCGTGAAACGGGGCCGGGAGGGG GGCCGAGCATCCAACGCGTGGCCGATGT | 235 |
| CENTG1 | NM_001222772 | 19 | 12 | - | 1015 | - | 0 | 37 | 1 | 0 | CGCGAATGCCGCCGCTGATAAACTTGAGCATCT TGCGGTCACGAGACGCCGTGGCGGATGT | 236 |
| CENTG1 | NM_001222772 | 19 | 12 | - | 1050 | + | 0 | 37 | 1 | 0 | CGCGAATGCCATCTTCACCAAGAGCACAGGAGG GCCTCCTGCCTCACGCGTGGCGGATGT | 237 |
| CENTG1 | NM_001222772 | 19 | 12 | - | 1085 | - | 0 | 37 | 1 | 0 | CGCGAATGCCAGAAGACAGGCTGGGGGGTCC GGGAAGGGGCCCAGCGCCGTGGCGGATGT | 238 |
| CENTG1 | NM_001222772 | 19 | 12 | - | 1120 | + | 0 | 37 | 1 | 0 | CGCGAATGCCCAGCGGGTCAGGAGCTGCTG GGCGCCGAGCTCACGCGTGGCGGATGT | 239 |
| CENTG1 | NM_001222772 | 19 | 12 | - | 1155 | - | 0 | 37 | 1 | 0 | CGCGAATGCCCTCAAGCCTGACTCAACTCACT AGGGGAAGCGCGACGCGTGGCGGATGT | 240 |
| PKN1 | NM_002741 | 1 | 19 | + | -56 | + | 2 | 37 | 1 | 0 | CGCGAATGCCGCTCCTCTTGGCCGCCCCTCCCTCC GCGCGGGACCCACGCCGTGGCGGATGT | 241 |
| PKN1 | NM_002741 | 1 | 19 | + | -25 | - | 0 | 37 | 1 | 0 | CGCGAATGCCCCGCTGGCCATGTCCTCCTGCCGC CCGCCAGGGTCACGCGTGGCGGATGT | 242 |
| PKN1 | NM_002741 | 1 | 19 | + | 9 | + | 0 | 37 | 1 | 0 | CGCCAATGCCGACGCCCTGCAGGTAGGCGCACC TGCGTCTGGAGTACGCGTGGCGGATGT | 243 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| PKN1 | NM_002741 | 1 | 19 | + | 41 | − | 32 | 37 | 1 | 0 | CGCGAATGCCGGGGTCCGCCGGCGCCGTCCGGT CCCCCGGGACTACGCCGTGGCGGATGT | 244 |
| PIK3CA | NM_006218 | 5 | 3 | + | 0 | + | 0 | 37 | 1 | 0 | CGCGAATGCCTATATAGAAGCTGTATAATGCT TGGGAGGATGCCACGCCGTGGCGGATGT | 245 |
| PIK3CA | NM_006218 | 5 | 3 | + | 35 | − | 0 | 37 | 1 | 0 | CGCGAATGCCAATAAAGGCTTTCTTTAGCCATC AACATCAAATTGACGCCGTGGCGGATGT | 246 |
| PIK3CA | NM_006218 | 5 | 3 | + | 70 | + | 0 | 37 | 1 | 0 | CGCGAATGCCCTCAACTGCCAATGGACTGTTTT ACAATGCCATCTACGCCGTGGCGGATGT | 247 |
| PIK3CA | NM_006218 | 5 | 3 | + | 105 | − | 0 | 37 | 1 | 0 | CGCGAATGCCATATATGGTAGCTGTGTGAAAT GCGTCTGAATAACGCCGTGGCGGATGT | 248 |
| PIK3CA | NM_006218 | 5 | 3 | + | 140 | + | 0 | 37 | 1 | 0 | CGCGAATGCCGAATGGAGAAAACATCTACAAAAT CCCTTTGGGTTAACGCCGTGGCGGATGT | 249 |
| PIK3CA | NM_006218 | 5 | 3 | + | 175 | − | 0 | 37 | 1 | 0 | CGCGAATGCCTGCACAAAGAATTTTATTCTGA GTGCACTATTTAACGCCGTGGCGGATGT | 250 |
| PIK3CA | NM_006218 | 5 | 3 | + | 210 | + | 0 | 37 | 1 | 0 | CGCGAATGCCACCTACGTGAATGTAAATATTCG AGACATTGATAAACGCCGTGGCGGATGT | 251 |
| PIK3CA | NM_006218 | 5 | 3 | + | 245 | − | 0 | 37 | 1 | 0 | CGCGAATGCCCTATAAAATAATAAGCATCAGCA TTTGACTTTACCACGCCGTGGCGGATGT | 252 |
| KSR2 | NM_173598 | 12 | 12 | − | −8 | + | 0 | 37 | 1 | 0 | CGCGAATGCCCCCTACGGATCCAGCAAGGTTAG TCCGACAGAGTACGCCGTGGCGGATGT | 253 |
| KSR2 | NM_173598 | 12 | 12 | − | 27 | − | 0 | 37 | 1 | 0 | CGCGAATGCCCTTCCGTAGAGGGTTGTTGATGT CACACGGAACGGACGCCGTGGCGGATGT | 254 |
| KSR2 | NM_173598 | 12 | 12 | − | 62 | + | 0 | 37 | 1 | 0 | CGCGAATGCCCCACCTGCTATTCAGACCTGCA CATCAGTCAGACGCCGTGGCGGATGT | 255 |
| KSR2 | NM_173598 | 12 | 12 | − | 97 | − | 0 | 37 | 1 | 0 | CGCGAATGCCGCCTTACTTGTTGATTTTGTTGG TTTTGGGGAGCACGCCGTGGCGGATGT | 256 |
| PDGFRA | NM_006206 | 2 | 4 | + | −46 | + | 0 | 37 | 1 | 0 | CGCGAATGCCTAATGCTGTTTTCTGTTGACTTTTG ACTTTTCTAGTACGCCGTGGCGGATGT | 257 |
| PDGFRA | NM_006206 | 2 | 4 | + | −11 | − | 0 | 37 | 1 | 0 | CGCGAATGCCGAACGCCGGATGGAAGTCCCCA TAGCTCTCGGAAACGCCGTGGCGGATGT | 258 |
| PDGFRA | NM_006206 | 2 | 4 | + | 24 | + | 0 | 37 | 1 | 0 | CGCGAATGCCCTGGTCTTAGGCTGTCTTCTCACA GGTACGGAGCCACGCCGTGGCGGATGT | 259 |
| PDGFRA | NM_006206 | 2 | 4 | + | 59 | − | 0 | 37 | 1 | 0 | CGCGAATGCCACAAGACACCCAAACAAGGAAC TCAGAGAGGACTGACGCCGTGGCGGATGT | 260 |
| EPHA4 | NM_004438 | 14 | 2 | − | 0 | − | 0 | 37 | 1 | 0 | CGCGAATGCCGTCCACCATCTGCTCCCCTGAACT TGATTTCAAATACGCCGTGGCGGATGT | 261 |
| EPHA4 | NM_004438 | 14 | 2 | − | 35 | + | 0 | 37 | 1 | 0 | CGCGAATGCCCTACTCCATTCCAAGTTCACAGA TGTCTCGTTGACACGCCGTGGCGGATGT | 262 |
| EPHA4 | NM_004438 | 14 | 2 | − | 70 | − | 0 | 37 | 1 | 0 | CGCGAATGCCCCCTCAGAATACAGGTGCCGCC AGGACATTTCCTACGCCGTGGCGGATGT | 263 |
| EPHA4 | NM_004438 | 14 | 2 | − | 105 | + | 0 | 37 | 1 | 0 | CGCGAATGCCGTCACCAGCTCCACATTTCTTGCA TACCACATTATACGCCGTGGCGGATGT | 264 |
| EPHA4 | NM_004438 | 14 | 2 | − | 140 | − | 0 | 37 | 1 | 0 | CGCGAATGCCCCCAGCAAGTGCCGACCCTGTGG AAGTGGGGTCCAACGCCGTGGCGGATGT | 265 |
| EPHA4 | NM_004438 | 14 | 2 | − | 175 | + | 0 | 37 | 1 | 0 | CCCGAATGCCTGGTCTTCAAGCCATTCTGCT GTGGGGTTAGACGCCGTGGCGGATGT | 266 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| EPHA4 | NM_004438 | 14 | 2 | - | 210 | + | 0 | 37 | 1 | 0 | CGCGAATGCCAAGTCTCCATCACTGACCTCTAGCTCATACCAATACGCGTGGCGGATGT | 267 |
| EPHA4 | NM_004438 | 14 | 2 | - | 245 | - | 0 | 37 | 1 | 0 | CGCGAATGCCGACACTCCATTCACAGCCCAGATTTCAAAGTGTAACGCGTGGCGGATGT | 268 |
| EPHA4 | NM_004438 | 14 | 2 | - | 280 | + | 0 | 37 | 1 | 0 | CGCGAATGCCAAATATAACCCTAACCCAGACCAATCAGTTTCTGACGCGTGGCGGATGT | 269 |
| EPHA4 | NM_004438 | 14 | 2 | - | 315 | - | 0 | 37 | 1 | 0 | CGCGAATGCCTCAATTCCTACCTGCTTGGTTGGTGGTCACAGTGAACGCGTGGCGGATGT | 270 |
| EPHA3 | NM_005233 | 11 | 3 | + | 0 | + | 0 | 37 | 1 | 0 | CGCGAATGCCGTGAATTTGGAGAGGTGTGCAGTGGTCGCTTAAAACGCGTGGCGGATGT | 271 |
| EPHA3 | NM_005233 | 11 | 3 | + | 35 | - | 0 | 37 | 1 | 0 | CGCGAATGCCTTAATGCCACTGAAATCTCTTTTTTTGAAGGAAGACGCGTGGCGGATGT | 272 |
| EPHA3 | NM_005233 | 11 | 3 | + | 70 | + | 0 | 37 | 1 | 0 | CGCGAATGCCGACCCTGAAAGTTGGCTACACAGAAAAGCAGAGGAACGCGTGGCGGATGT | 273 |
| EPHA3 | NM_005233 | 11 | 3 | + | 105 | - | 0 | 37 | 1 | 0 | CGCGAATGCCTGTCCCATAATGCTTGCTTCTCCCAGGAAGTCTCACGCGTGGCGGATGT | 274 |
| EPHA3 | NM_005233 | 11 | 3 | + | 140 | + | 0 | 37 | 1 | 0 | CGCGAATGCCTTTGACCACCCCAATATCATTCGACTGGAAGGAGTACGCGTGGCGGATGT | 275 |
| EPHA3 | NM_005233 | 11 | 3 | + | 175 | - | 0 | 37 | 1 | 0 | CGCGAATGCCAGTCTTATGACTACTTTACTTACTTTGGTAACAACGCGTGGCGGATGT | 276 |
| RB1 | NM_000321 | 23 | 13 | + | 0 | + | 0 | 37 | 1 | 0 | CGCGAATGCCACATTCAAACGTGTTTGATCAAAGAAGAGGAGTAACGCGTGGCGGATGT | 277 |
| RB1 | NM_000321 | 23 | 13 | + | 35 | - | 0 | 37 | 1 | 0 | CGCGAATGCCTGAAGACCGAGTTATAGAATACTATAATAGAATCAACGCGTGGCGGATGT | 278 |
| RB1 | NM_000321 | 23 | 13 | + | 70 | + | 0 | 37 | 1 | 0 | CGCGAATGCCTGCAGAGACTGAAAACAAATATTTTGCAGTATGCTACGCGTGGCGGATGT | 279 |
| RB1 | NM_000321 | 23 | 13 | + | 105 | - | 0 | 37 | 1 | 0 | CGCGAATGCCCCAATCAAAGGATACTTTTGACCTACCCTGTGGAACGCGTGGCGGATGT | 280 |
| RB1 | NM_000321 | 23 | 13 | + | 140 | + | 0 | 37 | 1 | 0 | CGCGAATGCCAAAAATCTAATGTAATGGGTCCACCAAAACATTAAACGCGTGGCGGATGT | 281 |
| RB1 | NM_000321 | 23 | 13 | + | 175 | - | 0 | 37 | 1 | 0 | CGCGAATGCCGGGCTAGAGCAAAAACAAAAAAGTAGATTATTTATACGCCGTGGCCGATGT | 282 |
| RB1 | NM_000321 | 23 | 13 | + | 210 | + | 0 | 37 | 1 | 0 | CGCGAATGCCCCTACCTTGTCACCAATACCTCACATTCCTGAAGACGCGTGGCGGATGT | 283 |
| RB1 | NM_000321 | 23 | 13 | + | 245 | - | 0 | 37 | 1 | 0 | CGCGAATGCCGAATCCTGAAGGGTGAACTAGGAAACTTGTAAGGGACGCGTGGCGGATGT | 284 |
| RB1 | NM_000321 | 23 | 13 | + | 280 | + | 0 | 37 | 1 | 0 | CGCGAATGCCCTGGAGGGAACATCTATATTTCACCCTGAAGAGTACGCGTGGCGGATGT | 285 |
| RB1 | NM_000321 | 23 | 13 | + | 315 | - | 0 | 37 | 1 | 0 | CGCGAATGCCGTTGGTTTGCAGACCTTCTGAAATTTTATATGGACGCGTGGCGGATGT | 286 |
| RB1 | NM_000321 | 23 | 13 | + | 350 | + | 0 | 37 | 1 | 0 | CGCGAATGCCAAAAATGACTCCAAGATCAAGTGTGTTTTCTCACGCGTGGCGGATGT | 287 |
| EPHB1 | NM_004441 | 3 | 3 | + | 0 | + | 0 | 37 | 1 | 0 | CGCGAATGCCTGGGAAGAAGTCAGTGCTACGATGAAAACCTGAAACGCGTGGCGGATGT | 288 |
| EPHB1 | NM_004441 | 3 | 3 | + | 35 | - | 0 | 37 | 1 | 0 | CGCGAATGCCCGAAGACATTGCACACCTGGTAGGTGCGGATGGTGACGCGTGGCGGATGT | 289 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| EPHB1 | NM_004441 | 3 | 3 | + | 70 | + | 0 | 37 | 1 | 0 | CGCGAATGCCAGCCCACCAGAACAATTGGCTG CTCACCACCTTCACGCGTGGCCGATGT | 290 |
| EPHB1 | NM_004441 | 3 | 3 | + | 105 | − | 0 | 37 | 1 | 0 | CGCGAATGCCTCTGTGTAGATGCGATGGGCCCC CCGCCGGTTGATACGCGTGGCCGATGT | 291 |
| EPHB1 | NM_004441 | 3 | 3 | + | 140 | + | 0 | 37 | 1 | 0 | CGCGAATGCGATGCGCTTCACTGTGAGAGACT GCAGCAGCCTCACGCGTGGCCGATGT | 292 |
| EPHB1 | NM_004441 | 3 | 3 | + | 175 | − | 0 | 37 | 1 | 0 | CGCGAATGCCGTTGAAGGTCTCCTTGCAGGATC CTGGGACATTAGACGCGTGGCCGATGT | 293 |
| EPHB1 | NM_004441 | 3 | 3 | + | 210 | + | 0 | 37 | 1 | 0 | CGCGAATGCCTTGTATTACTATGAGACTGACTCT GTCATTGCCACACGCGTGGCCGATGT | 294 |
| EPHB1 | NM_004441 | 3 | 3 | + | 245 | − | 0 | 37 | 1 | 0 | CGCGAATGCCGGTAGGGGCCTTCAGACCAGAA GGCTGACTTCTTGACGCGTGGCCGATGT | 295 |
| EPHB1 | NM_004441 | 3 | 3 | + | 280 | + | 0 | 37 | 1 | 0 | CGCGAATGCCTCAAAGTAGACACCATTGCTGCA GATGAGAGCTTCACGCGTGGCCGATGT | 296 |
| EPHB1 | NM_004441 | 3 | 3 | + | 315 | − | 0 | 37 | 1 | 0 | CGCGAATGCCACCTTCATCAGCCTTCCCCCAAA GTCCACTGGGAACGCGTGGCCGATGT | 297 |
| EPHB1 | NM_004441 | 3 | 3 | + | 350 | + | 0 | 37 | 1 | 0 | CGCGAATGCCAAACACAGAAGTCAGGAGCTTTG GGCCTCTTACTCACGCGTGGCCGATGT | 298 |
| EPHB1 | NM_004441 | 3 | 3 | + | 385 | − | 0 | 37 | 1 | 0 | CGCGAATGCCTCCATAATCCTGAAAAGCGAGGT AAAAACCATTCCACGCGTGGCCGATGT | 299 |
| EPHB1 | NM_004441 | 3 | 3 | + | 420 | + | 0 | 37 | 1 | 0 | CGCGAATGCCGCTGTATGTCTCTTTCTGTC CGTGTCTTCTTACGCGTGGCCGATGT | 300 |
| EPHB1 | NM_004441 | 3 | 3 | + | 455 | − | 0 | 37 | 1 | 0 | CGCGAATGCCCTGCAAAATTTTGCACAATGCTG GGACACTTTTTGACGCGTGGCCGATGT | 301 |
| EPHB1 | NM_004441 | 3 | 3 | + | 490 | + | 0 | 37 | 1 | 0 | CGCGAATGCCTGTTTCCAGAGACTATGACAGGG GCAGAGAGCACAACGCGTGGCCGATGT | 302 |
| EPHB1 | NM_004441 | 3 | 3 | + | 525 | − | 0 | 37 | 1 | 0 | CGCGAATGCCTTGGGGATGCATGTGCCCCGAGC AATCACCAGAGAACGCGTGGCCGATGT | 303 |
| EPHB1 | NM_004441 | 3 | 3 | + | 560 | + | 0 | 37 | 1 | 0 | CGCGAATGCCCGCAGAGAAGTGGACGTGCCCA TCAAACTCTACTACGCGTGGCCGATGT | 304 |
| EPHB1 | NM_004441 | 3 | 3 | + | 595 | − | 0 | 37 | 1 | 0 | CGCGAATGCCCCCAATAGGCACCATCATTCCC CATCCCCGTTGCACGCGTGGCCGATGT | 305 |
| EPHB1 | NM_004441 | 3 | 3 | + | 630 | + | 0 | 37 | 1 | 0 | CGCGAATGCCGATGCACCTGCAAGCCTGGCTA TGAGCCTGAGAAACGCGTGGCCGATGT | 306 |
| EPHB1 | NM_004441 | 3 | 3 | + | 665 | − | 0 | 37 | 1 | 0 | CGCGAATGCCAGAGGCTCCAAAGCTTACCCTTG CATGCCACGCTGACGCGTGGCCGATGT | 307 |
| NFKB1 | NM_003998 | 22 | 4 | + | 0 | + | 0 | 37 | 1 | 0 | CGCGAATGCCGAGACATGAAAACGCTGGCTGAA GATGTGAAGCTGACGCGTGGCCGATGT | 308 |
| NFKB1 | NM_003998 | 22 | 4 | + | 35 | − | 0 | 37 | 1 | 0 | CGCGAATGCCTTGGATCAGGAATTTCTAGTAA CTTATACAGCTGACGCGTGGCCGATGT | 309 |
| NFKB1 | NM_003998 | 22 | 4 | + | 70 | + | 0 | 37 | 1 | 0 | CGCGAATGCCCAAAAACTGGCTACTCTGGCGC AGAAATTAGGTCACGCGTGGCCGATGT | 310 |
| NFKB1 | NM_003998 | 22 | 4 | + | 105 | − | 0 | 37 | 1 | 0 | CGCGAATGCCAGGACTCAGCCGCCGAAGGCATTAT TAAGTATCCCACGCGTGGCCGATGT | 311 |
| NFKB1 | NM_003998 | 22 | 4 | + | 140 | + | 0 | 37 | 1 | 0 | CGCGAATGCCGCTGCTTCCTTCCAAAACACTTATGGA CAACTATGAGGTACGCGTGGCCGATGT | 312 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| RBBP8 | NM_002894 | 13 | 18 | + | -26 | + | 0 | 37 | 1 | 0 | CGCGAATGCCTTGCATGCTCTTTCCCTTTACCTAAGATGTATCCTACGCGTGGCGGATGT | 313 |
| RBBP8 | NM_002894 | 13 | 18 | + | 9 | - | 0 | 37 | 1 | 0 | CGCGAATGCCTGCTCCCGGATCTATACTCCACTGGATATTTTCAAACGCGTGGCGGATGT | 314 |
| RBBP8 | NM_002894 | 13 | 18 | + | 44 | + | 0 | 37 | 1 | 0 | CGCGAATGCCGACTTTCTCAGTATAAAATGAATGTTACTGTAATACGCGTGGCGGATGT | 315 |
| RBBP8 | NM_002894 | 13 | 18 | + | 79 | - | 0 | 37 | 1 | 0 | CGCGAATGCCGTTTTGGTTTTACTTTTTAACTTACCTTTGTATCTTACGCGTGGCGGATGT | 316 |
| NFKB1 | NM_003998 | 7 | 4 | + | 0 | + | 0 | 37 | 1 | 0 | CGCGAATGCCCTTCGCAAACCTGGGTATACTTCATGTGACAAAGAACGCGTGGCGGATGT | 317 |
| NFKB1 | NM_003998 | 7 | 4 | + | 35 | - | 0 | 37 | 1 | 0 | CGCGAATGCCTGTCATTCGTGCTTCCAGTGTTTCAAATACTTTTTACGCGTGGCGGATGT | 318 |
| NFKB1 | NM_003998 | 7 | 4 | + | 70 | + | 0 | 37 | 1 | 0 | CGCGAATGCCGAGGCGTGTATAAGGGCTATAATCCTGGACTCTTACGCGTGGCGGATGT | 319 |
| NFKB1 | NM_003998 | 7 | 4 | + | 105 | - | 0 | 37 | 1 | 0 | CGCGAATGCCCTTTCGTCTTGCAAATAGGCAAGGTCAGGGTGCACCACGCGTGGCGGATGT | 320 |
| NFKB1 | NM_003998 | 7 | 4 | + | 140 | + | 0 | 37 | 1 | 0 | CGCGAATGCCGTGAGGGGACCCGGCAGCTGGGAGGTAAGCATCATACGCGTGGCGGATGT | 321 |
| NFKB1 | NM_003998 | 10 | 4 | + | -24 | + | 0 | 37 | 1 | 0 | CGCGAATGCCACACTTCAATGTGATTGTTGCAGATGACATCCAGACGCGTGGCGGATGT | 322 |
| NFKB1 | NM_003998 | 10 | 4 | + | 11 | - | 0 | 37 | 1 | 0 | CGCGAATGCCACTCCACATTTCTCCTCTTCATAAATCGAATACGCGTGGCGGATGT | 323 |
| NFKB1 | NM_003998 | 10 | 4 | + | 46 | + | 0 | 37 | 1 | 0 | CGCGAATGCCCTGGGAAGGATTTGGAGATTTTCCCCACAGATGACGCGTGGCGGATGT | 324 |
| NFKB1 | NM_003998 | 10 | 4 | + | 81 | - | 0 | 37 | 1 | 0 | CGCGAATGCCTAATAATATAATAAATCACTTACTTGTCTATGAAACGCGTGGCGGATGT | 325 |
| PIK3CA | NM_006218 | 2 | 3 | + | 0 | + | 0 | 37 | 1 | 0 | CGCGAATGCCATGCCTCCACGACCATCATCAGGTGAACTGTGGGACGCGTGGCGGATGT | 326 |
| PIK3CA | NM_006218 | 2 | 3 | + | 35 | - | 0 | 37 | 1 | 0 | CGCGAATGCCATTCTACTAGGATTCTTGGGGCATCAAGTGATGACGCGTGGCGGATGT | 327 |
| PIK3CA | NM_006218 | 2 | 3 | + | 70 | + | 0 | 37 | 1 | 0 | CGCGAATGCCGTTTACTACCAAATGAATGATAGTGACTTTAGAAACGCGTGGCGGATGT | 328 |
| PIK3CA | NM_006218 | 2 | 3 | + | 105 | - | 0 | 37 | 1 | 0 | CGCGAATGCCTGCTTTATGGTTATTAATGTAGCCTCACGGAGGCAACGCGTGGCGGATGT | 329 |
| PIK3CA | NM_006218 | 2 | 3 | + | 140 | + | 0 | 37 | 1 | 0 | CGCGAATGCCTGAACTATTTAAAGAAGCAAGAAATACCCCTCACGCCTGGCGGATGT | 330 |
| PIK3CA | NM_006218 | 2 | 3 | + | 175 | - | 0 | 37 | 1 | 0 | CGCGAATGCCGAAAATGTAAGAAGATTCATCTTGAAGAAGTTGATACGCGTGGCGGATGT | 331 |
| PIK3CA | NM_006218 | 2 | 3 | + | 210 | + | 0 | 37 | 1 | 0 | CGCGAATGCCGTAAGTGTTACTCAAGAAGCAGAAAGGGAAGAATTACGCGTGGCGGATGT | 332 |
| PIK3CA | NM_006218 | 2 | 3 | + | 245 | - | 0 | 37 | 1 | 0 | CGCGAATGCCGCCGAAGGTCACAAAGTCGTCTTGTTTCATCAAAAACGCGTGGCGGATGT | 333 |
| PIK3CA | NM_006218 | 2 | 3 | + | 280 | + | 0 | 37 | 1 | 0 | CGCGAATGCCTTTTCAACCCTTTTAAAAGTAATTGAACCAGTACGCGTGGCGGATGT | 334 |
| PIK3CA | NM_006218 | 2 | 3 | + | 315 | - | 0 | 37 | 1 | 0 | CGCGAATGCCATTTCTCGATTGAGGATCTTTTCTTCACGGTTGCCACGCGTGGCGGATGT | 335 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| PIK3CA | NM_006218 | 2 | 3 | + | 350 | + | 0 | 37 | 1 | 0 | CGCGAATGCCTGGTATGATACAATATCCTATTCT AAAATGCAAATACGCGTGGCGGATGT | 336 |
| EPHA4 | NM_004438 | 10 | 2 | - | -44 | + | 13 | 37 | 1 | 0 | CGCGAATGCCGTGTTTGAAGGAAAATAATTCTCT TTTTAAAAAAACGCGTGGCGGATGT | 337 |
| EPHA4 | NM_004438 | 10 | 2 | - | -1 | - | 0 | 37 | 1 | 0 | CGCGAATGCCCGCTTCTTGTTTGGCTTTACTGTA TTTACTCCGTCACGCGTGGCGGATGT | 338 |
| EPHA4 | NM_004438 | 10 | 2 | - | 30 | + | 0 | 37 | 1 | 0 | CGCGAATGCCAGCGGATGAAGAGAAACATTTGA ATCAAGGTACAAACGCGTGGCGGATGT | 339 |
| EPHA4 | NM_004438 | 10 | 2 | - | 65 | - | 0 | 37 | 1 | 0 | CGCGAATGCCCATGCTCTAAAATAGAATTTTTT AATCCAATTTTACGCGTGGCGGATGT | 340 |
| NFKB1 | NM_003998 | 23 | 4 | + | 0 | + | 0 | 37 | 1 | 0 | CGCGAATGCCGTCTCTGGGGTACAGTCAGAGA GCTGGTGAGGCACGCGTGGCGGATGT | 341 |
| NFKB1 | NM_003998 | 23 | 4 | + | 35 | - | 0 | 37 | 1 | 0 | CGCGAATGCCCTTCAATTGCTTCGGTGTAGCCCA TTTGTCTCAGGACGCGTGGCGGATGT | 342 |
| NFKB1 | NM_003998 | 23 | 4 | + | 70 | + | 0 | 37 | 1 | 0 | CGCGAATGCCTGATCCAGGCAGCCTCCAGCCCA GTGAAGACCACCACGCGTGGCGGATGT | 343 |
| NFKB1 | NM_003998 | 23 | 4 | + | 105 | - | 0 | 37 | 1 | 0 | CGCGAATGCCGAGGCAGGCGAGAGAGGCAGCG AGTGGCCTGAGAACGCGTGGCGGATGT | 344 |
| NFKB1 | NM_003998 | 23 | 4 | + | 140 | + | 0 | 37 | 1 | 0 | CGCGAATGCCCACAAGGCAGCAGCAAATAGTAA AAAAAGACAAAACGCGTGGCGGATGT | 345 |
| NFKB1 | NM_003998 | 20 | 4 | + | -8 | + | 0 | 37 | 1 | 0 | CGCGAATGCCCTTCGCAGGAGCAGATCCCTGG TGGAGAACTTTGACGCGTGGCGGATGT | 346 |
| NFKB1 | NM_003998 | 20 | 4 | + | 27 | - | 0 | 37 | 1 | 0 | CGCGAATGCCATTTTCCCAAGAGTCATCCAGGT CATAGAGAGGCTACGCGTGGCGGATGT | 347 |
| NFKB1 | NM_003998 | 20 | 4 | + | 62 | + | 0 | 37 | 1 | 0 | CGCGAATGCCGAGGAGGATGAAGGAGTTG TGCCTGGAACCACACGCGTGGCGGATGT | 348 |
| NFKB1 | NM_003998 | 20 | 4 | + | 97 | - | 0 | 37 | 1 | 0 | CGCGAATGCCACTCACCTGCCAGCTGTGGCC ATATCTAGAGGCACGCGTGGCGGATGT | 349 |
| PIK3CA | NM_006218 | 4 | 3 | + | 0 | + | 0 | 37 | 1 | 0 | CGCGAATGCCGGCAAATAATAGTGGTGATCTGG GTAATAGTTTCTACGCGTGGCGGATGT | 350 |
| PIK3CA | NM_006218 | 4 | 3 | + | 35 | - | 0 | 37 | 1 | 0 | CGCGAATGCCATTTTCAGAGTATACTTCTGCTTG TCATTATTTGGACGCGTGGCGGATGT | 351 |
| PIK3CA | NM_006218 | 4 | 3 | + | 70 | + | 0 | 37 | 1 | 0 | CGCGAATGCCCAACCATGACTGTGTACCAGAAC AAGTAATTGCTGACGCGTGGCGGATGT | 352 |
| PIK3CA | NM_006218 | 4 | 3 | + | 105 | - | 0 | 37 | 1 | 0 | CGCGAATGCCTAGCAACATACTTCGAGTTTTTTT CCTGATTGCTTACGCGTGGCGGATGT | 353 |
| PIK3CA | NM_006218 | 4 | 3 | + | 140 | + | 0 | 37 | 1 | 0 | CGCGAATGCCTCCTCTGAACAACTAAAACTCTG TGTTTTAGAATAACGCGTGGCGGATGT | 354 |
| PIK3CA | NM_006218 | 4 | 3 | + | 175 | - | 0 | 37 | 1 | 0 | CGCGAATGCCCATCCACACACTTTTAAAATA TACTTGCCCTGAACGCGTGGCGGATGT | 355 |
| PIK3CA | NM_006218 | 4 | 3 | + | 210 | + | 0 | 37 | 1 | 0 | CGCGAATGCCCATGAATACTTCCTAGAAAATAT CCTCTGAGTCAGACGCGTGGCGGATGT | 356 |
| PIK3CA | NM_006218 | 4 | 3 | + | 241 | - | 9 | 37 | 1 | 0 | CGCGAATGCCTAATATTTGAAACTTGTTACTCA CCTTATACTGAACGCGTGGCGGATGT | 357 |
| GUCY2F | NM_001522 | 4 | X | - | -22 | + | 0 | 37 | 1 | 0 | CGCGAATGCCATGTCTCCTTCTTTTTGCAGCT TATCGCATTCAACGCGTGGCGGATGT | 358 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| GUCY2F | NM_001522 | 4 | X | - | 13 | - | 0 | 37 | 1 | 0 | CGCGAATGCCGATTTTGAAGAATTGTAACAGTGCTGAGACTGACAACGCGTGGCGATGT | 359 |
| GUCY2F | NM_001522 | 4 | X | - | 48 | + | 0 | 37 | 1 | 0 | CGCGAATGCCTGAGTGAGGCTATGAAGTGGAGCTTCGAGAAGAACGCGTGGCGATGT | 360 |
| GUCY2F | NM_001522 | 4 | X | - | 83 | - | 0 | 37 | 1 | 0 | CGCGAATGCCAAAAAACAAAAAGACATTATACCTTGAGCTCTGTACGCGTGGCGATGT | 361 |
| PKN1 | NM_002741 | 21 | 19 | + | 0 | + | 0 | 37 | 1 | 0 | CGCGAATGCCTCCCATTCCCAGGGGATGATGAGGAGGAGTCTTTACGCGTGGCGATGT | 362 |
| PKN1 | NM_002741 | 21 | 19 | + | 35 | - | 0 | 37 | 1 | 0 | CGCGAATGCCGGGGTAGCGAACCTCGTCGTTGACGATGTGTCGACGCGTGGCGATGT | 363 |
| PKN1 | NM_002741 | 21 | 19 | + | 70 | + | 0 | 37 | 1 | 0 | CGCGAATGCCGCTTCCTGTCGCCGAAGCCATCGGCATCATGAGAACGCGTGGCGATGT | 364 |
| PKN1 | NM_002741 | 21 | 19 | + | 105 | - | 0 | 37 | 1 | 0 | CGCGAATGCCCCCAGGCCGCCCCACCTCGGGGGTCCTCACCGTACGCGTGGCGATGT | 365 |
| PKN1 | NM_002741 | 21 | 19 | + | 140 | + | 0 | 37 | 1 | 0 | CGCGAATGCCAGGGGCAGTGGGGCCCAGGAGGGGACAGATCCTGAACGCGTGGCGATGT | 366 |
| PKN1 | NM_002741 | 21 | 19 | + | 175 | - | 0 | 37 | 1 | 0 | CGCGAATGCCTTCCTCCCAAGCAGCTTGGAGGAAGGAGCACTGTGACGCGTGGCGATGT | 367 |
| PKN1 | NM_002741 | 21 | 19 | + | 210 | + | 0 | 37 | 1 | 0 | CGCGAATGCCCCCAGACGGAGCCTGGGATCTAGCGAGAGATGACGCGTGGCGATGT | 368 |
| PKN1 | NM_002741 | 21 | 19 | + | 245 | - | 0 | 37 | 1 | 0 | CGCGAATGCCCACCCTGAAGAAGGGCTGTTTCTTCACATCTTCGACGCCTGGCGATGT | 369 |
| PIK3CA | NM_006218 | 20 | 3 | + | 0 | + | 0 | 37 | 1 | 0 | CGCGAATGCCATGTTTTGGTGTTCTTAATTATTTTACACGTTCATACGCGTGGCGATGT | 370 |
| PIK3CA | NM_006218 | 20 | 3 | + | 35 | - | 0 | 37 | 1 | 0 | CGCGAATGCCTCCCAAAATGAAGGTAGCTACACAGTATCCAGCACACGCGTGGCGATGT | 371 |
| PIK3CA | NM_006218 | 20 | 3 | + | 70 | + | 0 | 37 | 1 | 0 | CGCGAATGCCATTGGAGATCGTCACAATAGTAACATCATGGTGAAACGCGTGGCGATGT | 372 |
| PIK3CA | NM_006218 | 20 | 3 | + | 105 | - | 0 | 37 | 1 | 0 | CGCGAATGCCTTTAAACAGAGAAAACCATTACTTGTCCATCGTCTACGCGTGGCGATGT | 373 |
| PIK3CA | NM_006218 | 20 | 3 | + | 140 | + | 0 | 37 | 1 | 0 | CGCGAATGCCATGTTTTGGTGTTCTTAATTATTCAAGACATTTTACGCGTGGCGATGT | 374 |
| PIK3CA | NM_006218 | 20 | 3 | + | 175 | - | 0 | 37 | 1 | 0 | CGCGAATGCCAAGAAAATTATGTTATAGTTTGATATATGCAGATACACGCGTGGCGATGT | 375 |
| PIK3CA | NM_006218 | 20 | 3 | + | 210 | + | 0 | 37 | 1 | 0 | CGCGAATGCCATTTTGAAAGCTGTTTCATATAGATTTTGGACACACGCGTGGCGATGT | 376 |
| PIK3CA | NM_006218 | 20 | 3 | + | 245 | - | 0 | 37 | 1 | 0 | CGCGAATGCCTATAACCAAATTTTTCTTCTTGTGATCCAAAAAACGCGTGGCGATGT | 377 |
| PIK3CA | NM_006218 | 20 | 3 | + | 280 | + | 0 | 37 | 1 | 0 | CGCGAATGCCACGAGAACGTGTGCCATTTGTTTTGACACAGGATTACGCGTGGCGATGT | 378 |
| PIK3CA | NM_006218 | 20 | 3 | + | 315 | - | 0 | 37 | 1 | 0 | CGCGAATGCCCGCATTCTTGGCTCCTTTACTAATCACTATTAAGAACGCGTGGCGATGT | 379 |
| PIK3CA | NM_006218 | 20 | 3 | + | 350 | + | 0 | 37 | 1 | 0 | CGCGAATGCCACAAGACAAGAGAATTTGAGAGGTGAGCTGCAAAGACGCGTGGCGATGT | 380 |
| RBBP8 | NM_002894 | 4 | 18 | + | -22 | + | 0 | 37 | 1 | 0 | CGCGAATGCCTTATTTATTTTTGACCTTTAGAGATGCACAAAGAACGCGTGGCGATGT | 381 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| RBBP8 | NM_002894 | 4 | 18 | + | 13 | - | 0 | 37 | 1 | 0 | CGCGAATGCCCTCAGCTGTTGATTTTTGGTGAAGAATTCTTCTAGACGCGTGGCGGATGT | 382 |
| RBBP8 | NM_002894 | 4 | 18 | + | 48 | + | 0 | 37 | 1 | 0 | CGCGAATGCCGGAACAGCAGAAGTCCTTCATGAAACCATTAAAGACGCGTGGCGGATGT | 383 |
| RBBP8 | NM_002894 | 4 | 18 | + | 83 | - | 0 | 37 | 1 | 0 | CGCGAATGCCAAGACCTAAGTGCCAGACTCACCGATCTTCTAAAACGCGTGGCGGATGT | 384 |
| NTRK3 | NM_001012338 | 8 | 15 | - | -18 | + | 0 | 37 | 1 | 0 | CGCGAATGCCGTTTCTGTTCCTCACAGGTATCCATAGCAGTGGACGCGTGGCGGATGT | 385 |
| NTRK3 | NM_001012338 | 8 | 15 | - | 17 | - | 0 | 37 | 1 | 0 | CGCGAATGCCGAACCACCAACAGGACACAGGCAAAAGCAGCAAGTACGCGTGGCGGATGT | 386 |
| NTRK3 | NM_001012338 | 8 | 15 | - | 52 | + | 0 | 37 | 1 | 0 | CGCGAATGCCTCTTCGTCATGATCAACAAATATGGTCGACGGTCCACGCGTGGCGGATGT | 387 |
| NTRK3 | NM_001012338 | 8 | 15 | - | 87 | - | 0 | 37 | 1 | 0 | CGCGAATGCCAATGAAACTCCCACCTTACCCTTCATTCCAAATTTACGCGTGGCGGATGT | 388 |
| EPHA4 | NM_004438 | 6 | 2 | - | 0 | + | 0 | 37 | 1 | 0 | CGCGAATGCCAAAAATGATGGCAGATTTACAGTCATTCAGCTGGTACGCGTGGCGGATGT | 389 |
| EPHA4 | NM_004438 | 6 | 2 | - | 35 | - | 0 | 37 | 1 | 0 | CGCGAATGCCACTTCATCCAGACCCAATGCCACGAAGACATGCCACGCGTGGCGGATGT | 390 |
| EPHA4 | NM_004438 | 6 | 2 | - | 70 | + | 0 | 37 | 1 | 0 | CGCGAATGCCATTTATCTGATATGAGCTATGTGCATCGTGATCGACGCCGTGGCGGATGT | 391 |
| EPHA4 | NM_004438 | 6 | 2 | - | 105 | - | 0 | 37 | 1 | 0 | CGCGAATGCCACCAAGTTGCTGTTCACCAGGATGTTCCGTGCGGCCACGCCGTGGCGGATGT | 392 |
| EPHA4 | NM_004438 | 6 | 2 | - | 140 | + | 0 | 37 | 1 | 0 | CGCGAATGCCCTGCAAAGTGTCTGATTTTGGCATGTCCCAGTGCACGCGTGGCGGATGT | 393 |
| EPHA4 | NM_004438 | 6 | 2 | - | 175 | - | 0 | 37 | 1 | 0 | CGCGAATGCCCCCTGGTGTGTGTAAGCTGCTTCCGGATCATCCTCAAACGCGTGGCGGATGT | 394 |
| EPHA4 | NM_004438 | 6 | 2 | - | 210 | + | 0 | 37 | 1 | 0 | CGCGAATGCCGTAAGAAAGATCGGTGACATCTGGGCTTTCACTCTACGCGTGGCGGATGT | 395 |
| NTRK3 | NM_001012338 | 18 | 15 | - | 0 | + | 0 | 37 | 1 | 0 | CGCGAATGCCATGGATGTCTCTCTTTGCCCAGCCAAGTGTAGTTTACGCGTGGCGGATGT | 396 |
| NTRK3 | NM_001012338 | 18 | 15 | - | 35 | - | 0 | 37 | 1 | 0 | CGCGAATGCCCCAGCCAGACGCTTCCCAGCAAGAAAATCCCCAGACGCCTGGCGGATGT | 397 |
| NTRK3 | NM_001012338 | 18 | 15 | - | 70 | + | 0 | 37 | 1 | 0 | CGCGAATGCCACTATGTGGCTCCGTGGCTTGCCCTGCAAATACGCGTGGCGGATGT | 398 |
| NTRK3 | NM_001012338 | 18 | 15 | - | 105 | - | 0 | 37 | 1 | 0 | CGCGAATGCCCCGGCAATTGATCCAGTCTTGCTGCAGACACAACGCGTGGCGGATGT | 399 |
| NTRK3 | NM_001012338 | 18 | 15 | - | 140 | + | 0 | 37 | 1 | 0 | CGCGAATGCCGCCGACGATGGGAACCTCTTCCCCCTCCTGAAGACGCGTGGCGGATGT | 400 |
| NTRK3 | NM_001012338 | 18 | 15 | - | 175 | - | 0 | 37 | 1 | 0 | CGCGAATGCCACTGGCTTCCATTGCTGTTCCCTGAATCCTGCCACGCGTGGCGGATGT | 401 |
| NTRK3 | NM_001012338 | 18 | 15 | - | 210 | + | 0 | 37 | 1 | 0 | CGCGAATGCCCATCAACATCACGGACATCTCAAGGAATATCACTTCACGCGTGGCGGATGT | 402 |
| NTRK3 | NM_001012338 | 18 | 15 | - | 245 | - | 0 | 37 | 1 | 0 | CGCGAATGCCGAGGCAGGCTGGGAGCGGCCGCCTGACTTACATGACGCGTGGCGGATGT | 403 |
| PIK3CA | NM_006218 | 7 | 3 | + | -17 | + | 0 | 37 | 1 | 0 | CGCGAATGCCTTTAAAATTTTACATAGGTGGAATGAATGGCTGAAACGCGTGGCGGATGT | 404 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| PIK3CA | NM_006218 | 7 | 3 | + | 18 | − | 0 | 37 | 1 | 0 | CGCGAATGCCCAGCACGAGGAAGATCAGGAAT GTATATCATAAACGCGTGGCGATGT | 405 |
| PIK3CA | NM_006218 | 7 | 3 | + | 53 | + | 0 | 37 | 1 | 0 | CGCGAATGCCCTCGACTTTGCCTTTCCATTTGCT CTGTTAAAGCACGCGTGGCGATGT | 406 |
| PIK3CA | NM_006218 | 7 | 3 | + | 88 | − | 0 | 37 | 1 | 0 | CGCGAATGCCCTTCTGAAATACTTTACCTCTTTA GCACCCTTTCGACGCGTGGCGATGT | 407 |
| NTRK3 | NM_001012338 | 15 | 15 | − | −36 | + | 0 | 37 | 1 | 0 | CGCGAATGCCTGTTTAAAATTTCCCTTTATTTG TCAATCTTGCAACGCGTGGCGATGT | 408 |
| NTRK3 | NM_001012338 | 15 | 15 | − | −1 | − | 0 | 37 | 1 | 0 | CGCGAATGCCCGAGAGTGTGGTGAGCCGGTTAC TTGACAGGTTTCACGCGTGGCGATGT | 409 |
| NTRK3 | NM_001012338 | 15 | 15 | − | 34 | + | 0 | 37 | 1 | 0 | CGCGAATGCCTGCAGCTCTTCCAGACGCTGAG TCTTCGGGAATTACGCGTGGCGATGT | 410 |
| NTRK3 | NM_001012338 | 15 | 15 | − | 69 | − | 0 | 37 | 1 | 0 | CGCGAATGCCTTCAGTACCTGGACAGTCTTCAA AACCAAACTTACACGCGTGGCGATGT | 411 |
| PALB2 | NM_024675 | 6 | 16 | − | −27 | + | 0 | 37 | 1 | 0 | CGCGAATGCCAATTTTGGCTGCTTTGTTTATT TAGGTTCCAGTACGCGTGGCGATGT | 412 |
| PALB2 | NM_024675 | 6 | 16 | − | 8 | − | 0 | 37 | 1 | 0 | CGCGAATGCCGATTATACACATCAGGCACTGGA ACTATCTGTAATACGCGTGGCGATGT | 413 |
| PALB2 | NM_024675 | 6 | 16 | − | 43 | + | 0 | 37 | 1 | 0 | CGCGAATGCCTCGTGTGTAGCTTTGGGAAAT TTGGAAATCAGAACGCGTGGCGATGT | 414 |
| PALB2 | NM_024675 | 6 | 16 | − | 78 | − | 0 | 37 | 1 | 0 | CGCGAATGCCACAAATCACTCCTTGGGAATTAC ATACCTGATCTCACGCGTGGCGATGT | 415 |
| EPHB1 | NM_004441 | 16 | 3 | + | −16 | + | 0 | 37 | 1 | 0 | CCGGAATGCCGGCTCTTTCCTCCTAGAGACCTCC TGAGAATAGGCACGCGTGGCGATGT | 416 |
| EPHB1 | NM_004441 | 16 | 3 | + | 19 | − | 0 | 37 | 1 | 0 | CGCGAATGCCTTCAGGATCTTCTTCTGATGGCCT GCCAAGTGATACGCGTGGCGATGT | 417 |
| EPHB1 | NM_004441 | 16 | 3 | + | 54 | + | 0 | 37 | 1 | 0 | CGCGAATGCCCAGCATTCATTCTATGAGGGTCC AGATAAGTCAGTACGCGTGGCGATGT | 418 |
| EPHB1 | NM_004441 | 16 | 3 | + | 89 | − | 0 | 37 | 1 | 0 | CGCGAATGCCAAGAACAAGAGTTCTCATGCCA TTGCCGTTGTGACGCGTGGCGATGT | 419 |
| NFKB1 | NM_003998 | 11 | 4 | + | 0 | + | 0 | 37 | 1 | 0 | CCGGAATGCCTTTGCCATTGTCTTCAAAACTCCA AAGTATAAAGAACGCGTGGCGATGT | 420 |
| NFKB1 | NM_003998 | 11 | 4 | + | 35 | − | 0 | 37 | 1 | 0 | CCGGAATGCCGGACAAACACAGAGGCTGGTTTT GTAATATTAATAACGCGTGGCGATGT | 421 |
| NFKB1 | NM_003998 | 11 | 4 | + | 70 | + | 0 | 37 | 1 | 0 | CCGGAATGCCAGCTTCGGAGGAAATCTGACTTG GAAACTAGTGAAACGCGTGGCGATGT | 422 |
| NFKB1 | NM_003998 | 11 | 4 | + | 105 | − | 0 | 37 | 1 | 0 | CGCGAATGCCCCTTTGATTTCAGGATAGTAGAG GAAAGGTTTTGACGCGTGGCGATGT | 423 |
| PDGFRA | NM_006206 | 23 | 4 | + | 0 | + | 0 | 37 | 1 | 0 | CGCGAATGCCCTCGCAGACCTCGAAGAGAGTG CCATTGAGACGGACGCGTGGCGATGT | 424 |
| PDGFRA | NM_006206 | 23 | 4 | + | 35 | − | 0 | 37 | 1 | 0 | CGCGAATGCCGTCTCTCTCTTGATGAAGGTGG AACTGCTGAACACGCGTGGCGATGT | 425 |
| PDGFRA | NM_006206 | 23 | 4 | + | 70 | + | 0 | 37 | 1 | 0 | CGCGAATGCCAGAGACATTGAAGACATCGACAT GATGGAATGACATACGCGTGGCGATGT | 426 |
| PDGFRA | NM_006206 | 23 | 4 | + | 105 | − | 0 | 37 | 1 | 0 | CCGCGAATGCCAGCTGCTCTTCCACCAGTCTGAA GAGTCTATGCCGACGCGTGGCGATGT | 427 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| PDGFRA | NM_006206 | 23 | 4 | + | 140 | + | 0 | 37 | 1 | 0 | CGCGAATGCCTCCTGTAACTGGCGGATTCGAGG GGTTCCTTCCACACGCGTGGCGGATGT | 428 |
| RB1 | NM_000321 | 20 | 13 | + | 0 | + | 0 | 37 | 1 | 0 | CGCGAATGCCTGTATCGGCTAGCCTATCTCCGG CTAAATACACTTACGCGTGGCGGATGT | 429 |
| RB1 | NM_000321 | 20 | 13 | + | 35 | - | 0 | 37 | 1 | 0 | CGCGAATGCCTCTAATTCTGGGTGCTCAGACAG AAGGCGTTCACAACGCGTGGCGGATGT | 430 |
| RB1 | NM_000321 | 20 | 13 | + | 70 | + | 0 | 37 | 1 | 0 | CGCGAATGCCACATATCATCTGACCCTTTTCCA GCACACCCTGCACGCGTGGCGGATGT | 431 |
| RB1 | NM_000321 | 20 | 13 | + | 105 | - | 0 | 37 | 1 | 0 | CGCGAATGCCCAAATGCTGTCTCTCATGAGTTC ATACTCATTCTACGCGTGGCGGATGT | 432 |
| RB1 | NM_000321 | 20 | 13 | + | 140 | + | 0 | 37 | 1 | 0 | CGCGAATGCCGACCAAGTAAGAAAATCAAGCA CTTCACCTTCTCTACGCGTGGCGGATGT | 433 |
| NFKB1 | NM_003998 | 14 | 4 | + | 0 | + | 0 | 37 | 1 | 0 | CGCGAATGCCGAACCATGGACACTGAATCTAAA AAGGACCCTGAAACGCGTGGCGGATGT | 434 |
| NFKB1 | NM_003998 | 14 | 4 | + | 35 | - | 0 | 37 | 1 | 0 | CGCGAATGCCTTTACAGTGTTTTTGTCATCACTT TTGTCACACACCACGCGTGGCGGATGT | 435 |
| NFKB1 | NM_003998 | 14 | 4 | + | 70 | + | 0 | 37 | 1 | 0 | CGCGAATGCCCCCTCTTTGGGAAAGTTATTGAAA CCACAGAGCAAGACGCGTGGCGGATGT | 436 |
| NFKB1 | NM_003998 | 14 | 4 | + | 105 | - | 0 | 37 | 1 | 0 | CGCGAATGCCACATTCCAACGGTGGCCTCGC TGGGCTCCTGATACGCGTGGCGGATGT | 437 |
| NFKB1 | NM_003998 | 14 | 4 | + | 140 | + | 0 | 37 | 1 | 0 | CGCGAATGCCGAGGTCACTCTAACGTATGCAAC AGGAACAAAAGAACGCGTGGCGGATGT | 438 |
| NFKB1 | NM_003998 | 14 | 4 | + | 175 | - | 0 | 37 | 1 | 0 | CGCGAATGCCTGTGTCTCACTTACCCTGAACTC CAGCACTCTCTACGCGTGGCGGATGT | 439 |
| PALB2 | NM_024675 | 12 | 16 | - | 0 | + | 0 | 37 | 1 | 0 | CGCGAATGCCTTAAAGGAGAAATTAGACATTCTT GAAAAGGGAATAACGCGTGGCGGATGT | 440 |
| PALB2 | NM_024675 | 12 | 16 | - | 35 | - | 0 | 37 | 1 | 0 | CGCGAATGCCATTCACTTACCTGAAGGCGGGCT AGTGTCTTTGCTGACGCGTGGCGGATGT | 441 |
| PALB2 | NM_024675 | 12 | 16 | - | 70 | + | 0 | 37 | 1 | 0 | CGCGAATGCCCCGTATTCTCAAATTAAGGTGTAT AGTACAAACAAACGCGTGGCGGATGT | 442 |
| PALB2 | NM_024675 | 12 | 16 | - | 105 | - | 0 | 37 | 1 | 0 | CGCGAATGCCTTTAAAGTTTTATAGAGTCAAGA ACTGTTTTTAAAACGCGTGGCGGATGT | 443 |
| PALB2 | NM_024675 | 12 | 16 | - | 140 | + | 0 | 37 | 1 | 0 | CGCGAATGCCGAAAACGTATTTCTGGGCTGTT TTTGTCTCCTACGCGTGGCGGATGT | 444 |
| PALB2 | NM_024675 | 12 | 16 | - | 175 | - | 0 | 37 | 1 | 0 | CGCGAATGCCAGAATGCTTAATCTTTTCAGCTCT TTGGGCACGCTACGCGTGGCGGATGT | 445 |
| PALB2 | NM_024675 | 12 | 16 | - | 210 | + | 0 | 37 | 1 | 0 | CGCGAATGCCATTAAGAAAACAGTAGAAGAAC AAGATTGTTTGTCACGCCGTGGCGGATGT | 446 |
| PALB2 | NM_024675 | 12 | 16 | - | 245 | - | 0 | 37 | 1 | 0 | CGCGAATGCCCTGAGTGTTTTAGCTGCGGTGAG AGATCCTGCTACGCGTGGCGGATGT | 447 |
| PALB2 | NM_024675 | 12 | 16 | - | 280 | + | 0 | 37 | 1 | 0 | CGCGAATGCCGTAAATCTAGACCATTCACTTAT GCTGCTTTATTACGCGTGGCGGATGT | 448 |
| RPS6KA1 | NM_002953 | 20 | 1 | + | -11 | + | 0 | 37 | 1 | 0 | CGCGAATGCCCTTTTCTGCAGATATACTCCATTT GCCAACGTCCACGCGTGGCGGATGT | 449 |
| RPS6KA1 | NM_002953 | 20 | 1 | + | 24 | - | 0 | 37 | 1 | 0 | CGCGAATGCCCGATCCCGGTTAGGATTTCCTCT GGTGTGTCACTGACGCGTGGCGGATGT | 450 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| RPS6KA1 | NM_002953 | 20 | 1 | + | 59 | + | 0 | 37 | 1 | 0 | CGCGAATGCCGCAGTGGAAGTTTACCCTCAGTGGGGAAATTGACGCCTGGCCGATGT | 451 |
| RPS6KA1 | NM_002953 | 20 | 1 | + | 94 | - | 0 | 37 | 1 | 0 | CGCGAATGCCTACAGACTCACCTTGGCTGCTGCTCTGAAACTGTGTTACGCGTGGCGATGT | 452 |
| CENTG1 | NM_014770 | 17 | 12 | - | -40 | + | 0 | 37 | 1 | 0 | CGCGAATGCCGCCAGGAGCCTCCCCCTTACTGCCCTTCTCCCGTACGCCGTGGCCGATGT | 453 |
| CENTG1 | NM_014770 | 17 | 12 | - | -5 | - | 0 | 37 | 1 | 0 | CGCGAATGCCAAGTCCATTCCTGGCTATTGATCACAGCCTCGTAACGCGTGGCGATGT | 454 |
| CENTG1 | NM_014770 | 17 | 12 | - | 30 | + | 0 | 37 | 1 | 0 | CGCGAATGCCTGAGCCGCTCCATTCCTGAACTGCGCCTGGTAGGTACGCCGTGGCGATGT | 455 |
| EPHA3 | NM_005233 | 13 | 3 | + | 65 | - | 0 | 37 | 1 | 0 | CGCGAATGCCAGTCAGCCTTCCCTATAGGCAAGGGGACTTGGGTTACGCGTGGCGATGT | 456 |
| EPHA3 | NM_005233 | 13 | 3 | + | 0 | + | 0 | 37 | 1 | 0 | CGCGAATGCCAAACACGATGCCCAGTTTACTGTCATTCAGCTAGTACGCCTGGCCGATGT | 457 |
| EPHA3 | NM_005233 | 13 | 3 | + | 35 | - | 0 | 37 | 1 | 0 | CGCGAATGCCACTTCATGCCAGATGCTATCCCTCGAAGCATCCCACGCGTGGCGATGT | 458 |
| EPHA3 | NM_005233 | 13 | 3 | + | 70 | + | 0 | 37 | 1 | 0 | CGCGAATGCCACCTGTCAGACATGGGCTATGTTCACCGAGACCTCACGCCTGGCCGATGT | 459 |
| EPHA3 | NM_005233 | 13 | 3 | + | 105 | - | 0 | 37 | 1 | 0 | CGCGAATGCCACCAAGTTACTGTTGATCAAGATGTTCCGAGCAGCACGCCGTGGCCGATGT | 460 |
| EPHA3 | NM_005233 | 13 | 3 | + | 140 | + | 0 | 37 | 1 | 0 | CGCGAATGCCGTGTAAGTTTCTGATTTCGGACTTTCGCGTGTCCACGCGTGGCCGATGT | 461 |
| EPHA3 | NM_005233 | 13 | 3 | + | 175 | - | 0 | 37 | 1 | 0 | CGCGAATGCCTCTTGTTGTATAAGCAGCTTCTGGGTCATCCTCCAACGCGTGGCCGATGT | 462 |
| EPHA3 | NM_005233 | 13 | 3 | + | 210 | + | 0 | 37 | 1 | 0 | CGCGAATGCCGTGAGTAACTTAGATTTTTCTCCTTTTTTATCATTGACGCGTGGCCGATGT | 463 |
| EPHA3 | NM_005233 | 6 | 3 | + | -8 | + | 0 | 37 | 1 | 0 | CGCGAATGCCCTTTACAGCTCCATCACCTGTCCTGACGATTAAGAACGCGTGGCGATGT | 464 |
| EPHA3 | NM_005233 | 6 | 3 | + | 27 | - | 0 | 37 | 1 | 0 | CGCGAATGCCGGACAAAGAGATGCTATTTCTGGAGGTCCGATCTTACGCCTGGCCGATGT | 465 |
| EPHA3 | NM_005233 | 6 | 3 | + | 62 | + | 0 | 37 | 1 | 0 | CGCGAATGCCTGCAAGAACCTGAACATCCTAATGGGATCATATTACGCCGTGGCCGATGT | 466 |
| EPHA3 | NM_005233 | 6 | 3 | + | 97 | - | 0 | 37 | 1 | 0 | CGCGAATGCCTCCCCACCTTTTCATAGTATTTGACCTTCGTAGTCCACGCCGTGGCCGATGT | 467 |
| PDGFRA | NM_006206 | 7 | 4 | + | 0 | + | 0 | 37 | 1 | 0 | CGCGAATGCCAAAGGCATACACAATGCTGGAAGAAATCAAACGCGTGGCCGATGT | 468 |
| PDGFRA | NM_006206 | 7 | 4 | + | 35 | - | 0 | 37 | 1 | 0 | CGCGAATGCCCCGTCAAAGTGTACACCAATTTGATGGATGGGACTACGCCGTGGCCGATGT | 469 |
| PDGFRA | NM_006206 | 7 | 4 | + | 70 | + | 0 | 37 | 1 | 0 | CGCGAATGCCTCCCGAGGCACGCGGTGAAAGACAGTGGAGATTACACGCCGTGGCCGATGT | 470 |
| PDGFRA | NM_006206 | 7 | 4 | + | 105 | - | 0 | 37 | 1 | 0 | CGCGAATGCCTTGACCTCCCTGGTAGCCTGGCGGGCAGCACATTCACGCCGTGGCCGATGT | 471 |
| PDGFRA | NM_006206 | 7 | 4 | + | 140 | + | 0 | 37 | 1 | 0 | CGCGAATGCCAGAAATGAAGAAAGTCACTATTTCTGTCCATGGTTACGCCGTGGCCGATGT | 472 |
| PDGFRA | NM_006206 | 7 | 4 | + | 175 | - | 0 | 37 | 1 | 0 | CGCGAATGCCCAGAATGACATGACAACTGACATTTTAGAAAGCCGAATGACGCGTGGCCGATGT | 473 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit # BWA mismatch | Sequence with add-ons | SEQ ID NO: |
|---|---|---|---|---|---|---|---|---|---|---|---|
| PDGFRA | NM_006206 | 7 | 4 | + | 210 | + | 0 | 37 | 1 0 | CGCGAATGCCCTCGGATCCATATGTGTAATCATTATTAATGACGCCTGGCCGGATGT | 474 |
| PDGFRA | NM_006206 | 7 | 4 | + | 245 | − | 0 | 37 | 1 0 | CGCGAATGCCTTCAATGAAACCTTTCTGTACAGGGAAGAGTTTACGCGTGGCCGGATGT | 475 |
| PDGFRA | NM_006206 | 7 | 4 | + | 280 | + | 0 | 37 | 1 0 | CGCGAATGCCATCAAACCCACCTTCAGCCAGTTGGAAGCTGTCAAACGCCTGGCCGGATGT | 476 |
| PDGFRA | NM_006206 | 7 | 4 | + | 315 | − | 0 | 37 | 1 0 | CGCGAATGCCGCACCTCTACACACAAAATGTTTGACTTCATGCAGGACGCGTGGCCGGATGT | 477 |
| PDGFRA | NM_006206 | 7 | 4 | + | 350 | + | 0 | 37 | 1 0 | CGCGAATGCCGGGCCTACCCACCTCCCAGGATATCCTGGCTGAAAACGCGTGGCCGGATGT | 478 |
| PDGFRA | NM_006206 | 7 | 4 | + | 385 | − | 0 | 37 | 1 0 | CGCGAATGCCATCCAGTGAGATTTTCAATCAGAGTCAGATGTTTACGCGTGGCCGGATGT | 479 |
| PDGFRA | NM_006206 | 7 | 4 | + | 420 | + | 0 | 37 | 1 0 | CGCGAATGCCCACCACTGATGTGAAAAGATTCAGGAAATAAGGTACGCCTGGCCGGATGT | 480 |
| RET | NM_020630 | 14 | 10 | + | 0 | + | 0 | 37 | 1 0 | CGCGAATGCCGCCCGCTTCCTCCTCATCGTGAGTACGCCAAATACACGCGTGGCCGGATGT | 481 |
| RET | NM_020630 | 14 | 10 | + | 35 | − | 0 | 37 | 1 0 | CGCGAATGCCTTGCGGCTCTCGCGGAGAAGCCCCGCAGGGAGCCACGCCTGGCCGGATGT | 482 |
| RET | NM_020630 | 14 | 10 | + | 70 | + | 0 | 37 | 1 0 | CGCGAATGCCAGTGGGCCTGGCTACCTGGCAGTGGAGGCAGCCACGCCGTGGCCGGATGT | 483 |
| RET | NM_020630 | 14 | 10 | + | 105 | − | 0 | 37 | 1 0 | CGCGAATGCCCCCTCATCCGGTGGTCCAGGAGCTGGAGTTGCACGCCTGGCCGGATGT | 484 |
| RET | NM_020630 | 14 | 10 | + | 140 | + | 0 | 37 | 1 0 | CGCGAATGCCGCCCTCACCATGGGCGACCTCATCTCATTTGCCTGACGCGTGGCCGGATGT | 485 |
| RET | NM_020630 | 14 | 10 | + | 175 | − | 0 | 37 | 1 0 | CGCGAATGCCTCTCGGCCAGATACTCATCCCCTGTGAGATCTGCACGCGTGGCCGGATGT | 486 |
| RET | NM_020630 | 14 | 10 | + | 210 | + | 0 | 37 | 1 0 | CGCGAATGCCTGAAGGTGCGTCATATGGCTCTGCACCCAGCCAGACGCGTGGCCGGATGT | 487 |
| NFKB1 | NM_003998 | 18 | 4 | + | 0 | − | 0 | 37 | 1 0 | CGCGAATGCCGTCTGAATGCCATTCATCTAGCCATGATGAGCAATACGCGTGGCCGGATGT | 488 |
| NFKB1 | NM_003998 | 18 | 4 | + | 35 | + | 0 | 37 | 1 0 | CGCGAATGCCCCAGCGGCCACCAGCAGCAGCAAACATGGCAGGCTACGCCTGGCCGGATGT | 489 |
| NFKB1 | NM_003998 | 18 | 4 | + | 70 | − | 0 | 37 | 1 0 | CGCGAATGCCGGCTGACGTCAATGCTCAGGAGCAGAAGTCCGGCACGCCGTGGCCGGATGT | 490 |
| NFKB1 | NM_003998 | 18 | 4 | + | 105 | + | 0 | 37 | 1 0 | CGCGAATGCCGTTGTCGTCTCCACAGCCAGTGCAGTGCTGCACGCCTGGCCGGATGT | 491 |
| NFKB1 | NM_003998 | 18 | 4 | + | 140 | − | 0 | 37 | 1 0 | CGCGAATGCCATCTCATTGGCAGGCTGCCTGCTCCTGGAGTGAAACGCGTGGCCGGATGT | 492 |
| EPHA3 | NM_005233 | 15 | 3 | + | 0 | + | 0 | 37 | 1 0 | CGCGAATGCCGTAATTAAAGCTGTAGATGAGGGCTATCGACTGCCACGCGTGGCCGGATGT | 493 |
| EPHA3 | NM_005233 | 15 | 3 | + | 35 | − | 0 | 37 | 1 0 | CGCGAATGCCGCTGATACAAGGCAGCTGGGCAGTCCATGGGGTACGCGTGGCCGGATGT | 494 |
| EPHA3 | NM_005233 | 15 | 3 | + | 70 | + | 0 | 37 | 1 0 | CGCGAATGCCTGATGCTGGACTGCTGCAGAAAGACAGGAACAACGCGTGGCCGGATGT | 495 |
| EPHA3 | NM_005233 | 15 | 3 | + | 105 | − | 0 | 37 | 1 0 | CGCGAATGCCTCCAGAATACTAACAATCTGCTCAACTTGGGTCTACGCGTGGCCGGATGT | 496 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| EPHA3 | NM_005233 | 15 | 3 | + | 140 | + | 0 | 37 | 1 | 0 | CGCGAATGCCCAAGCTTATCCGGAATCCGGCAGCCTGAAGATCAACGCGTGGCGGATGT | 497 |
| EPHA3 | NM_005233 | 15 | 3 | + | 175 | − | 0 | 37 | 1 | 0 | CGCGAATGCCAAATTGAATGTGTCACCTTGCCGCTGCACTGTGACGCGTGGCCGGATGT | 498 |
| PKN1 | NM_002741 | 4 | 19 | + | −2 | + | 0 | 37 | 1 | 0 | CGCGAATGCCAGGACCGGAAGCTGCTGCTGACAGCCCAGAGATGACGCGTGGCCGGATGT | 499 |
| PKN1 | NM_002741 | 4 | 19 | + | 33 | − | 0 | 37 | 1 | 0 | CGCGAATGCCCGATGATGTCAATCTTGGTCTTACTGTCTGCAAACGCGTGGCCGGATGT | 500 |
| PKN1 | NM_002741 | 4 | 19 | + | 68 | + | 0 | 37 | 1 | 0 | CGCGAATGCCCATGCAACTCCGCCGGCGCTGCAGGCCGGCCAGCACGCGTGGCCGGATGT | 501 |
| PKN1 | NM_002741 | 4 | 19 | + | 103 | − | 0 | 37 | 1 | 0 | CGCGAATGCCACCTTGGCTGTCATCCGGGGCTGCCTGGTTCTCCAACGCGTGGCCGGATGT | 502 |
| EPHA4 | NM_004438 | 17 | 2 | − | −36 | + | 0 | 37 | 1 | 0 | CGCGAATCCCTTGGAAATTCATCTATTTTTCTTTTGTTTTTGCAACGCGTGGCGGATGT | 503 |
| EPHA4 | NM_004438 | 17 | 2 | − | −1 | − | 0 | 37 | 1 | 0 | CGCGAATGCCTCCCTGAACAGATCTGGAATCCAATAAGTAACACGCGTGGCCGGATGT | 504 |
| EPHA4 | NM_004438 | 17 | 2 | − | 34 | + | 0 | 37 | 1 | 0 | CGCGAATGCCACTTGGGTGGATAGCAAGCCCTCTGGAAGGAGGGACGCGTGGCCGGATGT | 505 |
| EPHA4 | NM_004438 | 17 | 2 | − | 69 | − | 0 | 37 | 1 | 0 | CGCGAATGCCTTTACCCTTTGGATCAGAGACAACTCAGGACTTAACGCGTGGCCGGATGT | 506 |
| PIK3CA | NM_006218 | 21 | 3 | + | 0 | + | 0 | 37 | 1 | 0 | CGCGAATGCCGTTTCAGGAGATGTGTTACAAGCTTATCTAGCTAACGCCTGGCCGGATGT | 507 |
| PIK3CA | NM_006218 | 21 | 3 | + | 35 | − | 0 | 37 | 1 | 0 | CGCGAATGCCGAAAAGATTTATGAAGAGATTGGCATGCTGCGAAAACGCGTGGCCGGATGT | 508 |
| PIK3CA | NM_006218 | 21 | 3 | + | 70 | + | 0 | 37 | 1 | 0 | CGCGAATGCCTCAATGATGCTTGGCTCTGGAATGCCAGAACTACAACGCGTGGCCGGATGT | 509 |
| PIK3CA | NM_006218 | 21 | 3 | + | 105 | − | 0 | 37 | 1 | 0 | CGCGAATGCCGGGTCTTTCGAATGTATGCAATGTCATCAAAAGATACGCCGTGGCCGGATGT | 510 |
| PIK3CA | NM_006218 | 21 | 3 | + | 140 | + | 0 | 37 | 1 | 0 | CGCGAATGCCTAGCCTTAGATAAAACTGAGCAAGAGGCTTTGGAGACGCGTGGCCGGATGT | 511 |
| PIK3CA | NM_006218 | 21 | 3 | + | 175 | − | 0 | 37 | 1 | 0 | CGCGAATGCCCATGATGTGCATCATTCATTTGTTTCATGAAATAACGCGTGGCCGGATGT | 512 |
| PIK3CA | NM_006218 | 21 | 3 | + | 210 | + | 0 | 37 | 1 | 0 | CGCGAATGCCTGCTGGACAACAAAAATGGATTGGATCTTCCACAACGCGTGGCCGGATGT | 513 |
| PIK3CA | NM_006218 | 21 | 3 | + | 245 | − | 0 | 37 | 1 | 0 | CGCGAATGCCGTTATCTTTTCAGTTCAATGCATGCTGTTTAATTGACGCGTGGCCGGATGT | 514 |
| GUCY2F | NM_001522 | 3 | X | − | 0 | − | 0 | 37 | 1 | 0 | CGCGAATGCCGGCAAAGGCACAGAGGAAACCTTCTGGCTGATTGACGCCGTGGCCGGATGT | 515 |
| GUCY2F | NM_001522 | 3 | X | − | 35 | − | 0 | 37 | 1 | 0 | CGCGAATGCCGGGCACAGGAAGGGGCTTCATGAAGCCTTTTTCACGCGTGGCCGGATGT | 516 |
| GUCY2F | NM_001522 | 3 | X | − | 70 | + | 0 | 37 | 1 | 0 | CGCGAATGCCCACCAGTGGACAAAGATGGGTAAGTGGAGTTCACACGCGTGGCCGGATGT | 517 |
| GUCY2F | NM_001522 | 3 | X | − | 105 | − | 0 | 37 | 1 | 0 | CGCGAATGCCGTGGCAGAGTATGGCATAGGAAGACTCCAATTAAACGCGTGGCCGGATGT | 518 |
| GUCY2F | NM_001522 | 3 | X | − | 140 | + | 0 | 37 | 1 | 0 | CGCGAATGCCACTTTCTTCACTACCTATTTGATGTCTCCCCTGCCACGCGTGGCCGGATGT | 519 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| GUCY2F | NM_001522 | 3 | X | - | 175 | - | 0 | 37 | 1 | CGCGAATGCCCCACTGGTTGCAGGCCATGGCCCACTTGCCTGCAGACGCGTGGCGCGATGT | 520 |
| GUCY2F | NM_001522 | 3 | X | - | 210 | + | 0 | 37 | 1 | CGCGAATGCCAGATTGCAGCCTTCCAAAGAAGAAAGCAGAAGATGCCGTGGCGCGATGT | 521 |
| GUCY2F | NM_001522 | 3 | X | - | 245 | - | 0 | 37 | 1 | CGCGAATGCCTGGCCATTACCTTATGGCTTGTTTCTCACCAACTGACGCGTGGCGCGATGT | 522 |
| RBBP8 | NM_002894 | 12 | 18 | + | 0 | + | 0 | 37 | 1 | CGCGAATGCCATTTTCAGATTCTACTTCAAAGACTCCTCCTCAAGACGCGTGGCGCGATGT | 523 |
| RBBP8 | NM_002894 | 12 | 18 | + | 35 | - | 0 | 37 | 1 | CGCGAATGCCAAATACAGGAGATGACACTCGAGTAGGTAATTCTTACGCGTGGCGCGATGT | 524 |
| RBBP8 | NM_002894 | 12 | 18 | + | 70 | + | 0 | 37 | 1 | CGCGAATGCCGGAGCTACCCTCTAGTATCAAAAGTGTTTAGATTTACGCGTGGCGCGATGT | 525 |
| RBBP8 | NM_002894 | 12 | 18 | + | 105 | - | 0 | 37 | 1 | CGCGAATGCCCAGGCTGTAAAAGAAGGGGACAAACTTGTATTCACGCGTGGCGCGATGT | 526 |
| RBBP8 | NM_002894 | 12 | 18 | + | 140 | + | 0 | 37 | 1 | CGCGAATGCCGGAAAAAAAACATCTGAAAACACTCCCCTTTTAGCACGCGTGGCGCGATGT | 527 |
| RBBP8 | NM_002894 | 12 | 18 | + | 175 | - | 0 | 37 | 1 | CGCGAATGCCGATCTAGTTTTTCTAATCTAGATATACAAGTGTTACGCGTGGCGCGATGT | 528 |
| RBBP8 | NM_002894 | 12 | 18 | + | 210 | + | 0 | 37 | 1 | CGCGAATGCCAAAATCTGAAGATAGTGCCCTTTTCACACATCACACGCGTGGCGCGATGT | 529 |
| RBBP8 | NM_002894 | 12 | 18 | + | 245 | - | 0 | 37 | 1 | CGCGAATGCCCTGGATAATGATCTTGTTCACTTCAGACCCAAGACACGCGTGGCGCGATGT | 530 |
| RBBP8 | NM_002894 | 12 | 18 | + | 280 | + | 0 | 37 | 1 | CGCGAATGCCTCATCTAATAAACAGATACTTATAATAAAATATACGCGTGGCGCGATGT | 531 |
| RBBP8 | NM_002894 | 12 | 18 | + | 315 | - | 0 | 37 | 1 | CGCGAATGCCACTCAGTCCTATTCTGTTCACCTAGGGATTCACTTACGCGTGGCGCGATGT | 532 |
| RBBP8 | NM_002894 | 12 | 18 | + | 350 | + | 0 | 37 | 1 | CGCGAATGCCACGGTAAAGATTCTAACACTGATAAACATTTGGAGACGCGTGGCGCGATGT | 533 |
| RBBP8 | NM_002894 | 12 | 18 | + | 385 | - | 0 | 37 | 1 | CGCGAATGCCCCTTTTGGATGTTCGGCCTCCCAATGATTTCAGGGACGCGTGGCGCGATGT | 534 |
| RBBP8 | NM_002894 | 12 | 18 | + | 420 | + | 0 | 37 | 1 | CGCGAATGCCGAAGAAAACTGAGGAAGAAAGTGAACATGAAGTAAACGCTGGCGCGATGT | 535 |
| RBBP8 | NM_002894 | 12 | 18 | + | 455 | - | 0 | 37 | 1 | CGCGAATGCCAGCATTTCTTTATCAAAAGAAGCTTGGGGCAGCACGCGTGGCGCGATGT | 536 |
| RBBP8 | NM_002894 | 12 | 18 | + | 490 | + | 0 | 37 | 1 | CGCGAATGCCTTCCCTTTTCAATGGATAATCAGTTTTCCATGAAACGCGTGGCGCGATGT | 537 |
| RBBP8 | NM_002894 | 12 | 18 | + | 525 | - | 0 | 37 | 1 | CGCGAATGCCACAGATCCAGAGGTTTATCCATCACACAGTCTCCAACGCGTGGCGCGATGT | 538 |
| RBBP8 | NM_002894 | 12 | 18 | + | 560 | + | 0 | 37 | 1 | CGCGAATGCCCTGATCGATTTTCAGCTATTCAGCGTCAAGAGAAACGCCGTGGCGCGATGT | 539 |
| RBBP8 | NM_002894 | 12 | 18 | + | 595 | - | 0 | 37 | 1 | CGCGAATGCCCTAAATTTGTTTTAGAAGTCTCACTTCCTTGGCTACGCGTGGCGCGATGT | 540 |
| RBBP8 | NM_002894 | 12 | 18 | + | 630 | + | 0 | 37 | 1 | CGCGAATGCCGCAAGTGACTCTTTATGAGGCTTTGAAGACCATTCACGCGTGGCGCGATGT | 541 |
| RBBP8 | NM_002894 | 12 | 18 | + | 665 | - | 0 | 37 | 1 | CGCGAATGCCATCGAGGCCTTACGGCTTGAGGAAAGCCCTTTGACGCGTGGCGCGATGT | 542 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| RBBP8 | NM_002894 | 12 | 18 | + | 700 | + | 0 | 37 | 1 | 0 | CGCGAATGCCGGCAACTGCACGTTGCCCAAAGATTCCCAGGGGACGCGTGGCGATGT | 543 |
| RBBP8 | NM_002894 | 12 | 18 | + | 735 | − | 0 | 37 | 1 | 0 | CGCGAATGCCCAGGGCTGAAGGATGATGCATTCCTGTGAACAGGCGTGGCGATGT | 544 |
| RBBP8 | NM_002894 | 12 | 18 | + | 770 | + | 0 | 37 | 1 | 0 | CGCGAATGCCTGAATAAATGCTCTCCAGACAATAAACCATCATTAACGCGTGGCGATGT | 545 |
| RBBP8 | NM_002894 | 12 | 18 | + | 805 | − | 0 | 37 | 1 | 0 | CGCGAATGCCGGAATTTTAAAGACAGCATTTTCTTCTTTTATTGACGCGTGGCGATGT | 546 |
| RBBP8 | NM_002894 | 12 | 18 | + | 840 | + | 0 | 37 | 1 | 0 | CGCGAATGCCCTACGTCCACGTGAAAGTTTGGAGACTGAGAATGACGCGTGGCGATGT | 547 |
| RBBP8 | NM_002894 | 12 | 18 | + | 875 | − | 0 | 37 | 1 | 0 | CGCGAATGCCTGAACATTTAACACAAACCTTTATGTCATCTAAAAACGCGTGGCGATGT | 548 |
| RBBP8 | NM_002894 | 12 | 18 | + | 910 | + | 0 | 37 | 1 | 0 | CGCGAATGCCAGGATTTTGATTAAAATGATTGCTTGTGATTTCATACGCGTGGCGATGT | 549 |
| RBBP8 | NM_002894 | 12 | 18 | + | 945 | − | 0 | 37 | 1 | 0 | CGCGAATGCCCAGCACTCTAAAACAGAAATAATTGTTAGCTCTAAACGCGTGGCGATGT | 550 |
| RBBP8 | NM_002894 | 12 | 18 | + | 980 | + | 0 | 37 | 1 | 0 | CGCGAATGCCGTTCTCATGAGCCAATAAAAATACAAACCAGGTCAACGCGTGGCGATGT | 551 |
| RBBP8 | NM_002894 | 12 | 18 | + | 1015 | − | 0 | 37 | 1 | 0 | CGCGAATGCCTGAAGAACTGATGCAAGTTCACATCCTCCATGGTCACGCGTGGCGATGT | 552 |
| RBBP8 | NM_002894 | 12 | 18 | + | 1050 | + | 0 | 37 | 1 | 0 | CGCGAATGCCGTTAAATCATGTAGAACTGGTAAATAAAGTCTCACGCCTGGCGATGT | 553 |
| RBBP8 | NM_002894 | 12 | 18 | + | 1085 | − | 0 | 37 | 1 | 0 | CGCGAATGCCCCCTGTTTATGGTGTACACACCTTGGTTGTTTTGTAACGCGTGGCGATGT | 554 |
| EPHB1 | NM_004441 | 5 | 3 | + | 0 | + | 0 | 37 | 1 | 0 | CGCGAATGCCGCGTCCCCATCAGTCCCGCAATGTTATCTCCATCACGCGTGGCGATGT | 555 |
| EPHB1 | NM_004441 | 5 | 3 | + | 35 | − | 0 | 37 | 1 | 0 | CGCGAATGCCGGGTGCCACTCCAGAATGATGGACGTCTCATTGACACGCGTGGCGATGT | 556 |
| EPHB1 | NM_004441 | 5 | 3 | + | 70 | + | 0 | 37 | 1 | 0 | CGCGAATGCCTCCAAGGAGACAGGTGGGCGGATGATGTGACCTTACGCGTGGCGATGT | 557 |
| EPHB1 | NM_004441 | 5 | 3 | + | 105 | − | 0 | 37 | 1 | 0 | CGCGAATGCCGCGGTCTGCCCGGCACTTTTTGCAGATGATGTTGTACGCGTGGCGATGT | 558 |
| EPHB1 | NM_004441 | 5 | 3 | + | 140 | + | 0 | 37 | 1 | 0 | CGCGAATGCCCGGAGCTGCTCCCGCTGTGACGACAATGTGAGTTACGCGTGGCGATGT | 559 |
| EPHB1 | NM_004441 | 5 | 3 | + | 175 | − | 0 | 37 | 1 | 0 | CGCGAATGCCTCTCCATCAGCAGCCTCTGGGCCTGCCTGGGCACACGCGTGGCGATGT | 560 |
| EPHB1 | NM_004441 | 5 | 3 | + | 210 | + | 0 | 37 | 1 | 0 | CGCGAATGCCCTGGAGACTCCATTGATGGCCTGCACACCCCTACACGCGTGGCGATGT | 561 |
| EPHB1 | NM_004441 | 5 | 3 | + | 245 | − | 0 | 37 | 1 | 0 | CGCGAATGCCTCAAAGGTCCCTTCCCCCACAGCGATGTCAAGGTACGCGTGGCGATGT | 562 |
| EPHB1 | NM_004441 | 5 | 3 | + | 280 | + | 0 | 37 | 1 | 0 | CGCGAATGCCGCCTCCAGAGTCCTTCCCCACAGCACGTCTGTCAACGCGTGGCGATGT | 563 |
| EPHB1 | NM_004441 | 5 | 3 | + | 315 | − | 0 | 37 | 1 | 0 | CGCGAATGCCGCCTGCCTGAGCTTACCGGCTTGGTTTGTGGTGATGTACGCGTGGCGATGT | 564 |
| RPS6KA1 | NM_002953 | 9 | 1 | + | 0 | + | 0 | 37 | 1 | 0 | CGCGAATGCCACTTTGCCTGAGCAAGAGGCCATTGACCACGAGACGCGTGGCGATGT | 565 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| RPS6KA1 | NM_002953 | 9 | 1 | + | 35 | − | 0 | 37 | 1 | 0 | CGCGAATGCCTACTCCACTGTCCCGCAGAAAGAATAGGCCTTCTTACGCGTGGCGATGT | 566 |
| RPS6KA1 | NM_002953 | 9 | 1 | + | 70 | + | 0 | 37 | 1 | 0 | CGCGAATGCCCATGCCCCTGAGGTCGTCAACCGCCAGGGCCACTACGCGTGGCGATGT | 567 |
| RPS6KA1 | NM_002953 | 9 | 1 | + | 105 | − | 0 | 37 | 1 | 0 | CGCGAATGCCAACACCCCATAGGACCACCAGTCCGCACTATGGGACGCGTGGCGATGT | 568 |
| RPS6KA1 | NM_002953 | 9 | 1 | + | 140 | + | 0 | 37 | 1 | 0 | CGCGAATGCCATGGTGAGTGCCCAGACAGGGGTAAAGGATCCAGCACGCGTGGCGATGT | 569 |
| RPS6KA1 | NM_001006665 | 1 | 1 | + | −2 | + | 0 | 37 | 1 | 0 | CGCGAATGCCGGATGGAGCAGGATCCCAAGCCGCCCCGTCTGCGGACGCGTGGCGATGT | 570 |
| RPS6KA1 | NM_001006665 | 1 | 1 | + | 33 | − | 0 | 37 | 1 | 0 | CGCGAATGCCTGCTTCCTGGAAGCCAGGGGATCAGGGCCCAGAGACGCGTGGCGATGT | 571 |
| RPS6KA1 | NM_001006665 | 1 | 1 | + | 68 | + | 0 | 37 | 1 | 0 | CGCGAATGCCGCCGCCCAGGATCAGCCAGACCTCTCTGCCTGTCCACGCGTGGCGATGT | 572 |
| RPS6KA1 | NM_001006665 | 1 | 1 | + | 103 | − | 0 | 37 | 1 | 0 | CGCGAATGCCCACCGAGTCCCGCTGGGGCCAGAGCCAGGGCCAGACGCGTGGCGATGT | 573 |
| GUCY2F | NM_001522 | 16 | X | − | −28 | + | 0 | 37 | 1 | 0 | CGCGAATGCCTTCTTCCTCTCCACTCTGCAGGCATCGAACGCGTGGCGATGT | 574 |
| GUCY2F | NM_001522 | 16 | X | − | 7 | − | 0 | 37 | 1 | 0 | CGCGAATGCCCGCAAAGTAAGGCAGACCATCATGGCAAAGGCAGGGCGCGTGGCGATGT | 575 |
| GUCY2F | NM_001522 | 16 | X | − | 42 | + | 0 | 37 | 1 | 0 | CGCGAATGCCTTATAGCCCTGCTGTCTATTAATGGATTTGCTTACACGCGTGGCGATGT | 576 |
| GUCY2F | NM_001522 | 16 | X | − | 77 | − | 0 | 37 | 1 | 0 | CGCGAATGCCTATATACAAAAATAACAAAAATGTACCTTATAAAACGCGTGGCGATGT | 577 |
| RBBP8 | NM_002894 | 5 | 18 | + | −14 | + | 0 | 37 | 1 | 0 | CGCGAATGCCGTTTGTTTCATAGGTTAAGAGCAGGCTTATGTGAACGCGTGGCGATGT | 578 |
| RBBP8 | NM_002894 | 5 | 18 | + | 21 | − | 0 | 37 | 1 | 0 | CGCGAATGCCTTTCCCATATGTTCTTCAGTTACTGCACAGCGAACGCGTGGCGATGT | 579 |
| RBBP8 | NM_002894 | 5 | 18 | + | 56 | + | 0 | 37 | 1 | 0 | CGCGAATGCCAACAGCACAAGAGTTTGAAAATATCCGGCAGCAGAATACGCGTGGCGATGT | 580 |
| RBBP8 | NM_002894 | 5 | 18 | + | 91 | − | 0 | 37 | 1 | 0 | CGCGAATGCCAAAGGAAACTCACTAAGTTCTGTAATAAGTTTAAGACGCGTGGCGATGT | 581 |
| KSR2 | NM_173598 | 3 | 12 | − | −5 | + | 0 | 37 | 1 | 0 | CGCGAATGCCAACAGCACAATCTGGTATGAACTCCACGCCAGGGAACGCGTGGCGATGT | 582 |
| KSR2 | NM_173598 | 3 | 12 | − | 30 | − | 0 | 37 | 1 | 0 | CGCGAATGCCTCTGGCAAATGGGCACAGGCATGTGAAAGGCCATACGCGTGGCGATGT | 583 |
| KSR2 | NM_173598 | 3 | 12 | − | 65 | + | 0 | 37 | 1 | 0 | CGCGAATGCCTTATTGCCTCTGCTGGTTGGGTCTAAACCCAACCTCACGCGTGGCGATGT | 584 |
| KSR2 | NM_173598 | 3 | 12 | − | 100 | − | 0 | 37 | 1 | 0 | CGCGAATGCCCTTACCAGATTTCTTTTCCCATGCCAATCTGGCTACGCGTGGCGATGT | 585 |
| EPHA7 | NM_004440 | 2 | 6 | − | 0 | + | 0 | 37 | 1 | 0 | CGCGAATGCCGCCAATAAGCCCTCTTCTGGATCAAAACACTCCTGACGCGTGGCGATGT | 586 |
| EPHA7 | NM_004440 | 2 | 6 | − | 35 | − | 0 | 37 | 1 | 0 | CGCGAATGCCTAGCCATTCTCCAACTGAACAAAAGTAGTGAAATTACGCGTGGCGATGT | 587 |
| EPHA7 | NM_004440 | 2 | 6 | − | 70 | + | 0 | 37 | 1 | 0 | CGCGAATGCCCAAGCTATTAAGATGGAAAGATATAAAGATATTTACGCGTGGCGATGT | 588 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| EPHA7 | NM_004440 | 2 | 6 | - | 105 | - | 0 | 37 | 1 | 0 | CGCGAATGCCCTACTGATTCAAGGGAATTGTAG CCAGCTGCCGTGACGCGTGGCCGATGT | 589 |
| EPHA7 | NM_004440 | 2 | 6 | - | 140 | + | 0 | 37 | 1 | 0 | CGCGAATGCCCCAGGATGACTATTGAGTAAGCT TAAACTCTAAACGCGTGGCCGATGT | 590 |
| RB1 | NM_000321 | 24 | 13 | + | -54 | + | 0 | 37 | 1 | 0 | CGCGAATGCCAAAATTGTATATGGTTTTTATT ACTAATTGGTAACGCGTGGCCGATGT | 591 |
| RB1 | NM_000321 | 24 | 13 | + | -19 | - | 0 | 37 | 1 | 0 | CGCGAATGCCAATTGATACTAAGATTCTGTCAA GTTAAGATGAAAACGCGTGGCCGATGT | 592 |
| RB1 | NM_000321 | 24 | 13 | + | 16 | + | 0 | 37 | 1 | 0 | CGCGAATGCCGGTGAATCATTCCGGGTCAGTAT TTTCTTTCTATGACGCGTGGCCGATGT | 593 |
| RB1 | NM_000321 | 24 | 13 | + | 51 | - | 0 | 37 | 1 | 0 | CGCGAATGCCTTTCTTTTTATACTTACAATGCATA CTATTATATTTACGCGTGGCCGATGT | 594 |
| EPHA4 | NM_004438 | 11 | 2 | - | -14 | + | 0 | 37 | 1 | 0 | CGCGAATGCCATTGTCATTCCCAGTGCCTTCCCG GATCATTGGAGACGCGTGGCCGATGT | 595 |
| EPHA4 | NM_004438 | 11 | 2 | - | 21 | - | 0 | 37 | 1 | 0 | CGCGAATGCCGACAGAGACCAGAAGGACTGTG GAGTTAGCCCCATACGCGTGGCCGATGT | 596 |
| EPHA4 | NM_004438 | 11 | 2 | - | 56 | + | 0 | 37 | 1 | 0 | CGCGAATGCCTCCGGCAGTGTGTGCTGGTGGT AATTCTCATTGCACGCGTGGCCGATGT | 597 |
| EPHA4 | NM_004438 | 11 | 2 | - | 91 | - | 0 | 37 | 1 | 0 | CGCGAATGCCGCTTCAGTGCTTACCTCCGGCTG ATGACAAAGCTACGCGTGGCCGATGT | 598 |
| EPHB1 | NM_004441 | 12 | 3 | + | 0 | + | 0 | 37 | 1 | 0 | CGCGAATGCCAAAATGACGGGCAGTTCACCGT GATCCAGCTTGTACGCGTGGCCGATGT | 599 |
| EPHB1 | NM_004441 | 12 | 3 | + | 35 | - | 0 | 37 | 1 | 0 | CGCGAATGCCACTTCATGCCAGCAGCGATGCCC CTGAGCATAACCACGCGTGGCCGATGT | 600 |
| EPHB1 | NM_004441 | 12 | 3 | + | 70 | + | 0 | 37 | 1 | 0 | CGCGAATGCCACCTGGCTGAGATGAATTATGTG CATCGGGACCTGACGCGTGGCCGATGT | 601 |
| EPHB1 | NM_004441 | 12 | 3 | + | 105 | - | 0 | 37 | 1 | 0 | CGCGAATGCCACCAGGTTACTGTTGACCAGAAT GTTCCTAGCAGCACGCGTGGCCGATGT | 602 |
| EPHB1 | NM_004441 | 12 | 3 | + | 140 | + | 0 | 37 | 1 | 0 | CGCGAATGCCGTGCAAGTGTCCGACTTTGGCC TCTCCCGCTACCACGCGTGGCCGATGT | 603 |
| EPHB1 | NM_004441 | 12 | 3 | + | 175 | - | 0 | 37 | 1 | 0 | CGCGAATGCCGCTGGTGGTAGGTGGGATCTGAGG TGTCATCCTGGAACGCGTGGCCGATGT | 604 |
| EPHB1 | NM_004441 | 12 | 3 | + | 210 | + | 0 | 37 | 1 | 0 | CGCGAATGCCTCCTTGGTGAGTCCTTCTTGGCAT TCTCAAGTAGAACGCGTGGCCGATGT | 605 |
| RB1 | NM_000321 | 26 | 13 | + | -45 | + | 0 | 37 | 1 | 0 | CGCGAATGCCATTTATAATACCACATGAAAATGT TTTGCATTTTTTACGCGTGGCCGATGT | 606 |
| RB1 | NM_000321 | 26 | 13 | + | -10 | - | 0 | 37 | 1 | 0 | CGCGAATGCCTTTGGACTCTCCTGGGAGATGTTT ACTGCAGATTAACGCGTGGCCGATGT | 607 |
| RB1 | NM_000321 | 26 | 13 | + | 25 | + | 0 | 37 | 1 | 0 | CGCGAATGCCTTTCAGCAGAAACTGGCAGAAAT GAGTAAGTACTTACGCGTGGCCGATGT | 608 |
| RB1 | NM_000321 | 26 | 13 | + | 60 | - | 0 | 37 | 1 | 0 | CGCGAATGCCAAACAATTGTTTATTCATTTACA CAAGGTGAAAAACGCGTGGCCGATGT | 609 |
| CHAF1A | NM_005483 | 12 | 19 | + | 0 | + | 0 | 37 | 1 | 0 | CGCGAATGCCGAGTGTCCGACCCTGAGAACCA TAAGGTCCGCCAACGCGTGGCCGATGT | 610 |
| CHAF1A | NM_005483 | 12 | 19 | + | 35 | - | 0 | 37 | 1 | 0 | CGCGAATGCCCCAGGAACTGCTCCCACTCCTTG GCCTTCAGTTTCACGCGTGGCCGATGT | 611 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit # BWA mismatch | Sequence with add-ons | SEQ ID NO: |
|---|---|---|---|---|---|---|---|---|---|---|---|
| CHAF1A | NM_005483 | 12 | 19 | + | 70 | + | 0 | 37 | 1 0 | CGCGAATGCCCTAAGGGGAAGCGCTTTCGCGTC CTGCAACCTGTGACGCGTGGCGGATGT | 612 |
| CHAF1A | NM_005483 | 12 | 19 | + | 105 | - | 0 | 37 | 1 0 | CGCGAATGCCCAGTCTCTGTCAGCCGCCCACAC GCAGCCGATCTTACGCGTGGCGGATGT | 613 |
| CHAF1A | NM_005483 | 12 | 19 | + | 140 | + | 0 | 37 | 1 0 | CGCGAATGCCCAGGCCGATGACCTGAAGGTAC TGCAGCAGTTGACGCGTGGCGGATGT | 614 |
| CHAF1A | NM_005483 | 12 | 19 | + | 175 | - | 0 | 37 | 1 0 | CGCGAATGCCCTCCTGGGCCGGCAGGGTCTCCA GGAAGCAGGCTGACGCGTGGCGGATGT | 615 |
| CHAF1A | NM_005483 | 12 | 19 | + | 210 | + | 0 | 37 | 1 0 | CGCGAATGCCGAGCAGACGCCCAAGGCCTCCAA GCGGGAGAGGAGACGCGTGGCGGATGT | 616 |
| CHAF1A | NM_005483 | 12 | 19 | + | 245 | - | 0 | 37 | 1 0 | CGCGAATGCCTGCCTGCCCCGCCCACACTCA CTCTGCTGTCTACGCGTGGCGGATGT | 617 |
| EPHA3 | NM_005233 | 10 | 3 | + | -7 | + | 0 | 37 | 1 0 | CGCGAATGCCCAAACAGTAAAACTTCCAGGTCT CAGGACTTATGTACGCGTGGCGGATGT | 618 |
| EPHA3 | NM_005233 | 10 | 3 | + | 28 | - | 0 | 37 | 1 0 | CGCGAATGCCCAGCTTGGGTAGGGTCTTTCATAT GTATGTGGGTCAACGCGTGGCGGATGT | 619 |
| EPHA3 | NM_005233 | 10 | 3 | + | 63 | + | 0 | 37 | 1 0 | CGCGAATGCCTTCATGAGTTTGCCAAGGAATTG GATGCCACCAACGCGTGGCGGATGT | 620 |
| EPHA3 | NM_005233 | 10 | 3 | + | 98 | - | 0 | 37 | 1 0 | CGCGAATGCCCTTGTTACCTGCTCCAACAACTTTA TCAATGGATATACGCGTGGCGGATGT | 621 |
| EPHA3 | NM_005233 | 4 | 3 | + | 0 | + | 0 | 37 | 1 0 | CGCGAATGCCCCTTGTCGACCAGGTTTCTACAAG GCATTGGATGTTACGCGTGGCGGATGT | 622 |
| EPHA3 | NM_005233 | 4 | 3 | + | 35 | - | 0 | 37 | 1 0 | CGCGAATGCCGAACTGTGAGGCGGGCACTTAGC ACACTTCATATATACGCGTGGCGGATGT | 623 |
| EPHA3 | NM_005233 | 4 | 3 | + | 70 | + | 0 | 37 | 1 0 | CGCGAATGCCTACTCAGGAAGATGGTTCAATGA ACTGCAGGTGTGACGCGTGGCGGATGT | 624 |
| EPHA3 | NM_005233 | 4 | 3 | + | 105 | - | 0 | 37 | 1 0 | CGCGAATGCCTGGAGGGTCTTTGTCTGCCCGGA AGTAATTATTCTACGCGTGGCGGATGT | 625 |
| EPHA3 | NM_005233 | 4 | 3 | + | 140 | + | 0 | 37 | 1 0 | CGCGAATGCCTCCATGGCTTGTACCCGTGAGTA GTTTTGCTGCAAACGCGTGGCGGATGT | 626 |
| RB1 | NM_000321 | 10 | 13 | + | -15 | + | 0 | 37 | 1 0 | CGCGAATGCCCTTTTCTTCTTTCAAGGTTGAAAAT CTTTCTAAACGACGCGTGGCGGATGT | 627 |
| RB1 | NM_000321 | 10 | 13 | + | 20 | - | 0 | 37 | 1 0 | CGCGAATGCCCTAGATCTTATTTTAAGATAAA TTTCTTCGTATACGCGTGGCGGATGT | 628 |
| RB1 | NM_000321 | 10 | 13 | + | 55 | + | 0 | 37 | 1 0 | CGCGAATGCCATGCAAGATTATTTTTGGATCAT GATAAAACTCTTACGCGTGGCGGATGT | 629 |
| RB1 | NM_000321 | 10 | 13 | + | 90 | - | 0 | 37 | 1 0 | CGCGAATGCCTACCATGTGCAATACCTGTCTAT AGAATCAGTCTGACGCGTGGCGGATGT | 630 |
| PIK3CA | NM_006218 | 15 | 3 | + | -16 | + | 0 | 37 | 1 0 | CGCGAATGCCCTTTTTTTTAATCAGTACAGAT GAAGTTTTTAGACGCGTGGCGGATGT | 631 |
| PIK3CA | NM_006218 | 15 | 3 | + | 19 | - | 0 | 37 | 1 0 | CGCGAATGCCAGCATCCATGAGAAATCTGGTCGCC TCATTGTCAAACGCGTGGCGGATGT | 632 |
| PIK3CA | NM_006218 | 15 | 3 | + | 54 | + | 0 | 37 | 1 0 | CGCGAATGCCCTACAGGGCTTTCTGTCCTCCTA AACCCTGCTCAACGCGTGGCGGATGT | 633 |
| PIK3CA | NM_006218 | 15 | 3 | + | 89 | - | 0 | 37 | 1 0 | CGCGAATGCCAACCCCAAGAAGTACCTGAGG TTTCCTAGTTGAACGCGTGGCGGATGT | 634 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit # BWA mismatch | Sequence with add-ons | SEQ ID NO: |
|---|---|---|---|---|---|---|---|---|---|---|---|
| EPHB1 | NM_004441 | 8 | 3 | + | -16 | + | 0 | 37 | 1 0 | CGCGAATGCCCCTCCTTTCTCACCTAGATGATTAC AAGTCAGAGCTACGCGTGGCGGATGT | 635 |
| EPHB1 | NM_004441 | 8 | 3 | + | 19 | - | 0 | 37 | 1 0 | CGCGAATGCCCTGCCGAGCCAGCAATCAGGGGC AGTGCTCTCCACGCGTGGCGGATGT | 636 |
| EPHB1 | NM_004441 | 8 | 3 | + | 54 | + | 0 | 37 | 1 0 | CGCGAATGCCCGCCGGGTCGTGTTCGTTGTG TCTTGGTGGCCACGCGTGGCGGATGT | 637 |
| EPHB1 | NM_004441 | 8 | 3 | + | 89 | - | 0 | 37 | 1 0 | CGCGAATGCCGAGTGGAGGACCTACCTGCTACA GACGATAGAGATACGCGTGGCGGATGT | 638 |
| EPHA7 | NM_004440 | 15 | 6 | - | 0 | + | 0 | 37 | 1 0 | CGCGAATGCCTGGGAAGAATTAGTGGTTTGGA TGAGAACTATACACGCGTGGCGGATGT | 639 |
| EPHA7 | NM_004440 | 15 | 6 | - | 35 | - | 0 | 37 | 1 0 | CGCGAATGCCCCATGACTTGGCACACCTGGTAT GTTCGTATCGGGACGCGTGGCGGATGT | 640 |
| EPHA7 | NM_004440 | 15 | 6 | - | 70 | + | 0 | 37 | 1 0 | CGCGAATGCCAGCCCAACCAAAACAACTGGCTG CGGACTAACTGACGCGTGGCGGATGT | 641 |
| EPHA7 | NM_004440 | 15 | 6 | - | 105 | - | 0 | 37 | 1 0 | CGCGAATGCCTACAAAAATCCTTTGTGCATTG CCTTTGGAAATACGCGTGGCGGATGT | 642 |
| EPHA7 | NM_004440 | 15 | 6 | - | 140 | + | 0 | 37 | 1 0 | CGCGAATGCCATTGAAATTCACCCTGAGGGATT GTAACAGTCTTCACGCGTGGCGGATGT | 643 |
| EPHA7 | NM_004440 | 15 | 6 | - | 175 | - | 0 | 37 | 1 0 | CGCGAATGCCATTAAATGTTTCCTTGCAAGTTCC CAGTACTCCAGACGCGTGGCGGATGT | 644 |
| EPHA7 | NM_004440 | 15 | 6 | - | 210 | + | 0 | 37 | 1 0 | CGCGAATGCCTTGTACTATTATGAAACAGACTA TGACACTGGCAGACGCGTGGCGGATGT | 645 |
| EPHA7 | NM_004440 | 15 | 6 | - | 245 | - | 0 | 37 | 1 0 | CGCGAATGCCTGTCTATTTTACATAGAGGTTTT CTCTTATATTCACGCGTGGCGGATGT | 646 |
| EPHA7 | NM_004440 | 15 | 6 | - | 280 | + | 0 | 37 | 1 0 | CGCGAATGCCCATTGCTGCCAGATGAAAGTTTT ACCCAAGGTGACACGCGTGGCGGATGT | 647 |
| EPHA7 | NM_004440 | 15 | 6 | - | 315 | - | 0 | 37 | 1 0 | CGCGAATGCCACCTCAGTGTTAAGCTTCATCTTT CTTTCACCAAGACGCGTGGCGGATGT | 648 |
| EPHA7 | NM_004440 | 15 | 6 | - | 350 | + | 0 | 37 | 1 0 | CGCGAATGCCGAGAGAGATTGGACCTTTGTCCA AAAAGGGATTCTACGCGTGGCGGATGT | 649 |
| EPHA7 | NM_004440 | 15 | 6 | - | 385 | - | 0 | 37 | 1 0 | CGCGAATGCCAGCTATCTGCAAGCCCTACATCCT GAAAGGCAAGATACGCGTGGCGGATGT | 650 |
| EPHA7 | NM_004440 | 15 | 6 | - | 420 | + | 0 | 37 | 1 0 | CGCGAATGCCTTGGTTTCTGTCAAAGTGTACTAC AAGAAGTCTGACGCGTGGCGGATGT | 651 |
| EPHA7 | NM_004440 | 15 | 6 | - | 455 | - | 0 | 37 | 1 0 | CGCGAATGCCTATCTGGAAAGATAGCTAAGTTC TCAATAATGGACACGCGTGGCGGATGT | 652 |
| EPHA7 | NM_004440 | 15 | 6 | - | 490 | + | 0 | 37 | 1 0 | CGCGAATGCCCAGTGACTGGTTCAGAATTTTCCT CTTTAGTCGAGACGCGTGGCGGATGT | 653 |
| EPHA7 | NM_004440 | 15 | 6 | - | 525 | - | 0 | 37 | 1 0 | CGCGAATGCCTCTTCCTCTGCACTGCTGACACAT GTCCCTGCAACACGCGTGGCGGATGT | 654 |
| EPHA7 | NM_004440 | 15 | 6 | - | 560 | + | 0 | 37 | 1 0 | CGCGAATGCCAGCGGAAAACGCCCCCAGGATGC ACTGCAGTGCAGACGCGTGGCGGATGT | 655 |
| EPHA7 | NM_004440 | 15 | 6 | - | 595 | - | 0 | 37 | 1 0 | CGCGAATGCCGATACATTTTCAATGGGCACTA ACCATTCCTTACGCGTGGCGGATGT | 656 |
| EPHA7 | NM_004440 | 15 | 6 | - | 630 | + | 0 | 37 | 1 0 | CGCGAATGCCTGCAAAGCAGGCTACCAGCAAAA AGGAGACACTTGACGCGTGGCGGATGT | 657 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit # BWA mismatch | Sequence with add-ons | SEQ ID NO: |
|---|---|---|---|---|---|---|---|---|---|---|---|
| EPHA7 | NM_004440 | 15 | 6 | - | 665 | - | 0 | 37 | 1 0 | CGCGAATGCCAGTGGAGTTTTAATAGGACACATTACTTACGTTCAACGCGTGGCCGATGT | 658 |
| PALB2 | NM_024675 | 8 | 16 | - | -34 | + | 0 | 37 | 1 0 | CGCGAATGCCGTGTAGACTAATGATGTGACTTTTGTTTTCACAGAACGCGTGGCCGATGT | 659 |
| PALB2 | NM_024675 | 8 | 16 | - | 1 | - | 0 | 37 | 1 0 | CGCGAATGCCTATGCTATCAGAAGCAGGAAGCTCTGCTGTTTCAGACGCCTGGCCGATGT | 660 |
| PALB2 | NM_024675 | 8 | 16 | - | 36 | + | 0 | 37 | 1 0 | CGCGAATGCCAACCCAGGCAACCTACAATTGGTTTCAGAGTTAAAACGCGTGGCCGATGT | 661 |
| PALB2 | NM_024675 | 8 | 16 | - | 71 | - | 0 | 37 | 1 0 | CGCGAATGCCGACACGAGACACTGGAAGAGAATATTCTTCTGACCACCGCGTGGCCGATGT | 662 |
| RET | NM_020630 | 3 | 10 | + | 0 | + | 0 | 37 | 1 0 | CGCGAATGCCACCGCGGCTTTCCCCTGCTCACCGTCTACCTCAAGACGCGTGGCCGATGT | 663 |
| RET | NM_020630 | 3 | 10 | + | 35 | - | 0 | 37 | 1 0 | CGCGAATGCCTCCCCTCCACGAAGGATGTGGGTGACAGGAAGACACGCGTGGCCGATGT | 664 |
| RET | NM_020630 | 3 | 10 | + | 70 | + | 0 | 37 | 1 0 | CGCGAATGCCGTGCCAGTGGCCAGGCTGTGCCCGCGTATACTTCTACGCGTGGCCGATGT | 665 |
| RET | NM_020630 | 3 | 10 | + | 105 | - | 0 | 37 | 1 0 | CGCGAATGCCGGAGCTGCAGGCTGGAAAGGAGGTGTTGAAGAAGGACACGCGTGGCCGATGT | 666 |
| RET | NM_020630 | 3 | 10 | + | 140 | + | 0 | 37 | 1 0 | CGCGAATGCCCTCAAGCCCCGGAGCTCTGCTTCCCAGAGACAAGACGCGTGGCCGATGT | 667 |
| RET | NM_020630 | 3 | 10 | + | 175 | - | 0 | 37 | 1 0 | CGCGAATGCCCTGGGGTCGGTTCTCCCGAATGCGGAAGGAGGCACGCGTGGCCGATGT | 668 |
| RET | NM_020630 | 3 | 10 | + | 210 | + | 0 | 37 | 1 0 | CGCGAATGCCGCACCTTCCACCAGTTCCGCTGCTGCCTGCAGCCTGTAGGCCACGCGTGGCCGATGT | 669 |
| RET | NM_020630 | 3 | 10 | + | 245 | - | 0 | 37 | 1 0 | CGCGAATGCCAGCCTGTAGGCCACGCTGATGTTGGGGCACAAGAACGCGTGGCCGATGT | 670 |
| RET | NM_020630 | 3 | 10 | + | 280 | + | 0 | 37 | 1 0 | CGCGAATGCCCCTGGAGGGTGAGTGCCGACCTTGTGGGCCGCCACGCGTGGCCGATGT | 671 |
| NTRK3 | NM_001012338 | 4 | 15 | - | 0 | - | 0 | 37 | 1 0 | CGCGAATGCCGGCCCATGGCCCAGATGCAATGATCCTTGTGATGACGCGTGGCCGATGT | 672 |
| NTRK3 | NM_001012338 | 4 | 15 | - | 35 | + | 0 | 37 | 1 0 | CGCGAATGCCGGAGCCCAGCTCACCCTTGGCCTGGCGTGTCACGCGTGGCCGATGT | 673 |
| NTRK3 | NM_001012338 | 4 | 15 | - | 70 | - | 0 | 37 | 1 0 | CGCGAATGCCTCCCAAATGCTCCACATTGCCAGTCAGATCCCCTCACGCCTGGCCGATGT | 674 |
| NTRK3 | NM_001012338 | 4 | 15 | - | 105 | + | 0 | 37 | 1 0 | CGCGAATGCCGCACAAAGTGCTGGGAGGCCAGGTACACCATACCCACCGCGTGGCCGATGT | 675 |
| NTRK3 | NM_001012338 | 4 | 15 | - | 140 | - | 0 | 37 | 1 0 | CGCGAATGCCACCAGACCTGGCCACCAGGAACTGCCTGGTTGGAACGCGTGGCCGATGT | 676 |
| NTRK3 | NM_001012338 | 4 | 15 | - | 175 | + | 0 | 37 | 1 0 | CGCGAATGCCATGCCGAAGTCCCAATCTTCACTAGCAGATTCGCACGCGTGGCCGATGT | 677 |
| NTRK3 | NM_001012338 | 4 | 15 | - | 210 | - | 0 | 37 | 1 0 | CGCGAATGCCGTCCAGAGATGTCTACAGCACGGATTATTACAGGACGCGTGGCCGATGT | 678 |
| PALB2 | NM_024675 | 9 | 16 | - | 0 | + | 0 | 37 | 1 0 | CGCGAATGCCGAAGAAAAGTCGTCATCAAAAAGAGGATTCCCTTACGCGTGGCCGATGT | 679 |
| PALB2 | NM_024675 | 9 | 16 | - | 35 | - | 0 | 37 | 1 0 | CGCGAATGCCCTCATCCAAGGATAAATAAGCACTATTACTCCAAGACGCGTGGCCGATGT | 680 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| PALB2 | NM_024675 | 9 | 16 | - | 70 | + | 0 | 37 | 1 | 0 | CGCGAATGCCTGATGCTTTCACGGCTCCATTTCATAGGGATGGAAACGCGTGGCGATGT | 681 |
| PALB2 | NM_024675 | 9 | 16 | - | 105 | - | 0 | 37 | 1 | 0 | CGCGAATGCCACTGAGAAAAGACAGTAGTTGCTTTAAACTCAGCAACGCGTGGCGATGT | 682 |
| PALB2 | NM_024675 | 9 | 16 | - | 140 | + | 0 | 37 | 1 | 0 | CGCGAATGCCATCACAGACTTTCAGTTACCTGATGAAGACTTTGACGCCGTGGCGATGT | 683 |
| PALB2 | NM_024675 | 9 | 16 | - | 175 | - | 0 | 37 | 1 | 0 | CGCGAATGCCCTGAGCAGGACTTCACTTTTTCAAGCTTAAGAGGTACGCGTGGCGATGT | 684 |
| PALB2 | NM_024675 | 9 | 16 | - | 210 | + | 0 | 37 | 1 | 0 | CGCGAATGCCAAAACCAGTGGAGCCCTTTGAGTCAAAAATGTTTACGCGTGGCGATGT | 685 |
| PALB2 | NM_024675 | 9 | 16 | - | 245 | - | 0 | 37 | 1 | 0 | CGCGAATGCCAAAATACAGCTTCCCTCTTTAAGATGTCTCTCCACGCGTGGCGGATGT | 686 |
| PALB2 | NM_024675 | 9 | 16 | - | 280 | + | 0 | 37 | 1 | 0 | CGCGAATGCCTCCAGAGGAACTGAGTCCTAAACGCATGGATACAGACGCGTGGCGATGT | 687 |
| PALB2 | NM_024675 | 9 | 16 | - | 315 | - | 0 | 37 | 1 | 0 | CGCGAATGCCTAGAACAATAAGTCCTCTTCTAAGTCCTCCATTTACGCGTGGCGATGT | 688 |
| PALB2 | NM_024675 | 9 | 16 | - | 350 | + | 0 | 37 | 1 | 0 | CGCAAACTCGCAACGCTTGGCGGATGTGCCAAATCACATCCCAAAAG | 689 |
| PALB2 | NM_024675 | 9 | 16 | - | 385 | - | 0 | 37 | 1 | 0 | CGCGAATGCCTGATGAAGAAAGGCCCGTCTTTGTATGCTGGCTTACGCGTGGCCGATGT | 690 |
| PALB2 | NM_024675 | 9 | 16 | - | 420 | + | 0 | 37 | 1 | 0 | CGCGAATGCCTATTACTTTATACTTCCTTTAAATACGGTTGCCCTACGCGTGGCGATGT | 691 |
| PALB2 | NM_024675 | 9 | 16 | - | 455 | - | 0 | 37 | 1 | 0 | CGCGAATGCCGAACACATGTCTGTGGTAGGCCTGTCATTATCACGCGTGGCGATGT | 692 |
| PALB2 | NM_024675 | 9 | 16 | - | 490 | + | 0 | 37 | 1 | 0 | CGCGAATGCCACCTGCTTTCCCCATCTTAGGTACTACTCCAGCTACGCGTGGCGATGT | 693 |
| PALB2 | NM_024675 | 9 | 16 | - | 525 | - | 0 | 37 | 1 | 0 | CGCGAATGCCTGTAGATGCTTTTCATAGGAGCCTTGAGGGCCAAACGCCTGGCGATGT | 694 |
| PALB2 | NM_024675 | 9 | 16 | - | 560 | + | 0 | 37 | 1 | 0 | CGCGAATGCCGAAGTTGCTGGACGAACTTGCTGCACACCCCAACTACGCGTGGCGATGT | 695 |
| PALB2 | NM_024675 | 9 | 16 | - | 595 | - | 0 | 37 | 1 | 0 | CGCGAATGCCCACTGGCAAGACAGACTGAGTCTTTCAAATGAGCAACGCGTGGCGATGT | 696 |
| PALB2 | NM_024675 | 9 | 16 | - | 630 | + | 0 | 37 | 1 | 0 | CGCGAATGCCATACTAAACAATTCGACAGTTCAGGCAGCCAGCAACGCGTGGCGATGT | 697 |
| PALB2 | NM_024675 | 9 | 16 | - | 665 | - | 0 | 37 | 1 | 0 | CGCGAATGCCTGCCTGCTGACACTTGCAGGGTGGTATGTGGTTTACGCGTGGCGATGT | 698 |
| PALB2 | NM_024675 | 9 | 16 | - | 700 | + | 0 | 37 | 1 | 0 | CGCGAATGCCAGGACAACCTACCTGTGACTGTGACTCTGTCCCACGCGCGTGGCGATGT | 699 |
| PALB2 | NM_024675 | 9 | 16 | - | 735 | - | 0 | 37 | 1 | 0 | CGCGAATGCCAAAGAAATGAATGACTCAATGGGTGGAGGTGTTCCTACGCGTGGCGATGT | 700 |
| PALB2 | NM_024675 | 9 | 16 | - | 770 | + | 0 | 37 | 1 | 0 | CGCGAATGCCAAAGAAAATCAGCTCTGTAGAAACACATGCCAGGACGCCGTGGCGATGT | 701 |
| PALB2 | NM_024675 | 9 | 16 | - | 805 | - | 0 | 37 | 1 | 0 | CGCGAATGCCTGGATTGTACCTGTTCGACGAATGTTTATGCAGCACGCGTGGCGATGT | 702 |
| PKN1 | NM_002741 | 12 | 19 | + | 0 | + | 0 | 37 | 1 | 0 | CGCGAATGCCGTCACCTTCCGCAACCCTGTCATTGAGAGGATTCCACGCGTGGCGATGT | 703 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| PKN1 | NM_002741 | 12 | 19 | + | 35 | - | 0 | 37 | 1 | 0 | CGCGAATGCCGCTTGGAGAAAATTTCTTCTGCCGTCGGAGCCGAACGCGTGGCCGATGT | 704 |
| PKN1 | NM_002741 | 12 | 19 | + | 70 | + | 0 | 37 | 1 | 0 | CGCGAATGCCAGCCAAGGTGAGAGGGTGCTCCAGGCTTCCTGGGGACGCGTGGCCGATGT | 705 |
| PKN1 | NM_002741 | 12 | 19 | + | 105 | - | 0 | 37 | 1 | 0 | CGCGAATGCCCACCCTCTACGCCGTGGCCGATGACCCCTGGCCTCTACGCCGTGGCCGATGT | 706 |
| PKN1 | NM_002741 | 12 | 19 | + | 140 | + | 0 | 37 | 1 | 0 | CGCGAATGCCACGCCTGCCCCGTCCCCCAGGGAAGGCGGTTCAGACGCGTGGCCGATGT | 707 |
| PKN1 | NM_002741 | 12 | 19 | + | 175 | - | 0 | 37 | 1 | 0 | CGCGAATGCCCACGTGGCGACATCGATGTTCATCTGCCTAGCACGACGCGTGGCCGATGT | 708 |
| PKN1 | NM_002741 | 12 | 19 | + | 210 | + | 0 | 37 | 1 | 0 | CGCGAATGCCGGTGCGCTGCTCCGGAGGCTCATCCCCAATGCCAACGCGTGGCCGATGT | 709 |
| PKN1 | NM_002741 | 12 | 19 | + | 245 | - | 0 | 37 | 1 | 0 | CGCGAATGCCTGAGAAGCCCAGGGCTAAAGGTGCCTGTGCCGACGCGTGGCCGATGT | 710 |
| PKN1 | NM_002741 | 12 | 19 | + | 280 | + | 0 | 37 | 1 | 0 | CGCGAATGCCGGATCCGAGGCCCCGGACCACGGGTAAGGAAGAGACGCGTGGCCGATGT | 711 |
| PKN1 | NM_002741 | 12 | 19 | + | 315 | - | 0 | 37 | 1 | 0 | CGCGAATGCCCCAGGCTTCAAGGGCCAGCCGGGACCATGGGCCACGCCGTGGCCGATGT | 712 |
| PKN1 | NM_002741 | 12 | 19 | + | 350 | + | 0 | 37 | 1 | 0 | CGCGAATGCCAGGGTCCTGGGTCCCAGACACACCCTCCTCTCGTCACGCGTGGCCGATGT | 713 |
| PKN1 | NM_002741 | 12 | 19 | + | 385 | - | 0 | 37 | 1 | 0 | CGCGAATGCCAGGTTCAGCTTCTCCACCGATATGTCACTGCAGCAACGCGTGGCCGATGT | 714 |
| PKN1 | NM_002741 | 12 | 19 | + | 420 | + | 0 | 37 | 1 | 0 | CGCGAATGCCCCGCACTGACTCGGACAGCTCACCTCAGAAGAGCTACGCGTGGCCGATGT | 715 |
| PKN1 | NM_002741 | 12 | 19 | + | 455 | - | 0 | 37 | 1 | 0 | CGCGAATGCCCACCAGGCTCGATGGGCTGGAAGGAGGATCCCGCGACGCGTGGCCGATGT | 716 |
| NTRK3 | NM_001012338 | 7 | 15 | - | 0 | + | 0 | 37 | 1 | 0 | CGCGAATGCCGTCCGTGGCTGTCATCAGTGGTGAGGAGGACTCAACGCGTGGCCGATGT | 717 |
| NTRK3 | NM_001012338 | 7 | 15 | - | 35 | - | 0 | 37 | 1 | 0 | CGCGAATGCCGTGATGCCGTGGTTGATGTGGTGCAGTGGGCTGCACGCGTGGCCGATGT | 718 |
| NTRK3 | NM_001012338 | 7 | 15 | - | 70 | + | 0 | 37 | 1 | 0 | CGCGAATGCCACGCCCTCGTCACTGATGCCGGGCCCGACTGCCGTGGCCGATGT | 719 |
| NTRK3 | NM_001012338 | 7 | 15 | - | 105 | - | 0 | 37 | 1 | 0 | CGCGAATGCCCTCAATGACAGGGATGCGAGTCATGCCAATGACCAACGCGTGGCCGATGT | 720 |
| NTRK3 | NM_001012338 | 7 | 15 | - | 140 | + | 0 | 37 | 1 | 0 | CGCGAATGCCAACCCCAGTACTTCCGTCAGGGACACAACTGCCGCATTCAACGCGTGGCCGATGT | 721 |
| NTRK3 | NM_001012338 | 7 | 15 | - | 175 | - | 0 | 37 | 1 | 0 | CGCGAATGCCGCATTCCATCCCAGTACTTACACGTGTCCGGCTTGACGCGTGGCCGATGT | 722 |
| RPS6KA1 | NM_002953 | 14 | 1 | + | -4 | + | 0 | 37 | 1 | 0 | CGCGAATGCCACAGATTCCCAGGCATCCCCCCCAGCGCTGGGGACACGCGTGGCCGATGT | 723 |
| RPS6KA1 | NM_002953 | 14 | 1 | + | 31 | - | 0 | 37 | 1 | 0 | CGCGAATGCCTGGCCACGAAGCTGAAGCCCCGGAACAGCTGATGGACGCGTGGCCGATGT | 724 |
| RPS6KA1 | NM_002953 | 14 | 1 | + | 66 | + | 0 | 37 | 1 | 0 | CGCGAATGCCCCGGCCTGATGAAGACGACGGCAAGCCTCGTGCCACGCGTGGCCGATGT | 725 |
| RPS6KA1 | NM_002953 | 14 | 1 | + | 101 | - | 0 | 37 | 1 | 0 | CGCGAATGCCCTCACCTGTACCACCGAGTGCAGGGTGCCTGCGGACGCGTGGCCGATGT | 726 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit mismatch | # BWA mismatch | Sequence with add-ons | SEQ ID NO: |
|---|---|---|---|---|---|---|---|---|---|---|---|---|
| GUCY2F | NM_001522 | 19 | X | - | 0 | + | 0 | 37 | 1 | 0 | CGCGAATGCCATGTTCCTGGACTCGGGCGCTT TTCTCGCCTTGTACGCGTGGCGGATGT | 727 |
| GUCY2F | NM_001522 | 19 | X | - | 35 | - | 0 | 37 | 1 | 0 | CGCGAATGCCGTCCCAGCAGTTTCCTGAAAGCC GAAAACCAGAGACGCGTGGCGGATGT | 728 |
| GUCY2F | NM_001522 | 19 | X | - | 70 | + | 0 | 37 | 1 | 0 | CGCGAATGCCACCATGGCCTTGCATCTGCCAAG TTCCTGTGGTGCACGCGTGGCGGATGT | 729 |
| GUCY2F | NM_001522 | 19 | X | - | 105 | - | 0 | 37 | 1 | 0 | CGCGAATGCCTGCTGCCGAAGGGACATGACAGA CAGAAGGCACAAACGCGTGGCGGATGT | 730 |
| GUCY2F | NM_001522 | 19 | X | - | 140 | + | 0 | 37 | 1 | 0 | CGCGAATGCCGTGTGGACACTCCCTACAAGA TAGGGGTGGTGGACGCGTGGCGGATGT | 731 |
| GUCY2F | NM_001522 | 19 | X | - | 175 | - | 0 | 37 | 1 | 0 | CGCGAATGCCGGCCTTTGAAAACAGCGAATCAC AAGCCCAAGGCACGCGTGGCGGATGT | 732 |
| GUCY2F | NM_001522 | 19 | X | - | 210 | + | 0 | 37 | 1 | 0 | CGCGAATGCCCTGCCTCGCCGAGGTTGCTGCCGATT AGCCATTGAGCGACGCGTGGCGGATGT | 733 |
| GUCY2F | NM_001522 | 19 | X | - | 245 | - | 0 | 37 | 1 | 0 | CGCGAATGCCAATAACTCAGGTCAAAAGATGGG TCCCGGTTGATTACGCGTGGCGGATGT | 734 |
| GUCY2F | NM_001522 | 19 | X | - | 280 | + | 0 | 37 | 1 | 0 | CGCGAATGCCCTTTTGAATACGTGATTCTCAATG AAGACTGCCAGACGCGTGGCGGATGT | 735 |
| GUCY2F | NM_001522 | 19 | X | - | 315 | - | 0 | 37 | 1 | 0 | CGCGAATGCCTGTGGGAAATGAAACTGGAGA GAGCCCTCGAAGTACGCGTGGCGGATGT | 736 |
| GUCY2F | NM_001522 | 19 | X | - | 350 | + | 0 | 37 | 1 | 0 | CGCGAATGCCCCAGATGCCTCAGGATTTATTG GACCTACCAACACGCGTGGCGGATGT | 737 |
| GUCY2F | NM_001522 | 19 | X | - | 385 | - | 0 | 37 | 1 | 0 | CGCGAATGCCGTTTCCCAGGAGCGAGGCTGCCT CCGAGTTCAAGTACGCGTGGCGGATGT | 738 |
| GUCY2F | NM_001522 | 19 | X | - | 420 | + | 0 | 37 | 1 | 0 | CGCGAATGCCAGCTGGGACAAAGGAATTTTCTC TTGGGCTTGTGTACGCGTGGCGGATGT | 739 |
| GUCY2F | NM_001522 | 19 | X | - | 455 | - | 0 | 37 | 1 | 0 | CGCGAATGCCTCGGGTAGCTAATTTATTGTCTA ATTCATAATTCACGCGTGGCGGATGT | 740 |
| GUCY2F | NM_001522 | 19 | X | - | 490 | + | 0 | 37 | 1 | 0 | CGCGAATGCCCCTTTTCTCCGGACACTCCCTTCTC CCATCCGGGTGACGCGTGGCGGATGT | 741 |
| GUCY2F | NM_001522 | 19 | X | - | 525 | - | 0 | 37 | 1 | 0 | CGCGAATGCCTGAGCCCACTGAGCCCACTGAAAATATTTCAT GACAGTTACAAGACGCGTGGCGGATGT | 742 |
| GUCY2F | NM_001522 | 19 | X | - | 560 | + | 0 | 37 | 1 | 0 | CGCGAATGCCTGCTGGAGTCATTTCCTCAGATG AAGACATTTGGGACGCGTGGCGGATGT | 743 |
| GUCY2F | NM_001522 | 19 | X | - | 595 | - | 0 | 37 | 1 | 0 | CGCGAATGCCCGAAGAGCACTTGCGACTCGAT TGGCTGTATGCAACGCGTGGCGGATGT | 744 |
| GUCY2F | NM_001522 | 19 | X | - | 630 | + | 0 | 37 | 1 | 0 | CGCGAATGCCAGCCACGCTTACCTGTAGGGGT CGTCCTGACCACACGCGTGGCGGATGT | 745 |
| GUCY2F | NM_001522 | 19 | X | - | 665 | - | 0 | 37 | 1 | 0 | CGCGAATGCCGAGGGCTTTCCGCATGCTTTGG CTGTCTTGTCCTACGCGTGGCGGATGT | 746 |
| GUCY2F | NM_001522 | 19 | X | - | 700 | + | 0 | 37 | 1 | 0 | CGCGAATGCCAGAGGATTCACCAGGCAGACAG AATTCGCAGTGAGACGCGTGGCGGATGT | 747 |
| CENTG1 | NM_014770 | 11 | 12 | + | 0 | + | 0 | 37 | 1 | 0 | CGCGAATGCCGCTAGTAACGGGGCCACACTAG CGACTACTCTTCACGCGTGGCGGATGT | 748 |
| CENTG1 | NM_014770 | 11 | 12 | + | 35 | - | 0 | 37 | 1 | 0 | CGCGAATGCCCCGGTGACCAACATTCGGTGAG GACGGGAGGGAAACGCGTGGCGGATGT | 749 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| CENTG1 | NM_014770 | 11 | 12 | - | 70 | + | 0 | 37 | 1 0 | CGCGAATGCCAGCTCCGAGCCGAGGCAGCTGCA GTGGCTGATTGACGCGTGGCGGATGT | 750 |
| CENTG1 | NM_014770 | 11 | 12 | - | 105 | - | 0 | 37 | 1 0 | CGCGAATGCCCGCTTGGCTGCCGGTGCAGGGA CCCTGGGGTGCTACGCGTGGCGGATGT | 751 |
| CENTG1 | NM_014770 | 11 | 12 | - | 140 | + | 0 | 37 | 1 0 | CGCGAATGCCCAGGACCAGCCTTTTTGCGGTAT TGGACATGGACAACGCGTGGCGGATGT | 752 |
| CENTG1 | NM_014770 | 11 | 12 | - | 175 | - | 0 | 37 | 1 0 | CGCGAATGCCGAGGTCATGGGGACAGGAGG ATGGGGGTCAGCACGCGTGGCGGATGT | 753 |
| CENTG1 | NM_014770 | 11 | 12 | - | 210 | + | 0 | 37 | 1 0 | CGCGAATGCCCCATCTTCCCTAGTCCCTAGACTC CTCTGTTGGGCACGCGTGGCGGATGT | 754 |
| CENTG1 | NM_014770 | 11 | 12 | - | 245 | - | 0 | 37 | 1 0 | CGCGAATGCCACTGATGTGACGATAGGGAAGAT AGATGAAGAAGGACGCGTGGCGGATGT | 755 |
| CENTG1 | NM_014770 | 11 | 12 | - | 280 | + | 0 | 37 | 1 0 | CGCGAATGCCGTATCCCTCTATCCATCCTCAAAC TGATTCCAATAACGCGTGGCGGATGT | 756 |
| CENTG1 | NM_014770 | 11 | 12 | - | 315 | - | 0 | 37 | 1 0 | CGCGAATGCCTCGGAGTCACTACCCCGACGA TTCTGGAATGGTACGCGTGGCGGATGT | 757 |
| CENTG1 | NM_014770 | 11 | 12 | - | 350 | + | 0 | 37 | 1 0 | CGCGAATGCCAACGAAGCTTGGATAGTCGGGGA GAGACAACAGGGACGCGTGGCGGATGT | 758 |
| CENTG1 | NM_014770 | 11 | 12 | - | 385 | - | 0 | 37 | 1 0 | CGCGAATGCCTCACTCACCTGTTGATGGGAT GGCTCGCCCACTACGCGTGGCGGATGT | 759 |
| CENTG1 | NM_014770 | 11 | 12 | - | 420 | + | 0 | 37 | 1 0 | CGCGAATGCCTCCAGGGCTGGGACAGCTAGG GGCAGCTGGTCTACGCGTGGCGGATGT | 760 |
| CENTG1 | NM_014770 | 11 | 12 | - | 455 | - | 0 | 37 | 1 0 | CGCGAATGCCAAGGGAAAGACACATGTGGGA AAAAGCCAACTAACGCGTGGCGGATGT | 761 |
| CENTG1 | NM_014770 | 11 | 12 | - | 490 | + | 0 | 37 | 1 0 | CGCGAATGCCTCTCCAGAGCTTCCTACTAAAAC GAAGTGGCAATTACGCGTGGCGGATGT | 762 |
| CENTG1 | NM_014770 | 11 | 12 | - | 525 | - | 0 | 37 | 1 0 | CGCGAATGCCGGTTACATATTTCTTCTTCCATTC TTTGTTCAAGGACGCGTGGCGGATGT | 763 |
| CENTG1 | NM_014770 | 11 | 12 | - | 560 | + | 0 | 37 | 1 0 | CGCGAATGCCCCTGTCCAGTAATGGCTTTCTACTC TACCACCCCAGACGCGTGGCGGATGT | 764 |
| CENTG1 | NM_014770 | 11 | 12 | - | 595 | - | 0 | 37 | 1 0 | CGCGAATGCCCCAATGTGGCCCAGTCTCTGCCA CTCACGTTAATAACGCGTGGCGGATGT | 765 |
| RBBP8 | NM_002894 | 8 | 18 | + | -18 | + | 0 | 37 | 1 0 | CGCGAATGCCATTTTTTCTCCCCTTAGAAATGA GAAAAGTTTCCACGCGTGGCGGATGT | 766 |
| RBBP8 | NM_002894 | 8 | 18 | + | 17 | - | 0 | 37 | 1 0 | CGCGAATGCCTCATTAGGATATATGTTGTGGATG AGTTGAAGACTTACGCGTGGCGGATGT | 767 |
| RBBP8 | NM_002894 | 8 | 18 | + | 52 | + | 0 | 37 | 1 0 | CGCGAATGCCAAATGAAATTCTAGTAGCTGACA CTTATGACCAAAACGCGTGGCGGATGT | 768 |
| RBBP8 | NM_002894 | 8 | 18 | + | 87 | - | 0 | 37 | 1 0 | CGCGAATGCCCTCAGTATCTTGCTTACTGGCCAT TGGAGATTGACACGCGTGGCGGATGT | 769 |
| NFKB1 | NM_003998 | 19 | 4 | + | -18 | + | 0 | 37 | 1 0 | CGCGAATGCCGTGTGGCCTGGATTGTAGGGTGA TGCCCATGGAACGCGTGGCGGATGT | 770 |
| NFKB1 | NM_003998 | 19 | 4 | + | 17 | - | 0 | 37 | 1 0 | CGCGAATGCCTATGCAGGGGTGTGGTTCCATCG TAGGTAGTACTGACGCGTGGCGGATGT | 771 |
| NFKB1 | NM_003998 | 19 | 4 | + | 52 | + | 0 | 37 | 1 0 | CGCGAATGCCTAGCAGCTGGGAGAGGTCCACC AGCTGGCTACGCGTGGCGGATGT | 772 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| NFKB1 | NM_003998 | 19 | 4 | + | 87 | - | 0 | 37 | 1 | CGCGAATGCCCGCCAGATCACCATCTTACCTGC TGCTTTGAAGACGCGTGGCGGATGT | 773 |
| GUCY2F | NM_001522 | 6 | X | - | 0 | - | 0 | 37 | 1 | CGCGAATGCCAGACCATTGGAGATGCCTACATG GTGGCTTCAGCACGCGTGGCGGATGT | 774 |
| GUCY2F | NM_001522 | 6 | X | - | 35 | + | 0 | 37 | 1 | CGCGAATGCCTCAGCTGCATGCCTACTGCCATTC CTCTTTGGGAGACGCGTGGCGGATGT | 775 |
| GUCY2F | NM_001522 | 6 | X | - | 70 | + | 0 | 37 | 1 | CGCGAATGCCGATTGCAAACATGTCCTTAGATA TCCTGAGCTCTGACGCGTGGCGGATGT | 776 |
| GUCY2F | NM_001522 | 6 | X | - | 105 | - | 0 | 37 | 1 | CGCGAATGCCCACTTCTGCATGTGCCCATCTT GAAAGTGCCCACACGCGTGGCGGATGT | 777 |
| GUCY2F | NM_001522 | 6 | X | - | 140 | + | 0 | 37 | 1 | CGCGAATGCCCCGGTCCGAATTCGAATTGGCCT TCACTCAGTAAACGCGTGGCGGATGT | 778 |
| RB1 | NM_000321 | 3 | 13 | + | -12 | + | 7 | 37 | 1 | CGCGAATGCCTTTGTTCCCAGGAGGTTATATT CAAAAGAAAAACGCGTGGCGGATGT | 779 |
| RB1 | NM_000321 | 3 | 13 | + | 23 | - | 0 | 37 | 1 | CGCGAATGCCCTGCTGCAATAAAGATACAGATT CCCACAGTTCCACGCGTGGCGGATGT | 780 |
| RB1 | NM_000321 | 3 | 13 | + | 58 | + | 0 | 37 | 1 | CGCGAATGCCTTGACCTTAGATGAGATGTCGTTC ACTTTACTGAGACGCGTGGCGGATGT | 781 |
| RB1 | NM_000321 | 3 | 13 | + | 93 | - | 0 | 37 | 1 | CGCGAATGCCAAGAAACTTACCTGATTTCTAT GTTTTCTGTAGACGCGTGGCGGATGT | 782 |
| RPS6KA1 | NM_002953 | 8 | 1 | + | -51 | + | 0 | 37 | 1 | CGCGAATGCCCCTCCACCACGCGTGGCGGATGT GGCCCTGACCACACGCGTGGCGGATGT | 783 |
| RPS6KA1 | NM_002953 | 8 | 1 | + | -16 | - | 0 | 37 | 1 | CGCGAATGCCCTTCCTCATCCAGAAGGATGCTGT AATAGAGAAATAACGCGTGGCGGATGT | 784 |
| RPS6KA1 | NM_002953 | 8 | 1 | + | 19 | + | 0 | 37 | 1 | CGCGAATGCCGGCCACATCAAACTCACTGGTGA GTGGAGGGCGCCACGCGTGGCGGATGT | 785 |
| RPS6KA1 | NM_002953 | 8 | 1 | + | 54 | - | 0 | 37 | 1 | CGCGAATGCCCCTTGTCTGTCTCTCCCCTGGGTC CCAGGGGCAACGCGTGGCGGATGT | 786 |
| RBBP8 | NM_002894 | 14 | 18 | - | -8 | + | 0 | 37 | 1 | CGCGAATGCCTTATTTAGGATGCCAGTCAGTCA AAATTAGGAGAACGCGTGGCGGATGT | 787 |
| RBBP8 | NM_002894 | 14 | 18 | - | 23 | - | 0 | 37 | 1 | CGCGAATGCCTAACCAATGTACAGTCCATGTCC ACTGTCTCTCTACGCGTGGCGGATGT | 788 |
| RBBP8 | NM_002894 | 14 | 18 | - | 58 | + | 0 | 37 | 1 | CGCGAATGCCGTGAAACCGTTCTTCTTAAAAATG AAGAAGCAAGAGACGCGTGGCGGATGT | 789 |
| RBBP8 | NM_002894 | 14 | 18 | - | 93 | - | 0 | 37 | 1 | CGCGAATGCCAAACAGATCTTACTTGAACTTTTT TCTCCCTTCTGACGCGTGGCGGATGT | 790 |
| KSR2 | NM_173598 | 4 | 12 | - | -4 | + | 0 | 37 | 1 | CGCGAATGCCCCCGGCGGAGGACAAACTGCG CATCCAGAATGCACGCGTGGCGGATGT | 791 |
| KSR2 | NM_173598 | 4 | 12 | - | 31 | - | 0 | 37 | 1 | CGCGAATGCCTGGCGATGATCTCTGTGCCAG GTGGCATAGCCAACGCGTGGCGGATGT | 792 |
| KSR2 | NM_173598 | 4 | 12 | - | 66 | + | 0 | 37 | 1 | CGCGAATGCCGCTGTCCCCGACACAGAGGAGG ATAAGCTCCCTACGCGTGGCGGATGT | 793 |
| KSR2 | NM_173598 | 4 | 12 | - | 101 | - | 0 | 37 | 1 | CGCGAATGCCTTACCCAAGGGCAAAGACGTCAG AGTGCTTGGAGACGCGTGGCGGATGT | 794 |
| PIK3CA | NM_006218 | 3 | 3 | + | 0 | + | 0 | 37 | 1 | CGCGAATGCCGTTTTGCTATCGGCATGCCAGTGT GTGAATTTGATACGCGTGGCGGATGT | 795 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| PIK3CA | NM_006218 | 3 | 3 | + | 35 | − | 0 | 37 | 1 | 0 | CGCGAATGCCCTTCGGAAGTCCTGTACTTCTGGATCTTTAACCATACGCGTGGCCGATGT | 796 |
| PIK3CA | NM_006218 | 3 | 3 | + | 70 | + | 0 | 37 | 1 | 0 | CGCGAATGCCAAATATTCTGAACGTTTGTAAAGAAGCTGTGATCACGCGTGGCCGATGT | 797 |
| PIK3CA | NM_006218 | 3 | 3 | + | 105 | − | 0 | 37 | 1 | 0 | CGCGAATGCCCATTGCTCTACTATGAGGTGAATTGAGGTCCTAAACGCGTGGCCGATGT | 798 |
| PIK3CA | NM_006218 | 3 | 3 | + | 140 | + | 0 | 37 | 1 | 0 | CGCGAATGCCTATGTCTATCCTCCAAATGTAGAATCTTCACCAGAACGCGTGGCCGATGT | 799 |
| PIK3CA | NM_006218 | 3 | 3 | + | 175 | − | 0 | 37 | 1 | 0 | CGCGAATGCCCTTTATCTAATTTATTATATATGTGCTTTGCAATACGCGTGGCCGATGT | 800 |
| PIK3CA | NM_006218 | 3 | 3 | + | 210 | + | 0 | 37 | 1 | 0 | CGCGAATGCCGTAAGAAAATGACTAATCTACTCTAATCATTACTAACGCGTGGCCGATGT | 801 |
| PIK3CA | NM_006218 | 3 | 3 | + | −22 | + | 0 | 37 | 1 | 0 | CGCGAATGCCATCTTGTCCTTTTGCTTTTCAGCCTCTGTAAGGGAACGCGTGGCCGATGT | 802 |
| KSR2 | NM_173598 | 6 | 12 | − | 13 | − | 0 | 37 | 1 | 0 | CGCGAATGCCATTTTGCCATCCCTCACAACGGAATAGAGCGTCGACGCGTGGCCGATGT | 803 |
| KSR2 | NM_173598 | 6 | 12 | − | 48 | + | 0 | 37 | 1 | 0 | CGCGAATGCCCGTTTTGGATGTCAACAAAACCAGGCAGATTGCTCACGCGTGGCCGATGT | 804 |
| KSR2 | NM_173598 | 6 | 12 | − | 83 | − | 0 | 37 | 1 | 0 | CGCGAATGCCAGGCCCAAGAGCCGACAGTACCTTCACAATTCTTACGCGTGGCCGATGT | 805 |
| KSR2 | NM_173598 | 6 | 12 | − | 0 | + | 0 | 37 | 1 | 0 | CGCGAATGCCGTGAAGTCAGCACTGTGCTTAAGCTGGATAACACAACGCCTGGCCGATGT | 806 |
| PKN1 | NM_002741 | 9 | 19 | + | 35 | − | 0 | 37 | 1 | 0 | CGCGAATGCCGGGCCACATGGCTTCCAAGACGTCTGCCCCACCACGCCGTGGCCGATGT | 807 |
| PKN1 | NM_002741 | 9 | 19 | + | 70 | + | 0 | 37 | 1 | 0 | CGCGAATGCCAATGCCTGGGACCCAGAGCTTCACTCTGGAGCTGGACGCGTGGCCGATGT | 808 |
| PKN1 | NM_002741 | 9 | 19 | + | 105 | − | 0 | 37 | 1 | 0 | CGCGAATGCCTAGGCCCTGCTGTCCTCCAACGCAGCTCACCCTTTACGCGTGGCCGATGT | 809 |
| PKN1 | NM_002741 | 9 | 19 | + | 140 | + | 0 | 37 | 1 | 0 | CGCGAATGCCGAGGAGGAGGGGTTCCATGCCTCTGGCACCCGTGAGACGCGTGGCCGATGT | 810 |
| PKN1 | NM_002741 | 9 | 19 | + | 175 | − | 0 | 37 | 1 | 0 | CGCGAATGCCTTCCCGTGCCTGGAGGGAGAGGAAGAGGGCCATCAACGCGTGGCCGATGT | 811 |
| PKN1 | NM_002741 | 9 | 19 | + | 210 | + | 0 | 37 | 1 | 0 | CGCGAATGCCCTGGAGTTGGCTGTGTTCTGGCGGGACCAGCGGGACGCGTGGCCGATGT | 812 |
| PKN1 | NM_002741 | 9 | 19 | + | 245 | − | 0 | 37 | 1 | 0 | CGCGAATGCCAATCCTCCAACTTCAGGAATTTGAGGGCACACAGGACGCGTGGCCGATGT | 813 |
| PKN1 | NM_002741 | 9 | 19 | + | 280 | + | 0 | 37 | 1 | 0 | CGCGAATGCCTCTTGGACAATGAGAGGCATGAGGTCCAGCTGGACACGCGTGGCCGATGT | 814 |
| PKN1 | NM_002741 | 9 | 19 | + | 315 | − | 0 | 37 | 1 | 0 | CGCGAATGCCTATACCTCAGCCACCAGGCAGCCCTGGGGTTCATACGCGTGGCCGATGT | 815 |
| CHAF1A | NM_005483 | 10 | 19 | + | 0 | + | 0 | 37 | 1 | 0 | CGCGAATGCCTGATGTCGTCATCGTCGTGAGCGTGGAAGGGCGACGACGCGTGGCCGATGT | 816 |
| CHAF1A | NM_005483 | 10 | 19 | + | 35 | − | 0 | 37 | 1 | 0 | CGCGAATGCCCTTCATCCTGCCAAACTTCCTCCTCGGGAACACACGCGTGGCCGATGT | 817 |
| CHAF1A | NM_005483 | 10 | 19 | + | 70 | + | 0 | 37 | 1 | 0 | CGCGAATGCCCTAACGCGTGGCCGATGTCCAGTTCTGTGAGAACCACCGGCCCTGCCCT | 818 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BwA score | BWA hit | # BWA mismatch | Sequence with add-ons | SEQ ID NO: |
|---|---|---|---|---|---|---|---|---|---|---|---|---|
| CHAF1A | NM_005483 | 10 | 19 | + | 105 | - | 0 | 37 | 1 | 0 | CGCGAATGCCGATGAGTGCCGTCTTCTTATTCC AGTACCCCAGACGCGCGTGGCGGATGT | 819 |
| CHAF1A | NM_005483 | 10 | 19 | + | 140 | + | 0 | 37 | 1 | 0 | CGCGAATGCCGCGCCGAGACCCCTGGGCCCAG GACACGGGCTAACGCGTGGCGGATGT | 820 |
| CHAF1A | NM_005483 | 10 | 19 | + | 175 | - | 0 | 37 | 1 | 0 | CGCGAATGCCTGAGGAGGTACGGGGACCGAGG CACTCTGGGCTAACGCGTGGCGGATGT | 821 |
| CHAF1A | NM_005483 | 10 | 19 | + | 210 | + | 0 | 37 | 1 | 0 | CGCGAATGCCCTGTGCCCCTTTCCTCCAGCCCA AAGACAGTGTACGCGTGGCGGATGT | 822 |
| CHAF1A | NM_005483 | 10 | 19 | + | 245 | - | 0 | 37 | 1 | 0 | CGCGAATGCCCAGGAGCTTCTGAGAAAGAAA CACATGGACTCACGCGTGGCGGATGT | 823 |
| CHAF1A | NM_005483 | 10 | 19 | + | 280 | + | 0 | 37 | 1 | 0 | CGCGAATGCCACTATGAGGTGGACAGTGATGAG GAGTGGGAGAAACGCGTGGCGGATGT | 824 |
| CHAF1A | NM_005483 | 10 | 19 | + | 315 | - | 0 | 37 | 1 | 0 | CGCGAATGCCCCCTCACTGTGGACAGGGACTC CCCAGGCTCCTCACGCGTGGCGGATGT | 825 |
| CHAF1A | NM_005483 | 10 | 19 | + | 350 | + | 0 | 37 | 1 | 0 | CGCGAATGCCGGTAAGGATGTGCCCCAGCTGTC TTCACTCACAGAACGCGTGGCGGATGT | 826 |
| PDGFRA | NM_006206 | 22 | 4 | + | 0 | + | 0 | 37 | 1 | 0 | CGCGAATGCCAGTTATGAAAAATTCACTGGA CTTCCTGAAGAGACGCGTGGCGGATGT | 827 |
| PDGFRA | NM_006206 | 22 | 4 | + | 35 | - | 0 | 37 | 1 | 0 | CGCGAATGCCAGTCCACACGCGTGCCACA GCAGGATGGTCAACGCGTGGCGGATGT | 828 |
| PDGFRA | NM_006206 | 22 | 4 | + | 70 | + | 0 | 37 | 1 | 0 | CGCGAATGCCCAGACAATGCATACATTGGTGTC ACCTACAAAAACACGCGTGGCGGATGT | 829 |
| PDGFRA | NM_006206 | 22 | 4 | + | 105 | - | 0 | 37 | 1 | 0 | CGCGAATGCCCAGACCACCCTCCCAGTCCTTCAG CTTGTCTTCCTCACGCGTGGCGGATGT | 830 |
| PDGFRA | NM_006206 | 22 | 4 | + | 140 | + | 0 | 37 | 1 | 0 | CGCGAATGCCGGATGAGCAGGAGACTGAGCGCTG ACAGTGGCTACAACGCGTGGCGGATGT | 831 |
| PDGFRA | NM_006206 | 22 | 4 | + | 175 | - | 0 | 37 | 1 | 0 | CGCGAATGCCCTCAGGGACCAGGGTCAATGTCAG GCAGAGGAATGAACGCGTGGCGGATGT | 832 |
| PDGFRA | NM_006206 | 22 | 4 | + | 210 | + | 0 | 37 | 1 | 0 | CGCGAATGCCGAGGAGGACCTGGGCAAGAGGA ACAGACACAGGTAACGCGTGGCCGATGT | 833 |
| PKN1 | NM_002741 | 19 | 19 | + | 0 | + | 0 | 37 | 1 | 0 | CGCGAATGCCCTTTTATTCCGCCTGCGTGGTGCT GGGCCTACAGTACGCGTGGCGGATGT | 834 |
| PKN1 | NM_002741 | 19 | 19 | + | 35 | - | 0 | 37 | 1 | 0 | CGCGAATGCCCACACACCTGTAGACGATCTTGT GTTCGTGAAGAAACGCGTGGCGGATGT | 835 |
| PKN1 | NM_002741 | 19 | 19 | + | 70 | + | 0 | 37 | 1 | 0 | CGCGAATGCCCGTGTGCATGCATGTGCACAC TGCCCGTTGTGGACGCGTGGCGGATGT | 836 |
| PKN1 | NM_002741 | 19 | 19 | + | 105 | - | 0 | 37 | 1 | 0 | CGCGAATGCCGGAAAGAGGGATGAGCGGGGT CTGGGTCCTGTCACGCCGTGGCGGATGT | 837 |
| PKN1 | NM_002741 | 19 | 19 | + | 140 | + | 0 | 37 | 1 | 0 | CGCGAATGCCACCCTCCAACCCCAACAGGGA CCTGAAGTTGGAACGCGTGGCGGATGT | 838 |
| PKN1 | NM_002741 | 19 | 19 | + | 175 | - | 0 | 37 | 1 | 0 | CGCGAATGCCTCTTGACGTAGCCCTCCGTGTCC AGAGCAAATTGACGCGTGGCGGATGT | 839 |
| PKN1 | NM_002741 | 19 | 19 | + | 210 | + | 0 | 37 | 1 | 0 | CGCGAATGCCTTCCCCCCCTTTGCCTCTGCAAG GAGGGTGAGGGGACGCGTGGCGGATGT | 840 |
| PKN1 | NM_002741 | 19 | 19 | + | 245 | - | 0 | 37 | 1 | 0 | CGCGAATGCCTTCCCTCCCCCTTTGTCTAAT CCAGAGGCCAGACGCGTGGCGGATGT | 841 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA hit score | # BWA mismatch | Sequence with add-ons | SEQ ID NO: |
|---|---|---|---|---|---|---|---|---|---|---|---|
| PKN1 | NM_002741 | 19 | 19 | + | 280 | + | 0 | 37 | 1 | CGCGAATGCCTGGGGTCCTAACCCTATTCGGG GTGCCCCACCACGCGTGGCCGATGT | 842 |
| PKN1 | NM_002741 | 19 | 19 | + | 315 | - | 0 | 37 | 1 | CGCGAATGCCGGTTGTCCACACAGCCAGCCCTG TCCCAGGGTCAGACGCCGTGGCCGATGT | 843 |
| PKN1 | NM_002741 | 19 | 19 | + | 350 | + | 0 | 37 | 1 | CGCGAATGCCCCACATTGGGCTGAGTGACTCCT CTGGCCCCCATAACGCCGTGGCCGATGT | 844 |
| PKN1 | NM_002741 | 19 | 19 | + | 385 | - | 0 | 37 | 1 | CGCGAATGCCAGCCCATCCCTGGGACAGCAAG GCCATGTGAGGTACGCCGTGGCCGATGT | 845 |
| PKN1 | NM_002741 | 19 | 19 | + | 420 | + | 0 | 37 | 1 | CGCGAATGCCATGGGACCGGACCAGCACATTC TGTGGGACCCGACGCCGTGGCCGATGT | 846 |
| PKN1 | NM_002741 | 19 | 19 | + | 455 | - | 0 | 37 | 1 | CGCGAATGCCGACGTGTCCGTCAGCACCTCAGG GGCCAGGAACTCACGCCGTGGCCGATGT | 847 |
| PKN1 | NM_002741 | 19 | 19 | + | 490 | + | 0 | 37 | 1 | CGCGAATGCCGTACACGCGAGCTGTGGACTGGT GGGGACTGGGTGACGCCGTGGCCGATGT | 848 |
| PKN1 | NM_002741 | 19 | 19 | + | 525 | - | 0 | 37 | 1 | CGCGAATGCCTCACCTCGCCAACCAGCAGCATCT CGTAGAGCAGCAACGCCGTGGCCGATGT | 849 |
| EPHA7 | NM_004440 | 10 | 6 | - | -16 | + | 0 | 37 | 1 | CGCGAATGCCTTTCTCTGTTTACAGCTACAGCT GTCTCCAGTGAACGCGTGGCCGATGT | 850 |
| EPHA7 | NM_004440 | 10 | 6 | - | 19 | - | 0 | 37 | 1 | CGCGAATGCCCAGCAACCACCAGCAATGATAATA ACAGGATTCTGTACGCCGTGGCCGATGT | 851 |
| EPHA7 | NM_004440 | 10 | 6 | - | 54 | + | 0 | 37 | 1 | CGCGAATGCCTAGCTGGGACCATCATTTGGTG TTCATGGTCTTTACGCCGTGGCCGATGT | 852 |
| EPHA7 | NM_004440 | 10 | 6 | - | 89 | - | 0 | 37 | 1 | CGCGAATGCCAACTTTGTTCTTACCTTCTCCCA ATGATGAAGCCACGCCGTGGCCGATGT | 853 |
| PIK3CA | NM_006218 | 11 | 3 | + | -29 | + | 0 | 37 | 1 | CGCGAATGCCTTTATGTTTATTTTGTTTCTCCCAC ACAGACTAACGCGTGGCCGATGT | 854 |
| PIK3CA | NM_006218 | 11 | 3 | + | 6 | - | 0 | 37 | 1 | CGCGAATGCCGCAATTTGGGTAGAATTTCGGGG ATAGTTACACAAACGCCGTGGCCGATGT | 855 |
| PIK3CA | NM_006218 | 11 | 3 | + | 39 | + | 0 | 37 | 1 | CGCGAATGCCGCTTCTGTCTGTTAAATGGAATTC TAGAGATGAAGACGCGTGGCCGATGT | 856 |
| PIK3CA | NM_006218 | 11 | 3 | + | 76 | - | 0 | 0 | 2 | CGCGAATGCCTTATCTAGTAATCTCAAACATAC ATTTACCTGGGCACGCGTGGCCGATGT | 857 |
| NTRK3 | NM_001012338 | 10 | 15 | - | -58 | + | 0 | 37 | 1 | CGCGAATGCCTGTTCTGTTCTGGTTTTTATTAA ATTTGTTAATTACCGTGGCCGATGT | 858 |
| NTRK3 | NM_001012338 | 10 | 15 | - | -23 | - | 0 | 37 | 1 | CGCGAATGCCTATCCGTGCTCTCTGCAAAAAA GGACAAAGAGATACGCCGTGGCCGATGT | 859 |
| NTRK3 | NM_001012338 | 10 | 15 | - | 12 | + | 0 | 37 | 1 | CGCGAATGCCACTTATCTTGTGTAAGTCTGCTT TACCTGTTGCTACGCCGTGGCCGATGT | 860 |
| NTRK3 | NM_001012338 | 10 | 15 | - | 47 | - | 0 | 37 | 1 | CGCGAATGCCTAGTTACCGATAGTATCAGAATA AATCAGTTTCAAACGCCGTGGCCGATGT | 861 |
| RBBP8 | NM_002894 | 9 | 18 | + | -21 | + | 0 | 37 | 1 | CGCGAATGCCTGGTTTATTATTTATTCTTAGAAG CACATGGAACAACGCGTGGCCGATGT | 862 |
| RBBP8 | NM_002894 | 9 | 18 | + | 14 | - | 0 | 37 | 1 | CGCGAATGCCAAATTAAAAGATGACTTATCAGG GGTATAGCTGCTACGCGTGGCCGATGT | 863 |
| RBBP8 | NM_002894 | 9 | 18 | + | 49 | + | 0 | 37 | 1 | CGCGAATGCCAGCTACAGTTGTTGCTGAAACAC TTGGACTTGGTGACGCGTGGCCGATGT | 864 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| RBBP8 | NM_002894 | 9 | 18 | + | 84 | - | 0 | 37 | 1 | 0 | CGCGAATGCCCCAAACTAAACAATTACTTACAG ATTCTTCTTGAAACGCGTGGCCGGATGT | 865 |
| CHAF1A | NM_005483 | 8 | 19 | + | 0 | + | 0 | 37 | 1 | 0 | CGCGAATGCCCACCCTGGCCGCGGCTCCTGTGGAA GTTTGCCCCTTACGCGTGGCCGGATGT | 866 |
| CHAF1A | NM_005483 | 8 | 19 | + | 35 | - | 0 | 37 | 1 | 0 | CGCGAATGCCGCCGAGGGGCCAGGACCATGTGC TCTTTAATTCAACGCGTGGCCGGATGT | 867 |
| CHAF1A | NM_005483 | 8 | 19 | + | 70 | + | 0 | 37 | 1 | 0 | CGCGAATGCCGTCGGACCGCTTTCCATCCAGAC CTCTGCAGTCAGACGCGTGGCCGGATGT | 868 |
| CHAF1A | NM_005483 | 8 | 19 | + | 105 | - | 0 | 37 | 1 | 0 | CGCGAATGCCAACTCGCCGCTCTCGTGGCCGGATGT GAGCTGTGTCCAGACGCGTGGCCGGATGT | 869 |
| CHAF1A | NM_005483 | 8 | 19 | + | 140 | + | 0 | 37 | 1 | 0 | CGCGAATGCCCTCCTTCTTGAAAGACCTCAAAG GCCGGCAGCCCCACGCGTGGCCGGATGT | 870 |
| CHAF1A | NM_005483 | 8 | 19 | + | 175 | - | 0 | 37 | 1 | 0 | CGCGAATGCCATTCCGGTGGAAACGTCGTGG GTCCGGACCTCAACGCGTGGCCGGATGT | 871 |
| CHAF1A | NM_005483 | 8 | 19 | + | 210 | + | 0 | 37 | 1 | 0 | CGCGAATGCCGCAGATATTTTAACAGGTCAGA GCCTGAGGAGGTACGCGTGGCCGGATGT | 872 |
| RPS6KA1 | NM_002953 | 17 | 1 | + | 0 | - | 0 | 37 | 1 | 0 | CGCGAATGCCGTGTATGATGATGGCAAACACGT GTACCTGGTGACACGCGTGGCCGGATGT | 873 |
| RPS6KA1 | NM_002953 | 17 | 1 | + | 35 | + | 0 | 37 | 1 | 0 | CGCGAATGCCTCTTGTCCAGCAGCTCCCCACCCC GCATCAGCTCTACGCGTGGCCGGATGT | 874 |
| RPS6KA1 | NM_002953 | 17 | 1 | + | 70 | - | 0 | 37 | 1 | 0 | CGCGAATGCCTCCTGCGGCAGAAGTTCTTCTCA GAGCGGGAGGCCACGCGTGGCCGGATGT | 875 |
| RPS6KA1 | NM_002953 | 17 | 1 | + | 105 | + | 0 | 37 | 1 | 0 | CGCGAATGCCTCCACAGTTTGCCAATGGTGTG CAGGACAAAGCTACGCGTGGCCGGATGT | 876 |
| RPS6KA1 | NM_002953 | 17 | 1 | + | 140 | - | 0 | 37 | 1 | 0 | CGCGAATGCCGTATCTGCACTCACAGGGGTGA GTCTGGATTCGGACGCGTGGCCGGATGT | 877 |
| EPHA7 | NM_004440 | 6 | 6 | - | -39 | + | 0 | 37 | 1 | 0 | CGCGAATGCCCAGGTTACGACTCCTGAAACTTT TTTTTTTAATTACGCGTGGCCGGATGT | 878 |
| EPHA7 | NM_004440 | 6 | 6 | - | -4 | - | 0 | 37 | 1 | 0 | CGCGAATGCCATGAACTCTATTACTATCATGACT GGTTTCCCTAAACGCGTGGCCGGATGT | 879 |
| EPHA7 | NM_004440 | 6 | 6 | - | 31 | + | 0 | 37 | 1 | 0 | CGCGAATGCCGGAAAATGGAGCCCTAGAATGCAT TTCTCAGGGTAAACGCGTGGCCGGATGT | 880 |
| EPHA7 | NM_004440 | 6 | 6 | - | 66 | - | 0 | 37 | 1 | 0 | CGCGAATGCCATAGTATATTTAGAATAAGTGGA TCACTTTGTACACGCGTGGCCGGATGT | 881 |
| RB1 | NM_000321 | 21 | 13 | + | -18 | + | 0 | 37 | 1 | 0 | CGCGAATGCCCATCAATTATTTATTACTAGATTATG ATGTGTTCCATACGCGTGGCCGGATGT | 882 |
| RB1 | NM_000321 | 21 | 13 | + | 17 | - | 0 | 37 | 1 | 0 | CGCGAATGCCTAAGGTCTATATTCTTCACTTTGC AATATGCCATACACGCGTGGCCGGATGT | 883 |
| RB1 | NM_000321 | 21 | 13 | + | 52 | + | 0 | 37 | 1 | 0 | CGCGAATGCCAATTCAAAATCATTGTAACAGCA TACAAGGATCTTACGCGTGGCCGGATGT | 884 |
| RB1 | NM_000321 | 21 | 13 | + | 87 | - | 0 | 37 | 1 | 0 | CGCGAATGCCTATGGAAAATTACCTACCTCCTG AACAGCATGAGGACGCGTGGCCGGATGT | 885 |
| KSR2 | NM_173598 | 11 | 12 | - | 0 | + | 0 | 37 | 1 | 0 | CGCGAATGCCGACCATCCCTGTCCCTTACCA GCCAGACTCCAGACGCGTGGCCGGATGT | 886 |
| KSR2 | NM_173598 | 11 | 12 | - | 35 | - | 0 | 37 | 1 | 0 | CGCGAATGCCAGGGCTGGAGGACGTCGTGGA GGAGGGGTGCTGACGCGTGGCCGGATGT | 887 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| KSR2 | NM_173598 | 11 | 12 | - | 70 | + | 0 | 37 | 1 | 0 | CGCGAATGCCCCTCGCCAGCACCCCCCTCCCTCCTAGTGCCACGACGCGTGGCGATGT | 888 |
| KSR2 | NM_173598 | 11 | 12 | - | 105 | - | 0 | 37 | 1 | 0 | CGCGAATGCCGTGCACTGTGGGAAGGTGTAGGGGAGAAGGCGACGCGTGGCGATGT | 889 |
| KSR2 | NM_173598 | 11 | 12 | - | 140 | + | 0 | 37 | 1 | 0 | CGCGAATGCCACGGCAGCAGAAGAACTTCAACCTGCCAGGTACCTACGCCGTGGCGATGT | 890 |
| RPS6KA1 | NM_002953 | 12 | 1 | + | -38 | + | 0 | 37 | 1 | 0 | CGCGAATGCCGCCAGGGACAGACCCTTCATTTGGGCTCTTTACGCGTGGCGATGT | 891 |
| RPS6KA1 | NM_002953 | 12 | 1 | + | -3 | - | 0 | 37 | 1 | 0 | CGCGAATGCCCTTGATTTCCTCGCCCATCAGGGCCGGAGCCTGACGCGTGGCGATGT | 892 |
| RPS6KA1 | NM_002953 | 12 | 1 | + | 32 | + | 0 | 37 | 1 | 0 | CGCGAATGCCCGACATGTCTTCTACTCCACCATTGACTGGAATGTACGCGTGGCGATGT | 893 |
| RPS6KA1 | NM_002953 | 12 | 1 | + | 67 | - | 0 | 37 | 1 | 0 | CGCGAATGCCCCTGGCCAGAGCCCTGTGTGGGTGGACACTCACGCGTGGCGATGT | 894 |
| PALB2 | NM_024675 | 2 | 16 | - | 0 | + | 0 | 37 | 1 | 0 | CGCGAATGCCGGGCTTCTCTTTATTGTCCTGAGTCATCCCTGTGCACGCGTGGCGATGT | 895 |
| PALB2 | NM_024675 | 2 | 16 | - | 35 | - | 0 | 37 | 1 | 0 | CGCGAATGCCGAAACACAGGGCTTCGCAACGACTCACTCTCTTTGACGCGTGGCGATGT | 896 |
| PALB2 | NM_024675 | 2 | 16 | - | 70 | + | 0 | 37 | 1 | 0 | CGCGAATGCCAGCTCATTGTGATTAACCCTAAGACGACTCTCAGCACGCGTGGCGATGT | 897 |
| PALB2 | NM_024675 | 2 | 16 | - | 105 | - | 0 | 37 | 1 | 0 | CGCGAATGCCTGCCTGAGGAAGACAGTACAGCATCACACCCACGCGTGGCGATGT | 898 |
| EPHA3 | NM_005233 | 16 | 3 | + | 140 | + | 0 | 37 | 1 | 0 | CGCGAATGCCGGCAGGCAAGTGTGCATAACTGCTACTCTATACGCGTGGCGATGT | 899 |
| EPHA3 | NM_005233 | 16 | 3 | + | 0 | + | 0 | 37 | 1 | 0 | CGCGAATGCCGCCATCAAAACTTCTTCTGGACCAAAGCAATGTGACGCGTGGCGATGT | 900 |
| EPHA3 | NM_005233 | 16 | 3 | + | 35 | - | 0 | 37 | 1 | 0 | CGCGAATGCCAAGCCAGTCACCTGTTGTGCGGAAGGTAGTGATATACGCGTGGCGATGT | 901 |
| EPHA3 | NM_005233 | 16 | 3 | + | 70 | + | 0 | 37 | 1 | 0 | CGCGAATGCCAATGGTGTCTGGACAGCACACTGCAAGGAAATCTTACGCGTGGCGATGT | 902 |
| EPHA3 | NM_005233 | 16 | 3 | + | 105 | - | 0 | 37 | 1 | 0 | CGCGAATGCCCTATTGTGTCACAAGACTGTACTCCACACCCGTGACGCGTGGCGATGT | 903 |
| EPHA3 | NM_005233 | 16 | 3 | + | 140 | + | 0 | 37 | 1 | 0 | CGCGAATGCCCCAAGATTTCCACAGAGTAAGAAAAAAAATTCATACGCGTGGCGATGT | 904 |
| RET | NM_020630 | 12 | 10 | + | 0 | + | 0 | 37 | 1 | 0 | CGCGAATGCCGAGGATCCAAAGTGGGAATTCCCTCGGAAGAACTTACGCGTGGCGATGT | 905 |
| RET | NM_020630 | 12 | 10 | + | 35 | - | 0 | 37 | 1 | 0 | CGCGAATGCCCAAATTGCCTTCTCCTAGAGTTTTTCCAAGAACCACGCGTGGCGATGT | 906 |
| RET | NM_020630 | 12 | 10 | + | 70 | + | 0 | 37 | 1 | 0 | CGCGAATGCCGAAAAGTGGTCAAGGCAACGGCCTTCCATCTGAAAACGCGTGGCGATGT | 907 |
| RET | NM_020630 | 12 | 10 | + | 105 | - | 0 | 37 | 1 | 0 | CGCGAATGCCCATCTTCACGGCCACCGTGGTGTACCCTGCTCTGCACGCGTGGCGATGT | 908 |
| RET | NM_020630 | 12 | 10 | + | 140 | + | 0 | 37 | 1 | 0 | CGCGAATGCCGCTGAAAGGTACCTGCCAGGCACAGCACAGTGCACGCGTGGCGATGT | 909 |
| RB1 | NM_000321 | 27 | 13 | + | -33 | + | 0 | 37 | 1 | 0 | CGCGAATGCCAATGCTGTTAACAGTTCTTCATCCTTTTCCAGCTACGCGTGGCGATGT | 910 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| RB1 | NM_000321 | 27 | 13 | + | 2 | − | 0 | 37 | 1 | 0 | CGCGAATGCCTTCATTTTCTGCTTTTGCATTCGTGTTCGAGTAGAACGCGTGGCGGATGT | 911 |
| RB1 | NM_000321 | 27 | 13 | + | 37 | + | 0 | 37 | 1 | 0 | CGCGAATGCCTGATAGCCATGGATACCTCAAACAAGAAGAGAAATACGCGTGGCGGATGT | 912 |
| RB1 | NM_000321 | 27 | 13 | + | 72 | − | 0 | 37 | 1 | 0 | CGCGAATGCCGTGTACACAGTGTCCACCAAGTCCTGAGATCCTCACGCGTGGCGGATGT | 913 |
| PKN1 | NM_002741 | 15 | 19 | + | 0 | + | 0 | 37 | 1 | 0 | CGCGAATGCCAGCTCCCCATCCAGGAATCCACTGCTCCGAGTACGCGTGGCGGATGT | 914 |
| PKN1 | NM_002741 | 15 | 19 | + | 35 | − | 0 | 37 | 1 | 0 | CGCGAATCCCGGCGGGGCCTGGGGTCTCCTGGGTCTCCGAAGGCACGCGTGGCGGATGT | 915 |
| PKN1 | NM_002741 | 15 | 19 | + | 70 | + | 0 | 37 | 1 | 0 | CGCGAATGCCTGTGCAGTGACACCACTCCCTGGCCCCTGTCCAACGCGTGGCGGATGT | 916 |
| PKN1 | NM_002741 | 15 | 19 | + | 105 | − | 0 | 37 | 1 | 0 | CGCGAATCCCCACTGGTGAGAACAAGGACAGCGGGCAGGGTGAGCGCTGGCGGATGT | 917 |
| PKN1 | NM_002741 | 15 | 19 | + | 140 | + | 0 | 37 | 1 | 0 | CGCGAATGCCCCTCTTCCACAGCCCCTGAGGAAGTCACCTCTGACGCGTGGCGGATGT | 918 |
| PKN1 | NM_002741 | 15 | 19 | + | 175 | − | 0 | 37 | 1 | 0 | CGCGAATGCCCCCAGCACCGCCAGGAACTTGAAATCTTCGAGGGTACGCGTGGCGGATGT | 919 |
| PKN1 | NM_002741 | 15 | 19 | + | 210 | + | 0 | 37 | 1 | 0 | CGCGAATGCCCCGGGGTCATTTTGGAAGGTGAGGTGGAGGGCAGACGCGTGGCGGATGT | 920 |
| PKN1 | NM_002741 | 15 | 19 | + | 245 | − | 0 | 37 | 1 | 0 | CGCGAATGCCCCGCCAGCCAGGCAGGGACCTGGGGGTCTCCCAATTCCACGCGTGGCGGATGT | 921 |
| PKN1 | NM_002741 | 15 | 19 | + | 280 | + | 0 | 37 | 1 | 0 | CGCGAATGCCCTAAAACACCCCTGCCCACTGTGGTTCCAGGTGCACGCGTGGCGGATGT | 922 |
| PKN1 | NM_002741 | 15 | 19 | + | 315 | − | 0 | 37 | 1 | 0 | CGCGAATGCCGAACAGCTCCCCACTGGGCCGGAATTCGGAGAGAACGCGTGGCGGATGT | 923 |
| PKN1 | NM_002741 | 15 | 19 | + | 350 | + | 0 | 37 | 1 | 0 | CGCGAATGCCGGCCATAAGGCTCTGAAGAAAGGGGACATTGTGGCACGCGTGGCGGATGT | 924 |
| PKN1 | NM_002741 | 15 | 19 | + | 385 | − | 0 | 37 | 1 | 0 | CGCGAATGCCCCACGGCAGGTCCCACCTCTCCACCTCGTCTCGGACGCGTGGCGGATGT | 925 |
| CHAF1A | NM_005483 | 1 | 19 | + | −44 | + | 0 | 37 | 1 | 0 | CGCGAATGCCCGCCCTCCGCCGCCTGAGAGGAGGTCGAGCTGCCACGCGTGGCGGATGT | 926 |
| CHAF1A | NM_005483 | 1 | 19 | + | −9 | − | 0 | 37 | 1 | 0 | CGCGAATGCCGCCCCGCCACTCCAGCTCTCCAGCATCGCCCCGGCACGCGTGGCGGATGT | 927 |
| CHAF1A | NM_005483 | 1 | 19 | + | 26 | + | 0 | 37 | 1 | 0 | CGCGAATGCCGCCGGCGCCAGGGAGCCGCCACAGGTCGTTCGACGCGTGGCGGATGT | 928 |
| CHAF1A | NM_005483 | 1 | 19 | + | 57 | − | 13 | 37 | 1 | 0 | CGCGAATGCCGCCGCCGCCCCCCCTTCCCCTCGGCGCGGGCCGAAACGCGTGGCGGATGT | 929 |
| GUCY2F | NM_001522 | 11 | X | − | 0 | + | 0 | 37 | 1 | 0 | CGCGAATGCCGGCATGAAGTACTTACACCACAGAGAGTTTGTTCACACGCGTGGCGGATGT | 930 |
| GUCY2F | NM_001522 | 11 | X | − | 35 | − | 0 | 37 | 1 | 0 | CGCGAATGCCCATCTACCACACAGTTTCGAGACTTAGCCTCCCAACGCGTGGCGGATGT | 931 |
| GUCY2F | NM_001522 | 11 | X | − | 70 | + | 0 | 37 | 1 | 0 | CGCGAATGCCGGCGTTTTGTACTAAAAGTGACAGATTATGCTTTACGCGTGGCGGATGT | 932 |
| GUCY2F | NM_001522 | 11 | X | − | 105 | − | 0 | 37 | 1 | 0 | CGCGAATGCCTCTTCAGAGAGTCTCAGCATTTCTAAGATGTCTTACGCGTGGCGGATGT | 933 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| GUCY2F | NM_001522 | 11 | X | - | 140 | + | 0 | 37 | 1 | 0 | CGCGAATGCCGAATCTTCTATGGAAGGTAAGCAATGAATGTACACGCGTGGCGGATGT | 934 |
| CENTG1 | NM_014770 | 8 | 12 | - | 0 | + | 0 | 37 | 1 | 0 | CGCGAATGCCGATTACATCCACAGTACCCACGGCAAGGAGATGGAACGCGTGGCGGATGT | 935 |
| CENTG1 | NM_014770 | 8 | 12 | - | 35 | - | 0 | 37 | 1 | 0 | CGCGAATGCCGCTTGCCCGGACTTTGACTGTTGTTCGCAGCAAGACGCGTGGCGGATGT | 936 |
| CENTG1 | NM_014770 | 8 | 12 | - | 70 | + | 0 | 37 | 1 | 0 | CGCGAATGCCGGCCCCCGAGGGCCATCTCTGCCTTTGGCCCTCAACGCGTGGCGGATGT | 937 |
| CENTG1 | NM_014770 | 8 | 12 | - | 105 | - | 0 | 37 | 1 | 0 | CGCGAATGCCGTCTCATGTCCTTGACCAGCCCGTTAATGCTGGCACGCGTGGCGGATGT | 938 |
| CENTG1 | NM_014770 | 8 | 12 | - | 140 | + | 0 | 37 | 1 | 0 | CGCGAATGCCTGTCCAGATGGGTGAAGGCCTGGGTGAGTAAGGTTACGCGTGGCGGATGT | 939 |
| CENTG1 | NM_014770 | 8 | 12 | - | 175 | - | 0 | 37 | 1 | 0 | CGCGAATGCCCCAGCCCTGGCCCCTCTTCTGCTCCTATGTCATAACGCGTGGCGGATGT | 940 |
| CENTG1 | NM_014770 | 8 | 12 | - | 210 | + | 0 | 37 | 1 | 0 | CGCGAATGCCGAAAAAGAGGGGTAAGAGGGAAGAGGGGCTGCAACGCGTGGCGGATGT | 941 |
| CENTG1 | NM_014770 | 8 | 12 | - | 245 | - | 0 | 37 | 1 | 0 | CGCGAATGCCGTCCTCTTTATCACCCAGCTTCCTACTCGCCCAGACGCGTGGCGGATGT | 942 |
| CENTG1 | NM_014770 | 8 | 12 | - | 280 | + | 0 | 37 | 1 | 0 | CGCGAATGCCCACATAAGGAATGGGGCCAGAAGAAAGAGGCTCACACGCGTGGCGGATGT | 943 |
| CENTG1 | NM_014770 | 8 | 12 | - | 315 | - | 0 | 37 | 1 | 0 | CGCGAATGCCAGTAGTGCTTCTGTCGAAGAAGATGAAAACCTCAACGCGTGGCGGATGT | 944 |
| CENTG1 | NM_014770 | 8 | 12 | - | 350 | + | 0 | 37 | 1 | 0 | CGCGAATGCCCCCATGCCAAGCCCTAGCCCCAGCCCAGTTCCCTTACGCGTGGCGGATGT | 945 |
| CENTG1 | NM_014770 | 8 | 12 | - | 385 | - | 0 | 37 | 1 | 0 | CGCGAATGCCGAGGTGTTTGGATGTCTGATCTGGTGGTGCTGCACGCGTGGCGGATGT | 946 |
| CENTG1 | NM_014770 | 8 | 12 | - | 420 | + | 0 | 37 | 1 | 0 | CGCGAATGCCTGAAGCCAGAACCGGAATTTGGCCCAGCCCTCAGCACGCGTGGCGGATGT | 947 |
| CENTG1 | NM_014770 | 8 | 12 | - | 455 | - | 0 | 37 | 1 | 0 | CGCGAATGCCAGACAGCAGATGAAGGTCATCCCCACTGACCCGTACGCGTGGCGGATGT | 948 |
| EPHA7 | NM_004440 | 8 | 6 | - | -7 | + | 0 | 37 | 1 | 0 | CGCGAATGCCATTACAGTTAAATTTCAGGCACCAAAACCTACATACGCGTGGCGGATGT | 949 |
| EPHA7 | NM_004440 | 8 | 6 | - | 28 | - | 0 | 37 | 1 | 0 | CGCGAATGCCCAGCTTCTATTTGGGTCCTCATAGGTTTCAGGGTCAACGCGTGGCGGATGT | 950 |
| EPHA7 | NM_004440 | 8 | 6 | - | 63 | + | 0 | 37 | 1 | 0 | CGCGAATGCCTCCATCAATTCGCCAAGGAGCTAGATGCCTCCTGTACGCGTGGCGGATGT | 951 |
| EPHA7 | NM_004440 | 8 | 6 | - | 98 | - | 0 | 37 | 1 | 0 | CGCGAATGCCGCCTTACCTGCCAATCACACGCTCAATTTAATACGCGTGGCGGATGT | 952 |
| EPHB1 | NM_004441 | 10 | 3 | + | -8 | + | 0 | 37 | 1 | 0 | CGCGAATGCCCAACAAGGCTCCCAGGATGAAGATCTACATTGACGCGTGGCGGATGT | 953 |
| EPHB1 | NM_004441 | 10 | 3 | + | 27 | - | 0 | 37 | 1 | 0 | CGCGAATGCCGACAGCTTCGTTGGGATCCTCGTAAGTGAAGGGGTACGCGTGGCGGATGT | 954 |
| EPHB1 | NM_004441 | 10 | 3 | + | 62 | + | 0 | 37 | 1 | 0 | CGCGAATGCCCGGAGTTTGCCAAGGAGATTGATGTATCTTTTGTACGCGTGGCGGATGT | 955 |
| EPHB1 | NM_004441 | 10 | 3 | + | 97 | - | 0 | 37 | 1 | 0 | CGCGAATGCCGAGCCATACCTGCTCCGATGACCTCTTCAATTTCACGCGTGGCGGATGT | 956 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| PIK3CA | NM_006218 | 9 | 3 | + | 0 | + | 0 | 37 | 1 | 0 | CGCGAATGCCGAACACTGTCCATTGGCATGGGG AATATAAACTTACGCGTGGCGGATGT | 957 |
| PIK3CA | NM_006218 | 9 | 3 | + | 35 | − | 0 | 37 | 1 | 0 | CGCGAATGCCTTTTTCCAGATACTAGAGTGTCTG TGTAATCAACACGCGTGGCGGATGT | 958 |
| PIK3CA | NM_006218 | 9 | 3 | + | 70 | + | 0 | 37 | 1 | 0 | CGCGAATGCCTGCTTTGAATCTTTGGCCAGTAC CTCATGATTAACGCGTGGCGGATGT | 959 |
| PIK3CA | NM_006218 | 9 | 3 | + | 105 | − | 0 | 37 | 1 | 0 | CGCGAATGCCGATCCAGTAACACCAATAGGGTT CAGACAAATCTTCACGCGTGGCGGATGT | 960 |
| PIK3CA | NM_006218 | 9 | 3 | + | 140 | + | 0 | 37 | 1 | 0 | CGCGAATGCCAAATCCAAATAAAGTAAGGTTTT TATTGTCATAAAACGCGTGGCGGATGT | 961 |
| PIK3CA | NM_006218 | 9 | 3 | + | 175 | − | 0 | 37 | 1 | 0 | CGCGAATGCCAGAGAGAAGGTTTGACTGCCATA AAAAATATCTAAACGCGTGGCGGATGT | 962 |
| PIK3CA | NM_006218 | 9 | 3 | + | 210 | + | 0 | 37 | 1 | 0 | CGCGAATGCCTATGTATATATAATAGCTTTCTT CCATCTCTTAGACGCGTGGCGGATGT | 963 |
| PIK3CA | NM_006218 | 9 | 3 | + | 245 | − | 0 | 37 | 1 | 0 | CGCGAATGCCAACCAGTCAAACTCCAACTCTAA GCATGGAGTTTCACGCGTGGCGGATGT | 964 |
| PIK3CA | NM_006218 | 9 | 3 | + | 280 | + | 0 | 37 | 1 | 0 | CGCGAATGCCCAGCAGTGTGGTAAAGTTCCCAG ATATGTCAGTGAACGCGTGGCGGATGT | 965 |
| PIK3CA | NM_006218 | 9 | 3 | + | 315 | − | 0 | 37 | 1 | 0 | CGCGAATGCCTTCTCGGGATACAGACCAATTGG CATGCTCTTCAAACGCGTGGCGGATGT | 966 |
| PIK3CA | NM_006218 | 9 | 3 | + | 350 | + | 0 | 37 | 1 | 0 | CGCGAATGCCGCAGGATTAGCTATTCCCACGC AGGACTGGTAAGACGCCTGGCGGATGT | 967 |
| RET | NM_020630 | 16 | 10 | + | −34 | − | 0 | 37 | 1 | 0 | CGCGAATGCCTAACTTCAATGTCTTTATTCCATC TTCTCTTTAGGACGCGTGGCGGATGT | 968 |
| RET | NM_020630 | 16 | 10 | + | 1 | + | 0 | 37 | 1 | 0 | CGCGAATGCCGGATTCAATTGCCATCCATTTAA CTGGAATCCGACACGCGTGGCGGATGT | 969 |
| RET | NM_020630 | 16 | 10 | + | 36 | − | 0 | 37 | 1 | 0 | CGCGAATGCCCTTTTTGATCATATCTACACCACG CAAAGTGATGTACGCGTGGCGGATGT | 970 |
| RET | NM_020630 | 16 | 10 | + | 71 | + | 0 | 37 | 1 | 0 | CGCGAATGCCAACCTCCACCCCAAGAGAGCAAC ACCCACACTTACACGCGTGGCGGATGT | 971 |
| PIK3CA | NM_006218 | 17 | 3 | + | −30 | + | 0 | 37 | 1 | 0 | CGCGAATGCCAAATGGTGATACATATATTTGA ATTTCAGATTTAACGCGTGGCGGATGT | 972 |
| PIK3CA | NM_006218 | 17 | 3 | + | 5 | − | 0 | 37 | 1 | 0 | CGCGAATGCCATACGAATAAATTTGAAGTGTTAG CATATCTTGCCGACGCGTGGCGGATGT | 973 |
| PIK3CA | NM_006218 | 17 | 3 | + | 40 | + | 0 | 37 | 1 | 0 | CGCGAATGCCTATGGAAAATATCTGGCAAAATC AAGGTCTTGATCACGCGTGGCGGATGT | 974 |
| PIK3CA | NM_006218 | 17 | 3 | + | 75 | − | 0 | 37 | 1 | 0 | CGCGAATGCCCACATACAGGTTGCCTTACTGG TTACCTACCGAAACGCGTGGCGGATGT | 975 |
| RB1 | NM_000321 | 4 | 13 | + | −10 | + | 0 | 37 | 1 | 0 | CGCGAATGCCCTTTTGTAGTGTCCATAAATTCT TTAACTTACTAACGCGTGGCGGATGT | 976 |
| RB1 | NM_000321 | 4 | 13 | + | 25 | − | 0 | 37 | 1 | 0 | CGCGAATGCCGCATTATCAACTTTGGTACTGGT ATCAATTCTTTACGCGTGGCGGATGT | 977 |
| RB1 | NM_000321 | 4 | 13 | + | 60 | + | 0 | 37 | 1 | 0 | CGCGAATGCCTATGTCAAGACTGTTGAAGAAGT ATGATGTATTGTACGCGTGGCGGATGT | 978 |
| RB1 | NM_000321 | 4 | 13 | + | 95 | − | 0 | 37 | 1 | 0 | CGCGAATGCCTTTACTTTACCTTTCCAATTTGCT GAAGAGTCAACGCGTGGCGGATGT | 979 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| RPS6KA1 | NM_002953 | 21 | 1 | + | -1 | + | 0 | 37 | 1 | 0 | CGCGAATGCCGGACCTGGTGTCCAAGATGCTACACGTGGATCCCACGCGTGGCGATGT | 980 |
| RPS6KA1 | NM_002953 | 21 | 1 | + | 34 | - | 0 | 37 | 1 | 0 | CGCGAATGCCATGCTGCAGAACCTGCTTAGCTGTGAGGCGCTGGGTTACGCGTGGCGATGT | 981 |
| RPS6KA1 | NM_002953 | 21 | 1 | + | 69 | + | 0 | 37 | 1 | 0 | CGCGAATGCCCATGGGTCACCCAGAAAGACAAGCTTCCCAAAGACGCGTGGCGATGT | 982 |
| RPS6KA1 | NM_002953 | 21 | 1 | + | 104 | - | 0 | 37 | 1 | 0 | CGCGAATGCCCCTTCACAAGCTGTAGGTCCTGGTGGGACAGCTGACGCGTGGCGATGT | 983 |
| NFKB1 | NM_003998 | 3 | 4 | + | -30 | + | 0 | 37 | 1 | 0 | CGCGAATGCCATTGAAACATTTAAATGTTCTTCTTTACAGATGTTACGCGTGGCGATGT | 984 |
| NFKB1 | NM_003998 | 3 | 4 | + | 5 | - | 0 | 37 | 1 | 0 | CGCGAATGCCTAAATATTGTATGAGTCAAAGAAGGATCCAAATGAACGCGTGGCGATGT | 985 |
| NFKB1 | NM_003998 | 3 | 4 | + | 40 | + | 0 | 37 | 1 | 0 | CGCGAATGCCATCCAGAAGTATTTCAACCACAGATGGCACTGCCAACGCGTGGCGATGT | 986 |
| NFKB1 | NM_003998 | 3 | 4 | + | 75 | - | 0 | 37 | 1 | 0 | CGCGAATGCCACAACAGGGTAACAGGGATGAGTTTTCTTACCTGTACGCGTGGCGATGT | 987 |
| EPHA3 | NM_005233 | 17 | 3 | + | -17 | + | 0 | 37 | 1 | 0 | CGCGAATGCCGTTTCTTTTTTTACAGTGACATGAAAAAGTTGACGCGTGGCGATGT | 988 |
| EPHA3 | NM_005233 | 17 | 3 | + | 18 | - | 0 | 37 | 1 | 0 | CGCGAATGCCTGATGATCTTCTCTGTGGCCCAACCACGGTGACAACGCGTGGCGATGT | 989 |
| EPHA3 | NM_005233 | 17 | 3 | + | 53 | + | 0 | 37 | 1 | 0 | CGCGAATGCCGTAGCATTAAAGCTCTAGAAACGCAATCAAAGAATACGCGTGGCGATGT | 990 |
| EPHA3 | NM_005233 | 17 | 3 | + | 88 | - | 0 | 37 | 1 | 0 | CGCGAATGCCCACTTCCGTCCCGTGCTTTACACGGAACTGGGCCACGCGTGGCGATGT | 991 |
| NTRK3 | NM_001007156 | 2 | 15 | - | -6 | + | 19 | 37 | 1 | 0 | CGCGAATGCCTGCCAGGGTCTTTTCAAACATAGACAATCATGGACGCGTGGCGATGT | 992 |
| NTRK3 | NM_001007156 | 2 | 15 | - | 33 | - | 35 | 37 | 1 | 0 | CGCGAATGCCTGGACTAGATGATCTCTATTGTCCTTCAAGTTTAACGCGTGGCGATGT | 993 |
| NTRK3 | NM_001007156 | 2 | 15 | - | 68 | + | 35 | 37 | 1 | 0 | CGCGAATGCCTCAACTCACTACTATATATGAGGAACCTGAGGTCCAACGCGTGGCGATGT | 994 |
| NTRK3 | NM_001007156 | 2 | 15 | - | 103 | - | 35 | 37 | 1 | 0 | CGCGAATGCCACCATGTGACCTTGGGTAAGACACTTCCCACCACTCACGCGTGGCGATGT | 995 |
| EPHA4 | NM_004438 | 3 | 2 | - | 0 | + | 0 | 37 | 1 | 0 | CGCGAATGCCACCTAACACTGCCTTGTTGGATCCAAGCTCCCCTGACGCGTGGCGATGT | 996 |
| EPHA4 | NM_004438 | 3 | 2 | - | 35 | - | 0 | 37 | 1 | 0 | CGCGAATGCCAGCCAATCGCCACTGACTACCACAGCAGAAATTACGCGTGGCGATGT | 997 |
| EPHA4 | NM_004438 | 3 | 2 | - | 70 | + | 0 | 37 | 1 | 0 | CGCGAATGCCAGGCCATTAAAATGGACCGGTATAAGGATAACTTACGCGTGGCGATGT | 998 |
| EPHA4 | NM_004438 | 3 | 2 | - | 105 | - | 0 | 37 | 1 | 0 | CGCGAATGCCCACAGCCTCAGTGTGTATAACAGCAGCTGTGACGCGTGGCGATGT | 999 |
| EPHA4 | NM_004438 | 3 | 2 | - | 140 | + | 0 | 37 | 1 | 0 | CGCGAATGCCTGCCACGTGAACCAGGAGTAAGTACTCAACGATGTACGCGTGGCGATGT | 1000 |
| EPHA3 | NM_005233 | 9 | 3 | + | -38 | + | 0 | 37 | 1 | 0 | CGCGAATGCCTTCCTCTTATGTGTTCGCTTTCTTGATTTACCTCACGCGTGGCGATGT | 1001 |
| EPHA3 | NM_005233 | 9 | 3 | + | -3 | - | 0 | 37 | 1 | 0 | CGCGAATGCCCTGCCCATGTTTGACTTATAGCCACAGAACCTGACGCGTGGCGATGT | 1002 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| EPHA3 | NM_005233 | 9 | 3 | + | 32 | + | 0 | 37 | 1 | 0 | CGCGAATGCCATGAAAAAGACTTCATTTTGGCAATGGGCATTGTACGCGTGGCCGATGT | 1003 |
| EPHA3 | NM_005233 | 9 | 3 | + | 67 | - | 0 | 37 | 1 | 0 | CGCGAATGCCGGTGAAGCAAAACAAAAGCCAAGTTTAGAACTTACGCGTGGCCGATGT | 1004 |
| EPHB1 | NM_004441 | 7 | 3 | + | 0 | + | 0 | 37 | 1 | 0 | CGCGAATGCCGAACACAATGAGTTCAACTCCTCCATGGCCAGGAGACGCGTGGCCGATGT | 1005 |
| EPHB1 | NM_004441 | 7 | 3 | + | 35 | - | 0 | 37 | 1 | 0 | CGCGAATGCCGCCGCAGCCCATCAATCCTTGCTGTGTTGGTCTGAACGCGTGGCCGATGT | 1006 |
| EPHB1 | NM_004441 | 7 | 3 | + | 70 | + | 0 | 37 | 1 | 0 | CGCGAATGCCCTGCATGGTATATGTGGTACAGGTGCGTGCCCGCACGCGTGGCCGATGT | 1007 |
| EPHB1 | NM_004441 | 7 | 3 | + | 105 | - | 0 | 37 | 1 | 0 | CGCGAATGCCATCTTGCCACTGAACTTGCCGTAGCCAGCACAGTACGCGTGGCCGATGT | 1008 |
| EPHB1 | NM_004441 | 7 | 3 | + | 140 | + | 0 | 37 | 1 | 0 | CGCGAATGCCGTGCTCTTCCAGACTCTGACTGACGGTAAGGGTCGGACGCGTGGCCGATGT | 1009 |
| RB1 | NM_000321 | 19 | 13 | + | 0 | + | 0 | 37 | 1 | 0 | CGCGAATGCCGTATCTTTCTCCTGTAAGATCTCCAAAGAAAAAGACGCGTGGCCGATGT | 1010 |
| RB1 | NM_000321 | 19 | 13 | + | 35 | - | 0 | 37 | 1 | 0 | CGCGAATGCCTCTGCATTTGCAGTAGAATTTACACGCGTAGTTGAACACGCGTGGCCGATGT | 1011 |
| RB1 | NM_000321 | 19 | 13 | + | 70 | + | 0 | 37 | 1 | 0 | CGCGAATGCCGAGACACAAGCAACCTCAGCCTTCCAGACCCAGAAACGCGTGGCCGATGT | 1012 |
| RB1 | NM_000321 | 19 | 13 | + | 105 | - | 0 | 37 | 1 | 0 | CGCGAATGCCTATAAACAGTGAAAGAGAGGTAGATTTCAATGCACGCGTGGCCGATGT | 1013 |
| RB1 | NM_000321 | 19 | 13 | + | 136 | + | 7 | 37 | 1 | 0 | CGCGAATGCCTATAAAAAGGTTAGTAGATGATTATTTCAAGAGACGCGTGGCCGATGT | 1014 |
| RBBP8 | NM_002894 | 18 | 18 | + | 0 | + | 0 | 37 | 1 | 0 | CGCGAATGCCTATTATGCAGATATGCCAGCAGAAGAAAGAGAAAACGCGTGGCCGATGT | 1015 |
| RBBP8 | NM_002894 | 18 | 18 | + | 35 | - | 0 | 37 | 1 | 0 | CGCGAATGCCAGCGGAATCGGTGTCTTGAGCAGGAAGCCAATTTCACGCGTGGCCGATGT | 1016 |
| RBBP8 | NM_002894 | 18 | 18 | + | 70 | + | 0 | 37 | 1 | 0 | CGCGAATGCCACATTCCACCCAACACCAGAGAATTTTGGAAACGCGTGGCCGATGT | 1017 |
| RBBP8 | NM_002894 | 18 | 18 | + | 105 | - | 0 | 37 | 1 | 0 | CGCGAATGCCCTTTCCATACAGTCTGAGTGGAAGGAAAACCAACACGCGTGGCCGATGT | 1018 |
| RBBP8 | NM_002894 | 18 | 18 | + | 136 | + | 9 | 37 | 1 | 0 | CGCGAATGCCAAAGAGGTGAGAGTATAGATTGTAACATTTTATAAACGCGTGGCCGATGT | 1019 |
| KSR2 | NM_173598 | 8 | 12 | - | -46 | + | 0 | 37 | 1 | 0 | CGCGAATGCCCCTGCCTTTTCACCTAGGGATCACGTTTATTTTTCACGCGTGGCCGATGT | 1020 |
| KSR2 | NM_173598 | 8 | 12 | - | -11 | - | 0 | 37 | 1 | 0 | CGCGAATGCCTGAAGTAATGGATTTCTTCCAAGCTGTAAAGAAACGCGTGGCCGATGT | 1021 |
| KSR2 | NM_173598 | 8 | 12 | - | 24 | + | 0 | 37 | 1 | 0 | CGCGAATGCCAATTGAAGTGAGCCAACGTCGGAGTGAGAATCACGCGTGGCCGATGT | 1022 |
| KSR2 | NM_173598 | 8 | 12 | - | 59 | - | 0 | 37 | 1 | 0 | CGCGAATGCCGGCAGTCCCTGGAAAATGTCGCTTCACTGCTCTCACGCGTGGCCGATGT | 1023 |
| RBBP8 | NM_002894 | 10 | 18 | + | -10 | + | 0 | 37 | 1 | 0 | CGCGAATGCCACTCTTGAAGGAAACTCAAGGTCCCATGAGCCCCCACGCGTGGCCGATGT | 1024 |
| RBBP8 | NM_002894 | 10 | 18 | + | 21 | - | 0 | 37 | 1 | 0 | CGCGAATGCCCCTTCCAGACAGTGGTAGAGCTCATCACCAAGGGACGCGTGGCCGATGT | 1025 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| RBBP8 | NM_002894 | 10 | 18 | + | 56 | + | 0 | 37 | 1 | 0 | CGCGAATGCCAAATCACAAGAAACAGCCTTTG AGAATTACAAACGCTGGCGGATGT | 1026 |
| RBBP8 | NM_002894 | 10 | 18 | + | 91 | − | 0 | 37 | 1 | 0 | CGCGAATGCCTGCCCTTAATTACCTTAAACTATC TTCAGTATTTCACGCGTGGCGGATGT | 1027 |
| RB1 | NM_000321 | 9 | 13 | + | −31 | + | 0 | 37 | 1 | 0 | CGCGAATGCCAATGATCATGTTGTAACTTCATCT TTTTCAGTGACGCGTGGCGGATGT | 1028 |
| RB1 | NM_000321 | 9 | 13 | + | 4 | − | 0 | 37 | 1 | 0 | CGCGAATGCCCATAAAAGGTATAAAATTTTTGA AATAAACATTTTACGCGTGGCGGATGT | 1029 |
| RB1 | NM_000321 | 9 | 13 | + | 39 | + | 0 | 37 | 1 | 0 | CGCGAATGCCAATTCTCTTGGACTTGTAACATCT AATGGACTTCCACGCGTGGCGGATGT | 1030 |
| RB1 | NM_000321 | 9 | 13 | + | 74 | − | 0 | 37 | 1 | 0 | CGCGAATGCCTAATATTTTATTAAATTTCCTTTC AGATTACCTTACGCGTGGCGGATGT | 1031 |
| RET | NM_020630 | 5 | 10 | + | 0 | + | 0 | 37 | 1 | 0 | CGCGAATCCGACACCGTGTGCCACCGTGCG TGTCTTCGATGCACGCGTGGCGGATGT | 1032 |
| RET | NM_020630 | 5 | 10 | + | 35 | − | 0 | 37 | 1 | 0 | CGCGAATGCCGCCTCACCAGCTCCCCTGATGCA GGTACCACGTCTACGCGTGGCGGATGT | 1033 |
| RET | NM_020630 | 5 | 10 | + | 70 | + | 0 | 37 | 1 | 0 | CGCGAATGCCGGTACACAAGCACGCTGCTCCCC GGGGACACCTGACGCCTGGCGGATGT | 1034 |
| RET | NM_020630 | 5 | 10 | + | 105 | − | 0 | 37 | 1 | 0 | CGCGAATGCCTTGGGCCAGTGTTCCACCGGAA GGTCTGTGTGACGCGCGTGGCGGATGT | 1035 |
| RET | NM_020630 | 5 | 10 | + | 140 | + | 0 | 37 | 1 | 0 | CGCGAATGCCCCGAGACCTCGGTCCAGGCCAACG GCAGCTTCGTGCACGCCTGGCGGATGT | 1036 |
| RET | NM_020630 | 5 | 10 | + | 175 | − | 0 | 37 | 1 | 0 | CGCGAATGCCCAGCCCCTCTTACTATAGTCATG TACGGTCGCCACGCGTGGCGGATGT | 1037 |
| PKN1 | NM_002741 | 22 | 19 | + | 0 | + | 0 | 37 | 1 | 0 | CGCGAATGCCACTCTGGCTGGAAGCCCTGTT GGCCCGGCGCTTACGCGTGGCGGATGT | 1038 |
| PKN1 | NM_002741 | 22 | 19 | + | 35 | − | 0 | 37 | 1 | 0 | CGCGAATGCCTCGCGCCGGACAGCGTGGCACA AAGGGCGTGGCACGCGTGGCGGATGT | 1039 |
| PKN1 | NM_002741 | 22 | 19 | + | 70 | + | 0 | 37 | 1 | 0 | CGCGAATGCCCCGACGTCAGCAACTTCGACGAG GAGTTCACCGGGACGCGTGGCGGATGT | 1040 |
| PKN1 | NM_002741 | 22 | 19 | + | 105 | − | 0 | 37 | 1 | 0 | CGCGAATGCCCCGCGTCGGGGCGGGCTCAG TGTGGGGCCTCACGCGTGGCGGATGT | 1041 |
| PKN1 | NM_002741 | 22 | 19 | + | 140 | + | 0 | 37 | 1 | 0 | CGCGAATGCCGCCCCTCACCAGCCGCGGAGCAGG CAGCCTTCCGACGCGTGGCGGATGT | 1042 |
| PKN1 | NM_002741 | 22 | 19 | + | 171 | − | 3 | 37 | 1 | 0 | CGCGAATGCCGGCTAGCAGCCCCGGCCACGAA GTCGAAGTCCAGACAACGCGTGGCGGATGT | 1043 |
| PIK3CA | NM_006218 | 13 | 3 | + | −18 | + | 0 | 23 | 1 | 1 | CGCGAATGCCTTTTTGGAATACCTAGGTCCTA AAATATGAACAACGCGTGGCGGATGT | 1044 |
| PIK3CA | NM_006218 | 13 | 3 | + | 17 | − | 0 | 0 | 2 | 0 | CGCGAATGCCTCAGTAAAAATCTCACAAGCAAG TTATCCAAATATACGCGTGGCGGATGT | 1045 |
| PIK3CA | NM_006218 | 13 | 3 | + | 52 | + | 0 | 0 | 2 | 0 | CGCGAATGCCAGAAAGCATTGACTAATCAAAGG ATTGGGCACTTTACGCGTGGCGGATGT | 1046 |
| PIK3CA | NM_006218 | 13 | 3 | + | 87 | − | 0 | 0 | 2 | 0 | CGCGAATGCCGAAAATAATTAGACTTACTTTAA ATGCCAAAGAAACGCGTGGCGGATGT | 1047 |
| PDGFRA | NM_006206 | 3 | 4 | + | 0 | + | 0 | 37 | 1 | 0 | CGCGAATGCCGGCTGAGCCTAATCCTCTGCCAG CTTTCATTACCCACGCGTGGCGGATGT | 1048 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| PDGFRA | NM_006206 | 3 | 4 | + | 35 | - | 0 | 37 | 1 | 0 | CGCGAATGCCTGCACAACCTTTTCATTTTCATTT GAAGGATAGAACGCGTGGCGATGT | 1049 |
| PDGFRA | NM_006206 | 3 | 4 | + | 70 | + | 0 | 37 | 1 | 0 | CGCGAATGCCGCTGAATTCATCCTTTTCTCTGAG ATGCTTTGGGGACGCGTGGCGATGT | 1050 |
| PDGFRA | NM_006206 | 3 | 4 | + | 105 | - | 0 | 37 | 1 | 0 | CGCGAATGCCTTCAGACATGGGGTACTGCCAGC TCACTTCACTCTACGCGTGGCGATGT | 1051 |
| PDGFRA | NM_006206 | 3 | 4 | + | 140 | + | 0 | 37 | 1 | 0 | CGCGAATGCCGAAGAGAGCTCCGATGTGAAAT CAGAAATGCCAAGAACGCGTGGCGATGT | 1052 |
| PDGFRA | NM_006206 | 3 | 4 | + | 175 | - | 0 | 37 | 1 | 0 | CGCGAATGCCCTTCCAAGACCGTCACAAAAGG CCGCTGTTGTTTACGCGTGGCGATGT | 1053 |
| PDGFRA | NM_006206 | 3 | 4 | + | 210 | + | 0 | 37 | 1 | 0 | CGCGAATGCCTGAGCAGTGCCTCGGCGCCCAC ACAGGGTTGTACACGCGTGGCGATGT | 1054 |
| PDGFRA | NM_006206 | 3 | 4 | + | 245 | - | 0 | 37 | 1 | 0 | CGCGAATGCCTTCTCTTCTCTCGAGTGTGGTTG TAATAGCAAGTACGCGTGGCGATGT | 1055 |
| PDGFRA | NM_006206 | 3 | 4 | + | 280 | + | 0 | 37 | 1 | 0 | CGCGAATGCCTGAGCTTGAAGGCAGGCACATTT ACATCTATGTGCACGCGTGGCGATGT | 1056 |
| PDGFRA | NM_006206 | 3 | 4 | + | 315 | - | 0 | 37 | 1 | 0 | CGCGAATGCCGAAGCTTGGTCCTGGAGACCCAG CCAACTCACCTGACGCGTGGCGATGT | 1057 |
| EPHA7 | NM_004440 | 16 | 6 | - | -38 | + | 0 | 37 | 1 | 0 | CGCGAATGCCTTTCATGTAACATATGGAAATAC AACTTCTTTTTACGCGTGGCGATGT | 1058 |
| EPHA7 | NM_004440 | 16 | 6 | - | -3 | - | 0 | 37 | 1 | 0 | CGCGAATGCCTGTTTGTTGTGCTTTAGAATCCAG CAGTAGTACTGACGCGTGGCGATGT | 1059 |
| EPHA7 | NM_004440 | 16 | 6 | - | 32 | + | 0 | 37 | 1 | 0 | CGCGAATGCCGAGTTGGAGTGGATTTCCTCTCC ACCCAATGCGGTACGCGTGGCGATGT | 1060 |
| EPHA7 | NM_004440 | 16 | 6 | - | 67 | - | 0 | 37 | 1 | 0 | CGCGAATGCCTTTAAAAAGTGATATTTTATGA TGAAAAAACTTACGCGTGGCGATGT | 1061 |
| KSR2 | NM_173598 | 7 | 12 | - | 0 | + | 0 | 37 | 1 | 0 | CGCGAATGCCAATGAAGAGGTCATGATGAGGC CAAGAGTCAGAACGCGTGGCGATGT | 1062 |
| KSR2 | NM_173598 | 7 | 12 | - | 35 | - | 0 | 37 | 1 | 0 | CGCGAATGCCAGAGAGGACAGGTTCATCTCC TCGAAGTCATCCACGCGTGGCGATGT | 1063 |
| KSR2 | NM_173598 | 7 | 12 | - | 70 | + | 0 | 37 | 1 | 0 | CGCGAATGCCCGCCCGAGCTTCCACGCAAG GCCAGCCAGACCACGCGTGGCGATGT | 1064 |
| KSR2 | NM_173598 | 7 | 12 | - | 105 | - | 0 | 37 | 1 | 0 | CGCGAATGCCTCAAGGGGATGTCCCACTCCTG AAGGAAGATGCTACGCGTGGCGATGT | 1065 |
| KSR2 | NM_173598 | 7 | 12 | - | 140 | + | 0 | 37 | 1 | 0 | CGCGAATGCCGCAGCTGGAGATCGGCGAGCTCA TTGGAAAGGGCCACGCGTGGCGATGT | 1066 |
| KSR2 | NM_173598 | 7 | 12 | - | 175 | - | 0 | 37 | 1 | 0 | CGCGAATGCCGCCATGCCGCAGCCCGTGGTACA CTTGCCCAAAGCACGCGTGGCGATGT | 1067 |
| KSR2 | NM_173598 | 7 | 12 | - | 210 | + | 0 | 37 | 1 | 0 | CGCGAATGCCGAGGTGCCATCCGGCTGATTGA CATTGAGAGGGACGCGTGGCGATGT | 1068 |
| KSR2 | NM_173598 | 7 | 12 | - | 245 | - | 0 | 37 | 1 | 0 | CGCGAATGCCCCCTCCCCCTTGAAGGCCTTGAGC TGTCCTCGTTGACGCGTGGCGATGT | 1069 |
| KSR2 | NM_173598 | 7 | 12 | - | 280 | + | 0 | 37 | 1 | 0 | CGCGAATGCCTGATGGCCTACAGGCAGACACGG CATGAGAACGTGACGCGTGGCGATGT | 1070 |
| KSR2 | NM_173598 | 7 | 12 | - | 315 | - | 0 | 37 | 1 | 0 | CGCGAATGCCTGAGGCGGCTCATGCCAGGCACC CATGAAAAGCACACGCGGTGGCGATGT | 1071 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| KSR2 | NM_173598 | 7 | 12 | − | 350 | + | 0 | 37 | 1 | 0 | CGCGAATGCCCCTGGCCATCATCACCAGGTCAG TTCCACTGGGCACGCGTGGCGGATGT | 1072 |
| GUCY2F | NM_001522 | 9 | X | − | 0 | + | 0 | 37 | 1 | 0 | CGCGAATGCCAAATCATAAACAGACTTAAGAAG CCTCCTCTGTGACGCGTGGCGGATGT | 1073 |
| GUCY2F | NM_001522 | 9 | X | − | 35 | − | 0 | 37 | 1 | 0 | CGCGAATGCCGAGGGCATGCTCAGGAGGAA CTACTGGTCTGTAACGCGTGGCGGATGT | 1074 |
| GUCY2F | NM_001522 | 9 | X | − | 70 | + | 0 | 37 | 1 | 0 | CGCGAATGCCAGAATGTCTCCAGCTGATGAAGC AGTGCTGGCTGACGCGTGGCGGATGT | 1075 |
| GUCY2F | NM_001522 | 9 | X | − | 105 | − | 0 | 37 | 1 | 0 | CGCGAATGCCTATTTCATCAAAAGTTGTCGTTG TTCTGCAGCCTACGCGTGGCGGATGT | 1076 |
| GUCY2F | NM_001522 | 9 | X | − | 140 | + | 0 | 37 | 1 | 0 | CGCGAATGCCTTTAACCAGGTAAGGACTCTGAA TCTTATCATTGCACGCGTGGCGGATGT | 1077 |
| RBBP8 | NM_002894 | 6 | 18 | + | −36 | + | 0 | 37 | 1 | 0 | CGCGAATGCCTATATATTTGCCTTCTTTTTCAC AATGTTTTTAAACGCGTGGCGGATGT | 1078 |
| RBBP8 | NM_002894 | 6 | 18 | + | −1 | − | 0 | 37 | 1 | 0 | CGCGAATGCCTTATTTCTTCCTGTAGAGTATTC CTTTCATTCACACGCGTGGCGGATGT | 1079 |
| RBBP8 | NM_002894 | 6 | 18 | + | 34 | + | 0 | 37 | 1 | 0 | CGCGAATGCCAAAGCTTTCTGAACAACTCCAGC AGAAAATTGAGTACGCCTGGCGGATGT | 1080 |
| RBBP8 | NM_002894 | 6 | 18 | + | 69 | − | 0 | 37 | 1 | 0 | CGCGAATGCCATAAAATAAAATAACAAGGTTGG AGGAAAATACTTACGCGTGGCGGATGT | 1081 |
| RB1 | NM_000321 | 1 | 13 | + | −6 | + | 2 | 37 | 1 | 0 | CGCGAATGCCGGCGTCATGCCGCCAAAACCCC CCGAAAACGCACGCGTGGCGGATGT | 1082 |
| RB1 | NM_000321 | 1 | 13 | + | 33 | − | 35 | 37 | 1 | 0 | CGCGAATGCCGGTGCCCGGGGTTCCGCGGCGC AGCGCGCGGTACGCGTGGCGGATGT | 1083 |
| RB1 | NM_000321 | 1 | 13 | + | 72 | + | 8 | 37 | 1 | 0 | CGCGAATGCCCCCGCCCCCCTCCTGAGGAGGA CCCAGAGCAGAGAACGCGTGGCGGATGT | 1084 |
| RB1 | NM_000321 | 1 | 13 | + | 103 | − | 0 | 37 | 1 | 0 | CGCGAATGCCCCTGACGAGAGCAGGTCCTCCG GGCCGCTGTCCTACGCGTGGCGGATGT | 1085 |
| PDGFRA | NM_006206 | 14 | 4 | + | −14 | + | 0 | 37 | 1 | 0 | CGCGAATGCCTATTCTTTCAACACCACGCCA GATCCAGTGAAAACGCGTGGCGGATGT | 1086 |
| PDGFRA | NM_006206 | 14 | 4 | + | 21 | − | 0 | 37 | 1 | 0 | CGCGAATGCCAGTCATTATCTTCAGTTCAGACAT GAGAGCTTGTTACGCCGTGGCGGATGT | 1087 |
| PDGFRA | NM_006206 | 14 | 4 | + | 56 | + | 0 | 37 | 1 | 0 | CGCGAATGCCCACCTGGGGCCACATTTGAACAT TGTAAACTTGCTACGCGTGGCGGATGT | 1088 |
| PDGFRA | NM_006206 | 14 | 4 | + | 91 | − | 0 | 37 | 1 | 0 | CGCGAATGCCGGTCAGTGAGCCCACCTGACTTG GTGCAGGCTCCCACGCGTGGCGGATGT | 1089 |
| CHAF1A | NM_005483 | 5 | 19 | + | 0 | + | 0 | 37 | 1 | 0 | CGCGAATGCCGATCAGGAGGCGTCTGGGCAAGCA GCTCAAGTTACGACGCGTGGCGGATGT | 1090 |
| CHAF1A | NM_005483 | 5 | 19 | + | 35 | − | 0 | 37 | 1 | 0 | CGCGAATGCCCCTCTTTCAGCTTCTCCTTTTCTTC CCTTTCTGCAACGCGTGGCGGATGT | 1091 |
| CHAF1A | NM_005483 | 5 | 19 | + | 66 | + | 4 | 37 | 1 | 0 | CGCGAATGCCGAGGAGGCCAAGCGGGCCAAGG AGAGGCAAGAAACGCGTGGCGGATGT | 1092 |
| CHAF1A | NM_005483 | 5 | 19 | + | 105 | − | 35 | 37 | 1 | 0 | CGCGAATGCCCTCCTTTCCTTAAGCTCCTTC TCTTCCTCCTTACGCGTGGCGGATGT | 1093 |
| CHAF1A | NM_005483 | 5 | 19 | + | 144 | + | 31 | 37 | 1 | 0 | CCCGAATGCCGAGAAGCGGGAGGAAGGATGAGA AGGAGAAGGCGGAACGCGTGGCGGATGT | 1094 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| CHAF1A | NM_005483 | 5 | 19 | + | 175 | - | 0 | 37 | 1 | 0 | CGCGAATGCCCTTGCGCCGCTCCTCCTTGAGCCGCTGCTTCTCCGACGCGTGGCGGATGT | 1095 |
| CHAF1A | NM_005483 | 5 | 19 | + | 210 | + | 0 | 37 | 1 | 0 | CGCGAATGCCGAGACAGGAAGCCCTGGAGTGAGTGTCTTGAACGCGTGGCGGATGT | 1096 |
| NFKB1 | NM_003998 | 2 | 4 | + | -54 | + | 17 | 37 | 1 | 0 | CGCGAATGCCGTTCATTCTAGTGTTACAGTTTTGTTTGTTTTGTACGCGTGGCGGATGT | 1097 |
| NFKB1 | NM_003998 | 2 | 4 | + | -15 | - | 0 | 37 | 1 | 0 | CGCGAATGCCTATGGATCATCTTCTGCCATTCTGAAGCTGTGTATACGCGTGGCGGATGT | 1098 |
| NFKB1 | NM_003998 | 2 | 4 | + | 20 | + | 0 | 37 | 1 | 0 | CGCGAATGCCTTTGGGAAGGCCTGAACAAGTAAGTGTCATAATCTACGCGTGGCGGATGT | 1099 |
| NFKB1 | NM_003998 | 2 | 4 | + | 55 | - | 0 | 37 | 1 | 0 | CGCGAATGCCTGAAATATGAATATATTTAAATAAAGTTATCAGTGACGCGTGGCGGATGT | 1100 |
| RET | NM_020630 | 11 | 10 | + | 0 | + | 0 | 37 | 1 | 0 | CGCACGGTGATCACGCGTGGCGGATGTCGCGAATGCCATCCACTGTGCGACGAGCTGTGC | 1101 |
| RET | NM_020630 | 11 | 10 | + | 35 | - | 0 | 37 | 1 | 0 | CGCGAATGCCACCGAGACGATGAAGGAGAAGAGGACAGCGGCTGCACGCGTGGCGGATGT | 1102 |
| RET | NM_020630 | 11 | 10 | + | 70 | + | 0 | 37 | 1 | 0 | CGCGAATGCCGCGTCGTCTGCCTTCTGCATCCACTGCTACCACAACGCGTGGCGGATGT | 1103 |
| RET | NM_020630 | 11 | 10 | + | 105 | - | 0 | 37 | 1 | 0 | CGCGAATGCCCTCAGCTGAGGAGATGGGCTGTGGGCAAACTACGCGTGGCGGATGT | 1104 |
| RET | NM_020630 | 11 | 10 | + | 140 | + | 0 | 37 | 1 | 0 | CGCGAATGCCATGACCTTCCGGAGGCCCGCCAGGCCTTCCGGTACGCGTGGCGGATGT | 1105 |
| RET | NM_020630 | 11 | 10 | + | 175 | - | 0 | 37 | 1 | 0 | CGCGAATGCCGCGAGGGCCGGCGGGCACCGAAGAGGAGTAGCTGACGCGTGGCGGATGT | 1106 |
| RET | NM_020630 | 11 | 10 | + | 210 | + | 0 | 37 | 1 | 0 | CGCGAATGCCTGACTCCATGGAGAACCAGGTCTCCGTGATGCCACGCGTGGCGGATGT | 1107 |
| RET | NM_020630 | 11 | 10 | + | 245 | - | 0 | 37 | 1 | 0 | CGCGAATGCCCCCTGCCCCGCAGGGACCCTCACCAGGATCTTGAAACGCGTGGCGGATGT | 1108 |
| NFKB1 | NM_003998 | 15 | 4 | + | 0 | + | 0 | 37 | 1 | 0 | CGCGAATGCCATAACCTCTTTCTAGAGAAGGCTATGCAGCTTGCAACGCGTGGCGGATGT | 1109 |
| NFKB1 | NM_003998 | 15 | 4 | + | 35 | - | 0 | 37 | 1 | 0 | CGCGAATGCCACCGCGTAGTCAAAAGGCATTGGCATGCCTTTACGCGTGGCGGATGT | 1110 |
| NFKB1 | NM_003998 | 15 | 4 | + | 70 | + | 0 | 37 | 1 | 0 | CGCGAATGCCGACAGGAGACGTGAAGATGCTGCTGGCCGTCCAGCACGCGTGGCGGATGT | 1111 |
| NFKB1 | NM_003998 | 15 | 4 | + | 105 | - | 0 | 37 | 1 | 0 | CGCGAATGCCGTCCCATTCTCATCCTGCACAGCAGTGAGATGGCACGCGTGGCGGATGT | 1112 |
| NFKB1 | NM_003998 | 15 | 4 | + | 140 | + | 0 | 37 | 1 | 0 | CGCGAATGCCAGGTAAGTCAGAACTTTTGCATGATAGGTTGTCTTACGCGTGGCGGATGT | 1113 |
| NTRK3 | NM_001012338 | 16 | 15 | - | -34 | - | 0 | 37 | 1 | 0 | CGCGAATGCCAGCTCTGCTGATCCTCTTTTTCTCTCGTCTAGGACGCGTGGCGGATGT | 1114 |
| NTRK3 | NM_001012338 | 16 | 15 | - | 1 | + | 0 | 37 | 1 | 0 | CGCGAATGCCGGCTGAATGCTCCGAAGTCCTGAGTTCTTGATGGTACGCGTGGCGGATGT | 1115 |
| NTRK3 | NM_001012338 | 16 | 15 | - | 36 | + | 0 | 37 | 1 | 0 | CGCGAATGCCAGAGCCTTTGCCAAGAACCCCCATTTGCGTTATACGCGTGGCGGATGT | 1116 |
| NTRK3 | NM_001012338 | 16 | 15 | - | 71 | - | 0 | 37 | 1 | 0 | CGCGAATGCCGTGCCCCAATCCCTGCAGCCCAGCTCTACTCACAACGCGTGGCGGATGT | 1117 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| NFKB1 | NM_003998 | 9 | 4 | + | -18 | + | 0 | 37 | 1 | 0 | CGCGAATGCCTTTTCCCCTGTGAACAGAAGCC CCCAATGCATCCACGCGTGGCGCGATGT | 1118 |
| NFKB1 | NM_003998 | 9 | 4 | + | 17 | - | 0 | 37 | 1 | 0 | CGCGAATGCCCCAGCTGTCCTGTCCATTCTTACA ATTTCAAGTTACGCGTGGCCGATGT | 1119 |
| NFKB1 | NM_003998 | 9 | 4 | + | 52 | + | 0 | 37 | 1 | 0 | CGCGAATGCCATGTGTGACTGGAGGGAGGAA AATTATCTTCTTTACGCGTGGCCGGATGT | 1120 |
| NFKB1 | NM_003998 | 9 | 4 | + | 87 | - | 0 | 37 | 1 | 0 | CGCGAATGCCTCACAGAATGTATTTACCTTTCTG AACTTTGTCACACGCGTGGCGGATGT | 1121 |
| CENTG1 | NM_014770 | 13 | 12 | + | -2 | + | 0 | 37 | 1 | 0 | CGCGAATGCCAGACAGGATCAGTGCTTCCTCCC CTCGGGTGGTGACGCGTGGCGGATGT | 1122 |
| CENTG1 | NM_014770 | 13 | 12 | - | 33 | - | 0 | 37 | 1 | 0 | CGCGAATGCCCATGTCCCGCACAGAGCTCTGG CACGAGCATCTCACGCGTGGCGGATGT | 1123 |
| CENTG1 | NM_014770 | 13 | 12 | - | 68 | + | 0 | 37 | 1 | 0 | CGCGAATGCCAAACGCTCAGCTACTATGAGAC TTGTGCAACCTAACGCGTGGCGGATGT | 1124 |
| CENTG1 | NM_014770 | 13 | 12 | - | 103 | - | 0 | 37 | 1 | 0 | CGCGAATGCCCACCCTCCTGGAAGACCCGATCC ACATTGAGCCCAACGCGTGGCGGATGT | 1125 |
| EPHA4 | NM_004438 | 16 | 2 | - | 0 | + | 0 | 37 | 1 | 0 | CGCGAATGCCTGGAGGAAGTGAGTATCATGGA TGAAAAAATACACGCGTGGCCGATGT | 1126 |
| EPHA4 | NM_004438 | 16 | 2 | - | 35 | - | 0 | 37 | 1 | 0 | CGCGAATGCCCCATCACATTGCACACTTGGTAG GTTCGGATTGGTACGCGTGGCCGATGT | 1127 |
| EPHA4 | NM_004438 | 16 | 2 | - | 70 | + | 0 | 37 | 1 | 0 | CGCGAATGCCAACCAGCCAGAGAATAACTGGCTA CGAACTGATTGGACGCGTGGCCGATGT | 1128 |
| EPHA4 | NM_004438 | 16 | 2 | - | 105 | - | 0 | 37 | 1 | 0 | CGCGAATGCCTCAATATACACCCTCTGAGCCCC TTCTCGGGTGATACGCGTGGCCGATGT | 1129 |
| EPHA4 | NM_004438 | 16 | 2 | - | 140 | + | 0 | 37 | 1 | 0 | CGCGAATGCCGATTAAATTCACCTTGAGGGACT GCAATAGTCTTCACGCGTGGCCGATGT | 1130 |
| EPHA4 | NM_004438 | 16 | 2 | - | 175 | - | 0 | 37 | 1 | 0 | CGCGAATGCCGTTAAACGTCTCTTGCAAGTCC CCATGACCCCGACGCGTGGCCGATGT | 1131 |
| EPHA4 | NM_004438 | 16 | 2 | - | 210 | + | 0 | 37 | 1 | 0 | CGCGAATGCCTGTACTACTATGAATCAGACAA CGACAAAGAGCGACGCGTGGCCGATGT | 1132 |
| EPHA4 | NM_004438 | 16 | 2 | - | 245 | - | 0 | 37 | 1 | 0 | CGCGAATGCCTGTCAATTTGACAAACTGGTTCT CTCTGATGAAAACGCGTGGCCGATGT | 1133 |
| EPHA4 | NM_004438 | 16 | 2 | - | 280 | + | 0 | 37 | 1 | 0 | CGCGAATGCCCCATTGCTGCTGATGAGAGCTTC ACCCAAGTGGACACGCGTGGCCGATGT | 1134 |
| EPHA4 | NM_004438 | 16 | 2 | - | 315 | - | 0 | 37 | 1 | 0 | CGCGAATGCCATCTCGGTGTTCAGCTTCATGATT CTGTCACCAATACGCGTGGCCGATGT | 1135 |
| EPHA4 | NM_004438 | 16 | 2 | - | 350 | + | 0 | 37 | 1 | 0 | CGCGAATGCCCCGGGATGTAGGGCCATTAAGCA AAAAGGGGTTTTACGCGTGGCCGATGT | 1136 |
| EPHA4 | NM_004438 | 16 | 2 | - | 385 | - | 0 | 37 | 1 | 0 | CGCGAATGCCGGCGATGCAGGCCCCCACATCCT GAAAAGCCAGGTACGCGTGGCCGATGT | 1137 |
| EPHA4 | NM_004438 | 16 | 2 | - | 420 | + | 0 | 37 | 1 | 0 | CGCGAATGCCCTGGTATCAGTCCGTGTGTTCTAT AAAAGTGTCCACGCGTGGCCGATGT | 1138 |
| EPHA4 | NM_004438 | 16 | 2 | - | 455 | - | 0 | 37 | 1 | 0 | CGCGAATGCCTCAGGAAACTGGGCCAGATTG CGACTGTGAGTTACGCGTGGCCGATGT | 1139 |
| EPHA4 | NM_004438 | 16 | 2 | - | 490 | + | 0 | 37 | 1 | 0 | CGCGAATGCCCATCACAGGGGCTGATACGTCT TCCCTGGTGGAAACGCGTGGCCGATGT | 1140 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BwA score | BWA hit | # BWA mismatch | Sequence with add-ons | SEQ ID NO: |
|---|---|---|---|---|---|---|---|---|---|---|---|---|
| EPHA4 | NM_004438 | 16 | 2 | - | 525 | - | 0 | 37 | 1 | 0 | CGCGAATGCCTTCTCTTCTGAGTTGTTGACACAG GAGCCTCGAACACGCGTGGCGATGT | 1141 |
| EPHA4 | NM_004438 | 16 | 2 | - | 560 | + | 0 | 37 | 1 | 0 | CGCGAATGCCAGATGCCAAAATGTACTGTG GGGCAGATGCGACGCGTGGCGATGT | 1142 |
| EPHA4 | NM_004438 | 16 | 2 | - | 595 | - | 0 | 37 | 1 | 0 | CGCGAATGCCGTTGCATAGGCAGTTGCCAATGG GTACCAGCCATTACGCGTGGCGATGT | 1143 |
| EPHA4 | NM_004438 | 16 | 2 | - | 630 | + | 0 | 37 | 1 | 0 | CGCGAATGCCGCTGGGCATGAGGAGCGAGCG GAGAATGCCAAGACGCGTGGCGATGT | 1144 |
| CENTG1 | NM_014770 | 12 | 12 | - | -15 | - | 0 | 37 | 1 | 0 | CGCGAATGCCGTCAACTCCCTCAGTGCCCAG AAGGTGTGACCACGCGTGGCGATGT | 1145 |
| CENTG1 | NM_014770 | 12 | 12 | - | 20 | + | 0 | 37 | 1 | 0 | CGCGAATGCCTTGCAGGCAGCCAGAAGCTGTTG CTGCTTGCGCAAACGCGTGGCGATGT | 1146 |
| CENTG1 | NM_014770 | 12 | 12 | - | 55 | + | 0 | 37 | 1 | 0 | CGCGAATGCCGTCCTGCCCAGCTCCCCAAGCC ACTCAGCTGCATACGCGTGGCGATGT | 1147 |
| CENTG1 | NM_014770 | 12 | 12 | - | 90 | - | 0 | 37 | 1 | 0 | CGCGAATGCCGAAACCCCAACTCACCTGGCCAG CTACCGGAGTGGACGCGTGGCGATGT | 1148 |
| PKN1 | NM_002741 | 16 | 19 | + | 0 | + | 0 | 37 | 1 | 0 | CGCGAATGCCCCCTGATGTGTGAGAAGCCGATAT TGGCGGCAGTGAACGCGTGGCGATGT | 1149 |
| PKN1 | NM_002741 | 16 | 19 | + | 35 | - | 0 | 37 | 1 | 0 | CGCGAATGCCGAAGAGGTTCACCAGGAAGGGG TGTCCCGCACTGGACGCGTGGCGATGT | 1150 |
| PKN1 | NM_002741 | 16 | 19 | + | 70 | + | 0 | 37 | 1 | 0 | CGCGAATGCCGGCTGCTGTTTCCAGACACCGGACA CGTGTCGCTTCGTACGCGTGGCGATGT | 1151 |
| PKN1 | NM_002741 | 16 | 19 | + | 105 | - | 0 | 37 | 1 | 0 | CGCGAATGCCGCAGCATCAGGTTCCCACCGGCC GAGTACTCCATCACGCGTGGCGATGT | 1152 |
| PKN1 | NM_002741 | 16 | 19 | + | 140 | + | 0 | 37 | 1 | 0 | CGCGAATGCCACATCCACAGCGACGTGTTCTCT GAGCCCCGTGCCACGCGTGGCGATGT | 1153 |
| PKN1 | NM_002741 | 16 | 19 | + | 175 | - | 0 | 37 | 1 | 0 | CGCGAATGCCGAGGCAGGGGCCGGGCTGGGG TCCAGGCTCACATACGCGTGGCGATGT | 1154 |
| GUCY2F | NM_001522 | 8 | X | - | 0 | + | 0 | 37 | 1 | 0 | CGCGAATGCCTTTAAACTTTTAATAAAGGGAA GAAGACCAATATACGCGTGGCGATGT | 1155 |
| GUCY2F | NM_001522 | 8 | X | - | 35 | - | 0 | 37 | 1 | 0 | CGCGAATGCCAATATTGCTCCAACATCCGAAGC ATAGAATCAATAACGCGTGGCGATGT | 1156 |
| GUCY2F | NM_001522 | 8 | X | - | 70 | + | 0 | 37 | 1 | 0 | CGCGAATGCCCTAGCAACTTGGAAGATTTGATT CGGGAGCCGACTACGCGTGGCGATGT | 1157 |
| GUCY2F | NM_001522 | 8 | X | - | 105 | - | 0 | 37 | 1 | 0 | CGCGAATGCCTTTTCCGTTTCTGTTTTTCAATTT CCAGCTCTTCACGCGTGGCGATGT | 1158 |
| GUCY2F | NM_001522 | 8 | X | - | 140 | + | 0 | 37 | 1 | 0 | CGCGAATGCCGCTTCTAACACAGATGCTACCAC CGTATGTGAGAAACGCGTGGCGATGT | 1159 |
| RET | NM_020630 | 19 | 10 | + | 0 | - | 0 | 37 | 1 | 0 | CGCGAATGCCGACTACTTGGACCTTGCGGCGTC CACTCCATCTGAACGCGTGGCGATGT | 1160 |
| RET | NM_020630 | 19 | 10 | + | 35 | + | 0 | 37 | 1 | 0 | CGCGAATGCCCCCTCCTCTGAGAGGCCGTCGTCA TAAATCAGGGAGACGCGTGGCGATGT | 1161 |
| RET | NM_020630 | 19 | 10 | + | 70 | - | 0 | 37 | 1 | 0 | CGCGAATGCCAGACACCGCTGTGACTGTAAT AATGCCCCCTCACGCGTGGCGATGT | 1162 |
| RET | NM_020630 | 19 | 10 | + | 105 | - | 0 | 37 | 1 | 0 | CGCGAATGCCTTGTTTTCAATCCATGTGGAAGG GAGGGCTGAGGACGCGTGGCGATGT | 1163 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| RET | NM_020630 | 19 | 10 | + | 140 | + | 0 | 37 | 1 | 0 | CGCGAATGCCACTCTATGGTAGAATTTCCATGCATTTACTAGATACGCCTGGCCGATGT | 1164 |
| RET | NM_020630 | 19 | 10 | + | 175 | - | 0 | 37 | 1 | 0 | CGCGAATGCCAGGAAGGATAGTGCAAAGGGGACAGCCGTCTAGAACGCGTGGCCGATGT | 1165 |
| RB1 | NM_000321 | 12 | 13 | + | -26 | + | 0 | 37 | 1 | 0 | CGCGAATGCCCATTTCCTATTTTTATCCCCTCTAGGACTGTTATACGCCGTGGCCGATGT | 1166 |
| RB1 | NM_000321 | 12 | 13 | + | 9 | - | 0 | 37 | 1 | 0 | CGCGAATGCCAATTTAAAATCATCATTAATTGTTGGATAGTGTTCACGCCGTGGCCGATGT | 1167 |
| RB1 | NM_000321 | 12 | 13 | + | 44 | + | 0 | 37 | 1 | 0 | CGCGAATGCCCAGCAAGTGATCAACCTTCAGAAAATCTGATTTCACGCCGTGGCCGATGT | 1168 |
| RB1 | NM_000321 | 12 | 13 | + | 79 | - | 0 | 37 | 1 | 0 | CGCGAATGCCTAAATAATGTTTCATATATGGCTTACGTTAAAATAACGCGTGGCCGATGT | 1169 |
| GUCY2F | NM_001522 | 14 | X | - | -4 | + | 0 | 37 | 1 | 0 | CGCGAATGCCACAGAGAGGAAGTCGTGCCAGTGTAAGCTTCCAGAACGCGTGGCCGATGT | 1170 |
| GUCY2F | NM_001522 | 14 | X | - | 31 | - | 0 | 37 | 1 | 0 | CGCGAATGCCTCTTGGGACCTTCCCACTTTGGACCTCTGAGGTAAACGCGTGGCCGATGT | 1171 |
| GUCY2F | NM_001522 | 14 | X | - | 66 | + | 0 | 37 | 1 | 0 | CGCGAATGCCCCTCCTTTTCTTCAGGGAGTCTAACTCCAGTACACGCCGTGGCCGATGT | 1172 |
| GUCY2F | NM_001522 | 14 | X | - | 101 | - | 0 | 37 | 1 | 0 | CGCGAATGCCTTACCTCATAAATCGCTATGTTGGAGTTTTCATAGACGCCGTGGCCGATGT | 1173 |
| RET | NM_020975 | 20 | 10 | + | 0 | + | 0 | 37 | 1 | 0 | CGCGAATGCCCATGTCAGACCCGAACTGGCCTGGAGAGAGTCCTACGCCTGGCCGATGT | 1174 |
| RET | NM_020975 | 20 | 10 | + | 35 | - | 0 | 37 | 1 | 0 | CGCGAATGCCCCAGTGTTAGTGCCATCAGCTCTCGTAGTGTACACGCCGTGGCCGATGT | 1175 |
| RET | NM_020975 | 20 | 10 | + | 70 | + | 0 | 37 | 1 | 0 | CGCGAATGCCGTTTCCAAGATATCCAAATGATAGTGTATATGCTAACGCCGTGGCCGATGT | 1176 |
| RET | NM_020975 | 20 | 10 | + | 105 | + | 0 | 37 | 1 | 0 | CGCGAATGCCCATTAATTTGCCGCTGAGGGTGAAAGCATCCAGTACGCCGTGGCCGATGT | 1177 |
| RET | NM_020975 | 20 | 10 | + | 140 | + | 0 | 37 | 1 | 0 | CGCGAATGCCGACACGTTTGATAGTTAACATTTCTTTGTGAAAGGACGCCGTGGCCGATGT | 1178 |
| CHAF1A | NM_005483 | 6 | 19 | + | -40 | + | 0 | 37 | 1 | 0 | CGCGAATGCCAAGCAAGCAAAGAGTCGGCTGAAATGTCATTTGCTGTTACGCCGTGGCCGATGT | 1179 |
| CHAF1A | NM_005483 | 6 | 19 | + | -5 | - | 0 | 37 | 1 | 0 | CGCGAATGCCTCCTCTTTTTCCTTTTTCCTCAAGTTTAGCCCTGTGACCCGTGCGATGT | 1180 |
| CHAF1A | NM_005483 | 6 | 19 | + | 30 | + | 0 | 37 | 1 | 0 | CGCGAATGCCAGAAGAGAAACGGTTAAGAGAAGAAGAAGGTAGACGCCGTGGCCGATGT | 1181 |
| CHAF1A | NM_005483 | 6 | 19 | + | 65 | - | 0 | 37 | 1 | 0 | CGCGAATGCCACGGGCTGGACGGGGAAGCTCTGTGGGAAACACTACGCCGTGGCCGATGT | 1182 |
| KSR2 | NM_173598 | 14 | 12 | - | -28 | + | 0 | 37 | 1 | 0 | CGCGAATGCCTTGAACATTTCTGTCTCTTTTCCACAGGTTTTCACGCCGTGGCCGATGT | 1183 |
| KSR2 | NM_173598 | 14 | 12 | - | 7 | - | 0 | 37 | 1 | 0 | CGCGAATGCCCAGACTGTGCACGTCTGAGACATCCAGTCTGGTACGCCTGGCCGATGT | 1184 |
| KSR2 | NM_173598 | 14 | 12 | - | 42 | + | 0 | 37 | 1 | 0 | CGCGAATGCCTGGGAAGGGATGCTTTTTGGCCTCAAGTGTAAAACGCCGTGGCCGATGT | 1185 |
| KSR2 | NM_173598 | 14 | 12 | - | 77 | - | 0 | 37 | 1 | 0 | CGCGAATGCCAAAGTCACTGCAGGGCACAGTCACTTACTTGCAGTACGCCGTGGCCGATGT | 1186 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| EPHA7 | NM_004440 | 9 | 6 | − | −42 | + | 0 | 37 | 1 | 0 | CGCGAATGCCAAGTAAATGACTGAGATTGTCACAAATTTGCTTTACGCGTGGCCGGATGT | 1187 |
| EPHA7 | NM_004440 | 9 | 6 | − | −7 | − | 0 | 37 | 1 | 0 | CGCGAATGCCTTGGTCAGCTTTGCTATAACCACAGTGCCTTGAAGACGCGTGGCCGGATGT | 1188 |
| EPHA7 | NM_004440 | 9 | 6 | − | 28 | + | 0 | 37 | 1 | 0 | CGCGAATGCCGAAGGCGATGAAGAGCTTTACTTTCATTGTAAGTGACGCCGTGGCCGGATGT | 1189 |
| EPHA7 | NM_004440 | 9 | 6 | − | 63 | − | 0 | 37 | 1 | 0 | CGCGAATGCCTTAATAGGGGTACATCATAATAAAGAAAAGCCAAAACGCGTGGCCGGATGT | 1190 |
| RPS6KA1 | NM_002953 | 10 | 1 | + | −34 | + | 0 | 37 | 1 | 0 | CGCGAATGCCGATCAGAGCCTGAATAGATCCTTGTCCTCTGCAGTACGCGTGGCCGGATGT | 1191 |
| RPS6KA1 | NM_002953 | 10 | 1 | + | 1 | − | 0 | 37 | 1 | 0 | CGCGAATGCCCCCCTGGAAGGGCAGGGAGCCCGTCAGCATCTCAAACGCGTGGCCGGATGT | 1192 |
| RPS6KA1 | NM_002953 | 10 | 1 | + | 36 | + | 0 | 37 | 1 | 0 | CGCGAATGCCAAGGACCCGAAGGAGACCATGACACTGATTCTGAAACGCTGGCCGGATGT | 1193 |
| RPS6KA1 | NM_002953 | 10 | 1 | + | 71 | − | 0 | 37 | 1 | 0 | CGCGAATGCCGAGTCCATTGTTATCAGGGCAGGGCTGGGGCTTACACGCGTGGCCGGATGT | 1194 |
| EPHA3 | NM_005233 | 5 | 3 | + | 0 | + | 0 | 37 | 1 | 0 | CGCGAATGCCGACCTCCATCTTCACCAAGAAATGTTATCTCTAATACGCCTGGCCGGATGT | 1195 |
| EPHA3 | NM_005233 | 5 | 3 | + | 35 | − | 0 | 37 | 1 | 0 | CGCGAATGCCCAACTCCAGTCCAGGATAACTGAGGTCTCGTTTATACGCGTGGCCGGATGT | 1196 |
| EPHA3 | NM_005233 | 5 | 3 | + | 70 | + | 0 | 37 | 1 | 0 | CGCGAATGCCGCCCCTGACACAGGAGGCCGGAAAGATGTTACTTACGCCTGGCCGGATGT | 1197 |
| EPHA3 | NM_005233 | 5 | 3 | + | 105 | − | 0 | 37 | 1 | 0 | CGCGAATGCCTATATTCCACCCACATTTTTACATATGATGTGAACGCGTGGCCGGATGT | 1198 |
| EPHA3 | NM_005233 | 5 | 3 | + | 140 | + | 0 | 37 | 1 | 0 | CGCGAATGCCAAACAGTGAGCCATGCAGCCCAAATGTCCGCTTACGCGTGGCCGGATGT | 1199 |
| EPHA3 | NM_005233 | 5 | 3 | + | 175 | − | 0 | 37 | 1 | 0 | CGCGAATGCCCCGTGGTTGTGGTGAGTCCAAACTGTCGAGGGAGGACGCGTGGCCGGATGT | 1200 |
| EPHA3 | NM_005233 | 5 | 3 | + | 210 | + | 0 | 37 | 1 | 0 | CGCGAATGCCTGACAGTGACAGACCTTCTGGCACATACTAACTACACGCGTGGCCGGATGT | 1201 |
| EPHA3 | NM_005233 | 5 | 3 | + | 245 | − | 0 | 37 | 1 | 0 | CGCGAATGCCTCTGACACCCATTAACGGCATCAATCTCAAAGGTACGCGTGGCCGGATGT | 1202 |
| EPHA3 | NM_005233 | 5 | 3 | + | 280 | + | 0 | 37 | 1 | 0 | CGCGAATGCCGCTGAGCTCCCACCAAGACAGTTTGCTGCGTCAACGCGTGGCCGGATGT | 1203 |
| EPHA3 | NM_005233 | 5 | 3 | + | 315 | − | 0 | 37 | 1 | 0 | CGCGAATGCCTAGTATGTACTCACCAGCCTGATTAGTTGTGATGCACGCGTGGCCGGATGT | 1204 |
| RET | NM_020630 | 10 | 10 | + | −10 | + | 0 | 37 | 1 | 0 | CGCGAATGCCCCTGCCCTCCAGGGGCAGCATTGTTGGGGACACGAACGCGTGGCCGGATGT | 1205 |
| RET | NM_020630 | 10 | 10 | + | 25 | − | 0 | 37 | 1 | 0 | CGCGAATGCCCATAGCCAGCTTTAATCCCCGGGCTCCCAGGCACGCCGTGGCCGGATGT | 1206 |
| RET | NM_020630 | 10 | 10 | + | 60 | + | 0 | 37 | 1 | 0 | CGCGAATGCCGACCTGCAACTGCTTCCCTGAGGAGGAGAAGTGCACGCGTGGCCGGATGT | 1207 |
| RET | NM_020630 | 10 | 10 | + | 95 | − | 0 | 37 | 1 | 0 | CGCGAATGCCACCCACTCACCCTGATGTCTTCGGGCTCCAGAAACGCGTGGCCGGATGT | 1208 |
| NFKB1 | NM_003998 | 13 | 4 | + | −25 | + | 0 | 37 | 1 | 0 | CGCGAATGCCTCATTGTTTTACTTGCCGTTTCAGGCTATAGCTTACGCGTGGCCGGATGT | 1209 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|------|------------|------|------------|-------------|---------------------------|--------------|----------------------|-----------|---------|----------------|----------------------|------------|
| NFKB1 | NM_003998 | 13 | 4 | + | 10 | − | 0 | 37 | 1 | 0 | CGCGAATGCCTAATCCCACCATAAGTAGGAAAT CCATAGTGTGGGACGCCGTGGCCGATGT | 1210 |
| NFKB1 | NM_003998 | 13 | 4 | + | 45 | + | 0 | 37 | 1 | 0 | CGCGAATGCCCTTTCCATCCTGAACTACTAAAT CTAATGCCGACGCGTGGCCGATGT | 1211 |
| NFKB1 | NM_003998 | 13 | 4 | + | 80 | − | 0 | 37 | 1 | 0 | CGCGAATGCCGTATTAAGAACAAAGCATTACTT ACCATGCTTCATACGCCGTGGCCGATGT | 1212 |
| RB1 | NM_000321 | 18 | 13 | + | −10 | + | 0 | 37 | 1 | 0 | CGCGAATGCCTTTCATATAGGATTCACCTTTATT TGATCTTTATTAACGCCGTGGCCGATGT | 1213 |
| RB1 | NM_000321 | 18 | 13 | + | 25 | − | 0 | 37 | 1 | 0 | CGCGAATGCCGTGATCAGTTGGTCCTTCTCGGTC CTTTGATTGTTACGCGTGGCCGATGT | 1214 |
| RB1 | NM_000321 | 18 | 13 | + | 60 | + | 0 | 37 | 1 | 0 | CGCGAATGCCCTTGAATCTGCTTGTCCTCTAAT CTTCCTCTCCAACGCGTGGCCGATGT | 1215 |
| RB1 | NM_000321 | 18 | 13 | + | 95 | − | 0 | 37 | 1 | 0 | CGCGAATGCCATTTTGCTTACATATCTGCTGCAG TGTGATTATTCACGCGTGGCCGATGT | 1216 |
| GUCY2F | NM_001522 | 5 | X | − | −20 | + | 0 | 37 | 1 | 0 | CGCGAATGCCAACCCCTGATACTCTATAGGGC CGTTGTTGTCGACGCGTGGCCGATGT | 1217 |
| GUCY2F | NM_001522 | 5 | X | − | 15 | − | 0 | 37 | 1 | 0 | CGCGAATGCCCAAGCAGTATCTGGGCATGGTGA GGCCCACACTCACGCCGTGGCCGATGT | 1218 |
| GUCY2F | NM_001522 | 5 | X | − | 50 | + | 0 | 37 | 1 | 0 | CGCGAATGCCTTTGGAGACACTGTGAACAGC TTCTCGATGGAACGCCGTGGCCGATGT | 1219 |
| GUCY2F | NM_001522 | 5 | X | − | 85 | − | 0 | 37 | 1 | 0 | CGCGAATGCCATCTCTATTAGGTACTCACGTA AGCCTGTAGATACGCGTGGCCGATGT | 1220 |
| EPHA7 | NM_004440 | 5 | 6 | − | 0 | + | 0 | 37 | 1 | 0 | CGCGAATGCCAAACATGATGGGCAATTTACAGT CATTCAGTTAGTACGCCGTGGCCGATGT | 1221 |
| EPHA7 | NM_004440 | 5 | 6 | − | 35 | − | 0 | 37 | 1 | 0 | CGCGAATGCCATCTCATTCCAGCACAATTCCTC TCAGCATTCCTACGCGTGGCCGATGT | 1222 |
| EPHA7 | NM_004440 | 5 | 6 | − | 70 | + | 0 | 37 | 1 | 0 | CGCGAATGCCATTTGGCTGATATGGGATATGTT CACAGGACCTTACGCCGTGGCCGATGT | 1223 |
| EPHA7 | NM_004440 | 5 | 6 | − | 105 | − | 0 | 37 | 1 | 0 | CGCGAATGCCACAGAGATTGCTGTTGACAAGAAT ATTGCGAGCTGCACGCCGTGGCCGATGT | 1224 |
| EPHA7 | NM_004440 | 5 | 6 | − | 140 | + | 0 | 37 | 1 | 0 | CGCGAATGCCTTGTAAAGTGTCAGATTTTGGCCT GTCCCGAGTTAACGCGTGGCCGATGT | 1225 |
| EPHA7 | NM_004440 | 5 | 6 | − | 175 | − | 0 | 37 | 1 | 0 | CGCGAATGCCCAGTAGTTGTATAGACAGCTTCTG GATCATCCTTACGCCGTGGCCGATGT | 1226 |
| NFKB1 | NM_003998 | 24 | 4 | + | 210 | + | 0 | 37 | 1 | 0 | CGCGAATGCCGTAAGAAAAGTCATTTACTGCA CTTCTTCATATATACGCCGTGGCCGATGT | 1227 |
| NFKB1 | NM_003998 | 24 | 4 | + | 0 | − | 0 | 37 | 1 | 0 | CGCGAATGCCACGAGCTCCGAGACAGTGACAGT GTCTGCGACAGCACGCCGTGGCCGATGT | 1228 |
| NFKB1 | NM_003998 | 24 | 4 | + | 35 | + | 0 | 37 | 1 | 0 | CGCGAATGCCGTAAAGCTGAGTTTGCGAAGGA TGTCTCCACGCCACGCGTGGCCGATGT | 1229 |
| NFKB1 | NM_003998 | 24 | 4 | + | 70 | − | 0 | 37 | 1 | 0 | CGCGAATGCCCCTTCTGACCAGTGTGCCT CACTGCTAACTCACGCGTGGCCGATGT | 1230 |
| NFKB1 | NM_003998 | 24 | 4 | + | 105 | + | 0 | 37 | 1 | 0 | CGCGAATGCCCCTTCCTGCCCATAATCATGGG GCATTTGTTGACGCGTGGCCGATGT | 1231 |
| NFKB1 | NM_003998 | 24 | 4 | + | 140 | − | 0 | 37 | 1 | 0 | CGCGAATGCCCCCTCTAGAAGGCAAAATTTAGCC TGTCACAATTTACGCCGTGGCCGATGT | 1232 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| RBBP8 | NM_203292 | 18 | 18 | + | -18 | + | 0 | 37 | 1 | 0 | CGCGAATGCCTTATGATTTGTTTTAAGGTTATATTAAGGAAGATACGCGTGGCGATGT | 1233 |
| RBBP8 | NM_203292 | 18 | 18 | + | 17 | - | 0 | 37 | 1 | 0 | CGCGAATGCCGGCTGACGTCTTTTTGACGAGGACAAGGATCAAGACGCCGTGGCGATGT | 1234 |
| RBBP8 | NM_203292 | 18 | 18 | + | 52 | + | 0 | 37 | 1 | 0 | CGCGAATGCCTTACAACGCAATATTTTCTCCAAAAGGCAAGGAGCACGCGTGGCGATGT | 1235 |
| RBBP8 | NM_203292 | 18 | 18 | + | 87 | - | 0 | 37 | 1 | 0 | CGCGAATGCCATCCTTCTGTTTCTGTTTCAACGTCTATGTCTTCTACGCGTGGCGATGT | 1236 |
| EPHA4 | NM_004438 | 2 | 2 | - | -12 | + | 0 | 37 | 1 | 0 | CGCGAATGCCCCCTATGTACAGGGACCTGGCAAGAATTGTATCAACGCGTGGCGATGT | 1237 |
| EPHA4 | NM_004438 | 2 | 2 | - | 23 | - | 0 | 37 | 1 | 0 | CGCGAATGCCACTGCTCAAAATCTTATTCTGGTGCGTGATGCTGACGCGTGGCGATGT | 1238 |
| EPHA4 | NM_004438 | 2 | 2 | - | 58 | + | 0 | 37 | 1 | 0 | CGCGAATGCCGTCCAGGCAATGCAACCCAAATGCAGCAGATGCAACGCGTGGCGATGT | 1239 |
| EPHA4 | NM_004438 | 2 | 2 | - | 93 | - | 0 | 37 | 1 | 0 | CGCGAATGCCATTCAGTACTGGCTCAGACGGGAACCATTCTGCCGACGCGTGGCGATGT | 1240 |
| RPS6KA1 | NM_002953 | 6 | 1 | + | 0 | + | 0 | 37 | 1 | 0 | CGCGAATGCCTACGTGACCGCGTCCGGACCAAGATGGAGAGACACGCGTGGCGATGT | 1241 |
| RPS6KA1 | NM_002953 | 6 | 1 | + | 35 | - | 0 | 37 | 1 | 0 | CGCGAATGCCTTCACCACGAATGGTGATTTACATCAGCCAGGATACGCGTGGCGATGT | 1242 |
| RPS6KA1 | NM_002953 | 6 | 1 | + | 70 | + | 0 | 37 | 1 | 0 | CGCGAATGCCGTCGCTGCACTATGGTAAAGCTTCTGGCCCTGCCTGAGACGCGTGGCGATGT | 1243 |
| RPS6KA1 | NM_002953 | 6 | 1 | + | 105 | - | 0 | 37 | 1 | 0 | CGCGAATGCCCCACAGGCAAGGCGAAGGATGGGTGGGTAGGAGACGCGTGGCGATGT | 1244 |
| RPS6KA1 | NM_002953 | 6 | 1 | + | 140 | + | 0 | 37 | 1 | 0 | CGCGAATGCCTCTGTACACTGTCCACCGCCTGCCTGGCTCCCTACGCGTGGCGATGT | 1245 |
| RPS6KA1 | NM_002953 | 6 | 1 | + | 175 | - | 0 | 37 | 1 | 0 | CGCGAATGCCGGCCCTTATGATCTTGCTTCTCCGGCCCTGGCTCCCTACGCGTGGCGATGT | 1246 |
| RPS6KA1 | NM_002953 | 6 | 1 | + | 210 | + | 0 | 37 | 1 | 0 | CGCGAATGCCGCCCGACTCTACCATTGCCTTTCTCCCTCTTCCCACGCGTGGCGATGT | 1247 |
| RPS6KA1 | NM_002953 | 6 | 1 | + | 245 | - | 0 | 37 | 1 | 0 | CGCGAATGCCGAATGAGATAGAGCTTGCCCTCGGTCTGGAAGGCTACGCGTGGCGATGT | 1248 |
| RPS6KA1 | NM_002953 | 6 | 1 | + | 280 | + | 0 | 37 | 1 | 0 | CGCGAATGCCTGACTTCCTGCCTGGGTGGGACCTCTTCACCCGGACGCGTGGCGATGT | 1249 |
| RPS6KA1 | NM_002953 | 6 | 1 | + | 315 | - | 0 | 37 | 1 | 0 | CGCGAATGCCTCTGGCAGTAGATGTCAGCTCACCTCTTTTGAGACGCGTGGCGATGT | 1250 |
| NTRK3 | NM_001007156 | 1 | 15 | - | -6 | + | 2 | 37 | 1 | 0 | CGCGAATGCCTTATAGGTTTCAGAGAAATTATGTTGAATCAATAACGCGTGGCGATGT | 1251 |
| NTRK3 | NM_001007156 | 1 | 15 | - | 25 | - | 0 | 37 | 1 | 0 | CGCGAATGCCGTTAAGAGGCTTGGAATGTCCGGGAAGGCTTATTACGCGTGGCGATGT | 1252 |
| NTRK3 | NM_001007156 | 1 | 15 | - | 60 | + | 0 | 37 | 1 | 0 | CGCGAATGCCATGGCATCTATGTTGAGGATGTCAATGTTTATTTCACGCGTGGCGATGT | 1253 |
| NTRK3 | NM_001007156 | 1 | 15 | - | 95 | - | 0 | 37 | 1 | 0 | CGCGAATGCCAAAAGGAGTTTTTAAAAGCCATGACGTCCTTTGCTACGCGTGGCGATGT | 1254 |
| RET | NM_020630 | 9 | 10 | + | -14 | + | 0 | 37 | 1 | 0 | CGCGAATGCCTGTCCTGTGCAGGGATCACCAGGAACTTCTCCAACGCGTGGCGATGT | 1255 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| RET | NM_020630 | 9 | 10 | + | 21 | - | 0 | 37 | 1 | 0 | CGCGAATGCCGCCGTCCGGGCAGGTCTTGGTGC TGGGAGAGCAGGACGCCTGGCGGATGT | 1256 |
| RET | NM_020630 | 9 | 10 | + | 56 | + | 0 | 37 | 1 | 0 | CGCGAATGCCCACTGCCGATGTTGTGGAGACCCA AGACATCAACATACGCGGCGGATGT | 1257 |
| RET | NM_020630 | 9 | 10 | + | 91 | - | 0 | 37 | 1 | 0 | CGCGAATGCCTTAAACCCTGCTTACGGAGGCAG TCCTGAGGGCAAACGCGTGGCGGATGT | 1258 |
| NTRK3 | NM_001012338 | 3 | 15 | - | -49 | + | 35 | 37 | 1 | 0 | CGCGAATGCCTTTCTAAGTTTTCTTCTAATATTA TTATTGTTTTGACGCGTGGCGGATGT | 1259 |
| NTRK3 | NM_001012338 | 3 | 15 | - | -14 | - | 35 | 37 | 1 | 0 | CGCGAATGCCATTTCCAGATGGATTAAAGAGCT AAACATAAAAAAACGCGTGGCGGATGT | 1260 |
| NTRK3 | NM_001012338 | 3 | 15 | - | 21 | + | 35 | 37 | 1 | 0 | CGCGAATGCCGATTTTTGTATATGGTGTGAGGT AGGTATCTAAGCACGCGTGGCGGATGT | 1261 |
| NTRK3 | NM_001012338 | 3 | 15 | - | 60 | - | 32 | 37 | 1 | 0 | CGCGAATGCCAAAGTGTTGGGACAATGAACTAT TCATTAAAAAAAACGCTGGCGGATGT | 1262 |
| EPHB1 | NM_004441 | 9 | 3 | + | -38 | + | 0 | 37 | 1 | 0 | CGCGAATGCCTGCCCCTGTGGCTGAGAGAGCCCC TCTTTTTATCCAACGCGTGGCGGATGT | 1263 |
| EPHB1 | NM_004441 | 9 | 3 | + | -3 | - | 0 | 37 | 1 | 0 | CGCGAATGCCTGTACACAGCCTCTTTGCTATAA GCCCGTTTCCTGACGCGTGGCGGATGT | 1264 |
| EPHB1 | NM_004441 | 9 | 3 | + | 32 | + | 0 | 37 | 1 | 0 | CGCGAATGCCGCGATAAGCTCCAGCATTACAGC ACAGGCCGAGGTACGCGTGGCGGATGT | 1265 |
| EPHB1 | NM_004441 | 9 | 3 | + | 67 | - | 0 | 37 | 1 | 0 | CGCGAATGCCGTGGGGGTCAGACACCCGGTCTC TGCTTTCTACTTACGCGTGGCGGATGT | 1266 |
| PIK3CA | NM_006218 | 12 | 3 | + | 0 | + | 0 | 37 | 1 | 0 | CGCGAATGCCCATGTATTGCTTGGTAAAAGATTG GCCTCCAATCAAACGCGTGGCGGATGT | 1267 |
| PIK3CA | NM_006218 | 12 | 3 | + | 35 | - | 0 | 37 | 2 | 0 | CGCGAATGCCAATTACAGTCCAGAAGTTCCATA GCCTGTTCAGTGTACGCGTGGCGGATGT | 1268 |
| PIK3CA | NM_006218 | 12 | 3 | + | 70 | + | 0 | 37 | 2 | 0 | CGCGAATGCCACCCAGATCCTATGGTTCGAGGT TTTGCTGTTCGGACGCGTGGCGGATGT | 1269 |
| PIK3CA | NM_006218 | 12 | 3 | + | 103 | - | 0 | 37 | 1 | 0 | CGCGAATGCCAAGTTTGTCATCTGTTAAATATTT TTCCAAGCACCACGCGTGGCGGATGT | 1270 |
| PALB2 | NM_024675 | 5 | 16 | - | 136 | + | 5 | 0 | 2 | 0 | CGCGAATGCCTTTTCTCAGTATTTAATTCAGCTAG TACAGGTAAAAACGCGTGGCGGATGT | 1271 |
| PALB2 | NM_024675 | 5 | 16 | - | 0 | + | 0 | 37 | 1 | 0 | CGCGAATGCCGGCATTGTTTTGTTCCTCTGATGA TGAAAGTGAAAACGCGTGGCGGATGT | 1272 |
| PALB2 | NM_024675 | 5 | 16 | - | 35 | - | 0 | 37 | 1 | 0 | CGCGAATGCCAGCTTTTATATTTCCAGACTTCAG TAGTACTTGCTACGCGTGGCGGATGT | 1273 |
| PALB2 | NM_024675 | 5 | 16 | - | 70 | + | 0 | 37 | 1 | 0 | CGCGAATGCCGTGCTTGGCCTGCCTGACAAAGAGAG GCTAGTTAGTAGACGCGTGGCGGATGT | 1274 |
| PALB2 | NM_024675 | 5 | 16 | - | 105 | - | 0 | 37 | 1 | 0 | CGCGAATGCCGACTTCTACTTGTTGATCAGAA AGGGTCCACTGACGCGTGGCGGATGT | 1275 |
| PALB2 | NM_024675 | 5 | 16 | - | 140 | + | 0 | 37 | 1 | 0 | CGCGAATGCCTTGCAGTTTGCAGAAGATGGAGGG TAAGAAAGCATACGCGTGGCGGATGT | 1276 |
| RPS6KA1 | NM_002953 | 18 | 1 | + | 0 | + | 0 | 37 | 1 | 0 | CGCGAATGCCGTTGCACAGGGACCTGAAGCC CAGCAACATCCTACGCGTGGCGGATGT | 1277 |
| RPS6KA1 | NM_002953 | 18 | 1 | + | 35 | - | 0 | 37 | 1 | 0 | CGCGAATGCCCAGGCACTCCGGATTCCCGGAC TCGTCCATACACGCGGTGGCGGATGT | 1278 |

TABLE 4-continued

Representative subset (2170) of a total of 1,148,286 Capture Probes Designed for Exon Capture of 25,341 Human Genes

| Gene | Transcript | Chromosome | Exon | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| RPS6KA1 | NM_002953 | 1 | 18 | + | 70 | + | 0 | 37 | 1 | 0 | CGCGAATGCCGCATCTGTGACTTTGGTTTTGCCAAACAGCTGCGGACGCGTGGCGGATGT | 1279 |
| RPS6KA1 | NM_002953 | 1 | 18 | + | 105 | - | 0 | 37 | 1 | 0 | CGCGAATGCCGTGTAGCAAGGTGTCATGAGGAGCCCATTCTCAGCACGCCGTGGCGGATGT | 1280 |
| RPS6KA1 | NM_002953 | 1 | 18 | + | 140 | + | 0 | 37 | 1 | 0 | CGCGAATGCCAGCCAACTTTGTGGCGCCTGAGGTGAGTGCCCAGACGCCGTGGCGGATGT | 1281 |
| PDGFRA | NM_006206 | 4 | 17 | + | -12 | - | 0 | 37 | 1 | 0 | CGCGAATGCCTCTTTCTGCAGACTCAGAAGTCAAAAACCCTTACGCGTGGCGGATGT | 1282 |
| PDGFRA | NM_006206 | 4 | 17 | + | 23 | + | 0 | 37 | 1 | 0 | CGCGAATGCCTCCAATAAAGTAAGGCCTTCTGAGTTATCATCTGAACGCGTGGCGGATGT | 1283 |
| PDGFRA | NM_006206 | 4 | 17 | + | 58 | - | 0 | 37 | 1 | 0 | CGCGAATGCCTTTGTTGAGCTTCACCTATCAAGTTGCCCGAGGAAACGCGTGGCGGATGT | 1284 |
| PDGFRA | NM_006206 | 4 | 17 | + | 93 | + | 0 | 37 | 1 | 0 | CGCGAATGCCCCTTGAACTTACATTTTTTGAAGCCAAAACTCCAACGCGTGGCGGATGT | 1285 |
| PALB2 | NM_024675 | 16 | 10 | - | 0 | + | 0 | 37 | 1 | 0 | CGCGAATGCCAACCTAAAAATAAAATATGTGTTTATGACAAGTTAACGCGTGGCGGATGT | 1286 |
| PALB2 | NM_024675 | 16 | 10 | - | 35 | - | 0 | 37 | 1 | 0 | CGCGAATGCCTCTCCAGTTTCTTCATCAAGATGGGTTTTGATGTGACGCGTGGCGGATGT | 1287 |
| PALB2 | NM_024675 | 16 | 10 | - | 70 | + | 0 | 37 | 1 | 0 | CGCGAATGCCAAAGACATCTATCACACTTGATGTTGGGCCTGAGTACGCGTGGCGGATGT | 1288 |
| PALB2 | NM_024675 | 16 | 10 | - | 105 | - | 0 | 37 | 1 | 0 | CGCGAATGCCAGTAATCCTCCTGGGCCATCTCCAGGGTTAAAGACGCCGTGGCGGATGT | 1289 |
| PALB2 | NM_024675 | 16 | 10 | - | 140 | + | 0 | 37 | 1 | 0 | CGCGAATGCCATACAAAGAACAGATGACACCCAAGAACATTTTCCACGCCGTGGCGGATGT | 1290 |
| PALB2 | NM_024675 | 16 | 10 | - | 175 | - | 0 | 37 | 1 | 0 | CGCGAATGCCGCTTTTGCTCACCACTAGGGTCACTGACCCTGTGGACGCCGTGGCGGATGT | 1291 |
| PALB2 | NM_024675 | 16 | 10 | - | 210 | + | 0 | 37 | 1 | 0 | CGCGAATGCCAGAAGCTGCCAAGCAGAAGAAAGAAGCAGCAGAAGACGCCGTGGCGGATGT | 1292 |
| PALB2 | NM_024675 | 16 | 10 | - | 245 | - | 0 | 37 | 1 | 0 | CGCGAATGCCAAGACACAGTCTCTCCTGTGAAATAAAATGTCCTACGCGTGGCGGATGT | 1293 |
| PALB2 | NM_024675 | 16 | 10 | - | 280 | + | 0 | 37 | 1 | 0 | CGCGAATGCCTGCACTGATTCACTCAGATTGTCTGGAAAAGACACGCCGTGGCGGATGT | 1294 |
| PALB2 | NM_024675 | 16 | 10 | - | 315 | - | 0 | 37 | 1 | 0 | CGCGAATGCCAGGATTTTTGCTACTGATTTCTTCCTGTTCCTTTAACGCGTGGCGGATGT | 1295 |
| PALB2 | NM_024675 | 16 | 10 | - | 350 | + | 0 | 37 | 1 | 0 | CGCGAATGCCGCTAGATCACCAGTAACTGAAATAAGAACTCACCTTACGCCGTGGCGGATGT | 1296 |
| PALB2 | NM_024675 | 16 | 10 | - | 385 | - | 0 | 37 | 1 | 0 | CGCGAATGCCCTGGAGAATCTGGAAGTTCAGATTTAAGACTTAAAACGCGTGGCGGATGT | 1297 |
| PALB2 | NM_024675 | 16 | 10 | - | 420 | + | 0 | 37 | 1 | 0 | CGCGAATGCCAACCAGTTACAGAAATTAATGAAGACAGTGTATTAACGCCGTGGCGGATGT | 1298 |
| PALB2 | NM_024675 | 16 | 10 | - | 455 | - | 0 | 37 | 1 | 0 | CGCGAATGCCTCAACACCTTTTCTGTTGGGCAGTTGGTGAATACGCGTGGCGGATGT | 1299 |
| PALB2 | NM_024675 | 16 | 10 | - | 490 | + | 0 | 37 | 1 | 0 | CGCGAATGCCTACATTCCTAAGAAAGACCTAATTTCACCAGGGCAACGCGTGGCGGATGT | 1300 |
| PALB2 | NM_024675 | 16 | 10 | - | 525 | - | 0 | 37 | 1 | 0 | CGCGAATGCCACCGCTATCTGATAGAGTCTGTAAAGGAACTGTAGACGCGTGGCGGATGT | 1301 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| PALB2 | NM_024675 | 10 | 16 | - | 559 | + | 0 | 37 | 1 | 0 | CGCGAATGCCTAGTAGTCAGCACCTTGAACACA TTCCTCCTAAAGACGCGTGGCCGGATGT | 1302 |
| PALB2 | NM_024675 | 10 | 16 | - | 595 | - | 0 | 37 | 1 | 0 | CGCGAATGCCTGTTTTTTAGGTCGTGAGTAGTAA GTTCACTGCTAACGCGTGGCCGGATGT | 1303 |
| PALB2 | NM_024675 | 10 | 16 | - | 630 | + | 0 | 37 | 1 | 0 | CGCGAATGCCTTAGATTTACTTCACCTGTAAGTT TGGAGGCACAAACGCGTGGCCGGATGT | 1304 |
| PALB2 | NM_024675 | 10 | 16 | - | 665 | - | 0 | 37 | 1 | 0 | CGCGAATGCCAGGAGGTTATCTGTAGAGACAGT CATTTTTTGCCACGCGTGGCCGGATGT | 1305 |
| PALB2 | NM_024675 | 10 | 16 | - | 700 | + | 0 | 37 | 1 | 0 | CGCGAATGCCTGTAAATAAAGCTATAAGTAAAA GTGGCCAACTGCACGCGTGGCCGGATGT | 1306 |
| PALB2 | NM_024675 | 10 | 16 | - | 735 | - | 0 | 37 | 1 | 0 | CGCGAATGCCACATGAAATATTTGCCTCTAAAT TAGAACTTGTGGACGCGTGGCCGGATGT | 1307 |
| PALB2 | NM_024675 | 10 | 16 | - | 770 | + | 0 | 37 | 1 | 0 | CGCGAATGCCTCTCTAAATGAACTCACCTACAA TAACTTACCAGCACGCGTGGCCGGATGT | 1308 |
| PALB2 | NM_024675 | 10 | 16 | - | 805 | - | 0 | 37 | 1 | 0 | CGCGAATGCCTTTGATTTGTTCTTTTAAGTTTTG GTTTTCATTTACGCGTGGCCGGATGT | 1309 |
| PALB2 | NM_024675 | 10 | 16 | - | 840 | + | 0 | 37 | 1 | 0 | CGCGAATGCCCAGAGAAATCTTTAAAATCTCCC AGTGACACTCTTACGCGTGGCCGGATGT | 1310 |
| PALB2 | NM_024675 | 10 | 16 | - | 875 | - | 0 | 37 | 1 | 0 | CGCGAATGCCATCTCACTTTCCTGAAGATTTCA TTCCTGCCATCACGCGTGGCCGGATGT | 1311 |
| PALB2 | NM_024675 | 10 | 16 | - | 910 | + | 0 | 37 | 1 | 0 | CGCGAATGCCTCTAAGTCAACCTAAGAGTCTTA GCCTGAAGCAAACGCGTGGCCGGATGT | 1312 |
| PALB2 | NM_024675 | 10 | 16 | - | 945 | - | 0 | 37 | 1 | 0 | CGCGAATGCCTGTGCCAAGAAATGTTTTCTGCAG AAAGAGGAGGACGCGTGGCCGGATGT | 1313 |
| PALB2 | NM_024675 | 10 | 16 | - | 980 | + | 0 | 37 | 1 | 0 | CGCGAATGCCGTGCCTGAAGGCCTTCTGTTTCT GCAGAATATTAACGCGTGGCCGGATGT | 1314 |
| PALB2 | NM_024675 | 10 | 16 | - | 1015 | - | 0 | 37 | 1 | 0 | CGCGAATGCCTCTGGCAATTGGACATGCTTCGT GTTGTTCTAACAACGCGTGGCCGGATGT | 1315 |
| PALB2 | NM_024675 | 10 | 16 | - | 1050 | + | 0 | 37 | 1 | 0 | CGCGAATGCCGGAAAGTAGCCGTGGAGGCTGTC ATTCAGAGTCATACGCGTGGCCGGATGT | 1316 |
| PALB2 | NM_024675 | 10 | 16 | - | 1085 | - | 0 | 37 | 1 | 0 | CGCGAATGCCTTTTATTTTAAACCCTTTTTTCT TGACATCCAAACGCGTGGCCGGATGT | 1317 |
| PALB2 | NM_024675 | 10 | 16 | - | 1120 | + | 0 | 37 | 1 | 0 | CGCGAATGCCTAAGGATGCAAGTAAAAATTTAA ACCTTTTCCAATGACGCGTGGCCGGATGT | 1318 |
| PALB2 | NM_024675 | 10 | 16 | - | 1155 | - | 0 | 37 | 1 | 0 | CGCGAATGCCGCCAGACATCCTAATTTCACTTTG GTCAGTTTCCTACGCGTGGCCGGATGT | 1319 |
| PALB2 | NM_024675 | 10 | 16 | - | 1190 | + | 0 | 37 | 1 | 0 | CGCGAATGCCACATGCACAGGACAACCAAGTTC AAGAACCTCTCAACGCGTGGCCGGATGT | 1320 |
| PALB2 | NM_024675 | 10 | 16 | - | 1225 | - | 0 | 37 | 1 | 0 | CGCGAATGCCCGGAGCTGACTTTAGTTAAT GAGAGAGATTTCACGCGTGGCCGGATGT | 1321 |
| PALB2 | NM_024675 | 10 | 16 | - | 1260 | + | 0 | 37 | 1 | 0 | CGCGAATGCCCTGGCCCACTGAAGATAATGAC TTGTCTAGGAAGACGCGTGGCCGGATGT | 1322 |
| PALB2 | NM_024675 | 10 | 16 | - | 1295 | - | 0 | 37 | 1 | 0 | CGCGAATGCCCCTGTGTATCTTCTACCAGGTGCT TGGGCAACTGCACGCGTGGCCGGATGT | 1323 |
| PALB2 | NM_024675 | 10 | 16 | - | 1330 | + | 0 | 37 | 1 | 0 | CGCGAATGCCAAAAAGAAAATCAGCCTGCACCC CAGCATCAGATCACGCGTGGCCGGATGT | 1324 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| PALB2 | NM_024675 | 10 | 16 | - | 1365 | - | 0 | 37 | 1 | CGCGAATGCCCGACAGGCTAGAAGTTGGCAAAAGTGGTTCACAATACGCGTGGCGGATGT | 1325 |
| PALB2 | NM_024675 | 10 | 16 | - | 1400 | + | 0 | 37 | 1 | CGCGAATGCCATTGTTAACAGGTCCAAGGAAGAAGTCACCTCACACGCGTGGCCGGATGT | 1326 |
| PALB2 | NM_024675 | 10 | 16 | - | 1435 | - | 0 | 37 | 1 | CGCGAATGCCTCCACTTGAATAAATAATTTTTCGTGCTGATATTTGACGCGTGGCGGATGT | 1327 |
| PALB2 | NM_024675 | 10 | 16 | + | 1466 | + | 11 | 37 | 1 | CGCGAATGCCGTGAAAGTAAATCAAGATGTGTTTGATGATGACGCGTGGCGGATGT | 1328 |
| RB1 | NM_000321 | 8 | 13 | + | 0 | + | 0 | 37 | 1 | CGCGAATGCCAAACAGCTGTTATACCATTAATGGTTCACCTGAACGCGTGGCGGATGT | 1329 |
| RB1 | NM_000321 | 8 | 13 | + | 35 | - | 0 | 37 | 1 | CGCGAATGCCATCCGTCACTCCTGTTCTGACCTCGCCTGGGTGTACGCGTGGCGGATGT | 1330 |
| RB1 | NM_000321 | 8 | 13 | + | 70 | + | 0 | 37 | 1 | CGCGAATGCCAGCAAACAACTAGAAATGATACAAGAATTATTGACGCGTGGCGGATGT | 1331 |
| RB1 | NM_000321 | 8 | 13 | - | 105 | - | 0 | 37 | 1 | CGCGAATGCCATCTATATTACATTCATGTTCTTTACAGAGAACTTACGCGTGGCGGATGT | 1332 |
| RB1 | NM_000321 | 8 | 13 | + | 140 | + | 0 | 37 | 1 | CGCGAATGCCGAGTAATTTAACTTCATGATTTCTTTAAAACAGTACGCGTGGCGGATGT | 1333 |
| RPS6KA1 | NM_002953 | 16 | 1 | + | 0 | + | 0 | 37 | 1 | CGCGAATGCCCAACTCCATGGGAAGAACCTGGTTTTAGTGACGACGCGTGGCGGATGT | 1334 |
| RPS6KA1 | NM_002953 | 16 | 1 | + | 35 | - | 0 | 37 | 1 | CGCGAATGCCAGAGACGCCACACCAATTGTCTCCTTTACCACGTAGACGCGTGGCGGATGT | 1335 |
| RPS6KA1 | NM_002953 | 16 | 1 | + | 70 | + | 0 | 37 | 1 | CGCGAATGCCACTCTGAGTGCAAGCGCTGTGTCCACAAGGCCACCACGCGTGGCGGATGT | 1336 |
| RPS6KA1 | NM_002953 | 16 | 1 | - | 105 | - | 0 | 37 | 1 | CGCGAATGCCGTCAGGAGGCCCACCTTGACAGCATACTCCATGTTACGCGTGGCGGATGT | 1337 |
| RPS6KA1 | NM_002953 | 16 | 1 | + | 140 | + | 0 | 37 | 1 | CGCGAATGCCCACGTCTCGGCCAAGGCTGCTGGGTTGGGGCAGGACGCGTGGCGGATGT | 1338 |
| RPS6KA1 | NM_002953 | 16 | 1 | + | 175 | - | 0 | 37 | 1 | CGCGAATGCCGAGCTCAGGCACCATCCCTCCCCACCAGACGGGAACGCGTGGCGGATGT | 1339 |
| RPS6KA1 | NM_002953 | 16 | 1 | + | 210 | + | 0 | 37 | 1 | CGCGAATGCCTGCAGATGTATGAAAGGTGTGTGGCCGAGACCTCCACGCGTGGCGGATGT | 1340 |
| RPS6KA1 | NM_002953 | 16 | 1 | + | 245 | - | 0 | 37 | 1 | CGCGAATGCCGGGTCCAGGGTCTTTTCTGGCCATGGAGCAGGCCAACGCGTGGCGGATGT | 1341 |
| RPS6KA1 | NM_002953 | 16 | 1 | + | 280 | + | 0 | 37 | 1 | CGCGAATGCCTGTCACCCTGACACTGCCACATGCACCCCTTTCTACGCGTGGCGGATGT | 1342 |
| RPS6KA1 | NM_002953 | 16 | 1 | + | 315 | - | 0 | 37 | 1 | CGCGAATGCCCTGAAGGATCCCGCCTTGCTCTTTATCAATGACCTTGAACGCGTGGCGGATGT | 1343 |
| RPS6KA1 | NM_002953 | 16 | 1 | + | 350 | + | 0 | 37 | 1 | CGCGAATGCCCCCCCACTCCACATCTTTCAGAGTTATGGCCAGCACGCGTGGCGGATGT | 1344 |
| RPS6KA1 | NM_002953 | 16 | 1 | + | 385 | - | 0 | 37 | 1 | CGCGAATGCCCTGCCTCGGCTTGGTCTCGGCCTGGATGATGTTGGGACGCGTGGCGGATGT | 1345 |
| EPHB1 | NM_004441 | 1 | 3 | + | -41 | + | 0 | 37 | 1 | CGCGAATGCCAGGAGCAGTAGTAGATAATCCAGCGGGCCCGTCGGACGCGTGGCCGGATGT | 1346 |
| EPHB1 | NM_004441 | 1 | 3 | + | -6 | - | 0 | 37 | 1 | CGCCATGCCGGACGCGTGGCCGATGTGGCCATGCCGGACGCGTGGCCGGATGT | 1347 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BwA score | # BWA BWA hit mismatch | Sequence with add-ons | SEQ ID NO: |
|---|---|---|---|---|---|---|---|---|---|---|---|
| EPHB1 | NM_004441 | 1 | 3 | + | 29 | + | 0 | 37 | 1 0 | CGCGAATGCCCCTGGCATCCGCAGTGGCTGCGA TGGAAGGTAACGACGCGTGGCGGATGT | 1348 |
| EPHB1 | NM_004441 | 1 | 3 | + | 64 | – | 0 | 37 | 1 0 | CGCGAATGCCCCGGCACCAGCAGCCAACTTGCT CCTGGAGGGTAACGCGTGGCGGATGT | 1349 |
| PALB2 | NM_024675 | 1 | 16 | – | 0 | + | 0 | 37 | 1 0 | CGCGAATGCCGTTCCTGGAAGGTGACGTGAAAG ATCACTGTGCAGACGCCGTGGCGGATGT | 1350 |
| PALB2 | NM_024675 | 1 | 16 | – | 35 | – | 0 | 37 | 1 0 | CGCGAATGCCCCAAATGCAATTGTTCCAGAAG TCAAGATTGCTGACGCGTGGCGGATGT | 1351 |
| PALB2 | NM_024675 | 1 | 16 | – | 70 | + | 0 | 37 | 1 0 | CGCGAATGCCGACTTACTTCTCCGTCAGTGTACT GCCCTCTCCCACGCGTGGCGGATGT | 1352 |
| PALB2 | NM_024675 | 1 | 16 | – | 105 | – | 0 | 37 | 1 0 | CGCGAATGCCATTTCACAAAAGACCAATGTTGG TCAAGACAGGTACGCGTGGCGGATGT | 1353 |
| PALB2 | NM_024675 | 1 | 16 | – | 140 | + | 0 | 37 | 1 0 | CGCGAATGCCGGTCGGGTACAGACTCTCATTTG CTGGCTGACAAACGCGTGGCGGATGT | 1354 |
| PALB2 | NM_024675 | 1 | 16 | – | 175 | – | 0 | 37 | 1 0 | CGCGAATGCCTATGAATAGTGGTATACAAATAT ATTTCCATCTTTTACGCGTGGCGGATGT | 1355 |
| PALB2 | NM_024675 | 1 | 16 | – | 210 | + | 0 | 37 | 1 0 | CGCGAATGCCAGTTAGGTAAGTAAAGTGAAAACACA ATTTTCTGATAACGCCTGGCGGATGT | 1356 |
| CENTG1 | NM_014770 | 6 | 12 | – | –6 | + | 0 | 37 | 1 0 | CGCGAATGCCCCTAAGACTGTACCCCATCTGGA GACCTGAGCCCCACGCGTGGCGGATGT | 1357 |
| CENTG1 | NM_014770 | 6 | 12 | – | 29 | + | 0 | 37 | 1 0 | CGCGAATGCCTTCACCATGGAGGACGAAGGAGGG GTTCCCGACTCAGACGCGTGGCGGATGT | 1358 |
| CENTG1 | NM_014770 | 6 | 12 | – | 64 | + | 0 | 37 | 1 0 | CGCGAATGCCGAAGCAGGAGGAGGAGAAAATTG ACAACACCATCCAACGCGTGGCGGATGT | 1359 |
| CENTG1 | NM_014770 | 6 | 12 | – | 99 | – | 0 | 37 | 1 0 | CGCGAATGCCCTCACCTTCAGCCTGCCCAGCCG AGCCTTCAGTCTACGCGTGGCGGATGT | 1360 |
| EPHA7 | NM_004440 | 11 | 6 | – | 0 | + | 0 | 37 | 1 0 | CGCGAATGCCGATCAAAGGGACGGACCTACTC AACAGTAAAAACACGCGTGGCGGATGT | 1361 |
| EPHA7 | NM_004440 | 11 | 6 | – | 35 | – | 0 | 37 | 1 0 | CGCGAATGCCGTTTCAGATTATTAATGAGGCT GAAGTAGACTTGACGCGTGGCGGATGT | 1362 |
| EPHA7 | NM_004440 | 11 | 6 | – | 70 | + | 0 | 37 | 1 0 | CGCGAATGCCCAGGAACAGTGTATGTTTTCCAG ATTCGGGCTTTTACGCGTGGCGGATGT | 1363 |
| EPHA7 | NM_004440 | 11 | 6 | – | 105 | – | 0 | 37 | 1 0 | CGCGAATGCCAGTCTGGGACTGTAATTTCCATA ACCAGCACCAGTACGCGTGGCGGATGT | 1364 |
| EPHA7 | NM_004440 | 11 | 6 | – | 140 | + | 0 | 37 | 1 0 | CGCGAATGCCTGATGTTGCTACACTAGGAGAAG CTACAGGTAAAACGCGTGGCGGATGT | 1365 |
| EPHA7 | NM_004440 | 11 | 6 | – | 175 | – | 0 | 37 | 1 0 | CGCGAATGCCGGAATCCAAACCAAAGGCATAAT TACCTTCAAACACGCGTGGCGGATGT | 1366 |
| RB1 | NM_000321 | 5 | 13 | + | –50 | + | 0 | 37 | 1 0 | CGCGAATGCCCTTCTAAATTACGAAAAATGTT AAAAGTCATAAACGCGTGGCGGATGT | 1367 |
| RB1 | NM_000321 | 5 | 13 | + | –15 | – | 0 | 37 | 1 0 | CGCGAATGCCAATATATAAGTTCACATGTCCTG AAAGAAAAACACGCGTGGCGGATGT | 1368 |
| RB1 | NM_000321 | 5 | 13 | + | 20 | + | 0 | 37 | 1 0 | CGCGAATGCCGACACAACCCAGCCAGTTCGTAA GTAGTTCACAGACGCGTGGCGGATGT | 1369 |
| RB1 | NM_000321 | 5 | 13 | + | 55 | – | 0 | 37 | 1 0 | CGCGAATGCCCATAAAAATCTTTTTTTAAGTG AAAAATAACATACGCGTGGCGGATGT | 1370 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| EPHA4 | NM_004438 | 4 | 2 | − | 0 | + | 0 | 37 | 1 | CGCGAATGCCGTGATTAAAGCCATTGAGGAAGG CTATCGGTTACCACGCGTGGCCGATGT | 1371 |
| EPHA4 | NM_004438 | 4 | 2 | − | 35 | − | 0 | 37 | 1 | CGCGAATGCCGCTGGTGGAGCCAATGGGGCAG TCCATTGAGGACGCGTGGCCGATGT | 1372 |
| EPHA4 | NM_004438 | 4 | 2 | − | 70 | + | 0 | 37 | 1 | CGCGAATGCCTGATGCTAGACTGCTGGCAGAAG GAGAGGAGCGACACGCGTGGCCGATGT | 1373 |
| EPHA4 | NM_004438 | 4 | 2 | − | 105 | − | 0 | 37 | 1 | CGCGAATGCCTCCAACATGTTGACAATCTGCCC AAATTTAGGCCTACGCGTGGCCGATGT | 1374 |
| EPHA4 | NM_004438 | 4 | 2 | − | 140 | + | 0 | 37 | 1 | CGCGAATGCCCAAACTCATCCGCAACCCCAACA GCTTGAAGAGGAACGCGTGGCCGATGT | 1375 |
| EPHA4 | NM_004438 | 4 | 2 | − | 175 | − | 0 | 37 | 1 | CGCGAATGCCAGTAAGCATGGCTGACCTGGAGC TCTCCGTCCTGACGCGTGGCCGATGT | 1376 |
| EPHA7 | NM_004440 | 1 | 6 | − | −12 | + | 0 | 37 | 1 | CGCGAATGCCTGTCTTTTTCAGGGATGTGATGA GTTTAGGGATCAACGCGTGGCCGATGT | 1377 |
| EPHA7 | NM_004440 | 1 | 6 | − | 23 | − | 0 | 37 | 1 | CGCGAATGCCGCTGCTCATGATTTTCTTTTGATG ACCAACCAGTGACGCGTGGCCGATGT | 1378 |
| EPHA7 | NM_004440 | 1 | 6 | − | 58 | + | 0 | 37 | 1 | CGCGAATGCCATTCAGACTATGAGAGACACAAT GCTACATTTACAACGCGTGGCCGATGT | 1379 |
| EPHA7 | NM_004440 | 1 | 6 | − | 93 | − | 0 | 37 | 1 | CGCGAATGCCGGAGAAATGCATATCACACTTGA ATGCCAGTTCCAACGCGTGGCCGATGT | 1380 |
| RPS6KA1 | NM_002953 | 11 | 1 | + | −26 | + | 0 | 37 | 1 | CGCGAATGCCTTGATGAGTCCCGGGGCTGTTT CAGGGCGAAGCTACGCGTGGCCGATGT | 1381 |
| RPS6KA1 | NM_002953 | 11 | 1 | + | 9 | − | 0 | 37 | 1 | CGCGAATGCCTCTGGGCTTCAGTGCTCAGAAAC TGGGGCATGCCTACGCGTGGCCGATGT | 1382 |
| RPS6KA1 | NM_002953 | 11 | 1 | + | 44 | + | 0 | 37 | 1 | CGCGAATGCCGCCTCTTCGGGCCCTGTTCAAG CGGAATCCTGCCACGCGTGGCCGATGT | 1383 |
| RPS6KA1 | NM_002953 | 11 | 1 | + | 79 | − | 0 | 37 | 1 | CGCGAATGCCCCTCCCTGAGCTGGGCTGCTT ACCGAGCCGGTTACGCGTGGCCGATGT | 1384 |
| EPHB1 | NM_004441 | 2 | 3 | + | −38 | + | 0 | 37 | 1 | CGCGAATGCCCTTGTTTTTGTTTATTCGTTTTTCT TTTTAATCTAACGCGTGGCCGATGT | 1385 |
| EPHB1 | NM_004441 | 2 | 3 | + | −3 | − | 0 | 37 | 1 | CGCGAATGCCTGCAGTAGCCGTTCTGGTGTCCA TTAACGTTTCTGACGCGTGGCCGATGT | 1386 |
| EPHB1 | NM_004441 | 2 | 3 | + | 32 | + | 0 | 37 | 1 | CGCGAATGCCGAGCTGGGCTGGACGGCCAATCC TGCGTCCGGGTACGCGTGGCCGATGT | 1387 |
| EPHB1 | NM_004441 | 2 | 3 | + | 67 | − | 0 | 37 | 1 | CGCGAATGCCCATAGCAGGACTGAAAGACGAAT GGTTTGATACTCACGCGTGGCCGATGT | 1388 |
| PDGFRA | NM_006206 | 19 | 4 | + | −14 | + | 0 | 37 | 1 | CGCGAATGCCCTCTTCCTTGCAGACCTTTCTGC CCGTGAAGTGGACGCGTGGCCGATGT | 1389 |
| PDGFRA | NM_006206 | 19 | 4 | + | 21 | − | 0 | 37 | 1 | CGCGAATGCCGTGTAGAGGTTGTCAAAGATGCT CTCAGGAGCCATACGCGTGGCCGATGT | 1390 |
| PDGFRA | NM_006206 | 19 | 4 | + | 56 | + | 0 | 37 | 1 | CGCGAATGCCCACACTGAGTGATGTCTGGTCTT ATGGCATTTCGCACGCGTGGCCGATGT | 1391 |
| PDGFRA | NM_006206 | 19 | 4 | + | 91 | − | 0 | 37 | 1 | CGCGAATGCCTCAGGCCCATACCAAGGGAAA AGATCTCCAGAACGCGTGGCCGATGT | 1392 |
| CENTG1 | NM_014770 | 5 | 12 | − | 0 | + | 0 | 37 | 1 | CGCGAATGCCAGGAAACTTTGAGTTCCTGATC GTGTCCAGCACGACGCGTGGCCGATGT | 1393 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit mismatch | Sequence with add-ons | SEQ ID NO: |
|---|---|---|---|---|---|---|---|---|---|---|---|
| CENTG1 | NM_014770 | 5 | 12 | - | 35 | - | 0 | 37 | 1 | 0 | CGCGAATGCCTCAAAACTGGCTGCCTCAAAGTG CCACGTCTGACCACGCGTGGCGCGATGT | 1394 |
| CENTG1 | NM_014770 | 5 | 12 | - | 70 | + | 0 | 37 | 1 | 0 | CGCGAATGCCGGAGCGGATGCCTGGGTCCAGG CATCGAGAGTCACGCGTGGCGCGATGT | 1395 |
| CENTG1 | NM_014770 | 5 | 12 | - | 105 | - | 0 | 37 | 1 | 0 | CGCGAATGCCGCTGCTTCACAGCATTGCAGAC TGCTAGGATCTACGCGTGGCGCGATGT | 1396 |
| CENTG1 | NM_014770 | 5 | 12 | - | 140 | + | 0 | 37 | 1 | 0 | CGCGAATGCCAAGGTCAAGGTAAGAGTTTGAGG TGGAGTGAGGAACGCGTGGCGCGATGT | 1397 |
| CENTG1 | NM_014770 | 5 | 12 | - | 175 | - | 0 | 37 | 1 | 0 | CGCGAATGCCTGGCCGTCAGCACCAGGGTCAGT TCCTGCGGCCAGACGCGTGGCGCGATGT | 1398 |
| CENTG1 | NM_014770 | 5 | 12 | - | 210 | + | 0 | 37 | 1 | 0 | CGCGAATGCCTTGGCAACGACACGGCCGAAGTC GTGTGAGGAGAGCGCGTGGCGCGATGT | 1399 |
| CENTG1 | NM_014770 | 5 | 12 | - | 245 | - | 0 | 37 | 1 | 0 | CGCGAATGCCCTCCAAGCCCCACCTCCTTCTCAG ACACCCTGCTACGCGTGGCGCGATGT | 1400 |
| CENTG1 | NM_014770 | 5 | 12 | - | 280 | + | 0 | 37 | 1 | 0 | CGCGAATGCCCAGAGTCAGTGCCAACCCAAAC CCTCTCTGCAGCACGCGTGGCGCGATGT | 1401 |
| CENTG1 | NM_014770 | 5 | 12 | - | 315 | - | 0 | 37 | 1 | 0 | CGCGAATGCCGATGGCCACGCGCTCGCTTTGGC TGTCTGTGCGAACGCGTGGCGCGATGT | 1402 |
| CENTG1 | NM_014770 | 5 | 12 | - | 350 | + | 0 | 37 | 1 | 0 | CGCGAATGCCCAGGCGATCCGAACGCAAGG GGAATTCAATCTGACGCGTGGCGCGATGT | 1403 |
| CENTG1 | NM_014770 | 5 | 12 | - | 385 | - | 0 | 37 | 1 | 0 | CGCGAATGCCCCCTCCTGCACTCACTGGGGCC CCGCAGTCCACGACGCGTGGCGCGATGT | 1404 |
| CENTG1 | NM_014770 | 5 | 12 | - | 420 | + | 0 | 37 | 1 | 0 | CGCGAATGCCAGCGAGGGGCTAGGGAGTGT AGTGAATGCCGACGCGTGGCGCGATGT | 1405 |
| CENTG1 | NM_014770 | 5 | 12 | - | 455 | - | 0 | 37 | 1 | 0 | CGCGAATGCCGTAGAGGTCGGCTCCAGCCGGG CAGCACAGGCACACGCGTGGCGCGATGT | 1406 |
| CENTG1 | NM_014770 | 5 | 12 | - | 490 | + | 0 | 37 | 1 | 0 | CGCGAATGCCGTCTTCCGCAGACCCCACGTG GGCCAGCTTGAAACGCGTGGCGCGATGT | 1407 |
| CENTG1 | NM_014770 | 5 | 12 | - | 525 | - | 0 | 37 | 1 | 0 | CGCGAATGCCTGCCAGAACACTCGATGCAGATG AGGGCGCCCAGGACGCGTGGCGCGATGT | 1408 |
| CENTG1 | NM_014770 | 5 | 12 | - | 560 | + | 0 | 37 | 1 | 0 | CGCGAATGCCTCCACCGCCAACCTGGGCACACAC CTGTCCCCGCGTTACGCGTGGCGCGATGT | 1409 |
| CENTG1 | NM_014770 | 5 | 12 | - | 595 | - | 0 | 37 | 1 | 0 | CGCGAATGCCAGCTCCCGTGGCCAGTCGTCCAA GTCCAGCGAGCGACGCGTGGCGCGATGT | 1410 |
| CENTG1 | NM_014770 | 5 | 12 | - | 633 | + | 0 | 37 | 1 | 0 | CGCGAATGCCCCTGGTCGTGACGGCTATTGGCA ACGACACGGCCACGCGTGGCGCGATGT | 1411 |
| CENTG1 | NM_014770 | 5 | 12 | - | 665 | - | 0 | 37 | 1 | 0 | CGCGAATGCCCACGCCTCGGCTGTCGCTTTCCC ACACGCGGTTGACGCGTGGCGCGATGT | 1412 |
| CENTG1 | NM_014770 | 5 | 12 | - | 700 | + | 0 | 37 | 1 | 0 | CGCGAATGCCGCCAAGCCCTCGCGGGACTCTTC GCGGTAAGCGTGACGCGTGGCGCGATGT | 1413 |
| CENTG1 | NM_014770 | 5 | 12 | - | 735 | - | 0 | 37 | 1 | 0 | CGCGAATGCCACACCCTCAGCAACCCTCCCCC GCTCTGTTCCCTACGCGTGGCGCGATGT | 1414 |
| CENTG1 | NM_014770 | 5 | 12 | - | 770 | + | 0 | 37 | 1 | 0 | CGCGAATGCCGGAACCTGAGACGGTCCGTGG GTAGGGCAGAACGCGTGGCGCGATGT | 1415 |
| CENTG1 | NM_014770 | 5 | 12 | - | 805 | - | 0 | 37 | 1 | 0 | CGCGAATGCCAACGAAAAGGCTCTAGGGACC CCAGCCAGGACACGCGTGGCGCGATGT | 1416 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| CENTG1 | NM_014770 | 5 | 12 | - | 840 | + | 0 | 37 | 1 | 0 | CGCGAATGCCATCCCTGGTCTTGCAGGGAGAG CCGAGTCGTGACGCCTGGCCGATGT | 1417 |
| CENTG1 | NM_014770 | 5 | 12 | - | 875 | - | 0 | 37 | 1 | 0 | CGCGAATGCCCAGGAACAGTAGCTGCTCGTA CTTGGCGCGAATACGCGTGGCCGATGT | 1418 |
| CENTG1 | NM_014770 | 5 | 12 | - | 910 | + | 0 | 37 | 1 | 0 | CGCGAATGCCGCGTGAGCACCTGGAGGAGC CCTGGGCCGCCACGCGTGGCCGATGT | 1419 |
| CENTG1 | NM_014770 | 5 | 12 | - | 945 | - | 0 | 37 | 1 | 0 | CGCGAATGCCAGCCACGTCCTGGGCCTGCACGG CGCCCACAGCTACGCGTGGCCGATGT | 1420 |
| CENTG1 | NM_014770 | 5 | 12 | - | 980 | + | 0 | 37 | 1 | 0 | CGCGAATGCCACCGTTCTCCTGCTTTTGGCCCAT GCGCGACACGGACGCGTGGCCGATGT | 1421 |
| CENTG1 | NM_014770 | 5 | 12 | - | 1015 | - | 0 | 37 | 1 | 0 | CGCGAATGCCCGCAGCTGTGGGTCCTCTACGCTG GTGTGAGCGCACGCGTGGCCGATGT | 1422 |
| CENTG1 | NM_014770 | 5 | 12 | - | 1050 | + | 0 | 37 | 1 | 0 | CGCGAATGCCGCTCCCCACTCCACCTGGCCGCC GAGCTCGCCCACACGCGTGGCCGATGT | 1423 |
| CENTG1 | NM_014770 | 5 | 12 | - | 1085 | - | 0 | 37 | 1 | 0 | CGCGAATGCCTCACGTACCCACAGCAGCAGTTG CGTGATGACGACACGCGTGGCCGATGT | 1424 |
| CENTG1 | NM_014770 | 5 | 12 | - | 1120 | + | 0 | 37 | 1 | 0 | CGCGAATGCCGCTGGGGGAGGAAAGGGGGTC TTTGAGGCTTCATACGCGTGGCCGATGT | 1425 |
| CENTG1 | NM_014770 | 5 | 12 | - | 1155 | - | 0 | 37 | 1 | 0 | CGCGAATGCCAATTTCGGGCTTTCCCGCGCCAG GCGTTTTCCGAGACGCGTGGCCGATGT | 1426 |
| CENTG1 | NM_014770 | 5 | 12 | - | 1190 | + | 0 | 37 | 1 | 0 | CGCGAATGCCCCCAGAGGACCCGGAAGTAG GCTTGGGCCATGTGACGCGTGGCCGATGT | 1427 |
| CENTG1 | NM_014770 | 5 | 12 | - | 1225 | - | 0 | 37 | 1 | 0 | CGCGAATGCCGTCCCAGGGCCCCACACCCGG CGCCGCCTCCCCACGCGTGGCCGATGT | 1428 |
| CENTG1 | NM_014770 | 5 | 12 | - | 1260 | + | 0 | 37 | 1 | 0 | CGCGAATGCCGGCGGTCACGCGGCCGTTTCCG CCCTCTAGTACGACGCGTGGCCGATGT | 1429 |
| CENTG1 | NM_014770 | 5 | 12 | - | 1295 | - | 0 | 37 | 1 | 0 | CGCGAATGCCGGCCGCTTGGGCGTCACGGGCCG CCACGTCCGGCACGCGTGGCCGATGT | 1430 |
| CENTG1 | NM_014770 | 5 | 12 | - | 1330 | + | 0 | 37 | 1 | 0 | CGCGAATGCCACGGCGTGTTTACGCCCGCCA GGCTGGAAGCCAACGCGTGGCCGATGT | 1431 |
| CENTG1 | NM_014770 | 5 | 12 | - | 1365 | - | 0 | 37 | 1 | 0 | CGCGAATGCCGGCAGCCGTGCTGGAGAAGGATG TCGGCGCACAGCACGCGTGGCCGATGT | 1432 |
| CENTG1 | NM_014770 | 5 | 12 | - | 1400 | + | 0 | 37 | 1 | 0 | CGCGAATGCCCGGGTGAGGGCGGCCAGCGCGGC CACCACGCCAGCGCCGTGGCCGATGT | 1433 |
| CENTG1 | NM_014770 | 5 | 12 | - | 1435 | - | 0 | 37 | 1 | 0 | CGCGAATGCCCTGGGCGTGGCGTGATGCTGGG CGTGGTGCCGCCACGCGTGGCCGATGT | 1434 |
| CENTG1 | NM_014770 | 5 | 12 | - | 1470 | + | 0 | 37 | 1 | 0 | CGCGAATGCCGGCAACTATACCAGCAGCGCCG CTAGCGTGGCCGCACGCGTGGCCGATGT | 1435 |
| CENTG1 | NM_014770 | 5 | 12 | - | 1505 | - | 0 | 37 | 1 | 0 | CGCGAATGCCGGCAACTATACCAGCCAACCG GGGCGTCGGCCGCACGCGTGGCCGATGT | 1436 |
| EPHA7 | NM_004440 | 13 | 6 | - | 0 | + | 0 | 37 | 1 | 0 | CGCGAATGCCGGCCTCCATCTGCCACCAGAAC CTCATTTCAACACGCGTGGCCGATGT | 1437 |
| EPHA7 | NM_004440 | 13 | 6 | - | 35 | - | 0 | 37 | 1 | 0 | CGCGAATGCCGAGACTCCATTCCAAACTTACTGT GGTTTGGTTGATACGCGTGGCCGATGT | 1438 |
| EPHA7 | NM_004440 | 13 | 6 | - | 70 | + | 0 | 37 | 1 | 0 | CGCGAATGCCTCCTGCAGACAATGGGGAAGAA ACGATGTGACCTTACGCGTGGCCGATGT | 1439 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| EPHA7 | NM_004440 | 13 | 6 | - | 105 | - | 0 | 37 | 1 | 0 | CGCGAATGCCCTGCTCCCAACTGCACCGCTTACACAATATTCTGTACGCGTGGCCGGATGT | 1440 |
| EPHA7 | NM_004440 | 13 | 6 | - | 140 | - | 0 | 37 | 1 | 0 | CGCGAATGCCGGCGAATGTGTTCCCTGTGGGAGTAACATTGGATAACGCGTGGCCGGATGT | 1441 |
| EPHA7 | NM_004440 | 13 | 6 | - | 175 | - | 0 | 37 | 1 | 0 | CGCGAATGCCATAGTTATCCTCTAATCCAGTCTGCTGGGGCATGACGCGTGGCCGGATGT | 1442 |
| EPHA7 | NM_004440 | 13 | 6 | - | 210 | - | 0 | 37 | 1 | 0 | CGCGAATGCCTCACTGTCATGGACCTGCTAGCCCACGCTAATTATACGCGTGGCCGGATGT | 1443 |
| EPHA7 | NM_004440 | 13 | 6 | - | 245 | - | 0 | 37 | 1 | 0 | CGCGAATGCCTCAGAAACTCCATTTACAGCTTCAACTTCAAAAGTACGCGTGGCCGGATGT | 1444 |
| EPHA7 | NM_004440 | 13 | 6 | - | 280 | - | 0 | 37 | 1 | 0 | CGCGAATGCCTTAAGCCGATCCCAGAGGCTCTTTGCTGTGTCAACGCGTGGCCGGATGT | 1445 |
| EPHA7 | NM_004440 | 13 | 6 | - | 315 | - | 0 | 37 | 1 | 0 | CGCGAATGCCAACACAAAACATACCTGCTTGACCAGTGGTGATACACGCGTGGCCGGATGT | 1446 |
| CHAF1A | NM_005483 | 7 | 19 | + | -36 | + | 0 | 37 | 1 | 0 | CGCGAATGCCTCTTCCTCTTTCTCATCACCATCTCTTAACATCACAACGCGTGGCCGGATGT | 1447 |
| CHAF1A | NM_005483 | 7 | 19 | + | -1 | - | 0 | 37 | 1 | 0 | CGCGAATGCCACCTCGTGATTTCGGCCTTCTCTGCTTTAATGCGACGCGTGGCCGGATGT | 1448 |
| CHAF1A | NM_005483 | 7 | 19 | + | 34 | + | 0 | 37 | 1 | 0 | CGCGAATGCCTCTTCCAGAAACCAAAGACTCCACAGGCCCCAAGACGCGTGGCCGGATGT | 1449 |
| CHAF1A | NM_005483 | 7 | 19 | + | 69 | - | 0 | 37 | 1 | 0 | CGCGAATGCCCTGAAACCAAAGCAAAGCAGCCGGCTTGCTCACACGCGTGGCCGGATGT | 1450 |
| PKN1 | NM_002741 | 6 | 19 | + | 0 | + | 0 | 37 | 1 | 0 | CGCGAATGCCGCCAGGAGAGAAATTAACAGAATCCAACCAGAAGCTACGCGTGGCCGGATGT | 1451 |
| PKN1 | NM_002741 | 6 | 19 | + | 35 | - | 0 | 37 | 1 | 0 | CGCGAATGCCCAAGTCTCCGCTCCAGAGCCTCCCGCAGCCCCACGCGTGGCCGGATGT | 1452 |
| PKN1 | NM_002741 | 6 | 19 | + | 70 | + | 0 | 37 | 1 | 0 | CGCGAATGCCGGGAGCTGCCCCGACCACCCCAAGGGGCCGGCTGACGCGTGGCCGGATGT | 1453 |
| PKN1 | NM_002741 | 6 | 19 | + | 105 | - | 0 | 37 | 1 | 0 | CGCGAATGCCCAGCGGCAGGAGGCCGCAGCGAGCTCTTCTCGCAGACGCGTGGCCGGATGT | 1454 |
| PKN1 | NM_002741 | 6 | 19 | + | 140 | + | 0 | 37 | 1 | 0 | CGCGAATGCCCTTCAGCACCCCCTGGCCGGGCCCTTTCCCGCAACGCGTGGCCGGATGT | 1455 |
| PKN1 | NM_002741 | 6 | 19 | + | 175 | - | 0 | 37 | 1 | 0 | CGCGAATGCCGAGCGGCGGCGGCTTGCACAGGGTGCTGAGTGCGACGCGTGGCCGGATGT | 1456 |
| PKN1 | NM_002741 | 6 | 19 | + | 210 | + | 0 | 37 | 1 | 0 | CGCGAATGCCACAGGTGGGTCTGAGACCCTACCCACCCCTGCAGACGCGTGGCCGGATGT | 1457 |
| EPHA3 | NM_005233 | 2 | 3 | + | -38 | - | 0 | 37 | 1 | 0 | CGCGAATGCCTGTTATTAACTGTGTTTGTATTATGTTTTATTTACGCGTGGCCGGATGT | 1458 |
| EPHA3 | NM_005233 | 2 | 3 | + | -3 | + | 0 | 37 | 1 | 0 | CGCGAATGCCCCCTTGAATTGTTTTTGAATCCAGTAGATTGACTAACGCGTGGCCGGATGT | 1459 |
| EPHA3 | NM_005233 | 2 | 3 | + | 32 | + | 0 | 37 | 1 | 0 | CGCGAATGCCGAGCTGGGCTGACATCTCTTATCCATCACATGGGTACGCGTGGCCGGATGT | 1460 |
| EPHA3 | NM_005233 | 2 | 3 | + | 67 | + | 0 | 37 | 1 | 0 | CGCGAATGCCGAGAAAATGTTTCCTTGTGATAGTTTATTGAACTCACGCGTGGCCGGATGT | 1461 |
| KSR2 | NM_173598 | 5 | 12 | - | -3 | + | 0 | 37 | 1 | 0 | CGCGAATGCCAGGGCATGGCTACCTCCACGCCAAGGGAATCCTACGCGTGGCCGGATGT | 1462 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| KSR2 | NM_173598 | 5 | 12 | - | 32 | - | 0 | 37 | 1 | 0 | CGCGAATGCCCATAGAAGACGTTCTTTGACTTG AGTTCCTTGTGTACGCCGTGGCGGATGT | 1463 |
| KSR2 | NM_173598 | 5 | 12 | - | 67 | + | 0 | 37 | 1 | 0 | CGCGAATGCCACAACGCAAAGTGGTCATCACG GACTTTGACTTCACGCCGTGGCGGATGT | 1464 |
| KSR2 | NM_173598 | 5 | 12 | - | 102 | - | 0 | 37 | 1 | 0 | CGCGAATGCCCACCTGCCAGCTGCAGCACCCC AGAAATGCTGAAACGCCGTGGCGGATGT | 1465 |
| RPS6KA1 | NM_002953 | 1 | 1 | + | -38 | + | 0 | 37 | 1 | 0 | CGCGAATGCCGGCCGCCGGAGGAGCGCGGGTG ACCTGCGGCGGCACGCGTGGCGGATGT | 1466 |
| RPS6KA1 | NM_002953 | 1 | 1 | + | -3 | - | 0 | 37 | 1 | 0 | CGCGAATCCGGCCAGGGCTCCTTGAGCTGGGC GAGCGGCATCTCACGCGTGGCGGATGT | 1467 |
| RPS6KA1 | NM_002953 | 1 | 1 | + | 32 | + | 0 | 37 | 1 | 0 | CGCGAATGCCGCTCATGGAGCTAGTGCCTCTGG ACCCGGAGGTGAACGCGTGGCGGATGT | 1468 |
| RPS6KA1 | NM_002953 | 1 | 1 | + | 63 | - | 27 | 37 | 1 | 0 | CGCGAATCCGCCGCGGGCCCCGTCCCCGCC CCGCTCACTCACGCGTGGCGGATGT | 1469 |
| KSR2 | NM_173598 | 18 | 12 | - | 0 | + | 0 | 37 | 1 | 0 | CGCGAATGCCGAAATCTCCCCCGGCCAGCTGAG CTGGAGGACTTACGCCGTGGCGGATGT | 1470 |
| KSR2 | NM_173598 | 18 | 12 | - | 35 | - | 0 | 37 | 1 | 0 | CGCGAATGCCCAGTCTCCACACCTGTTCATCC GTCATCTTCCAAGACGCCGTGGCGGATGT | 1471 |
| KSR2 | NM_173598 | 18 | 12 | - | 70 | + | 0 | 37 | 1 | 0 | CGCGAATGCTGAGAAATACGGAGCCAACCG GGAGGAGTGTGCCACGCGTGGCGGATGT | 1472 |
| KSR2 | NM_173598 | 18 | 12 | - | 105 | - | 0 | 37 | 1 | 0 | CGCGAATGCCACATTCCTGAGGCAGGAGGAGGA GGCGTTGAGGCGACGCGTGGCGGATGT | 1473 |
| KSR2 | NM_173598 | 18 | 12 | - | 140 | + | 0 | 37 | 1 | 0 | CGCGAATGCCCCACATGTCAGGTGAGCAGGCCC CGGGGTCGGGGAACGCGTGGCGGATGT | 1474 |
| GUCY2F | NM_001522 | 10 | X | - | 0 | - | 0 | 37 | 1 | 0 | CGCGAATGCCAGCTGCTGTGGACGGCCCCTGAA CTGTTGAGAGCTACGCCGTGGCGGATGT | 1475 |
| GUCY2F | NM_001522 | 10 | X | - | 35 | + | 0 | 37 | 1 | 0 | CGCGAATGCCTCTCTCCTCCAAAAGAACCTAACCT GCTGCCTCTTGGACGCCGTGGCGGATGT | 1476 |
| GUCY2F | NM_001522 | 10 | X | - | 70 | - | 0 | 37 | 1 | 0 | CGCGAATGCCTGTCTATAGCTTTGCCATCATCAT GCAAGAAGTGAACGCGTGGCGGATGT | 1477 |
| GUCY2F | NM_001522 | 10 | X | - | 105 | + | 0 | 37 | 1 | 0 | CGCGAATGCCAGATCCATCATGCAGAATGGGG TACCCCGACCAACGCCGTGGCGGATGT | 1478 |
| GUCY2F | NM_001522 | 10 | X | - | 140 | - | 0 | 37 | 1 | 0 | CGCGAATGCCCCAGCTCAAGGTAAGCGGAGGT GAGAAAAGGCCACGCCGTGGCGGATGT | 1479 |
| PKN1 | NM_002741 | 2 | 19 | + | 0 | + | 0 | 37 | 1 | 0 | CGCGAATGCCAGTGAGCCTCGCAGCTGGTCCCT GCTAGAGCAGCTTACGCCGTGGCGGATGT | 1480 |
| PKN1 | NM_002741 | 2 | 19 | + | 35 | - | 0 | 37 | 1 | 0 | CGCGAATGCCCCCGGGGCCGCCAGGTCTGCC CGGCCCAGGCCCACGCCGTGGCGGATGT | 1481 |
| PKN1 | NM_002741 | 2 | 19 | + | 70 | + | 0 | 37 | 1 | 0 | CGCGAATGCCTACAGCAGCTGGAGCTGGAG CGGGAGCCGGCCACGCCGTGGCGGATGT | 1482 |
| PKN1 | NM_002741 | 2 | 19 | + | 105 | - | 0 | 37 | 1 | 0 | CGCGAATGCCTCCTTCCAGCTTCAGCTCCTTGCGG ATTTCCCCGACGCGTGGCGGATGT | 1483 |
| PKN1 | NM_002741 | 2 | 19 | + | 140 | + | 0 | 37 | 1 | 0 | CGCGAATGCCGGTGCTGAGAACCTGCGGCGG CCACCATGACCACGCCGTGGCGGATGT | 1484 |
| PKN1 | NM_002741 | 2 | 19 | + | 175 | - | 0 | 37 | 1 | 0 | CGCGAATGCCCAGCAGCAGCTCTACGGGCCCA GGTGCGCCCAACGCGTGGCGGATGT | 1485 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| PKN1 | NM_002741 | 2 | 19 | + | 210 | + | 0 | 37 | 1 | 0 | CGCGAATGCCCGGGGCTCCTCGCGCCGCCTCGACCTGCTGCACCAACGCCTGGGCCGATGT | 1486 |
| PKN1 | NM_002741 | 2 | 19 | + | 245 | - | 0 | 37 | 1 | 0 | CGCGAATGCCGAAGCACCACGTGGGCGTGCAGCTCCTGCAGCTGCACGCGGTGGCCGATGT | 1487 |
| PKN1 | NM_002741 | 2 | 19 | + | 280 | + | 0 | 37 | 1 | 0 | CGCGAATGCCCCGACCCGGCGGGCCACCCACGGTGAGCTGGGATGCACGCGGTGGCCGATGT | 1488 |
| RBBP8 | NM_002894 | 7 | 18 | + | 0 | + | 0 | 37 | 1 | 0 | CGCGAATGCCGAATGATCAAACAGCATCAAGCAGCTGAGCTTGAAATACGCGGTGGCCGATGT | 1489 |
| RBBP8 | NM_002894 | 7 | 18 | + | 35 | - | 0 | 37 | 1 | 0 | CGCGAATGCCTGTTATCCGTGAATCTGAATAACGTCTTCCTCACGCGTGGCCGATGT | 1490 |
| RBBP8 | NM_002894 | 7 | 18 | + | 70 | + | 0 | 37 | 1 | 0 | CGCGAATGCCGCCTTCTCATTTTCTGGCGTTAACCGGCTACGAAGACGCGTGGCCGATGT | 1491 |
| RBBP8 | NM_002894 | 7 | 18 | + | 105 | - | 0 | 37 | 1 | 0 | CGCGAATGCCTTTGTTCTTATGTATCGGACATGGGGGTTCTCCTTTACGCGTGGCCGATGT | 1492 |
| RBBP8 | NM_002894 | 7 | 18 | + | 140 | + | 0 | 37 | 1 | 0 | CGCGAATGCCCACATACTAAATTGGACCACTCTGTGTGTGCAAATACGCGTGGCCGATGT | 1493 |
| RBBP8 | NM_002894 | 7 | 18 | + | 175 | - | 0 | 37 | 1 | 0 | CGCGAATGCCAACCAGAGAACTAAAATACAACTCCAACTCTTACACGCCTGGCCGATGT | 1494 |
| EPHB1 | NM_004441 | 13 | 3 | + | 0 | + | 0 | 37 | 1 | 0 | CGCGAATGCCGAGGGAAGATCCCTGTGAGATGGACAGCTCCAGAACGCCGTGGCCGATGT | 1495 |
| EPHB1 | NM_004441 | 13 | 3 | + | 35 | - | 0 | 37 | 1 | 0 | CGCGAATGCCCCTGGCTGAAGTGAACTTGCGGTAGGCGATGGCCACGCCTGGCCGATGT | 1496 |
| EPHB1 | NM_004441 | 13 | 3 | + | 70 | + | 0 | 37 | 1 | 0 | CGCGAATGCCACGTTTGGAGCTATGGGATCGTCATGTGGAAGTCACGCCGTGGCCGATGT | 1497 |
| EPHB1 | NM_004441 | 13 | 3 | + | 105 | - | 0 | 37 | 1 | 0 | CGCGAATGCCGACATATCCCAATAGGGGTCTCTCTCCAAATGACATACGCCTGGCCGATGT | 1498 |
| EPHB1 | NM_004441 | 13 | 3 | + | 140 | + | 0 | 37 | 1 | 0 | CGCGAATGCCCAACCAAGATGTGAGTGTCAGCAGCACTTGGTCACACGCCGTGGCCGATGT | 1499 |
| PDGFRA | NM_006206 | 12 | 4 | + | -4 | + | 0 | 37 | 1 | 0 | CGCGAATGCCATAGAAACCGAGTATGAAATTCGCTGGAGGGTCAACGCCTGGCCGATGT | 1500 |
| PDGFRA | NM_006206 | 12 | 4 | + | 31 | - | 0 | 37 | 1 | 0 | CGCGAATGCCAATATATTCATGTCCATCTGGGCTGATTGATTCAAACGCGTGGCCGATGT | 1501 |
| PDGFRA | NM_006206 | 12 | 4 | + | 66 | + | 0 | 37 | 1 | 0 | CGCGAATGCCTATGTGGACCCGATGCAGCTGCCTTATGACTCAAGACGCCTGGCCGATGT | 1502 |
| PDGFRA | NM_006206 | 12 | 4 | + | 101 | - | 0 | 37 | 1 | 0 | CGCGAATGCCTACCAAGCACTAGTCCATCTCTTGGAAACTCCCATACGCCTGGCCGATGT | 1503 |
| RET | NM_020630 | 7 | 10 | + | 0 | + | 0 | 37 | 1 | 0 | CGCGAATGCCCATCGGGAAAGTCTGTGTGGAAAACTGCCCAGGCATTACGCCTGGCCGATGT | 1504 |
| RET | NM_020630 | 7 | 10 | + | 35 | - | 0 | 37 | 1 | 0 | CGCGAATGCCAGGAATGCAGCTTGTACTGGACGTTGATGCCACTGACGCCTGGCCGATGT | 1505 |
| RET | NM_020630 | 7 | 10 | + | 70 | + | 0 | 37 | 1 | 0 | CGCGAATGCCCTGGTGCCAACTGCAGCACGCTAGGGGTGGTCACCACGCCGTGGCCGATGT | 1506 |
| RET | NM_020630 | 7 | 10 | + | 105 | - | 0 | 37 | 1 | 0 | CGCGAATGCCTTCACAAACAGGATCCCCGAGGTGTCCTCGGCTGAACGCGTGGCCGATGT | 1507 |
| RET | NM_020630 | 7 | 10 | + | 140 | + | 0 | 37 | 1 | 0 | CGCGAATGCCTGACACCAAGGCCCTGCGGCGCCCAAGTGCCGACGCCGTGGCCGATGT | 1508 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit mismatch | # BWA Sequence with add-ons | SEQ ID NO: |
|---|---|---|---|---|---|---|---|---|---|---|---|
| RET | NM_020630 | 7 | 10 | + | 175 | - | 0 | 37 | 1 | 0 | CGCGAATGCCCTGCTGGTCGTGGCCACCACCATGTAGTGAAGTTACGCCGTGGCCGATGT | 1509 |
| RET | NM_020630 | 7 | 10 | + | 210 | + | 0 | 37 | 1 | 0 | CGCGAATGCCCACCTCTAGGCAGGCCCAGGCCCAGCTGCTTGTAACACGCCGTGGCCGATGT | 1510 |
| RET | NM_020630 | 7 | 10 | + | 245 | - | 0 | 37 | 1 | 0 | CGCGAATGCCCTCCCTGGAGCAGGCACTCACATGACCCCTCCACTACGCCGTGGCCGATGT | 1511 |
| EPHA7 | NM_004440 | 3 | 6 | - | 0 | + | 0 | 37 | 1 | 0 | CGCGAATGCCGTTATAAAAGCAATAGAAGAAGGTTATCGTTACCACGCCGTGGCCGATGT | 1512 |
| EPHA7 | NM_004440 | 3 | 6 | - | 35 | - | 0 | 37 | 1 | 0 | CGCGAATCCGCTGGTGAAGGCCAGCTGGGCAGTCCATGGTGCTACGCCGTGGCCGATGT | 1513 |
| EPHA7 | NM_004440 | 3 | 6 | - | 70 | + | 0 | 37 | 1 | 0 | CGCGAATGCCTAATGTTGGATTGTTGGCAAAAGGAGCGTGCTGAAACGCGTGGCCGATGT | 1514 |
| EPHA7 | NM_004440 | 3 | 6 | - | 105 | - | 0 | 37 | 1 | 0 | CGCGAATGCCTCTAGAATTCCAACTATCGTTCAAATTTTGGCCTACGCGTGGCCGATGT | 1515 |
| EPHA7 | NM_004440 | 3 | 6 | - | 140 | + | 0 | 37 | 1 | 0 | CGCGAATGCCCAAAATGATTCGAAACCCAAATAGTCTGAAAACTCACGCCGTGGCCGATGT | 1516 |
| EPHA7 | NM_004440 | 3 | 6 | - | 175 | - | 0 | 37 | 1 | 0 | CGCGAATGCCCTTAGGCATTCTTACCTACTACAAGTTCCAGGGACGCCGTGGCCGATGT | 1517 |
| IRS4 | NM_003604 | 1 | X | - | 0 | + | 0 | 37 | 1 | 0 | CGCGAATGCCATGGCGAGTTGCTCCTTCACTCGCAACCAAGCGACACGCCGTGGCCGATGT | 1518 |
| IRS4 | NM_003604 | 1 | X | - | 35 | - | 0 | 37 | 1 | 0 | CGCGAATGCCCCGTCTTAGCACAGTGTGACCACCCCGCTTCTTACGCCGTGGCCGATGT | 1519 |
| IRS4 | NM_003604 | 1 | X | - | 70 | + | 0 | 37 | 1 | 0 | CGCGAATGCCCCGTCCCAATGAGTGCGGTCGGCTTAGTCTTCTTACGCCGTGGCCGATGT | 1520 |
| IRS4 | NM_003604 | 1 | X | - | 105 | - | 0 | 37 | 1 | 0 | CGCGAATGCCCCGGTCCCAATGAGTGCGGTCGGGGTTCCCGAGGAACGCCGTGGCCGATGT | 1521 |
| IRS4 | NM_003604 | 1 | X | - | 140 | + | 0 | 37 | 1 | 0 | CGCGAATGCCGTCGTCTTGTCCGGAGCCATGTGGCTCTCCACGGACGCCGTGGCCGATGT | 1522 |
| IRS4 | NM_003604 | 1 | X | - | 175 | - | 0 | 37 | 1 | 0 | CGCGAATGCCCTCTTCGACTCGGAGTCTGACCGGGAGCCAGTGGACGCCGTGGCCGATGT | 1523 |
| IRS4 | NM_003604 | 1 | X | - | 210 | + | 0 | 37 | 1 | 0 | CGCGAATGCCGAGGACTGCCCGTCGGGGAGGAAGTCTGCAAACGACGCCGTGGCCGATGT | 1524 |
| IRS4 | NM_003604 | 1 | X | - | 245 | - | 0 | 37 | 1 | 0 | CGCGAATGCCGCCTGTGCCCATGCTTCTGTTTTCCGCAGGTAGCCGACGCCGTGGCCGATGT | 1525 |
| IRS4 | NM_003604 | 1 | X | - | 280 | + | 0 | 37 | 1 | 0 | CGCGAATGCCGCTACTTCGTGTCTCAAACTCGAGACTGCTGACGCCACGCCGTGGCCGATGT | 1526 |
| IRS4 | NM_003604 | 1 | X | - | 315 | - | 0 | 37 | 1 | 0 | CGCGAATGCCTTCCTGCATTTTCGTAGTATTCCAGCCGAGCTGGACGCCGTGGCCGATGT | 1527 |
| IRS4 | NM_003604 | 1 | X | - | 350 | + | 0 | 37 | 1 | 0 | CGCGAATGCCGTTCCGCACAGTGTCCGCCCGCGGCGTGCAGACGCGGTGGCCGATGT | 1528 |
| IRS4 | NM_003604 | 1 | X | - | 385 | - | 0 | 37 | 1 | 0 | CGCGAATGCCCGCGCTGACGCGTGGCCGATGTGCGCCCGCGCTGACGCGTGGCCGATGT | 1529 |
| IRS4 | NM_003604 | 1 | X | - | 420 | + | 0 | 37 | 1 | 0 | CGCGAATGCCCTCATTCCACCCGGCCGCGTGATCACCCTATACCAACGCGTGGCCGATGT | 1530 |
| IRS4 | NM_003604 | 1 | X | - | 455 | - | 0 | 37 | 1 | 0 | CGCGAATGCCACCTTGCATCTGCTGCTGGCTCACGAAAAGCCACGCGTGGCCGATGT | 1531 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| IRS4 | NM_003604 | 1 | X | − | 490 | + | 0 | 37 | 1 0 | CGCGAATGCCACCGACCACCTCATTGCTCTTTCA CCCAAGACGAAACGCGTGGCGGATGT | 1532 |
| IRS4 | NM_003604 | 1 | X | − | 525 | − | 0 | 37 | 1 0 | CGCGAATGCCTGCTCCCGACTCGTTCTCGGCCACC ATCGCGAAGTAACGCGTGGCGGATGT | 1533 |
| IRS4 | NM_003604 | 1 | X | − | 560 | + | 0 | 37 | 1 0 | CGCGAATGCCGGAAAGCTGGTACTTGCTGCTCA GCCGCTCATCCACGCGTGGCGGATGT | 1534 |
| IRS4 | NM_003604 | 1 | X | − | 595 | − | 0 | 37 | 1 0 | CGCGAATGCCGCCGAGCGTGCCGCAGCGGCGGC GCTTGCTCTCGAACGCGTGGCGGATGT | 1535 |
| IRS4 | NM_003604 | 1 | X | − | 630 | + | 0 | 37 | 1 0 | CGCGAATGCCGCCCAGCCGACGCCGGAGAGCCGG CCGCGCTGGCGCGCCACGCGTGGCGGATGT | 1536 |
| IRS4 | NM_003604 | 1 | X | − | 665 | − | 0 | 37 | 1 0 | CGCGAATGCCCATCTTTATAGAAGGGTGGCTCC GCCGCCGCTGCCACGCGTGGCGGATGT | 1537 |
| IRS4 | NM_003604 | 1 | X | − | 700 | + | 0 | 37 | 1 0 | CGCGAATGCCTGTGCAGGTAATAGTCAAACCC AGGGGCTGGGACGCGTGGCGGATGT | 1538 |
| IRS4 | NM_003604 | 1 | X | − | 735 | − | 0 | 37 | 1 0 | CGCGAATGCCCACAGCCGGAACACGCCGCTCAG CTCTTTCTGTGACGCGTGGCGGATGT | 1539 |
| IRS4 | NM_003604 | 1 | X | − | 770 | + | 0 | 37 | 1 0 | CGCGAATGCCTCTAACCGACGAGGAGGTCGTGT TTGTGAGGCTGAACGCGTGGCGGATGT | 1540 |
| IRS4 | NM_003604 | 1 | X | − | 805 | + | 0 | 37 | 1 0 | CGCGAATGCCCAGGAGCTGGACGACCACGCTGG CCACTTCGGTGTACGCGTGGCGGATGT | 1541 |
| IRS4 | NM_003604 | 1 | X | − | 840 | + | 0 | 37 | 1 0 | CGCGAATGCCAGCATCCGTCGCTGTGGACACTC GGAGCAGTATTTACGCGTGGCGGATGT | 1542 |
| IRS4 | NM_003604 | 1 | X | − | 875 | − | 0 | 37 | 1 0 | CGCGAATGCCGACCGATGACAGTGGACCTGCCT ACTTCCAAGAAGACGCGTGGCGGATGT | 1543 |
| IRS4 | NM_003604 | 1 | X | − | 910 | + | 0 | 37 | 1 0 | CGCGAATGCCCGGAGAGCTCTGGATGCAGGTC GATGACTGTGTGACGCGTGGCGGATGT | 1544 |
| IRS4 | NM_003604 | 1 | X | − | 945 | − | 0 | 37 | 1 0 | CGCGAATGCCTTCTCCAAAACAGCTCATGCAT GTTTTGGGCAACACGCGTGGCGGATGT | 1545 |
| IRS4 | NM_003604 | 1 | X | − | 980 | + | 0 | 37 | 1 0 | CGCGAATGCCGATGAGAGCCTTGTGTGCAGACG AATACAGAGCCCACGCGTGGCGGATGT | 1546 |
| IRS4 | NM_003604 | 1 | X | − | 1015 | − | 0 | 37 | 1 0 | CGCGAATGCCGTGGGCGCCGATGCTGATGCTGT AGCTGCCGCAGCACGCGTGGCGGATGT | 1547 |
| IRS4 | NM_003604 | 1 | X | − | 1050 | + | 0 | 37 | 1 0 | CGCGAATGCCCTGTTAACCCTGCTGTCCGCTAG GAGGCACCTGGGACGCGTGGCGGATGT | 1548 |
| IRS4 | NM_003604 | 1 | X | − | 1085 | − | 0 | 37 | 1 0 | CGCGAATGCCTTCTGAGCCAGCCTCCCGGCTCG AGCGGCACCAAGACGCGTGGCGGATGT | 1549 |
| IRS4 | NM_003604 | 1 | X | − | 1120 | + | 0 | 37 | 1 0 | CGCGAATGCCGGTCCCGCTTTGAGCAGTTTTGCC ACCTCAGGGCCCACGCGTGGCGGATGT | 1550 |
| IRS4 | NM_003604 | 1 | X | − | 1155 | − | 0 | 37 | 1 0 | CGCGAATGCCCTGGTGAAAAGCATCTCGTCTTC CCCGTCCCGATACGCGTGGCGGATGT | 1551 |
| IRS4 | NM_003604 | 1 | X | − | 1190 | + | 0 | 37 | 1 0 | CGCGAATGCCGCGTTCGTAACACCCAGCGAGC CTGTGGCCCACTACGCGTGGCGGATGT | 1552 |
| IRS4 | NM_003604 | 1 | X | − | 1225 | − | 0 | 37 | 1 0 | CGCGAATGCCGCGCCCTCTGGGCAGGTGCAGTC TTCCTCGCCTGGACGCGTGGCGGATGT | 1553 |
| IRS4 | NM_003604 | 1 | X | − | 1260 | + | 0 | 37 | 1 0 | CGCGAATGCCAGGTCAAGGAGGAGCCGGTTTCAGT GCCGGCCAGCTTACGCGTGGCGGATGT | 1554 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| IRS4 | NM_003604 | 1 | X | − | 1295 | − | 0 | 37 | 1 | CGCGAATGCCGGGACTGCTGGGCTGGTGCT AAGCGGCGAAAACGCCTGGCGGATGT | 1555 |
| IRS4 | NM_003604 | 1 | X | − | 1330 | + | 0 | 37 | 1 | CGCGAATGCCGGCACCCTGCAGAAGCCCGAAC AATGGAGCTCGACGCGTGGCGGATGT | 1556 |
| IRS4 | NM_003604 | 1 | X | − | 1365 | − | 0 | 37 | 1 | CGCGAATGCCTTGCCAGAGCCAGAACCAGACAC TTCAGAAGACAGCGCCTGGCGGATGT | 1557 |
| IRS4 | NM_003604 | 1 | X | − | 1400 | + | 0 | 37 | 1 | CGCGAATGCCCTTTGGGGAGGAAGGCAATCCCC AGGGCAAAGAAGACGCGTGGCGGATGT | 1558 |
| IRS4 | NM_003604 | 1 | X | − | 1435 | + | 0 | 37 | 1 | CGCGAATGCCCATAGGCATGTAGTCACCTCCGC TTCCTTCTGATACGCTGGCGGATGT | 1559 |
| IRS4 | NM_003604 | 1 | X | − | 1470 | + | 0 | 37 | 1 | CGCGAATGCCAACAATTGGGCTCAGGAAATGG CCGGGCTCAGGACGCGTGGCGGATGT | 1560 |
| IRS4 | NM_003604 | 1 | X | − | 1505 | − | 0 | 37 | 1 | CGCGAATGCCTACTGGACGCCTTGGCCATTGAG CCCTGGCCACTTACGCGTGGCGGATGT | 1561 |
| IRS4 | NM_003604 | 1 | X | − | 1540 | + | 0 | 37 | 1 | CGCGAATGCCGCCATAGCTCGGGAGGAAACCAG TGTTCAGGCGAGACGCGTGGCGGATGT | 1562 |
| IRS4 | NM_003604 | 1 | X | − | 1575 | − | 0 | 37 | 1 | CGCGAATGCCCCCATTTGAGCCCTGACCACCTCG GGATCCCTGTCACGCCTGGCCGGATGT | 1563 |
| IRS4 | NM_003604 | 1 | X | − | 1610 | + | 0 | 37 | 1 | CGCGAATGCCCCAGGGCTCAGGAGGAAACCAGT GCTCTAAGATGACGCCGTGGCCGGATGT | 1564 |
| IRS4 | NM_003604 | 1 | X | − | 1645 | − | 0 | 37 | 1 | CGCGAATGCCACCACCTGAACCCTGCCCACCTG CGGTGCCCTGGCCACGCCTGGCCGGATGT | 1565 |
| IRS4 | NM_003604 | 1 | X | − | 1680 | + | 0 | 37 | 1 | CGCGAATGCCGGCCAGAGACCTGGAGGTGGGC ATGGCTCAGGTGGACGCCGTGGCCGGATGT | 1566 |
| IRS4 | NM_003604 | 1 | X | − | 1715 | − | 0 | 37 | 1 | CGCGAATGCCCACCTGAGCCATGGCCATCTCCA GGTCCCTGGCCAACGCGTGGCCGGATGT | 1567 |
| IRS4 | NM_003604 | 1 | X | − | 1750 | + | 0 | 37 | 1 | CGCGAATGCCGTGGCAAGAACTCTGGGGGGGC AAAGGCTCAGGAACGCCTGGCCGGATGT | 1568 |
| IRS4 | NM_003604 | 1 | X | − | 1785 | − | 0 | 37 | 1 | CGCGAATGCCCCACGTTCACCATCACCATCGGA TCCTTTCCCACTACGCCTGGCCGGATGT | 1569 |
| IRS4 | NM_003604 | 1 | X | − | 1820 | + | 0 | 37 | 1 | CGCGAATGCCAAAATCTGAAGAAAAGATCCT ATTTTGGCAAATACGCCTGGCCGGATGT | 1570 |
| IRS4 | NM_003604 | 1 | X | − | 1855 | − | 0 | 37 | 1 | CGCGAATGCCAGGTGGTGGCATTTGCTGTTGCTT GCTTTGAGTTAACCGTGGCCGGATGT | 1571 |
| IRS4 | NM_003604 | 1 | X | − | 1890 | + | 0 | 37 | 1 | CGCGAATGCCCACCACCTCCTCCTCCACCCCCA CCAGCTGAGGACGCCGTGGCCGGATGT | 1572 |
| IRS4 | NM_003604 | 1 | X | − | 1925 | − | 0 | 37 | 1 | CGCGAATGCCTGAATCTTCCCCCAGACTTCCTT TTCCACCAGTTACGCGTGGCCGGATGT | 1573 |
| IRS4 | NM_003604 | 1 | X | − | 1960 | + | 0 | 37 | 1 | CGCGAATGCCGACTTTATTTTGTGTTGACAGAG GAGCCAGAAAACGCCGTGGCCGGATGT | 1574 |
| IRS4 | NM_003604 | 1 | X | − | 1995 | − | 0 | 37 | 1 | CGCGAATGCCCTGCATCTTTCACTTCTTTGGCT TCTTTGCATTCACGCGTGGCCGGATGT | 1575 |
| IRS4 | NM_003604 | 1 | X | − | 2030 | + | 0 | 37 | 1 | CGCGAATGCCGATCCCAGAAGTGCAGCTCGAG GTCCCACAGAGACGCCGTGGCCGGATGT | 1576 |
| IRS4 | NM_003604 | 1 | X | − | 2065 | − | 0 | 37 | 1 | CGCGAATGCCGTATGGGTCATCCTCATCTTCATC AAAAGCTCTGGACGCGTGGCCGGATGT | 1577 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| IRS4 | NM_003604 | 1 | X | - | 2100 | + | 0 | 37 | 1 | 0 | CGCGAATGCCGTGCCAATGAGGCCAGGGTGGCCACCCCTCTTGTACGCGTGGCCGATGT | 1578 |
| IRS4 | NM_003604 | 1 | X | - | 2135 | - | 0 | 37 | 1 | 0 | CGCGAATGCCTTTGAGGAGCCATTGGCATATAATCACTGAGCTTACGCGTGGCCGATGT | 1579 |
| IRS4 | NM_003604 | 1 | X | - | 2170 | + | 0 | 37 | 1 | 0 | CGCGAATGCCATGTCTCTGCTTCAAAAAGCGCCACTCTCGATCCACGCGTGGCCGATGT | 1580 |
| IRS4 | NM_003604 | 1 | X | - | 2205 | - | 0 | 37 | 1 | 0 | CGCGAATGCCAACATCATCATGTACCCTCTTGAATCTTCAAAAGGACGCGTGGCCGATGT | 1581 |
| IRS4 | NM_003604 | 1 | X | - | 2240 | + | 0 | 37 | 1 | 0 | CGCGAATGCCTCCCAGAGTGAGCCACCACCTGCTCCGAGTCCTCACGCGTGGCCGATGT | 1582 |
| IRS4 | NM_003604 | 1 | X | - | 2275 | - | 0 | 37 | 1 | 0 | CGCGAATGCCTGAGTCATCCTCTTTATTAGTATCAGGTGCTTTGACGCGTGGCCGATGT | 1583 |
| IRS4 | NM_003604 | 1 | X | - | 2310 | + | 0 | 37 | 1 | 0 | CGCGAATGCCAAGGACAATGACAGTGAGAGTGACTACATGTTATACGCTGGCCGGATGT | 1584 |
| IRS4 | NM_003604 | 1 | X | - | 2345 | - | 0 | 37 | 1 | 0 | CGCGAATGCCTGGGTTTTTTGGAATTGCACCGGCTCCAGGAGCCACGCGTGGCCGATGT | 1585 |
| IRS4 | NM_003604 | 1 | X | - | 2380 | + | 0 | 37 | 1 | 0 | CGCGAATGCCGAAATCCTCAGGTGGCTCTTCCTCCAAAGTTGACGCCTGGCCGATGT | 1586 |
| IRS4 | NM_003604 | 1 | X | - | 2415 | - | 0 | 37 | 1 | 0 | CGCGAATGCCCTCGAAAAGGGTTTGGTAGAGAGAAGTAGGAGCTTACGCGTGGCCGATGT | 1587 |
| IRS4 | NM_003604 | 1 | X | - | 2450 | + | 0 | 37 | 1 | 0 | CGCGAATGCCCCTTTGGGACAGAATGACAACAGTGAGTATGACGCGTGGCCGATGT | 1588 |
| IRS4 | NM_003604 | 1 | X | - | 2485 | - | 0 | 37 | 1 | 0 | CGCGAATGCCGCCCCTCCCCAGGAACTTTCCAGGTAACATTGGCACGCGTGGCCGATGT | 1589 |
| IRS4 | NM_003604 | 1 | X | - | 2520 | + | 0 | 37 | 1 | 0 | CGCGAATGCCCTAGACAAAGAAGTCTCCTATAACTGGGACCCCAAACGCGTGGCCGATGT | 1590 |
| IRS4 | NM_003604 | 1 | X | - | 2555 | - | 0 | 37 | 1 | 0 | CGCGAATGCCATGATCCCTCACTGAAGGCTTTGAAGCTGCATCTACGCGTGGCCGATGT | 1591 |
| IRS4 | NM_003604 | 1 | X | - | 2590 | + | 0 | 37 | 1 | 0 | CGCGAATGCCTCTCAAAGCCTGAGATGGGGATCACCTTCAAAGACGCGTGGCCGATGT | 1592 |
| IRS4 | NM_003604 | 1 | X | - | 2625 | - | 0 | 37 | 1 | 0 | CGCGAATGCCTTAGCTTTATTCTTGGGGCTCATGATCTGAAGGACGCGTGGCCGATGT | 1593 |
| IRS4 | NM_003604 | 1 | X | - | 2660 | + | 0 | 37 | 1 | 0 | CGCGAATGCCGAGACCTAACCGACTTCTTTTATTACAAAAGGATACGCGTGGCCGATGT | 1594 |
| IRS4 | NM_003604 | 1 | X | - | 2695 | - | 0 | 37 | 1 | 0 | CGCGAATGCCATGTGTGGGCTTTTGTGGTTTTGGCTTGATTTTATACGCGTGGCCGATGT | 1595 |
| IRS4 | NM_003604 | 1 | X | - | 2730 | + | 0 | 37 | 1 | 0 | CGCGAATGCCGAGCAGAGAGAAGCTGACAGCTCTAGTGACTACGCGTGGCCGATGT | 1596 |
| IRS4 | NM_003604 | 1 | X | - | 2765 | - | 0 | 37 | 1 | 0 | CGCGAATGCCGTGTATTGCTCTCTCTTTTAGTGAAGTCCATGTTGACGCGTGGCCGATGT | 1597 |
| IRS4 | NM_003604 | 1 | X | - | 2800 | + | 0 | 37 | 1 | 0 | CGCGAATGCCCAGCTCCCTCTACTCAAGGACTACCAGATTCGTGGACGCGTGGCCGATGT | 1598 |
| IRS4 | NM_003604 | 1 | X | - | 2835 | - | 0 | 37 | 1 | 0 | CGCGAATGCCGAAAAGCTGACTGTCTGGGTTCAGCAATTATGCCACGCGTGGCCGATGT | 1599 |
| IRS4 | NM_003604 | 1 | X | - | 2870 | + | 0 | 37 | 1 | 0 | CGCGAATGCCTAATTATGTGAATGTTGAGTTTGGAGTGCCATTTCACGCGTGGCCGATGT | 1600 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| IRS4 | NM_003604 | 1 | X | - | 2905 | - | 0 | 37 | 1 | 0 | CGCGAATGCCTCTTAAAGATCTGAGAGGTCGT TTGCTGGATTTGACGCCTGGCCGATGT | 1601 |
| IRS4 | NM_003604 | 1 | X | - | 2940 | + | 0 | 37 | 1 | 0 | CGCGAATGCCGCTATACCACGTGCCAACCCTT ATCTCTGACAGACGCCGTGGCCGATGT | 1602 |
| IRS4 | NM_003604 | 1 | X | - | 2975 | + | 0 | 37 | 1 | 0 | CGCGAATGCCCACTGAGGGGAAGGGAGGAAG TGGCCACCTAGCAACGCGTGGCCGATGT | 1603 |
| IRS4 | NM_003604 | 1 | X | - | 3010 | + | 0 | 37 | 1 | 0 | CGCGAATGCCCTACAGGTAGCAATGCTATTGAG GAAGAGGGTGACACGCGTGGCCGATGT | 1604 |
| IRS4 | NM_003604 | 1 | X | - | 3045 | - | 0 | 37 | 1 | 0 | CGCGAATGCCGGTGTCATTGCTGAGTTGAAAAT TACTTCAATGTAACGCGTGGCCGATGT | 1605 |
| IRS4 | NM_003604 | 1 | X | - | 3080 | + | 0 | 37 | 1 | 0 | CGCGAATGCCAGCCATGCTCTTTGCTGACAGTG CCATTCGCTATGACGCGTGGCCGATGT | 1606 |
| IRS4 | NM_003604 | 1 | X | - | 3115 | - | 0 | 37 | 1 | 0 | CGCGAATGCCTGGGTCGACCACATAGATTCGAC CTGTTTCAGCATACGCCTGGCCGATGT | 1607 |
| IRS4 | NM_003604 | 1 | X | - | 3150 | + | 0 | 37 | 1 | 0 | CGCGAATGCCTTTTCTGAGTGCTGTATGGATATT TCTCTCTCCCACGCGTGGCCGATGT | 1608 |
| IRS4 | NM_003604 | 1 | X | - | 3185 | - | 0 | 37 | 1 | 0 | CGCGAATGCCGCCTAGCTACAGTGGTGGTTCA GAACATCGGCTGACGCCTGGCCGATGT | 1609 |
| IRS4 | NM_003604 | 1 | X | - | 3220 | + | 0 | 37 | 1 | 0 | CGCGAATGCCTGCTGCAGGAAGAAGAGCAGGA GAGAAGACGCCCAACGCGTGGCCGATGT | 1610 |
| IRS4 | NM_003604 | 1 | X | - | 3255 | - | 0 | 37 | 1 | 0 | CGCGAATGCCCTGGCTGCTGCAAAGAAACTTTG AGAACGGCTTTGACGCCTGGCCGATGT | 1611 |
| IRS4 | NM_003604 | 1 | X | - | 3290 | + | 0 | 37 | 1 | 0 | CGCGAATGCCAGCCGCTGTCTCTGCTTTTCCAAC AGACAGCCTGACGCCGTGGCCGATGT | 1612 |
| IRS4 | NM_003604 | 1 | X | - | 3325 | - | 0 | 37 | 1 | 0 | CGCGAATGCCGACAGCCGGGCGTGAGGATGGG GAAAGGTCTCTTCACGCCGTGGCCGATGT | 1613 |
| IRS4 | NM_003604 | 1 | X | - | 3360 | + | 0 | 37 | 1 | 0 | CGCGAATGCCGTTCGGCTGCTGCAGAGCCGACTTT AGCCCTCAGCCAACGCCTGGCCGATGT | 1614 |
| IRS4 | NM_003604 | 1 | X | - | 3395 | - | 0 | 37 | 1 | 0 | CGCGAATGCCGGGCTGCGCGGAGCGCCGAGGC CGCAGCTACAACTACGCCGTGGCCGATGT | 1615 |
| IRS4 | NM_003604 | 1 | X | - | 3430 | + | 0 | 37 | 1 | 0 | CGCGAATGCCGGGCATCGGCCGCCAGAGCCGCA GCTGCTGATTTACGCCGTGGCCGATGT | 1616 |
| IRS4 | NM_003604 | 1 | X | - | 3465 | - | 0 | 37 | 1 | 0 | CGCGAATGCCGCAACAGGTTGAAACCAGCGGGC AGAGGCGGAGTCACGCCGTGGCCGATGT | 1617 |
| IRS4 | NM_003604 | 1 | X | - | 3500 | + | 0 | 37 | 1 | 0 | CGCGAATGCCTAATGCTGCTGATGCCGAAGCAG TAAGGGGAGCCCCACGCCGTGGCCGATGT | 1618 |
| IRS4 | NM_003604 | 1 | X | - | 3535 | - | 0 | 37 | 1 | 0 | CGCGAATGCCGTGGGCTCCAGGGTTCGAGCCAC CGGCAACGTCTTACGCGTGGCCGATGT | 1619 |
| IRS4 | NM_003604 | 1 | X | - | 3570 | + | 0 | 37 | 1 | 0 | CGCGAATGCCAACCATCTGCAAACTTTGCCAG AGTTGATAACCACGCGTGGCCGATGT | 1620 |
| IRS4 | NM_003604 | 1 | X | - | 3605 | - | 0 | 37 | 1 | 0 | CGCGAATGCCCCGGAGCGGCAGCTGCCAGCGGCA GCCCCGCCAGCCACGCCGTGGCCGATGT | 1621 |
| IRS4 | NM_003604 | 1 | X | - | 3640 | + | 0 | 37 | 1 | 0 | CGCGAATGCCAACCACCCTCGCAGTCGCCGG GTGCCAAGACCCACGCCGTGGCCGATGT | 1622 |
| IRS4 | NM_003604 | 1 | X | - | 3675 | - | 0 | 37 | 1 | 0 | CGCGAATGCCGTTCGTCGTTGTCAGAATCT TCTCTCTCCGGACGCGTGGCCGATGT | 1623 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| IRS4 | NM_003604 | 1 | X | - | 3710 | + | 0 | 37 | 1 | 0 | CGCGAATGCCTCACGTGAGAATGGATTTGCCAGACGTGATAATCACGCGTGGCGATGT | 1624 |
| IRS4 | NM_003604 | 1 | X | - | 3745 | - | 0 | 37 | 1 | 0 | CGCGAATGCCCTAAAATTACCGACCTCTTTTGGGAGAGTCGAACTACGCGTGGCGATGT | 1625 |
| RET | NM_020630 | 1 | 10 | + | -34 | + | 0 | 37 | 1 | 0 | CGCGAATGCCGTCCCTCCAGCCGTGGCCCCAGCGCGCACGGGCGAACGCGTGGCGATGT | 1626 |
| RET | NM_020630 | 1 | 10 | + | 1 | - | 0 | 37 | 1 | 0 | CGCGAATGCCACGCAGCCCCGGCGGCACCGGACGTCGCCTTCGCCAACGCGTGGCGATGT | 1627 |
| RET | NM_020630 | 1 | 10 | + | 40 | + | 25 | 37 | 1 | 0 | CGCGAATGCCTGTTGCTGCTGCTGCCGCTGCTAGGCAAAGGTACGCGTGGCGATGT | 1628 |
| RET | NM_020630 | 1 | 10 | + | 71 | - | 0 | 37 | 1 | 0 | CGCGAATGCCCCCTGCCGGGAGCCGGCGGCCGGCAGAACTCACCTACGCGTGGCGATGT | 1629 |
| EPHA3 | NM_005233 | 14 | 3 | + | 0 | + | 0 | 37 | 1 | 0 | CGCGAATGCCGGAGGGAAGATCCAATCAGGTGGACATCACCAGAACGCGTGGCGATGT | 1630 |
| EPHA3 | NM_005233 | 14 | 3 | + | 35 | - | 0 | 37 | 1 | 0 | CGCGAATGCCCCGCTGGCTGACGTGAACTTGCGGTAGGCTATAGCTACGCGTGGCGATGT | 1631 |
| EPHA3 | NM_005233 | 14 | 3 | + | 70 | + | 0 | 37 | 1 | 0 | CGCGAATGCCATGTATGGAGTTATGGGATTGTTCTCTGGAGGTGACGCCTGGCGGATGT | 1632 |
| EPHA3 | NM_005233 | 14 | 3 | + | 105 | - | 0 | 37 | 1 | 0 | CGCGAATGCCGACATCTCCCAGTATGGTCTCTCTCCATAAGACATACGCGTGGCGATGT | 1633 |
| EPHA3 | NM_005233 | 14 | 3 | + | 140 | + | 0 | 37 | 1 | 0 | CGCGAATGCCCAATCAGAGATGTAAGTATTTGTGGTCTATGAGTTAACGCCTGGCGGATGT | 1634 |
| RB1 | NM_000321 | 2 | 13 | + | -6 | + | 0 | 37 | 1 | 0 | CGCGAATGCCTGTAGGCTTGAGTTTGAAGAAACAGAAGAACCTGACGCCGTGGCGGATGT | 1635 |
| RB1 | NM_000321 | 2 | 13 | + | 29 | - | 0 | 37 | 1 | 0 | CGCGAATGCCTGTATCTTTAATTTCTGACATAATGCAGTAAAATACGCGTGGCGGATGT | 1636 |
| RB1 | NM_000321 | 2 | 13 | + | 64 | + | 0 | 37 | 1 | 0 | CGCGAATGCCGATCATGTCAGAGAGAGCTTGGTTAACTTGGAACGCGTGGCGGATGT | 1637 |
| RB1 | NM_000321 | 2 | 13 | + | 99 | - | 0 | 37 | 1 | 0 | CGCGAATGCCTCCTTACCAATACTCCATCCACAGATGAAACTTTCACGCCGTGGCGGATGT | 1638 |
| RB1 | NM_000321 | 7 | 13 | + | -14 | + | 0 | 37 | 1 | 0 | CGCGAATGCCCATTTTTTTCAGGGAAGTATTACAAATGAAGACGCGTGGCGGATGT | 1639 |
| RB1 | NM_000321 | 7 | 13 | + | 21 | - | 0 | 37 | 1 | 0 | CGCGAATGCCACATAGACATTAACTGAAATGAAATCACCAGATCATACGCCGTGGCGGATGT | 1640 |
| RB1 | NM_000321 | 7 | 13 | + | 56 | + | 0 | 37 | 1 | 0 | CGCGAATGCCTTGACTATATTTTATTAAACTCTCACCTCCCATACGCGTGGCGGATGT | 1641 |
| RB1 | NM_000321 | 7 | 13 | + | 91 | - | 0 | 37 | 1 | 0 | CGCGAATGCCCAAATTAAATACTTACTATATGGTTCTTTGACAACACGCCGTGGCGGATGT | 1642 |
| GUCY2F | NM_001522 | 17 | X | - | 0 | + | 0 | 37 | 1 | 0 | CGCGAATGCCGTTTCACCGTTGTTTGAACCATCTACAATTCAATACGCCGTGGCGGATGT | 1643 |
| GUCY2F | NM_001522 | 17 | X | - | 35 | - | 0 | 37 | 1 | 0 | CGCGAATGCCCTATAGCATTATTCATGGCTTGTGCGATAAGTAAACGCGTGGCGGATGT | 1644 |
| GUCY2F | NM_001522 | 17 | X | - | 70 | + | 0 | 37 | 1 | 0 | CGCAGCCTGGTTACGCGTGGCGATGTGCCAAGAAATGGACAGGCTGGTGCT | 1645 |
| GUCY2F | NM_001522 | 17 | X | - | 105 | - | 0 | 37 | 1 | 0 | CGCGAATGCCTTGAATCCATGAACTGCATGTTTCTGGAATGCTGACGCGTGGCGCATGT | 1646 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit # BWA mismatch | Sequence with add-ons | SEQ ID NO: |
|---|---|---|---|---|---|---|---|---|---|---|---|
| GUCY2F | NM_001522 | 17 | X | - | 140 | + | 0 | 37 | 1 0 | CGCGAATGCCCCAGTTGATGAGGACAGATTCAAATGGAAATGCCTTTCAAGTTGGCGGATGT | 1647 |
| GUCY2F | NM_001522 | 17 | X | - | 175 | - | 0 | 37 | 1 0 | CGCGAATGCCTTTCAAGTTGGTGTCCAGGATTACATATTCTGAAAACGCCGTGGCCGATGT | 1648 |
| GUCY2F | NM_001522 | 17 | X | - | 210 | + | 0 | 37 | 1 0 | CGCGAATGCCAATGGGAACTCCATAGCACCTACACTGTGACATACGCCGTGGCCGATGT | 1649 |
| GUCY2F | NM_001522 | 17 | X | - | 245 | - | 0 | 37 | 1 0 | CGCGAATGCCTAGGGGTCCCTCCGAAACGTAGCAGCTCCATTCCACGCGTGGCCGATGT | 1650 |
| GUCY2F | NM_001522 | 17 | X | - | 280 | + | 0 | 37 | 1 0 | CGCGAATGCCTTCACTTCCCTGGTGGCAGGCCCCCTAGAGCAGATACGCCGTGGCCGATGT | 1651 |
| GUCY2F | NM_001522 | 17 | X | - | 315 | - | 0 | 37 | 1 0 | CGCGAATGCCTGCAGATCTTCCCTTCTGCAAACCAGCATTTTGCACGCGTGGCCGATGT | 1652 |
| GUCY2F | NM_001522 | 17 | X | - | 350 | + | 0 | 37 | 1 0 | CGCGAATGCCTGAGGTAAGGAATGCAAAATCACTAGTAGTCAATACGCCGTGGCCGATGT | 1653 |
| EPHA4 | NM_004438 | 13 | 2 | - | -8 | + | 0 | 37 | 1 0 | CGCGAATGCCTCTAACAGCACCATCATCCATTGCTTTGGTCCAGGACGCCGTGGCCGATGT | 1654 |
| EPHA4 | NM_004438 | 13 | 2 | - | 27 | - | 0 | 37 | 1 0 | CGCGAATGCCAGCCAGTGCCACACTGTATCTTGTGACTTCTTTAGACGCCGTGGCCGATGT | 1655 |
| EPHA4 | NM_004438 | 13 | 2 | - | 62 | + | 0 | 37 | 1 0 | CGCGAATGCCTGCTGGAACCAGATCGGCCCAATGGGTAATCCTACGCCGTGGCCGATGT | 1656 |
| EPHA4 | NM_004438 | 13 | 2 | - | 97 | - | 0 | 37 | 1 0 | CGCGAATGCCGTAATACCTTCTCATAATACTTGACTTCATATTCCACGCGTGGCCGATGT | 1657 |
| GUCY2F | NM_001522 | 15 | X | - | -22 | + | 0 | 37 | 1 0 | CGCGAATGCCTCTGATTTCATGTTTGTTTTAGCGTCGTATAAATACGCGTGGCCGATGT | 1658 |
| GUCY2F | NM_001522 | 15 | X | - | 13 | - | 0 | 37 | 1 0 | CGCGAATGCCAGAATTCTATTGGTCCTTTGATCAACTGGATTTTACGCGTGGCCGATGT | 1659 |
| GUCY2F | NM_001522 | 15 | X | - | 48 | + | 0 | 37 | 1 0 | CGCGAATGCCACTGACTTTGGAGGATGTAACGTTTATCAATCCCCACGCCGTGGCCGATGT | 1660 |
| GUCY2F | NM_001522 | 15 | X | - | 83 | - | 0 | 37 | 1 0 | CGCGAATGCCAAAGAGGATATCTCCTTACCTTACTGCCAAAGTACGCCGTGGCCGATGT | 1661 |
| GUCY2F | NM_001522 | 12 | X | - | 0 | + | 0 | 37 | 1 0 | CGCGAATGCCATGAAGGACTTGCGTCATGAGAATATTAACCCTTTACGCCGTGGCCGATGT | 1662 |
| GUCY2F | NM_001522 | 12 | X | - | 35 | - | 0 | 37 | 1 0 | CGCGAATGCCTGCAAACATCCCCGAATCATAGAAGAAACCCAATACGCCGTGGCCGATGT | 1663 |
| GUCY2F | NM_001522 | 12 | X | - | 70 | + | 0 | 37 | 1 0 | CGCGAATGCCTTGTGACAGAAATCTGTTCCCGAGGGAGCCTAGAAACGCCGTGGCCGATGT | 1664 |
| GUCY2F | NM_001522 | 12 | X | - | 105 | - | 0 | 37 | 1 0 | CGCGAATGCCCAGTCAAGTTTCACATCTTGATTTGTCAGTATGTCACGCCGTGGCCGATGT | 1665 |
| GUCY2F | NM_001522 | 12 | X | - | 140 | + | 0 | 37 | 1 0 | CGCGAATGCCGATGTTTAAATCATCACTCTTGCTGGATCTCATAAACGCCGTGGCCGATGT | 1666 |
| GUCY2F | NM_001522 | 12 | X | - | 175 | - | 0 | 37 | 1 0 | CGCGAATGCCAAAATCCAAGATTTCCTCAGTCTTCCCATTAACCTTACGCGGTGGCCGATGT | 1667 |
| KSR2 | NM_173598 | 9 | 12 | - | -34 | + | 0 | 37 | 1 0 | CGCGAATGCCTTTTTTTCTGAGTGTTCAATCTCTGTTTTCAGACGCGTGGCCGATGT | 1668 |
| KSR2 | NM_173598 | 9 | 12 | - | 1 | - | 0 | 37 | 1 0 | CGCGAATGCCGCGCCCGGGTCCGGCGTCCGGCACCGGCCACCAACGCGTGGCCGATGT | 1669 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| KSR2 | NM_173598 | 9 | 12 | - | 36 | + | 0 | 37 | 1 0 | CGCGAATGCCCCCAGTGCATCCTGCATCCGGTG ACCTCGAATCCAACGCGTGGCGGATGT | 1670 |
| KSR2 | NM_173598 | 9 | 12 | - | 71 | - | 0 | 37 | 1 0 | CGCGAATGCCGGGAAAGGGGAAGATGTCTCTG TCTCACTTACATACGCGTGGCGGATGT | 1671 |
| RBBP8 | NM_002894 | 16 | 18 | + | -35 | + | 0 | 37 | 1 0 | CGCGAATGCCACATTAGTTTGTAATGTGCATGT TTTATTTATAGACGCGTGGCGGATGT | 1672 |
| RBBP8 | NM_002894 | 16 | 18 | + | 0 | - | 0 | 37 | 1 0 | CGCGAATGCCTTTCTGCTTGACTTTGTCTTGTTT ATCACCATGAGACGCGTGGCGGATGT | 1673 |
| RBBP8 | NM_002894 | 16 | 18 | + | 35 | + | 0 | 37 | 1 0 | CGCGAATGCCGCGTTTGTGGAGCCGTATTTTAA AGGTGATGAAAGACGCGTGGCGGATGT | 1674 |
| RBBP8 | NM_002894 | 16 | 18 | + | 70 | - | 0 | 37 | 1 0 | CGCGAATGCCAGTCACATTGCTGGTATAAATAA AAACCAACTTACACGCGTGGCGGATGT | 1675 |
| PDGFRA | NM_006206 | 18 | 4 | + | -8 | + | 0 | 37 | 1 0 | CGCGAATGCCCCATGCAGTGTGTCCACCGTGAT CTGGCTGCTCGCACGCGTGGCGGATGT | 1676 |
| PDGFRA | NM_006206 | 18 | 4 | + | 27 | - | 0 | 37 | 1 0 | CGCGAATGCCATCTTCACAATTTTCCTTGTGCC AGGAGGACGTTACGCGTGGCGGATGT | 1677 |
| PDGFRA | NM_006206 | 18 | 4 | + | 62 | + | 0 | 37 | 1 0 | CGCGAATGCCCTGTGACTTTGGCCTGGCCAGAG ACATCATGCATGACGCGTGGCGGATGT | 1678 |
| PDGFRA | NM_006206 | 18 | 4 | + | 97 | - | 0 | 37 | 1 0 | CGCGAATGCCAGGACGTACACTGCCTTTCGACA CATAGTTCGAATACGCGTGGCGGATGT | 1679 |
| RPS6KA1 | NM_002953 | 22 | 1 | + | -8 | + | 0 | 37 | 1 0 | CGCGAATGCCTCTTTCAGGGAGCCATGCTGCC ACGTACTTCCGAACGCGTGGCGGATGT | 1680 |
| RPS6KA1 | NM_002953 | 22 | 1 | + | 27 | - | 0 | 37 | 1 0 | CGCGAATGCCGGCTTCAGCTCGGGGGTGGGCTT GGAGCTGTTGAGACGCGTGGCGGATGT | 1681 |
| RPS6KA1 | NM_002953 | 22 | 1 | + | 62 | + | 0 | 37 | 1 0 | CGCGAATGCCCATCGAGTCATCCATCCTGGCCC AGCGGCGAGTGAACGCGTGGCGGATGT | 1682 |
| RPS6KA1 | NM_002953 | 22 | 1 | + | 97 | - | 0 | 37 | 1 0 | CGCGAATGCCCCTGGTCCTCACAGGGTGGTGG ATGGCAACTTCCACGCGTGGCGGATGT | 1683 |
| EPHA3 | NM_005233 | 1 | 3 | + | -26 | + | 0 | 37 | 1 0 | CGCGAATGCCACTGCCCCTCTGCACCAGC AACATGGATTGTACGCGTGGCGGATGT | 1684 |
| EPHA3 | NM_005233 | 1 | 3 | + | 9 | - | 0 | 37 | 1 0 | CGCGAATGCCACAGAGCAGCTGAGAAGGAGA GGATGGAGAGCTGACGCCTGGCCGATGT | 1685 |
| EPHA3 | NM_005233 | 1 | 3 | + | 44 | + | 0 | 37 | 1 0 | CGCGAATGCCTCTCGACAGCTTCGGGAACTGA TTCCGCAGCTTACGCGTGGCGGATGT | 1686 |
| EPHA3 | NM_005233 | 1 | 3 | + | 79 | - | 0 | 37 | 1 0 | CGCGAATGCCTCCGTGCGTCGCGGTACCTGGCT TACTTCATTGGACGCGTGGCGGATGT | 1687 |
| PIK3CA | NM_006218 | 16 | 3 | + | -9 | + | 0 | 37 | 1 0 | CGCGAATGCCATTTTAAAGGCTTGAAGAGTGTC GAATTATGTCCTACGCGTGGCGGATGT | 1688 |
| PIK3CA | NM_006218 | 16 | 3 | + | 26 | - | 0 | 37 | 1 0 | CGCGAATGCCGTTCTCCCAATTCAACCACAGTG GCCTTTTGCAGACGCGTGGCGGATGT | 1689 |
| PIK3CA | NM_006218 | 16 | 3 | + | 61 | + | 0 | 37 | 1 0 | CGCGAATGCCCCAGACATCATGTCAGAGTTACT GTTTCAGACAAACGCGTGGCGGATGT | 1690 |
| PIK3CA | NM_006218 | 16 | 3 | + | 96 | - | 0 | 37 | 1 0 | CGCGAATGCCCTTCCTTACCATCCCCATTTTTAA AGATGATCTCAACGCGTGGCGGATGT | 1691 |
| EPHB1 | NM_004441 | 4 | 3 | + | 0 | + | 0 | 37 | 1 0 | CGCGAATGCCCTTGCCCTGCAGGGACATTCAAG GCCAGCCAGGAAACGCGTGGCGGATGT | 1692 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit mismatch | # BWA Sequence with add-ons | SEQ ID NO: |
|---|---|---|---|---|---|---|---|---|---|---|---|
| EPHB1 | NM_004441 | 4 | 3 | + | 35 | - | 0 | 37 | 1 | 0 | CGCGAATGCCCGCTGTTGGAGGGGCAGTGGGA GCAGCCTTCAGCACGCGTGGCGCGATGT | 1693 |
| EPHB1 | NM_004441 | 4 | 3 | + | 70 | + | 0 | 37 | 1 | 0 | CGCGAATGCCCTCCCTGCAGAGGCGTCTCCCA TCTGCACCTGTCACGCGTGGCGCGATGT | 1694 |
| EPHB1 | NM_004441 | 4 | 3 | + | 105 | - | 0 | 37 | 1 | 0 | CGCGAATGCCTGGAGGTCAAAGTCCGCTCGT AATAACCGTCACGCCGTGGCGCGATGT | 1695 |
| EPHB1 | NM_004441 | 4 | 3 | + | 140 | + | 0 | 37 | 1 | 0 | CGCGAATGCCGAAGTGGCATGCACTAGTAAGTG TCTAGTAATGGCACGCGTGGCGCGATGT | 1696 |
| KSR2 | NM_173598 | 2 | 12 | - | -3 | + | 0 | 37 | 1 | 0 | CGCGAATGCCTAGGACATTCTTCTTCTTCTGCTGG GCCTTTGAACAACGCGTGGCGGATGT | 1697 |
| KSR2 | NM_173598 | 2 | 12 | - | 32 | - | 0 | 37 | 1 | 0 | CGCGAATGCCTGTCCATGAGCTTGGTGAAGGTA GGTCTCTCTTCTACGCGTGGCGCGATGT | 1698 |
| KSR2 | NM_173598 | 2 | 12 | - | 67 | + | 0 | 37 | 1 | 0 | CGCGAATGCCTGCTGGAGAAACTGCCAAAGCGA AACCGTCGCCTGACGCGTGGCGCGATGT | 1699 |
| KSR2 | NM_173598 | 2 | 12 | - | 102 | - | 0 | 37 | 1 | 0 | CGCGAATGCCTACTCTGCAGACTTCCAGAAATG TCCAGGGTGAGAACGCCGTGGCGGATGT | 1700 |
| KSR2 | NM_173598 | 2 | 12 | - | 0 | + | 0 | 37 | 1 | 0 | CGCGAATGCCGAGGCAACGCTTTCAAACAAGAC TGGACCATCCAGACGCCGTGGCGGATGT | 1701 |
| KSR2 | NM_173598 | 17 | 12 | - | 35 | - | 0 | 37 | 1 | 0 | CGCGAATGCCGGATTGTCTCCTTCCCCGTCT GTCGTGGGCCAACGCGTGGCGGATGT | 1702 |
| KSR2 | NM_173598 | 17 | 12 | - | 70 | + | 0 | 37 | 1 | 0 | CGCGAATGCCCGTGTGCCCCGGAGCCCACCC CGTGGATCCGCAACGCGTGGCGGATGT | 1703 |
| KSR2 | NM_173598 | 17 | 12 | - | 105 | - | 0 | 37 | 1 | 0 | CGCGAATGCCCTTGACGGGACCCTGGGGCTCT GGGAGAGATGGGACGCCGTGGCGGATGT | 1704 |
| KSR2 | NM_173598 | 17 | 12 | - | 140 | + | 0 | 37 | 1 | 0 | CGCGAATGCCTGCGTCCAGCACTATTGTCACAC CAGCCCCACTCCACGCGTGGCGGATGT | 1705 |
| KSR2 | NM_173598 | 17 | 12 | - | 175 | - | 0 | 37 | 1 | 0 | CGCGAATGCCTAAGCCTTGTCACGTGGGTGTAC ACAGGGGCCCCGACGCGTGGCGGATGT | 1706 |
| KSR2 | NM_173598 | 17 | 12 | - | 210 | + | 0 | 37 | 1 | 0 | CGCGAATGCCCCGTGGACGCCTACCCGGCTTG TGCCCGCCCCGACGCGTGGCGGATGT | 1707 |
| KSR2 | NM_173598 | 17 | 12 | - | 245 | - | 0 | 37 | 1 | 0 | CGCGAATGCCGATGGGGCAGGGAACCGTGGC CCGACTCCAGTGCACGCGTGGCCGATGT | 1708 |
| KSR2 | NM_173598 | 17 | 12 | - | 280 | + | 0 | 37 | 1 | 0 | CGCGAATGCCGCCCCGGAGCGGCCACGCGGTC GCACCCCCGCACGCGTGGCGGATGT | 1709 |
| KSR2 | NM_173598 | 17 | 12 | - | 315 | - | 0 | 37 | 1 | 0 | CGCGAATGCCCGGCGGGTCACGGTGGTGACGA TGTTGGGGGTGCACGCGTGGCGGATGT | 1710 |
| KSR2 | NM_173598 | 17 | 12 | - | 350 | + | 0 | 37 | 1 | 0 | CGCGAATGCCGGCACGCCGCCCATGAGGAAGA AGAACAAGCTGAAACGCGTGGCGGATGT | 1711 |
| KSR2 | NM_173598 | 17 | 12 | - | 385 | - | 0 | 37 | 1 | 0 | CGCGAATGCCGTTTTCGGAGAGGGCGGTGGG GTCCCCGGGGCATACGCGTGGCGGATGT | 1712 |
| KSR2 | NM_173598 | 17 | 12 | - | 420 | + | 0 | 37 | 1 | 0 | CGCGAATGCCTGATACACTTGATCCCGGATTC ACCGCGTGCATACGCGTGGCGGATGT | 1713 |
| KSR2 | NM_173598 | 17 | 12 | - | 455 | - | 0 | 37 | 1 | 0 | CGCGAATGCCCGTGCCCAGCTGGAACTCGTG GGATTTGCTCCGACGCGTGGCGGATGT | 1714 |
| KSR2 | NM_173598 | 17 | 12 | - | 490 | + | 0 | 37 | 1 | 0 | CGCGAATGCCCGTGGACGAGGCCCACACGCCCA AGTGAGTGCGATACGCGTGGCGGATGT | 1715 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| KSR2 | NM_173598 | 10 | 12 | - | -49 | + | 0 | 37 | 1 | 0 | CGCGAATGCCCGATGTCTCCCTGGGACACTCA CTTTGATGTTTACGCGTGGCCGATGT | 1716 |
| KSR2 | NM_173598 | 10 | 12 | - | -14 | - | 0 | 37 | 1 | 0 | CGCGAATGCCTGTATTTGTAGTAGTGGGATGCTT GCAAAAGAAGACGCGTGGCCGATGT | 1717 |
| KSR2 | NM_173598 | 10 | 12 | - | 21 | + | 0 | 37 | 1 | 0 | CGCGAATGCCAGCAGCAGTTCATCTTCCCAGT GAGTTTCATGTGACGCGTGGCCGATGT | 1718 |
| KSR2 | NM_173598 | 10 | 12 | - | 56 | - | 0 | 37 | 1 | 0 | CGCGAATGCCCAGCGGGCTTGTTCAGAAGGGG CTGCTTCCAGCTACGCGTGGCCGATGT | 1719 |
| EPHA3 | NM_005233 | 8 | 3 | + | -18 | + | 0 | 37 | 1 | 0 | CGCGAATGCCTTCTCTTCAACCTCACAGCTTTCT CCATCTCTGGTACGCGTGGCCGATGT | 1720 |
| EPHA3 | NM_005233 | 8 | 3 | + | 17 | - | 0 | 37 | 1 | 0 | CGCGAATGCCGTGAAATGCCGATCATGACCAC TTGGCTACTTTCACGCGTGGCCGATGT | 1721 |
| EPHA3 | NM_005233 | 8 | 3 | + | 52 | + | 0 | 37 | 1 | 0 | CGCGAATCCGGCAGTAGCAATTATTCCTCA CTGTTGTCATCTACGCGTGGCCGATGT | 1722 |
| EPHA3 | NM_005233 | 8 | 3 | + | 87 | - | 0 | 37 | 1 | 0 | CGCGAATGCCAAACAGACTGTGAACTCACCTCC CAATCAAAACATACGCGTGGCCGATGT | 1723 |
| KSR2 | NM_173598 | 19 | 12 | - | 0 | + | 0 | 37 | 1 | 0 | CCGGCAGCTGTCACGCCGTGGCCGATGT CGCGAATGCCAGCAAGCTGGTGAAGTACTTCAG | 1724 |
| KSR2 | NM_173598 | 19 | 12 | - | 35 | - | 0 | 37 | 1 | 0 | CGCGAATGCCCGTTGCCGCTCCTGCAAGCTACC TTCTTTTTGCAGACGCGTGGCCGATGT | 1725 |
| KSR2 | NM_173598 | 19 | 12 | - | 70 | + | 0 | 37 | 1 | 0 | CGCGAATGCCCGGAGCTTGACGCGTGGCCGATGT CTACGGCACTGACGCCTGGCCGATGT | 1726 |
| KSR2 | NM_173598 | 19 | 12 | - | 105 | - | 0 | 37 | 1 | 0 | CGCGAATGCCTCCAGGACCCTCCTTGCCACATC GACGATTCGGAAACGCGTGGCCGATGT | 1727 |
| KSR2 | NM_173598 | 19 | 12 | - | 140 | + | 0 | 37 | 1 | 0 | CGCGAATGCCGGTGACCTGGACGCGTGGGGCCCCTGTGT CCCCTGCCCCTTACGCGTGGCCGATGT | 1728 |
| NTRK3 | NM_001012338 | 1 | 15 | - | 0 | + | 0 | 37 | 1 | 0 | CGCGAATGCCGTCATTGAGTGCATTACCCAAGG TCGTGTTTTGGAACGCGTGGCCGATGT | 1729 |
| NTRK3 | NM_001012338 | 1 | 15 | - | 35 | - | 0 | 37 | 1 | 0 | CGCGAATGCCCATCGTACACCTCTTTGGGCAG ACTCGGGGCCGCACGCGTGGCCGATGT | 1730 |
| NTRK3 | NM_001012338 | 1 | 15 | - | 70 | + | 0 | 37 | 1 | 0 | CGCGAATGCCTCATGCTGGGGTGCTGGCCAGAGG GAACCACAGCAGACGCCTGGCCGATGT | 1731 |
| NTRK3 | NM_001012338 | 1 | 15 | - | 105 | - | 0 | 37 | 1 | 0 | CGCGAATGCCTGGAGGATTTTGTAGATCTCCTTG ATGTTCAACGACGCGTGGCCGATGT | 1732 |
| NTRK3 | NM_001012338 | 1 | 15 | - | 140 | + | 0 | 37 | 1 | 0 | CGCGAATGCCTGCTTTGGGAAGGCCACCCCAA TCTACCTGGACACGCGTGGCCGATGT | 1733 |
| NTRK3 | NM_001012338 | 1 | 15 | - | 175 | - | 0 | 37 | 1 | 0 | CGCGAATGCCTGAATTCATGACCACCAGCCACC ACTAGCCAAGAAACGCGTGGCCGATGT | 1734 |
| CENTG1 | NM_014770 | 16 | 12 | - | 0 | + | 0 | 37 | 1 | 0 | CGCGAATGCCGTGTCTGGCATGCCAGGAG TGGGAAGTCATCACGCGTGGCCGATGT | 1735 |
| CENTG1 | NM_014770 | 16 | 12 | - | 35 | - | 0 | 37 | 1 | 0 | CGCGAATGCCCCTGGTATGAGCCAGTCAGGAAT CGGTGGATGAGCACGCGTGGCCGATGT | 1736 |
| CENTG1 | NM_014770 | 16 | 12 | - | 70 | + | 0 | 37 | 1 | 0 | CGCGAATGCCTGCTGAGAAGACAGAGAGTGA GTTCTGAAGAGCCCACGCGTGGCCGATGT | 1737 |
| CENTG1 | NM_014770 | 16 | 12 | - | 105 | - | 0 | 37 | 1 | 0 | CGCGAATGCCTCCTGGATCCCTGACCCCAATGG TTAGCTTACTATACGCGTGGCCGATGT | 1738 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit mismatch | # BWA mismatch | Sequence with add-ons | SEQ ID NO: |
|---|---|---|---|---|---|---|---|---|---|---|---|---|
| CENTG1 | NM_014770 | 16 | 12 | - | 140 | + | 0 | 37 | 1 | 0 | CGCGAATGCCGTGAGATTCAATGATTAGGCAGTGTGGAGACCAGGACGCGTGGCGCAGT | 1739 |
| CENTG1 | NM_014770 | 16 | 12 | - | 175 | - | 0 | 37 | 1 | 0 | CGCGAATGCCCAGTGCTTTTGCTATTATGGCCTCATCCTTCCCACGCGTGGCGATGT | 1740 |
| CENTG1 | NM_014770 | 16 | 12 | - | 210 | + | 0 | 37 | 1 | 0 | CGCGAATGCCGAGCATGGGAGGTTTGGTGACCTGTCACCTCTGAACGCGTGGCGATGT | 1741 |
| CENTG1 | NM_014770 | 16 | 12 | - | 245 | - | 0 | 37 | 1 | 0 | CGCGAATGCCCTCACCTGTCCAGAAGAGTTGAAGGGGTAACAGGACGCGTGGCGATGT | 1742 |
| CENTG1 | NM_014770 | 16 | 12 | - | 280 | + | 0 | 37 | 1 | 0 | CGCGAATGCCCAGTACAAGAAAGAAATGTTGGTGGATGGACAGACACGCGTGGCGATGT | 1743 |
| CENTG1 | NM_014770 | 16 | 12 | - | 315 | - | 0 | 37 | 1 | 0 | CGCGAATGCCGTGCCCCAGCTTCCTCTCGGATTAGCACCAGATGTACGCGTGGCGATGT | 1744 |
| CENTG1 | NM_014770 | 16 | 12 | - | 350 | + | 0 | 37 | 1 | 0 | CGCGAATGCCCTGATGCCAAGGTGAGGGTGGAGGTGGTGGGGACACGCGTGGCGATGT | 1745 |
| CENTG1 | NM_014770 | 16 | 12 | - | 385 | - | 0 | 37 | 1 | 0 | CGCGAATGCCCCCTCCTTTGCCAGTGCTGACCCAGCCAGCCTACGCGTGGCGATGT | 1746 |
| CENTG1 | NM_014770 | 16 | 12 | - | 420 | + | 0 | 37 | 1 | 0 | CGCGAATGCCGCTCTGGTTTCCCAGGTCTTCATCTGGATTGGGTCACGCGTGGCGATGT | 1747 |
| CENTG1 | NM_014770 | 16 | 12 | - | 455 | - | 0 | 37 | 1 | 0 | CGCGAATGCCGAGCAAATGGAAAGTCAGACAGGTCTACTTCCTTGACGCGTGGCGATGT | 1748 |
| CENTG1 | NM_014770 | 16 | 12 | - | 490 | + | 0 | 37 | 1 | 0 | CGCGAATGCCCCTCACTCCCCGCAAGTTCTCAGGCTGGGCAGATGACGCGTGGCGATGT | 1749 |
| CENTG1 | NM_014770 | 16 | 12 | - | 525 | - | 0 | 37 | 1 | 0 | CGCGAATGCCGTTCTCATCCTCCAGGCTGAAGACGAAGATCACAGACGCGTGGCGATGT | 1750 |
| CENTG1 | NM_014770 | 16 | 12 | - | 560 | + | 0 | 37 | 1 | 0 | CGCGAATGCCAGTTTCCAGGCTGTGAGCCGTCTCCATGGGCAGTACGCGTGGCGATGT | 1751 |
| CENTG1 | NM_014770 | 16 | 12 | - | 595 | - | 0 | 37 | 1 | 0 | CGCGAATGCCCAGGCCTCCTGTCCCTCCCCGCGAAGGGAACTCACGCGTGGCGATGT | 1752 |
| CENTG1 | NM_014770 | 16 | 12 | - | 630 | + | 0 | 37 | 1 | 0 | CGCGAATGCCCCTTGGCACTGGTGGGGACACAAGGTAAGGAGGGGACGCGTGGCGATGT | 1753 |
| RPS6KA1 | NM_002953 | 3 | 1 | + | -12 | + | 0 | 37 | 1 | 0 | CGCGAATGCCTCCCTCCATCAGGATGAGGGCGTCCTCAAGGAGATACGCGTGGCGATGT | 1754 |
| RPS6KA1 | NM_002953 | 3 | 1 | + | 23 | - | 0 | 37 | 1 | 0 | CGCGAATGCCTCTCAGAGCCAGCCTTGACGTGGTGCCTGATGGAGACGCGTGGCGATGT | 1755 |
| RPS6KA1 | NM_002953 | 3 | 1 | + | 58 | + | 0 | 37 | 1 | 0 | CGCGAATGCCAGGCTGATCCATCCCATTTCGAGCTCCTCAAGGTTACGCGTGGCGATGT | 1756 |
| RPS6KA1 | NM_002953 | 3 | 1 | + | 93 | - | 0 | 37 | 1 | 0 | CGCGAATGCCCATCTGAGATGCACAATAAAACAGTCCCTGGCCAGACGCGTGGCGATGT | 1757 |
| PIK3CA | NM_006218 | 14 | 3 | + | 0 | + | 0 | 23 | 1 | 1 | CGCGAATGCCATCTGAGATGCACAATAAAACAGTTAGCCAGGTACGCGTGGCGATGT | 1758 |
| PIK3CA | NM_006218 | 14 | 3 | + | 35 | - | 0 | 0 | 2 | 0 | CGCGAATGCCACATGCCACGACAATAGGACTCCAAAAGCAGCCAAACGCGTGGCGATGT | 1759 |
| PIK3CA | NM_006218 | 14 | 3 | + | 70 | + | 0 | 0 | 2 | 0 | CGCGAATGCCGGATGTATTTGAAGCACCTGAATAGGCAAGTCGACGCGTGGCGATGT | 1760 |
| PIK3CA | NM_006218 | 14 | 3 | + | 105 | - | 0 | 23 | 1 | 1 | CGCGAATGCCGAATGTCAGTTAAGTTAATGAGCTTTTCCATTGCCACGCGTGGCGATGT | 1761 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| PIK3CA | NM_006218 | 14 | 3 | + | 139 | + | 0 | 37 | 1 | 0 | CGCGAATGCCCTCAAACAGGAGGAAGAAGGATGAACACAAAAGGTACGCGTGGCGATGT | 1762 |
| EPHA7 | NM_004440 | 7 | 6 | − | 0 | + | 0 | 37 | 1 | 0 | CGCGAATGCCGAGAATTCGGTGAAGTCTGCAGTGGCCGTTTGAAAACGCGGCGGATGT | 1763 |
| EPHA7 | NM_004440 | 7 | 6 | − | 35 | − | 0 | 37 | 1 | 0 | CGCGAATGCCTTTATGGCTACTGCAACATCTCTTTTCCCTGAAGACGCGTGGCGATGT | 1764 |
| EPHA7 | NM_004440 | 7 | 6 | − | 70 | + | 0 | 37 | 1 | 0 | CGCGAATGCCAACCCTGAAAGTTGGTTACACAGAAAAACAAAGGAACGCGTGGCGATGT | 1765 |
| EPHA7 | NM_004440 | 7 | 6 | − | 105 | − | 0 | 37 | 1 | 0 | CGCGAATGCCTCCCCATGATGCTTGCTTCACACAAAAGTCTCACGCGTGGCGATGT | 1766 |
| EPHA7 | NM_004440 | 7 | 6 | − | 140 | + | 0 | 37 | 1 | 0 | CGCGAATGCCTTTGACCACCCGAATGTTGTCCATTTGGAAGGGTACGCGTGGCGATGT | 1767 |
| EPHA7 | NM_004440 | 7 | 6 | − | 175 | − | 0 | 37 | 1 | 0 | CGCGAATGCCAATAAAGATATAACCAATATCTACCTCTTGTAACAACGCGTGGCGATGT | 1768 |
| CENTG1 | NM_014770 | 18 | 12 | − | 0 | + | 0 | 37 | 1 | 0 | CGCGAATGCCATGCATGCCCAGAGGCAGTTCGTTGTAGCTGCAGTACGCGTGGCGATGT | 1769 |
| CENTG1 | NM_014770 | 18 | 12 | − | 35 | − | 0 | 37 | 1 | 0 | CGCGAATGCCGTTGGCCACCTCATGTCGTCTGACTTCGCTCTCACGCGTGGCGATGT | 1770 |
| CENTG1 | NM_014770 | 18 | 12 | − | 70 | + | 0 | 37 | 1 | 0 | CGCGAATGCCAGGCTCTAAACCGCCTCAGGAAGCTGGCAGAGAACGCGTGGCGATGT | 1771 |
| CENTG1 | NM_014770 | 18 | 12 | − | 105 | − | 0 | 37 | 1 | 0 | CGCGAATGCCCTGGATGCTGTCCTGAGTTCGGGTCGTCCACGCCGTGGCGATGT | 1772 |
| CENTG1 | NM_014770 | 18 | 12 | − | 140 | + | 0 | 37 | 1 | 0 | CGCGAATGCCCTCATTGACACAGCATTCGAGGTAAGAGAAAGGTCAACGCGTGGCGATGT | 1773 |
| IRS1 | NM_005544 | 2 | 2 | − | 0 | + | 0 | 37 | 1 | 0 | CGCGAATGCCATGGCGAGCCCTCGGAGAGCGATGGCTTCTCGGAACGCCTGGCGATGT | 1774 |
| IRS1 | NM_005544 | 2 | 2 | − | 35 | − | 0 | 37 | 1 | 0 | CGCGAATGCCTCTTGGGTTTGCCAGGTAGCCCACCTTGCCCACGACGCGTGGCGATGT | 1775 |
| IRS1 | NM_005544 | 2 | 2 | − | 70 | + | 0 | 37 | 1 | 0 | CGCGAATGCCGATGCACAAACGCTTCTTCGTACTGCGCGGCCACGCGTGGCGATGT | 1776 |
| IRS1 | NM_005544 | 2 | 2 | − | 105 | − | 0 | 37 | 1 | 0 | CGCGAATGCCTAGTACTCGAGGCGCGCCGGGCCCCAGCCTCGCTACGCCTGGCGATGT | 1777 |
| IRS1 | NM_005544 | 2 | 2 | − | 140 | + | 0 | 37 | 1 | 0 | CGCGAATGCCCGAGAACGAAGAAGAAGTGGCGGCACAAGTCGAGCGCCGTGGCGATGT | 1778 |
| IRS1 | NM_005544 | 2 | 2 | − | 175 | − | 0 | 37 | 1 | 0 | CGCGAATGCCGAAGCAGCTTCAAGGGGATCGAGCGTTTGGGGGACGCGTGGCGATGT | 1779 |
| IRS1 | NM_005544 | 2 | 2 | − | 210 | + | 0 | 37 | 1 | 0 | CGCGAATGCCAACATCAACAAGCGGGCTGACTCCAAGAACAAGCACGCGTGGCGATGT | 1780 |
| IRS1 | NM_005544 | 2 | 2 | − | 245 | − | 0 | 37 | 1 | 0 | CGCGAATGCCAAAGTGCTCGTTCCCGGGTGTAGAGAGCCCACCAGGACGCGTGGCGATGT | 1781 |
| IRS1 | NM_005544 | 2 | 2 | − | 280 | + | 0 | 37 | 1 | 0 | CGCGAATGCCCCATCGCGGCGGACAGCGAGGCCGAGCAAGACAGCACGCGTGGCGATGT | 1782 |
| IRS1 | NM_005544 | 2 | 2 | − | 315 | − | 0 | 37 | 1 | 0 | CGCGAATGCCCGACGGTTGCAGCTGTAGGAGAGCCTGGTACCAACGCGTGGCGATGT | 1783 |
| IRS1 | NM_005544 | 2 | 2 | − | 350 | + | 0 | 37 | 1 | 0 | CGCGAATGCCTAAGGGCCACCACGACGAGCTGCGGCCCTGGGACGCGTGGCGATGT | 1784 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| IRS1 | NM_005544 | 2 | 2 | − | 385 | − | 0 | 37 | 1 | 0 | CGCGAATGCCGGAGCTGCCGCTGCAGCTGCCCCCACCACCTCCCGACGCGTGGCGCGATGT | 1785 |
| IRS1 | NM_005544 | 2 | 2 | − | 420 | + | 0 | 37 | 1 | 0 | CGCGAATGCCGGCCTTGTTGTGAGGCTGGGGAGGACTTGAGCTACGGACGCGTGGCGGATGT | 1786 |
| IRS1 | NM_005544 | 2 | 2 | − | 455 | − | 0 | 37 | 1 | 0 | CGCGAATGCCAGACCCTTTGAATGCGGGTCCTGGGGCACGTCAACGCGTGGCGGATGT | 1787 |
| IRS1 | NM_005544 | 2 | 2 | − | 490 | + | 0 | 37 | 1 | 0 | CGCGAATGCCGGCAAGTGATCCTGAAGCCCAAGGGCCTGGGTCAGACGCGTGGCGGATGT | 1788 |
| IRS1 | NM_005544 | 2 | 2 | − | 525 | − | 0 | 37 | 1 | 0 | CGCGAATGCCAGGCAAAGGCGGTAGATACCAATCAGGTTCTTTGTACGCGTGGCGGATGT | 1789 |
| IRS1 | NM_005544 | 2 | 2 | − | 560 | + | 0 | 37 | 1 | 0 | CGCGAATGCCGACCAGCAAGACCATCAGCTTCGTGAAGCTGAAACTACGCGTGGCGGATGT | 1790 |
| IRS1 | NM_005544 | 2 | 2 | − | 595 | − | 0 | 37 | 1 | 0 | CGCGAATGCCGTTCATCAGCTGCAGCACCACGGCCGCTGCCTCCGACGCGTGGCGGATGT | 1791 |
| IRS1 | NM_005544 | 2 | 2 | − | 630 | + | 0 | 37 | 1 | 0 | CGCGAATGCCATCAGGCGCTGTGGCCACTCGGAAAACTTCTTCTTACGCGTGGCGGATGT | 1792 |
| IRS1 | NM_005544 | 2 | 2 | − | 665 | − | 0 | 37 | 1 | 0 | CGCGAATGCCCGGGCCCCGTCACGGCAGAACGGCCCACCTCGATGACGCGTGGCGGATGT | 1793 |
| IRS1 | NM_005544 | 2 | 2 | − | 700 | + | 0 | 37 | 1 | 0 | CGCGAATGCCGGGAGTTCTGGATGCAGTGGATGACTCTGTGGTGACGCGTGGCGGATGT | 1794 |
| IRS1 | NM_005544 | 2 | 2 | − | 735 | − | 0 | 37 | 1 | 0 | CGCGAATGCCATGGCCTTCCAGGATGGTCTCGTGCATGTTCTGGGCACGCGTGGCGGATGT | 1795 |
| IRS1 | NM_005544 | 2 | 2 | − | 770 | + | 0 | 37 | 1 | 0 | CGCGAATGCCGCGGGGCCATGAGTGATGAGTTCCGCCCTCCGCATGCGCGTGGCGGATGT | 1796 |
| IRS1 | NM_005544 | 2 | 2 | − | 805 | − | 0 | 37 | 1 | 0 | CGCGAATGCCGATGGGGTTAGAGCAGTTGGACGAGGACTGGCTCTACGCGTGGCGGATGT | 1797 |
| IRS1 | NM_005544 | 2 | 2 | − | 840 | + | 0 | 37 | 1 | 0 | CGCGAATGCCAGCGTCCCCCTCCGCCCGCACCATCTCAACAATCCACGCGTGGCGGATGT | 1798 |
| IRS1 | NM_005544 | 2 | 2 | − | 875 | − | 0 | 37 | 1 | 0 | CGCGAATGCCGTGATCGCGGGTCAGCCCCACCTGGCTGGCGGGACGCGTGGCGGATGT | 1799 |
| IRS1 | NM_005544 | 2 | 2 | − | 910 | + | 0 | 37 | 1 | 0 | CGCGAATGCCGCACTGAGAGCATCACCGCCACCTCCCCGGCCAGCACGCGTGGCGGATGT | 1800 |
| IRS1 | NM_005544 | 2 | 2 | − | 945 | − | 0 | 37 | 1 | 0 | CGCGAATGCCCCGACACGGAAGGAGCCTGGCTTCCCGCCCACCATACGCGTGGCGGATGT | 1801 |
| IRS1 | NM_005544 | 2 | 2 | − | 980 | + | 0 | 37 | 1 | 0 | CGCGAATGCCCGCCTCCAGTGACGGCGAAGGCACCATGTCCCGCCACGCGTGGCGGATGT | 1802 |
| IRS1 | NM_005544 | 2 | 2 | − | 1015 | − | 0 | 37 | 1 | 0 | CGCGAATGCCGCTGGGACTCACAGGGCTGCCGTCCACCGAGGCTGACGCGTGGCGGATGT | 1803 |
| IRS1 | NM_005544 | 2 | 2 | − | 1050 | + | 0 | 37 | 1 | 0 | CGCGAATGCCACCAAGAACCACGCCCACCGGCATCGGGGCAGACGCGTGGCGGATGT | 1804 |
| IRS1 | NM_005544 | 2 | 2 | − | 1085 | − | 0 | 37 | 1 | 0 | CGCGAATGCCCGTGTGGTTGAGCGGGGGGTGCAGCCGGCGACGCGTGGCGGATGT | 1805 |
| IRS1 | NM_005544 | 2 | 2 | − | 1120 | + | 0 | 37 | 1 | 0 | CGCGAATGCCCATCCCCATGCCGGCTTCCCGCTGCTCGCCTTCGACGCGTGGCGGATGT | 1806 |
| IRS1 | NM_005544 | 2 | 2 | − | 1155 | − | 0 | 37 | 1 | 0 | CGCGAATGCCGTGCTACTGGACGACAGACTGACCGGGCTGTGGCACGCGGTGGCGGATGT | 1807 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| IRS1 | NM_005544 | 2 | 2 | - | 1190 | + | 0 | 37 | 1 | 0 | CGCGAATGCCCAGTGCCAGTGGCCATGCCTCCACCTCGG ATTGTCTTCCACGCGTGGCGGATGT | 1808 |
| IRS1 | NM_005544 | 2 | 2 | - | 1225 | - | 0 | 37 | 1 | 0 | CGCGAATGCCCGGGGAACCAGACACCGAAGCA CTAGAATGCCGTGACGCGTGGCGGATGT | 1809 |
| IRS1 | NM_005544 | 2 | 2 | - | 1260 | + | 0 | 37 | 1 | 0 | CGCGAATGCCAGCGATGCGCGTTTCATCTCCTC GGATGAGTATGACGCGTGGCGGATGT | 1810 |
| IRS1 | NM_005544 | 2 | 2 | - | 1295 | - | 0 | 37 | 1 | 0 | CGCGAATGCCTGCGGAAGGAACTCCGGAAATCG CAGGGACTGGAGACGCGTGGCGGATGT | 1811 |
| IRS1 | NM_005544 | 2 | 2 | - | 1330 | + | 0 | 37 | 1 | 0 | CGCGAATGCCGTGTCACTCCGGATTCCCTGGGC CACACCCACCAACGCGTGGCGGATGT | 1812 |
| IRS1 | NM_005544 | 2 | 2 | - | 1365 | - | 0 | 37 | 1 | 0 | CGCGAATGCCCAGATATAGTTGCTTAGCTCCTCC TCACCGCGGCACGCGTGGCGGATGT | 1813 |
| IRS1 | NM_005544 | 2 | 2 | - | 1400 | + | 0 | 37 | 1 | 0 | CGCGAATGCCCATGGGTGGCAAGGGCCCTCCA CCCTGACCGCCCACGCGTGGCGGATGT | 1814 |
| IRS1 | NM_005544 | 2 | 2 | - | 1435 | - | 0 | 37 | 1 | 0 | CGCGAATGCCATTGCCACCCCGAGACAAAATGT AGTGACCGTTGGACGCGTGGCGGATGT | 1815 |
| IRS1 | NM_005544 | 2 | 2 | - | 1470 | + | 0 | 37 | 1 | 0 | CGCGAATGCCGGCCACCGCTGCACCCCAGGAAC AGGCTTGGGACGCACGCGTGGCGGATGT | 1816 |
| IRS1 | NM_005544 | 2 | 2 | - | 1505 | - | 0 | 37 | 1 | 0 | CGCGAATGCCCACTGGCTGCTTCATCCCCAGCC AAGGCTGGACTCACGCGTGGCGGATGT | 1817 |
| IRS1 | NM_005544 | 2 | 2 | - | 1540 | + | 0 | 37 | 1 | 0 | CGCGAATGCCCTGCAGATCTGGATAATCGGTTC CGAAAGAGAACTACGCGTGGCGGATGT | 1818 |
| IRS1 | NM_005544 | 2 | 2 | - | 1575 | - | 0 | 37 | 1 | 0 | CGCGAATGCCTGTGGGTAATGTAGGGGATGT GCCTGCCGAGTGACGCGTGGCGGATGT | 1819 |
| IRS1 | NM_005544 | 2 | 2 | - | 1610 | + | 0 | 37 | 1 | 0 | CGCGAATGCCGAAGACCCCGTCCCAGTCCTCAG TGGCTTCCATTGACGCGTGGCGGATGT | 1820 |
| IRS1 | NM_005544 | 2 | 2 | - | 1645 | - | 0 | 37 | 1 | 0 | CGCGAATGCCTGTGTGGGTAGGCAGGCATCATCT CTGTGTACTCCTACGCGTGGCGGATGT | 1821 |
| IRS1 | NM_005544 | 2 | 2 | - | 1680 | + | 0 | 37 | 1 | 0 | CGCGAATGCCGGAGGTGCCAGTGGAGGCCGACT GCCGGGACACAGACGCGTGGCGGATGT | 1822 |
| IRS1 | NM_005544 | 2 | 2 | - | 1715 | - | 0 | 37 | 1 | 0 | CGCGAATGCCCTGGGTAGGAGCGGGTGGCACG AAGGCCGAGTGCACGCGTGGCGGATGT | 1823 |
| IRS1 | NM_005544 | 2 | 2 | - | 1750 | + | 0 | 37 | 1 | 0 | CGCGAATGCCAGGAGGGTCTGGAAATGCACCCC TTGGAGCCTCGGACGCGTGGCGGATGT | 1824 |
| IRS1 | NM_005544 | 2 | 2 | - | 1785 | - | 0 | 37 | 1 | 0 | CGCGAATGCCTGGAGGGTGGAGCTGTCTGGGCG GTGGTGCCCCCACGCGTGGCGGATGT | 1825 |
| IRS1 | NM_005544 | 2 | 2 | - | 1820 | + | 0 | 37 | 1 | 0 | CGCGAATGCCCACGGATGATGGCTACATGCCCA TGTCCCAGGGACGCGTGGCGGATGT | 1826 |
| IRS1 | NM_005544 | 2 | 2 | - | 1855 | - | 0 | 37 | 1 | 0 | CGCGAATGCCTCCACTGCCCTTTCGGCCACTGG GCACTGGGCCAACGCGTGGCGGATGT | 1827 |
| IRS1 | NM_005544 | 2 | 2 | - | 1890 | + | 0 | 37 | 1 | 0 | CGCGAATGCCGACTATATGCCCATGAGCCCCAA GAGCGTATCTGCACGCGTGGCGGATGT | 1828 |
| IRS1 | NM_005544 | 2 | 2 | - | 1925 | - | 0 | 37 | 1 | 0 | CGCGAATGCCGATGGCCTCTGATGGGATTGATG ATCTGCTGTGGGACGCGTGGCGGATGT | 1829 |
| IRS1 | NM_005544 | 2 | 2 | - | 1960 | + | 0 | 37 | 1 | 0 | CGCGAATGCCCCCAGAGAGTGACCCCAATGGC TACATGATGATGACGCGTGGCGGATGT | 1830 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BwA score | BWA hit | # BWA mismatch | Sequence with add-ons | SEQ ID NO: |
|---|---|---|---|---|---|---|---|---|---|---|---|---|
| IRS1 | NM_005544 | 2 | 2 | - | 1995 | - | 0 | 37 | 1 | 0 | CGCGAATGCCCCTCCAATGTCAGGAGAGCAGCC ACCGCTGGGGAACGCGTGGCGGATGT | 1831 |
| IRS1 | NM_005544 | 2 | 2 | - | 2030 | + | 23 | 37 | 1 | 0 | CGCGAATGCCTGGCCCCAGCAGCAGCAGCAGCA GCACAACGCGCCGTGGCCGATGT | 1832 |
| IRS1 | NM_005544 | 2 | 2 | - | 2065 | - | 0 | 37 | 1 | 0 | CGCGAATGCCTGTCCACAGCTTTCCATAGCTGGT CCCGGAGGGAACGCGTGGCGGATGT | 1833 |
| IRS1 | NM_005544 | 2 | 2 | - | 2100 | + | 0 | 37 | 1 | 0 | CGCGAATGCCAACGGGTAGGGGCCCACCACTC TCATGTCTTGCCACGCGTGGCGGATGT | 1834 |
| IRS1 | NM_005544 | 2 | 2 | - | 2135 | - | 0 | 37 | 1 | 0 | CGCGAATGCCTACCACCCTGCTCTCCACTGGG GGTTTGGGTGAACGCGTGGCGGATGT | 1835 |
| IRS1 | NM_005544 | 2 | 2 | - | 2170 | + | 0 | 37 | 1 | 0 | CGCGAATGCCAGCTCTTACCTTGCACAGGTGAC TACATGAACATGACGCGTGGCGGATGT | 1836 |
| IRS1 | NM_005544 | 2 | 2 | - | 2205 | - | 0 | 37 | 1 | 0 | CGCGAATCCGAGGGGCTGCTGTGTTGGAGTC CCCACTGGTGAACGCGTGGCGGATGT | 1837 |
| IRS1 | NM_005544 | 2 | 2 | - | 2240 | + | 0 | 37 | 1 | 0 | CGCGAATGCCCGACTGCTACTACGGCCCTGAGG ACCCCCAGCACACGCGTGGCGGATGT | 1838 |
| IRS1 | NM_005544 | 2 | 2 | - | 2275 | - | 0 | 37 | 1 | 0 | CGCGAATGCCGGATCTTGGCAATGAGTAGTAGG AGAGGACTGGCTACGCCTGGCGGATGT | 1839 |
| IRS1 | NM_005544 | 2 | 2 | - | 2310 | + | 0 | 37 | 1 | 0 | CGCGAATGCCTTTAAGCACACCCAGCGCCCCGG GGAGCCGAGGAACGCGTGGCCGATGT | 1840 |
| IRS1 | NM_005544 | 2 | 2 | - | 2345 | - | 0 | 37 | 1 | 0 | CGCGAATGCCTAGTGGAAAGGCGGAGGTGCTGA TGCCGGGCACCCCACGCGTGGCCGATGT | 1841 |
| IRS1 | NM_005544 | 2 | 2 | - | 2380 | + | 0 | 37 | 1 | 0 | CGCGAATGCCGCTCGTCTGTCGCCTTTCTCTATGCTG CAACAGCAGATACGCGTGGCGGATGT | 1842 |
| IRS1 | NM_005544 | 2 | 2 | - | 2415 | - | 0 | 37 | 1 | 0 | CGCGAATGCCCCCAGGCTGTCGCTGCTGGTGGA AGAGGAAGAATCACGCGTGGCGGATGT | 1843 |
| IRS1 | NM_005544 | 2 | 2 | - | 2450 | + | 0 | 37 | 1 | 0 | CGCGAATGCCTGGGGATACTCCGGGGCTAGGC TGGAGCCCAGCCACGCGTGGCCGATGT | 1844 |
| IRS1 | NM_005544 | 2 | 2 | - | 2485 | - | 0 | 37 | 1 | 0 | CGCGAATGCCATGGGCTGCAGAACCTGATGGT GGGGATGTGGAAACGCGTGGCGGATGT | 1845 |
| IRS1 | NM_005544 | 2 | 2 | - | 2520 | + | 0 | 37 | 1 | 0 | CGCGAATGCCCTGCCTGAAAGGTGGACACAGC TGCTCAGACCAAACGCGTGGCGGATGT | 1846 |
| IRS1 | NM_005544 | 2 | 2 | - | 2555 | - | 0 | 37 | 1 | 0 | CGCGAATGCCCCAGGACGACGCTCGTGGGCCGG GCCAGGCCGGCTAACGCGTGGCCGATGT | 1847 |
| IRS1 | NM_005544 | 2 | 2 | - | 2590 | + | 0 | 37 | 1 | 0 | CGCGAATGCCGGATCCAAGGCCAGCCAGCACCTTA CCTCGGGCCCGAACGCGTGGCGGATGT | 1848 |
| IRS1 | NM_005544 | 2 | 2 | - | 2629 | - | 18 | 37 | 1 | 0 | CGCGAATGCCTGGAGGTGCAGCAAGGGCTGCT GCTGCTGCTACGCGTGGCGGATGT | 1849 |
| IRS1 | NM_005544 | 2 | 2 | - | 2660 | + | 0 | 37 | 1 | 0 | CGCGAATGCCTCCAGACCCAAGAGCCCGGGGG AATATGTCAATAACGCGTGGCCGATGT | 1850 |
| IRS1 | NM_005544 | 2 | 2 | - | 2695 | - | 0 | 37 | 1 | 0 | CGCGAATGCCAGACAAGTAGCCAGACTGATCAC TCCCAAATTCAAACGCGTGGCCGATGT | 1851 |
| IRS1 | NM_005544 | 2 | 2 | - | 2730 | + | 0 | 37 | 1 | 0 | CGCGAATGCCCGGCCCGTGGCTTTCCACAGCTC ACTTCTGTCAGACGCGTGGCCGATGT | 1852 |
| IRS1 | NM_005544 | 2 | 2 | - | 2765 | - | 0 | 37 | 1 | 0 | CGCGAATGCCCCTCTTGGGACTGGCTGGAGC TGGGATGACACACGCGTGGCCGATGT | 1853 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| IRS1 | NM_005544 | 2 | 2 | - | 2800 | + | 0 | 37 | 1 | 0 | CGCGAATGCCAAGAGACTGGCACTGAGGAGTAC ATGAAGATGGACACGCGTGGCGATGT | 1854 |
| IRS1 | NM_005544 | 2 | 2 | - | 2835 | - | 0 | 37 | 1 | 0 | CGCGAATGCCCTCTCCTGCCAGGCTGCCCTCCG GCCCGCCCAGACGCGTGGCGATGT | 1855 |
| IRS1 | NM_005544 | 2 | 2 | - | 2870 | + | 0 | 37 | 1 | 0 | CGCGAATGCCACTGGGGTCGAGATGGGCAGAC TGGCCCTGCACACGCGTGGCGATGT | 1856 |
| IRS1 | NM_005544 | 2 | 2 | - | 2905 | - | 0 | 37 | 1 | 0 | CGCGAATGCCCCGGGTAGGCCTGCAAATGCTAG CAGCCCCGGAGACGCGTGGCGATGT | 1857 |
| IRS1 | NM_005544 | 2 | 2 | - | 2940 | + | 0 | 37 | 1 | 0 | CGCGAATGCCGCAGTGCCCAGCAGCCGGGGTGA CTACATGACCATACGCGTGGCGATGT | 1858 |
| IRS1 | NM_005544 | 2 | 2 | - | 2975 | - | 0 | 37 | 1 | 0 | CGCGAATGCCTGTCCACCTAGCTCTGACGCGGGA CAACTCATCTGACGCGTGGCGATGT | 1859 |
| IRS1 | NM_005544 | 2 | 2 | - | 3010 | + | 0 | 37 | 1 | 0 | CGCGAATGCCCCTCCGCCAGCTGCCCTGTAAGC TATGCTGACATGACGCGTGGCGATGT | 1860 |
| IRS1 | NM_005544 | 2 | 2 | - | 3045 | - | 0 | 37 | 1 | 0 | CGCGAATGCCGGCAGGCTCACCTCCTCTGCAGC AATGCCTGTTCGACGCGTGGCGATGT | 1861 |
| IRS1 | NM_005544 | 2 | 2 | - | 3080 | + | 0 | 37 | 1 | 0 | CGCGAATGCCCAGGGCCACCATGGCTGCTGCCT CCTCATCCTCAGACGCGTGGCGATGT | 1862 |
| IRS1 | NM_005544 | 2 | 2 | - | 3115 | - | 0 | 37 | 1 | 0 | CGCGAATGCCTCGCCCCTTGAGGCCCAGTCGGGG AAGCAGAGGCTGACGCGTGGCGATGT | 1863 |
| IRS1 | NM_005544 | 2 | 2 | - | 3150 | + | 0 | 37 | 1 | 0 | CGCGAATGCCGCCAGAGCTGGCTGCCCACTCGTC CCTGCTGGGGGACGCCTGGCCGATGT | 1864 |
| IRS1 | NM_005544 | 2 | 2 | - | 3185 | - | 0 | 37 | 1 | 0 | CGCGAATGCCGGGTGAAGGCGCTCATGCCCCCA GGTCCTTGTGGGACGCGTGGCGATGT | 1865 |
| IRS1 | NM_005544 | 2 | 2 | - | 3220 | + | 0 | 37 | 1 | 0 | CGCGAATGCCGGGTGAACCTCAGTCCTAACCGC AACCAGAGTGCCACGCGTGGCCGATGT | 1866 |
| IRS1 | NM_005544 | 2 | 2 | - | 3255 | - | 0 | 37 | 1 | 0 | CGCGAATGCCCCCGGCACCCTTGTGGGTCTGC ACGGATCACTTTACGCGTGGCCGATGT | 1867 |
| IRS1 | NM_005544 | 2 | 2 | - | 3290 | + | 0 | 37 | 1 | 0 | CGCGAATGCCGAGGCATAGCTCCGAGACTTTCT CCTCAACACCCAACGCGTGGCCGATGT | 1868 |
| IRS1 | NM_005544 | 2 | 2 | - | 3325 | - | 0 | 37 | 1 | 0 | CGCGAATGCCTCCAAGGGCACTGTGTTGCCCA CCCGGGTGGCACACGCGTGGCCGATGT | 1869 |
| IRS1 | NM_005544 | 2 | 2 | - | 3360 | + | 0 | 37 | 1 | 0 | CGCGAATGCCGGGGGGCACAGTAGGGGGCG GTGGCGGTAGCAGACGCCGTGGCCGATGT | 1870 |
| IRS1 | NM_005544 | 2 | 2 | - | 3395 | - | 0 | 37 | 1 | 0 | CGCGAATGCCCAGAGCTGTGGCGTTTCACATCC TCGCTGCTGCGACGCGTGGCCGATGT | 1871 |
| IRS1 | NM_005544 | 2 | 2 | - | 3430 | + | 0 | 37 | 1 | 0 | CGCGAATGCCCTTTCCTTTGAGAATGTGGCTG AGGCCTGGGGAGACGCGTGGCCGATGT | 1872 |
| IRS1 | NM_005544 | 2 | 2 | - | 3465 | - | 0 | 37 | 1 | 0 | CGCGAATGCCCACAGTTTGGCTGGCTCCTTGGG GGCTCCCCAAGACGCGTGGCCGATGT | 1873 |
| IRS1 | NM_005544 | 2 | 2 | - | 3500 | + | 0 | 37 | 1 | 0 | CGCGAATGCCTGGGGTTGCTGGGGTTTGGAGA ATGGTCTTAACTACGCGTGGCCGATGT | 1874 |
| IRS1 | NM_005544 | 2 | 2 | - | 3535 | - | 0 | 37 | 1 | 0 | CGCGAATGCCCTGTTTGAAGTCCTTGACCAAAT CCAGGTCTATGTACGCGTGGCCGATGT | 1875 |
| IRS1 | NM_005544 | 2 | 2 | - | 3570 | + | 0 | 37 | 1 | 0 | CGCGAATGCCTCCACGCGTGGCGATGT ACCGCAGCCTCCAGGAGTGCACCCCTGA | 1876 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit mismatch | # BWA mismatch | Sequence with add-ons | SEQ ID NO: |
|---|---|---|---|---|---|---|---|---|---|---|---|---|
| IRS1 | NM_005544 | 2 | 2 | - | 3605 | - | 0 | 37 | 1 | 0 | CGCGAATGCCCCTGCCCAGGGGTTGATGAGGGGGTGGGGTGGGACGCGTGGCGGATGT | 1877 |
| IRS1 | NM_005544 | 2 | 2 | - | 3640 | + | 0 | 37 | 1 | 0 | CGCGAATGCCGTGAGAGCAGCTCCACCCGCGCTCAAGTGAGGATACGCGTGGCGGATGT | 1878 |
| IRS1 | NM_005544 | 2 | 2 | - | 3675 | + | 0 | 37 | 1 | 0 | CGCGAATGCCTGCTTCTGGAAACTGATGCTGGCATAGGCCTTAAACGCGTGGCGGATGT | 1879 |
| IRS1 | NM_005544 | 2 | 2 | - | 3710 | + | 0 | 37 | 1 | 0 | CGCGAATGCCGCCAGAGGACCGTCAGTAGCTCAACTGGACATCACACGCGTGGCGGATGT | 1880 |
| RBBP8 | NM_002894 | 3 | 18 | + | -48 | - | 0 | 37 | 1 | 0 | CGCGAATGCCCATAAAGGAACTGTTGTAGAAGTAATACCTTTTCTACGCGTGGCGGATGT | 1881 |
| RBBP8 | NM_002894 | 3 | 18 | + | -13 | + | 0 | 37 | 1 | 0 | CGCGAATGCCTTGGTTACTTTTACTTGTAAACCTGAAAGTAAAAACGCGTGGCGGATGT | 1882 |
| RBBP8 | NM_002894 | 3 | 18 | + | 22 | + | 0 | 37 | 1 | 0 | CGCGAATGCCGCTAAAACAGGAACGAATCTTGTAAGTATCAGTATACGCGTGGCGGATGT | 1883 |
| RBBP8 | NM_002894 | 3 | 18 | + | 57 | - | 0 | 37 | 1 | 0 | CGCGAATGCCTATCAACTACTCTATAAATAACACATGAGTATTACACGCGTGGCGGATGT | 1884 |
| NTRK3 | NM_001012338 | 11 | 15 | - | 0 | + | 0 | 37 | 1 | 0 | CGCGAATGCCCCGCCACCACAAACTGATGCAGTGCTCCAGGCGCAGACGCGTGGCGGATGT | 1885 |
| NTRK3 | NM_001012338 | 11 | 15 | - | 35 | - | 0 | 37 | 1 | 0 | CGCGAATGCCTGCAACCCCCACCAACGCTGCACTGGCTGCACAACGCCTGGCGGATGT | 1886 |
| NTRK3 | NM_001012338 | 11 | 15 | - | 70 | + | 0 | 37 | 1 | 0 | CGCGAATGCCCATGGATGATCTTGGACTCCCGCAGAGGCTGCCCATACGCGTGGCGGATGT | 1887 |
| NTRK3 | NM_001012338 | 11 | 15 | - | 105 | - | 0 | 37 | 1 | 0 | CGCGAATGCCGTGGAATACTACCAAGAGGAGAGATTTCCGAGGGACGCCGTGGCGGATGT | 1888 |
| NTRK3 | NM_001012338 | 11 | 15 | - | 140 | + | 0 | 37 | 1 | 0 | CGCGAATGCCTTGTGTAGTGGGTGGGCTTGTTGAAGAGCAGGCAGACGCCTGGCGGATGT | 1889 |
| NTRK3 | NM_001012338 | 11 | 15 | - | 175 | - | 0 | 37 | 1 | 0 | CGCGAATGCCATGGCAACTATACCCTCATTGCCAAAAACCACTGACGCGTGGCGGATGT | 1890 |
| NTRK3 | NM_001012338 | 11 | 15 | - | 210 | + | 0 | 37 | 1 | 0 | CGCGAATGCCAGGAAGTGCCATTGATGGTCTGGTTGGCTGTGCCACGCGTGGCGGATGT | 1891 |
| NTRK3 | NM_001012338 | 11 | 15 | - | 245 | - | 0 | 37 | 1 | 0 | CGCGAATGCCAAGGAGCCTTTCCAGTGAGGGCAGCGTAGCTGACGCGTGGCGGATGT | 1892 |
| NTRK3 | NM_001012338 | 11 | 15 | - | 280 | + | 0 | 37 | 1 | 0 | CGCGAATGCCGTGGCACCCCTTACCCGGCATGATGGTGATTCTACGCCGTGGCGGATGT | 1893 |
| PDGFRA | NM_006206 | 21 | 4 | + | 0 | + | 0 | 37 | 1 | 0 | CGCGAATGCCATCCGGTACCCACTCTTGATCTTATTGTAGAAAGTACGCGTGGCGGATGT | 1894 |
| PDGFRA | NM_006206 | 21 | 4 | + | 35 | - | 0 | 37 | 1 | 0 | CGCGAATGCCCGGCCAAGCCTGACCACCGCTACCAGTGAAGTGTGAGACGCGTGGCGGATGT | 1895 |
| PDGFRA | NM_006206 | 21 | 4 | + | 70 | + | 0 | 37 | 1 | 0 | CGCGAATGCCGACTGTGAACACAGGCCCCCGGGATGGGAAGGAGACGCGTGGCGGATGT | 1896 |
| PDGFRA | NM_006206 | 21 | 4 | + | 105 | - | 0 | 37 | 1 | 0 | CGCGAATGCCTGGGTCTAGGGGAGGGAGGGGCCCTGAGACTTACGCGTGGCGGATGT | 1897 |
| PDGFRA | NM_006206 | 21 | 4 | + | 140 | + | 0 | 37 | 1 | 0 | CGCGAATGCCCTGTGGGACAGAACTCAAGAGTGGCACAGGGGACGCGTGGCGGATGT | 1898 |
| PDGFRA | NM_006206 | 21 | 4 | + | 175 | - | 0 | 37 | 1 | 0 | | 1899 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| PDGFRA | NM_006206 | 21 | 4 | + | 210 | + | 0 | 37 | 1 | 0 | CGCGAATGCCCTACGAGATCATGGTGAAATGCTGAACAGTGAGCACGCGTGGCGGATGT | 1900 |
| PDGFRA | NM_006206 | 21 | 4 | + | 245 | - | 0 | 37 | 1 | 0 | CGCGAATGCCCTCACTCAGGTGGTAAAAGGAGGGTCTCTTCCCGACGCGTGGCGGATGT | 1901 |
| PDGFRA | NM_006206 | 21 | 4 | + | 280 | + | 0 | 37 | 1 | 0 | CGCGAATGCCATTGTGGAGAATCTGCTGCCTGGACAATATAAAAACGCGTGGCGGATGT | 1902 |
| PDGFRA | NM_006206 | 21 | 4 | + | 315 | - | 0 | 37 | 1 | 0 | CGCGAATGCCATCCAGACCTTTCCACCCACAGATCCAAACACCACGCGTGGCGGATGT | 1903 |
| PDGFRA | NM_006206 | 9 | 4 | + | -6 | + | 0 | 37 | 1 | 0 | CGCGAATGCCCTTGCAGTTCCTTCATCCATTCTGGACTTGGTCGATACGGTGGCGGATGT | 1904 |
| PDGFRA | NM_006206 | 9 | 4 | + | 29 | - | 0 | 37 | 1 | 0 | CGCGAATGCCCTCACCGTCTGTCCCCAGTTGAGCCATGGTGATCACGCGTGGCGGATGT | 1905 |
| PDGFRA | NM_006206 | 9 | 4 | + | 64 | + | 0 | 37 | 1 | 0 | CGCGAATGCCGTCACAGCTGAAGGCACGCCGCTTCCTGATATTGACGCGTGGCGGATGT | 1906 |
| PDGFRA | NM_006206 | 9 | 4 | + | 99 | - | 0 | 37 | 1 | 0 | CGCGAATGCCTCCATACTTCTTAATATCTTTGCATATCATCCACTACGCGTGGCGGATGT | 1907 |
| PDGFRA | NM_006206 | 13 | 4 | + | -18 | + | 0 | 37 | 1 | 0 | CGCGAATGCCGATTCTGCCTGCCCACAGGTCGGGTCTTGGGGTCTACGCGTGGCGGATGT | 1908 |
| PDGFRA | NM_006206 | 13 | 4 | + | 17 | - | 0 | 37 | 1 | 0 | CGCGAATGCCTAGGCTGTTCCTTCAACCACCTTCCAAACGCTCACGCGTGGCGGATGT | 1909 |
| PDGFRA | NM_006206 | 13 | 4 | + | 52 | + | 0 | 37 | 1 | 0 | CGCGAATGCCTGATTAAGCCGTCCCAACCTGTCATGAAAGTTGACGCCTGGCGGATGT | 1910 |
| PDGFRA | NM_006206 | 13 | 4 | + | 87 | - | 0 | 37 | 1 | 0 | CGCGAATGCCCAGGAAGGAGCACTTACGTTTAGCATCTTCACTGACGCGTGGCGGATGT | 1911 |
| GUCY2F | NM_001522 | 13 | X | - | -25 | + | 0 | 37 | 1 | 0 | CGCGAATGCCTTCATTCTCCTCTTTTCTTTCTAGGGTGATTGGGACGCGTGGCGGATGT | 1912 |
| GUCY2F | NM_001522 | 13 | X | - | 10 | - | 0 | 37 | 1 | 0 | CGCGAATGCCTCCAAAATCTCCAAGGAGAACTTTTTCAGCCACACACGCGTGGCGGATGT | 1913 |
| GUCY2F | NM_001522 | 13 | X | - | 45 | + | 0 | 37 | 1 | 0 | CGCGAATGCCGACCTTAAGTCCATCAAATCAAGAGCAAGTGATGTACGCGTGGCGGATGT | 1914 |
| GUCY2F | NM_001522 | 13 | X | - | 80 | - | 0 | 37 | 1 | 0 | CGCGAATGCCTTACATAAACGAAGATTTCTCATACCATTTCGAACACGCGTGGCGGATGT | 1915 |
| NTRK3 | NM_001012338 | 17 | 15 | - | -32 | + | 0 | 37 | 1 | 0 | CGCGAATGCCGGCTGACCGTTACCTTTCCTCCTCCCCTGCAGACAACGCGTGGCGGATGT | 1916 |
| NTRK3 | NM_001012338 | 17 | 15 | - | 3 | - | 0 | 37 | 1 | 0 | CGCGAATGCCCGTTGAGCGTGTGAAGACTGCGCCAGTTCTATGACGCGGATGT | 1917 |
| NTRK3 | NM_001012338 | 17 | 15 | - | 38 | + | 0 | 37 | 1 | 0 | CGCGAATGCCTGGACATGGAGCTCTACACCGGACTTCAAAAGACGCGTGGCGGATGT | 1918 |
| NTRK3 | NM_001012338 | 17 | 15 | - | 73 | - | 0 | 37 | 1 | 0 | CGCGAATGCCGGAAAGGCTCTCTGTGGCCGGGTGTACTCACAGACGCGTGGCGGATGT | 1919 |
| CHAF1A | NM_005483 | 2 | 19 | + | -44 | + | 0 | 37 | 1 | 0 | CGCGAATGCCTTTGCAGAATTTAACAGTTTACCCTTTGACACTTTACGCGTGGCGGATGT | 1920 |
| CHAF1A | NM_005483 | 2 | 19 | + | -9 | - | 0 | 37 | 1 | 0 | CGCGAATGCCAGCTGGTCTATCTTTGCAATCCATGGCTGCAATAACGCGTGGCGGATGT | 1921 |
| CHAF1A | NM_005483 | 2 | 19 | + | 26 | + | 0 | 37 | 1 | 0 | CGCGAATGCCTTTCAGTTAAGAAGTTAATACAAGTAATTATTTACGCGTGGCGGATGT | 1922 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| CHAF1A | NM_005483 | 2 | 19 | + | 61 | - | 0 | 37 | 1 | 0 | CGCGAATGCCACTATAAACTACGAACAACTCTT TAACCCATTTCCACGCGTGGCGGATGT | 1923 |
| PKN1 | NM_002741 | 5 | 19 | + | 0 | + | 0 | 37 | 1 | 0 | CGCGAATGCCGGAGTCCTGACCTGGGGCTGTG GAGCTGCGCATCACGCCGTGGCGGATGT | 1924 |
| PKN1 | NM_002741 | 5 | 19 | + | 35 | - | 0 | 37 | 1 | 0 | CGCGAATGCCGCGTGCTCCACTCGGAAGTGGTG CCGCAGTCTTCACGCCGTGGCGGATGT | 1925 |
| PKN1 | NM_002741 | 5 | 19 | + | 70 | + | 0 | 37 | 1 | 0 | CGCGAATGCCGGTGGCCCAGGGTGCCAAGAAC GTACTGCCGTGCACGCGTGGCGGATGT | 1926 |
| PKN1 | NM_002741 | 5 | 19 | + | 105 | - | 0 | 37 | 1 | 0 | CGCGAATGCCGACTGCCTTGCGGTCCGGGGCCT TGGCAGCGCTGAACGCGTGGCGGATGT | 1927 |
| PKN1 | NM_002741 | 5 | 19 | + | 140 | + | 0 | 37 | 1 | 0 | CGCGAATGCCAGCGAGGTGAGGGGCGGAGCTTT CATTAGAGGCGGACGCGTGGCGGATGT | 1928 |
| KSR2 | NM_173598 | 20 | 12 | - | -24 | + | 0 | 37 | 1 | 0 | CGCGAATGCCCAGCAGTGCGAACTGGTCCAAAA CATGATAGACTTACGCTGGCGGATGT | 1929 |
| KSR2 | NM_173598 | 20 | 12 | - | 11 | - | 0 | 37 | 1 | 0 | CGCGAATGCCATTTGGTCCTAAGCCCTTCCAGT TGGAGAATGCTCACGCGTGGCGGATGT | 1930 |
| KSR2 | NM_173598 | 20 | 12 | - | 46 | + | 1 | 37 | 1 | 0 | CGCGAATGCCGTGCTACCTCCAACGACCTCACA CAAAAGAAATCACGCCGTGGCGGATGT | 1931 |
| KSR2 | NM_173598 | 20 | 12 | - | 77 | - | 0 | 37 | 1 | 0 | CGCGAATGCCTCCGGATTACGCCGTGGCGGATGT AGGGTCCGATTACGCCGTGGCGGATGT | 1932 |
| EPHA7 | NM_004440 | 17 | 6 | - | -22 | + | 0 | 37 | 1 | 0 | CGCGAATGCCAAATAAACTGCTCATGCACCA TGGTTTTTCAAAACGCCTGGCGGATGT | 1933 |
| EPHA7 | NM_004440 | 17 | 6 | - | 13 | - | 0 | 37 | 1 | 0 | CGCGAATGCCGATGTAGCATAAAATATCCATG AAGGTACCGAGACGCGTGGCGGATGT | 1934 |
| EPHA7 | NM_004440 | 17 | 6 | - | 48 | + | 0 | 37 | 1 | 0 | CGCGAATGCCTGCTGCTCCGCTTTGCACACAC AGGGGAGGCGCAACGCGTGGCGGATGT | 1935 |
| EPHA7 | NM_004440 | 17 | 6 | - | 83 | - | 0 | 37 | 1 | 0 | CGCGAATGCCTTTGCTTTCCCATCACCTTACCTT CCTTCGCAGCCACGCGTGGCGGATGT | 1936 |
| NFKB1 | NM_003998 | 16 | 4 | + | -12 | + | 0 | 37 | 1 | 0 | CGCGAATGCCTTTTCATTCCAGTGTCTTACACTT AGCAATCATCCACGCGTGGCGGATGT | 1937 |
| NFKB1 | NM_003998 | 16 | 4 | + | 23 | - | 0 | 37 | 1 | 0 | CGCGAATGCCTTCTAGTAGATCCCTCACAAGTT GAGAATGAAGGTACGCGTGGCGGATGT | 1938 |
| NFKB1 | NM_003998 | 16 | 4 | + | 58 | + | 0 | 37 | 1 | 0 | CGCGAATGCCGTCACATCTGGTTTGATTTCTGAT GACATTATCAAACGCGTGGCGGATGT | 1939 |
| NFKB1 | NM_003998 | 16 | 4 | + | 93 | - | 0 | 37 | 1 | 0 | CGCGAATGCCGATTTCTGCTTACCTGGTACAGAT CATTTCTCATGACGCGTGGCGGATGT | 1940 |
| EPHA4 | NM_004438 | 15 | 2 | - | 0 | + | 0 | 37 | 1 | 0 | CGCGAATGCCCTTGCAAATTGGATATTACAAG GCTCTCTCCACGACGCGTGGCGGATGT | 1941 |
| EPHA4 | NM_004438 | 15 | 2 | - | 35 | - | 0 | 37 | 1 | 0 | CGCGAATGCCTAGTGTGGGGTGGGCACTTGGC ACAGGTGCATCACGCCGTGGCGGATGT | 1942 |
| EPHA4 | NM_004438 | 15 | 2 | - | 70 | + | 0 | 37 | 1 | 0 | CGCGAATGCCCTCTGTCTGGAAGGAGCCACCT CGTGCACCTGTGACGCGTGGCGGATGT | 1943 |
| EPHA4 | NM_004438 | 15 | 2 | - | 105 | - | 0 | 37 | 1 | 0 | CGCGAATGCCGCAGCATCGTTGTCAGCTCTGA AAAAGCCTCGGTACGCGTGGCGGATGT | 1944 |
| EPHA4 | NM_004438 | 15 | 2 | - | 140 | + | 0 | 37 | 1 | 0 | CGCGAATGCCCTATGCCCTGCCACCCGTAAGTT GTATGCTTGTCTACGCCGTGGCGGATGT | 1945 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| RB1 | NM_000321 | 11 | 13 | + | -31 | + | 0 | 37 | 1 | 0 | CGCGAATGCCTATGTGAATGACTTCACTTATTGTTATTTAGTTTACGCGTGGCGATGT | 1946 |
| RB1 | NM_000321 | 11 | 13 | + | 4 | - | 0 | 37 | 1 | 0 | CGCGAATGCCTCAAGGTTACTTTTTCGTGGTGTTCTCTGTGTTCACGCGTGGCGATGT | 1947 |
| RB1 | NM_000321 | 11 | 13 | + | 39 | + | 0 | 37 | 1 | 0 | CGCGAATGCCTGAAGAGGTGAATGTAATTCCTCCACACACTCCAGACGCCGTGGCGATGT | 1948 |
| RB1 | NM_000321 | 11 | 13 | + | 70 | - | 11 | 37 | 1 | 0 | CGCGAATGCCTATAATTAAAAGTAGGAAAATTCATACCTAACTGGACGCGTGGCGATGT | 1949 |
| EPHA4 | NM_004438 | 8 | 2 | - | 0 | + | 0 | 37 | 1 | 0 | CGCGAATGCCGTGAATTTGGTGAGGTATGCAGTGGGCGTTCAAAACGCGTGGCGATGT | 1950 |
| EPHA4 | NM_004438 | 8 | 2 | - | 35 | - | 0 | 37 | 1 | 0 | CGCGAATGCCTTGATAGCCACACAGATCTCTCTCTTGCCAGGCACACGCGTGGCGATGT | 1951 |
| EPHA4 | NM_004438 | 8 | 2 | - | 70 | + | 0 | 37 | 1 | 0 | CGCGAATGCCGACTCTGAAAGCTGGTTATACAGACAAACAGAGGAACGCGTGGCGATGT | 1952 |
| EPHA4 | NM_004438 | 8 | 2 | - | 105 | - | 0 | 37 | 1 | 0 | CGCGAATGCCCTGTCCCATGATGCTGGCCTCACTCAGGAAGTCTCACGCGTGGCGATGT | 1953 |
| EPHA4 | NM_004438 | 8 | 2 | - | 140 | + | 0 | 37 | 1 | 0 | CGCGAATGCCTTTGACCATCCGAACATCATTCACTTGGAAGGGTACGCGTGGCGATGT | 1954 |
| EPHA4 | NM_004438 | 8 | 2 | - | 175 | - | 0 | 37 | 1 | 0 | CGCGAATGCCTTGTAAAGGGGTGACCCACGTACATTAGTGACCACGCGTGGCGATGT | 1955 |
| RB1 | NM_000321 | 14 | 13 | + | -42 | + | 0 | 37 | 1 | 0 | CGCGAATGCCCTAAAATAGCAGCTCTTATTTTCTTTTTGTTTGACGCGTGGCGATGT | 1956 |
| RB1 | NM_000321 | 14 | 13 | + | -7 | - | 0 | 37 | 1 | 0 | CGCGAATGCCAATACAAGCGAACTCCAAGTTTGTATCGCTACAAAACGCGTGGCGATGT | 1957 |
| RB1 | NM_000321 | 14 | 13 | + | 28 | + | 0 | 37 | 1 | 0 | CGCGAATGCCACCGAGTAATGAATCCATGCTTAAATCAGTAAGTACGCGTGGCGATGT | 1958 |
| RB1 | NM_000321 | 14 | 13 | + | 59 | - | 8 | 37 | 1 | 0 | CGCGAATGCCGCCCGGCTGAAATTTTTTATATTGTTTTTAACTTACGCGTGGCGATGT | 1959 |
| PALB2 | NM_024675 | 13 | 16 | - | -46 | + | 0 | 37 | 1 | 0 | CGCGAATGCCGCCTGGGGTCGGCGACGCTGCTCTTTCGTTCTGACGCGTGGCGATGT | 1960 |
| PALB2 | NM_024675 | 13 | 16 | - | -11 | - | 0 | 37 | 1 | 0 | CGCGAATGCCGGGCTTCCCGGAGGCTCGTCCATCGGGCAGCCGAACGCCTGGCGATGT | 1961 |
| PALB2 | NM_024675 | 13 | 16 | - | 24 | + | 0 | 37 | 1 | 0 | CGCGAATGCCCTCAGCTGTGAGGAGGAGAAAAGTGCCCGGGGTACGCCTGGCGATGT | 1962 |
| PALB2 | NM_024675 | 13 | 16 | - | 59 | - | 0 | 37 | 1 | 0 | CGCGAATGCCAAGCGGGTCAGAGTCCTCGTCCGCCCCTTCCCGCACGCGTGGCGATGT | 1963 |
| EPHA3 | NM_005233 | 12 | 3 | + | -39 | + | 0 | 37 | 1 | 0 | CGCGAATGCCACTGTACTGATTATTATTATTATTTACTGTATATACGCGTGGCGATGT | 1964 |
| EPHA3 | NM_005233 | 12 | 3 | + | -4 | - | 0 | 37 | 1 | 0 | CGCGAATGCCATGTATTCTGACAATCATAACTGGCTTACCTAGACGCGTGGCGATGT | 1965 |
| EPHA3 | NM_005233 | 12 | 3 | + | 31 | + | 0 | 37 | 1 | 0 | CGCGAATGCCGGAGAATGGTTCCTTGGATAGTTTCCTACGTGAAACGCGTGGCGATGT | 1966 |
| EPHA3 | NM_005233 | 12 | 3 | + | 66 | - | 0 | 37 | 1 | 0 | CGCGAATGCCATTTATTCATATATATGTATGTGTGTCATCTTACGCGTGGCGATGT | 1967 |
| RB1 | NM_000321 | 13 | 13 | + | -12 | + | 0 | 37 | 1 | 0 | CGCGAATGCCTACCTCCTAAAGAACTGCACAGTGAATCCAAAAGACGCGTGGCGATGT | 1968 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatches | Sequence with add-ons | SEQ ID NO: |
|---|---|---|---|---|---|---|---|---|---|---|---|
| RB1 | NM_000321 | 13 | 13 | + | 23 | − | 0 | 37 | 1 | 0 | CGCGAATGCCTGTATCCTATATCCTTCACTCTTTTCAGTATACTTACGCGTGGCGGATGT | 1969 |
| RB1 | NM_000321 | 13 | 13 | + | 58 | + | 0 | 37 | 1 | 0 | CGCGAATGCCTCTTTAAAGAGAAATTTGCTAAAGCTGTGGACAGACGCGTGGCGGATGT | 1970 |
| RB1 | NM_000321 | 13 | 13 | + | 93 | − | 0 | 37 | 1 | 0 | CGCGAATGCCATTCAAGTTACCTGTGATCCAATTTCACACAACCACGCGTGGCGGATGT | 1971 |
| RPS6KA1 | NM_002953 | 2 | 1 | + | −48 | + | 0 | 37 | 1 | 0 | CGCGAATGCCGGTGTAAGTTCTGACAGTGCTCCCCCAATCTCCTACGCGTGGCGGATGT | 1972 |
| RPS6KA1 | NM_002953 | 2 | 1 | + | −13 | − | 0 | 37 | 1 | 0 | CGCGAATGCCCTTCCCCTGAGGTCTGTCCATTCTGGAAAAGAGAAACGCGTGGCGGATGT | 1973 |
| RPS6KA1 | NM_002953 | 2 | 1 | + | 22 | + | 0 | 37 | 1 | 0 | CGCGAATGCCAAGCTGGACTTCAGCCGTCCAAGGTGAGGACCATGACGCGTGGCGGATGT | 1974 |
| RPS6KA1 | NM_002953 | 2 | 1 | + | 57 | − | 0 | 37 | 1 | 0 | CGCGAATGCCAGGATCCCCACAGCCCCTGCTCAGGGTGCTGGCACGCGTGGCGGATGT | 1975 |
| RB1 | NM_000321 | 6 | 13 | + | −36 | + | 0 | 37 | 1 | 0 | CGCGAATGCCTTCCTGTTTTTTTTCTGCTTTCTATTTGTTTAATAACGCGTGGCGGATGT | 1976 |
| RB1 | NM_000321 | 6 | 13 | + | −1 | − | 0 | 37 | 1 | 0 | CGCGAATGCCTAGCACCATGCAGAATTTATTTCAGTAGATATCCACGCGTGGCGGATGT | 1977 |
| RB1 | NM_000321 | 6 | 13 | + | 34 | + | 0 | 37 | 1 | 0 | CGCGAATGCCAAAGTTCTTGGATCACATTTTTATTAGCTAAAGGACGCGTGGCGGATGT | 1978 |
| RB1 | NM_000321 | 6 | 13 | + | 69 | − | 0 | 37 | 1 | 0 | CGCGAATGCCTGAAATATTAGCATTTAATAAATATAATGAACTTAACGCGTGGCGGATGT | 1979 |
| CHAF1A | NM_005483 | 15 | 19 | + | −20 | + | 0 | 37 | 1 | 0 | CGCGAATGCCCTTCCCTTCTTGCCCTGCAGAGTCCAAGCCCCGTACGCGTGGCGGATGT | 1980 |
| CHAF1A | NM_005483 | 15 | 19 | + | 15 | − | 0 | 37 | 1 | 0 | CGCGAATGCCCCCACCACCCCCAGCTCCGGAAGCGCTCCACACGCGTGGCGGATGT | 1981 |
| CHAF1A | NM_005483 | 15 | 19 | + | 50 | + | 0 | 37 | 1 | 0 | CGCGAATGCCGTGACACCGGCAAGGCCACCCTGACCTCGAGCCCACGCGTGGCGGATGT | 1982 |
| CHAF1A | NM_005483 | 15 | 19 | + | 85 | − | 0 | 37 | 1 | 0 | CGCGAATGCCACATACGTCACCCCTGCTCTCAGGATGCACCCAGTACGCGTGGCGGATGT | 1983 |
| RET | NM_020630 | 18 | 10 | + | −20 | + | 0 | 37 | 1 | 0 | CGCGAATGCCCTGTCTGCTCTTCCACCAGGTACCGCCTGATGCTACGCGTGGCGGATGT | 1984 |
| RET | NM_020630 | 18 | 10 | + | 15 | − | 0 | 37 | 1 | 0 | CGCGAATGCCCCGGCCTTTTGTCCGGCTCCTGCTTCCAGCATTGCACGCGTGGCGGATGT | 1985 |
| RET | NM_020630 | 18 | 10 | + | 50 | + | 0 | 37 | 1 | 0 | CGCGAATGCCTGTTTGCGGACATCAGCAAAGACCTGGAGAAGATGACGCGTGGCGGATGT | 1986 |
| RET | NM_020630 | 18 | 10 | + | 85 | − | 0 | 37 | 1 | 0 | CGCGAATGCCAATTGGACCCAGGCACTCACTCTCCTCTTAACCATACGCGTGGCGGATGT | 1987 |
| NFKB1 | NM_003998 | 17 | 4 | + | 0 | + | 0 | 37 | 1 | 0 | CGCGAATGCCACGCCCTTGCACTTGGCAGTGATCACTAAGCAGGAACGCGTGGCGGATGT | 1988 |
| NFKB1 | NM_003998 | 17 | 4 | + | 35 | − | 0 | 37 | 1 | 0 | CGCGAATGCCCCCAGCCCCTCAGCAAATCCTCCACCATCTACGCGTGGCGGATGT | 1989 |
| NFKB1 | NM_003998 | 17 | 4 | + | 70 | + | 0 | 37 | 1 | 0 | CGCGAATGCCACCTGAGCCTTCTGACCGCTTGGGTAACTCTGTTACGCGTGGCGGATGT | 1990 |
| NFKB1 | NM_003998 | 17 | 4 | + | 105 | − | 0 | 37 | 1 | 0 | CGCGAATGCCACTTTATCATGTCCTTTCTTTGGCAGCTAGGTCAAACGCGTGGCGGATGT | 1991 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| NFKB1 | NM_003998 | 17 | 4 | + | 140 | + | 0 | 37 | 1 | 0 | CGCGAATGCCTCTCAGTATCTTACTCAAGCACAAAAAGGCAGCACACGCCTGGCCGATGT | 1992 |
| NFKB1 | NM_003998 | 17 | 4 | + | 175 | - | 0 | 37 | 1 | 0 | CGCGAATGCCTCTCTTACCGTCCCCGTTGGGGTGGTCAAGAAGTAACGCGTGGCCGATGT | 1993 |
| NFKB1 | NM_003998 | 5 | 4 | + | -20 | + | 0 | 37 | 1 | 0 | CGCGAATGCCCTTAACGTTCACCTTTGCAGAGAGGATTTCGTTTCACGCCTGGCCGATGT | 1994 |
| NFKB1 | NM_003998 | 5 | 4 | + | 15 | - | 0 | 37 | 1 | 0 | CGCGAATGCCAGTCCACCATGGGATGGGCCTTCACATACATAACGACGCGTGGCCGATGT | 1995 |
| NFKB1 | NM_003998 | 5 | 4 | + | 50 | + | 0 | 37 | 1 | 0 | CGCGAATGCCACCTGGTGCCTCTAGTGAAAAGAACAAGAGTCTTACGCGTGGCCGATGT | 1996 |
| NFKB1 | NM_003998 | 5 | 4 | + | 85 | - | 0 | 37 | 1 | 0 | CGCGAATGCCGGAGAGCTACCACCAAACTTACTTTGACCTGGGGTACGCGTGGCCGATGT | 1997 |
| EPHB1 | NM_004441 | 11 | 3 | + | 0 | + | 0 | 37 | 1 | 0 | CGCGAATGCCGGAGTTTGGAGAAGTGTACAAGGGGCGTTTGAAAACGCGTGGCCGATGT | 1998 |
| EPHB1 | NM_004441 | 11 | 3 | + | 35 | - | 0 | 37 | 1 | 0 | CGCGAATGCCTTGATGCCCACGTAGATTTCCCTCTTGCCTGCAGACGCGTGGCCGATGT | 1999 |
| EPHB1 | NM_004441 | 11 | 3 | + | 70 | + | 0 | 37 | 1 | 0 | CGCGAATGCCGACCTCACGCCTGGCCGATGTAGAAGCAGCGTCACGCCTGGCCGATGT | 2000 |
| EPHB1 | NM_004441 | 11 | 3 | + | 105 | - | 0 | 37 | 1 | 0 | CGCGAATGCCCTGGCCCATGATGCTCCGCCTACTCAGAAAGTCCCACGCCTGGCCGATGT | 2001 |
| EPHB1 | NM_004441 | 11 | 3 | + | 140 | + | 0 | 37 | 1 | 0 | CGCGAATGCCTTCGACCATCCTAACATCATTCGCCTGGAGGGTGTACGCGTGGCCGATGT | 2002 |
| EPHB1 | NM_004441 | 11 | 3 | + | 175 | - | 0 | 37 | 1 | 0 | CGCGAATGCCCTGTGATGATCATGACAGGCCGACTCTTGGTGACCACGCGTGGCCGATGT | 2003 |
| EPHB1 | NM_004441 | 11 | 3 | + | 210 | + | 0 | 37 | 1 | 0 | CGCGAATGCCAGTTCATGGAGAATGGTGCATTGGATTCTTTCCTCACGCCTGGCCGATGT | 2004 |
| EPHB1 | NM_004441 | 11 | 3 | + | 245 | - | 0 | 37 | 1 | 0 | CGCGAATGCCAGTGCATCATCAAACCCTGAGTTGCTCTTACCCTACGCCTGGCCGATGT | 2005 |
| EPHB1 | NM_004441 | 15 | 3 | + | 0 | + | 0 | 37 | 1 | 0 | CGCGAATGCCGCCTTCCCAGCCCCTGCTCGACCGCTCCATCCAGACGCGTGGCCGATGT | 2006 |
| EPHB1 | NM_004441 | 15 | 3 | + | 35 | - | 0 | 37 | 1 | 0 | CGCGAATGCCGAGCCAGTCATCCACGGTGGTAAAGGCCGTGAAGTACGCCTGGCCGATGT | 2007 |
| EPHB1 | NM_004441 | 15 | 3 | + | 70 | + | 0 | 37 | 1 | 0 | CGCGAATGCCAGCGCCATCAAAATGGTCCAGTACAGGGACAGCTTACGCCTGGCCGATGT | 2008 |
| EPHB1 | NM_004441 | 15 | 3 | + | 105 | - | 0 | 37 | 1 | 0 | CGCGAATGCCTGACCAGCTGAGGGAGGTGAAGCCAGCAGTGAGACGCCGTGGCCGATGT | 2009 |
| EPHB1 | NM_004441 | 15 | 3 | + | 140 | + | 0 | 37 | 1 | 0 | CGCGAATGCCCCCAGATGACATCAGAGTAAGTGATGAGAATCTACGCGTGGCCGATGT | 2010 |
| PIK3CA | NM_006218 | 6 | 3 | + | -27 | + | 0 | 37 | 1 | 0 | CGCGAATGCCTAGTATATACCTACTTTTTCTTTTAGATCTATGTACGCGTGGCCGATGT | 2011 |
| PIK3CA | NM_006218 | 6 | 3 | + | 8 | - | 0 | 37 | 1 | 0 | CGCGAATGCCATAAGGGTTCTCCTCCATGGTAGATACCTGTTCGAACGCGTGGCCGATGT | 2012 |
| PIK3CA | NM_006218 | 6 | 3 | + | 43 | + | 0 | 37 | 1 | 0 | CGCGAATGCCGTGACAATGTGAACACTCAAAGAGTACCTTGTTCCACGCGTGGCCGATGT | 2013 |
| PIK3CA | NM_006218 | 6 | 3 | + | 78 | - | 0 | 37 | 1 | 0 | CGCGAATGCCGAAATATAAATCTATATACTTCCTTACCTGGATTACGCGTGGCCGATGT | 2014 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| NTRK3 | NM_001012338 | 6 | 15 | - | -4 | + | 0 | 37 | 1 | 0 | CGCGAATGCCACAGATGTGCAGCACATTAAGAGGAGAGACATCGTACGCGTGGCGGATGT | 2015 |
| NTRK3 | NM_001012338 | 6 | 15 | - | 31 | - | 0 | 37 | 1 | 0 | CGCGAATGCCTTCCAAAGGCTCCCTCACCCAGTTCTCGCTTCAGCACGCGTGGCGGATGT | 2016 |
| NTRK3 | NM_001012338 | 6 | 15 | - | 66 | + | 0 | 37 | 1 | 0 | CGCGAATGCCAGGTCTTCCTGGCCGAGTGCTACAACCTCAGCCCGACGCGTGGCGGATGT | 2017 |
| NTRK3 | NM_001012338 | 6 | 15 | - | 101 | - | 0 | 37 | 1 | 0 | CGCGAATGCCTTTACCTTCACAGCCACAAGCATCTTGTCCTTGGTACGCGTGGCGGATGT | 2018 |
| CHAF1A | NM_005483 | 14 | 19 | + | -22 | + | 0 | 37 | 1 | 0 | CGCGAATCCGCCGTGTACCCTGTCTGTCCAGATTTGGTGTGAAGACGCGTGGCGGATGT | 2019 |
| CHAF1A | NM_005483 | 14 | 19 | + | 9 | - | 6 | 37 | 1 | 0 | CGCGAATGCCTCCTCCGTGTCTGCCTGGAAGCCGTCCATGTCTTCACGCGTGGCGGATGT | 2020 |
| CHAF1A | NM_005483 | 14 | 19 | + | 52 | + | 9 | 37 | 1 | 0 | CGCGAATCCAGGAGGAGGGCGACTGTATGATCGTGGATGTCCGACGCGTGGCGGATGT | 2021 |
| CHAF1A | NM_005483 | 14 | 19 | + | 83 | - | 0 | 37 | 1 | 0 | CGCGAATGCCGCTATCTACAGCCCTTCTCACCCGCAGCATCCGGACGCGTGGCGGATGT | 2022 |
| NFKB1 | NM_003998 | 8 | 4 | + | 0 | + | 0 | 37 | 1 | 0 | CGCGAATGCCATGCCCCACCACGCTGAGGTCCATCTCCAAGCAGCTTCGACGCGTGGCGGATGT | 2023 |
| NFKB1 | NM_003998 | 8 | 4 | + | 35 | - | 0 | 37 | 1 | 0 | CGCGAATGCCGCTCATGTTTACAGCTTTTCTTCCTTGGTCTGCTACGCGTGGCGGATGT | 2024 |
| NFKB1 | NM_003998 | 8 | 4 | + | 70 | + | 0 | 37 | 1 | 0 | CGCGAATGCCGCTCATGTTTACAGCTTTTCTTCCGGATAGCACTGACGCGTGGCGGATGT | 2025 |
| NFKB1 | NM_003998 | 8 | 4 | + | 105 | - | 0 | 37 | 1 | 0 | CGCGAATGCCTGATACCACGGGTTCCAGGCGCCTTGTGAAGCTCACGCGTGGCGGATGT | 2026 |
| NFKB1 | NM_003998 | 8 | 4 | + | 140 | + | 0 | 37 | 1 | 0 | CGCGAATGCCGACGCCATCTATGACAGTAGTGAGTACTTCACTTCACGCGTGGCGGATGT | 2027 |
| RPS6KA1 | NM_002953 | 13 | 1 | + | -18 | + | 0 | 37 | 1 | 0 | CGCGAATGCCGCCCACCCACTGTGCAGAAGCTATACCGTCGTGAACGCGTGGCGGATGT | 2028 |
| RPS6KA1 | NM_002953 | 13 | 1 | + | 17 | - | 0 | 37 | 1 | 0 | CGCGAATGCCGTGAGCCACTGCTGGCTTGAAGGGTGGCTTGATCACGCGTGGCGGATGT | 2029 |
| RPS6KA1 | NM_002953 | 13 | 1 | + | 52 | + | 0 | 37 | 1 | 0 | CGCGAATGCCCTGATGACACCTTCTACTTTGACACCGAGTTCACGACGCGTGGCGGATGT | 2030 |
| RPS6KA1 | NM_002953 | 13 | 1 | + | 87 | - | 0 | 37 | 1 | 0 | CGCGAATGCCAAACAGATAAGGAGCACCCTTGGGTGTGCGGAACGCGTGGCGGATGT | 2031 |
| EPHB1 | NM_004441 | 14 | 3 | + | 0 | + | 0 | 37 | 1 | 0 | CGCGAATGCCGTCATCAATGCCATGCAGAGCAGGACTACCGGCTGCCACGCGTGGCGGATGT | 2032 |
| EPHB1 | NM_004441 | 14 | 3 | + | 35 | - | 0 | 37 | 1 | 0 | CGCGAATGCCGCTGGTGTAGAGCGCTGGACAGTCCATGGTGGGACGCGTGGCGGATGT | 2033 |
| EPHB1 | NM_004441 | 14 | 3 | + | 70 | + | 0 | 37 | 1 | 0 | CGCGAATGCCTCATGCTGGACTGTTGCAGAAGGACCGGAACAGCACGCGTGGCGGATGT | 2034 |
| EPHB1 | NM_004441 | 14 | 3 | + | 105 | - | 0 | 37 | 1 | 0 | CGCGAATGCCTAGGGTGTTGCAATCTCCGCAAACCGGGGCCGACGCGTGGCGGATGT | 2035 |
| EPHB1 | NM_004441 | 14 | 3 | + | 140 | + | 0 | 37 | 1 | 0 | CGCGAATGCCTAAGATGATCCGGAACCCGGATGTCTCAAGACTGACGCGTGGCGGATGT | 2036 |
| EPHB1 | NM_004441 | 14 | 3 | + | 175 | - | 0 | 37 | 1 | 0 | CGCGAATGCCGTTTCACTGACTCACGCGCGGTGATGGTTGCCAACGCGTGGCGGATGT | 2037 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| NTRK3 | NM_001012338 | 12 | 15 | - | 0 | + | 0 | 37 | 1 | CGCGAATGCCACCAATCTGAACTGGACCAATGT TCATGCCATCAAACGCCTGGCCGATGT | 2038 |
| NTRK3 | NM_001012338 | 12 | 15 | - | 35 | - | 0 | 37 | 1 | CGCGAATGCCCATTGTCCTCACTCGTCACATTCA CAGCGTCAAGACGCCGTGGCCGATGT | 2039 |
| NTRK3 | NM_001012338 | 12 | 15 | - | 70 | + | 0 | 37 | 1 | CGCGAATGCCGCTTCACCCTGACGTGCATTGCA GAGAACGTGGTGACGCCGTGGCCGATGT | 2040 |
| NTRK3 | NM_001012338 | 12 | 15 | - | 105 | - | 0 | 37 | 1 | CGCGAATGCCTAGACAGTGAGGGCAACACTGGC AATGCTCATGCCACGCGTGGCCGATGT | 2041 |
| NTRK3 | NM_001012338 | 12 | 15 | - | 140 | + | 0 | 37 | 1 | CGCGAATGCCCTGTAAGTGCATGTTATTGTGGG GGATGGCTGTGTACGCCGTGGCCGATGT | 2042 |
| EPHA7 | NM_004440 | 4 | 6 | - | 0 | - | 0 | 37 | 1 | CGCGAATGCCGGTGGAAAAATTCCAGTAAGGTG GACAGCACCGAACGCGTGGCCGATGT | 2043 |
| EPHA7 | NM_004440 | 4 | 6 | - | 35 | + | 0 | 37 | 1 | CGCGAATGCCCACTGGCTGATGTGAATTTCCGG TACTGGATGCCTACGCCTGGCCGATGT | 2044 |
| EPHA7 | NM_004440 | 4 | 6 | - | 70 | - | 0 | 37 | 1 | CGCGAATGCCATGTATGGAGCTATGGAATAGTC ATGTGGGAAGTTACGCCGTGGCCGATGT | 2045 |
| EPHA7 | NM_004440 | 4 | 6 | - | 105 | + | 0 | 37 | 1 | CGCGAATGCCGACATGTCCAATAAGGTCTTTC TCCATAAGACATACGCCTGGCCGATGT | 2046 |
| EPHA7 | NM_004440 | 4 | 6 | - | 140 | - | 0 | 37 | 1 | CGCGAATGCCAAATCAAGATGTAGGTGTTACAT TCATTTAAACAACGCCGTGGCCGATGT | 2047 |
| EPHA7 | NM_004440 | 14 | 6 | - | 0 | + | 0 | 37 | 1 | CGCGAATGCCCCTGTGGCCGTGGGTTCACAAG TCTTCCTCTCAAACGCCTGGCCGATGT | 2048 |
| EPHA7 | NM_004440 | 14 | 6 | - | 35 | - | 0 | 37 | 1 | CGCGAATGCCAAACTGTGAGTTGGACAACGAGA GCACTGAAGATCACGCCGTGGCCGATGT | 2049 |
| EPHA7 | NM_004440 | 14 | 6 | - | 70 | + | 0 | 37 | 1 | CGCGAATGCCTTCTGATAAAGAAGAGGCTCCTCCA GATGTGAATGTGACGCCTGGCCGATGT | 2050 |
| EPHA7 | NM_004440 | 14 | 6 | - | 105 | - | 0 | 37 | 1 | CGCGAATGCCTGTGGGTCAGATGGAGCCCTGT AATACCCATCTTACGCCTGGCCGATGT | 2051 |
| EPHA7 | NM_004440 | 14 | 6 | - | 140 | + | 0 | 37 | 1 | CGCGAATGCCTACGTTGCGTGCACAAGTGAGTT GTATTATGAAAGACGCCTGGCCGATGT | 2052 |
| NFKB1 | NM_003998 | 12 | 4 | + | 0 | + | 0 | 37 | 1 | CGCGAATGCCATAAAGAAGAAGTGCAGAGGAA ACGTCAGAAGCTTCACGCCGTGGCCGATGT | 2053 |
| NFKB1 | NM_003998 | 12 | 4 | + | 35 | - | 0 | 37 | 1 | CGCGAATGCCCTACCACCGCCGAAACTATCCGA AAAATTGGGCATACGCCTGGCCGATGT | 2054 |
| NFKB1 | NM_003998 | 12 | 4 | + | 70 | + | 0 | 37 | 1 | CGCGAATGCCTGGTGCTGGAGCTGGAGGCGGAG GCATGTTTGGTAACGCCGTGGCCGATGT | 2055 |
| NFKB1 | NM_003998 | 12 | 4 | + | 105 | - | 0 | 37 | 1 | CGCGAATGCCACCTGTACTTCCAGTGCCCCTCC TCCACCGCCACACGCCGTGGCCGATGT | 2056 |
| NFKB1 | NM_003998 | 12 | 4 | + | 140 | + | 0 | 37 | 1 | CGCGAATGCCCAGGTACAAAAATACTTATTCT TCCTAAACTTTACGCCGTGGCCGATGT | 2057 |
| NFKB1 | NM_003998 | 21 | 4 | + | -36 | - | 0 | 37 | 1 | CGCGAATGCCATGTATAACGATTTCTGGTGTTTT TCTTTCCAACAACGCCGTGGCCGATGT | 2058 |
| NFKB1 | NM_003998 | 21 | 4 | + | -1 | + | 0 | 37 | 1 | CGCGAATGCCGCTCATATGGTTTCCCATTTAATA TGTCAAATACCACGCCGTGGCCGATGT | 2059 |
| NFKB1 | NM_003998 | 21 | 4 | + | 34 | - | 0 | 37 | 1 | CGCGAATGCCCAGAGTTTACATCTGATGATTTA CTAGCACAAGGTACGCCGTGGCCGATGT | 2060 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| NFKB1 | NM_003998 | 21 | 4 | + | 69 | - | 0 | 37 | 1 | 0 | CGCGAATGCCATAATGTTAAGAGAATCTGGTTTTATCACAACCCACGCTGGCCGGATGT | 2061 |
| EPHA4 | NM_004438 | 7 | 2 | - | -39 | + | 0 | 37 | 1 | 0 | CGCGAATGCCCTCATCAAAGGTTTGTGTTTTCTTTCTGAAAACTACGCGTGGCCGGATGT | 2062 |
| EPHA4 | NM_004438 | 7 | 2 | - | -4 | - | 0 | 37 | 1 | 0 | CGCGAATGCCATGTACTTCTGTTATGATCATTACTGGTTTACCTAGACGCGTGGCCGGATGT | 2063 |
| EPHA4 | NM_004438 | 7 | 2 | - | 31 | + | 0 | 37 | 1 | 0 | CGCGAATGCCGGAGAATGGCTCCTTGGATGCATTCCTCAGGTATACGCGTGGCCGGATGT | 2064 |
| EPHA4 | NM_004438 | 7 | 2 | - | 66 | - | 0 | 37 | 1 | 0 | CGCGAATGCCTACCAACATTCTTGGGTTTAATATAAAGTAGTCACACGCGTGGCCGGATGT | 2065 |
| RET | NM_020630 | 17 | 10 | + | -1 | + | 0 | 37 | 1 | 0 | CGCGAATGCCGATGGTCTTTTGGTGTCCTGCTGTGGGAGATGTGACGCGTGGCCGGATGT | 2066 |
| RET | NM_020630 | 17 | 10 | + | 34 | - | 0 | 37 | 1 | 0 | CGCGAATGCCGGAGGAATCCCAGGATAGGGGTTTCCCCTAGGGTACGCGTGGCCGGATGT | 2067 |
| RET | NM_020630 | 17 | 10 | + | 69 | + | 0 | 37 | 1 | 0 | CGCGAATGCCTGAGCGCTCTTCAACCTTCTGAAGACCGGCCACCACGCGTGGCCGGATGT | 2068 |
| RET | NM_020630 | 17 | 10 | + | 104 | - | 0 | 37 | 1 | 0 | CGCGAATGCCCATCTCCTCGCTGCAGTTGTCTGGCCTCTCCATCCACGCGTGGCCGGATGT | 2069 |
| EPHA4 | NM_004438 | 12 | 2 | - | 0 | + | 0 | 37 | 1 | 0 | CGCGAATGCCGATCAGAATGAGCGAAGCTATCGTATAGTTCGACACGCGTGGCCGGATGT | 2070 |
| EPHA4 | NM_004438 | 12 | 2 | - | 35 | - | 0 | 37 | 1 | 0 | CGCGAATGCCGGTTCAGCCTTTGATATCTGTGTTCCTGGCAGCTACGCGTGGCCGGATGT | 2071 |
| EPHA4 | NM_004438 | 12 | 2 | - | 70 | + | 0 | 37 | 1 | 0 | CGCGAATGCCCTCTCACTTCTATGTTTTCCACGTGCAGCCAGGACGCGTGGCCGGATGT | 2072 |
| EPHA4 | NM_004438 | 12 | 2 | - | 105 | - | 0 | 37 | 1 | 0 | CGCGAATGCCAAGGGCTCACTGAAGTCTCCATAGCCAGCTGCTGTACGCGTGGCCGGATGT | 2073 |
| EPHA4 | NM_004438 | 12 | 2 | - | 140 | + | 0 | 37 | 1 | 0 | CGCGAATGCCGGAGGTTACAACCAACACAGGTAACAAGGACCACCACGCGTGGCCGGATGT | 2074 |
| KSR2 | NM_173598 | 1 | 12 | - | -66 | + | 0 | 37 | 1 | 0 | CGCGAATGCCACAACGGATGACATCATCATGTCCTTGTGACCTTACGCGTGGCCGGATGT | 2075 |
| KSR2 | NM_173598 | 1 | 12 | - | -31 | - | 0 | 37 | 1 | 0 | CGCGAATGCCCAGCCTGAGTGGGGAGAGAAGGGAGAGAGTGGTGACGCCGTGGCCGGATGT | 2076 |
| KSR2 | NM_173598 | 1 | 12 | - | 4 | + | 0 | 37 | 1 | 0 | CGCGAATGCCTGACCTTTGACCATCGGGACGGCGCCCAGCTGCCTACGCCGTGGCCGGATGT | 2077 |
| KSR2 | NM_173598 | 1 | 12 | - | 39 | - | 0 | 37 | 1 | 0 | CGCGAATGCCAGGACAGAGTAGGGAGGGAGAGGTGACGGAGCCACCGCTGGCCGGATGT | 2078 |
| PALB2 | NM_024675 | 7 | 16 | - | 0 | + | 0 | 37 | 1 | 0 | CGCGAATGCCAATCCTTCAGGTTCCTGTTCCGTAGATGTGAGTGCACGCGTGGCCGGATGT | 2079 |
| PALB2 | NM_024675 | 7 | 16 | - | 35 | - | 0 | 37 | 1 | 0 | CGCGAATGCCATGGCTCTTTACAACCGGCTCTTTCCCAAAACATGACGCGTGGCCGGATGT | 2080 |
| PALB2 | NM_024675 | 7 | 16 | - | 70 | + | 0 | 37 | 1 | 0 | CGCGAATGCCGTATCATAACTGCTTGCGAAGATGTAGTTTCTTACGCGTGGCCGGATGT | 2081 |
| PALB2 | NM_024675 | 7 | 16 | - | 105 | - | 0 | 37 | 1 | 0 | CGCGAATGCCAGTTTTCCACTGCCAAGCATCCAGAGCTTTCCAACGCGTGGCCGGATGT | 2082 |
| PALB2 | NM_024675 | 7 | 16 | - | 140 | + | 0 | 37 | 1 | 0 | CGCGAATGCCTTATACCTGGCACTTCCAGAGGTAAGTGGGAATCACGCGTGGCCGGATGT | 2083 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BwA score | BWA hit | # BWA mismatch | Sequence with add-ons | SEQ ID NO: |
|---|---|---|---|---|---|---|---|---|---|---|---|---|
| PIK3CA | NM_006218 | 18 | 3 | + | 0 | + | 0 | 37 | 1 | 0 | CGCGAATGCCAATGTTACCTTATGGTTGTCTGTCAATCGGTGACTACGCGTGGCGGATGT | 2084 |
| PIK3CA | NM_006218 | 18 | 3 | + | 35 | - | 0 | 37 | 1 | 0 | CGCGAATGCCGTGAGAATTTCGCACCACCTCAATAAGTCCCACACGCGTGGCGGATGT | 2085 |
| PIK3CA | NM_006218 | 18 | 3 | + | 70 | + | 0 | 37 | 1 | 0 | CGCGAATGCCACTATTATGCAAATTCAGTGCAAAGGCGGCTTGAAACGCCGTGGCGGATGT | 2086 |
| PIK3CA | NM_006218 | 18 | 3 | + | 105 | - | 0 | 37 | 1 | 0 | CGCGAATGCCGATGTAGTGTGTGGCTGTTGAACTGCAGTGCACTTACGCGTGGCGGATGT | 2087 |
| PIK3CA | NM_006218 | 18 | 3 | + | 140 | + | 0 | 37 | 1 | 0 | CGCGAATGCCAGTGGCTCAAAGACAAGAACAAAGGAGAAATGTGAACGCGTGGCGGATGT | 2088 |
| CENTG1 | NM_001122772 | 6 | 12 | - | -36 | + | 24 | 37 | 1 | 0 | CGCGAATGCCCATTCTATCTCTATCTCCTTCGCTTCGGGAACCAACGCGTGGCGGATGT | 2089 |
| CENTG1 | NM_001122772 | 6 | 12 | - | -5 | - | 0 | 37 | 1 | 0 | CGCGAATGCCAGGATTTTAGTTTCCACATTTTGCGCTTGGCTGGTACGCGTGGCGGATGT | 2090 |
| CENTG1 | NM_001122772 | 6 | 12 | - | 30 | + | 0 | 37 | 1 | 0 | CGCGAATGCCTTGGTAGTTTAAGAAATATTTATAAAGCAGTAACACGCGTGGCGGATGT | 2091 |
| CENTG1 | NM_001122772 | 6 | 12 | - | 65 | - | 0 | 37 | 1 | 0 | CGCGAATGCCCACCCCAGCTGACGCGCCCTCCCGGCTCCCACTTACGCGTGGCGGATGT | 2092 |
| EPHA7 | NM_004440 | 12 | 6 | - | -8 | + | 0 | 37 | 1 | 0 | CGCGAATGCCCCAAACAGCTCCCTCGCAAGTGAGTGGAGTAATGAACGCGTGGCGGATGT | 2093 |
| EPHA7 | NM_004440 | 12 | 6 | - | 27 | - | 0 | 37 | 1 | 0 | CGCGAATGCCGGAAAGCTCGACACTCCGCTGCAGTACTCTCTCCTACGCGTGGCGGATGT | 2094 |
| EPHA7 | NM_004440 | 12 | 6 | - | 62 | + | 0 | 37 | 1 | 0 | CGCGAATGCCTGCAGGAACCAGAGCATCCCAATGGAGTCATCACGCGTGGCGGATGT | 2095 |
| EPHA7 | NM_004440 | 12 | 6 | - | 97 | - | 0 | 37 | 1 | 0 | CGCGAATGCCCACTTCTTCTGTAATACTGATTTCATATTCTACGCGTGGCGGATGT | 2096 |
| PDGFRA | NM_006206 | 15 | 4 | + | 0 | + | 0 | 37 | 1 | 0 | CGCGAATGCCGCCCCATTACATCATCACAGAGTATTGCTTCTATACGCGTGGCGGATGT | 2097 |
| PDGFRA | NM_006206 | 15 | 4 | + | 35 | - | 0 | 37 | 1 | 0 | CGCGAATGCCTCCCTATTCTTATGCAAATAGTTGACCAAATCTCACGCGTGGCGGATGT | 2098 |
| PDGFRA | NM_006206 | 15 | 4 | + | 70 | + | 0 | 37 | 1 | 0 | CGCGAATGCCTAGCTTCTGAGCCACCACCCAGAGAAGCCAAAGAACGCCTGGCGGATGT | 2099 |
| PDGFRA | NM_006206 | 15 | 4 | + | 105 | - | 0 | 37 | 1 | 0 | CGCGAATGCCATCAGCAGGGTTCAATCAAAGATATCCAGCTCTTACGCCTGGCGGATGT | 2100 |
| PDGFRA | NM_006206 | 15 | 4 | + | 140 | + | 0 | 37 | 1 | 0 | CGCGAATGCCGAAAGACACGGAGGTGGGTGCAAAGAGAGATGTTACGCCTGGCGGATGT | 2101 |
| RET | NM_020630 | 8 | 10 | + | -7 | + | 0 | 37 | 1 | 0 | CGCGAATGCCCCTGCAGATGTGGCCGAGGAGGCGGGCTGCCCCTACGCGTGGCGGATGT | 2102 |
| RET | NM_020630 | 8 | 10 | + | 28 | - | 0 | 37 | 1 | 0 | CGCGAATGCCCACACTCCAGCCGTCTCTTGCTGACTGCAGGACACGCGTGGCGGATGT | 2103 |
| RET | NM_020630 | 8 | 10 | + | 63 | + | 0 | 37 | 1 | 0 | CGCGAATGCCAGGAGTGTGGCGCCTGGGCTCCCAACAGCAGGACGCGTGGCGGATGT | 2104 |
| RET | NM_020630 | 8 | 10 | + | 98 | - | 0 | 37 | 1 | 0 | CGCGAATGCCGGCTTACCTTTGCCATCCTCCTTGCCTCCACTCCACACGCGTGGCGGATGT | 2105 |
| PDGFRA | NM_006206 | 4 | 4 | + | 0 | + | 0 | 37 | 1 | 0 | CGCGAATGCCACCAGATGTAGCCTTTGTACCTCTAGGAATGACGCGTGGCGGATGT | 2106 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| PDGFRA | NM_006206 | 4 | 4 | + | 35 | − | 0 | 37 | 1 | 0 | CGCGAATGCCGCAGAATCATCATCCTCCACGATGACTAAATAATCACGCGTGGCCGATGT | 2107 |
| PDGFRA | NM_006206 | 4 | 4 | + | 70 | + | 0 | 37 | 1 | 0 | CGCGAATGCCCATTATACCTTGTCGCACAACTGATCCCGAGACTCACGCGTGGCCGATGT | 2108 |
| PDGFRA | NM_006206 | 4 | 4 | + | 105 | − | 0 | 37 | 1 | 0 | CGCGAATGCCAGGTACCACCCCCTCACTGTTGTGTAAGGTTACAGACGCGTGGCCGATGT | 2109 |
| PDGFRA | NM_006206 | 4 | 4 | + | 140 | + | 0 | 37 | 1 | 0 | CGCGAATGCCGCCTCCTACGACAGCAGACAGGGCTTTAATGGACACGCGTGGCCGATGT | 2110 |
| PDGFRA | NM_006206 | 4 | 4 | + | 175 | − | 0 | 37 | 1 | 0 | CGCGAATGCCCGTGGCCTCACAGATATAGGGCCCTACAGTGAAGACGCGTGGCCGATGT | 2111 |
| PDGFRA | NM_006206 | 4 | 4 | + | 210 | + | 0 | 37 | 1 | 0 | CGCGAATGCCTCAAAGGAAAGAAGTTCCAGACCATCCCATTTAATACGCGTGGCCGATGT | 2112 |
| PDGFRA | NM_006206 | 4 | 4 | + | 245 | − | 0 | 37 | 1 | 0 | CGCGAATGCCAAGGAGATGATACAAGTACCTTTTAAAGCATAAACACGCGTGGCCGATGT | 2113 |
| RET | NM_020630 | 15 | 10 | + | −8 | + | 0 | 37 | 1 | 0 | CGCGAATGCCCCTCACAGCTCGTTCATCGGACTTGGCAGCAGACGCGTGGCCGATGT | 2114 |
| RET | NM_020630 | 15 | 10 | + | 27 | − | 0 | 37 | 1 | 0 | CGCGAATGCCATCTTCATCTTCCGCCCCTCAGCTACCAGAGATGTTACGCGTGGCCGATGT | 2115 |
| RET | NM_020630 | 15 | 10 | + | 62 | + | 0 | 37 | 1 | 0 | CGCGAATGCCTTCGGATTTCGGCTTGTCCCGAGATGTTTATGAAGACGCGTGGCCGATGT | 2116 |
| RET | NM_020630 | 15 | 10 | + | 97 | − | 0 | 37 | 1 | 0 | CGCGAATGCCCACTGGGCACCTGCCTCCTCTTCACGTAGGAATCCTACGCCTGGCCGATGT | 2117 |
| RPS6KA1 | NM_002953 | 19 | 1 | + | −32 | + | 0 | 37 | 1 | 0 | CGCGAATGCCCAGACTGACCACCTCCCCTGCCCTGTTGCCAGGTGACGCGTGGCCGATGT | 2118 |
| RPS6KA1 | NM_002953 | 19 | 1 | + | 3 | − | 0 | 37 | 1 | 0 | CGCGAATGCCATGTCGCAGCCTTCATCGTAGCCCTGGCGCTTCAGACGCGTGGCCGATGT | 2119 |
| RPS6KA1 | NM_002953 | 19 | 1 | + | 38 | + | 0 | 37 | 1 | 0 | CGCGAATGCCTGGAGCCTGGGCATTCTGCTGTACACCATGCTGGACGCGTGGCCGATGT | 2120 |
| RPS6KA1 | NM_002953 | 19 | 1 | + | 73 | − | 0 | 37 | 1 | 0 | CGCACTCACCCTGACGCGTGGCCGATGGGCCAATGCCGTGGGAAGGGTCCAGGCCAGG | 2121 |
| RB1 | NM_000321 | 16 | 13 | + | −2 | + | 0 | 37 | 1 | 0 | CGCGAATGCCAGGAAGAAGAACGATTATCCATTCAAAATTTTAGGACGCGTGGCCGATGT | 2122 |
| RB1 | NM_000321 | 16 | 13 | + | 31 | − | 33 | 37 | 1 | 0 | CGCGAATGCCGAAAAAATTTTTTACTAAAAGTAAAAATTTACCACGCGTGGCCGATGT | 2123 |
| RB1 | NM_000321 | 16 | 13 | + | 74 | + | 31 | 37 | 1 | 0 | CGCGAATGCCGAAGTAAGTATTTTATAATCTTTTTTTTTCCTTACGCGTGGCCGATGT | 2124 |
| RB1 | NM_000321 | 16 | 13 | + | 105 | − | 0 | 37 | 1 | 0 | CGCGAATGCCATGAAAAATGTTGTCATTCAGAAGTTTGCTAAAGGACGCGTGGCCGATGT | 2125 |
| RB1 | NM_000321 | 16 | 13 | + | 140 | + | 0 | 37 | 1 | 0 | CGCGAATGCCATGTCTTTATTGGCGTGCGCTTTGAGGTTGTAATACGCGTGGCCGATGT | 2126 |
| RB1 | NM_000321 | 16 | 13 | + | 175 | − | 0 | 37 | 1 | 0 | CGCGAATGCCCATTTATGAAAATTTAACTTACTGCTATATGTGGCCACGCGTGGCCGATGT | 2127 |
| RPS6KA1 | NM_002953 | 7 | 1 | + | −16 | + | 0 | 37 | 1 | 0 | CGCGAATGCCCTCTGTCTTTTGCAGTGATGTTACGGAGGAGCGCGTGGCCGATGT | 2128 |
| RPS6KA1 | NM_002953 | 7 | 1 | + | 19 | − | 0 | 37 | 1 | 0 | CGCGAATGCGCCCAGCCAGCTCAGCCAGTAAAACTTCACATACGCGGCCGATGT | 2129 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| RPS6KA1 | NM_002953 | 7 | 1 | + | 54 | + | 0 | 37 | 1 | 0 | CGCGAATGCCCTGGATCACCTGCACAGCCTGGG TATCATTTACAGACGCGCTGGCGGATGT | 2130 |
| RPS6KA1 | NM_002953 | 7 | 1 | + | 89 | - | 0 | 37 | 1 | 0 | CGCGAATGCCCTGGAGGCTTCACTCACTTCTCA GGCTTGAGGTCTACGCGTGGCGGATGT | 2131 |
| PKN1 | NM_002741 | 3 | 19 | + | 0 | + | 0 | 37 | 1 | 0 | CGCGAATGCCATGCCCCCAGTCCCCTGGTGCG GGTGGCCCCACCACGCGTGGCGGATGT | 2132 |
| PKN1 | NM_002741 | 3 | 19 | + | 35 | - | 0 | 37 | 1 | 0 | CGCGAATGCCAGGCCCGCCACGCGGCTCAGGTT GGTGGCCAGCAACGCGTGGCGGATGT | 2133 |
| PKN1 | NM_002741 | 3 | 19 | + | 70 | + | 0 | 37 | 1 | 0 | CGCGAATGCCGGAGAAGCAGTTGGCCATTGAGC TGAAGGTGAAGCACGCGTGGCGGATGT | 2134 |
| PKN1 | NM_002741 | 3 | 19 | + | 105 | - | 0 | 37 | 1 | 0 | CGCGAATGCCATTGCTGTAGGTCTGGATCATGTT CTCCGCCCCTACGCGTGGCGGATGT | 2135 |
| PKN1 | NM_002741 | 3 | 19 | + | 140 | + | 0 | 37 | 1 | 0 | CGCGAATGCCGGCAGCACCAAGGTGAGGCAGC ACGTGCACACAACGCGTGGCGGATGT | 2136 |
| PDGFRA | NM_006206 | 16 | 4 | + | 0 | + | 0 | 37 | 1 | 0 | CGCGAATGCCCTATGTTATTTTATCTTTTGAAAA CAATGGTGACATACGCGTGGCGGATGT | 2137 |
| PDGFRA | NM_006206 | 16 | 4 | + | 35 | - | 0 | 37 | 1 | 0 | CGCGAATGCCATATCTGTGTAGTATCAGCCTGCTT CATGTCATGTACGCGTGGCGGATGT | 2138 |
| PDGFRA | NM_006206 | 16 | 4 | + | 70 | + | 0 | 37 | 1 | 0 | CGCGAATGCCGTCCCCATGCTAGAAAGGAAAGA GGTTTCTAAATAACGCGTGGCGGATGT | 2139 |
| PDGFRA | NM_006206 | 16 | 4 | + | 105 | - | 0 | 37 | 1 | 0 | CGCGAATGCCCTGGACGATCATAGAGTGATCTC TGGATGTCGGAAACGCCTGGCGGATGT | 2140 |
| PDGFRA | NM_006206 | 16 | 4 | + | 140 | + | 0 | 37 | 1 | 0 | CGCGAATGCCCCTCATATAAGAAGAAATCTATG TTAGGTAAAGTATACGCGTGGCGGATGT | 2141 |
| RB1 | NM_000321 | 25 | 13 | + | 0 | + | 0 | 37 | 1 | 0 | CGCGAATGCCCACTTCTGAGAAGTTCCAGAAAAT AAATCAGATGTATACGCCTGGCGGATGT | 2142 |
| RB1 | NM_000321 | 25 | 13 | + | 35 | - | 0 | 37 | 1 | 0 | CGCGAATGCCAGCACTTCTTTTGAGCACACGG TCGCTGTTACATACGCGTGGCGGATGT | 2143 |
| RB1 | NM_000321 | 25 | 13 | + | 70 | + | 0 | 37 | 1 | 0 | CGCGAATGCCAAGGAAGCAACCTCCTAAACCA CTGAAAAAACTAACGCGTGGCGGATGT | 2144 |
| RB1 | NM_000321 | 25 | 13 | + | 105 | - | 0 | 37 | 1 | 0 | CGCGAATGCCCCATCTGCTTCATCTGATCCTTCA ATATCAAAGCGACGCGTGGCGGATGT | 2145 |
| RB1 | NM_000321 | 25 | 13 | + | 140 | + | 0 | 37 | 1 | 0 | CGCGAATGCCAAGGTAGGAACCAGTTTTGAATG TTTTCCAGTAGCACGCGTGGCGGATGT | 2146 |
| PKN1 | NM_213560 | 1 | 19 | + | -50 | + | 0 | 37 | 1 | 0 | CGCGAATGCCGGTGGGGCTGAGGTTCAGGAAGA GGGCGGGGCCCTACGCGTGGCGGATGT | 2147 |
| PKN1 | NM_213560 | 1 | 19 | + | -15 | - | 0 | 37 | 1 | 0 | CGCGAATGCCGGGTTATTGGCCTCCGCCATCCT GGGTCCGGCTGACGCGTGGCGGATGT | 2148 |
| PKN1 | NM_213560 | 1 | 19 | + | 20 | + | 0 | 37 | 1 | 0 | CGCGAATGCCCTCGGAGCAGGAGCTGGAGGTGG GGTCCAGGGTCCACGCGTGGCGGATGT | 2149 |
| PKN1 | NM_213560 | 1 | 19 | + | 55 | - | 0 | 37 | 1 | 0 | CGCGAATGCCGCCACTTGGGCGCCCCCTTCTGCC TGCCCCACAGACGCGTGGCGGATGT | 2150 |
| PDGFRA | NM_006206 | 10 | 4 | + | 0 | + | 0 | 37 | 1 | 0 | CGCGAATGCCATGTAATAATGAAACTTCCTGGA CTATTTTGGCCAACGCGTGGCGGATGT | 2151 |
| PDGFRA | NM_006206 | 10 | 4 | + | 35 | - | 0 | 37 | 1 | 0 | CGCGAATGCCCGAGTGGATCTCCGTGATGATGT TTGAGACATTGTACGCGTGGCGGATGT | 2152 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| PDGFRA | NM_006206 | 10 | 4 | + | 70 | + | 0 | 37 | 1 | 0 | CGCGAATGCCCGAGACAGGAGTACCGTGGAGG GCCGTGTGACTTTACGCGTGGCGGATGT | 2153 |
| PDGFRA | NM_006206 | 10 | 4 | + | 105 | − | 0 | 37 | 1 | 0 | CGCGAATGCCGGCATCCACGGCGATGGTCTCC TCCACTTTGGCGACGCGTGGCGGATGT | 2154 |
| PDGFRA | NM_006206 | 10 | 4 | + | 140 | + | 0 | 37 | 1 | 0 | CGCGAATGCCTGCTAAGAATCTCCTTGGAGCT GAGAACCAGAGACGCGTGGCGGATGT | 2155 |
| PDGFRA | NM_006206 | 10 | 4 | + | 175 | − | 0 | 37 | 1 | 0 | CGCGAATGCCCTGTTGAGGAACTCACTGGGAGC CACCAGCTTCAGACGCGTGGCGGATGT | 2156 |
| NTRK3 | NM_001012338 | 14 | 15 | − | 0 | + | 0 | 37 | 1 | 0 | CGCGAATGCCGCAGTTGAGCAGCAGAACTTTTCA ACTGCAGCTGTGACGCGTGGCGGATGT | 2157 |
| NTRK3 | NM_001012338 | 14 | 15 | − | 35 | − | 0 | 37 | 1 | 0 | CGCGAATGCCCCCCTGCTCCTGCCAGAGCTGCA TCCACGCGATGTACGCGTGGCGGATGT | 2158 |
| NTRK3 | NM_001012338 | 14 | 15 | − | 70 | + | 0 | 37 | 1 | 0 | CGCGAATGCCGAGGCCAAGCTCAACAGCCAGA ACCTCTACTGCATACGCGTGGCGGATGT | 2159 |
| NTRK3 | NM_001012338 | 14 | 15 | − | 105 | − | 0 | 37 | 1 | 0 | CGCGAATGCCTCGCGGAAGAGAGAAGCTGGGA GCCATCAGCGTTGACGCGTGGCGGATGT | 2160 |
| NTRK3 | NM_001012338 | 14 | 15 | − | 140 | + | 0 | 37 | 1 | 0 | CGCGAATGCCTGAACATCAGTCAGTGTGTGAG TGAGTGCCGCCACGCGTGGCGGATGT | 2161 |
| CHAF1A | NM_005483 | 3 | 19 | + | 0 | + | 0 | 37 | 1 | 0 | CGCGAATGCCCCCCGTCTGCCGTTAAGCGCCTG AATCTTGTCCCACGCGTGGCGGATGT | 2162 |
| CHAF1A | NM_005483 | 3 | 19 | + | 35 | − | 0 | 37 | 1 | 0 | CGCGAATGCCCCCTGATCGTCTGACATGTCATC GGCTTTCCCCTTACGCGTGGCGGATGT | 2163 |
| CHAF1A | NM_005483 | 3 | 19 | + | 70 | + | 0 | 37 | 1 | 0 | CGCGAATGCCTACTTCTGTGCAAAGTAAAAGCC CCGATTTAGAGGACGCGTGGCGGATGT | 2164 |
| CHAF1A | NM_005483 | 3 | 19 | + | 105 | − | 0 | 37 | 1 | 0 | CGCGAATGCCCACATGACAGTGTTTTCCAAGG TGTCCAAAGAGGACGCGTGGCGGATGT | 2165 |
| CHAF1A | NM_005483 | 3 | 19 | + | 140 | + | 0 | 37 | 1 | 0 | CGCGAATGCCGGTTCTGACATAGACTTTAGACC GAAACTTGTCAAACGCGTGGCGGATGT | 2166 |
| CHAF1A | NM_005483 | 3 | 19 | + | 175 | − | 0 | 37 | 1 | 0 | CGCGAATGCCTATTTCTTAAAAGTTATCTAAG GGACCCTTCCGACGCGTGGCGGATGT | 2167 |
| CHAF1A | NM_005483 | 3 | 19 | + | 210 | + | 0 | 37 | 1 | 0 | CGCGAATGCCGAATCGAAACAGTATTGGCCAG AGCACAGTCATCACGCGTGGCGGATGT | 2168 |
| CHAF1A | NM_005483 | 3 | 19 | + | 245 | − | 0 | 37 | 1 | 0 | CGCGAATGCCTCTGGCTGCTGCTCATTCGAGTCCTCT GTCAAATCAATACGCGTGGCGGATGT | 2169 |
| CHAF1A | NM_005483 | 3 | 19 | + | 280 | + | 0 | 37 | 1 | 0 | CGCGAATGCCAGTCTTGTGGACCACAATAAAC TAAATTCTGAAGACGCGTGGCGGATGT | 2170 |
| CHAF1A | NM_005483 | 3 | 19 | + | 315 | − | 0 | 37 | 1 | 0 | CGCGAATGCCTCGCTGCCTGGCCATTTATTGCCTCCCT GGAGGGAGGACGCGTGGCGGATGT | 2171 |
| CHAF1A | NM_005483 | 3 | 19 | + | 350 | + | 0 | 37 | 1 | 0 | CGCGAATGCCAAGACACTGGGATCAGCAGG GGTTGTTGAAGGCACGCGTGGCGGATGT | 2172 |
| CHAF1A | NM_005483 | 3 | 19 | + | 385 | − | 0 | 37 | 1 | 0 | CGCGAATGCCTCTCCAGGAAATGCCAACTTG TCGTTCTGAATGACGCGTGGCGGATGT | 2173 |
| CHAF1A | NM_005483 | 3 | 19 | + | 420 | + | 0 | 37 | 1 | 0 | CGCGAATGCCCCCTTTCAGACATTCCTTGCAAA ACAGAGGAGGACGCGTGGCGGATGT | 2174 |
| CHAF1A | NM_005483 | 3 | 19 | + | 455 | − | 0 | 37 | 1 | 0 | CGCGAATGCCTCCTCCTCCCTGCCACCTCCA CAGCCAACCACGCGTGGCGGATGT | 2175 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | # BWA hit mismatch | Sequence with add-ons | SEQ ID NO: |
|---|---|---|---|---|---|---|---|---|---|---|---|
| CHAF1A | NM_005483 | 3 | 19 | + | 490 | + | 0 | 37 | 1 | 0 | CGCGAATGCCCTCCCAGGAATGTTCGCCACGA GCTGCCCGGAGCACGCGTGGCCGGATGT | 2176 |
| CHAF1A | NM_005483 | 3 | 19 | + | 525 | - | 0 | 37 | 1 | 0 | CGCGAATGCCCTTCCTTTCTGGGCACATTCTCGG GCCACTCGTCAACGCGTGGCCGGATGT | 2177 |
| CHAF1A | NM_005483 | 3 | 19 | + | 560 | + | 0 | 37 | 1 | 0 | CGCGAATGCCAGGACAGTTGGAGTGAAGCTGG GGGCATCCTGTTACGCCGTGGCCGGATGT | 2178 |
| CHAF1A | NM_005483 | 3 | 19 | + | 595 | - | 0 | 37 | 1 | 0 | CGCGAATGCCTGTCCTGCAAGACCACCATAGGC ACTTCCCTTTGACGCGTGGCCGGATGT | 2179 |
| CHAF1A | NM_005483 | 3 | 19 | + | 630 | + | 0 | 37 | 1 | 0 | CGCGAATGCCTCTTGGCTGTGAGACACCGCAA ATCAAGTCCCTTACGCCGTGGCCGGATGT | 2180 |
| CHAF1A | NM_005483 | 3 | 19 | + | 665 | - | 0 | 37 | 1 | 0 | CGCGAATGCCTCAGGGGTCATGTTCTTGCCTTGG GGTGTGCTGGACGCGTGGCCGGATGT | 2181 |
| CHAF1A | NM_005483 | 3 | 19 | + | 700 | + | 0 | 37 | 1 | 0 | CGCGAATGCCGAGTGAGGTGCTGGAATCTTTCC CCGAAGAGACTACGCCGTGGCCGGATGT | 2182 |
| CHAF1A | NM_005483 | 3 | 19 | + | 735 | - | 0 | 37 | 1 | 0 | CGCGAATGCCAGAGGAGAGCTTCAGGGACGAA TGGCTGAGTACAGACGCGTGGCCGGATGT | 2183 |
| CHAF1A | NM_005483 | 3 | 19 | + | 770 | + | 0 | 37 | 1 | 0 | CGCGAATGCCTCCACCAGCTCGCCCGAGGGCC GCCTGCTCCCCACGCCGTGGCCGGATGT | 2184 |
| CHAF1A | NM_005483 | 3 | 19 | + | 805 | - | 0 | 37 | 1 | 0 | CGCGAATGCCAGTGGGGAAGGACTGGTACTG CTGTGCTGCTTTACGCCGTGGCCGGATGT | 2185 |
| CHAF1A | NM_005483 | 3 | 19 | + | 840 | + | 0 | 37 | 1 | 0 | CGCGAATGCCCCACGCCCCTCCCAGAGTGAGT ATCTCCATGGAACGCCGTGGCCGGATGT | 2186 |
| EPHA4 | NM_004438 | 18 | 2 | - | -24 | + | 0 | 37 | 1 | 0 | CGCGAATGCCGAGCAGCGTTGGCACCGCGAAC CATGGCTGGGATACGCCGTGGCCGGATGT | 2187 |
| EPHA4 | NM_004438 | 18 | 2 | - | 11 | - | 0 | 37 | 1 | 0 | CGCGAATGCCTCCCGAAGAGACACGAAAATAG GGCGAAATAGAAAACGCCGTGGCCGGATGT | 2188 |
| EPHA4 | NM_004438 | 18 | 2 | - | 46 | + | 0 | 37 | 1 | 0 | CGCGAATGCCTTTGCGACGCGTCACAGGTTCC AGGGTATACCCCACGCCGTGGCCGGATGT | 2189 |
| EPHA4 | NM_004438 | 18 | 2 | - | 81 | - | 0 | 37 | 1 | 0 | CGCGAATGCCCACAGAAAGGCCGCCTCCCGCTCTT ACCTTCATTCGCACGCCGTGGCCGGATGT | 2190 |
| GUCY2F | NM_001522 | 18 | X | - | 0 | + | 0 | 37 | 1 | 0 | CGCGAATGCCTAATCATCATGTGTATGCATTCA GCTTTGATTGGGACGCCGTGGCCGGATGT | 2191 |
| GUCY2F | NM_001522 | 18 | X | - | 35 | - | 0 | 37 | 1 | 0 | CGCGAATGCCTGAGCACATTCCAAGAGATGCAT CTGAGTCTCTCCACGCCGTGGCCGGATGT | 2192 |
| GUCY2F | NM_001522 | 18 | X | - | 70 | + | 0 | 37 | 1 | 0 | CGCGAATGCCTGATCTGAAAATGACTGATGAA CCTACGTCTTTGACGCCGTGGCCGGATGT | 2193 |
| GUCY2F | NM_001522 | 18 | X | - | 105 | - | 0 | 37 | 1 | 0 | CGCGAATGCCATAAGGTAAACTGTAGAGCAGGG CATCATAAGGAACACCCACGCCGTGGCCGGATGT | 2194 |
| GUCY2F | NM_001522 | 18 | X | - | 140 | + | 0 | 37 | 1 | 0 | CGCGAATGCCAAGCACACCCCTACCGGTCCT AAGGAACAACCCACGCCGTGGCCGGATGT | 2195 |
| GUCY2F | NM_001522 | 18 | X | - | 175 | - | 0 | 37 | 1 | 0 | CGCGAATGCCTTGGTCAACACTGCATCATAGGCT TCCCGGAGCTTTACGCCGTGGCCGGATGT | 2196 |
| GUCY2F | NM_001522 | 18 | X | - | 210 | + | 0 | 37 | 1 | 0 | CGCGAATGCCTTACAGTGGAGTCCCAAGAAAAG ACCTTCTATCAAACGCCGTGGCCGGATGT | 2197 |
| GUCY2F | NM_001522 | 18 | X | - | 245 | - | 0 | 37 | 1 | 0 | CGCGAATGCCGGAATTTCACCTTCTTGCTGCTGCC TCTGTGAAGGCACGCCGTGGCCGGATGT | 2198 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| GUCY2F | NM_001522 | 18 | X | - | 280 | + | 0 | 37 | 1 | 0 | CGCGAATGCCTGAGAAGCTGGAGTTCGATCAAGTAAGTACACATTACGCCTGGCGGATGT | 2199 |
| CHAF1A | NM_005483 | 11 | 19 | + | -24 | + | 0 | 37 | 1 | 0 | CGCGAATGCCCTCTTTTTTTTTTTCTCCTTTTGAGGATGATGATGAACGCGTGGCGGATGT | 2200 |
| CHAF1A | NM_005483 | 11 | 19 | + | 11 | - | 0 | 37 | 1 | 0 | CGCGAATGCCAACCATCGTCCTCATCTTCATCCTCTCCCATGTCGACGCGTGGCGGATGT | 2201 |
| CHAF1A | NM_005483 | 11 | 19 | + | 46 | + | 0 | 37 | 1 | 0 | CGCGAATGCCTCTTTGTGCCCCATGGTACCTGTCTGAGGACGAAACGCGTGGCGGATGT | 2202 |
| CHAF1A | NM_005483 | 11 | 19 | + | 81 | - | 0 | 37 | 1 | 0 | CGCGAATGCCGACCTCCCCCTTCACTCCCTCACCTCTGTCACACACGCGTGGCGGATGT | 2203 |
| RET | NM_020630 | 6 | 10 | + | 0 | + | 0 | 37 | 1 | 0 | CGCGAATGCCGGCTGGTTCTCAACCGGAACCTCTCCATCTCGAGACGCGTGGCGGATGT | 2204 |
| RET | NM_020630 | 6 | 10 | + | 35 | - | 0 | 37 | 1 | 0 | CGCGAATGCCTCATTGACCAGCACCGCCAGCTGCATGGTGCGGTTACGCGTGGCGGATGT | 2205 |
| RET | NM_020630 | 6 | 10 | + | 70 | + | 0 | 37 | 1 | 0 | CGCGAATGCCCTCAGACTTCCAGGGCCCAGGAGCGGGCGTCCTCTACGCGTGGCGGATGT | 2206 |
| RET | NM_020630 | 6 | 10 | + | 105 | - | 0 | 37 | 1 | 0 | CGCGAATGCCGTGACCGGCAGCAGCACCGACACGTTGAAGTGGAGCAACGCGTGGCGGATGT | 2207 |
| RET | NM_020630 | 6 | 10 | + | 140 | + | 0 | 37 | 1 | 0 | CGCGAATGCCCTGCACCTGCCCAGTACCTACTCCCTCCCTGAGACGCCGTGGCGGATGT | 2208 |
| RET | NM_020630 | 6 | 10 | + | 175 | - | 0 | 37 | 1 | 0 | CGCGAATGCCATGGGCTCACCTGGGCAAATCGGCGAGCCCTCCTGACGCCTGGCGGATGT | 2209 |
| NTRK3 | NM_001012338 | 9 | 15 | - | -38 | + | 0 | 37 | 1 | 0 | CGCGAATGCCAGCTAACTGTCCTCCTCCTTTTGTGTTTGGTTTACGCCGTGGCGGATGT | 2210 |
| NTRK3 | NM_001012338 | 9 | 15 | - | -3 | - | 0 | 37 | 1 | 0 | CGCGAATGCCAGTGATAGGAGGTGTGGGACTCACTTCGTCAACTGACGCGTGGCGGATGT | 2211 |
| NTRK3 | NM_001012338 | 9 | 15 | - | 32 | + | 0 | 37 | 1 | 0 | CGCGAATGCCGTGACCCACAACCAGAAGAAGACACTTTTGGGGTACGCCGTGGCGGATGT | 2212 |
| NTRK3 | NM_001012338 | 9 | 15 | - | 67 | - | 0 | 37 | 1 | 0 | CGCGAATGCCCAGTCAACACACTCCTTTGACCAAGAAGTGACTCACGCCGTGGCGGATGT | 2213 |
| PDGFRA | NM_006206 | 5 | 4 | + | -4 | + | 0 | 37 | 1 | 0 | CGCGAATGCCATAGCAACATCAGAGCTGGATCTAGAAATGGAAGCACGCCTGGCGGATGT | 2214 |
| PDGFRA | NM_006206 | 5 | 4 | + | 31 | - | 0 | 37 | 1 | 0 | CGCGAATGCCCAATCGTTCCCCTGACTTATACACGGTTTTAAGAACGCCGTGGCGGATGT | 2215 |
| PDGFRA | NM_006206 | 5 | 4 | + | 66 | + | 0 | 37 | 1 | 0 | CGCGAATGCCTGGTCACCTGTCTGTTTTTAACAATGAGGTGGTTACGCCGTGGCGGATGT | 2216 |
| PDGFRA | NM_006206 | 5 | 4 | + | 101 | - | 0 | 37 | 1 | 0 | CGCGAATGCCCCTACCACTTCTCCAGGGTAAGTCCATTGAAGGTCACGCCGTGGCGGATGT | 2217 |
| RET | NM_020630 | 13 | 10 | + | -16 | + | 0 | 37 | 1 | 0 | CGCGAATGCCTGTGCTGCATTTCAGAGAACGCCTCCCCGAGTGACGCCGTTGGCGGATGT | 2218 |
| RET | NM_020630 | 13 | 10 | + | 19 | - | 0 | 37 | 1 | 0 | CGCGAATGCCTCAGGACGTTGAACTCTGACAGCAGTCTCCGACACGCCGGCGGATGT | 2219 |
| RET | NM_020630 | 13 | 10 | + | 54 | + | 0 | 37 | 1 | 0 | CGCGAATGCCAGCAGGTCAACCACCCACATGTCATCAAATGTATACGCCGTGGCGGATGT | 2220 |
| RET | NM_020630 | 13 | 10 | + | 89 | - | 0 | 37 | 1 | 0 | CGCGAATGCCCTGCAGCTGCCTTACCATCCTGGCTGCAGCCCCACGCGTGGCGGATGT | 2221 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| PALB2 | NM_024675 | 3 | 16 | - | -26 | + | 0 | 37 | 1 | 0 | CGCGAATGCCCAGCTTATTATTTTGTTATCTAAGGAATTAAAACGCGTGGCGATGT | 2222 |
| PALB2 | NM_024675 | 3 | 16 | - | 9 | - | 0 | 37 | 1 | 0 | CGCGAATGCCCATCAATGTGCATCTTTTTCAGGAGTTGACCAGTTACGCGTGGCGATGT | 2223 |
| PALB2 | NM_024675 | 3 | 16 | - | 44 | + | 0 | 37 | 1 | 0 | CGCGAATGCCATTCTTACCAAGCTTCAGTCTGTCACAAAGCCTATACGCGTGGCGATGT | 2224 |
| PALB2 | NM_024675 | 3 | 16 | - | 79 | - | 0 | 37 | 1 | 0 | CGCGAATGCCAGTGGTCCCAGCCAGTCATTACTTACCATTTCAGAACGCGTGGCGATGT | 2225 |
| EPHA4 | NM_004438 | 5 | 2 | - | 0 | + | 0 | 37 | 1 | 0 | CGCGAATGCCGTGGCAAGATTCCTATCCGGTGGACTGCGCCAGAACGCGTGGCGATGT | 2226 |
| EPHA4 | NM_004438 | 5 | 2 | - | 35 | - | 0 | 37 | 1 | 0 | CGCGAATGCCCACTTGCTGATGTGAATTTACGATAGGCAATGCTACGCGTGGCGATGT | 2227 |
| EPHA4 | NM_004438 | 5 | 2 | - | 70 | + | 0 | 37 | 1 | 0 | CGCGAATCCATGTATGGAGCTATGGAATCGTTATGTGGGAAGTGACGCGTGGCGATGT | 2228 |
| EPHA4 | NM_004438 | 5 | 2 | - | 105 | - | 0 | 37 | 1 | 0 | CGCGAATGCCGACATATCCCAATAGGGCCTCTCCCCGTACGACACATACGCGTGGCGATGT | 2229 |
| EPHA4 | NM_004438 | 5 | 2 | - | 140 | + | 0 | 37 | 1 | 0 | CGCGAATGCCCAATCAAGATGTAAGTCTATGTTCTGAAATATAACGCGTGGCGATGT | 2230 |
| NTRK3 | NM_001012338 | 13 | 15 | - | 0 | + | 0 | 37 | 1 | 0 | CGCGAATGCCACCTTCCTGAGATCAGCGTGAGCCACGTCAACCTGACGCGTGGCGATGT | 2231 |
| NTRK3 | NM_001012338 | 13 | 15 | - | 35 | - | 0 | 37 | 1 | 0 | CGCGAATGCCCAATGGCTCTGATCAAACAGCGTTGTCACCCTGATGTGACTACGCGTGGCGATGT | 2232 |
| NTRK3 | NM_001012338 | 13 | 15 | - | 70 | + | 0 | 37 | 1 | 0 | CGCGAATGCCGTGAGTGTTGATGACTGCAGCCCAGTGACTATCCACGCGTGGCGATGT | 2233 |
| NTRK3 | NM_001012338 | 13 | 15 | - | 105 | - | 0 | 37 | 1 | 0 | CGCGAATGCCCAGGTAGCCATCCTGGGCTTCAGCCCCATCAGGAGACGCGTGGCGATGT | 2234 |
| NTRK3 | NM_001012338 | 13 | 15 | - | 140 | + | 0 | 37 | 1 | 0 | CGCGAATGCCGTGAGGGTCTGCCCTTCCGCTGCGCCCCGGACAGCACGCGTGGCGATGT | 2235 |
| RET | NM_020630 | 4 | 10 | + | 0 | - | 0 | 37 | 1 | 0 | CGCGAATGCCTCGCGCTCCAGGCCCAGGCGCGTGCTCACCTCCAGACGCGTGGCGATGT | 2236 |
| RET | NM_020630 | 4 | 10 | + | 35 | + | 0 | 37 | 1 | 0 | CGCGAATGCCGCGGAGAAGTACGAGCTGGTGGCCCGTGTGCAACGCGTGGCCGATGT | 2237 |
| RET | NM_020630 | 4 | 10 | + | 70 | - | 0 | 37 | 1 | 0 | CGCGAATGCCCATCACCACCTCCTCGCGCGCGCCGCGTGCCGTGCCATCGGACGCGTGGCGATGT | 2238 |
| RET | NM_020630 | 4 | 10 | + | 105 | + | 0 | 37 | 1 | 0 | CGCGAATGCCGTGCCCTTCCCGGTGACCGTGTACGACGAGCGGAACGCGTGGCGATGT | 2239 |
| RET | NM_020630 | 4 | 10 | + | 140 | - | 0 | 37 | 1 | 0 | CGCGAATGCCCGGTGTCGACGCCCGGGAAGGTGGGGCGCCCGAGACGCGTGGCGATGT | 2240 |
| RET | NM_020630 | 4 | 10 | + | 175 | + | 0 | 37 | 1 | 0 | CGCGAATGCCCAGCCGCCGTGTGTGGAGTTCAAGCGAAGGAGGTGACGCGTGGCGATGT | 2241 |
| RET | NM_020630 | 4 | 10 | + | 210 | - | 0 | 37 | 1 | 0 | CGCGAATGCCATCAGTTGCTGAATCTCAAAAAGGGCTGCACAGCGCGTGGCGATGT | 2242 |
| GUCY2F | NM_001522 | 7 | X | - | 0 | + | 0 | 37 | 1 | 0 | CGCGAATGCCGTACAAGGTGACCAAGTCAAAGCCCTCAGGTTCAAACGCGTGGCGATGT | 2243 |
| GUCY2F | NM_001522 | 7 | X | - | 35 | - | 0 | 37 | 1 | 0 | CGCGAATGCCGTACAAGGTGACCAAGTCAAAGCCCTCAGGTTCAAACGCGTGGCGATGT | 2244 |

TABLE 4-continued

Representative subset (2170) of a total of 1,148,286 Capture Probes Designed for Exon Capture of 25,341 Human Genes

| Gene | Transcript | Exon | Chromosome | Gene strand | Distance from exon 5 edge | Oligo strand | # repeat nucleotides | BWA score | BWA hit | # BWA mismatch | Sequence with add-ons | SEQ ID NO: |
|---|---|---|---|---|---|---|---|---|---|---|---|---|
| GUCY2F | NM_001522 | 7 | X | − | 70 | + | 0 | 37 | 1 | 0 | CGCGAATGCCTTCAGCGACCATTGTGGGCTTCACAACCATTTCAGCACGCGTGGCGGATGT | 2245 |
| GUCY2F | NM_001522 | 7 | X | − | 105 | − | 0 | 37 | 1 | 0 | CGCGAATGCCTCAGAAGATCCACGACCTCAATGGGCTCACTCATGACGCGTGGCGGATGT | 2246 |
| GUCY2F | NM_001522 | 7 | X | − | 140 | + | 0 | 37 | 1 | 0 | CGCGAATGCCATGACCTTGTACACACTCTTTGATGCAATAATTGGCACGCGTGGCGGATGT | 2247 |
| GUCY2F | NM_001522 | 7 | X | − | 175 | − | 0 | 37 | 1 | 0 | CGCGAATGCCCCTGCTAATTAACCTACCTTGTAGACATCATGACTACGCGTGGCGGATGT | 2248 |
| NTRK3 | NM_001012338 | 5 | 15 | − | 0 | + | 0 | 37 | 1 | 0 | CGCGAATGCCGCCCTGAAGGATCCCACCCTGGCTGCCCGGAAGGAAACGCGTGGCGGATGT | 2249 |
| NTRK3 | NM_001012338 | 5 | 15 | − | 35 | − | 0 | 37 | 1 | 0 | CGCGAATGCCGCAGGTTGGTGAGCAGCTCGGCCTCCCTCTGGAAAACGCGTGGCGGATGT | 2250 |
| NTRK3 | NM_001012338 | 5 | 15 | − | 70 | + | 0 | 37 | 1 | 0 | CGCGAATGCCAGCATGACGCACATTGTCAAGTTCTATGGAGTGTGCACGCGTGGCGGATGT | 2251 |
| NTRK3 | NM_001012338 | 5 | 15 | − | 105 | − | 0 | 37 | 1 | 0 | CGCGAATGCCTATTCAAAGACCATGATGAGGGGGTCCCCATCGCCACGCGTGGCGGATGT | 2252 |
| NTRK3 | NM_001012338 | 5 | 15 | − | 140 | + | 0 | 37 | 1 | 0 | CGCGAATGCCCATGAAGCATGGAGACCTGAATAAGTTCCTCAGGTACGCGTGGCGGATGT | 2253 |

While the preferred embodiment of the invention has been illustrated and described, it will be appreciated that various changes can be made therein without departing from the spirit and scope of the invention.

What is claimed:

1. A method for generating a population of single-stranded nucleic acid probes, each probe comprising a predetermined nucleotide sequence, the method comprising:
   a) providing a starting population of linear double-stranded nucleic acid precursor molecules each precursor molecule having (i) a probe region having the predetermined sequence which is flanked at a 5' and a 3' end by a first and a second restriction enzyme recognition sequence for generating ligation substrates and for ligating a plurality of the double-stranded nucleic acid precursor molecules into head-to-tail concatemers (ii) the 5' flanking region including the first restriction enzyme recognition sequence and (iii) the 3' flanking region including the second restriction enzyme recognition sequence;
   b) contacting the 5' and 3' flanking regions of the linear double-stranded nucleic acid precursor molecules with a first and a second restriction enzyme to cleave the first and second restriction enzyme recognition sequences so as to generate ligation substrates;
   c) ligating the ligation substrates together so as to generate a plurality of random head-to-tail concatemers;
   d) amplifying the plurality of head-to-tail concatemers;
   e) contacting the amplified head-to-tail concatemers with the first and second restriction enzymes so as to release a plurality of double-stranded monomer linear precursor molecules; and
   f) selectively removing one strand of the double-stranded monomer linear precursor molecules so as to generate a population of single-stranded nucleic acid probes, each probe comprising the predetermined nucleotide sequence.

2. The method of claim 1, wherein the single-stranded nucleic acid probes further comprise a region which hybridizes to a capture nucleic acid molecule.

3. The method of claim 1, wherein the members of the starting population of the linear double-stranded nucleic acid precursor molecules each comprise the same nucleotide sequence in the 5' flanking region or each comprise the same nucleotide sequence in the 3' flanking region.

4. The method of claim 1, wherein the 3' flanking region further comprises a third restriction enzyme recognition sequence.

5. The method of claim 1, wherein the members of the starting population of the linear double-stranded nucleic acid precursor molecules each comprise the same predetermined sequences or different predetermined sequences.

6. The method of claim 1, wherein the ligation substrates of step (b) comprise overhanging nucleic acid ends capable of annealing together.

7. The method of claim 1, wherein the first or second restriction enzyme recognition sequence is cleaved by a type II restriction enzyme.

8. The method of claim 1, wherein the first or second restriction enzyme recognition sequence is cleaved by a Bsm1 enzyme.

9. The method of claim 1, wherein each predetermined nucleotide sequence in the population of linear double-stranded nucleic acid precursor molecules comprise a nucleotide sequence which is at least 95% identical to at least a portion of a sense or anti-sense strand of a target nucleic acid sequence.

10. The method of claim 9, wherein the predetermined sequence hybridizes to one target sequence or hybridizes to different target sequences.

11. The method of claim 9, wherein the predetermined sequences in the population of linear double-stranded nucleic acid precursor molecules hybridize to at least 10 different exon nucleotide sequences.

12. The method of claim 9, wherein the predetermined sequences in the population of linear double-stranded nucleic acid precursor molecules hybridize to at least 1000 different exon nucleotide sequences.

13. The method of claim 9, wherein the predetermined sequences hybridize to the target sequence at an interval of at least every 35 bases across the target sequence.

14. The method of claim 9, wherein the predetermined sequences hybridize to the target sequence of interest at an interval of one base across the target sequence.

15. The method of claim 1, wherein the probe region comprises 20-200 nucleotides.

16. The method of claim 1, wherein the predetermined nucleotide sequence comprises 10-50 nucleotides.

17. The method of claim 2, wherein the region of the single-stranded nucleic acid probe which hybridizes to the capture nucleic acid molecule comprises 10-50 nucleotides.

18. The method of claim 1, wherein the amplifying according to step (d) comprises isothermal amplification.

19. The method of claim 18, wherein the amplifying according to step (d) comprises random amplification primers.

20. The method of claim 19, wherein the random amplification primers each comprise a random 7-mer oligonucleotide and two additional nitroindole residues at the 5' end.

21. The method of claim 19, wherein the random amplification primers each comprise a random 7-mer oligonucleotide and a phosphorothioate linkage to the 3' end.

22. The method of claim 1, wherein the selectively removing one strand from the double-stranded monomer linear precursor molecules comprises:
  a) contacting the released precursor molecules of step (e) with alkaline phosphatase;
  b) contacting the released precursor molecules of step (e) with a third restriction enzyme which cleaves the third restriction enzyme recognition sequence; and
  c) contacting the released precursor molecules of step (e) with an exonuclease so as to selectively degrade the one strand of the double-stranded monomer linear precursor molecules.

23. The method of claim 22, wherein the exonuclease is lambda exonuclease.

24. The method of claim 2, wherein the capture nucleic acid molecule further comprises a protein binding partner.

25. The method of claim 24, wherein the protein binding partner is biotin.

26. The method of claim 1, wherein each single-stranded nucleic acid probe comprises (i) the predetermined nucleotide sequence having a nucleotide sequence which is at least 95% identical to at least a portion of a sense or an anti-sense strand of a target nucleic acid sequence and (ii) a region which hybridizes to a capture nucleic acid molecule.

27. The method of claim 1, wherein the starting population of linear double-stranded nucleic acid precursor molecules is generated by steps comprising:
  a) providing a population of a first single-stranded nucleic acid molecule comprising the 5' flanking region, the probe region which comprises the predetermined sequence, and the capture sequence;
  b) providing a population of a second single-stranded nucleic acid molecules comprising the sequence which is complementary to the capture sequence, and the 3' flanking region;
  c) annealing the first and second populations of the single-stranded nucleic acid molecules to form a nucleic acid duplex having overhanging 5' ends; and
  d) conducting a polymerase-dependent strand extension reaction on the overhanging 5' ends so as to generate the population of double-stranded nucleic acid precursor molecules.

28. A method for enriching a target nucleic acid sequence of interest from a nucleic acid library, comprising:
  a) contacting the population of single-stranded nucleic acid probes of claim 1 with the nucleic acid library having at least one target nucleic acid sequence of interest to form a mixture having unhybridized nucleic acid sequences and duplexes, each duplex having the single-stranded nucleic acid probe hybridized to the target nucleic acid sequence of interest;
  b) contacting the duplexes with a population of capture nucleic acid molecules to form complexes having the single-stranded nucleic acid probe hybridized to the target nucleic acid sequence of interest and hybridized to the capture nucleic acid molecule;
  c) separating the complex from the mixture; and
  d) eluting the target nucleic acid sequence of interest from the complex.

* * * * *

```
                         SEQUENCE LISTING

<160> NUMBER OF SEQ ID NOS: 2253

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 1
acgcgtggcg gatgt                                                          15

<210> SEQ ID NO 2
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 2
cgcgaatgcc                                                                10

<210> SEQ ID NO 3
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 3
cgcgaatgcc ggtgcccgag gctcccgcga cgctcacgcg ctcctacgcg tggcggatgt         60

<210> SEQ ID NO 4
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 4
cgcgaatgcc atgagcgacg tggctattgt gaaggagggt tggctacgcg tggcggatgt         60

<210> SEQ ID NO 5
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 5
cgcgaatgcc ccagccctgg cagcgggtac taacctcgtt tgtgcacgcg tggcggatgt         60

<210> SEQ ID NO 6
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 6
cgcgaatgcc gcctggggag ggagagatgg gggtagtagc cccagacgcg tggcggatgt         60

<210> SEQ ID NO 7
```

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 7
cgcgaatgcc ctacagacgt gcgggtggtg agagccacgc acactacgcg tggcggatgt    60

<210> SEQ ID NO 8
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 8
cgcgaatgcc gggagtacat caagacctgg cggccacgct acttcacgcg tggcggatgt    60

<210> SEQ ID NO 9
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 9
cgcgaatgcc ttgtagccaa tgaaggtgcc atcattcttg aggagacgcg tggcggatgt    60

<210> SEQ ID NO 10
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 10
cgcgaatgcc ggagcggccg caggatgtgg accaacgtga ggctcacgcg tggcggatgt    60

<210> SEQ ID NO 11
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 11
cgcgaatgcc gggatactta cgcgccacag agaagttgtt gagggacgcg tggcggatgt    60

<210> SEQ ID NO 12
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 12
cgcgaatgcc cttggcctct cgggattcag atttgggggg ttggcacgcg tggcggatgt    60

<210> SEQ ID NO 13
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 13
```
cgcgaatgcc ctgcgggcag gcagagcctc tgtctgcgtg catccacgcg tggcggatgt    60

<210> SEQ ID NO 14
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 14
cgcgaatgcc agtgccagct gatgaagacg gagcggcccc ggcccacgcg tggcggatgt    60

<210> SEQ ID NO 15
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 15
cgcgaatgcc gtggtccact gcaggcagcg gatgatgaag gtgttacgcg tggcggatgt    60

<210> SEQ ID NO 16
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 16
cgcgaatgcc tgtcatcgaa cgcaccttcc atgtggagac tcctgacgcg tggcggatgt    60

<210> SEQ ID NO 17
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 17
cgcgaatgcc cctggcctgg ccgccacagc ccacgtaccg ctcctacgcg tggcggatgt    60

<210> SEQ ID NO 18
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 18
cgcgaatgcc ctgcaggagg tcaggtgagg ctgcaggcct gtaccacgcg tggcggatgt    60

<210> SEQ ID NO 19
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 19
cgcgaatgcc ggaggagtgg acaaccgcca tccagactgt ggctgacgcg tggcggatgt    60

<210> SEQ ID NO 20
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 20
cgcgaatgcc gtccatctcc tcctcctcct gcttcttgag gccgtacgcg tggcggatgt    60

<210> SEQ ID NO 21
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 21
cgcgaatgcc ttccggtcgg gctcacccag tgacaactca ggggcacgcg tggcggatgt    60

<210> SEQ ID NO 22
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 22
cgcgaatgcc gcttgggctt ggccagggac acctccatct cttcaacgcg tggcggatgt    60

<210> SEQ ID NO 23
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 23
cgcgaatgcc accgcgtggt gaggcctgtc cccacttctg cctgtacgcg tggcggatgt    60

<210> SEQ ID NO 24
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 24
cgcgaatgcc ctatgggcag gcaccagggt cagcaagcgg cgctgacgcg tggcggatgt    60

<210> SEQ ID NO 25
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 25
cgcgaatgcc accatgaacg agtttgagta cctgaagctg ctgggacgcg tggcggatgt    60

<210> SEQ ID NO 26
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 26
cgcgaatgcc ccttcaccag gatcaccttg ccgaaagtgc ccttgacgcg tggcggatgt    60
```

<210> SEQ ID NO 27
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 27
cgcgaatgcc agaaggccac aggccgctac tacgccatga agatcacgcg tggcggatgt    60

<210> SEQ ID NO 28
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 28
cgcgaatgcc ggccccacct tggccacgat gacttccttc ttgagacgcg tggcggatgt    60

<210> SEQ ID NO 29
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 29
cgcgaatgcc ctgtaaagca gggctgggtg agctgccacc ccgcaacgcg tggcggatgt    60

<210> SEQ ID NO 30
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 30
cgcgaatgcc gacgaggtgg cccacacact caccgagaac cgcgtacgcg tggcggatgt    60

<210> SEQ ID NO 31
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 31
cgcgaatgcc tcactgtgag gaagggtgc ctggagttct gcaggacgcg tggcggatgt    60

<210> SEQ ID NO 32
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 32
cgcgaatgcc gtgggagccc agatggggct gaagggctgg ggccaacgcg tggcggatgt    60

<210> SEQ ID NO 33
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 33
cgcgaatgcc ctgcaaggaa ggggagctgg aactgcggcc ccacaacgcg tggcggatgt    60

<210> SEQ ID NO 34
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 34
cgcgaatgcc gccctgaagt actctttcca gacccacgac cgcctacgcg tggcggatgt    60

<210> SEQ ID NO 35
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 35
cgcgaatgcc cctcgccccc gttggcgtac tccatgacaa agcagacgcg tggcggatgt    60

<210> SEQ ID NO 36
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 36
cgcgaatgcc taggggctgg ggctgcgggg gatggacttc gcggcacgcg tggcggatgt    60

<210> SEQ ID NO 37
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 37
cgcgaatgcc ctgcgggagg cgcaacctga ggcacagccg tggctacgcg tggcggatgt    60

<210> SEQ ID NO 38
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 38
cgcgaatgcc ctgttcttcc acctgtcccg ggagcgtgtg ttctcacgcg tggcggatgt    60

<210> SEQ ID NO 39
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 39
cgcgaatgcc caatctcagc gccatagaag cgggcccggt cctcgacgcg tggcggatgt    60

-continued

```
<210> SEQ ID NO 40
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 40
cgcgaatgcc tgtcagccct ggactacctg cactcggaga agaacacgcg tggcggatgt      60

<210> SEQ ID NO 41
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 41
cgcgaatgcc gcccgccagc gcaccttgag gtcccggtac accacacgcg tggcggatgt      60

<210> SEQ ID NO 42
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 42
cgcgaatgcc ctaggggaaa ggtggcctca ggtcagtgcc gccagacgcg tggcggatgt      60

<210> SEQ ID NO 43
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 43
cgcgaatgcc ctggagaacc tcatgctgga caaggacggg cacatacgcg tggcggatgt      60

<210> SEQ ID NO 44
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 44
cgcgaatgcc tcccctcctt gcacagcccg aagtctgtga tcttaacgcg tggcggatgt      60

<210> SEQ ID NO 45
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 45
cgcgaatgcc tcaaggacgg tgccaccatg aagacctttt gcggcacgcg tggcggatgt      60

<210> SEQ ID NO 46
<211> LENGTH: 60
<212> TYPE: DNA
<213> ORGANISM: Artificial Sequence
<220> FEATURE:
<223> OTHER INFORMATION: Synthetic oligonucleotide
```

```
<400> SEQUENCE: 46
cgcgaatgcc ggggcgcaca cctcgggggc caggtactca ggtgtacgcg tggcggatgt      60

<210> SEQ ID NO 47
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 47
cgcgaatgcc ctgcacgggt ggcagatggg caggactcgg catcaacgcg tggcggatgt      60

<210> SEQ ID NO 48
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 48
cgcgaatgcc gtgctggagg acaatgacta cggccgtgca gtggaacgcg tggcggatgt      60

<210> SEQ ID NO 49
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 49
cgcgaatgcc tcatctcgta catgaccacg cccagccccc accagacgcg tggcggatgt      60

<210> SEQ ID NO 50
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 50
cgcgaatgcc tgtgcggtcg cctgcccttc tacaaccagg accatacgcg tggcggatgt      60

<210> SEQ ID NO 51
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 51
cgcgaatgcc atctcctcca tgaggatgag ctcaaaaagc ttctcacgcg tggcggatgt      60

<210> SEQ ID NO 52
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 52
cgcgaatgcc ccgcttcccg cgcacgcttg gtcccgaggc caagtacgcg tggcggatgt      60

<210> SEQ ID NO 53
<211> LENGTH: 60
```

```
<212> TYPE: DNA
<213> ORGANISM: Artificial Sequence
<220> FEATURE:
<223> OTHER INFORMATION: Synthetic oligonucleotide

<400> SEQUENCE: 53
cgcgaatgcc cttggggtcc ttcttgagca gccctgaaag caaggacgcg tggcggatgt    60

<210> SEQ ID NO 54
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 54
cgcgaatgcc cagaggtgag ggccgcccat cccagctaca ggctaacgcg tggcggatgt    60

<210> SEQ ID NO 55
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 55
cgcgaatgcc ctgcaggcag gaaacaaggc cacagtgtcg gtaccacgcg tggcggatgt    60

<210> SEQ ID NO 56
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 56
cgcgaatgcc gcttggcggg ggctccgagg acgccaagga gatcaacgcg tggcggatgt    60

<210> SEQ ID NO 57
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 57
cgcgaatgcc ctgccacacg ataccggcaa agaagcgatg ctgcaacgcg tggcggatgt    60

<210> SEQ ID NO 58
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 58
cgcgaatgcc cacgtgtacg agaagaaggt gcggctgctc cccgcacgcg tggcggatgt    60

<210> SEQ ID NO 59
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 59
```
cgcgaatgcc ctgcagaggt gggcagacgg gacagtcatg agcttacgcg tggcggatgt    60

<210> SEQ ID NO 60
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 60
cgcgaatgcc ctcagcccac ccttcaagcc ccaggtcacg tcggaacgcg tggcggatgt    60

<210> SEQ ID NO 61
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 61
cgcgaatgcc ccgtgaactc ctcatcaaaa tacctggtgt cagtcacgcg tggcggatgt    60

<210> SEQ ID NO 62
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 62
cgcgaatgcc cccagatgat caccatcaca ccacctgacc aaggtacgcg tggcggatgt    60

<210> SEQ ID NO 63
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 63
cgcgaatgcc ctgtgggtgt agacagctca gaccccggtg ccccaacgcg tggcggatgt    60

<210> SEQ ID NO 64
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 64
cgcgaatgcc atgacagcat ggagtgtgtg gacagcgagc gcaggacgcg tggcggatgt    60

<210> SEQ ID NO 65
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 65
cgcgaatgcc ccgctggccg agtaggagaa ctggggggaag tggggacgcg tggcggatgt    60

<210> SEQ ID NO 66
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 66
cgcgaatgcc cacggcctga ggcggcggtg gactgcgctg gacgaacgcg tggcggatgt    60

<210> SEQ ID NO 67
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 67
gaggtcggca ttcttataat tgctcgaagg ggtccacatc cgccacgcgt    50

<210> SEQ ID NO 68
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 68
gaggtcggca ttcaagctta attgctcgaa ggggtccaca tccgccacgc gt    52

<210> SEQ ID NO 69
<211> LENGTH: 95
<212> TYPE: DNA
<213> ORGANISM: Artificial Sequence
<220> FEATURE:
<223> OTHER INFORMATION: Synthetic oligonucleotide

<400> SEQUENCE: 69
cgcgaatgcc ggtgcccgag gctcccgcga cgctcacgcg ctcctacgcg tggcggatgt    60
ggacccctcc gagcaattat aagaatgccg acctc    95

<210> SEQ ID NO 70
<211> LENGTH: 95
<212> TYPE: DNA
<213> ORGANISM: Artificial Sequence
<220> FEATURE:
<223> OTHER INFORMATION: Synthetic oligonucleotide

<400> SEQUENCE: 70
gaggtcggca ttcttataat tgctcgaagg ggtccacatc cgccacgcgt aggagcgcgt    60
gagcgtcgcg ggagcctcgg gcaccggcat tcgcg    95

<210> SEQ ID NO 71
<211> LENGTH: 97
<212> TYPE: DNA
<213> ORGANISM: Artificial Sequence
<220> FEATURE:
<223> OTHER INFORMATION: Synthetic oligonucleotide

<400> SEQUENCE: 71
cgcgaatgcc ggtgcccgag gctcccgcga cgctcacgcg ctcctacgcg tggcggatgt    60
ggacccctcc gagcaattaa gcttgaatgc cgacctc    97

<210> SEQ ID NO 72
<211> LENGTH: 97
<212> TYPE: DNA
<213> ORGANISM: Artificial Sequence
<220> FEATURE:

<223> OTHER INFORMATION: Synthetic oligonucleotide

<400> SEQUENCE: 72
gaggtcggca ttcaagctta attgctcgaa ggggtccaca tccgccacgc gtaggagcgc     60
gtgagcgtcg cgggagcctc gggcaccggc attcgcg     97

<210> SEQ ID NO 73
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 73
ggtgcccgag gctcccgcga cgctcacgcg ctcctacgcg tggcggatgt ggacccctcc     60
gagcaattat aagaatgcc     79

<210> SEQ ID NO 74
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 74
cattcttata attgctcgaa ggggtccaca tccgccacgc gtaggagcgc gtgagcgtcg     60
cgggagcctc gggcaccgg     79

<210> SEQ ID NO 75
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 75
ggtgcccgag gctcccgcga cgctcacgcg ctcctacgcg tggcggatgt ggacccctcc     60
gagcaattaa gcttgaatgc c     81

<210> SEQ ID NO 76
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 76
cattcaagct taattgctcg aagggggtcca catccgccac gcgtaggagc gcgtgagcgt     60
cgcgggagcc tcgggcaccg g     81

<210> SEQ ID NO 77
<211> LENGTH: 7
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: [nitroindole]2 at 5' end
<220> FEATURE:
<221> NAME/KEY: misc_feature
<222> LOCATION: (1)..(7)
<223> OTHER INFORMATION: any n is A, C, G, or T
<220> FEATURE:

```
<221> NAME/KEY: misc_feature
<222> LOCATION: (6)..(7)
<223> OTHER INFORMATION: site of phosphothioate bond

<400> SEQUENCE: 77 nnnnnnn                                                              7

<210> SEQ ID NO 78
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 78
ggtgcccgag gctcccgcga cgctcacgcg ctcctacgcg tggcggatgt ggacccctta    60
gagcaatta                                                            69

<210> SEQ ID NO 79

<400> SEQUENCE: 79

000

<210> SEQ ID NO 80
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 80
acgcgtggcg gatgtggacc ccttcgagca atta                                34

<210> SEQ ID NO 81
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 81
taattgctcg aagggtcca catccgccac gcgt                                 34

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
aatgatacgg cgaccaccga                                                20

<210> SEQ ID NO 83
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 83
caagcagaag acggcatacg                                                20

<210> SEQ ID NO 84
```

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 84
cgcgaatgcc cctctgtgta acaggctgtt ctcttctctc tgtagacgcg tggcggatgt      60

<210> SEQ ID NO 85
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 85
cgcgaatgcc gatctgcggg gaccagcgtg gcactgacag tgtgtacgcg tggcggatgt      60

<210> SEQ ID NO 86
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 86
cgcgaatgcc cctcgcagag atctcggcaa ctccatcaag cacagacgcg tggcggatgt      60

<210> SEQ ID NO 87
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 87
cgcgaatgcc aagtaggcac cagtgcacac aggaatccag cctacacgcg tggcggatgt      60

<210> SEQ ID NO 88
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 88
cgcgaatgcc tcctggccca gctgctgccg ctcctgcacg gcaatacgcg tggcggatgt      60

<210> SEQ ID NO 89
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 89
cgcgaatgcc tggaactccc ggatgatgac cttgctcccg ttcacacgcg tggcggatgt      60

<210> SEQ ID NO 90
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 90
```
cgcgaatgcc ggagcactgc cgccggggac tgctcagcaa ccacaacgcg tggcggatgt    60

<210> SEQ ID NO 91
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 91
cgcgaatgcc caggtaggtg gtggaggggc tccgcgggct gccggacgcg tggcggatgt    60

<210> SEQ ID NO 92
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 92
cgcgaatgcc cacaccccca cccccagcga ggatgccgcc atcccacgcg tggcggatgt    60

<210> SEQ ID NO 93
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 93
cgcgaatgcc tctcggaaat gagccgcttg agccgggact tagagacgcg tggcggatgt    60

<210> SEQ ID NO 94
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 94
cgcgaatgcc actcagtgta tgagaagcgg cctgacttca ggatgacgcg tggcggatgt    60

<210> SEQ ID NO 95
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 95
cgcgaatgcc aagctctgta gcacctgcgg gtgcacgtac cagcaacgcg tggcggatgt    60

<210> SEQ ID NO 96
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 96
cgcgaatgcc ccagcaggag cacctgcccg tgccgtgcca gtggaacgcg tggcggatgt    60

<210> SEQ ID NO 97
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 97
cgcgaatgcc ctctttgggg gccgagggca ccgatgtcac atagcacgcg tggcggatgt    60

<210> SEQ ID NO 98
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 98
cgcgaatgcc gacagtggca gcgtcccctc cacggggccc agccaacgcg tggcggatgt    60

<210> SEQ ID NO 99
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 99
cgcgaatgcc ccgctgactt cctcttcagc gagatgggag tgcccacgcg tggcggatgt    60

<210> SEQ ID NO 100
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 100
cgcgaatgcc gcagcatgtg catcacccaa ttcatgaaga agcgcacgcg tggcggatgt    60

<210> SEQ ID NO 101
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 101
cgcgaatgcc acctgcccac cccacctcac ctggccgtcg tgcctacgcg tggcggatgt    60

<210> SEQ ID NO 102
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 102
cgcgaatgcc atgaagaaag aaaaatgaat gatagcttgg aagatacgcg tggcggatgt    60

<210> SEQ ID NO 103
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 103
cgcgaatgcc gattcatact cttcatgtgt tgtccgatca aacatacgcg tggcggatgt    60
```

<210> SEQ ID NO 104
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 104
cgcgaatgcc ctgtttggca gacagtttct cccaagcagc agatgacgcg tggcggatgt    60

<210> SEQ ID NO 105
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 105
cgcgaatgcc tagtttcttt gtggcagtag acaattcctc ctcttacgcg tggcggatgt    60

<210> SEQ ID NO 106
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 106
cgcgaatgcc cacagtaaga ttttttctg tttaattatg gcttcacgcg tggcggatgt    60

<210> SEQ ID NO 107
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 107
cgcgaatgcc atttaattca tttttccccc agagagacta gcttgacgcg tggcggatgt    60

<210> SEQ ID NO 108
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 108
cgcgaatgcc tttttccgaa ccacctcaat atgaggaaaa ttttgacgcg tggcggatgt    60

<210> SEQ ID NO 109
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 109
cgcgaatgcc agaggagaga agaaaactgc ttgggcacac gtgtaacgcg tggcggatgt    60

<210> SEQ ID NO 110
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 110
cgcgaatgcc agtatctaca ttagtactta caatttcaca ttcctacgcg tggcggatgt     60

<210> SEQ ID NO 111
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 111
cgcgaatgcc tttttttaaa aggtatcgaa gcaaattaaa gctgaacgcg tggcggatgt     60

<210> SEQ ID NO 112
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 112
cgcgaatgcc agtataatgg ccactgtctt cttccttagc acggaacgcg tggcggatgt     60

<210> SEQ ID NO 113
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 113
cgcgaatgcc attgtagctc aaaatgaaga tgctgtgaag agctaacgcg tggcggatgt     60

<210> SEQ ID NO 114
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 114
cgcgaatgcc ccctttacat accttgagtt aacagttcaa aagtaacgcg tggcggatgt     60

<210> SEQ ID NO 115
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 115
cgcgaatgcc gaagtacatc tcagaatctt gattctggaa cagatacgcg tggcggatgt     60

<210> SEQ ID NO 116
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 116
cgcgaatgcc aaattaagca cattcagaat ccatgggaaa gacaaacgcg tggcggatgt     60

```
<210> SEQ ID NO 117
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 117
cgcgaatgcc aaaagccttt gatttttaca aagtgatcga aagttacgcg tggcggatgt    60

<210> SEQ ID NO 118
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 118
cgcgaatgcc catttctctt gtcaagttgc cttctgcttt gataaacgcg tggcggatgt    60

<210> SEQ ID NO 119
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 119
cgcgaatgcc ataaaacatt tagaacgatg tgaacatcga atcatacgcg tggcggatgt    60

<210> SEQ ID NO 120
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 120
cgcgaatgcc tttagctact tactgagagc catgcaaggg attccacgcg tggcggatgt    60

<210> SEQ ID NO 121
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 121
cgcgaatgcc caggaacaag aaacaagtta taccattctg agggcacgcg tggcggatgt    60

<210> SEQ ID NO 122
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 122
cgcgaatgcc gcttgaggct actgatggta acatttgtgc ctcttacgcg tggcggatgt    60

<210> SEQ ID NO 123
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 123
cgcgaatgcc ctgacactat atacgtattc caaatccgag cccgaacgcg tggcggatgt    60

<210> SEQ ID NO 124
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 124
cgcgaatgcc aacttgcggc tgttcgtccc atatccagcg gctgtacgcg tggcggatgt    60

<210> SEQ ID NO 125
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 125
cgcgaatgcc tgagtttgaa actagtccag actgtatgta ttattacgcg tggcggatgt    60

<210> SEQ ID NO 126
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 126
cgcgaatgcc gcaagatccc tgcccctcc tctagactgc attgaacgcg tggcggatgt     60

<210> SEQ ID NO 127
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 127
cgcgaatgcc tggcattggg cctctacttc tcgagggatg cttacacgcg tggcggatgt    60

<210> SEQ ID NO 128
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 128
cgcgaatgcc gtgccggctg cctggtccac atacagcttc tcccaacgcg tggcggatgt    60

<210> SEQ ID NO 129
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 129
cgcgaatgcc gcccttgctg tacgtccatg ccctgcggga cgcccacgcg tggcggatgt    60

<210> SEQ ID NO 130
<211> LENGTH: 60

<212> TYPE: DNA
<213> ORGANISM: Artificial Sequence
<220> FEATURE:
<223> OTHER INFORMATION: Synthetic oligonucleotide

<400> SEQUENCE: 130
cgcgaatgcc atgctggccc aggcggaagc tgggcacctc ctcagacgcg tggcggatgt    60

<210> SEQ ID NO 131
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 131
cgcgaatgcc ctctacggca cgtaccgcac acggctgcat gagaaacgcg tggcggatgt    60

<210> SEQ ID NO 132
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 132
cgcgaatgcc ggaggccggt gtcctcctgg atgcagatcc agttgacgcg tggcggatgt    60

<210> SEQ ID NO 133
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 133
cgcgaatgcc tctaccttaa ccggagcctg gaccatagct cctggacgcg tggcggatgt    60

<210> SEQ ID NO 134
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 134
cgcgaatgcc ggggcggctc ccttactgcg gacactgagc ttctcacgcg tggcggatgt    60

<210> SEQ ID NO 135
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 135
cgcgaatgcc ttttacagag taacagacta gctagagaca atgaaacgcg tggcggatgt    60

<210> SEQ ID NO 136
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 136

-continued cgcgaatgcc attgctttga gctgttcttt gtcattttcc cttaaacgcg tggcggatgt    60

<210> SEQ ID NO 137
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 137
cgcgaatgcc ttctacacga gatcctctct ctgaaatcac tgagcacgcg tggcggatgt    60

<210> SEQ ID NO 138
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 138
cgcgaatgcc cacttacctg tgactccata gaaaatcttt ctcctacgcg tggcggatgt    60

<210> SEQ ID NO 139
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 139
cgcgaatgcc gcctctctct cttgtcacgt agccctgcgt tctgaacgcg tggcggatgt    60

<210> SEQ ID NO 140
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 140
cgcgaatgcc ccaacagcac caggactgca gcagccaccg tgagtacgcg tggcggatgt    60

<210> SEQ ID NO 141
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 141
cgcgaatgcc tgattgtgat catctcactt attgtcctgg ttgtcacgcg tggcggatgt    60

<210> SEQ ID NO 142
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 142
cgcgaatgcc tagttttatg agaaaatatc tacctgtttc caaatacgcg tggcggatgt    60

<210> SEQ ID NO 143
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 143
cgcgaatgcc gagaagcctc acagtttctt ttggtttctg tttgtacgcg tggcggatgt    60

<210> SEQ ID NO 144
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 144
cgcgaatgcc ttgaaggtat gggccatctg ctaaaaacaa aaacaacgcg tggcggatgt    60

<210> SEQ ID NO 145
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 145
cgcgaatgcc atattagagc aacctaaaca ggtaagatta aagggacgcg tggcggatgt    60

<210> SEQ ID NO 146
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 146
cgcgaatgcc tattagacac tggaatctaa catttaaagt cccacacgcg tggcggatgt    60

<210> SEQ ID NO 147
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 147
cgcgaatgcc gtttatcact caggtgtaag aacatatgtg gacccacgcg tggcggatgt    60

<210> SEQ ID NO 148
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 148
cgcgaatgcc ctcgcactgc ttggttggga tcttcgtacg taaagacgcg tggcggatgt    60

<210> SEQ ID NO 149
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 149
cgcgaatgcc agtttgccaa agaaattgac gcatcctgca ttaagacgcg tggcggatgt    60

<210> SEQ ID NO 150
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 150
cgcgaatgcc ctcagacact taccaactcc tataactttt tcaatacgcg tggcggatgt    60

<210> SEQ ID NO 151
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 151
cgcgaatgcc ttttaattac agaggcaaag aaaaccaatt tttgaacgcg tggcggatgt    60

<210> SEQ ID NO 152
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 152
cgcgaatgcc ctcagcaaaa gttagtatag tctcctcagg gggcaacgcg tggcggatgt    60

<210> SEQ ID NO 153
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 153
cgcgaatgcc gtccaaggga tgcaagaagc tctgcttggt actacacgcg tggcggatgt    60

<210> SEQ ID NO 154
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 154
cgcgaatgcc agcttaccaa ataacaatgt tgttcataat agtagacgcg tggcggatgt    60

<210> SEQ ID NO 155
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 155
cgcgaatgcc tgggaagaga tcagtggtgt ggatgaacat tacacacgcg tggcggatgt    60

<210> SEQ ID NO 156
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 156
cgcgaatgcc ccatgacatt gcacacctgg taagtcctga tgggtacgcg tggcggatgt    60

<210> SEQ ID NO 157
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 157
cgcgaatgcc accacagtca aaacaattgg ctgagaacaa actggacgcg tggcggatgt    60

<210> SEQ ID NO 158
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 158
cgcgaatgcc tccacataaa tcttctgagc tgagttcctg gggacacgcg tggcggatgt    60

<210> SEQ ID NO 159
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 159
cgcgaatgcc gctcaagttc actctacgag actgcaatag cattcacgcg tggcggatgt    60

<210> SEQ ID NO 160
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 160
cgcgaatgcc gttgaatgtc tccttgcaag ttcctaaaac caatgacgcg tggcggatgt    60

<210> SEQ ID NO 161
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 161
cgcgaatgcc ctgtactaca tggagtctga tgatgatcat ggggtacgcg tggcggatgt    60

<210> SEQ ID NO 162
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 162
cgcgaatgcc tgtcaatctt tgtaaactga tgctctcgaa atttcacgcg tggcggatgt    60

<210> SEQ ID NO 163

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 163
cgcgaatgcc ccattgcagc tgatgaaagt ttcactcaaa tggatacgcg tggcggatgt      60

<210> SEQ ID NO 164
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 164
cgcgaatgcc atctcagtgt tgagcttcag aatacggtcc ccaagacgcg tggcggatgt      60

<210> SEQ ID NO 165
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 165
cgcgaatgcc tagagaagta ggtcctgtca acaagaaggg attttacgcg tggcggatgt      60

<210> SEQ ID NO 166
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 166
cgcgaatgcc ggcaacacaa gcaccaacat cttgaaatgc caaatacgcg tggcggatgt      60

<210> SEQ ID NO 167
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 167
cgcgaatgcc ttggtgtctg tgagagtata cttcaaaaag tgcccacgcg tggcggatgt      60

<210> SEQ ID NO 168
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 168
cgcgaatgcc tgtctggaaa catagccaga ttcttcactg taaatacgcg tggcggatgt      60

<210> SEQ ID NO 169
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 169
```
cgcgaatgcc cggtacccat ggactcccag tccctggtgg aggttacgcg tggcggatgt    60

<210> SEQ ID NO 170
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 170
cgcgaatgcc tcttcctcct tagaattgtt gacacaagac cctctacgcg tggcggatgt    60

<210> SEQ ID NO 171
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 171
cgcgaatgcc tcctccaagg atgtactgca gtacagaagg cgaatacgcg tggcggatgt    60

<210> SEQ ID NO 172
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 172
cgcgaatgcc agcattgcag gaacacttgc caatgggtac aagccacgcg tggcggatgt    60

<210> SEQ ID NO 173
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 173
cgcgaatgcc ggctatgaag aaagaggttt tatgtgccaa ggtaaacgcg tggcggatgt    60

<210> SEQ ID NO 174
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 174
cgcgaatgcc tatccatctt tctctctctt tatctttctc aggttacgcg tggcggatgt    60

<210> SEQ ID NO 175
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 175
cgcgaatgcc ggcttctttg gtgcatttgt tgtggcactt taaccacgcg tggcggatgt    60

<210> SEQ ID NO 176
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 176
cgcgaatgcc caccctgtc atcttctgat catccaccga ggaggacgcg tggcggatgt    60

<210> SEQ ID NO 177
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 177
cgcgaatgcc ccctgcccc tagggcagta agtgttaaat agttaacgcg tggcggatgt    60

<210> SEQ ID NO 178
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 178
cgcgaatgcc gtgggaggac acaccatgct ccccattcgc tggatacgcg tggcggatgt    60

<210> SEQ ID NO 179
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 179
cgcgaatgcc tagtgaactt ccggtacatg atgctttcag gaggcacgcg tggcggatgt    60

<210> SEQ ID NO 180
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 180
cgcgaatgcc cagagagtga tgtatggagc ttcggggtga tcctcacgcg tggcggatgt    60

<210> SEQ ID NO 181
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 181
cgcgaatgcc aaccatggct gctttccata ggtgaagatc tcccaacgcg tggcggatgt    60

<210> SEQ ID NO 182
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 182
cgcgaatgcc ccaactctca aacacggagg taaaaggggg gtgcgacgcg tggcggatgt    60
```

<210> SEQ ID NO 183
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 183
cgcgaatgcc ctgccctgct tcctgctctg ccttctcagg tcttcacgcg tggcggatgt    60

<210> SEQ ID NO 184
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 184
cgcgaatgcc tgcccactgt caggccgggt gactttccgc accagacgcg tggcggatgt    60

<210> SEQ ID NO 185
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 185
cgcgaatgcc cctgtatgct atgaaggtgc tgaagaaggc aacgcacgcg tggcggatgt    60

<210> SEQ ID NO 186
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 186
cgcgaatgcc gttctgcaca gggaggtgtc cccactcacc tttcaacgcg tggcggatgt    60

<210> SEQ ID NO 187
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 187
cgcgaatgcc ggaccctgga ggtacgagtg gtgggctgca gagacacgcg tggcggatgt    60

<210> SEQ ID NO 188
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 188
cgcgaatgcc gaggggtag ggttccacgg gatggtctct gggagacgcg tggcggatgt    60

<210> SEQ ID NO 189
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 189
cgcgaatgcc aatgggggga cctgggaccc cagacagccg cccccacgcg tggcggatgt    60

<210> SEQ ID NO 190
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 190
cgcgaatgcc gctgtaaagg ccccgggctg ggcggctcag gaaggacgcg tggcggatgt    60

<210> SEQ ID NO 191
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 191
cgcgaatgcc cgaagcggaa gcctcagtgg ccggagcagc ctcaaacgcg tggcggatgt    60

<210> SEQ ID NO 192
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 192
cgcgaatgcc acgatgccca ctcactggtg ttctcggctt ctgctacgcg tggcggatgt    60

<210> SEQ ID NO 193
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 193
cgcgaatgcc agccaagaag aagagcaaac ccttgaacct caagaacgcg tggcggatgt    60

<210> SEQ ID NO 194
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 194
cgcgaatgcc ggggatgttc tcgcagctgc ctacgctgct gtggaacgcg tggcggatgt    60

<210> SEQ ID NO 195
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 195
cgcgaatgcc tctcagcagc gctccccgct gctgtccgag cgctcacgcg tggcggatgt    60

-continued

```
<210> SEQ ID NO 196
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 196
cgcgaatgcc ggaaaggtgc gtgtcccaca agaaggagc ggaggacgcg tggcggatgt      60

<210> SEQ ID NO 197
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 197
cgcgaatgcc tgccttccac ccctcctgtt cacactgagg ccaacacgcg tggcggatgt      60

<210> SEQ ID NO 198
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 198
cgcgaatgcc agtgcagccc ggcagggtga cttacttgca gagaaacgcg tggcggatgt      60

<210> SEQ ID NO 199
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 199
cgcgaatgcc tgaaataacc cgtgtttaaa gataaacgtc ttctgacgcg tggcggatgt      60

<210> SEQ ID NO 200
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 200
cgcgaatgcc tagagccttt gacgaatttc ttagttatct gaaaaacgcg tggcggatgt      60

<210> SEQ ID NO 201
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 201
cgcgaatgcc cagagaagaa caagctcaga ctgcaaagag taagaacgcg tggcggatgt      60

<210> SEQ ID NO 202
<211> LENGTH: 60
<212> TYPE: DNA
<213> ORGANISM: Artificial Sequence
<220> FEATURE:
<223> OTHER INFORMATION: Synthetic oligonucleotide
```

```
<400> SEQUENCE: 202
cgcgaatgcc gcacagcagg ttaattttct atttcaggga aaatgacgcg tggcggatgt      60

<210> SEQ ID NO 203
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 203
cgcgaatgcc gagcatatta agcaagatga acatctcggg aagcaacgcg tggcggatgt      60

<210> SEQ ID NO 204
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 204
cgcgaatgcc actagatgta tctgcagagt tagggcttcc acagcacgcg tggcggatgt      60

<210> SEQ ID NO 205
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 205
cgcgaatgcc gactttaagg acctttggac aaaactaaaa gaatgacgcg tggcggatgt      60

<210> SEQ ID NO 206
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 206
cgcgaatgcc aagaaaagat tttaccttgt acttctctat catgaacgcg tggcggatgt      60

<210> SEQ ID NO 207
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 207
cgcgaatgcc atgagccggg gcgcgggcgc gcttcagcgc cggacacgcg tggcggatgt      60

<210> SEQ ID NO 208
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 208
cgcgaatgcc gcttaaccag ggtcagcgag atgaggtagg tcgttacgcg tggcggatgt      60

<210> SEQ ID NO 209
<211> LENGTH: 60
```

```
<212> TYPE: DNA
<213> ORGANISM: Artificial Sequence
<220> FEATURE:
<223> OTHER INFORMATION: Synthetic oligonucleotide

<400> SEQUENCE: 209
cgcgaatgcc aagctcgagt cggtgcctcc gccgccgcct tctccacgcg tggcggatgt    60

<210> SEQ ID NO 210
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 210
cgcgaatgcc ctcggagcct ctggcaccgg cggcgccggc cgcggacgcg tggcggatgt    60

<210> SEQ ID NO 211
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 211
cgcgaatgcc cgagactggg gatcctggca gcccccgagg cgcggacgcg tggcggatgt    60

<210> SEQ ID NO 212
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 212
cgcgaatgcc gaagagacgt tcgtgccgct tcttgcccgg ctcctacgcg tggcggatgt    60

<210> SEQ ID NO 213
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 213
cgcgaatgcc caccggcagg atgcgctgtg gatcagcacg agcagacgcg tggcggatgt    60

<210> SEQ ID NO 214
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 214
cgcgaatgcc acagggctgg gggctccgcg cccccggtgc ccgcgacgcg tggcggatgt    60

<210> SEQ ID NO 215
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 215
```
cgcgaatgcc ccccggctcc ggccagtccg gcccgcccag tctccacgcg tggcggatgt    60

<210> SEQ ID NO 216
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 216
cgcgaatgcc acggcccaga gggagaggcg gcggccggga gcgggacgcg tggcggatgt    60

<210> SEQ ID NO 217
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 217
cgcgaatgcc ccctccggga cccccgctct ccgggggact gagccacgcg tggcggatgt    60

<210> SEQ ID NO 218
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 218
cgcgaatgcc ggaggaggtg ggggcgcccc caggcttggg gtcggacgcg tggcggatgt    60

<210> SEQ ID NO 219
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 219
cgcgaatgcc cggcgccccc tgctcagcag cccgagctgg ggcggacgcg tggcggatgt    60

<210> SEQ ID NO 220
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 220
cgcgaatgcc ggatgccgcc gcccgcccgg ccttcgggct ccgggacgcg tggcggatgt    60

<210> SEQ ID NO 221
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 221
cgcgaatgcc ctggctcatc ctctccgcac cctggcaccg gcagcacgcg tggcggatgt    60

<210> SEQ ID NO 222
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 222
cgcgaatgcc ggagccggcg gaggaggcgc caccttgagc ctccgacgcg tggcggatgt    60

<210> SEQ ID NO 223
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 223
cgcgaatgcc caagccttgc aagaccgtga ccacgagtgg agccaacgcg tggcggatgt    60

<210> SEQ ID NO 224
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 224
cgcgaatgcc caggcggcta cccgcgccct tgccccgcc ggcttacgcg tggcggatgt     60

<210> SEQ ID NO 225
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 225
cgcgaatgcc tcatggcccg aaagcgaggg caagcccagg gtcaaacgcg tggcggatgt    60

<210> SEQ ID NO 226
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 226
cgcgaatgcc ccgaagctcc agtcccggcg ctgctctttg accccacgcg tggcggatgt    60

<210> SEQ ID NO 227
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 227
cgcgaatgcc tctctgccgc cgccaccgcc gccgccgccg ggggaacgcg tggcggatgt    60

<210> SEQ ID NO 228
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 228
cgcgaatgcc ccgaccccac cagaggtcga agctgtagag cccccacgcg tggcggatgt    60
```

```
<210> SEQ ID NO 229
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 229
cgcgaatgcc ggctggggct ggagcccgag ggaagttgtc ccctcacgcg tggcggatgt      60

<210> SEQ ID NO 230
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 230
cgcgaatgcc gtcactgttg tccaaggtct tactcttgcc tttccacgcg tggcggatgt      60

<210> SEQ ID NO 231
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 231
cgcgaatgcc ttgcatccgg gaccgcctgc cggctctcct cctccacgcg tggcggatgt      60

<210> SEQ ID NO 232
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 232
cgcgaatgcc cagtggctgg actcggagtt ggtgggaggg ttagcacgcg tggcggatgt      60

<210> SEQ ID NO 233
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 233
cgcgaatgcc ctgtcaccgc tgcttccgcg cagcccccg ggcctacgcg tggcggatgt       60

<210> SEQ ID NO 234
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 234
cgcgaatgcc cccggagctg gaggctccag agtgattgga ggtgcacgcg tggcggatgt      60

<210> SEQ ID NO 235
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 235
cgcgaatgcc gctgaaacgg ggccgggagg ggggccgagc atccaacgcg tggcggatgt    60

<210> SEQ ID NO 236
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 236
cgcgaatgcc gccgctgata aacttgagca tcttgcggtc acgagacgcg tggcggatgt    60

<210> SEQ ID NO 237
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 237
cgcgaatgcc atcttcacca agagcacagg agggcctcct ggctcacgcg tggcggatgt    60

<210> SEQ ID NO 238
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 238
cgcgaatgcc cagaagacag gctgggggt ccgggaaggg gcccgacgcg tggcggatgt    60

<210> SEQ ID NO 239
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 239
cgcgaatgcc gcagcgggtc cagggagctg ctgggcgccg agctcacgcg tggcggatgt    60

<210> SEQ ID NO 240
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 240
cgcgaatgcc ctcaagccct gactcaactc actagggaa gcgcgacgcg tggcggatgt    60

<210> SEQ ID NO 241
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 241
cgcgaatgcc gctcctctgg ccgcccctcc ctccgcgcgg ggaccacgcg tggcggatgt    60

<210> SEQ ID NO 242

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 242
cgcgaatgcc cgctggccat gtcctcctgc cgcccgccag gggtcacgcg tggcggatgt    60

<210> SEQ ID NO 243
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 243
cgcgaatgcc gacgccgtgc aggtaggcgc acctgcgtct ggagtacgcg tggcggatgt    60

<210> SEQ ID NO 244
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 244
cgcgaatgcc ggggtccgcc ggcgccgtcc ggtcgccccg ggactacgcg tggcggatgt    60

<210> SEQ ID NO 245
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 245
cgcgaatgcc tatataagaa gctgtataat gcttgggagg atgccacgcg tggcggatgt    60

<210> SEQ ID NO 246
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 246
cgcgaatgcc aataaaggct ttctttagcc atcaacatca aattgacgcg tggcggatgt    60

<210> SEQ ID NO 247
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 247
cgcgaatgcc ctcaactgcc aatggactgt tttacaatgc catctacgcg tggcggatgt    60

<210> SEQ ID NO 248
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 248
```
cgcgaatgcc atatatggtg tagctgtgga aatgcgtctg gaataacgcg tggcggatgt    60

<210> SEQ ID NO 249
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 249
cgcgaatgcc gaatggagaa acatctacaa aatcccttttg ggttaacgcg tggcggatgt    60

<210> SEQ ID NO 250
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 250
cgcgaatgcc tgcacaaaga atttttattc tgagtgcact atttaacgcg tggcggatgt    60

<210> SEQ ID NO 251
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 251
cgcgaatgcc acctacgtga atgtaaatat tcgagacatt gataaacgcg tggcggatgt    60

<210> SEQ ID NO 252
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 252
cgcgaatgcc ctataaaata ataagcatca gcatttgact ttaccacgcg tggcggatgt    60

<210> SEQ ID NO 253
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 253
cgcgaatgcc ccctacggat ccagcaaggt tagtccggac agagtacgcg tggcggatgt    60

<210> SEQ ID NO 254
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 254
cgcgaatgcc cttccgtaga gggttgttga tgtcacacgg aacggacgcg tggcggatgt    60

<210> SEQ ID NO 255
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 255
cgcgaatgcc ccacctcgct attcagacct gcacatcagt cagacacgcg tggcggatgt    60

<210> SEQ ID NO 256
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 256
cgcgaatgcc gccttacctt gttgattttg ttggttttgg ggagcacgcg tggcggatgt    60

<210> SEQ ID NO 257
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 257
cgcgaatgcc taatgctgtt tctgttgact tttgactttt ctagtacgcg tggcggatgt    60

<210> SEQ ID NO 258
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 258
cgcgaatgcc gaacgccgga tgggaagtcc ccatagctct gggaaacgcg tggcggatgt    60

<210> SEQ ID NO 259
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 259
cgcgaatgcc ctggtcttag gctgtcttct cacaggtacg gagccacgcg tggcggatgt    60

<210> SEQ ID NO 260
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 260
cgcgaatgcc acaagacacc caaacaagga actcagagag gactgacgcg tggcggatgt    60

<210> SEQ ID NO 261
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 261
cgcgaatgcc gtccaccatc tgctcccctg aacttgattt caaatacgcg tggcggatgt    60
```

<210> SEQ ID NO 262
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 262
cgcgaatgcc ctactccatt ccaagttcac agatgtctcg ttgacacgcg tggcggatgt    60

<210> SEQ ID NO 263
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 263
cgcgaatgcc ccctcagaat acaggtggcc gccaggacat ttcctacgcg tggcggatgt    60

<210> SEQ ID NO 264
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 264
cgcgaatgcc gtcaccagct ccacatttct tgcataccac attatacgcg tggcggatgt    60

<210> SEQ ID NO 265
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 265
cgcgaatgcc cccagcaagt gccgaccctg tggaagtggg gtccaacgcg tggcggatgt    60

<210> SEQ ID NO 266
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 266
cgcgaatgcc tggtggtctt caagccattc tgctgtgggg tgtagacgcg tggcggatgt    60

<210> SEQ ID NO 267
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 267
cgcgaatgcc aagtctccat cactgacctc ctagctcata ccaatacgcg tggcggatgt    60

<210> SEQ ID NO 268
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 268
cgcgaatgcc gacactccat tcacagccca gatttcaaag gtgtaacgcg tggcggatgt    60

<210> SEQ ID NO 269
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 269
cgcgaatgcc caaatataac cctaacccag accaatcagt ttctgacgcg tggcggatgt    60

<210> SEQ ID NO 270
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 270
cgcgaatgcc tcaattccta cctgcttggt tggtggtcac agtgaacgcg tggcggatgt    60

<210> SEQ ID NO 271
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 271
cgcgaatgcc gtgaatttgg agaggtgtgc agtggtcgct taaaaacgcg tggcggatgt    60

<210> SEQ ID NO 272
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 272
cgcgaatgcc ttaatggcca ctgaaatctc tttttttgaa ggaagacgcg tggcggatgt    60

<210> SEQ ID NO 273
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 273
cgcgaatgcc gaccctgaaa gttggctaca cagaaaagca gaggaacgcg tggcggatgt    60

<210> SEQ ID NO 274
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 274
cgcgaatgcc ctgtcccata atgcttgctt ctcccaggaa gtctcacgcg tggcggatgt    60

```
<210> SEQ ID NO 275
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 275
cgcgaatgcc tttgaccacc ccaatatcat tcgactggaa ggagtacgcg tggcggatgt      60

<210> SEQ ID NO 276
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 276
cgcgaatgcc aggtcttatg actactttac ttactttggg taacaacgcg tggcggatgt      60

<210> SEQ ID NO 277
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 277
cgcgaatgcc acattcaaac gtgttttgat caaagaagag gagtaacgcg tggcggatgt      60

<210> SEQ ID NO 278
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 278
cgcgaatgcc tgaagaccga gttatagaat actataatag aatcaacgcg tggcggatgt      60

<210> SEQ ID NO 279
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 279
cgcgaatgcc tgcagagact gaaaacaaat attttgcagt atgctacgcg tggcggatgt      60

<210> SEQ ID NO 280
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 280
cgcgaatgcc ccaatcaaag gatactttg acctaccctg gtggaacgcg tggcggatgt      60

<210> SEQ ID NO 281
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 281
cgcgaatgcc aaaaatctaa tgtaatgggt ccaccaaaac attaaacgcg tggcggatgt    60

<210> SEQ ID NO 282
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 282
cgcgaatgcc gggctagagc aaaaacaaaa aagtagatta tttatacgcg tggcggatgt    60

<210> SEQ ID NO 283
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 283
cgcgaatgcc cctaccttgt caccaatacc tcacattcct cgaagacgcg tggcggatgt    60

<210> SEQ ID NO 284
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 284
cgcgaatgcc gaatccgtaa gggtgaacta ggaaacttgt aagggacgcg tggcggatgt    60

<210> SEQ ID NO 285
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 285
cgcgaatgcc ctggagggaa catctatatt tcacccctga agagtacgcg tggcggatgt    60

<210> SEQ ID NO 286
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 286
cgcgaatgcc gttggtgttg gcagaccttc tgaaatttta tatggacgcg tggcggatgt    60

<210> SEQ ID NO 287
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 287
cgcgaatgcc aaaaatgact ccaagatcaa ggtgtgtgtt ttctcacgcg tggcggatgt    60

<210> SEQ ID NO 288
<211> LENGTH: 60

```
<212> TYPE: DNA
<213> ORGANISM: Artificial Sequence
<220> FEATURE:
<223> OTHER INFORMATION: Synthetic oligonucleotide

<400> SEQUENCE: 288
cgcgaatgcc tgggaagaag tcagtggcta cgatgaaaac ctgaaacgcg tggcggatgt    60

<210> SEQ ID NO 289
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 289
cgcgaatgcc cgaagacatt gcacacctgg taggtgcgga tggtgacgcg tggcggatgt    60

<210> SEQ ID NO 290
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 290
cgcgaatgcc agcccaacca gaacaattgg ctgctcacca ccttcacgcg tggcggatgt    60

<210> SEQ ID NO 291
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 291
cgcgaatgcc tctgtgtaga tgcgatgggc cccccgccgg ttgatacgcg tggcggatgt    60

<210> SEQ ID NO 292
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 292
cgcgaatgcc gatgcgcttc actgtgagag actgcagcag cctccacgcg tggcggatgt    60

<210> SEQ ID NO 293
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 293
cgcgaatgcc gttgaaggtc tccttgcagg atcctgggac attagacgcg tggcggatgt    60

<210> SEQ ID NO 294
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 294
```
cgcgaatgcc ttgtattact atgagactga ctctgtcatt gccacacgcg tggcggatgt    60

<210> SEQ ID NO 295
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 295
cgcgaatgcc ggtagggggc ctcagaccag aaggctgact tcttgacgcg tggcggatgt    60

<210> SEQ ID NO 296
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 296
cgcgaatgcc tcaaagtaga caccattgct gcagatgaga gcttcacgcg tggcggatgt    60

<210> SEQ ID NO 297
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 297
cgcgaatgcc accttcatca gccttccccc aaagtccacc tgggaacgcg tggcggatgt    60

<210> SEQ ID NO 298
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 298
cgcgaatgcc aaacacagaa gtcaggagct ttgggcctct tactcacgcg tggcggatgt    60

<210> SEQ ID NO 299
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 299
cgcgaatgcc tccataatcc tgaaaagcga ggtaaaaacc attccacgcg tggcggatgt    60

<210> SEQ ID NO 300
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 300
cgcgaatgcc gcctgtatgt ctcttctttc tgtccgtgtc ttcttacgcg tggcggatgt    60

<210> SEQ ID NO 301
<211> LENGTH: 60
<212> TYPE: DNA
<213> ORGANISM: Artificial Sequence -continued

```
<220> FEATURE:
<223> OTHER INFORMATION: Synthetic oligonucleotide

<400> SEQUENCE: 301
cgcgaatgcc ctgcaaaatt ttgcacaatg ctgggacact ttttgacgcg tggcggatgt    60

<210> SEQ ID NO 302
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 302
cgcgaatgcc tgtttccaga gactatgaca ggggcagaga gcacaacgcg tggcggatgt    60

<210> SEQ ID NO 303
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 303
cgcgaatgcc ttggggatgc atgtgccccg agcaatcacc agagaacgcg tggcggatgt    60

<210> SEQ ID NO 304
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 304
cgcgaatgcc cgcagaggaa gtggacgtgc ccatcaaact ctactacgcg tggcggatgt    60

<210> SEQ ID NO 305
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 305
cgcgaatgcc cccaataggc accatccatt ccccatcccc gttgcacgcg tggcggatgt    60

<210> SEQ ID NO 306
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 306
cgcgaatgcc cgatgcacct gcaagcctgg ctatgagcct gagaaacgcg tggcggatgt    60

<210> SEQ ID NO 307
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 307
cgcgaatgcc agaggctcca aagcttaccc ttgcatgcca cgctgacgcg tggcggatgt    60
```

<210> SEQ ID NO 308
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 308
cgcgaatgcc gagacatgaa acagctggct gaagatgtga agctgacgcg tggcggatgt    60

<210> SEQ ID NO 309
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 309
cgcgaatgcc tctggatcag gaatttctag taacttatac agctgacgcg tggcggatgt    60

<210> SEQ ID NO 310
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 310
cgcgaatgcc caaaaactgg gctactctgg cgcagaaatt aggtcacgcg tggcggatgt    60

<210> SEQ ID NO 311
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 311
cgcgaatgcc aggactcagc cggaaggcat tattaagtat ccccaacgcg tggcggatgt    60

<210> SEQ ID NO 312
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 312
cgcgaatgcc gctccttcca aaacacttat ggacaactat gaggtacgcg tggcggatgt    60

<210> SEQ ID NO 313
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 313
cgcgaatgcc ttgcatgctc tttcccttta cctaagatgt atcctacgcg tggcggatgt    60

<210> SEQ ID NO 314
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 314
cgcgaatgcc tgctcccgga tctatactcc actggatatt ttcaaacgcg tggcggatgt    60

<210> SEQ ID NO 315
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 315
cgcgaatgcc gacctttctc agtataaaat ggatgttact gtaatacgcg tggcggatgt    60

<210> SEQ ID NO 316
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 316
cgcgaatgcc gttttggttt tactttttaa cttacctttg tatctacgcg tggcggatgt    60

<210> SEQ ID NO 317
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 317
cgcgaatgcc cttcgcaaac ctgggtatac ttcatgtgac aaagaacgcg tggcggatgt    60

<210> SEQ ID NO 318
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 318
cgcgaatgcc tgtcattcgt gcttccagtg tttcaaatac ttttacgcg tggcggatgt    60

<210> SEQ ID NO 319
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 319
cgcgaatgcc gaggcgtgta taaggggcta taatcctgga ctcttacgcg tggcggatgt    60

<210> SEQ ID NO 320
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 320
cgcgaatgcc cttctgcttg caaataggca aggtcagggt gcaccacgcg tggcggatgt    60

<210> SEQ ID NO 321

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 321
cgcgaatgcc gtggagggga ccggcagctg ggaggtaagc atcatacgcg tggcggatgt    60

<210> SEQ ID NO 322
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 322
cgcgaatgcc acacttcaat gtgattgttt gcagatgaca tccagacgcg tggcggatgt    60

<210> SEQ ID NO 323
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 323
cgcgaatgcc actccaccat tttcttcctc ttcataaaat cgaatacgcg tggcggatgt    60

<210> SEQ ID NO 324
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 324
cgcgaatgcc ctgggaagga tttggagatt tttcccccac agatgacgcg tggcggatgt    60

<210> SEQ ID NO 325
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 325
cgcgaatgcc taataataat aataaatcac ttacttgtct atgaaacgcg tggcggatgt    60

<210> SEQ ID NO 326
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 326
cgcgaatgcc atgcctccac gaccatcatc aggtgaactg tggggacgcg tggcggatgt    60

<210> SEQ ID NO 327
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 327
```

```
cgcgaatgcc attctactag gattcttggg ggcatcaagt ggatgacgcg tggcggatgt    60
```

<210> SEQ ID NO 328
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 328

```
cgcgaatgcc gtttactacc aaatggaatg atagtgactt tagaaacgcg tggcggatgt    60
```

<210> SEQ ID NO 329
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 329

```
cgcgaatgcc tgctttatgg ttattaatgt agcctcacgg aggcaacgcg tggcggatgt    60
```

<210> SEQ ID NO 330
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 330

```
cgcgaatgcc tgaactattt aaagaagcaa gaaaataccc cctccacgcg tggcggatgt    60
```

<210> SEQ ID NO 331
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 331

```
cgcgaatgcc gaaaatgtaa gaagattcat cttgaagaag ttgatacgcg tggcggatgt    60
```

<210> SEQ ID NO 332
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 332

```
cgcgaatgcc gtaagtgtta ctcaagaagc agaaagggaa gaattacgcg tggcggatgt    60
```

<210> SEQ ID NO 333
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 333

```
cgcgaatgcc gccgaaggtc acaaagtcgt cttgtttcat caaaaacgcg tggcggatgt    60
```

<210> SEQ ID NO 334
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 334
cgcgaatgcc ttttcaacc cttttttaaaa gtaattgaac cagtaacgcg tggcggatgt    60

<210> SEQ ID NO 335
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 335
cgcgaatgcc atttctcgat tgaggatctt ttcttcacgg ttgccacgcg tggcggatgt    60

<210> SEQ ID NO 336
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 336
cgcgaatgcc tggtatgata caatatccta ttctaaaatg caaatacgcg tggcggatgt    60

<210> SEQ ID NO 337
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 337
cgcgaatgcc gtgtttgagg aaaataattc tcttttttaa aaaaaacgcg tggcggatgt    60

<210> SEQ ID NO 338
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 338
cgcgaatgcc cgcttcttgt ttggctttac tgtatttact ccgtcacgcg tggcggatgt    60

<210> SEQ ID NO 339
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 339
cgcgaatgcc agcggatgaa gagaaacatt tgaatcaagg tacaaacgcg tggcggatgt    60

<210> SEQ ID NO 340
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 340
cgcgaatgcc catgctctaa aaatagaatt ttttaatcca attttacgcg tggcggatgt    60
```

<210> SEQ ID NO 341
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 341
cgcgaatgcc gtctctgggg gtacagtcag agagctggtg gaggcacgcg tggcggatgt    60

<210> SEQ ID NO 342
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 342
cgcgaatgcc cttcaattgc ttcggtgtag cccatttgtc tcaggacgcg tggcggatgt    60

<210> SEQ ID NO 343
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 343
cgcgaatgcc tgatccaggc agcctccagc ccagtgaaga ccaccacgcg tggcggatgt    60

<210> SEQ ID NO 344
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 344
cgcgaatgcc gaggcaggcg agagaggcag cgagtgggcc tgagaacgcg tggcggatgt    60

<210> SEQ ID NO 345
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 345
cgcgaatgcc cacaaggcag caaataggta aaaaaaaga caaaaacgcg tggcggatgt    60

<210> SEQ ID NO 346
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 346
cgcgaatgcc cttcgcagga gcagatcccc tggtggagaa ctttgacgcg tggcggatgt    60

<210> SEQ ID NO 347
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 347
cgcgaatgcc attttcccaa gagtcatcca ggtcatagag aggctacgcg tggcggatgt    60

<210> SEQ ID NO 348
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 348
cgcgaatgcc gcaggagagg atgaaggagt tgtgcctgga accacacgcg tggcggatgt    60

<210> SEQ ID NO 349
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 349
cgcgaatgcc cactcacctg ccagctggtg gccatatcta gaggcacgcg tggcggatgt    60

<210> SEQ ID NO 350
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 350
cgcgaatgcc ggcaaataat agtggtgatc tgggtaatag tttctacgcg tggcggatgt    60

<210> SEQ ID NO 351
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 351
cgcgaatgcc attttcagag tatacttctg cttgtcatta tttggacgcg tggcggatgt    60

<210> SEQ ID NO 352
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 352
cgcgaatgcc caaccatgac tgtgtaccag aacaagtaat tgctgacgcg tggcggatgt    60

<210> SEQ ID NO 353
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 353
cgcgaatgcc tagcaacata cttcgagttt ttttcctgat tgcttacgcg tggcggatgt    60

```
<210> SEQ ID NO 354
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 354
cgcgaatgcc tcctctgaac aactaaaact ctgtgtttta gaataacgcg tggcggatgt      60

<210> SEQ ID NO 355
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 355
cgcgaatgcc cacatccaca cacttttaaa atatacttgc cctgaacgcg tggcggatgt      60

<210> SEQ ID NO 356
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 356
cgcgaatgcc atgaatactt cctagaaaaa tatcctctga gtcagacgcg tggcggatgt      60

<210> SEQ ID NO 357
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 357
cgcgaatgcc taatattttg aaacttgtta ctcaccttat actgaacgcg tggcggatgt      60

<210> SEQ ID NO 358
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 358
cgcgaatgcc catgtctctc cttcttttgc agcttatcgc attcaacgcg tggcggatgt      60

<210> SEQ ID NO 359
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 359
cgcgaatgcc gattttgaag aattgtaaca gtgctgagac tgacaacgcg tggcggatgt      60

<210> SEQ ID NO 360
<211> LENGTH: 60
<212> TYPE: DNA
<213> ORGANISM: Artificial Sequence
<220> FEATURE:
<223> OTHER INFORMATION: Synthetic oligonucleotide
```

```
<400> SEQUENCE: 360
cgcgaatgcc tgagtgaggg ctatgaagtg gagcttcgag gaagaacgcg tggcggatgt    60

<210> SEQ ID NO 361
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 361
cgcgaatgcc caaaaaacaa aaagacatta taccttgagc tctgtacgcg tggcggatgt    60

<210> SEQ ID NO 362
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 362
cgcgaatgcc tccccattcc caggggatga tgaggaggag gtcttacgcg tggcggatgt    60

<210> SEQ ID NO 363
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 363
cgcgaatgcc gggggtagcg aacctcgtcg ttgacgatgc tgtcgacgcg tggcggatgt    60

<210> SEQ ID NO 364
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 364
cgcgaatgcc gcttcctgtc ggccgaagcc atcggcatca tgagaacgcg tggcggatgt    60

<210> SEQ ID NO 365
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 365
cgcgaatgcc ccccaggccc gccccacgtc gggggtcctc accctacgcg tggcggatgt    60

<210> SEQ ID NO 366
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 366
cgcgaatgcc aggggcagtg gggcccagga ggggacagat cctgaacgcg tggcggatgt    60

<210> SEQ ID NO 367
<211> LENGTH: 60
```

<212> TYPE: DNA
<213> ORGANISM: Artificial Sequence
<220> FEATURE:
<223> OTHER INFORMATION: Synthetic oligonucleotide

<400> SEQUENCE: 367
cgcgaatgcc ttcctccgaa gcagcttgga ggaaggagca ctgtgacgcg tggcggatgt    60

<210> SEQ ID NO 368
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 368
cgcgaatgcc cccagagcgg aggctgggat ctagcgagag agatgacgcg tggcggatgt    60

<210> SEQ ID NO 369
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 369
cgcgaatgcc caccctgaag aagggctgtt tcttcacatc ttctgacgcg tggcggatgt    60

<210> SEQ ID NO 370
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 370
cgcgaatgcc atatgatgca gccattgacc tgtttacacg ttcatacgcg tggcggatgt    60

<210> SEQ ID NO 371
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 371
cgcgaatgcc tcccaaaatg aaggtagcta cacagtatcc agcacacgcg tggcggatgt    60

<210> SEQ ID NO 372
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 372
cgcgaatgcc attggagatc gtcacaatag taacatcatg gtgaaacgcg tggcggatgt    60

<210> SEQ ID NO 373
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 373
cgcgaatgcc tttaaacaga gaaaaccatt acttgtccat cgtctacgcg tggcggatgt    60

<210> SEQ ID NO 374
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 374
cgcgaatgcc atgttttggt gttcttaatt tattcaagac attttacgcg tggcggatgt    60

<210> SEQ ID NO 375
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 375
cgcgaatgcc aagaaattat gttatagttt gatatatgca gatacacgcg tggcggatgt    60

<210> SEQ ID NO 376
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 376
cgcgaatgcc attttgaaa gctgtttcat atagattttg gacacacgcg tggcggatgt    60

<210> SEQ ID NO 377
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 377
cgcgaatgcc ttataaccaa attttttctt cttgtgatcc aaaaaacgcg tggcggatgt    60

<210> SEQ ID NO 378
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 378
cgcgaatgcc acgagaacgt gtgccatttg ttttgacaca ggattacgcg tggcggatgt    60

<210> SEQ ID NO 379
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 379
cgcgaatgcc gcattcttgg gctccttttac taatcactat taagaacgcg tggcggatgt    60

<210> SEQ ID NO 380
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 380
cgcgaatgcc acaaagacaa gagaatttga gaggtgagct cgagcacgcg tggcggatgt    60

<210> SEQ ID NO 381
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 381
cgcgaatgcc ttatttattt tttgaccttt agagatgcac aaagaacgcg tggcggatgt    60

<210> SEQ ID NO 382
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 382
cgcgaatgcc ctcagctgtt gatttttggt gaagaattct tctagacgcg tggcggatgt    60

<210> SEQ ID NO 383
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 383
cgcgaatgcc ggaacagcag aaagtccttc atgaaaccat taagacgcg tggcggatgt     60

<210> SEQ ID NO 384
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 384
cgcgaatgcc aagacctaag tgccagactc accgatcttc taaaaacgcg tggcggatgt    60

<210> SEQ ID NO 385
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 385
cgcgaatgcc gtttctggtt cctcacaggt atccatagca gttggacgcg tggcggatgt    60

<210> SEQ ID NO 386
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 386
cgcgaatgcc gaaccaccaa caggacacag gcaaaagcag caagtacgcg tggcggatgt    60
```

<210> SEQ ID NO 387
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 387
cgcgaatgcc tcttcgtcat gatcaacaaa tatggtcgac ggtccacgcg tggcggatgt    60

<210> SEQ ID NO 388
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 388
cgcgaatgcc aatgaaactc ccaccttacc cttcattcca aatttacgcg tggcggatgt    60

<210> SEQ ID NO 389
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 389
cgcgaatgcc aaaaatgatg gcagatttac agtcattcag ctggtacgcg tggcggatgt    60

<210> SEQ ID NO 390
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 390
cgcgaatgcc acttcatccc agacccaatg ccacgaagca tgcccacgcg tggcggatgt    60

<210> SEQ ID NO 391
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 391
cgcgaatgcc atttatctga tatgagctat gtgcatcgtg atctgacgcg tggcggatgt    60

<210> SEQ ID NO 392
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 392
cgcgaatgcc accaagttgc tgttcaccag gatgttccgt gcggcacgcg tggcggatgt    60

<210> SEQ ID NO 393
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 393
cgcgaatgcc ctgcaaagtg tctgattttg gcatgtcccg agtgcacgcg tggcggatgt    60

<210> SEQ ID NO 394
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 394
cgcgaatgcc cctggtggtg taagctgctt ccggatcatc ctcaaacgcg tggcggatgt    60

<210> SEQ ID NO 395
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 395
cgcgaatgcc gtaagaaaga tcggtgacat ctgggctttc actctacgcg tggcggatgt    60

<210> SEQ ID NO 396
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 396
cgcgaatgcc atggatgtct ctctttgccc agccaagtgt agtttacgcg tggcggatgt    60

<210> SEQ ID NO 397
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 397
cgcgaatgcc ccagccagac gcttcccagc aagaaaatcc gccagacgcg tggcggatgt    60

<210> SEQ ID NO 398
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 398
cgcgaatgcc actatgtggg ctccgtgctg gcttgccctg caaatacgcg tggcggatgt    60

<210> SEQ ID NO 399
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 399
cgcgaatgcc cgccggcaat tgatctcagt cttgctgcag acacaacgcg tggcggatgt    60

<210> SEQ ID NO 400

-continued

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 400
cgcgaatgcc gccggacgat gggaacctct tccccctcct ggaagacgcg tggcggatgt    60

<210> SEQ ID NO 401
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 401
cgcgaatgcc actggcgttc ccattgctgt tccctgaatc ctgccacgcg tggcggatgt    60

<210> SEQ ID NO 402
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 402
cgcgaatgcc atcaacatca cggacatctc aaggaatatc acttcacgcg tggcggatgt    60

<210> SEQ ID NO 403
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 403
cgcgaatgcc gaggcaggct ggggagcggc cgcctgactt acatgacgcg tggcggatgt    60

<210> SEQ ID NO 404
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 404
cgcgaatgcc tttaaaattt tacataggtg gaatgaatgg ctgaaacgcg tggcggatgt    60

<210> SEQ ID NO 405
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 405
cgcgaatgcc cagcacgagg aagatcagga atgtatatat cataaacgcg tggcggatgt    60

<210> SEQ ID NO 406
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 406
```
cgcgaatgcc ctcgactttg cctttccatt tgctctgtta aaggcacgcg tggcggatgt    60

<210> SEQ ID NO 407
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 407
cgcgaatgcc cttctgaaat actttacctc tttagcaccc tttcgacgcg tggcggatgt    60

<210> SEQ ID NO 408
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 408
cgcgaatgcc tgttttaaaa tttccctttta tttgtcaatc ttgcaacgcg tggcggatgt    60

<210> SEQ ID NO 409
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 409
cgcgaatgcc cgagagtgtg gtgagccggt tacttgacag gtttcacgcg tggcggatgt    60

<210> SEQ ID NO 410
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 410
cgcgaatgcc tggcagctct tccagacgct gagtcttcgg gaattacgcg tggcggatgt    60

<210> SEQ ID NO 411
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 411
cgcgaatgcc ttcagtacct ggacagtctt caaaaccaaa cttacacgcg tggcggatgt    60

<210> SEQ ID NO 412
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 412
cgcgaatgcc aattttttggc tgctttgttt tatttaggtt ccagtacgcg tggcggatgt    60

<210> SEQ ID NO 413
<211> LENGTH: 60
<212> TYPE: DNA

<213> ORGANISM: Artificial Sequence
<220> FEATURE:
<223> OTHER INFORMATION: Synthetic oligonucleotide

<400> SEQUENCE: 413
cgcgaatgcc gattatacac atcaggcact ggaactatct gtaatacgcg tggcggatgt    60

<210> SEQ ID NO 414
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 414
cgcgaatgcc tcgtgtgtgt agctttggga aatttggaaa tcagaacgcg tggcggatgt    60

<210> SEQ ID NO 415
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 415
cgcgaatgcc acaaatcact ccttgggaat tacatacctg atctcacgcg tggcggatgt    60

<210> SEQ ID NO 416
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 416
cgcgaatgcc ggctctttcc tcctagagac ctcctgagaa taggcacgcg tggcggatgt    60

<210> SEQ ID NO 417
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 417
cgcgaatgcc ttcaggatct tcttctgatg gcctgccaag gtgatacgcg tggcggatgt    60

<210> SEQ ID NO 418
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 418
cgcgaatgcc cagcattcat tctatgaggg tccagataag tcagtacgcg tggcggatgt    60

<210> SEQ ID NO 419
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 419
cgcgaatgcc aagaaacaag agttctcatg ccattgccgt tggtgacgcg tggcggatgt    60

<210> SEQ ID NO 420
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 420
cgcgaatgcc tttgccattg tcttcaaaac tccaaagtat aaagaacgcg tggcggatgt    60

<210> SEQ ID NO 421
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 421
cgcgaatgcc ggacaaacac agaggctggt tttgtaatat taataacgcg tggcggatgt    60

<210> SEQ ID NO 422
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 422
cgcgaatgcc agcttcggag gaaatctgac ttggaaacta gtgaaacgcg tggcggatgt    60

<210> SEQ ID NO 423
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 423
cgcgaatgcc cctttgattt caggatagta gaggaaaggt tttggacgcg tggcggatgt    60

<210> SEQ ID NO 424
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 424
cgcgaatgcc ctcgcagacc tctgaagaga gtgccattga gacggacgcg tggcggatgt    60

<210> SEQ ID NO 425
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 425
cgcgaatgcc gtcctctctc ttgatgaagg tggaactgct ggaacacgcg tggcggatgt    60

<210> SEQ ID NO 426
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 426
cgcgaatgcc gagaccattg aagacatcga catgatggat gacatacgcg tggcggatgt    60

<210> SEQ ID NO 427
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 427
cgcgaatgcc agctgtcttc caccaggtct gaagagtcta tgccgacgcg tggcggatgt    60

<210> SEQ ID NO 428
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 428
cgcgaatgcc tcctgtaact ggcggattcg aggggttcct tccacacgcg tggcggatgt    60

<210> SEQ ID NO 429
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 429
cgcgaatgcc tgtatcggct agcctatctc cggctaaata cacttacgcg tggcggatgt    60

<210> SEQ ID NO 430
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 430
cgcgaatgcc tctaattctg ggtgctcaga cagaaggcgt tcacaacgcg tggcggatgt    60

<210> SEQ ID NO 431
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 431
cgcgaatgcc acatatcatc tggacccttt tccagcacac cctgcacgcg tggcggatgt    60

<210> SEQ ID NO 432
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 432
cgcgaatgcc caaatgcctg tctctcatga gttcatactc attctacgcg tggcggatgt    60

<210> SEQ ID NO 433
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 433
cgcgaatgcc gaccaagtaa gaaaatcaag cacttcacct tctctacgcg tggcggatgt    60

<210> SEQ ID NO 434
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 434
cgcgaatgcc gaaccatgga cactgaatct aaaaaggacc ctgaaacgcg tggcggatgt    60

<210> SEQ ID NO 435
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 435
cgcgaatgcc tttacagtgt ttttgtcatc acttttgtca caaccacgcg tggcggatgt    60

<210> SEQ ID NO 436
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 436
cgcgaatgcc cctctttggg aaagttattg aaaccacaga gcaagacgcg tggcggatgt    60

<210> SEQ ID NO 437
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 437
cgcgaatgcc accattccca acggtggcct cgctgggctc ctgatacgcg tggcggatgt    60

<210> SEQ ID NO 438
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 438
cgcgaatgcc gaggtcactc taacgtatgc aacaggaaca aagaacgcg tggcggatgt    60

<210> SEQ ID NO 439
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 439
cgcgaatgcc tgtgtgctca cttaccctga actccagcac tctctacgcg tggcggatgt    60

<210> SEQ ID NO 440
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 440
cgcgaatgcc ttaaaggaga aattagcatt cttgaaaagg gaataacgcg tggcggatgt    60

<210> SEQ ID NO 441
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 441
cgcgaatgcc attcacttac ctgaaggcgg gctagtgtct tgctgacgcg tggcggatgt    60

<210> SEQ ID NO 442
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 442
cgcgaatgcc cgtattctca aattaaggtg ttatagtaca aacaaacgcg tggcggatgt    60

<210> SEQ ID NO 443
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 443
cgcgaatgcc tttaaagttt tatagagtca agaactgttt ttaaaacgcg tggcggatgt    60

<210> SEQ ID NO 444
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 444
cgcgaatgcc gaaaacgtat ttctggggct gttttttgtct cctctacgcg tggcggatgt    60

<210> SEQ ID NO 445
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 445
cgcgaatgcc agaatgctta atcttttcag ctctttgggc acgctacgcg tggcggatgt    60

<210> SEQ ID NO 446
<211> LENGTH: 60

```
<212> TYPE: DNA
<213> ORGANISM: Artificial Sequence
<220> FEATURE:
<223> OTHER INFORMATION: Synthetic oligonucleotide

<400> SEQUENCE: 446
cgcgaatgcc attaagaaaa cagtagaaga acaagattgt ttgtcacgcg tggcggatgt    60

<210> SEQ ID NO 447
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 447
cgcgaatgcc ctgagtgttt tagctgcggt gagagatcct gctgaacgcg tggcggatgt    60

<210> SEQ ID NO 448
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 448
cgcgaatgcc gtaaatctag accattcact tatgcctgct ttattacgcg tggcggatgt    60

<210> SEQ ID NO 449
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 449
cgcgaatgcc cttttctgca gatatactcc atttgccaac ggtccacgcg tggcggatgt    60

<210> SEQ ID NO 450
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 450
cgcgaatgcc cgatccgggt taggatttcc tctggtgtgt cactgacgcg tggcggatgt    60

<210> SEQ ID NO 451
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 451
cgcgaatgcc gcagtgggaa gtttaccctc agtgggggaa attggacgcg tggcggatgt    60

<210> SEQ ID NO 452
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 452
```
cgcgaatgcc tacagactca ccttggctgt ctctgaaact gtgttacgcg tggcggatgt    60

<210> SEQ ID NO 453
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 453
cgcgaatgcc gccaggagcc tcccctctta ctgcccttct cccgtacgcg tggcggatgt    60

<210> SEQ ID NO 454
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 454
cgcgaatgcc aagtccattc ctggctattg atcacagcct ctgtaacgcg tggcggatgt    60

<210> SEQ ID NO 455
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 455
cgcgaatgcc tgagccgctc cattcctgaa ctgcgcctgg taggtacgcg tggcggatgt    60

<210> SEQ ID NO 456
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 456
cgcgaatgcc aggtcagcct tccctatagg caaggggact gggttacgcg tggcggatgt    60

<210> SEQ ID NO 457
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 457
cgcgaatgcc aaacacgatg cccagtttac tgtcattcag ctagtacgcg tggcggatgt    60

<210> SEQ ID NO 458
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 458
cgcgaatgcc acttcatgcc agatgctatc cctcgaagca tccccacgcg tggcggatgt    60

<210> SEQ ID NO 459
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 459
cgcgaatgcc acctgtcaga catgggctat gttcaccgag acctcacgcg tggcggatgt      60

<210> SEQ ID NO 460
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 460
cgcgaatgcc accaagttac tgttgatcaa gatgttccga gcagcacgcg tggcggatgt      60

<210> SEQ ID NO 461
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 461
cgcgaatgcc gtgtaaggtt tctgatttcg gactttcgcg tgtccacgcg tggcggatgt      60

<210> SEQ ID NO 462
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 462
cgcgaatgcc tcttgttgta taagcagctt ctgggtcatc ctccaacgcg tggcggatgt      60

<210> SEQ ID NO 463
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 463
cgcgaatgcc gtgagtaact tagattttct cctttttat cattgacgcg tggcggatgt      60

<210> SEQ ID NO 464
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 464
cgcgaatgcc ctttacagct ccatcacctg tcctgacgat taagaacgcg tggcggatgt      60

<210> SEQ ID NO 465
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 465
cgcgaatgcc ggacaaagag atgctatttc tggaggtccg atcttacgcg tggcggatgt      60
```

<210> SEQ ID NO 466
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 466
cgcgaatgcc tggcaagaac ctgaacatcc taatgggatc atattacgcg tggcggatgt        60

<210> SEQ ID NO 467
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 467
cgcgaatgcc tccccacctt ttcatagtat ttgacctcgt agtccacgcg tggcggatgt        60

<210> SEQ ID NO 468
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 468
cgcgaatgcc aaaggcaaag gcatcacaat gctggaagaa atcaaacgcg tggcggatgt        60

<210> SEQ ID NO 469
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 469
cgcgaatgcc ccgtcaaagt gtacaccaat ttgatggatg ggactacgcg tggcggatgt        60

<210> SEQ ID NO 470
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 470
cgcgaatgcc tccccgaggc cacggtgaaa gacagtggag attacacgcg tggcggatgt        60

<210> SEQ ID NO 471
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 471
cgcgaatgcc ttgacctccc tggtagcctg gcgggcagca cattcacgcg tggcggatgt        60

<210> SEQ ID NO 472
<211> LENGTH: 60
<212> TYPE: DNA
<213> ORGANISM: Artificial Sequence
<220> FEATURE:
<223> OTHER INFORMATION: Synthetic oligonucleotide

```
<400> SEQUENCE: 472
cgcgaatgcc agaaatgaag aaagtcacta tttctgtcca tggtaacgcg tggcggatgt    60

<210> SEQ ID NO 473
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 473
cgcgaatgcc cagcatggac aactgacatt ttagaaagcg gaatgacgcg tggcggatgt    60

<210> SEQ ID NO 474
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 474
cgcgaatgcc ctcgggatcc atatgtggta atcattattt aatggacgcg tggcggatgt    60

<210> SEQ ID NO 475
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 475
cgcgaatgcc ttcaatgaaa cctttctctg tacagggaag agtttacgcg tggcggatgt    60

<210> SEQ ID NO 476
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 476
cgcgaatgcc atcaaaccca ccttcagcca gttggaagct gtcaaacgcg tggcggatgt    60

<210> SEQ ID NO 477
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 477
cgcgaatgcc gcacctctac aacaaaatgt ttgacttcat gcaggacgcg tggcggatgt    60

<210> SEQ ID NO 478
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 478
cgcgaatgcc gggcctaccc acctcccagg atatcctggc tgaaaacgcg tggcggatgt    60

<210> SEQ ID NO 479
```

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 479
cgcgaatgcc atctcagtga gattttcaat cagagtcaga ttgttacgcg tggcggatgt    60

<210> SEQ ID NO 480
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 480
cgcgaatgcc caccactgat gtggaaaaga ttcaggaaat aaggtacgcg tggcggatgt    60

<210> SEQ ID NO 481
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 481
cgcgaatgcc gcccgctcct cctcatcgtg gagtacgcca aatacacgcg tggcggatgt    60

<210> SEQ ID NO 482
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 482
cgcgaatgcc ttgcggctct cgcggaggaa gccccgcagg gagccacgcg tggcggatgt    60

<210> SEQ ID NO 483
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 483
cgcgaatgcc agtggggcct ggctacctgg gcagtggagg cagccacgcg tggcggatgt    60

<210> SEQ ID NO 484
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 484
cgcgaatgcc ccgctcatcc gggtggtcca gggagctgga gttgcacgcg tggcggatgt    60

<210> SEQ ID NO 485
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 485
```

```
cgcgaatgcc gccctcacca tgggcgacct catctcattt gcctgacgcg tggcggatgt    60
```

<210> SEQ ID NO 486
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 486

```
cgcgaatgcc tctcggccag atactgcatc ccctgtgaga tctgcacgcg tggcggatgt    60
```

<210> SEQ ID NO 487
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 487

```
cgcgaatgcc tgaaggtgcg tgcatatggc tctgcaccca gccagacgcg tggcggatgt    60
```

<210> SEQ ID NO 488
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 488

```
cgcgaatgcc gtctgaatgc cattcatcta gccatgatga gcaatacgcg tggcggatgt    60
```

<210> SEQ ID NO 489
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 489

```
cgcgaatgcc ccagcggcca ccagcagcag caaacatggc aggctacgcg tggcggatgt    60
```

<210> SEQ ID NO 490
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 490

```
cgcgaatgcc ggctgacgtc aatgctcagg agcagaagtc cgggcacgcg tggcggatgt    60
```

<210> SEQ ID NO 491
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 491

```
cgcgaatgcc gttgtcgtgc tccacagcca ggtgcagtgc tgtgcacgcg tggcggatgt    60
```

<210> SEQ ID NO 492
<211> LENGTH: 60
<212> TYPE: DNA

<213> ORGANISM: Artificial Sequence
<220> FEATURE:
<223> OTHER INFORMATION: Synthetic oligonucleotide

<400> SEQUENCE: 492
cgcgaatgcc atctcattgg caggctgcct gctcctggag gtgaaacgcg tggcggatgt    60

<210> SEQ ID NO 493
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 493
cgcgaatgcc gtaattaaag ctgtagatga gggctatcga ctgccacgcg tggcggatgt    60

<210> SEQ ID NO 494
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 494
cgcgaatgcc gctgatacaa ggcagctggg cagtccatgg ggggtacgcg tggcggatgt    60

<210> SEQ ID NO 495
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 495
cgcgaatgcc tgatgctgga ctgctggcag aaagacagga acaacacgcg tggcggatgt    60

<210> SEQ ID NO 496
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 496
cgcgaatgcc tccagaatac taacaatctg ctcaaacttg ggtctacgcg tggcggatgt    60

<210> SEQ ID NO 497
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 497
cgcgaatgcc caagcttatc cggaatcccg gcagcctgaa gatcaacgcg tggcggatgt    60

<210> SEQ ID NO 498
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 498
cgcgaatgcc aaattgaatg tgtcaccttg cggctgcact ggtgaacgcg tggcggatgt    60

<210> SEQ ID NO 499
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 499
cgcgaatgcc aggaccggaa gctgctgctg acagcccagc agatgacgcg tggcggatgt    60

<210> SEQ ID NO 500
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 500
cgcgaatgcc cggatgatgt caatcttggt cttactgtcc tgcaaacgcg tggcggatgt    60

<210> SEQ ID NO 501
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 501
cgcgaatgcc catgcaactc cgccgggcgc tgcaggccgg ccagcacgcg tggcggatgt    60

<210> SEQ ID NO 502
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 502
cgcgaatgcc accttgggtg tcatccgggg ctgcctggtt ctccaacgcg tggcggatgt    60

<210> SEQ ID NO 503
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 503
cgcgaatgcc ttggaaattc atctattttt cttttgtttt ttgcaacgcg tggcggatgt    60

<210> SEQ ID NO 504
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 504
cgcgaatgcc tctccctgaa cagatctgga atccaataag gtaacacgcg tggcggatgt    60

<210> SEQ ID NO 505
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 505
cgcgaatgcc acttgggtgg atagcaagcc ctctggaagg aggggacgcg tggcggatgt     60

<210> SEQ ID NO 506
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 506
cgcgaatgcc tttacccttt ggatcagaga gcaactcagg acttaacgcg tggcggatgt     60

<210> SEQ ID NO 507
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 507
cgcgaatgcc gtttcaggag atgtgttaca aggcttatct agctaacgcg tggcggatgt     60

<210> SEQ ID NO 508
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 508
cgcgaatgcc gaaaagattt atgaagagat tggcatgctg tcgaaacgcg tggcggatgt     60

<210> SEQ ID NO 509
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 509
cgcgaatgcc tcaatgatgc ttggctctgg aatgccagaa ctacaacgcg tggcggatgt     60

<210> SEQ ID NO 510
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 510
cgcgaatgcc gggtctttcg aatgtatgca atgtcatcaa aagatacgcg tggcggatgt     60

<210> SEQ ID NO 511
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 511
cgcgaatgcc tagccttaga taaaactgag caagaggctt tggagacgcg tggcggatgt     60

```
<210> SEQ ID NO 512
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 512
cgcgaatgcc ccatgatgtg catcattcat ttgtttcatg aaataacgcg tggcggatgt      60

<210> SEQ ID NO 513
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 513
cgcgaatgcc tggctggaca acaaaaatgg attggatctt ccacaacgcg tggcggatgt      60

<210> SEQ ID NO 514
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 514
cgcgaatgcc gttatctttt cagttcaatg catgctgttt aattgacgcg tggcggatgt      60

<210> SEQ ID NO 515
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 515
cgcgaatgcc ggcaaaggca cagaggaaac cttctggctg attggacgcg tggcggatgt      60

<210> SEQ ID NO 516
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 516
cgcgaatgcc ggggcacagg aaggggcttc atgaagcctt ttttcacgcg tggcggatgt      60

<210> SEQ ID NO 517
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 517
cgcgaatgcc caccagtgga caaagatggg taagtggagt tcacaacgcg tggcggatgt      60

<210> SEQ ID NO 518
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 518
cgcgaatgcc gtggcagagt atggcatagg aagactccaa ttaaaacgcg tggcggatgt    60

<210> SEQ ID NO 519
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 519
cgcgaatgcc actttcttca ctacctattt gatgtctccc ctgccacgcg tggcggatgt    60

<210> SEQ ID NO 520
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 520
cgcgaatgcc ccactggttg caggccatgg cccacttgcc tgcagacgcg tggcggatgt    60

<210> SEQ ID NO 521
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 521
cgcgaatgcc agattgcagc cttccaaaga agaaaagcag aaaggacgcg tggcggatgt    60

<210> SEQ ID NO 522
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 522
cgcgaatgcc tggccattac cttatggctt gtttctcacc aactgacgcg tggcggatgt    60

<210> SEQ ID NO 523
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 523
cgcgaatgcc attttcagat tctacttcaa agactcctcc tcaagacgcg tggcggatgt    60

<210> SEQ ID NO 524
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 524
cgcgaatgcc aaatacagga gatgacactc gagtaggtaa ttcttacgcg tggcggatgt    60

<210> SEQ ID NO 525
<211> LENGTH: 60

<212> TYPE: DNA
<213> ORGANISM: Artificial Sequence
<220> FEATURE:
<223> OTHER INFORMATION: Synthetic oligonucleotide

<400> SEQUENCE: 525
cgcgaatgcc ggagctacct ctagtatcaa aagtggttta gatttacgcg tggcggatgt    60

<210> SEQ ID NO 526
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 526
cgcgaatgcc caggctgtaa aagagaaggg gacaaacttg tattcacgcg tggcggatgt    60

<210> SEQ ID NO 527
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 527
cgcgaatgcc ggaaaaaaaa acatctgaaa acactccctt ttagcacgcg tggcggatgt    60

<210> SEQ ID NO 528
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 528
cgcgaatgcc gatctagttt tttctaatct agatatacaa gtgttacgcg tggcggatgt    60

<210> SEQ ID NO 529
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 529
cgcgaatgcc aaaatctgaa gatagtgccc ttttcacaca tcacaacgcg tggcggatgt    60

<210> SEQ ID NO 530
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 530
cgcgaatgcc ctggataatg atcttgttca cttcagaccc aagacacgcg tggcggatgt    60

<210> SEQ ID NO 531
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 531
cgcgaatgcc tcatctaata aacagatact tataaataaa aatatacgcg tggcggatgt    60

<210> SEQ ID NO 532
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 532
cgcgaatgcc actcagtcct attctgttca cctagggatt cacttacgcg tggcggatgt    60

<210> SEQ ID NO 533
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 533
cgcgaatgcc acggtaaaga ttctaacact gataaacatt tggagacgcg tggcggatgt    60

<210> SEQ ID NO 534
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 534
cgcgaatgcc cttttggatg ttcggcctcc caatgatttc aggggacgcg tggcggatgt    60

<210> SEQ ID NO 535
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 535
cgcgaatgcc gaagaaaact gaggaagaaa gtgaacatga agtaaacgcg tggcggatgt    60

<210> SEQ ID NO 536
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 536
cgcgaatgcc agcattttct ttatcaaaag aagcttgggg gcagcacgcg tggcggatgt    60

<210> SEQ ID NO 537
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 537
cgcgaatgcc ttccctttc caatggataa tcagttttcc atgaaacgcg tggcggatgt    60

<210> SEQ ID NO 538
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 538
cgcgaatgcc acagatccag aggtttatcc atcacacagt ctccaacgcg tggcggatgt      60

<210> SEQ ID NO 539
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 539
cgcgaatgcc ctgatcgatt ttcagctatt cagcgtcaag agaaaacgcg tggcggatgt      60

<210> SEQ ID NO 540
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 540
cgcgaatgcc ctaaatttgt ttttagaagt ctcacttcct tggctacgcg tggcggatgt      60

<210> SEQ ID NO 541
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 541
cgcgaatgcc gcaagtgact ctttatgagg ctttgaagac cattcacgcg tggcggatgt      60

<210> SEQ ID NO 542
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 542
cgcgaatgcc atctgaggcc ttacggcttg aggaaaagcc ctttgacgcg tggcggatgt      60

<210> SEQ ID NO 543
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 543
cgcgaatgcc ggcaactgca cgttgcccaa agattcccca ggggaacgcg tggcggatgt      60

<210> SEQ ID NO 544
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 544
cgcgaatgcc agggctgaag gatgatgcat tcctgtgaac agggcacgcg tggcggatgt      60
```

```
<210> SEQ ID NO 545
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 545
cgcgaatgcc tgaataaatg ctctccagac aataaaccat cattaacgcg tggcggatgt    60

<210> SEQ ID NO 546
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 546
cgcgaatgcc ggaattttaa agacagcatt ttcttctttt atttgacgcg tggcggatgt    60

<210> SEQ ID NO 547
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 547
cgcgaatgcc tctacgtcca cgtgaaagtt tggagactga gaatgacgcg tggcggatgt    60

<210> SEQ ID NO 548
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 548
cgcgaatgcc tgaacattta acacaaacct ttatgtcatc taaaaacgcg tggcggatgt    60

<210> SEQ ID NO 549
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 549
cgcgaatgcc aggattttga ttaaaatgat tgcttgtgat ttcatacgcg tggcggatgt    60

<210> SEQ ID NO 550
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 550
cgcgaatgcc cagcactcta aaacagaaat aattgttagc tctaaacgcg tggcggatgt    60

<210> SEQ ID NO 551
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 551
cgcgaatgcc gttctcatga gccaataaaa atacaaacca ggtcaacgcg tggcggatgt    60

<210> SEQ ID NO 552
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 552
cgcgaatgcc tgaagaactg atgcaagttc acatcctcca tggtcacgcg tggcggatgt    60

<210> SEQ ID NO 553
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 553
cgcgaatgcc gttaaatcca tgtagaactg gtaaaataaa gtctcacgcg tggcggatgt    60

<210> SEQ ID NO 554
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 554
cgcgaatgcc cctgtttatg gtgtacacac cttggttgtt ttgtaacgcg tggcggatgt    60

<210> SEQ ID NO 555
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 555
cgcgaatgcc gcgtcccatc aggtccccgc aatgttatct ccatcacgcg tggcggatgt    60

<210> SEQ ID NO 556
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 556
cgcgaatgcc gggtgccact ccagaatgat ggacgtctca ttgacacgcg tggcggatgt    60

<210> SEQ ID NO 557
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 557
cgcgaatgcc tccaagggag acaggtgggc gggatgatgt gacctacgcg tggcggatgt    60

<210> SEQ ID NO 558

<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 558
cgcgaatgcc gcggtctgcc cggcactttt tgcagatgat gttgtacgcg tggcggatgt    60

<210> SEQ ID NO 559
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 559
cgcgaatgcc cggagctgct cccgctgtga cgacaatgtg gagttacgcg tggcggatgt    60

<210> SEQ ID NO 560
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 560
cgcgaatgcc cgcggcactc cgtcaggccc agctgcctgg gcacaacgcg tggcggatgt    60

<210> SEQ ID NO 561
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 561
cgcgaatgcc tctccatcag cagcctgtgg gcccacaccc cctacacgcg tggcggatgt    60

<210> SEQ ID NO 562
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 562
cgcgaatgcc ctggagactc cattgatggc ctggatgtca aggtacgcg tggcggatgt    60

<210> SEQ ID NO 563
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 563
cgcgaatgcc caagagtccc ttcccccac agcacgtctc tgtcaacgcg tggcggatgt    60

<210> SEQ ID NO 564
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 564
cgcgaatgcc gcctccagac ttaccggctt ggtttgtggt gatgtacgcg tggcggatgt    60

<210> SEQ ID NO 565
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 565
cgcgaatgcc actttggcct gagcaaagag gccattgacc acgagacgcg tggcggatgt    60

<210> SEQ ID NO 566
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 566
cgcgaatgcc tactccactg tcccgcagaa agaataggcc ttcttacgcg tggcggatgt    60

<210> SEQ ID NO 567
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 567
cgcgaatgcc catggcccct gaggtcgtca accgccaggg ccactacgcg tggcggatgt    60

<210> SEQ ID NO 568
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 568
cgcgaatgcc caacacccca taggaccacc agtccgcact atgggacgcg tggcggatgt    60

<210> SEQ ID NO 569
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 569
cgcgaatgcc atggtgagtg cccagacagg ggtaaaggat ccagcacgcg tggcggatgt    60

<210> SEQ ID NO 570
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 570
cgcgaatgcc ggatggagca ggatcccaag ccgccccgtc tgcggacgcg tggcggatgt    60

<210> SEQ ID NO 571
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 571
cgcgaatgcc tgcttcctgg gaagccaggg gatcagggcc cagagacgcg tggcggatgt     60

<210> SEQ ID NO 572
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 572
cgcgaatgcc gcggcccagg atcagccaga cctctctgcc tgtccacgcg tggcggatgt     60

<210> SEQ ID NO 573
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 573
cgcgaatgcc caccgagtcc cgctgggggc cagagccagg gccagacgcg tggcggatgt     60

<210> SEQ ID NO 574
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 574
cgcgaatgcc ttcttcctct tcctctcact ctctgcaggc atcgaacgcg tggcggatgt     60

<210> SEQ ID NO 575
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 575
cgcgaatgcc gcaaagtaag gcagaccatc atggcaaagg cagggacgcg tggcggatgt     60

<210> SEQ ID NO 576
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 576
cgcgaatgcc ttatagccct gctgtctatt aatggatttg cttacacgcg tggcggatgt     60

<210> SEQ ID NO 577
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 577
cgcgaatgcc tatatacaaa aataacaaaa aatgtacctt ataaaacgcg tggcggatgt     60
```

<210> SEQ ID NO 578
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 578
cgcgaatgcc gttttgtttc ataggttaag agcaggctta tgtgaacgcg tggcggatgt    60

<210> SEQ ID NO 579
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 579
cgcgaatgcc ttttccgcat atgttcttca gttactgcac agcgaacgcg tggcggatgt    60

<210> SEQ ID NO 580
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 580
cgcgaatgcc aacagcaaga gtttgaaaat atccggcagc agaatacgcg tggcggatgt    60

<210> SEQ ID NO 581
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 581
cgcgaatgcc aaaggaaact cactaagttc tgtaataagt ttaagacgcg tggcggatgt    60

<210> SEQ ID NO 582
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 582
cgcgaatgcc aacagcacaa tctggtatga actccacgcc agggaacgcg tggcggatgt    60

<210> SEQ ID NO 583
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 583
cgcgaatgcc ttattgcctc tgctggttgg gtcttgaaag gccatacgcg tggcggatgt    60

<210> SEQ ID NO 584
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 584
cgcgaatgcc tctggcaaat gggcacaggc atgaaaccca acctcacgcg tggcggatgt    60

<210> SEQ ID NO 585
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 585
cgcgaatgcc cttaccgaga tttcttttcc catgccaatc tggctacgcg tggcggatgt    60

<210> SEQ ID NO 586
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 586
cgcgaatgcc gccaataagc cctcttctgg atcaaaacac tcctgacgcg tggcggatgt    60

<210> SEQ ID NO 587
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 587
cgcgaatgcc tagccattct ccaactgaac aaaaggtagt gaaatacgcg tggcggatgt    60

<210> SEQ ID NO 588
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 588
cgcgaatgcc caagctatta agatggaaag atataaagat aatttacgcg tggcggatgt    60

<210> SEQ ID NO 589
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 589
cgcgaatgcc ctactgattc aagggaattg tagccagctg ccgtgacgcg tggcggatgt    60

<210> SEQ ID NO 590
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 590
cgcgaatgcc ccaggatgac tattgagtaa gcttaaactc ttaaaacgcg tggcggatgt    60

<210> SEQ ID NO 591
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 591
cgcgaatgcc caaaattgta tatggttttt tattactaat tggtaacgcg tggcggatgt    60

<210> SEQ ID NO 592
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 592
cgcgaatgcc aattgatact aagattctgt caagttaaga tgaaacgcg tggcggatgt    60

<210> SEQ ID NO 593
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 593
cgcgaatgcc ggtgaatcat tcggggtgag tattttcttt ctatgacgcg tggcggatgt    60

<210> SEQ ID NO 594
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 594
cgcgaatgcc tttcttttat acttacaatg catactatta tatttacgcg tggcggatgt    60

<210> SEQ ID NO 595
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 595
cgcgaatgcc attgtcattc ccagtgcctt cccggatcat tggagacgcg tggcggatgt    60

<210> SEQ ID NO 596
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 596
cgcgaatgcc gacagagacc agaaggactg tggagttagc cccatacgcg tggcggatgt    60

<210> SEQ ID NO 597
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 597
cgcgaatgcc tcgggcagtg tggtgctggt ggtaattctc attgcacgcg tggcggatgt    60

<210> SEQ ID NO 598
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 598
cgcgaatgcc gcttcagtgc ttacctccgg ctgatgacaa aagctacgcg tggcggatgt    60

<210> SEQ ID NO 599
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 599
cgcgaatgcc caaaatgacg ggcagttcac cgtgatccag cttgtacgcg tggcggatgt    60

<210> SEQ ID NO 600
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 600
cgcgaatgcc acttcatgcc agcagcgatg ccctgagca tacccacgcg tggcggatgt    60

<210> SEQ ID NO 601
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 601
cgcgaatgcc acctggctga gatgaattat gtgcatcggg acctgacgcg tggcggatgt    60

<210> SEQ ID NO 602
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 602
cgcgaatgcc accaggttac tgttgaccag aatgttccta gcagcacgcg tggcggatgt    60

<210> SEQ ID NO 603
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 603
cgcgaatgcc gtgcaaggtg tccgactttg gcctctcccg ctaccacgcg tggcggatgt    60

<210> SEQ ID NO 604
<211> LENGTH: 60

<212> TYPE: DNA
<213> ORGANISM: Artificial Sequence
<220> FEATURE:
<223> OTHER INFORMATION: Synthetic oligonucleotide

<400> SEQUENCE: 604
cgcgaatgcc gctggtgtag gtgggatctg aggtgtcatc ctggaacgcg tggcggatgt    60

<210> SEQ ID NO 605
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 605
cgcgaatgcc tccttggtga gtccttcttg gcattctcaa gtagaacgcg tggcggatgt    60

<210> SEQ ID NO 606
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 606
cgcgaatgcc atttataaat acacatgaaa tgttttgcat tttttacgcg tggcggatgt    60

<210> SEQ ID NO 607
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 607
cgcgaatgcc tttggactct cctgggagat gtttactgca gattaacgcg tggcggatgt    60

<210> SEQ ID NO 608
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 608
cgcgaatgcc tttcagcaga aactggcaga aatgagtaag tacttacgcg tggcggatgt    60

<210> SEQ ID NO 609
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 609
cgcgaatgcc aaacaattgt ttatttcatt tacacaaggt gaaaaacgcg tggcggatgt    60

<210> SEQ ID NO 610
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 610
cgcgaatgcc gagtgtgccg accctgagaa ccataaggtc cgccaacgcg tggcggatgt    60

<210> SEQ ID NO 611
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 611
cgcgaatgcc ccaggaactc gtcccactcc ttggccttca gtttcacgcg tggcggatgt    60

<210> SEQ ID NO 612
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 612
cgcgaatgcc ctaaggggaa gcgctttcgc gtcctgcaac ctgtgacgcg tggcggatgt    60

<210> SEQ ID NO 613
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 613
cgcgaatgcc cagtctctgt cagccgccca cacgcagccg atcttacgcg tggcggatgt    60

<210> SEQ ID NO 614
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 614
cgcgaatgcc cgcaggcgat gacctgaagg tactgcagca gttcgacgcg tggcggatgt    60

<210> SEQ ID NO 615
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 615
cgcgaatgcc ctcctgggcc ggcagggtct ccaggaagca ggctgacgcg tggcggatgt    60

<210> SEQ ID NO 616
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 616
cgcgaatgcc gagcagacgc ccaaggcctc caagcgggag aggagacgcg tggcggatgt    60

<210> SEQ ID NO 617
<211> LENGTH: 60
<212> TYPE: DNA
<213> ORGANISM: Artificial Sequence -continued
<220> FEATURE:
<223> OTHER INFORMATION: Synthetic oligonucleotide

<400> SEQUENCE: 617
cgcgaatgcc tggcctggcc ccgcccacac tcactctgct cgtctacgcg tggcggatgt    60

<210> SEQ ID NO 618
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 618
cgcgaatgcc caaacagtaa aacttccagg tctcaggact tatgtacgcg tggcggatgt    60

<210> SEQ ID NO 619
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 619
cgcgaatgcc cagcttgggt agggtcttca tatgtatgtg ggtcaacgcg tggcggatgt    60

<210> SEQ ID NO 620
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 620
cgcgaatgcc ttcatgagtt tgccaaggaa ttggatgcca ccaacacgcg tggcggatgt    60

<210> SEQ ID NO 621
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 621
cgcgaatgcc tggttacctg ctccaacaac tttatcaatg gatatacgcg tggcggatgt    60

<210> SEQ ID NO 622
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 622
cgcgaatgcc cttgtcgacc aggtttctac aaggcattgg atggtacgcg tggcggatgt    60

<210> SEQ ID NO 623
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 623
cgcgaatgcc gaactgtgag gcgggcactt agcacacttc atattacgcg tggcggatgt    60

<210> SEQ ID NO 624
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 624
cgcgaatgcc tactcaggaa gatggttcaa tgaactgcag gtgtgacgcg tggcggatgt    60

<210> SEQ ID NO 625
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 625
cgcgaatgcc tggagggtct ttgtctgccc ggaagtaatt attctacgcg tggcggatgt    60

<210> SEQ ID NO 626
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 626
cgcgaatgcc tccatggctt gtacccgtga gtagttttgc tgcaaacgcg tggcggatgt    60

<210> SEQ ID NO 627
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 627
cgcgaatgcc cttttttctt tcaaggttga aaatctttct aaacgacgcg tggcggatgt    60

<210> SEQ ID NO 628
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 628
cgcgaatgcc ctagatcttt attttaaga taaatttctt cgtatacgcg tggcggatgt    60

<210> SEQ ID NO 629
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 629
cgcgaatgcc atgcaagatt atttttggat catgataaaa ctcttacgcg tggcggatgt    60

<210> SEQ ID NO 630
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 630
cgcgaatgcc taccatgtgc aatacctgtc tatagaatca gtctgacgcg tggcggatgt    60

<210> SEQ ID NO 631
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 631
cgcgaatgcc cttttttttt aatcaggtac agatgaagtt tttagacgcg tggcggatgt    60

<210> SEQ ID NO 632
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 632
cgcgaatgcc agcatccatg aaatctggtc gcctcatttg ctcaaacgcg tggcggatgt    60

<210> SEQ ID NO 633
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 633
cgcgaatgcc ctacagggct ttctgtctcc tctaaaccct gctcaacgcg tggcggatgt    60

<210> SEQ ID NO 634
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 634
cgcgaatgcc aaccccccaag aaagtacctg aggtttccta gttgaacgcg tggcggatgt    60

<210> SEQ ID NO 635
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 635
cgcgaatgcc cctctttctc acctagatga ttacaagtca gagctacgcg tggcggatgt    60

<210> SEQ ID NO 636
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 636
cgcgaatgcc ctgccgagcc agcaatcagg ggcagctgct ccctcacgcg tggcggatgt    60

<210> SEQ ID NO 637

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 637
cgcgaatgcc cggccggggt cgtgttcgtt gtgtccttgg tggccacgcg tggcggatgt    60

<210> SEQ ID NO 638
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 638
cgcgaatgcc gagtggagga cctacctgct acagacgata gagatacgcg tggcggatgt    60

<210> SEQ ID NO 639
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 639
cgcgaatgcc tgggaagaaa ttagtggttt ggatgagaac tatacacgcg tggcggatgt    60

<210> SEQ ID NO 640
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 640
cgcgaatgcc ccatgacttg gcacacctgg tatgttcgta tcgggacgcg tggcggatgt    60

<210> SEQ ID NO 641
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 641
cgcgaatgcc agcccaacca aaacaactgg ctgcggacta actggacgcg tggcggatgt    60

<210> SEQ ID NO 642
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 642
cgcgaatgcc tctacaaaaa tcctttgtgc attgcctttg gaaatacgcg tggcggatgt    60

<210> SEQ ID NO 643
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 643
```

```
cgcgaatgcc attgaaattc accctgaggg attgtaacag tcttcacgcg tggcggatgt    60
```

<210> SEQ ID NO 644
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 644

```
cgcgaatgcc attaaatgtt tccttgcaag ttcccagtac tccagacgcg tggcggatgt    60
```

<210> SEQ ID NO 645
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 645

```
cgcgaatgcc ttgtactatt atgaaacaga ctatgacact ggcagacgcg tggcggatgt    60
```

<210> SEQ ID NO 646
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 646

```
cgcgaatgcc tgtctatttt tacatagagg ttttctctta tattcacgcg tggcggatgt    60
```

<210> SEQ ID NO 647
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 647

```
cgcgaatgcc ccattgctgc agatgaaagt tttacccaag gtgacacgcg tggcggatgt    60
```

<210> SEQ ID NO 648
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 648

```
cgcgaatgcc acctcagtgt taagcttcat ctttctttca ccaagacgcg tggcggatgt    60
```

<210> SEQ ID NO 649
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 649

```
cgcgaatgcc gagagagatt ggacctttgt ccaaaaaggg attctacgcg tggcggatgt    60
```

<210> SEQ ID NO 650
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 650
cgcgaatgcc agctatgcaa gcccctacat cctgaaaggc aagatacgcg tggcggatgt    60

<210> SEQ ID NO 651
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 651
cgcgaatgcc ttggtttctg tcaaagtgta ctacaagaag tgctgacgcg tggcggatgt    60

<210> SEQ ID NO 652
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 652
cgcgaatgcc tatctggaaa gatagctaag ttctcaataa tggacacgcg tggcggatgt    60

<210> SEQ ID NO 653
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 653
cgcgaatgcc cagtgactgg ttcagaattt tcctctttag tcagacgcg tggcggatgt    60

<210> SEQ ID NO 654
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 654
cgcgaatgcc tcttcctctg cactgctgac acatgtccct cgaacacgcg tggcggatgt    60

<210> SEQ ID NO 655
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 655
cgcgaatgcc agcggaaaac gcccccagga tgcactgcag tgcagacgcg tggcggatgt    60

<210> SEQ ID NO 656
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 656
cgcgaatgcc gatacatttt ccaatgggca ctaaccattc tccttacgcg tggcggatgt    60
```

<210> SEQ ID NO 657
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 657
cgcgaatgcc tgcaaagcag gctaccagca aaaggagac acttgacgcg tggcggatgt      60

<210> SEQ ID NO 658
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 658
cgcgaatgcc agtggagttt aataggaca cattacttac gttcaacgcg tggcggatgt      60

<210> SEQ ID NO 659
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 659
cgcgaatgcc gtgtagacta atgatgtgac ttttgttttc acagaacgcg tggcggatgt      60

<210> SEQ ID NO 660
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 660
cgcgaatgcc tatgctatca gaagcaggaa gctctgctgt ttcagacgcg tggcggatgt      60

<210> SEQ ID NO 661
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 661
cgcgaatgcc aacccaggca acctacaatt ggtttcagag ttaaaacgcg tggcggatgt      60

<210> SEQ ID NO 662
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 662
cgcgaatgcc gacacgagac actggaagag aatattcttc tgaccacgcg tggcggatgt      60

<210> SEQ ID NO 663
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 663
cgcgaatgcc accgcggctt tcccctgctc accgtctacc tcaagacgcg tggcggatgt    60

<210> SEQ ID NO 664
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 664
cgcgaatgcc tcgccctcac gaagggatgt gggtgacagg aagacacgcg tggcggatgt    60

<210> SEQ ID NO 665
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 665
cgcgaatgcc gtgccagtgg ccaggctgtg cccgcgtata cttctacgcg tggcggatgt    60

<210> SEQ ID NO 666
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 666
cgcgaatgcc ggagctgcag gctggaaagg aggtgttgaa gaaggacgcg tggcggatgt    60

<210> SEQ ID NO 667
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 667
cgcgaatgcc ctcaagcccc gggagctctg cttcccagag acaagacgcg tggcggatgt    60

<210> SEQ ID NO 668
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 668
cgcgaatgcc ctggggtcg gttctcccga atgcggaagg agggcacgcg tggcggatgt    60

<210> SEQ ID NO 669
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 669
cgcgaatgcc gcaccttcca ccagttccgc ctgctgcctg tgcagacgcg tggcggatgt    60

<210> SEQ ID NO 670
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 670
cgcgaatgcc agcctgtagg ccacgctgat gttggggcac aagaaacgcg tggcggatgt    60

<210> SEQ ID NO 671
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 671
cgcgaatgcc cctggagggt gagtgccgac cttgtggggc cgcccacgcg tggcggatgt    60

<210> SEQ ID NO 672
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 672
cgcgaatgcc ggcccatggg ccagatgcaa tgatccttgt ggatgacgcg tggcggatgt    60

<210> SEQ ID NO 673
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 673
cgcgaatgcc gagccccagc tcacccttgg cctggcgtgg ctgtcacgcg tggcggatgt    60

<210> SEQ ID NO 674
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 674
cgcgaatgcc tcccaaatgc tccacattgc cagtcagatc gcctcacgcg tggcggatgt    60

<210> SEQ ID NO 675
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 675
cgcgaatgcc gcacaaagtg ctgggaggcc aggtacacca tacccacgcg tggcggatgt    60

<210> SEQ ID NO 676
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 676
cgcgaatgcc accgagacct ggccaccagg aactgcctgg ttggaacgcg tggcggatgt    60

<210> SEQ ID NO 677
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 677
cgcgaatgcc atgccgaagt ccccaatctt cactagcaga ttcgcacgcg tggcggatgt    60

<210> SEQ ID NO 678
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 678
cgcgaatgcc gtccagagat gtctacagca cggattatta cagggacgcg tggcggatgt    60

<210> SEQ ID NO 679
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 679
cgcgaatgcc ggaagaaaag tcgtcatcaa aaagaggatt cccttacgcg tggcggatgt    60

<210> SEQ ID NO 680
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 680
cgcgaatgcc tcatccaagg ataaataagc actattactc caagaacgcg tggcggatgt    60

<210> SEQ ID NO 681
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 681
cgcgaatgcc tgatgctttc acggctccat ttcataggga tggaacgcg tggcggatgt    60

<210> SEQ ID NO 682
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 682
cgcgaatgcc actgagaaaa gacagtagtt gctttaaact cagcaacgcg tggcggatgt    60

<210> SEQ ID NO 683
<211> LENGTH: 60

```
<212> TYPE: DNA
<213> ORGANISM: Artificial Sequence
<220> FEATURE:
<223> OTHER INFORMATION: Synthetic oligonucleotide

<400> SEQUENCE: 683
cgcgaatgcc atcacagact ttcagttacc tgatgaagac tttggacgcg tggcggatgt    60

<210> SEQ ID NO 684
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 684
cgcgaatgcc ctgagcagga cttcactttt tcaagcttaa gaggtacgcg tggcggatgt    60

<210> SEQ ID NO 685
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 685
cgcgaatgcc aaaaaccagt ggagcccttt gagtcaaaaa tgtttacgcg tggcggatgt    60

<210> SEQ ID NO 686
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 686
cgcgaatgcc aaaatacagc ttccctcttt aagatgtctc tctccacgcg tggcggatgt    60

<210> SEQ ID NO 687
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 687
cgcgaatgcc tccagaggaa ctgagtccta aacgcatgga tacagacgcg tggcggatgt    60

<210> SEQ ID NO 688
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 688
cgcgaatgcc tagaacaata aggtcctctt ctaagtcctc catttacgcg tggcggatgt    60

<210> SEQ ID NO 689
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 689
```
cgcgaatgcc ccaggaaaat cacatcccaa aaggccaaac tcgcaacgcg tggcggatgt    60

<210> SEQ ID NO 690
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 690
cgcgaatgcc tggatgaaga aaggcccgtc tttgtatgct ggcttacgcg tggcggatgt    60

<210> SEQ ID NO 691
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 691
cgcgaatgcc tattacttta tactccttta aatacggttg cgcctacgcg tggcggatgt    60

<210> SEQ ID NO 692
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 692
cgcgaatgcc gaacacatgt ctgtggtagg cctgtcatta tcatcacgcg tggcggatgt    60

<210> SEQ ID NO 693
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 693
cgcgaatgcc acctgctttc cccatcttag gtactactcc agcctacgcg tggcggatgt    60

<210> SEQ ID NO 694
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 694
cgcgaatgcc tgtagatgct ttttcatagg agccttgagg gccaaacgcg tggcggatgt    60

<210> SEQ ID NO 695
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 695
cgcgaatgcc gaagttgctg gacgaacttg ctgcacaccc caactacgcg tggcggatgt    60

<210> SEQ ID NO 696
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 696
cgcgaatgcc cactggcaag acagactgag tctttcaaat gagcaacgcg tggcggatgt    60

<210> SEQ ID NO 697
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 697
cgcgaatgcc atactaaaca attcgacagt tcaggcagcc cagcaacgcg tggcggatgt    60

<210> SEQ ID NO 698
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 698
cgcgaatgcc tgcctgcctg acacttgcag ggtggtatgt ggtttacgcg tggcggatgt    60

<210> SEQ ID NO 699
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 699
cgcgaatgcc aggacaacct acctgtgact gtgactctgt cccgcacgcg tggcggatgt    60

<210> SEQ ID NO 700
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 700
cgcgaatgcc aaaagtgaat gactcaatgg gtggaggtgt tcctgacgcg tggcggatgt    60

<210> SEQ ID NO 701
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 701
cgcgaatgcc aaagaaaatc agctctgtag aaacacatgc caggaacgcg tggcggatgt    60

<210> SEQ ID NO 702
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 702
cgcgaatgcc tggattgtac ctgttcgacg gaatgtttat gcagcacgcg tggcggatgt    60
```

<210> SEQ ID NO 703
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 703
cgcgaatgcc gtcaccttcc gcaaccctgt cattgagagg attccacgcg tggcggatgt    60

<210> SEQ ID NO 704
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 704
cgcgaatgcc gcttggagaa aattttcttc tgccgtcgga gccgaacgcg tggcggatgt    60

<210> SEQ ID NO 705
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 705
cgcgaatgcc agcaaggtga gagggtgctc caggcttcct gggggacgcg tggcggatgt    60

<210> SEQ ID NO 706
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 706
cgcgaatgcc caccctccat gacactccca ggacccctgg cctctacgcg tggcggatgt    60

<210> SEQ ID NO 707
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 707
cgcgaatgcc acgcctgccc cgtcccccca gggaaggcgt tccagacgcg tggcggatgt    60

<210> SEQ ID NO 708
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 708
cgcgaatgcc cacgtggcga catcgatgtt catctgccta gcacgacgcg tggcggatgt    60

<210> SEQ ID NO 709
<211> LENGTH: 60
<212> TYPE: DNA
<213> ORGANISM: Artificial Sequence
<220> FEATURE:
<223> OTHER INFORMATION: Synthetic oligonucleotide -continued

<400> SEQUENCE: 709
cgcgaatgcc ggtgcggctg ctccggaggc tcatccccaa tgccaacgcg tggcggatgt    60

<210> SEQ ID NO 710
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 710
cgcgaatgcc tggagaagcc ccagggctaa aggtgcctgt gcccgacgcg tggcggatgt    60

<210> SEQ ID NO 711
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 711
cgcgaatgcc ggatccgagg cccggaccac ggggtaagga aggagacgcg tggcggatgt    60

<210> SEQ ID NO 712
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 712
cgcgaatgcc cgcaggcttc aaggggcagc cgggaccatg gggccacgcg tggcggatgt    60

<210> SEQ ID NO 713
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 713
cgcgaatgcc agggtcctgg gtcccagaca caccctcctc tcgtcacgcg tggcggatgt    60

<210> SEQ ID NO 714
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 714
cgcgaatgcc aggttcagct tctccaccga tatgtcactg cagcaacgcg tggcggatgt    60

<210> SEQ ID NO 715
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 715
cgcgaatgcc cggcactgac tcggacagct cacctcagaa gagctacgcg tggcggatgt    60

<210> SEQ ID NO 716

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 716
cgcgaatgcc caccaggctc gatgggctgg aaggaggatc ccgcgacgcg tggcggatgt    60

<210> SEQ ID NO 717
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 717
cgcgaatgcc gtcccgtggc tgtcatcagt ggtgaggagg actcaacgcg tggcggatgt    60

<210> SEQ ID NO 718
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 718
cgcgaatgcc gtgatgccgt ggttgatgtg gtgcagtggg ctggcacgcg tggcggatgt    60

<210> SEQ ID NO 719
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 719
cgcgaatgcc cacgccctcg tcactggatg ccgggcccga cactgacgcg tggcggatgt    60

<210> SEQ ID NO 720
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 720
cgcgaatgcc ctcaatgaca gggatgcgag tcatgccaat gaccaacgcg tggcggatgt    60

<210> SEQ ID NO 721
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 721
cgcgaatgcc aaccccagt acttccgtca gggacacaac tgccaacgcg tggcggatgt    60

<210> SEQ ID NO 722
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 722
```
cgcgaatgcc gcattccatc ccagtactta cacgtgtccg gcttgacgcg tggcggatgt    60

<210> SEQ ID NO 723
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 723
cgcgaatgcc acagattccc caggcatccc ccccagcgct ggggcacgcg tggcggatgt    60

<210> SEQ ID NO 724
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 724
cgcgaatgcc tggccacgaa gctgaagccc cggaacagct gatggacgcg tggcggatgt    60

<210> SEQ ID NO 725
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 725
cgcgaatgcc ccggcctgat ggaagacgac ggcaagcctc gtgccacgcg tggcggatgt    60

<210> SEQ ID NO 726
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 726
cgcgaatgcc ctcacctgta ccaccgagtg caggggtgcc tgcggacgcg tggcggatgt    60

<210> SEQ ID NO 727
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 727
cgcgaatgcc atgttcctgg gactcgggcg cttttctcgc cttgtacgcg tggcggatgt    60

<210> SEQ ID NO 728
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 728
cgcgaatgcc gtcccagcag tttcctgaaa gccgcaaacc agagaacgcg tggcggatgt    60

<210> SEQ ID NO 729
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 729
cgcgaatgcc accatggcct tgcatctgcc aagttcctgt ggtgcacgcg tggcggatgt    60

<210> SEQ ID NO 730
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 730
cgcgaatgcc tgctgcggaa gggacatgac agacagaagg cacaaacgcg tggcggatgt    60

<210> SEQ ID NO 731
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 731
cgcgaatgcc ggtgtggaca ctcccctaca agatagggt ggtggacgcg tggcggatgt    60

<210> SEQ ID NO 732
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 732
cgcgaatgcc ggcctttgaa aacagcgaat cacaagccca agggcacgcg tggcggatgt    60

<210> SEQ ID NO 733
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 733
cgcgaatgcc ctgcctgagg ttgctgcgcg attagccatt gagcgacgcg tggcggatgt    60

<210> SEQ ID NO 734
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 734
cgcgaatgcc aataactcag gtcaaaagat gggtcccggt tgattacgcg tggcggatgt    60

<210> SEQ ID NO 735
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 735
cgcgaatgcc cttttgaata cgtgattctc aatgaagact gccagacgcg tggcggatgt    60
```

<210> SEQ ID NO 736
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 736
cgcgaatgcc tggtgggaaa tgaaactgga gagagccctc gaagtacgcg tggcggatgt    60

<210> SEQ ID NO 737
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 737
cgcgaatgcc ccagatggcc tcaggattta ttggacctac caaccacgcg tggcggatgt    60

<210> SEQ ID NO 738
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 738
cgcgaatgcc gtttcccagg agcgaggctg cctcgcagta gccagacgcg tggcggatgt    60

<210> SEQ ID NO 739
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 739
cgcgaatgcc agctgggaca aaggaatttt ctcttgggct tgtgtacgcg tggcggatgt    60

<210> SEQ ID NO 740
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 740
cgcgaatgcc tcgggtagct aattttattg tctaattcat aattcacgcg tggcggatgt    60

<210> SEQ ID NO 741
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 741
cgcgaatgcc cctttctcg gacactccct tctcccatcc gggtgacgcg tggcggatgt    60

<210> SEQ ID NO 742
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 742
cgcgaatgcc tgagcccact ggaaatattt catgacagtt acaagacgcg tggcggatgt     60

<210> SEQ ID NO 743
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 743
cgcgaatgcc tgctggagtc atttcctcag atgaagacat ttgggacgcg tggcggatgt     60

<210> SEQ ID NO 744
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 744
cgcgaatgcc ccgaagagca cttgcgactc gattggctgt atgcaacgcg tggcggatgt     60

<210> SEQ ID NO 745
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 745
cgcgaatgcc agccacggct tacctgtagg ggtcgtcctg accacacgcg tggcggatgt     60

<210> SEQ ID NO 746
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 746
cgcgaatgcc ggagggcttt ccgcatgctt tggctgtctt gtcctacgcg tggcggatgt     60

<210> SEQ ID NO 747
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 747
cgcgaatgcc agaggattca ccaggcagac agaattcgca gtgagacgcg tggcggatgt     60

<210> SEQ ID NO 748
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 748
cgcgaatgcc gctagtaacg ggggccacac tagcgactac tcttcacgcg tggcggatgt     60

<210> SEQ ID NO 749
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 749
cgcgaatgcc cccggtgacc aacattcggt gaggacggga gggaaacgcg tggcggatgt    60

<210> SEQ ID NO 750
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 750
cgcgaatgcc agctccgagc cgaggcagct gcagtggctg gattgacgcg tggcggatgt    60

<210> SEQ ID NO 751
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 751
cgcgaatgcc cgcttggctg cccggtgcag ggaccctggg gtgctacgcg tggcggatgt    60

<210> SEQ ID NO 752
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 752
cgcgaatgcc caggaccagc cttttttgcgg tattggacat ggacaacgcg tggcggatgt    60

<210> SEQ ID NO 753
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 753
cgcgaatgcc gcaggtcatg ggggacagga ggatgggggt cagcaacgcg tggcggatgt    60

<210> SEQ ID NO 754
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 754
cgcgaatgcc ccatcttccc tagtccctag actcctctgt tgggcacgcg tggcggatgt    60

<210> SEQ ID NO 755
<211> LENGTH: 60
<212> TYPE: DNA
<213> ORGANISM: Artificial Sequence
<220> FEATURE:
<223> OTHER INFORMATION: Synthetic oligonucleotide

```
<400> SEQUENCE: 755
cgcgaatgcc actgatgtga cgatagggaa gatagatgaa gaaggacgcg tggcggatgt    60

<210> SEQ ID NO 756
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 756
cgcgaatgcc gtatccctct atccatcctc aaactgattc caataacgcg tggcggatgt    60

<210> SEQ ID NO 757
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 757
cgcgaatgcc tctcggagtc actaccccga cgattctgga atggtacgcg tggcggatgt    60

<210> SEQ ID NO 758
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 758
cgcgaatgcc aacgaagctt ggatagtcgg ggagagacaa cagggacgcg tggcggatgt    60

<210> SEQ ID NO 759
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 759
cgcgaatgcc tcactcacct gtttgatggg gatggctcgc ccactacgcg tggcggatgt    60

<210> SEQ ID NO 760
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 760
cgcgaatgcc tccaggggct gggacaggct aggggcagct ggtctacgcg tggcggatgt    60

<210> SEQ ID NO 761
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 761
cgcgaatgcc aaggggaaag acacatgtgg gaaaaaagcc aactaacgcg tggcggatgt    60

<210> SEQ ID NO 762
<211> LENGTH: 60
```

<212> TYPE: DNA
<213> ORGANISM: Artificial Sequence
<220> FEATURE:
<223> OTHER INFORMATION: Synthetic oligonucleotide

<400> SEQUENCE: 762
cgcgaatgcc tctccagagc ttcctactaa aacgaagtgg caattacgcg tggcggatgt    60

<210> SEQ ID NO 763
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 763
cgcgaatgcc ggttacatat ttcttcttcc attctttgtt caaggacgcg tggcggatgt    60

<210> SEQ ID NO 764
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 764
cgcgaatgcc ctgtccagta atggctttct actctaccac cccagacgcg tggcggatgt    60

<210> SEQ ID NO 765
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 765
cgcgaatgcc ccaatgtggc ccagtctctg ccactcacgt taataacgcg tggcggatgt    60

<210> SEQ ID NO 766
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 766
cgcgaatgcc attttttct ccccttagaa atgagaaaag tttccacgcg tggcggatgt    60

<210> SEQ ID NO 767
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 767
cgcgaatgcc tcattaggat tatgttgtgg atgagttgaa gacttacgcg tggcggatgt    60

<210> SEQ ID NO 768
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 768
cgcgaatgcc aaatgaaatt ctagtagctg acacttatga ccaaaacgcg tggcggatgt    60

<210> SEQ ID NO 769
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 769
cgcgaatgcc ctcagtatct tgcttactgg ccattggaga ttgacacgcg tggcggatgt    60

<210> SEQ ID NO 770
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 770
cgcgaatgcc gtgtgggctg gattgtaggg tgatgcccat gtggaacgcg tggcggatgt    60

<210> SEQ ID NO 771
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 771
cgcgaatgcc tatgcagggg tgtggttcca tcgtaggtag tactgacgcg tggcggatgt    60

<210> SEQ ID NO 772
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 772
cgcgaatgcc tagcagctgg gagagggtcc accaggctgg cagctacgcg tggcggatgt    60

<210> SEQ ID NO 773
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 773
cgcgaatgcc cgccagatca ccatcttacc tgctgctttg agaagacgcg tggcggatgt    60

<210> SEQ ID NO 774
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 774
cgcgaatgcc agaccattgg agatgcctac atggtggctt caggcacgcg tggcggatgt    60

<210> SEQ ID NO 775
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 775
cgcgaatgcc tcagctgcat gcctactgcc attcctcttt gggagacgcg tggcggatgt    60

<210> SEQ ID NO 776
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 776
cgcgaatgcc gattgcaaac atgtccttag atatcctgag ctctgacgcg tggcggatgt    60

<210> SEQ ID NO 777
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 777
cgcgaatgcc cacttctggc atgtgccgca tcttgaaagt gcccaacgcg tggcggatgt    60

<210> SEQ ID NO 778
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 778
cgcgaatgcc ccggtccgaa ttcgaattgg ccttcactca ggtaaacgcg tggcggatgt    60

<210> SEQ ID NO 779
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 779
cgcgaatgcc ttttgttccc agggaggtta tattcaaaag aaaaaacgcg tggcggatgt    60

<210> SEQ ID NO 780
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 780
cgcgaatgcc ctgctgcaat aaagatacag attccccaca gttccacgcg tggcggatgt    60

<210> SEQ ID NO 781
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 781
cgcgaatgcc ttgacctaga tgagatgtcg ttcactttta ctgagacgcg tggcggatgt    60
```

<210> SEQ ID NO 782
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 782
cgcgaatgcc aagaaacttt acctgatttc tatgtttttc tgtagacgcg tggcggatgt    60

<210> SEQ ID NO 783
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 783
cgcgaatgcc cacccacacg gccacagctg aggggccctg accacacgcg tggcggatgt    60

<210> SEQ ID NO 784
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 784
cgcgaatgcc ctcctcatcc agaaggatgc tgtaatagag aaataacgcg tggcggatgt    60

<210> SEQ ID NO 785
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 785
cgcgaatgcc ggccacatca aactcactgg tgagtggagg gcgccacgcg tggcggatgt    60

<210> SEQ ID NO 786
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 786
cgcgaatgcc ccttgtcctg tcctcccctg ggtcccgagg gggcaacgcg tggcggatgt    60

<210> SEQ ID NO 787
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 787
cgcgaatgcc ttatttagga tggcagtcag tcaaaattag gaggaacgcg tggcggatgt    60

<210> SEQ ID NO 788
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 788
cgcgaatgcc taaccaatgt acagtccatg tccactgtct ctcctacgcg tggcggatgt    60

<210> SEQ ID NO 789
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 789
cgcgaatgcc gtgaaaccgt tctcttaaaa atgaagaagc aagagacgcg tggcggatgt    60

<210> SEQ ID NO 790
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 790
cgcgaatgcc aaacagatct tacttgaact tttttctccc ttctgacgcg tggcggatgt    60

<210> SEQ ID NO 791
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 791
cgcgaatgcc ccaggcggga ggacaaactg cgcatccaga atggcacgcg tggcggatgt    60

<210> SEQ ID NO 792
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 792
cgcgaatgcc tggcggatga tctctggtgc caggtggcat agccaacgcg tggcggatgt    60

<210> SEQ ID NO 793
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 793
cgcgaatgcc gctgtccccc gacacagagg aggataagct cccctacgcg tggcggatgt    60

<210> SEQ ID NO 794
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 794
cgcgaatgcc ttacccaagg gcaaagacgt cagagtgctt ggagaacgcg tggcggatgt    60

<210> SEQ ID NO 795

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 795
cgcgaatgcc gttttgctat cggcatgcca gtgtgtgaat ttgatacgcg tggcggatgt    60

<210> SEQ ID NO 796
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 796
cgcgaatgcc cttcggaagt cctgtacttc tggatcttta accatacgcg tggcggatgt    60

<210> SEQ ID NO 797
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 797
cgcgaatgcc aaatattctg aacgtttgta aagaagctgt ggatcacgcg tggcggatgt    60

<210> SEQ ID NO 798
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 798
cgcgaatgcc cattgctcta ctatgaggtg aattgaggtc cctaaacgcg tggcggatgt    60

<210> SEQ ID NO 799
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 799
cgcgaatgcc tatgtctatc ctccaaatgt agaatcttca ccagaacgcg tggcggatgt    60

<210> SEQ ID NO 800
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 800
cgcgaatgcc ctttatctaa tttattatat atgtgctttg gcaatacgcg tggcggatgt    60

<210> SEQ ID NO 801
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 801
```

```
cgcgaatgcc gtaagaaaat gactaatcta ctctaatcat tactaacgcg tggcggatgt    60

<210> SEQ ID NO 802
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 802
cgcgaatgcc atcttgtcct tttgcttttc agcctctgta agggaacgcg tggcggatgt    60

<210> SEQ ID NO 803
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 803
cgcgaatgcc attttggcat ccctcacaac ggaatagagc gtccgacgcg tggcggatgt    60

<210> SEQ ID NO 804
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 804
cgcgaatgcc cgttttggat gtcaacaaaa ccaggcagat tgctcacgcg tggcggatgt    60

<210> SEQ ID NO 805
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 805
cgcgaatgcc aggcccaaga gccgacagta ccttcacaat ttcttacgcg tggcggatgt    60

<210> SEQ ID NO 806
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 806
cgcgaatgcc gtgaagtcag cactgtgctt aagctggata acacaacgcg tggcggatgt    60

<210> SEQ ID NO 807
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 807
cgcgaatgcc gggccacatg gcttccaaga cgtctgcccc accacacgcg tggcggatgt    60

<210> SEQ ID NO 808
<211> LENGTH: 60
<212> TYPE: DNA
```

```
<213> ORGANISM: Artificial Sequence
<220> FEATURE:
<223> OTHER INFORMATION: Synthetic oligonucleotide

<400> SEQUENCE: 808
cgcgaatgcc caatgcctgg gaccagagct tcactctgga gctggacgcg tggcggatgt    60

<210> SEQ ID NO 809
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 809
cgcgaatgcc taggccctgc tgtcctccaa cgcagctcac cctttacgcg tggcggatgt    60

<210> SEQ ID NO 810
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 810
cgcgaatgcc gaggaggagg ggttccatgc ctctggcacc ctgagacgcg tggcggatgt    60

<210> SEQ ID NO 811
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 811
cgcgaatgcc ttcccgtgcc tggagggaga ggaagagggc catcaacgcg tggcggatgt    60

<210> SEQ ID NO 812
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 812
cgcgaatgcc ctggagttgg ctgtgttctg gcgggaccag cggggacgcg tggcggatgt    60

<210> SEQ ID NO 813
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 813
cgcgaatgcc aatcctccaa cttcaggaat ttgagggcac acaggacgcg tggcggatgt    60

<210> SEQ ID NO 814
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 814
cgcgaatgcc tcttggacaa tgagaggcat gaggtgcagc tggacacgcg tggcggatgt    60
```

<210> SEQ ID NO 815
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 815
cgcgaatgcc tatacctcag ccaccaggca gccctggggt tccatacgcg tggcggatgt    60

<210> SEQ ID NO 816
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 816
cgcgaatgcc tgatgtcgtc atcgtggagc gtgggaaggg cgacgacgcg tggcggatgt    60

<210> SEQ ID NO 817
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 817
cgcgaatgcc cttcatcctg ccaaacttcc tcctctcggg aacacacgcg tggcggatgt    60

<210> SEQ ID NO 818
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 818
cgcgaatgcc ctcctgcagt tctgtgagaa ccaccggcct gcctaacgcg tggcggatgt    60

<210> SEQ ID NO 819
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 819
cgcgaatgcc ggatgagtgc cgtcttctta ttccaggtac cccagacgcg tggcggatgt    60

<210> SEQ ID NO 820
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 820
cgcgaatgcc gcgcgcgaga cccctgggcc caggacacgg tgagcacgcg tggcggatgt    60

<210> SEQ ID NO 821
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 821
cgcgaatgcc tgaggaggta cggggacgga ggcactctgg ggctaacgcg tggcggatgt    60

<210> SEQ ID NO 822
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 822
cgcgaatgcc ctgtgcccct ttcctccagc cccaaagaca gttgtacgcg tggcggatgt    60

<210> SEQ ID NO 823
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 823
cgcgaatgcc ccaggagctt ctgagaaaag aaacacatgg gactcacgcg tggcggatgt    60

<210> SEQ ID NO 824
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 824
cgcgaatgcc actatgaggt ggacagtgat gaggagtggg aagaaacgcg tggcggatgt    60

<210> SEQ ID NO 825
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 825
cgcgaatgcc ccctcactgt gggacaggga ctccccaggc tcctcacgcg tggcggatgt    60

<210> SEQ ID NO 826
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 826
cgcgaatgcc ggtaaggatg tgccccagct gtcttcactc acagaacgcg tggcggatgt    60

<210> SEQ ID NO 827
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 827
cgcgaatgcc agttatgaaa aaattcacct ggacttcctg aagagacgcg tggcggatgt    60

```
<210> SEQ ID NO 828
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 828
cgcgaatgcc agtccacacg catgcgtgcc acagcaggat ggtcaacgcg tggcggatgt      60

<210> SEQ ID NO 829
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 829
cgcgaatgcc cagacaatgc atacattggt gtcacctaca aaaacacgcg tggcggatgt      60

<210> SEQ ID NO 830
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 830
cgcgaatgcc agaccaccct cccagtcctt cagcttgtct tcctcacgcg tggcggatgt      60

<210> SEQ ID NO 831
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 831
cgcgaatgcc ggatgagcag agactgagcg ctgacagtgg ctacaacgcg tggcggatgt      60

<210> SEQ ID NO 832
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 832
cgcgaatgcc ctcagggaca gggtcaatgt caggcagagg aatgaacgcg tggcggatgt      60

<210> SEQ ID NO 833
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 833
cgcgaatgcc gaggaggacc tgggcaagag gaacagacac aggtaacgcg tggcggatgt      60

<210> SEQ ID NO 834
<211> LENGTH: 60
<212> TYPE: DNA
<213> ORGANISM: Artificial Sequence
<220> FEATURE:
<223> OTHER INFORMATION: Synthetic oligonucleotide
```

```
<400> SEQUENCE: 834
cgcgaatgcc cttttattcc gcctgcgtgg tgctgggcct acagtacgcg tggcggatgt    60

<210> SEQ ID NO 835
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 835
cgcgaatgcc cacacacctg tagacgatct tgtgttcgtg aagaaacgcg tggcggatgt    60

<210> SEQ ID NO 836
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 836
cgcgaatgcc cgtgtgtgca tgcatgtgca cactgcccgt tgtggacgcg tggcggatgt    60

<210> SEQ ID NO 837
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 837
cgcgaatgcc ggaaagaggg atgagcgggg gtctgggtcc tgtccacgcg tggcggatgt    60

<210> SEQ ID NO 838
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 838
cgcgaatgcc acccctccaa cccccaacag ggacctgaag ttggaacgcg tggcggatgt    60

<210> SEQ ID NO 839
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 839
cgcgaatgcc tcttgacgta gccctcggtg tccaggagca aattgacgcg tggcggatgt    60

<210> SEQ ID NO 840
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 840
cgcgaatgcc tcgcagactt tggcctctgc aaggagggtg aggggacgcg tggcggatgt    60

<210> SEQ ID NO 841
<211> LENGTH: 60
```

```
<212> TYPE: DNA
<213> ORGANISM: Artificial Sequence
<220> FEATURE:
<223> OTHER INFORMATION: Synthetic oligonucleotide

<400> SEQUENCE: 841
cgcgaatgcc ttccttcccc ctcctttgtc taatccagag gccagacgcg tggcggatgt    60

<210> SEQ ID NO 842
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 842
cgcgaatgcc tggggtccct aaccctattc ggggtgcccc ccaccacgcg tggcggatgt    60

<210> SEQ ID NO 843
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 843
cgcgaatgcc ggttgtccac acagccagcc ctgtcccagg gtcagacgcg tggcggatgt    60

<210> SEQ ID NO 844
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 844
cgcgaatgcc ccacattggg ctgagtgact cctctggccc ccataacgcg tggcggatgt    60

<210> SEQ ID NO 845
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 845
cgcgaatgcc agcccatccc tggggacagc aaggccatgt gaggtacgcg tggcggatgt    60

<210> SEQ ID NO 846
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 846
cgcgaatgcc atggggaccg gaccagcaca ttctgtggga ccccgacgcg tggcggatgt    60

<210> SEQ ID NO 847
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 847
```
cgcgaatgcc gacgtgtccg tcagcacctc aggggccagg aactcacgcg tggcggatgt    60

<210> SEQ ID NO 848
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 848
cgcgaatgcc gtacacgcga gctgtggact ggtggggact gggtgacgcg tggcggatgt    60

<210> SEQ ID NO 849
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 849
cgcgaatgcc tctcacctcg ccaaccagca tctcgtagag cagcaacgcg tggcggatgt    60

<210> SEQ ID NO 850
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 850
cgcgaatgcc tttcctctgt ttacagctac agctgtctcc agtgaacgcg tggcggatgt    60

<210> SEQ ID NO 851
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 851
cgcgaatgcc cagcaaccac agcaatgata ataacaggat tctgtacgcg tggcggatgt    60

<210> SEQ ID NO 852
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 852
cgcgaatgcc tagctgggac catcattttg gtgttcatgg tctttacgcg tggcggatgt    60

<210> SEQ ID NO 853
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 853
cgcgaatgcc aactttgtgt tctaccttct cccaatgatg aagccacgcg tggcggatgt    60

<210> SEQ ID NO 854
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 854
cgcgaatgcc tttatgttta ttttgtttct cccacacaga cactaacgcg tggcggatgt    60

<210> SEQ ID NO 855
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 855
cgcgaatgcc gcaatttggg tagaatttcg gggatagtta cacaaacgcg tggcggatgt    60

<210> SEQ ID NO 856
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 856
cgcgaatgcc gcttctgtct gttaaatgga attctagaga tgaagacgcg tggcggatgt    60

<210> SEQ ID NO 857
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 857
cgcgaatgcc ttatctagta atctcaaaca tacatttacc tgggcacgcg tggcggatgt    60

<210> SEQ ID NO 858
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 858
cgcgaatgcc tgtgtctgtt ctggttttta ttaaatttgt taattacgcg tggcggatgt    60

<210> SEQ ID NO 859
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 859
cgcgaatgcc tatccgtgct ctctgcaaaa aaaggacaaa gagatacgcg tggcggatgt    60

<210> SEQ ID NO 860
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 860
cgcgaatgcc actttatctt gtgtaagtct gctttacctg ttgctacgcg tggcggatgt    60

<210> SEQ ID NO 861
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 861
cgcgaatgcc tagttaccga tagtatcaga ataaatcagt ttcaaacgcg tggcggatgt    60

<210> SEQ ID NO 862
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 862
cgcgaatgcc tggtttatta tttattctta gaagcacatg gaacaacgcg tggcggatgt    60

<210> SEQ ID NO 863
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 863
cgcgaatgcc aaattaaaag atgacttatc aggggtatag ctgctacgcg tggcggatgt    60

<210> SEQ ID NO 864
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 864
cgcgaatgcc agctacagtt gttgctgaaa cacttggact tggtgacgcg tggcggatgt    60

<210> SEQ ID NO 865
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 865
cgcgaatgcc ccaaactaaa caattactta cagattcttc ttgaaacgcg tggcggatgt    60

<210> SEQ ID NO 866
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 866
cgcgaatgcc accctggccg gctcctgtgg gaagtttgcc cccttacgcg tggcggatgt    60

<210> SEQ ID NO 867
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 867
cgcgaatgcc gccgaggggc caggaccatg tgctctttaa tttcaacgcg tggcggatgt    60

<210> SEQ ID NO 868
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 868
cgcgaatgcc gtcggaccgc tttccatcca gacctctgca gtcagacgcg tggcggatgt    60

<210> SEQ ID NO 869
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 869
cgcgaatgcc aactcgccgc tctgctgctg gaggagctgg tccagacgcg tggcggatgt    60

<210> SEQ ID NO 870
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 870
cgcgaatgcc ctccttcttg aaagacctca aggccggca gccccacgcg tggcggatgt    60

<210> SEQ ID NO 871
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 871
cgcgaatgcc attccgggtg gaaacgtgcg tgggtccgga cctcaacgcg tggcggatgt    60

<210> SEQ ID NO 872
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 872
cgcgaatgcc gcagatattt ttaacaggtc agagcctgag gaggtacgcg tggcggatgt    60

<210> SEQ ID NO 873
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 873
cgcgaatgcc gtgtatgatg atggcaaaca cgtgtacctg gtgacacgcg tggcggatgt    60

<210> SEQ ID NO 874

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 874
cgcgaatgcc tcttgtccag cagctcccca ccccgcatca gctctacgcg tggcggatgt      60

<210> SEQ ID NO 875
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 875
cgcgaatgcc tcctgcggca gaagttcttc tcagagcggg aggccacgcg tggcggatgt      60

<210> SEQ ID NO 876
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 876
cgcgaatgcc tccacagttt tgccaatggt gtgcaggaca aagctacgcg tggcggatgt      60

<210> SEQ ID NO 877
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 877
cgcgaatgcc gtatctgcac tcacaggggg tgagtctgga ttcggacgcg tggcggatgt      60

<210> SEQ ID NO 878
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 878
cgcgaatgcc caggttacga ctcctgaaac tttttttttt taattacgcg tggcggatgt      60

<210> SEQ ID NO 879
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 879
cgcgaatgcc atgaactcta ttactatcat gactggtttc cctaaacgcg tggcggatgt      60

<210> SEQ ID NO 880
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 880
```
cgcgaatgcc ggaaaatgga gccctagatg catttctcag ggtaaacgcg tggcggatgt    60

<210> SEQ ID NO 881
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 881
cgcgaatgcc atagtatatt tagaataagt ggatcacttt ggtacacgcg tggcggatgt    60

<210> SEQ ID NO 882
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 882
cgcgaatgcc catcaattta tttactagat tatgatgtgt tccatacgcg tggcggatgt    60

<210> SEQ ID NO 883
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 883
cgcgaatgcc taaggtctat attcttcact ttgcatatgc catacacgcg tggcggatgt    60

<210> SEQ ID NO 884
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 884
cgcgaatgcc aattcaaaat cattgtaaca gcatacaagg atcttacgcg tggcggatgt    60

<210> SEQ ID NO 885
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 885
cgcgaatgcc tatggaaaat tacctacctc ctgaacagca tgaggacgcg tggcggatgt    60

<210> SEQ ID NO 886
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 886
cgcgaatgcc gaccacatcc ctgtcccttaccagccagac tccagacgcg tggcggatgt    60

<210> SEQ ID NO 887
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 887
cgcgaatgcc agggcgtgga ggacgtcgtg gaggaggggt tgctgacgcg tggcggatgt    60

<210> SEQ ID NO 888
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 888
cgcgaatgcc cctcgccagc acccccctc cctcctagtg ccacgacgcg tggcggatgt    60

<210> SEQ ID NO 889
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 889
cgcgaatgcc gtgcactgtg gggaagggtg taggggagaa ggcggacgcg tggcggatgt    60

<210> SEQ ID NO 890
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 890
cgcgaatgcc acggcagcag aagaacttca acctgccagg tacctacgcg tggcggatgt    60

<210> SEQ ID NO 891
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 891
cgcgaatgcc gccagccagg gacagaccct tcatttgggc tctttacgcg tggcggatgt    60

<210> SEQ ID NO 892
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 892
cgcgaatgcc cttgatttcc tctgccccat cagggccgga gcctgacgcg tggcggatgt    60

<210> SEQ ID NO 893
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 893
cgcgaatgcc cggcatgtct tctactccac cattgactgg aatgtacgcg tggcggatgt    60
```

<210> SEQ ID NO 894
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 894
cgcgaatgcc ccctggccag agccctggtg tgggtggaca cactcacgcg tggcggatgt    60

<210> SEQ ID NO 895
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 895
cgcgaatgcc gggcttctct ttattgtcct gagtcatccc tgtgcacgcg tggcggatgt    60

<210> SEQ ID NO 896
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 896
cgcgaatgcc gaaacacagg gcttcgcaac gactcactct ctttgacgcg tggcggatgt    60

<210> SEQ ID NO 897
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 897
cgcgaatgcc agctcattgt gattaaccct aagacgactc tcagcacgcg tggcggatgt    60

<210> SEQ ID NO 898
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 898
cgcgaatgcc tgccctggag gaagacagta cagcatcaca cccacacgcg tggcggatgt    60

<210> SEQ ID NO 899
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 899
cgcgaatgcc ggctggcagg caagtgtgca taactgctac tctatacgcg tggcggatgt    60

<210> SEQ ID NO 900
<211> LENGTH: 60
<212> TYPE: DNA
<213> ORGANISM: Artificial Sequence
<220> FEATURE:

```
<223> OTHER INFORMATION: Synthetic oligonucleotide

<400> SEQUENCE: 900
cgcgaatgcc gccatcaaac cttcttctgg accaaagcaa tgtggacgcg tggcggatgt    60

<210> SEQ ID NO 901
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 901
cgcgaatgcc aagccagtca cctgttgtgc ggaaggtagt gatatacgcg tggcggatgt    60

<210> SEQ ID NO 902
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 902
cgcgaatgcc aatggtgtct ggacagcaca ctgcaaggaa atcttacgcg tggcggatgt    60

<210> SEQ ID NO 903
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 903
cgcgaatgcc ctattgtgtc acaagaactg tactccacac ccgtgacgcg tggcggatgt    60

<210> SEQ ID NO 904
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 904
cgcgaatgcc ccaagatttc cacagagtaa gaaaaaaaaa ttcatacgcg tggcggatgt    60

<210> SEQ ID NO 905
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 905
cgcgaatgcc gaggatccaa agtgggaatt ccctcggaag aacttacgcg tggcggatgt    60

<210> SEQ ID NO 906
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 906
cgcgaatgcc caaattcgcc ttctcctaga gttttttccaa gaaccacgcg tggcggatgt    60
```

```
<210> SEQ ID NO 907
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 907
cgcgaatgcc gaaaagtggt caaggcaacg gccttccatc tgaaaacgcg tggcggatgt    60

<210> SEQ ID NO 908
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 908
cgcgaatgcc atcttcacgg ccaccgtggt gtaccctgct ctgccacgcg tggcggatgt    60

<210> SEQ ID NO 909
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 909
cgcgaatgcc gctgaaaggt acctgccagg cacaggcaca gtgccacgcg tggcggatgt    60

<210> SEQ ID NO 910
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 910
cgcgaatgcc aatgctgtta acagttcttc atccttttc cagctacgcg tggcggatgt     60

<210> SEQ ID NO 911
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 911
cgcgaatgcc ttcattttct gcttttgcat tcgtgttcga gtagaacgcg tggcggatgt    60

<210> SEQ ID NO 912
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 912
cgcgaatgcc tgatagcatg gatacctcaa acaaggaaga gaaatacgcg tggcggatgt    60

<210> SEQ ID NO 913
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 913
cgcgaatgcc gtgtacacag tgtccaccaa ggtcctgaga tcctcacgcg tggcggatgt        60

<210> SEQ ID NO 914
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 914
cgcgaatgcc agctccccca tccaggaatc cactgctccc gagctacgcg tggcggatgt        60

<210> SEQ ID NO 915
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 915
cgcgaatgcc gggcggggcc tggggtctcc tgggtctccg aaggcacgcg tggcggatgt        60

<210> SEQ ID NO 916
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 916
cgcgaatgcc tgtgcaggtg acaccactcc ctggccccct gtccaacgcg tggcggatgt        60

<210> SEQ ID NO 917
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 917
cgcgaatgcc ccactggtga aacaaggac agcgggcagg ggtggacgcg tggcggatgt        60

<210> SEQ ID NO 918
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 918
cgcgaatgcc cctctctcca cagccctctg aggaagtcac ctctgacgcg tggcggatgt        60

<210> SEQ ID NO 919
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 919
cgcgaatgcc cccagcaccg ccaggaactt gaaatcttcg agggtacgcg tggcggatgt        60

<210> SEQ ID NO 920
<211> LENGTH: 60

<212> TYPE: DNA
<213> ORGANISM: Artificial Sequence
<220> FEATURE:
<223> OTHER INFORMATION: Synthetic oligonucleotide

<400> SEQUENCE: 920
cgcgaatgcc ccggggtcat tttgggaagg tgaggtggag ggcagacgcg tggcggatgt    60

<210> SEQ ID NO 921
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 921
cgcgaatgcc cggccagcca gggacctggg gggtctccca attccacgcg tggcggatgt    60

<210> SEQ ID NO 922
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 922
cgcgaatgcc ctaaaaccac ccctgcccac tgtggttcca ggtgcacgcg tggcggatgt    60

<210> SEQ ID NO 923
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 923
cgcgaatgcc gaacagctcc ccactgggcc ggaattcgga gaggaacgcg tggcggatgt    60

<210> SEQ ID NO 924
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 924
cgcgaatgcc gccatcaagg ctctgaagaa aggggacatt gtggcacgcg tggcggatgt    60

<210> SEQ ID NO 925
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 925
cgcgaatgcc ccacggcagg tccccacctc tccacctcgt ctcggacgcg tggcggatgt    60

<210> SEQ ID NO 926
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 926
cgcgaatgcc cgcgcctccg ccgcctgaga ggaggtcgag ctgccacgcg tggcggatgt    60

<210> SEQ ID NO 927
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 927
cgcgaatgcc gccccgcact ccagctcctc cagcatcgcc ccggcacgcg tggcggatgt    60

<210> SEQ ID NO 928
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 928
cgcgaatgcc gcccggcgcc aggggagccg ccacaggtcg gttcgacgcg tggcggatgt    60

<210> SEQ ID NO 929
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 929
cgcgaatgcc gccgcgcccc cccttccccct cggcgcgggc ccgaaacgcg tggcggatgt    60

<210> SEQ ID NO 930
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 930
cgcgaatgcc ggcatgaagt acttacacca cagagagttt gttcaacgcg tggcggatgt    60

<210> SEQ ID NO 931
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 931
cgcgaatgcc catctaccac acagtttcga gactttagcc tcccaacgcg tggcggatgt    60

<210> SEQ ID NO 932
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 932
cgcgaatgcc ggcgttttgt actaaaagtg acagattatg gctttacgcg tggcggatgt    60

<210> SEQ ID NO 933
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 933
cgcgaatgcc tcttcagaga gtctcagcat ttctaagatg tcgttacgcg tggcggatgt    60

<210> SEQ ID NO 934
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 934
cgcgaatgcc ggaatcttct atggaaggta agcaatgaat tgtacacgcg tggcggatgt    60

<210> SEQ ID NO 935
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 935
cgcgaatgcc gattacatcc acagtaccca cggcaaggag atggaacgcg tggcggatgt    60

<210> SEQ ID NO 936
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 936
cgcgaatgcc gcttgcccgg gactttgact gttgttcgca gcaagacgcg tggcggatgt    60

<210> SEQ ID NO 937
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 937
cgcgaatgcc ggcccccgag ggccatctct gcctttggcc cctcaacgcg tggcggatgt    60

<210> SEQ ID NO 938
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 938
cgcgaatgcc gtgctcatgt ccttgacgag cccgttaatg ctggcacgcg tggcggatgt    60

<210> SEQ ID NO 939
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 939
cgcgaatgcc tgtccagatg ggtgaaggcc tgggtgagta aggttacgcg tggcggatgt    60
```

<210> SEQ ID NO 940
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 940
cgcgaatgcc cccagccctg gcccctcttc tgctcctatg tcataacgcg tggcggatgt    60

<210> SEQ ID NO 941
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 941
cgcgaatgcc gaaaagagg ggtaagaggg aagaggggc tggcaacgcg tggcggatgt    60

<210> SEQ ID NO 942
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 942
cgcgaatgcc gtccctcttt atcacccagc ttcctactcg cccagacgcg tggcggatgt    60

<210> SEQ ID NO 943
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 943
cgcgaatgcc cacataagga atggggccag aagaaagagg ctcacacgcg tggcggatgt    60

<210> SEQ ID NO 944
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 944
cgcgaatgcc agtagtggct tctgtcggaa gaagatgaaa cctcaacgcg tggcggatgt    60

<210> SEQ ID NO 945
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 945
cgcgaatgcc cccatgccaa gccctagccc cagccccagt tccctacgcg tggcggatgt    60

<210> SEQ ID NO 946
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 946
cgcgaatgcc gcaggtgttt ggatgtctga tctggtggtg gctgcacgcg tggcggatgt    60

<210> SEQ ID NO 947
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 947
cgcgaatgcc tgaagccaga ccggaatttg gcccgagccc tcagcacgcg tggcggatgt    60

<210> SEQ ID NO 948
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 948
cgcgaatgcc agacagcaga tggaaggtca tccccactga cccgtacgcg tggcggatgt    60

<210> SEQ ID NO 949
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 949
cgcgaatgcc attacagtta aatttccagg caccaaaacc tacatacgcg tggcggatgt    60

<210> SEQ ID NO 950
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 950
cgcgaatgcc cagctctatt tgggtcctca taggtttcag ggtcaacgcg tggcggatgt    60

<210> SEQ ID NO 951
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 951
cgcgaatgcc tccatcaatt cgccaaggag ctagatgcct cctgtacgcg tggcggatgt    60

<210> SEQ ID NO 952
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 952
cgcgaatgcc gccttacctg caccaatcac acgctcaatt ttaatacgcg tggcggatgt    60

<210> SEQ ID NO 953

-continued

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 953
cgcgaatgcc ccaacaaggc tccccaggga tgaagatcta cattgacgcg tggcggatgt     60

<210> SEQ ID NO 954
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 954
cgcgaatgcc gacagcttcg ttgggatcct cgtaagtgaa ggggtacgcg tggcggatgt     60

<210> SEQ ID NO 955
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 955
cgcgaatgcc cgggagtttg ccaaggagat tgatgtatct tttgtacgcg tggcggatgt     60

<210> SEQ ID NO 956
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 956
cgcgaatgcc gagccatacc tgctccgatg acctcttcaa ttttcacgcg tggcggatgt     60

<210> SEQ ID NO 957
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 957
cgcgaatgcc gaacactgtc cattggcatg gggaaatata aacttacgcg tggcggatgt     60

<210> SEQ ID NO 958
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 958
cgcgaatgcc tttttccaga tactagagtg tctgtgtaat caaacacgcg tggcggatgt     60

<210> SEQ ID NO 959
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 959
```

```
cgcgaatgcc tggctttgaa tctttggcca gtacctcatg gattaacgcg tggcggatgt    60
```

<210> SEQ ID NO 960
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 960

```
cgcgaatgcc gatccagtaa caccaatagg gttcagcaaa tcttcacgcg tggcggatgt    60
```

<210> SEQ ID NO 961
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 961

```
cgcgaatgcc aaatccaaat aaagtaaggt ttttattgtc ataaaacgcg tggcggatgt    60
```

<210> SEQ ID NO 962
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 962

```
cgcgaatgcc agagagaagg tttgactgcc ataaaaaata tctaaacgcg tggcggatgt    60
```

<210> SEQ ID NO 963
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 963

```
cgcgaatgcc tatgtatata taatagcttt tcttccatct cttagacgcg tggcggatgt    60
```

<210> SEQ ID NO 964
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 964

```
cgcgaatgcc aaccagtcaa actccaactc taagcatgga gtttcacgcg tggcggatgt    60
```

<210> SEQ ID NO 965
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 965

```
cgcgaatgcc cagcagtgtg gtaaagttcc cagatatgtc agtgaacgcg tggcggatgt    60
```

<210> SEQ ID NO 966
<211> LENGTH: 60
<212> TYPE: DNA

<213> ORGANISM: Artificial Sequence
<220> FEATURE:
<223> OTHER INFORMATION: Synthetic oligonucleotide

<400> SEQUENCE: 966
cgcgaatgcc ttctcgggat acagaccaat tggcatgctc ttcaaacgcg tggcggatgt    60

<210> SEQ ID NO 967
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 967
cgcgaatgcc gcaggattta gctattccca cgcaggactg gtaagacgcg tggcggatgt    60

<210> SEQ ID NO 968
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 968
cgcgaatgcc taacttcaat gtctttattc catcttctct ttaggacgcg tggcggatgt    60

<210> SEQ ID NO 969
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 969
cgcgaatgcc ggattcaatt gccatccatt taactggaat ccgacacgcg tggcggatgt    60

<210> SEQ ID NO 970
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 970
cgcgaatgcc cttttgatc atatctacac cacgcaaagt gatgtacgcg tggcggatgt    60

<210> SEQ ID NO 971
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 971
cgcgaatgcc aacctccacc ccaagagagc aacacccaca cttacacgcg tggcggatgt    60

<210> SEQ ID NO 972
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 972
cgcgaatgcc aaatggtgat acatattatt tgaatttcag atttaacgcg tggcggatgt    60

<210> SEQ ID NO 973
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 973
cgcgaatgcc atacgaataa tttgaagtgt tagcatatct tgccgacgcg tggcggatgt    60

<210> SEQ ID NO 974
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 974
cgcgaatgcc tatggaaaat atctggcaaa atcaaggtct tgatcacgcg tggcggatgt    60

<210> SEQ ID NO 975
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 975
cgcgaatgcc caacatacag gttgccttac tggttaccta ccgaaacgcg tggcggatgt    60

<210> SEQ ID NO 976
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 976
cgcgaatgcc tcctttgtag tgtccataaa ttctttaact tactaacgcg tggcggatgt    60

<210> SEQ ID NO 977
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 977
cgcgaatgcc gcattatcaa ctttggtact ggtatcaatt tctttacgcg tggcggatgt    60

<210> SEQ ID NO 978
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 978
cgcgaatgcc tatgtcaaga ctgttgaaga agtatgatgt attgtacgcg tggcggatgt    60

<210> SEQ ID NO 979
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 979
cgcgaatgcc tttactttac ctttccaatt tgctgaagag tgcaaacgcg tggcggatgt      60

<210> SEQ ID NO 980
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 980
cgcgaatgcc ggacctggtg tccaagatgc tacacgtgga tccccacgcg tggcggatgt      60

<210> SEQ ID NO 981
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 981
cgcgaatgcc atgctgcaga acctgcttag ctgtgaggcg ctggtacgcg tggcggatgt      60

<210> SEQ ID NO 982
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 982
cgcgaatgcc ccatgggtca cccagaaaga caagcttccc caaagacgcg tggcggatgt      60

<210> SEQ ID NO 983
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 983
cgcgaatgcc ccttcacaag ctgtaggtcc tggtgggaca gctggacgcg tggcggatgt      60

<210> SEQ ID NO 984
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 984
cgcgaatgcc attgaaacat ttaaatgttc ttctttacag atgttacgcg tggcggatgt      60

<210> SEQ ID NO 985
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 985
cgcgaatgcc taaatattgt atgagtcaaa gaaggatcca atgaacgcg tggcggatgt      60

-continued

```
<210> SEQ ID NO 986
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 986
cgcgaatgcc atccagaagt atttcaacca cagatggcac tgccaacgcg tggcggatgt    60

<210> SEQ ID NO 987
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 987
cgcgaatgcc acaacagggt aacagggatg agttttctta cctgtacgcg tggcggatgt    60

<210> SEQ ID NO 988
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 988
cgcgaatgcc gttttctttt tttacagtga catgaaaaag gttggacgcg tggcggatgt    60

<210> SEQ ID NO 989
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 989
cgcgaatgcc tgatgatctt cttctgtggc ccaaccacgg tgacaacgcg tggcggatgt    60

<210> SEQ ID NO 990
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 990
cgcgaatgcc gtagcattaa agctctagaa acgcaatcaa agaatacgcg tggcggatgt    60

<210> SEQ ID NO 991
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 991
cgcgaatgcc cacttccgtc ccgtgcttta cacgggaact gggccacgcg tggcggatgt    60

<210> SEQ ID NO 992
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 992
cgcgaatgcc tgccaggggt cttttcaaac atagacaatc atgggacgcg tggcggatgt    60

<210> SEQ ID NO 993
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 993
cgcgaatgcc tgggactaga tgatctctat tgtccttcaa gtttaacgcg tggcggatgt    60

<210> SEQ ID NO 994
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 994
cgcgaatgcc tcaactcact atatatga ggaacctgag gtccaacgcg tggcggatgt    60

<210> SEQ ID NO 995
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 995
cgcgaatgcc caccatgtga ccttgggtaa gacacttccc cactcacgcg tggcggatgt    60

<210> SEQ ID NO 996
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 996
cgcgaatgcc acctaacact gccttgttgg atccaagctc ccctgacgcg tggcggatgt    60

<210> SEQ ID NO 997
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 997
cgcgaatgcc gagccaatcg cccactgata ccacagcaga gaattacgcg tggcggatgt    60

<210> SEQ ID NO 998
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 998
cgcgaatgcc caggccatta aaatggaccg gtataaggat aacttacgcg tggcggatgt    60

<210> SEQ ID NO 999
<211> LENGTH: 60

```
<212> TYPE: DNA
<213> ORGANISM: Artificial Sequence
<220> FEATURE:
<223> OTHER INFORMATION: Synthetic oligonucleotide

<400> SEQUENCE: 999
cgcgaatgcc ccacagcctc tagtgtggta taaccagcag ctgtgacgcg tggcggatgt    60

<210> SEQ ID NO 1000
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1000
cgcgaatgcc tgcacgtgaa ccaggagtaa gtactcaacg atgtaacgcg tggcggatgt    60

<210> SEQ ID NO 1001
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1001
cgcgaatgcc ttcctcttat gtgttcgctt tccttgattt acctcacgcg tggcggatgt    60

<210> SEQ ID NO 1002
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1002
cgcgaatgcc ctgccccatg ttttgactta tagccacaga acctgacgcg tggcggatgt    60

<210> SEQ ID NO 1003
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1003
cgcgaatgcc atgaaaaaag acttcatttt ggcaatgggc attgtacgcg tggcggatgt    60

<210> SEQ ID NO 1004
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1004
cgcgaatgcc ggtgaagcaa aacaaaaagc caagtttaga aacttacgcg tggcggatgt    60

<210> SEQ ID NO 1005
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1005
```

```
cgcgaatgcc gaacacaatg agttcaactc ctccatggcc aggagacgcg tggcggatgt    60
```

<210> SEQ ID NO 1006
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1006

```
cgcgaatgcc gccgcagccc atcaatcctt gctgtgttgg tctgaacgcg tggcggatgt    60
```

<210> SEQ ID NO 1007
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1007

```
cgcgaatgcc ctggcatggt atatgtggta caggtgcgtg cccgcacgcg tggcggatgt    60
```

<210> SEQ ID NO 1008
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1008

```
cgcgaatgcc atcttgccac tgaacttgcc gtagccagca acagtacgcg tggcggatgt    60
```

<210> SEQ ID NO 1009
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1009

```
cgcgaatgcc gtgcttccag actctgactg acggtaaggg tcgggacgcg tggcggatgt    60
```

<210> SEQ ID NO 1010
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1010

```
cgcgaatgcc gtatctttct cctgtaagat ctccaaagaa aaagacgcg tggcggatgt    60
```

<210> SEQ ID NO 1011
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1011

```
cgcgaatgcc tgcatttgca gtagaattta cacgcgtagt tgaacacgcg tggcggatgt    60
```

<210> SEQ ID NO 1012
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 1012
cgcgaatgcc gagacacaag caacctcagc cttccagacc cagaaacgcg tggcggatgt    60

<210> SEQ ID NO 1013
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1013
cgcgaatgcc tataaaacag tgaaagagag gtagatttca atggcacgcg tggcggatgt    60

<210> SEQ ID NO 1014
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1014
cgcgaatgcc tataaaaaag gttagtagat gattattttc aagagacgcg tggcggatgt    60

<210> SEQ ID NO 1015
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1015
cgcgaatgcc tattatgcag atatgccagc agaagaaaga gaaaaacgcg tggcggatgt    60

<210> SEQ ID NO 1016
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1016
cgcgaatgcc agcggaatcg gtgtcttgag caggaagcca atttcacgcg tggcggatgt    60

<210> SEQ ID NO 1017
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1017
cgcgaatgcc acattccacc caacacacca gagaattttt gggaaacgcg tggcggatgt    60

<210> SEQ ID NO 1018
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1018
cgcgaatgcc ctttccatac aagtctgagt ggaaggaaaa ccaacacgcg tggcggatgt    60
```

<210> SEQ ID NO 1019
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1019
cgcgaatgcc aaagaggtga gagtatagat tgtaacattt tataaacgcg tggcggatgt    60

<210> SEQ ID NO 1020
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1020
cgcgaatgcc cctgcctttt cacctaggga tcacgtttat ttttcacgcg tggcggatgt    60

<210> SEQ ID NO 1021
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1021
cgcgaatgcc tgaagtaatg gatttccttc caagctgtaa agaaaacgcg tggcggatgt    60

<210> SEQ ID NO 1022
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1022
cgcgaatgcc aattgaagtg gagccaacgt cggaggtgag aatcaacgcg tggcggatgt    60

<210> SEQ ID NO 1023
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1023
cgcgaatgcc gggcagtccc tggaaaatgt cgcttcactg ctctcacgcg tggcggatgt    60

<210> SEQ ID NO 1024
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1024
cgcgaatgcc actcttgaag gaaactcaag gtcccatgag cccccacgcg tggcggatgt    60

<210> SEQ ID NO 1025
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1025
cgcgaatgcc ccttccagac agtggtagag ctcatcacca aggggacgcg tggcggatgt    60

<210> SEQ ID NO 1026
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1026
cgcgaatgcc aaatcacaag aaacagcctt ttgaggaatc tacaaacgcg tggcggatgt    60

<210> SEQ ID NO 1027
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1027
cgcgaatgcc tgcccttaat taccttaaac tatcttcagt atttcacgcg tggcggatgt    60

<210> SEQ ID NO 1028
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1028
cgcgaatgcc aatgatcatg ttgtaacttc atcttttca ggtgaacgcg tggcggatgt    60

<210> SEQ ID NO 1029
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1029
cgcgaatgcc cataaaaggt ataaaatttt tgaaataaac attttacgcg tggcggatgt    60

<210> SEQ ID NO 1030
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1030
cgcgaatgcc aattctcttg gacttgtaac atctaatgga cttccacgcg tggcggatgt    60

<210> SEQ ID NO 1031
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1031
cgcgaatgcc taatatttta ttaaatttcc tttcagatta cctctacgcg tggcggatgt    60

<210> SEQ ID NO 1032

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1032
cgcgaatgcc gacaccgtgg tggccacgct gcgtgtcttc gatgcacgcg tggcggatgt    60

<210> SEQ ID NO 1033
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1033
cgcgaatgcc gcctcaccag ctcccctgat gcaggtacca cgtctacgcg tggcggatgt    60

<210> SEQ ID NO 1034
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1034
cgcgaatgcc ggtacacaag cacgctgctc cccggggaca cctggacgcg tggcggatgt    60

<210> SEQ ID NO 1035
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1035
cgcgaatgcc ttgggccagt gttccacccg gaaggtctgc tgggcacgcg tggcggatgt    60

<210> SEQ ID NO 1036
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1036
cgcgaatgcc cgagacctcg gtccaggcca acggcagctt cgtgcacgcg tggcggatgt    60

<210> SEQ ID NO 1037
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1037
cgcgaatgcc ccagcccctc ttactatagt catgtacggt cgcccacgcg tggcggatgt    60

<210> SEQ ID NO 1038
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1038
```

```
cgcgaatgcc actctgggct gggaagccct gttggcccgg cgcctacgcg tggcggatgt    60
```

<210> SEQ ID NO 1039
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1039

```
cgcgaatgcc tgcggccgga cagcgtgggc acaaagggcg gtggcacgcg tggcggatgt    60
```

<210> SEQ ID NO 1040
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1040

```
cgcgaatgcc ccgacgtcag caacttcgac gaggagttca ccgggacgcg tggcggatgt    60
```

<210> SEQ ID NO 1041
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1041

```
cgcgaatgcc cgcgcgtcgc ggggcgggct cagtgtgggg gcctcacgcg tggcggatgt    60
```

<210> SEQ ID NO 1042
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1042

```
cgcgaatgcc gccctcaca gccgcggagc aggcagcctt cctggacgcg tggcggatgt    60
```

<210> SEQ ID NO 1043
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1043

```
cgcgaatgcc ggctagcagc ccccggccac gaagtcgaag tccagacgcg tggcggatgt    60
```

<210> SEQ ID NO 1044
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1044

```
cgcgaatgcc tttttggaa tcacctaggt cctaaaatat gaacaacgcg tggcggatgt    60
```

<210> SEQ ID NO 1045
<211> LENGTH: 60
<212> TYPE: DNA

<213> ORGANISM: Artificial Sequence
<220> FEATURE:
<223> OTHER INFORMATION: Synthetic oligonucleotide

<400> SEQUENCE: 1045
cgcgaatgcc tcagtaaaaa tctcacaagc aagttatcca aatatacgcg tggcggatgt    60

<210> SEQ ID NO 1046
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1046
cgcgaatgcc agaaagcatt gactaatcaa aggattgggc actttacgcg tggcggatgt    60

<210> SEQ ID NO 1047
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1047
cgcgaatgcc gaaaataatt agacttactt taaatgccaa agaaacgcg tggcggatgt     60

<210> SEQ ID NO 1048
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1048
cgcgaatgcc ggctgagcct aatcctctgc cagctttcat tacccacgcg tggcggatgt    60

<210> SEQ ID NO 1049
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1049
cgcgaatgcc tgcacaacct tttcattttc atttggaagg atagaacgcg tggcggatgt    60

<210> SEQ ID NO 1050
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1050
cgcgaatgcc gctgaattca tccttttctc tgagatgctt tggggacgcg tggcggatgt    60

<210> SEQ ID NO 1051
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1051
cgcgaatgcc ttcagacatg gggtactgcc agctcacttc actctacgcg tggcggatgt    60

<210> SEQ ID NO 1052
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1052
cgcgaatgcc gaagagagct ccgatgtgga aatcagaaat gaagaacgcg tggcggatgt    60

<210> SEQ ID NO 1053
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1053
cgcgaatgcc cttccaagac cgtcacaaaa aggccgctgt tgtttacgcg tggcggatgt    60

<210> SEQ ID NO 1054
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1054
cgcgaatgcc tgagcagtgc ctcggcggcc cacacagggt tgtacacgcg tggcggatgt    60

<210> SEQ ID NO 1055
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1055
cgcgaatgcc ttctcttctg tctgagtgtg gttgtaatag caagtacgcg tggcggatgt    60

<210> SEQ ID NO 1056
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1056
cgcgaatgcc tgagcttgaa ggcaggcaca tttacatcta tgtgcacgcg tggcggatgt    60

<210> SEQ ID NO 1057
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1057
cgcgaatgcc gaagcttggt cctggagacc cagccaactc acctgacgcg tggcggatgt    60

<210> SEQ ID NO 1058
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 1058
cgcgaatgcc tttcatgtaa catatggaaa tacaactttc tttttacgcg tggcggatgt    60

<210> SEQ ID NO 1059
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1059
cgcgaatgcc tgtttgttgt gctttagaat ccagcagtag tactgacgcg tggcggatgt    60

<210> SEQ ID NO 1060
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1060
cgcgaatgcc gagttggagt ggatttcctc tccacccaat ggggtacgcg tggcggatgt    60

<210> SEQ ID NO 1061
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1061
cgcgaatgcc tttaaaaaag tgatatttta tgatgaaaaa aacttacgcg tggcggatgt    60

<210> SEQ ID NO 1062
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1062
cgcgaatgcc aatgaagagg tccatgatga ggccgaagag tcagaacgcg tggcggatgt    60

<210> SEQ ID NO 1063
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1063
cgcgaatgcc agaggaggga caggttcatc tcctcgaagt catccacgcg tggcggatgt    60

<210> SEQ ID NO 1064
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1064
cgcgaatgcc cggcccggag cttcccacgc aaggccagcc agaccacgcg tggcggatgt    60

```
<210> SEQ ID NO 1065
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1065
cgcgaatgcc tcaaagggga tgtcccactc ctgaaggaag atgctacgcg tggcggatgt    60

<210> SEQ ID NO 1066
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1066
cgcgaatgcc gcagctggag atcggcgagc tcattggaaa gggccacgcg tggcggatgt    60

<210> SEQ ID NO 1067
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1067
cgcgaatgcc gccatgccag cggccgtggt acacttgccc aaagcacgcg tggcggatgt    60

<210> SEQ ID NO 1068
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1068
cgcgaatgcc gaggtggcca tccggctgat tgacattgag agggaacgcg tggcggatgt    60

<210> SEQ ID NO 1069
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1069
cgcgaatgcc cctcccgctt gaaggccttg agctggtcct cgttgacgcg tggcggatgt    60

<210> SEQ ID NO 1070
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1070
cgcgaatgcc tgatggccta caggcagaca cggcatgaga acgtgacgcg tggcggatgt    60

<210> SEQ ID NO 1071
<211> LENGTH: 60
<212> TYPE: DNA
<213> ORGANISM: Artificial Sequence
<220> FEATURE:
<223> OTHER INFORMATION: Synthetic oligonucleotide
```

```
<400> SEQUENCE: 1071
cgcgaatgcc tgaggcgggc tcatgcaggc acccatgaaa agcacacgcg tggcggatgt    60

<210> SEQ ID NO 1072
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1072
cgcgaatgcc cctggccatc atcaccaggt cagttccacc tgggcacgcg tggcggatgt    60

<210> SEQ ID NO 1073
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1073
cgcgaatgcc aaatcataaa cagacttaag aagcctcctc ctgtgacgcg tggcggatgt    60

<210> SEQ ID NO 1074
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1074
cgcgaatgcc ggaggggcat gctcaggagg aactactggt ctgtaacgcg tggcggatgt    60

<210> SEQ ID NO 1075
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1075
cgcgaatgcc agaatgtctc cagctgatga agcagtgctg ggctgacgcg tggcggatgt    60

<210> SEQ ID NO 1076
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1076
cgcgaatgcc tatttcatca aaagttggtc gttgttctgc agcctacgcg tggcggatgt    60

<210> SEQ ID NO 1077
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1077
cgcgaatgcc tttaaccagg taaggactct gaatcttatc attgcacgcg tggcggatgt    60

<210> SEQ ID NO 1078
<211> LENGTH: 60
```

```
<212> TYPE: DNA
<213> ORGANISM: Artificial Sequence
<220> FEATURE:
<223> OTHER INFORMATION: Synthetic oligonucleotide

<400> SEQUENCE: 1078
cgcgaatgcc tatattattt gccttctttt tcacattgtt tttaaacgcg tggcggatgt    60

<210> SEQ ID NO 1079
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1079
cgcgaatgcc ttattttctt cctgtagagt attcctttca ttcacacgcg tggcggatgt    60

<210> SEQ ID NO 1080
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1080
cgcgaatgcc aaagctttct gaacaactcc agcagaaaat tgagtacgcg tggcggatgt    60

<210> SEQ ID NO 1081
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1081
cgcgaatgcc ataaaataaa ataacaaggt tggaggaaaa tacttacgcg tggcggatgt    60

<210> SEQ ID NO 1082
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1082
cgcgaatgcc ggcgtcatgc cgcccaaaac cccccgaaaa acggcacgcg tggcggatgt    60

<210> SEQ ID NO 1083
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1083
cgcgaatgcc ggtgccgggg gttccgcggc ggcagcggcg gcggtacgcg tggcggatgt    60

<210> SEQ ID NO 1084
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1084
```
cgcgaatgcc ccgccgcccc ctcctgagga ggacccagag caggaacgcg tggcggatgt    60

<210> SEQ ID NO 1085
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1085
cgcgaatgcc cctgacgaga ggcaggtcct ccgggccgct gtcctacgcg tggcggatgt    60

<210> SEQ ID NO 1086
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1086
cgcgaatgcc tattctttca acagccacgg ccagatccag tgaaaacgcg tggcggatgt    60

<210> SEQ ID NO 1087
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1087
cgcgaatgcc agtcattatc ttcagttcag acatgagagc ttgttacgcg tggcggatgt    60

<210> SEQ ID NO 1088
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1088
cgcgaatgcc cacctggggc cacatttgaa cattgtaaac ttgctacgcg tggcggatgt    60

<210> SEQ ID NO 1089
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1089
cgcgaatgcc ggtcagtgag cccacctgac ttggtgcagg ctcccacgcg tggcggatgt    60

<210> SEQ ID NO 1090
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1090
cgcgaatgcc gatcaggagc gtctgggcaa gcagctcaag ttacgacgcg tggcggatgt    60

<210> SEQ ID NO 1091
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1091
cgcgaatgcc cctctttcag cttctccttt tcttcccttt ctgcaacgcg tggcggatgt    60

<210> SEQ ID NO 1092
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1092
cgcgaatgcc gaggaggcca agcgggccaa ggaggaggcc aagaaacgcg tggcggatgt    60

<210> SEQ ID NO 1093
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1093
cgcgaatgcc ctctcctttt ccttaagctc cttctcttcc tccttacgcg tggcggatgt    60

<210> SEQ ID NO 1094
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1094
cgcgaatgcc gagaagcggg agaaggatga gaaggagaag gcggaacgcg tggcggatgt    60

<210> SEQ ID NO 1095
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1095
cgcgaatgcc cttgcgccgc tcctccttga gccgctgctt ctccgacgcg tggcggatgt    60

<210> SEQ ID NO 1096
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1096
cgcgaatgcc gagagacagg aagccctgga gtgagtgtcc ttggaacgcg tggcggatgt    60

<210> SEQ ID NO 1097
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1097
cgcgaatgcc gttcattcta gtgttacagt tttgttttgt tttgtacgcg tggcggatgt    60

<210> SEQ ID NO 1098
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1098
cgcgaatgcc tatggatcat cttctgccat tctgaagctg tgtatacgcg tggcggatgt    60

<210> SEQ ID NO 1099
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1099
cgcgaatgcc tttgggaagg cctgaacaag taagtgtcat aatctacgcg tggcggatgt    60

<210> SEQ ID NO 1100
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1100
cgcgaatgcc tgaaatatga atatatttaa ataaagttat cagtgacgcg tggcggatgt    60

<210> SEQ ID NO 1101
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1101
cgcgaatgcc atccactgtg cgacgagctg tgccgcacgg tgatcacgcg tggcggatgt    60

<210> SEQ ID NO 1102
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1102
cgcgaatgcc accgagacga tgaaggagaa gaggacagcg gctgcacgcg tggcggatgt    60

<210> SEQ ID NO 1103
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1103
cgcgaatgcc gctgctgtct gccttctgca tccactgcta ccacaacgcg tggcggatgt    60

<210> SEQ ID NO 1104
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1104
cgcgaatgcc ctcagctgag gagatgggtg gcttgtgggc aaactacgcg tggcggatgt    60

<210> SEQ ID NO 1105
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1105
cgcgaatgcc atgaccttcc ggaggcccgc ccaggccttc ccggtacgcg tggcggatgt    60

<210> SEQ ID NO 1106
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1106
cgcgaatgcc gcgagggccg gcgggcaccg gaagaggagt agctgacgcg tggcggatgt    60

<210> SEQ ID NO 1107
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1107
cgcgaatgcc tggactccat ggagaaccag gtctccgtgg atgccacgcg tggcggatgt    60

<210> SEQ ID NO 1108
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1108
cgcgaatgcc ccctgccccg cagggaccct caccaggatc ttgaaacgcg tggcggatgt    60

<210> SEQ ID NO 1109
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1109
cgcgaatgcc ataacctctt tctagagaag gctatgcagc ttgcaacgcg tggcggatgt    60

<210> SEQ ID NO 1110
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1110
cgcgaatgcc accgcgtagt cgaaaagggc attggcatgc ctcttacgcg tggcggatgt    60

<210> SEQ ID NO 1111

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1111
cgcgaatgcc gacaggagac gtgaagatgc tgctggccgt ccagcacgcg tggcggatgt     60

<210> SEQ ID NO 1112
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1112
cgcgaatgcc gtccccattc tcatcctgca cagcagtgag atggcacgcg tggcggatgt     60

<210> SEQ ID NO 1113
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1113
cgcgaatgcc aggtaagtca gaactttgc atgataggtt gtcctacgcg tggcggatgt      60

<210> SEQ ID NO 1114
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1114
cgcgaatgcc gagctctgct gatcctcttt ttctctctgt ctaggacgcg tggcggatgt     60

<210> SEQ ID NO 1115
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1115
cgcgaatgcc ggctgaatgc tccgaagtcc tgagttcttg atggtacgcg tggcggatgt     60

<210> SEQ ID NO 1116
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1116
cgcgaatgcc cagagccttt gccaagaacc cccatttgcg ttataacgcg tggcggatgt     60

<210> SEQ ID NO 1117
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1117
```

```
cgcgaatgcc gtgcccccaa tccctgcagc ccagctctac tcacaacgcg tggcggatgt    60

<210> SEQ ID NO 1118
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1118
cgcgaatgcc ttttcccct gtgaacagaa gcccccaatg catccacgcg tggcggatgt    60

<210> SEQ ID NO 1119
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1119
cgcgaatgcc ccagctgtcc tgtccattct tacaattttc aagttacgcg tggcggatgt    60

<210> SEQ ID NO 1120
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1120
cgcgaatgcc atgtgtgact ggaggggagg aaatttatct tctttacgcg tggcggatgt    60

<210> SEQ ID NO 1121
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1121
cgcgaatgcc tcacagaatg tatttacctt tctgaacttt gtcacacgcg tggcggatgt    60

<210> SEQ ID NO 1122
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1122
cgcgaatgcc agacaggatc agtgcttcct cccctcgggt ggtggacgcg tggcggatgt    60

<210> SEQ ID NO 1123
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1123
cgcgaatgcc catgtccgcg cacagagctc tggcacgagc atctcacgcg tggcggatgt    60

<210> SEQ ID NO 1124
<211> LENGTH: 60
<212> TYPE: DNA
```

<213> ORGANISM: Artificial Sequence
<220> FEATURE:
<223> OTHER INFORMATION: Synthetic oligonucleotide

<400> SEQUENCE: 1124
cgcgaatgcc aaacgctgca gctactatga gacttgtgca acctaacgcg tggcggatgt    60

<210> SEQ ID NO 1125
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1125
cgcgaatgcc caccctcctg aagacccga tccacattga gcccaacgcg tggcggatgt    60

<210> SEQ ID NO 1126
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1126
cgcgaatgcc tgggaggaag tgagtatcat ggatgaaaaa aatacacgcg tggcggatgt    60

<210> SEQ ID NO 1127
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1127
cgcgaatgcc ccatcacatt gcacacttgg taggttcgga ttggtacgcg tggcggatgt    60

<210> SEQ ID NO 1128
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1128
cgcgaatgcc aacccagcca gaataactgg ctacgaactg attggacgcg tggcggatgt    60

<210> SEQ ID NO 1129
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1129
cgcgaatgcc tcaatataca ccctctgagc cccttctcgg gtgatacgcg tggcggatgt    60

<210> SEQ ID NO 1130
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1130
cgcgaatgcc gattaaattc accttgaggg actgcaatag tcttcacgcg tggcggatgt    60

<210> SEQ ID NO 1131
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1131
cgcgaatgcc gttaaacgtc tccttgcaag tccccatgac gcccgacgcg tggcggatgt    60

<210> SEQ ID NO 1132
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1132
cgcgaatgcc ctgtactact atgaatcaga caacgacaaa gagcgacgcg tggcggatgt    60

<210> SEQ ID NO 1133
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1133
cgcgaatgcc tgtcaatttt gacaaactgg ttctctctga tgaaaacgcg tggcggatgt    60

<210> SEQ ID NO 1134
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1134
cgcgaatgcc ccattgctgc tgatgagagc ttcacccaag tggacacgcg tggcggatgt    60

<210> SEQ ID NO 1135
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1135
cgcgaatgcc atctcggtgt tcagcttcat gattctgtca ccaatacgcg tggcggatgt    60

<210> SEQ ID NO 1136
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1136
cgcgaatgcc ccgggatgta gggccattaa gcaaaaggg gttttacgcg tggcggatgt    60

<210> SEQ ID NO 1137
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 1137
cgcgaatgcc ggcgatgcag gcccccacat cctgaaaagc caggtacgcg tggcggatgt    60

<210> SEQ ID NO 1138
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1138
cgcgaatgcc ctggtatcag tccgtgtgtt ctataaaaag tgtccacgcg tggcggatgt    60

<210> SEQ ID NO 1139
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1139
cgcgaatgcc tgtcaggaaa ctgggccaga ttgcggactg tgagtacgcg tggcggatgt    60

<210> SEQ ID NO 1140
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1140
cgcgaatgcc ccatcacagg ggctgatacg tcttccctgg tggaaacgcg tggcggatgt    60

<210> SEQ ID NO 1141
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1141
cgcgaatgcc ttctcttctg agttgttgac acaggagcct cgaacacgcg tggcggatgt    60

<210> SEQ ID NO 1142
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1142
cgcgaatgcc agatgtgcca aaaatgtact gtggggcaga tggtgacgcg tggcggatgt    60

<210> SEQ ID NO 1143
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1143
cgcgaatgcc gttgcatagg cagttgccaa tgggtaccag ccattacgcg tggcggatgt    60

```
<210> SEQ ID NO 1144
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1144
cgcgaatgcc gctgggcatg aggagcggag cggagaatgc caaggacgcg tggcggatgt    60

<210> SEQ ID NO 1145
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1145
cgcgaatgcc gtcaactccc ctcagtggcc cagaaggtgg tgaccacgcg tggcggatgt    60

<210> SEQ ID NO 1146
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1146
cgcgaatgcc ttgcaggcag ccagaagctg ttgctgcttg cgcaaacgcg tggcggatgt    60

<210> SEQ ID NO 1147
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1147
cgcgaatgcc gtccctgccc agctccccaa gccactcagc tgcatacgcg tggcggatgt    60

<210> SEQ ID NO 1148
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1148
cgcgaatgcc gaaaccccaa ctcacctggc cagctaccgg agtggacgcg tggcggatgt    60

<210> SEQ ID NO 1149
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1149
cgcgaatgcc cctgatgtgt gagaagcgga tattggcggc agtgaacgcg tggcggatgt    60

<210> SEQ ID NO 1150
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 1150
cgcgaatgcc gaagaggttc accaggaagg ggtgtcccgc actggacgcg tggcggatgt    60

<210> SEQ ID NO 1151
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1151
cgcgaatgcc ggctgtttcc agacaccgga gcacgtgtgc ttcgtacgcg tggcggatgt    60

<210> SEQ ID NO 1152
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1152
cgcgaatgcc gcagcatcag gtccccaccg gccgagtact ccatcacgcg tggcggatgt    60

<210> SEQ ID NO 1153
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1153
cgcgaatgcc acatccacag cgacgtgttc tctgagcccc gtgccacgcg tggcggatgt    60

<210> SEQ ID NO 1154
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1154
cgcgaatgcc gaggcagggg cccgggctgg ggtccaggct cacatacgcg tggcggatgt    60

<210> SEQ ID NO 1155
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1155
cgcgaatgcc tttaaaactt ttaataaagg gaagaagacc aatatacgcg tggcggatgt    60

<210> SEQ ID NO 1156
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1156
cgcgaatgcc aatattgctc caacatccga agcatagaat caataacgcg tggcggatgt    60

<210> SEQ ID NO 1157
<211> LENGTH: 60

```
<212> TYPE: DNA
<213> ORGANISM: Artificial Sequence
<220> FEATURE:
<223> OTHER INFORMATION: Synthetic oligonucleotide

<400> SEQUENCE: 1157
cgcgaatgcc ctagcaactt ggaagatttg attcgggagc ggactacgcg tggcggatgt      60

<210> SEQ ID NO 1158
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1158
cgcgaatgcc ttttccgttt tctgtttttc aatttccagc tcttcacgcg tggcggatgt      60

<210> SEQ ID NO 1159
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1159
cgcgaatgcc gcttctaaca cagatgctac caccgtatgt gagaaacgcg tggcggatgt      60

<210> SEQ ID NO 1160
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1160
cgcgaatgcc gactacttgg accttgcggc gtccactcca tctgaacgcg tggcggatgt      60

<210> SEQ ID NO 1161
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1161
cgcgaatgcc cctcctctga gaggccgtcg tcataaatca gggagacgcg tggcggatgt      60

<210> SEQ ID NO 1162
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1162
cgcgaatgcc agacaccgct ggtggactgt aataatgccc ccctcacgcg tggcggatgt      60

<210> SEQ ID NO 1163
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1163
```
cgcgaatgcc ttgttttcaa tccatgtgga agggagggct cgaggacgcg tggcggatgt    60

<210> SEQ ID NO 1164
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1164
cgcgaatgcc actctatggt agaatttccc atgcatttac tagatacgcg tggcggatgt    60

<210> SEQ ID NO 1165
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1165
cgcgaatgcc aggaaggata gtgcaaaggg gacagcggtg ctagaacgcg tggcggatgt    60

<210> SEQ ID NO 1166
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1166
cgcgaatgcc cattttccta tttttatccc ctctaggact gttatacgcg tggcggatgt    60

<210> SEQ ID NO 1167
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1167
cgcgaatgcc aatttaaaat catcattaat tgttggatag tgttcacgcg tggcggatgt    60

<210> SEQ ID NO 1168
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1168
cgcgaatgcc cagcaagtga tcaaccttca gaaaatctga tttccacgcg tggcggatgt    60

<210> SEQ ID NO 1169
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1169
cgcgaatgcc taaataatgt ttcatatatg gcttacgtta aaataacgcg tggcggatgt    60

<210> SEQ ID NO 1170
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1170
cgcgaatgcc acagagagga agtcgtgcca gtgtaagctt ccagaacgcg tggcggatgt    60

<210> SEQ ID NO 1171
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1171
cgcgaatgcc tcttggggac ctcccacttt ggacctctga ggtaaacgcg tggcggatgt    60

<210> SEQ ID NO 1172
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1172
cgcgaatgcc ctctcctttt cttcagggag tctaactcca gctacacgcg tggcggatgt    60

<210> SEQ ID NO 1173
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1173
cgcgaatgcc ttacctcata aatcgctatg ttggagtttt catagacgcg tggcggatgt    60

<210> SEQ ID NO 1174
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1174
cgcgaatgcc gcatgtcaga cccgaactgg cctggagaga gtcctacgcg tggcggatgt    60

<210> SEQ ID NO 1175
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1175
cgcgaatgcc ccagtgttag tgccatcagc tctcgtgagt ggtacacgcg tggcggatgt    60

<210> SEQ ID NO 1176
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1176
cgcgaatgcc gtttccaaga tatccaaatg atagtgtata tgctaacgcg tggcggatgt    60

<210> SEQ ID NO 1177
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1177
cgcgaatgcc cattaatttt gccgctgagg gtgaaagcat ccagtacgcg tggcggatgt      60

<210> SEQ ID NO 1178
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1178
cgcgaatgcc gacacgtttg atagttaaca tttctttgtg aaaggacgcg tggcggatgt      60

<210> SEQ ID NO 1179
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1179
cgcgaatgcc aagcaaagag tcggctgaaa tgtcatttgc tgtctacgcg tggcggatgt      60

<210> SEQ ID NO 1180
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1180
cgcgaatgcc tcctttttcc tttttcctc aagtttagcc ctgtgacgcg tggcggatgt       60

<210> SEQ ID NO 1181
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1181
cgcgaatgcc agaagagaaa cggttaagag aagaagagaa ggtagacgcg tggcggatgt      60

<210> SEQ ID NO 1182
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1182
cgcgaatgcc acgggctggg acggggaagc tctgtgggaa acactacgcg tggcggatgt      60

<210> SEQ ID NO 1183
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1183
cgcgaatgcc ttgaacattt tctgtctctt ttccacaggt tttccacgcg tggcggatgt    60

<210> SEQ ID NO 1184
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1184
cgcgaatgcc cagactgtgc acgtctgaga catccagtac ttggtacgcg tggcggatgt    60

<210> SEQ ID NO 1185
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1185
cgcgaatgcc tgggaaaggg atgcttttttg gcctcaagtg taaaaacgcg tggcggatgt    60

<210> SEQ ID NO 1186
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1186
cgcgaatgcc aaagtcactg cagggcacag tcacttactt gcagtacgcg tggcggatgt    60

<210> SEQ ID NO 1187
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1187
cgcgaatgcc aagtaaaatg actgagattg tcacaaattt gctttacgcg tggcggatgt    60

<210> SEQ ID NO 1188
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1188
cgcgaatgcc ttggtcagct ttgctataac cacagtgcct tgaagacgcg tggcggatgt    60

<210> SEQ ID NO 1189
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1189
cgcgaatgcc gaaggcgatg aagagcttta ctttcattgt aagtgacgcg tggcggatgt    60

<210> SEQ ID NO 1190

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1190
cgcgaatgcc ttaatagggg tacatcataa taaagaaaag ccaaaacgcg tggcggatgt    60

<210> SEQ ID NO 1191
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1191
cgcgaatgcc gatcagagcc tgaatagatc cttgtcctct gcagtacgcg tggcggatgt    60

<210> SEQ ID NO 1192
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1192
cgcgaatgcc ccctggaag ggcagggagc ccgtcagcat ctcaaacgcg tggcggatgt     60

<210> SEQ ID NO 1193
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1193
cgcgaatgcc aaggaccgga aggagaccat gacactgatt ctgaaacgcg tggcggatgt    60

<210> SEQ ID NO 1194
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1194
cgcgaatgcc gagtccattg ttatcagggc agggctgggg cttacacgcg tggcggatgt    60

<210> SEQ ID NO 1195
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1195
cgcgaatgcc gacctccatc ttcaccaaga aatgttatct ctaatacgcg tggcggatgt    60

<210> SEQ ID NO 1196
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1196
```

-continued cgcgaatgcc caactccagt ccaggataac tgaggtctcg tttatacgcg tggcggatgt    60

<210> SEQ ID NO 1197
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1197
cgcgaatgcc gccctggac acaggaggcc ggaaagatgt tacctacgcg tggcggatgt    60

<210> SEQ ID NO 1198
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1198
cgcgaatgcc tatattccac ccacattttt tacatatgat gttgaacgcg tggcggatgt    60

<210> SEQ ID NO 1199
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1199
cgcgaatgcc aaacagtgtg agccatgcag cccaaatgtc cgcttacgcg tggcggatgt    60

<210> SEQ ID NO 1200
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1200
cgcgaatgcc ccgtggtgtt ggtgagtcca aactgtcgag ggaggacgcg tggcggatgt    60

<210> SEQ ID NO 1201
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1201
cgcgaatgcc tgacagtgac agaccttctg gcacatacta actacacgcg tggcggatgt    60

<210> SEQ ID NO 1202
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1202
cgcgaatgcc tctgacaccc cattaacggc atcaatctca aaggtacgcg tggcggatgt    60

<210> SEQ ID NO 1203
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 1203
cgcgaatgcc gctgagctcc ccaccaagac agtttgctgc ggtcaacgcg tggcggatgt    60

<210> SEQ ID NO 1204
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1204
cgcgaatgcc tagtatgtac tcaccagcct gattagttgt gatgcacgcg tggcggatgt    60

<210> SEQ ID NO 1205
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1205
cgcgaatgcc ctgccctcag ggggcagcat tgttggggga cacgaacgcg tggcggatgt    60

<210> SEQ ID NO 1206
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1206
cgcgaatgcc catagccagc tttaatcccc cggggctccc caggcacgcg tggcggatgt    60

<210> SEQ ID NO 1207
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1207
cgcgaatgcc gcacctgcaa ctgcttccct gaggaggaga agtgcacgcg tggcggatgt    60

<210> SEQ ID NO 1208
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1208
cgcgaatgcc acccactcac cctggatgtc ttcgggctcg cagaaacgcg tggcggatgt    60

<210> SEQ ID NO 1209
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1209
cgcgaatgcc tcatttgttt tacttgccgt ttcagggtat agcttacgcg tggcggatgt    60
```

<210> SEQ ID NO 1210
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1210
cgcgaatgcc taatcccacc ataagtagga aatccatagt gtgggacgcg tggcggatgt    60

<210> SEQ ID NO 1211
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1211
cgcgaatgcc ctttccatcc tggaactact aaatctaatg ctgggacgcg tggcggatgt    60

<210> SEQ ID NO 1212
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1212
cgcgaatgcc gtattaagaa caaagcatta cttaccatgc ttcatacgcg tggcggatgt    60

<210> SEQ ID NO 1213
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1213
cgcgaatgcc tttcatatag gattcacctt tatttgatct tattaacgcg tggcggatgt    60

<210> SEQ ID NO 1214
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1214
cgcgaatgcc gtgatcagtt ggtccttctc ggtcctttga ttgttacgcg tggcggatgt    60

<210> SEQ ID NO 1215
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1215
cgcgaatgcc cttgaatctg cttgtcctct taatcttcct ctccaacgcg tggcggatgt    60

<210> SEQ ID NO 1216
<211> LENGTH: 60
<212> TYPE: DNA
<213> ORGANISM: Artificial Sequence
<220> FEATURE:

```
<223> OTHER INFORMATION: Synthetic oligonucleotide

<400> SEQUENCE: 1216
cgcgaatgcc attttgctta catatctgct gcagtgtgat tattcacgcg tggcggatgt      60

<210> SEQ ID NO 1217
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1217
cgcgaatgcc aaccccctga tactctatag ggccggttgt tgctgacgcg tggcggatgt      60

<210> SEQ ID NO 1218
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1218
cgcgaatgcc caagcagtat ctgggcatgg tgaggcccac cactcacgcg tggcggatgt      60

<210> SEQ ID NO 1219
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1219
cgcgaatgcc tttggagaca ctgtgaacac agcttctcgg atggaacgcg tggcggatgt      60

<210> SEQ ID NO 1220
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1220
cgcgaatgcc atctctctat taggtactca cgtaagcctg tagatacgcg tggcggatgt      60

<210> SEQ ID NO 1221
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1221
cgcgaatgcc aaacatgatg ggcaatttac agtcattcag ttagtacgcg tggcggatgt      60

<210> SEQ ID NO 1222
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1222
cgcgaatgcc atctcattcc agcagcaatt cctctcagca ttcctacgcg tggcggatgt      60
```

```
<210> SEQ ID NO 1223
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1223
cgcgaatgcc atttggctga tatgggatat gttcacaggg accttacgcg tggcggatgt    60

<210> SEQ ID NO 1224
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1224
cgcgaatgcc acgagattgc tgttgacaag aatattgcga gctgcacgcg tggcggatgt    60

<210> SEQ ID NO 1225
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1225
cgcgaatgcc ttgtaaagtg tcagattttg gcctgtcccg agttaacgcg tggcggatgt    60

<210> SEQ ID NO 1226
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1226
cgcgaatgcc agtagttgta tagacagctt ctggatcatc ctctaacgcg tggcggatgt    60

<210> SEQ ID NO 1227
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1227
cgcgaatgcc gtaagaaaaa gtcatttact gcacttcttc atattacgcg tggcggatgt    60

<210> SEQ ID NO 1228
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1228
cgcgaatgcc acgagctccg agacagtgac agtgtctgcg acagcacgcg tggcggatgt    60

<210> SEQ ID NO 1229
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 1229
cgcgaatgcc gtaaagctga gtttgcggaa ggatgtctcc acgccacgcg tggcggatgt    60

<210> SEQ ID NO 1230
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1230
cgcgaatgcc cgagtctctg accagtggtg cctcactgct aactcacgcg tggcggatgt    60

<210> SEQ ID NO 1231
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1231
cgcgaatgcc tccttcctgc ccataatcat ggggcatttt gttgaacgcg tggcggatgt    60

<210> SEQ ID NO 1232
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1232
cgcgaatgcc cctctagaag gcaaaattta gcctgctgac aatttacgcg tggcggatgt    60

<210> SEQ ID NO 1233
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1233
cgcgaatgcc ttatgatttg ttttttaaggt tatattaagg aagatacgcg tggcggatgt    60

<210> SEQ ID NO 1234
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1234
cgcgaatgcc ggctgacgtc tttttggacg aggacaagga tcaagacgcg tggcggatgt    60

<210> SEQ ID NO 1235
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1235
cgcgaatgcc ttacaacgca atattttctc caaaaggcaa ggagcacgcg tggcggatgt    60

<210> SEQ ID NO 1236
<211> LENGTH: 60

```
<212> TYPE: DNA
<213> ORGANISM: Artificial Sequence
<220> FEATURE:
<223> OTHER INFORMATION: Synthetic oligonucleotide

<400> SEQUENCE: 1236
cgcgaatgcc atccttctgt ttctgtttca acgtctatgt cttctacgcg tggcggatgt    60

<210> SEQ ID NO 1237
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1237
cgcgaatgcc ccctatgtac agggacctgg caagaattgg tatcaacgcg tggcggatgt    60

<210> SEQ ID NO 1238
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1238
cgcgaatgcc actgctcaaa atcttattct ggtgcgtgat ggctgacgcg tggcggatgt    60

<210> SEQ ID NO 1239
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1239
cgcgaatgcc gtccaggcaa tgcgaaccca aatgcagcag atgcaacgcg tggcggatgt    60

<210> SEQ ID NO 1240
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1240
cgcgaatgcc attcagtact ggctcagacg ggaaccattc tgccgacgcg tggcggatgt    60

<210> SEQ ID NO 1241
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1241
cgcgaatgcc tacgtgaccg cgtccggacc aagatggaga gagacacgcg tggcggatgt    60

<210> SEQ ID NO 1242
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1242
```

```
cgcgaatgcc ttcaccacga atgggtgatt tacatcagcc aggatacgcg tggcggatgt      60
```

<210> SEQ ID NO 1243
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1243

```
cgcgaatgcc gctgcactat ggtaaagctt ctggccctgc ctgagacgcg tggcggatgt      60
```

<210> SEQ ID NO 1244
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1244

```
cgcgaatgcc ccacaggcaa gggcgaagga tgggtggggt aggagacgcg tggcggatgt      60
```

<210> SEQ ID NO 1245
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1245

```
cgcgaatgcc tctgtacact gtcccaccgc ctgcctggca ggccaacgcg tggcggatgt      60
```

<210> SEQ ID NO 1246
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1246

```
cgcgaatgcc ggccttatga tctgcttctc cggccctggc tccctacgcg tggcggatgt      60
```

<210> SEQ ID NO 1247
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1247

```
cgcgaatgcc gcgccgactc taccattgcc tttctccctc ttcccacgcg tggcggatgt      60
```

<210> SEQ ID NO 1248
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1248

```
cgcgaatgcc gaatgagata gagcttgccc tcggtctgga aggctacgcg tggcggatgt      60
```

<210> SEQ ID NO 1249
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1249
cgcgaatgcc tggacttcct gcgtggtggg gacctcttca cccggacgcg tggcggatgt    60

<210> SEQ ID NO 1250
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1250
cgcgaatgcc tctggcagta gatgtcagct cacctctttt gagagacgcg tggcggatgt    60

<210> SEQ ID NO 1251
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1251
cgcgaatgcc ttataggttt cagagaaatt atgttgaatc caataacgcg tggcggatgt    60

<210> SEQ ID NO 1252
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1252
cgcgaatgcc ggttaagagg cttggaatgt ccgggaaggc ttattacgcg tggcggatgt    60

<210> SEQ ID NO 1253
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1253
cgcgaatgcc atggcatcta tgttgaggat gtcaatgttt atttcacgcg tggcggatgt    60

<210> SEQ ID NO 1254
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1254
cgcgaatgcc aaaaggagtt tttaaaagcc atgacgtcct ttgctacgcg tggcggatgt    60

<210> SEQ ID NO 1255
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1255
cgcgaatgcc tgtgtcctgt gcagggatca ccaggaactt ctccaacgcg tggcggatgt    60

<210> SEQ ID NO 1256
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1256
cgcgaatgcc gccgtcgggg caggtcttgg tgctgggaga gcaggacgcg tggcggatgt        60

<210> SEQ ID NO 1257
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1257
cgcgaatgcc cactgcgatg ttgtggagac ccaagacatc aacatacgcg tggcggatgt        60

<210> SEQ ID NO 1258
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1258
cgcgaatgcc ttaaaccctg cttacggagg cagtcctgag ggcaaacgcg tggcggatgt        60

<210> SEQ ID NO 1259
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1259
cgcgaatgcc tttctaagtt ttcttctaat attattattg ttttgacgcg tggcggatgt        60

<210> SEQ ID NO 1260
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1260
cgcgaatgcc atttccagat ggattaaaga gctaaacata aaaaaacgcg tggcggatgt        60

<210> SEQ ID NO 1261
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1261
cgcgaatgcc gatttttgta tatggtgtga ggtaggtatc taagcacgcg tggcggatgt        60

<210> SEQ ID NO 1262
<211> LENGTH: 60
<212> TYPE: DNA
<213> ORGANISM: Artificial Sequence
<220> FEATURE:
<223> OTHER INFORMATION: Synthetic oligonucleotide -continued

<400> SEQUENCE: 1262
cgcgaatgcc aaagtgttgg gacaatgaac tattcattaa aaaaaacgcg tggcggatgt    60

<210> SEQ ID NO 1263
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1263
cgcgaatgcc tgccctgtgg ctgagagagc ccctcttttt atccaacgcg tggcggatgt    60

<210> SEQ ID NO 1264
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1264
cgcgaatgcc tgtacacagc ctctttgcta taagcccgtt tcctgacgcg tggcggatgt    60

<210> SEQ ID NO 1265
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1265
cgcgaatgcc gcgataagct ccagcattac agcacaggcc gaggtacgcg tggcggatgt    60

<210> SEQ ID NO 1266
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1266
cgcgaatgcc gtgggggtca gacaccgggt ctctgctttc tacttacgcg tggcggatgt    60

<210> SEQ ID NO 1267
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1267
cgcgaatgcc atgtattgct tggtaaaaga ttggcctcca atcaaacgcg tggcggatgt    60

<210> SEQ ID NO 1268
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1268
cgcgaatgcc aattacagtc cagaagttcc atagcctgtt caggtacgcg tggcggatgt    60

<210> SEQ ID NO 1269

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1269
cgcgaatgcc acccagatcc tatggttcga ggttttgctg ttcggacgcg tggcggatgt    60

<210> SEQ ID NO 1270
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1270
cgcgaatgcc aagtttgtca tctgttaaat atttttccaa gcaccacgcg tggcggatgt    60

<210> SEQ ID NO 1271
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1271
cgcgaatgcc tttctcagta tttaattcag ctagtacagg taaaaacgcg tggcggatgt    60

<210> SEQ ID NO 1272
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1272
cgcgaatgcc ggcattgttt tgttcctctg atgatgaaag tgaaaacgcg tggcggatgt    60

<210> SEQ ID NO 1273
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1273
cgcgaatgcc agcttttata tttccagact tcagtagtac ttgctacgcg tggcggatgt    60

<210> SEQ ID NO 1274
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1274
cgcgaatgcc gtgcttggcc tgacaaagag gaggctagtt agtagacgcg tggcggatgt    60

<210> SEQ ID NO 1275
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1275
```
cgcgaatgcc tgacttctac ttgttgatca gaaagggtcc cactgacgcg tggcggatgt    60

<210> SEQ ID NO 1276
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1276
cgcgaatgcc tgacgtttgc agaagatgga gggtaagaaa agcatacgcg tggcggatgt    60

<210> SEQ ID NO 1277
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1277
cgcgaatgcc gttgtgcaca gggacctgaa gcccagcaac atcctacgcg tggcggatgt    60

<210> SEQ ID NO 1278
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1278
cgcgaatgcc gcaggcactc gggattcccg gactcgtcca catacacgcg tggcggatgt    60

<210> SEQ ID NO 1279
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1279
cgcgaatgcc gcatctgtga ctttggtttt gccaaacagc tgcggacgcg tggcggatgt    60

<210> SEQ ID NO 1280
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1280
cgcgaatgcc gtgtagcaag gtgtcatgag gagcccattc tcagcacgcg tggcggatgt    60

<210> SEQ ID NO 1281
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1281
cgcgaatgcc agccaacttt gtggcgcctg aggtgagtgg cccagacgcg tggcggatgt    60

<210> SEQ ID NO 1282
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 1282
cgcgaatgcc tcttttctgc agactcagaa gtcaaaaacc tccttacgcg tggcggatgt      60

<210> SEQ ID NO 1283
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1283
cgcgaatgcc tccaataaag taaggccttc tgagttatca tctgaacgcg tggcggatgt      60

<210> SEQ ID NO 1284
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1284
cgcgaatgcc tttgttgagc ttcacctatc aagttgcccg aggaaacgcg tggcggatgt      60

<210> SEQ ID NO 1285
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1285
cgcgaatgcc ccttgaactt acatttttg aagccaaaaa ctccaacgcg tggcggatgt      60

<210> SEQ ID NO 1286
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1286
cgcgaatgcc aacctaaaaa taaatatgt gtttatgaca agttaacgcg tggcggatgt      60

<210> SEQ ID NO 1287
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1287
cgcgaatgcc tctccagttt cttcatcaag atgggttttg atgtgacgcg tggcggatgt      60

<210> SEQ ID NO 1288
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1288
cgcgaatgcc aaagacatct atcacacttg atgttgggcc tgagtacgcg tggcggatgt      60
```

<210> SEQ ID NO 1289
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1289
cgcgaatgcc aggtaatcct cctgggccat ctccagggtt aaaggacgcg tggcggatgt     60

<210> SEQ ID NO 1290
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1290
cgcgaatgcc atacaaagaa cagatgacac ccaagaacat tttccacgcg tggcggatgt     60

<210> SEQ ID NO 1291
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1291
cgcgaatgcc gcttttgctc accactaggg tcactgaccc tgtggacgcg tggcggatgt     60

<210> SEQ ID NO 1292
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1292
cgcgaatgcc agaagctgcc aagcagaaga aagaagcagc agaagacgcg tggcggatgt     60

<210> SEQ ID NO 1293
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1293
cgcgaatgcc aagacacagt ctctctcctg tgaaataaat gtcctacgcg tggcggatgt     60

<210> SEQ ID NO 1294
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1294
cgcgaatgcc tggcactgat tcactcagat tgtctgggaa aagacacgcg tggcggatgt     60

<210> SEQ ID NO 1295
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 1295
cgcgaatgcc aggattttg ctactgattt cttcctgttc ctttaacgcg tggcggatgt    60

<210> SEQ ID NO 1296
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1296
cgcgaatgcc gctagatcac cagtaactga aataagaact cacctacgcg tggcggatgt    60

<210> SEQ ID NO 1297
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1297
cgcgaatgcc ctggagaatc tggaagttca gatttaagac ttaaaacgcg tggcggatgt    60

<210> SEQ ID NO 1298
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1298
cgcgaatgcc aaccagttac agaaattaat gaagacagtg tattaacgcg tggcggatgt    60

<210> SEQ ID NO 1299
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1299
cgcgaatgcc tcaacacctt tttctggttg ggcagttggt ggaatacgcg tggcggatgt    60

<210> SEQ ID NO 1300
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1300
cgcgaatgcc tacattccta agaagaccta atttcaccag ggcgaacgcg tggcggatgt    60

<210> SEQ ID NO 1301
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1301
cgcgaatgcc accgctatct gatagagtct gtaaaggaac tgtagacgcg tggcggatgt    60

```
<210> SEQ ID NO 1302
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1302
cgcgaatgcc tagtagtcag caccttgaac acattcctcc taaagacgcg tggcggatgt    60

<210> SEQ ID NO 1303
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1303
cgcgaatgcc tgttttttag gtcgtgagta gtaagttcac tgctaacgcg tggcggatgt    60

<210> SEQ ID NO 1304
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1304
cgcgaatgcc ttagatttac ttcacctgta agtttggagg cacaaacgcg tggcggatgt    60

<210> SEQ ID NO 1305
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1305
cgcgaatgcc aggaggttat ctgtagagac agtcattttt ttgccacgcg tggcggatgt    60

<210> SEQ ID NO 1306
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1306
cgcgaatgcc tgtaaataaa gctataagta aaagtggcca actgcacgcg tggcggatgt    60

<210> SEQ ID NO 1307
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1307
cgcgaatgcc acatgaaata tttgcctcta aattagaact tgtggacgcg tggcggatgt    60

<210> SEQ ID NO 1308
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 1308
cgcgaatgcc tctctaaatg aactcaccta caataactta ccagcacgcg tggcggatgt    60

<210> SEQ ID NO 1309
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1309
cgcgaatgcc tttgattttg ttcttttaag ttttggtttt catttacgcg tggcggatgt    60

<210> SEQ ID NO 1310
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1310
cgcgaatgcc cagagaaatc tttaaaatct cccagtgaca ctcttacgcg tggcggatgt    60

<210> SEQ ID NO 1311
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1311
cgcgaatgcc atctcacttt cctgaagatt tcattcctg ccatcacgcg tggcggatgt    60

<210> SEQ ID NO 1312
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1312
cgcgaatgcc tctaagtcaa cctaagagtc ttagcctgga agcaaacgcg tggcggatgt    60

<210> SEQ ID NO 1313
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1313
cgcgaatgcc tgtgcaagaa tgttttctg cagaaagagg agaggacgcg tggcggatgt    60

<210> SEQ ID NO 1314
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1314
cgcgaatgcc gtgcctgaag gccttctgtt tcctgcagaa tattaacgcg tggcggatgt    60

<210> SEQ ID NO 1315
<211> LENGTH: 60

-continued

```
<212> TYPE: DNA
<213> ORGANISM: Artificial Sequence
<220> FEATURE:
<223> OTHER INFORMATION: Synthetic oligonucleotide

<400> SEQUENCE: 1315
cgcgaatgcc tctggcaatt ggacatgctt cgtgttgttc taacaacgcg tggcggatgt      60

<210> SEQ ID NO 1316
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1316
cgcgaatgcc ggaaagtagc cgtggaggct gtcattcaga gtcatacgcg tggcggatgt      60

<210> SEQ ID NO 1317
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1317
cgcgaatgcc tttttatttt taaacccttt tttcttgaca tccaaacgcg tggcggatgt      60

<210> SEQ ID NO 1318
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1318
cgcgaatgcc taaggatgca agtaaaaatt taaacctttc caatgacgcg tggcggatgt      60

<210> SEQ ID NO 1319
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1319
cgcgaatgcc gccagacatc ctaatttcac tttggtcagt ttcctacgcg tggcggatgt      60

<210> SEQ ID NO 1320
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1320
cgcgaatgcc acatgcacag gacaaccaag ttcaagaacc tctcaacgcg tggcggatgt      60

<210> SEQ ID NO 1321
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1321
```
cgcgaatgcc cgggagagct gactttagtt aatgagagaa gtttcacgcg tggcggatgt    60

<210> SEQ ID NO 1322
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1322
cgcgaatgcc ctgggcccac tgaagataat gacttgtcta ggaagacgcg tggcggatgt    60

<210> SEQ ID NO 1323
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1323
cgcgaatgcc cctgtgtatc ttctaccagg tgcttgggca actgcacgcg tggcggatgt    60

<210> SEQ ID NO 1324
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1324
cgcgaatgcc aaaaagaaaa tcagcctgca ccccagcatc agatcacgcg tggcggatgt    60

<210> SEQ ID NO 1325
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1325
cgcgaatgcc cgacaggcta gaagttggca aaagtggttc acaatacgcg tggcggatgt    60

<210> SEQ ID NO 1326
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1326
cgcgaatgcc attgttaaca ggtccaagga agaagtcacc tcacaacgcg tggcggatgt    60

<210> SEQ ID NO 1327
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1327
cgcgaatgcc tcacttgaat aaataatttt tcgtgctgat atttgacgcg tggcggatgt    60

<210> SEQ ID NO 1328
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1328
cgcgaatgcc gtgaaaggta aatcaagatg tgtttgatga tgatgacgcg tggcggatgt    60

<210> SEQ ID NO 1329
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1329
cgcgaatgcc aaacagctgt tatacccatt aatggttcac ctcgaacgcg tggcggatgt    60

<210> SEQ ID NO 1330
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1330
cgcgaatgcc atccgtgcac tcctgttctg acctcgcctg ggtgtacgcg tggcggatgt    60

<210> SEQ ID NO 1331
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1331
cgcgaatgcc agcaaaacaa ctagaaaatg atacaagaat tattgacgcg tggcggatgt    60

<210> SEQ ID NO 1332
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1332
cgcgaatgcc atctatatta cattcatgtt ctttacagag aacttacgcg tggcggatgt    60

<210> SEQ ID NO 1333
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1333
cgcgaatgcc gaggtaattt aacttcatga tttctttaaa acagtacgcg tggcggatgt    60

<210> SEQ ID NO 1334
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1334
cgcgaatgcc caactccatg ggaagaacct ggttttagt gacggacgcg tggcggatgt    60

<210> SEQ ID NO 1335
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1335
cgcgaatgcc aggagcccac accaattgtc tcctttacca cgtagacgcg tggcggatgt    60

<210> SEQ ID NO 1336
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1336
cgcgaatgcc actctgagtg caagcgctgt gtccacaagg ccaccacgcg tggcggatgt    60

<210> SEQ ID NO 1337
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1337
cgcgaatgcc gtcaggaggc ccaccttgac agcatactcc atgttacgcg tggcggatgt    60

<210> SEQ ID NO 1338
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1338
cgcgaatgcc cacgtctcgg ccaaggctgc tgggttgggg gcaggacgcg tggcggatgt    60

<210> SEQ ID NO 1339
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1339
cgcgaatgcc gagctcaggc accatccctc cccaccagac ggggaacgcg tggcggatgt    60

<210> SEQ ID NO 1340
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1340
cgcgaatgcc tgcagatgta tgaaaggtgt gtggccgaga cctccacgcg tggcggatgt    60

<210> SEQ ID NO 1341
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1341
cgcgaatgcc gggtccaggg tcctttctgg ccatggagca ggccaacgcg tggcggatgt    60

<210> SEQ ID NO 1342
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1342
cgcgaatgcc tgtcaccctg acactgccac atgcaccccc tttctacgcg tggcggatgt    60

<210> SEQ ID NO 1343
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1343
cgcgaatgcc ctgaaggatc ccgcttgctc ttatcaatga cctgaacgcg tggcggatgt    60

<210> SEQ ID NO 1344
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1344
cgcgaatgcc aagagattga gattcttctg cggtatggcc agcacacgcg tggcggatgt    60

<210> SEQ ID NO 1345
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1345
cgcgaatgcc cccccactca catctttcag agtgatgatg ttgggacgcg tggcggatgt    60

<210> SEQ ID NO 1346
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1346
cgcgaatgcc ctgcctcggc ttggtctcgg cctgcgggcc gtcggacgcg tggcggatgt    60

<210> SEQ ID NO 1347
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1347
cgcgaatgcc aggagcagta gtagataatc cagggccatc gccggacgcg tggcggatgt    60

<210> SEQ ID NO 1348

-continued

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1348
cgcgaatgcc cctggcatcc gcagtggctg cgatggaagg taacgacgcg tggcggatgt      60

<210> SEQ ID NO 1349
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1349
cgcgaatgcc ccggcaccag cagccaactt gctccgtgga gggtaacgcg tggcggatgt      60

<210> SEQ ID NO 1350
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1350
cgcgaatgcc gttcctggaa ggtgacgtga aagatcactg tgcagacgcg tggcggatgt      60

<210> SEQ ID NO 1351
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1351
cgcgaatgcc ccaaatggca attgttccag aagtcaagat tgctgacgcg tggcggatgt      60

<210> SEQ ID NO 1352
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1352
cgcgaatgcc gacttacttc tcggtcagtg tactgccctc ctcccacgcg tggcggatgt      60

<210> SEQ ID NO 1353
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1353
cgcgaatgcc atttcacaaa agaccaatgt tggtcagaga caggtacgcg tggcggatgt      60

<210> SEQ ID NO 1354
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1354
```
cgcgaatgcc ggtcgggtac agactctcat ttgctggctg gacaaacgcg tggcggatgt    60

<210> SEQ ID NO 1355
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1355
cgcgaatgcc tatgaatagt ggtatacaaa tatatttcca tctttacgcg tggcggatgt    60

<210> SEQ ID NO 1356
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1356
cgcgaatgcc agttagggta aagtgaaaac acaattttct ggataacgcg tggcggatgt    60

<210> SEQ ID NO 1357
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1357
cgcgaatgcc cctaagactg tacccatct ggagacctga gccccacgcg tggcggatgt    60

<210> SEQ ID NO 1358
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1358
cgcgaatgcc ttcaccatgg gagaaggagg gggttcccga ctcagacgcg tggcggatgt    60

<210> SEQ ID NO 1359
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1359
cgcgaatgcc gaagcagagg aggaaaaaat tgacaacacc atccaacgcg tggcggatgt    60

<210> SEQ ID NO 1360
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1360
cgcgaatgcc ctcaccttca gcctgcccag ccgagccttc agtctacgcg tggcggatgt    60

<210> SEQ ID NO 1361
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 1361
cgcgaatgcc gatcaaaggg aacggaccta ctcaacagta aaaacacgcg tggcggatgt    60

<210> SEQ ID NO 1362
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1362
cgcgaatgcc gtttcagatt attaatggag gctgaagtag acttgacgcg tggcggatgt    60

<210> SEQ ID NO 1363
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1363
cgcgaatgcc caggaacagt gtatgttttc cagattcggg cttttacgcg tggcggatgt    60

<210> SEQ ID NO 1364
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1364
cgcgaatgcc agtctgggac tgtaatttcc ataaccagca gcagtacgcg tggcggatgt    60

<210> SEQ ID NO 1365
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1365
cgcgaatgcc tgatgttgct acactagagg aagctacagg taaaaacgcg tggcggatgt    60

<210> SEQ ID NO 1366
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1366
cgcgaatgcc ggaatccaaa ccaaaggcat aattaccttc aaacaacgcg tggcggatgt    60

<210> SEQ ID NO 1367
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1367
cgcgaatgcc cttctaaatt acgaaaaaat gttaaaaagt cataaacgcg tggcggatgt    60
```

<210> SEQ ID NO 1368
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1368
cgcgaatgcc aatatataag ttcacatgtc ctgaaaagaa aaacaacgcg tggcggatgt    60

<210> SEQ ID NO 1369
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1369
cgcgaatgcc tgacacaacc cagcagttcg taagtagttc acagaacgcg tggcggatgt    60

<210> SEQ ID NO 1370
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1370
cgcgaatgcc cataaaaatc ttttttttta agtgaaaaat aacatacgcg tggcggatgt    60

<210> SEQ ID NO 1371
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1371
cgcgaatgcc gtgattaaag ccattgagga aggctatcgg ttaccacgcg tggcggatgt    60

<210> SEQ ID NO 1372
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1372
cgcgaatgcc gctggtggag cgcaatgggg cagtccattg gagggacgcg tggcggatgt    60

<210> SEQ ID NO 1373
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1373
cgcgaatgcc tgatgctaga ctgctggcag aaggagagga gcgacacgcg tggcggatgt    60

<210> SEQ ID NO 1374
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 1374
cgcgaatgcc tccaacatgt tgacaatctg cccaaattta ggcctacgcg tggcggatgt        60

<210> SEQ ID NO 1375
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1375
cgcgaatgcc caaactcatc cgcaaccccca acagcttgaa gaggaacgcg tggcggatgt        60

<210> SEQ ID NO 1376
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1376
cgcgaatgcc agtaagcatg gctgacctgg agctctccgt ccctgacgcg tggcggatgt        60

<210> SEQ ID NO 1377
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1377
cgcgaatgcc tgtctttttc agggatgtga tgagtttagg gatcaacgcg tggcggatgt        60

<210> SEQ ID NO 1378
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1378
cgcgaatgcc gctgctcatg attttctttt gatgaccaac cagtgacgcg tggcggatgt        60

<210> SEQ ID NO 1379
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1379
cgcgaatgcc attcagacta tgagagcaca aatgctacat ttacaacgcg tggcggatgt        60

<210> SEQ ID NO 1380
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1380
cgcgaatgcc ggagaaatgc atatcacact tgaatgccag ttccaacgcg tggcggatgt        60

```
<210> SEQ ID NO 1381
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1381
cgcgaatgcc ttgatgagtc ccgggggctg tttcagggcg aagctacgcg tggcggatgt      60

<210> SEQ ID NO 1382
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1382
cgcgaatgcc tctgggcttc agtgctcaga aactggggca tgcctacgcg tggcggatgt      60

<210> SEQ ID NO 1383
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1383
cgcgaatgcc gcctcttgcg ggccctgttc aagcggaatc ctgccacgcg tggcggatgt      60

<210> SEQ ID NO 1384
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1384
cgcgaatgcc cctcccctga gctggggctg cttaccgagc cggttacgcg tggcggatgt      60

<210> SEQ ID NO 1385
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1385
cgcgaatgcc ttgtttttgt ttattcgttt tttctttta atctaacgcg tggcggatgt      60

<210> SEQ ID NO 1386
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1386
cgcgaatgcc tgcagtagcc gttctggtgt ccattaacgt ttctgacgcg tggcggatgt      60

<210> SEQ ID NO 1387
<211> LENGTH: 60
<212> TYPE: DNA
<213> ORGANISM: Artificial Sequence
<220> FEATURE:
<223> OTHER INFORMATION: Synthetic oligonucleotide
```

```
<400> SEQUENCE: 1387
cgcgaatgcc gagctgggct ggacggccaa tcctgcgtcc ggggtacgcg tggcggatgt    60

<210> SEQ ID NO 1388
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1388
cgcgaatgcc catagcagga ctgaaagacg aatggtttga tactcacgcg tggcggatgt    60

<210> SEQ ID NO 1389
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1389
cgcgaatgcc ctccttcctt gcagaccttt ctgcccgtga agtggacgcg tggcggatgt    60

<210> SEQ ID NO 1390
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1390
cgcgaatgcc gtgtagaggt tgtcaaagat gctctcagga gccatacgcg tggcggatgt    60

<210> SEQ ID NO 1391
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1391
cgcgaatgcc cacactgagt gatgtctggt cttatggcat tctgcacgcg tggcggatgt    60

<210> SEQ ID NO 1392
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1392
cgcgaatgcc tgtcaggccc ataccaaggg aaaagatctc ccagaacgcg tggcggatgt    60

<210> SEQ ID NO 1393
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1393
cgcgaatgcc aggaaaactt tgagttcctg atcgtgtcca gcacgacgcg tggcggatgt    60

<210> SEQ ID NO 1394
<211> LENGTH: 60
```

<212> TYPE: DNA
<213> ORGANISM: Artificial Sequence
<220> FEATURE:
<223> OTHER INFORMATION: Synthetic oligonucleotide

<400> SEQUENCE: 1394
cgcgaatgcc tcaaaactgg ctgcctcaaa gtgccacgtc tgaccacgcg tggcggatgt    60

<210> SEQ ID NO 1395
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1395
cgcgaatgcc ggagcgggat gcctgggtcc aggccatcga gagtcacgcg tggcggatgt    60

<210> SEQ ID NO 1396
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1396
cgcgaatgcc gctgctctca cagcattgca gactggctag gatctacgcg tggcggatgt    60

<210> SEQ ID NO 1397
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1397
cgcgaatgcc aaggtcaagg taagagtttg aggtggagtg gaggaacgcg tggcggatgt    60

<210> SEQ ID NO 1398
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1398
cgcgaatgcc tggccgtcag caccagggtc agttcctgcg gccagacgcg tggcggatgt    60

<210> SEQ ID NO 1399
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1399
cgcgaatgcc ttggcaacga cacggccgaa gtcgtgtgag aggagacgcg tggcggatgt    60

<210> SEQ ID NO 1400
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1400
cgcgaatgcc ctccaagccc cacctccttc tcagacacct ctgctacgcg tggcggatgt    60

<210> SEQ ID NO 1401
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1401
cgcgaatgcc gcagagtcag tgccaaccca aaccctctct gcagcacgcg tggcggatgt    60

<210> SEQ ID NO 1402
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1402
cgcgaatgcc gatggccacg gcctcgcttt ggctgtctgt gcgcaacgcg tggcggatgt    60

<210> SEQ ID NO 1403
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1403
cgcgaatgcc caggcgatcc ggaacgccaa ggggaattca atctgacgcg tggcggatgt    60

<210> SEQ ID NO 1404
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1404
cgcgaatgcc cctcctggca ctcactgggg gccccgcagt ccacgacgcg tggcggatgt    60

<210> SEQ ID NO 1405
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1405
cgcgaatgcc cagcggaggg gctagggagt gtagtgaatg ccgggacgcg tggcggatgt    60

<210> SEQ ID NO 1406
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1406
cgcgaatgcc gtagaggtcg gctcccagcc gggcagcaca ggcacacgcg tggcggatgt    60

<210> SEQ ID NO 1407
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 1407
cgcgaatgcc gctccttccg cagacccac gtgggccagc ttgaaacgcg tggcggatgt    60

<210> SEQ ID NO 1408
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1408
cgcgaatgcc tgccagaaca ctcgatgcag atgagggcgc ccaggacgcg tggcggatgt    60

<210> SEQ ID NO 1409
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1409
cgcgaatgcc tccaccgcaa cctgggcaca cacctgtccc gcgttacgcg tggcggatgt    60

<210> SEQ ID NO 1410
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1410
cgcgaatgcc agctcccgtg gccagtcgtc caagtccagc gagcgacgcg tggcggatgt    60

<210> SEQ ID NO 1411
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1411
cgcgaatgcc cctggtgctg acggctattg gcaacgacac ggccaacgcg tggcggatgt    60

<210> SEQ ID NO 1412
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1412
cgcgaatgcc acggcctcgc gtgtcgcttt cccacacgcg gttggacgcg tggcggatgt    60

<210> SEQ ID NO 1413
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1413
cgcgaatgcc gccaagccct cgcgggactc ttcgcggtaa gcgtgacgcg tggcggatgt    60
```

<210> SEQ ID NO 1414
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1414
cgcgaatgcc acaccctcag caaccctccc cccgctctgt tccctacgcg tggcggatgt     60

<210> SEQ ID NO 1415
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1415
cgcgaatgcc gcgaacctga dacggtcccg tgggtagggg cagaaacgcg tggcggatgt     60

<210> SEQ ID NO 1416
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1416
cgcgaatgcc caacggaaaa ggctctaggg accccagcc aggacacgcg tggcggatgt     60

<210> SEQ ID NO 1417
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1417
cgcgaatgcc atccctggtc ttgcagggag gagcgcgagt cgtggacgcg tggcggatgt     60

<210> SEQ ID NO 1418
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1418
cgcgaatgcc gccaggaaca gtagctgctc gtacttggcg cgaatacgcg tggcggatgt     60

<210> SEQ ID NO 1419
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1419
cgcgaatgcc gccgctgagc acctcggagg agccgctggg ccgccacgcg tggcggatgt     60

<210> SEQ ID NO 1420
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1420
cgcgaatgcc agccacgtcc tgggcctgca cggcggccca cagctacgcg tggcggatgt    60

<210> SEQ ID NO 1421
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1421
cgcgaatgcc accgttctcc tgcttttggc ccatgcgcga cacggacgcg tggcggatgt    60

<210> SEQ ID NO 1422
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1422
cgcgaatgcc gcagctgtgg gtcctctacg ctggtgtcga gcggcacgcg tggcggatgt    60

<210> SEQ ID NO 1423
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1423
cgcgaatgcc gctccccact ccacctggcg gccgagctcg cccacacgcg tggcggatgt    60

<210> SEQ ID NO 1424
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1424
cgcgaatgcc tcacgtaccc acagcagcag ttgcgtgatg acgacacgcg tggcggatgt    60

<210> SEQ ID NO 1425
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1425
cgcgaatgcc gctgggggga ggaaaggggg tctttgaggc ttcatacgcg tggcggatgt    60

<210> SEQ ID NO 1426
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1426
cgcgaatgcc aatttcgggc tttcccgcgc caggcgtttt ccgagacgcg tggcggatgt    60

<210> SEQ ID NO 1427

<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1427
cgcgaatgcc cccagaggga ccccggaagt aggcttggcc atgtgacgcg tggcggatgt   60

<210> SEQ ID NO 1428
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1428
cgcgaatgcc gtccccaggg cgcccacacc cggcgccgcc tccccacgcg tggcggatgt   60

<210> SEQ ID NO 1429
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1429
cgcgaatgcc gcgcggtcac gcggccgttt ccgccctcta gtacgacgcg tggcggatgt   60

<210> SEQ ID NO 1430
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1430
cgcgaatgcc gcggccctgg gcgtcacggg ccgccacgtc cgcgcacgcg tggcggatgt   60

<210> SEQ ID NO 1431
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1431
cgcgaatgcc acggcgctgt tctacgcccg ccaggctgga agccaacgcg tggcggatgt   60

<210> SEQ ID NO 1432
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1432
cgcgaatgcc ggcagccgtg ctggagaagg atgtcggcgc acagcacgcg tggcggatgt   60

<210> SEQ ID NO 1433
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1433

```
cgcgaatgcc cgggtgaggg cggcagcgcg gccaccacgc ccagcacgcg tggcggatgt    60
```

<210> SEQ ID NO 1434
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1434

```
cgcgaatgcc ctgggcgtgg cggtgatgct gggcgtggtg gccgcacgcg tggcggatgt    60
```

<210> SEQ ID NO 1435
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1435

```
cgcgaatgcc cccccgccgc cggagcagcg ccgctagcgt gggccacgcg tggcggatgt    60
```

<210> SEQ ID NO 1436
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1436

```
cgcgaatgcc gggcaactat accagcgcaa ccggggcgtc ggcgcacgcg tggcggatgt    60
```

<210> SEQ ID NO 1437
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1437

```
cgcgaatgcc ggcctccatc tgcaccacag aacctcattt tcaacacgcg tggcggatgt    60
```

<210> SEQ ID NO 1438
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1438

```
cgcgaatgcc ggactccatt ccaaacttac tgtggtttgg ttgatacgcg tggcggatgt    60
```

<210> SEQ ID NO 1439
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1439

```
cgcgaatgcc tcctgcagac aatgggggaa gaaacgatgt gacctacgcg tggcggatgt    60
```

<210> SEQ ID NO 1440
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 1440
cgcgaatgcc ctgctcccaa ctgcaccgct tacacaatat tctgtacgcg tggcggatgt    60

<210> SEQ ID NO 1441
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1441
cgcgaatgcc ggcgaatgtg ttccctgtgg gagtaacatt ggataacgcg tggcggatgt    60

<210> SEQ ID NO 1442
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1442
cgcgaatgcc catagttatc ctctaatcca gtctgctggg gcatgacgcg tggcggatgt    60

<210> SEQ ID NO 1443
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1443
cgcgaatgcc tcactgtcat ggacctgcta gcccacgcta attatacgcg tggcggatgt    60

<210> SEQ ID NO 1444
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1444
cgcgaatgcc tcagaaactc catttacagc ttcaacttca aaagtacgcg tggcggatgt    60

<210> SEQ ID NO 1445
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1445
cgcgaatgcc cttaagccga tcccagaggc tctttgctgc tgtcaacgcg tggcggatgt    60

<210> SEQ ID NO 1446
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1446
cgcgaatgcc aacacaaaac atacctgctt gaccagtggt gatacacgcg tggcggatgt    60
```

<210> SEQ ID NO 1447
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1447
cgcgaatgcc tctcctcttt ctcatcacca tctcttaaca tcacaacgcg tggcggatgt    60

<210> SEQ ID NO 1448
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1448
cgcgaatgcc acctcgtgat ttcggccttc tctgctttaa tgcgcacgcg tggcggatgt    60

<210> SEQ ID NO 1449
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1449
cgcgaatgcc tcttccagaa accaaagact ccacaggccc caagacgcg tggcggatgt    60

<210> SEQ ID NO 1450
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1450
cgcgaatgcc ctgaaaccca aaagcaaagg cagccggctg ctcacacgcg tggcggatgt    60

<210> SEQ ID NO 1451
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1451
cgcgaatgcc gcccaggaga aattaacaga atccaaccag aagctacgcg tggcggatgt    60

<210> SEQ ID NO 1452
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1452
cgcgaatgcc caagtctccg ctccagagcc tcccgcagca gccccacgcg tggcggatgt    60

<210> SEQ ID NO 1453
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 1453
cgcgaatgcc gggagctgcc cgccgaccac cccaagggc ggctgacgcg tggcggatgt    60

<210> SEQ ID NO 1454
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1454
cgcgaatgcc gcagcggagg aggccgcagc gagctcttct cgcagacgcg tggcggatgt    60

<210> SEQ ID NO 1455
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1455
cgcgaatgcc cttcagcacc cgcctggccg ggccctttcc cgccaacgcg tggcggatgt    60

<210> SEQ ID NO 1456
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1456
cgcgaatgcc gagcggcgcg ggcttgcaca gggtgctgta gtgcgacgcg tggcggatgt    60

<210> SEQ ID NO 1457
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1457
cgcgaatgcc acaggtgggt ctgagaccct accccacccc tgcagacgcg tggcggatgt    60

<210> SEQ ID NO 1458
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1458
cgcgaatgcc tgttattaac tgtgtttgtg tattatgttt tatttacgcg tggcggatgt    60

<210> SEQ ID NO 1459
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1459
cgcgaatgcc cccttgaatt gttttttgaat ccagtagatt gactaacgcg tggcggatgt    60

```
<210> SEQ ID NO 1460
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1460
cgcgaatgcc gagctgggct ggatctctta tccatcacat ggggtacgcg tggcggatgt    60

<210> SEQ ID NO 1461
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1461
cgcgaatgcc gagaaaatgt ttccttgtga tagtttattg aactcacgcg tggcggatgt    60

<210> SEQ ID NO 1462
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1462
cgcgaatgcc cagggcatgg gctacctcca cgccaaggga atcctacgcg tggcggatgt    60

<210> SEQ ID NO 1463
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1463
cgcgaatgcc catagaagac gttctttgac ttgaggtcct tgtgtacgcg tggcggatgt    60

<210> SEQ ID NO 1464
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1464
cgcgaatgcc acaacggcaa agtggtcatc acggactttg gactcacgcg tggcggatgt    60

<210> SEQ ID NO 1465
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1465
cgcgaatgcc cacctgccag cctgcagcac cccagaaatg ctgaaacgcg tggcggatgt    60

<210> SEQ ID NO 1466
<211> LENGTH: 60
<212> TYPE: DNA
<213> ORGANISM: Artificial Sequence
<220> FEATURE:
<223> OTHER INFORMATION: Synthetic oligonucleotide
```

```
<400> SEQUENCE: 1466
cgcgaatgcc ggccgccgga ggagcgcggg tgacctggcg gcggcacgcg tggcggatgt    60

<210> SEQ ID NO 1467
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1467
cgcgaatgcc ggccagggct ccttgagctg ggcgagcggc atctcacgcg tggcggatgt    60

<210> SEQ ID NO 1468
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1468
cgcgaatgcc gctcatggag ctagtgcctc tggacccgga ggtgaacgcg tggcggatgt    60

<210> SEQ ID NO 1469
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1469
cgcgaatgcc gccgcgggcg cccgtccccc gccccgctca ctcacacgcg tggcggatgt    60

<210> SEQ ID NO 1470
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1470
cgcgaatgcc gaaatctccc ccggccagct gagcctggag gacctacgcg tggcggatgt    60

<210> SEQ ID NO 1471
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1471
cgcgaatgcc cagtctcgca cacctgttca tccgtcatct ccaagacgcg tggcggatgt    60

<210> SEQ ID NO 1472
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1472
cgcgaatgcc tggagaaata cggagccaac cgggaggagt gtgccacgcg tggcggatgt    60

<210> SEQ ID NO 1473
<211> LENGTH: 60
```

```
<212> TYPE: DNA
<213> ORGANISM: Artificial Sequence
<220> FEATURE:
<223> OTHER INFORMATION: Synthetic oligonucleotide

<400> SEQUENCE: 1473
cgcgaatgcc acattcctga ggcaggagag ggaggcgttg aggcgacgcg tggcggatgt      60

<210> SEQ ID NO 1474
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1474
cgcgaatgcc ccacatgtca ggtgagcagg ccccggggtc ggggaacgcg tggcggatgt      60

<210> SEQ ID NO 1475
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1475
cgcgaatgcc agctgctgtg dacggcccct gaactgttga gagctacgcg tggcggatgt      60

<210> SEQ ID NO 1476
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1476
cgcgaatgcc tctcctgcaa aagaacctaa cctgctgcct cttggacgcg tggcggatgt      60

<210> SEQ ID NO 1477
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1477
cgcgaatgcc tgtctatagc tttgccatca tcatgcaaga agtgaacgcg tggcggatgt      60

<210> SEQ ID NO 1478
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1478
cgcgaatgcc cagatccatc atgcagaatg gggtaccccg gaccaacgcg tggcggatgt      60

<210> SEQ ID NO 1479
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1479
```
cgcgaatgcc ccagctcaag gtaagcggga ggtgagaaaa gggccacgcg tggcggatgt    60

<210> SEQ ID NO 1480
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1480
cgcgaatgcc agtgagcctc gcagctggtc cctgctagag cagctacgcg tggcggatgt    60

<210> SEQ ID NO 1481
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1481
cgcgaatgcc ccccggggc cgccaggtct gccccggcca ggcccacgcg tggcggatgt    60

<210> SEQ ID NO 1482
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1482
cgcgaatgcc tacagcagca gctggagctg gagcgggagc ggctgacgcg tggcggatgt    60

<210> SEQ ID NO 1483
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1483
cgcgaatgcc tccttcagct tcagctcctt gcggatttcc cgccgacgcg tggcggatgt    60

<210> SEQ ID NO 1484
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1484
cgcgaatgcc gggtgctgag aacctgcggc gggccaccac tgaccacgcg tggcggatgt    60

<210> SEQ ID NO 1485
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1485
cgcgaatgcc cagcagcagc tctacggggc ccaggctgcg gcccaacgcg tggcggatgt    60

<210> SEQ ID NO 1486
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1486
cgcgaatgcc cggggctcct cgcgccgcct cgacctgctg caccaacgcg tggcggatgt    60

<210> SEQ ID NO 1487
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1487
cgcgaatgcc gaagcaccac gtgggcgtgc agctcctgca gctgcacgcg tggcggatgt    60

<210> SEQ ID NO 1488
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1488
cgcgaatgcc ccgacccggc ggccacccac ggtgagctgg gatgcacgcg tggcggatgt    60

<210> SEQ ID NO 1489
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1489
cgcgaatgcc gaatgatcaa cagcatcaag cagctgagct tgaatacgcg tggcggatgt    60

<210> SEQ ID NO 1490
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1490
cgcgaatgcc tgttatcggt gaatctggaa taacgtcttc ctcacacgcg tggcggatgt    60

<210> SEQ ID NO 1491
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1491
cgcgaatgcc gccttctcat tttctggcgt taaccggcta cgaagacgcg tggcggatgt    60

<210> SEQ ID NO 1492
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1492
cgcgaatgcc tttgttctat gtatcggaca tgggggttct cctttacgcg tggcggatgt    60

<210> SEQ ID NO 1493
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1493
cgcgaatgcc cacatactaa attggagcac tctgtgtgtg caaatacgcg tggcggatgt    60

<210> SEQ ID NO 1494
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1494
cgcgaatgcc aaccagagaa ctaaaataca actccaactc ttaccacgcg tggcggatgt    60

<210> SEQ ID NO 1495
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1495
cgcgaatgcc ggagggaaga tccctgtgag atggacagct ccagaacgcg tggcggatgt    60

<210> SEQ ID NO 1496
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1496
cgcgaatgcc cgctggctga agtgaacttg cggtaggcga tggccacgcg tggcggatgt    60

<210> SEQ ID NO 1497
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1497
cgcgaatgcc acgtttggag ctatgggatc gtcatgtggg aagtcacgcg tggcggatgt    60

<210> SEQ ID NO 1498
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1498
cgcgaatgcc gacatatccc aatagggtct ctctccaaat gacatacgcg tggcggatgt    60

<210> SEQ ID NO 1499
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1499
cgcgaatgcc caaccaagat gtgagtgtca gcagcacttg gtcacacgcg tggcggatgt    60

<210> SEQ ID NO 1500
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1500
cgcgaatgcc atagaaaccg aggtatgaaa ttcgctggag ggtcaacgcg tggcggatgt    60

<210> SEQ ID NO 1501
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1501
cgcgaatgcc aatatattca tgtccatctg ggctgattga ttcaaacgcg tggcggatgt    60

<210> SEQ ID NO 1502
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1502
cgcgaatgcc tatgtggacc cgatgcagct gccttatgac tcaagacgcg tggcggatgt    60

<210> SEQ ID NO 1503
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1503
cgcgaatgcc taccaagcac tagtccatct cttggaaact cccatacgcg tggcggatgt    60

<210> SEQ ID NO 1504
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1504
cgcgaatgcc atcgggaaag tctgtgtgga aaactgccag gcattacgcg tggcggatgt    60

<210> SEQ ID NO 1505
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1505
cgcgaatgcc aggaatgcag cttgtactgg acgttgatgc cactgacgcg tggcggatgt    60

<210> SEQ ID NO 1506

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1506
cgcgaatgcc ctggtgccaa ctgcagcacg ctaggggtgg tcaccacgcg tggcggatgt     60

<210> SEQ ID NO 1507
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1507
cgcgaatgcc ttcacaaaca ggatccccga ggtgtcctcg gctgaacgcg tggcggatgt     60

<210> SEQ ID NO 1508
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1508
cgcgaatgcc tgacaccaag gccctgcggc ggcccaagtg tgccgacgcg tggcggatgt     60

<210> SEQ ID NO 1509
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1509
cgcgaatgcc ctgctggtcg gtggccacca ccatgtagtg aagttacgcg tggcggatgt     60

<210> SEQ ID NO 1510
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1510
cgcgaatgcc acctctaggc aggcccaggc ccagctgctt gtaacacgcg tggcggatgt     60

<210> SEQ ID NO 1511
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1511
cgcgaatgcc ctccctggag caggcactca catgacccct ccactacgcg tggcggatgt     60

<210> SEQ ID NO 1512
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1512
```
cgcgaatgcc gttataaaag caatagaaga aggttatcgt ttaccacgcg tggcggatgt    60

<210> SEQ ID NO 1513
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1513
cgcgaatgcc gctggtgaag gccagctggg cagtccatgg gtgctacgcg tggcggatgt    60

<210> SEQ ID NO 1514
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1514
cgcgaatgcc taatgttgga ttgttggcaa aaggagcgtg ctgaaacgcg tggcggatgt    60

<210> SEQ ID NO 1515
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1515
cgcgaatgcc tctagaattc caactatctg ttcaaatttt ggcctacgcg tggcggatgt    60

<210> SEQ ID NO 1516
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1516
cgcgaatgcc caaaatgatt cgaaacccaa atagtctgaa aactcacgcg tggcggatgt    60

<210> SEQ ID NO 1517
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1517
cgcgaatgcc cttaggcatt tcttacctac tacaagttcc cagggacgcg tggcggatgt    60

<210> SEQ ID NO 1518
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1518
cgcgaatgcc atggcgagtt gctccttcac tcgcgaccaa gcgacacgcg tggcggatgt    60

<210> SEQ ID NO 1519
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 1519
cgcgaatgcc ccgctgccgc cgctgctgca cctcttagtc ttcttacgcg tggcggatgt      60

<210> SEQ ID NO 1520
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1520
cgcgaatgcc cagctctagc agcagtggtg accaccccgc ttcttacgcg tggcggatgt      60

<210> SEQ ID NO 1521
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1521
cgcgaatgcc ccggtcccaa tgagtgcggt cggggttccc gaggaacgcg tggcggatgt      60

<210> SEQ ID NO 1522
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1522
cgcgaatgcc gtcgtcttgt ccgggagcca tgtggctctc cacggacgcg tggcggatgt      60

<210> SEQ ID NO 1523
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1523
cgcgaatgcc ctcttcggac tcggagtctg accgggagcc agtggacgcg tggcggatgt      60

<210> SEQ ID NO 1524
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1524
cgcgaatgcc gaggacctgc ccgtcgggga ggaagtctgc aaacgacgcg tggcggatgt      60

<210> SEQ ID NO 1525
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1525
cgcgaatgcc gcctgtgccc atgcttctgt ttccgcaggt agccgacgcg tggcggatgt      60
```

<210> SEQ ID NO 1526
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1526
cgcgaatgcc gctacttcgt gctcaaactc gagactgctg acgccacgcg tggcggatgt    60

<210> SEQ ID NO 1527
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1527
cgcgaatgcc ttcctggcat tttcgtagta ttccagccga gctggacgcg tggcggatgt    60

<210> SEQ ID NO 1528
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1528
cgcgaatgcc gttccggcac agtgtccgcg ccgcggcggc tgcagacgcg tggcggatgt    60

<210> SEQ ID NO 1529
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1529
cgcgaatgcc cgggggatc gcggcgccag aggcggccgc cgctgacgcg tggcggatgt    60

<210> SEQ ID NO 1530
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1530
cgcgaatgcc ctcattccac cgcggcgcgt gatcaccct a taccaacgcg tggcggatgt    60

<210> SEQ ID NO 1531
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1531
cgcgaatgcc accttgcatc tgctcgctgg ctcacggaaa agcacacgcg tggcggatgt    60

<210> SEQ ID NO 1532
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 1532
cgcgaatgcc accgacacct cattgctctt ttcacccaag acgaaacgcg tggcggatgt    60

<210> SEQ ID NO 1533
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1533
cgcgaatgcc tgctccgact cgttctcggc caccatcgcg aagtaacgcg tggcggatgt    60

<210> SEQ ID NO 1534
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1534
cgcgaatgcc ggaaagctgg tacttgctgc tcagccgcct catccacgcg tggcggatgt    60

<210> SEQ ID NO 1535
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1535
cgcgaatgcc gccgagcgtg ccgcagcggc ggcgcttgct ctcgaacgcg tggcggatgt    60

<210> SEQ ID NO 1536
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1536
cgcgaatgcc gcgcagccgg acggagagcc ggccgcgctg gcggcacgcg tggcggatgt    60

<210> SEQ ID NO 1537
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1537
cgcgaatgcc catctttata gaagggtggc tccgccgccg ctgccacgcg tggcggatgt    60

<210> SEQ ID NO 1538
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1538
cgcgaatgcc tgtggcaggt aatagtcaaa cccaggggc tggggacgcg tggcggatgt    60

```
<210> SEQ ID NO 1539
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1539
cgcgaatgcc cacagccgga acacgccgct cagctctttt ctgtgacgcg tggcggatgt    60

<210> SEQ ID NO 1540
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1540
cgcgaatgcc tctaaccgac gaggaggtcg tgtttgtgag gctgaacgcg tggcggatgt    60

<210> SEQ ID NO 1541
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1541
cgcgaatgcc caggagctgg acgaccacgc tggccacttc ggtgtacgcg tggcggatgt    60

<210> SEQ ID NO 1542
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1542
cgcgaatgcc agcatccgtc gctgtggaca ctcggagcag tatttacgcg tggcggatgt    60

<210> SEQ ID NO 1543
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1543
cgcgaatgcc gaccgatgac agtggacctg cctacttcca agaagacgcg tggcggatgt    60

<210> SEQ ID NO 1544
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1544
cgcgaatgcc cgggagagct ctggatgcag gtcgatgact gtgtgacgcg tggcggatgt    60

<210> SEQ ID NO 1545
<211> LENGTH: 60
<212> TYPE: DNA
<213> ORGANISM: Artificial Sequence
<220> FEATURE:
<223> OTHER INFORMATION: Synthetic oligonucleotide
```

```
<400> SEQUENCE: 1545
cgcgaatgcc ttctccaaaa acagctcatg catgttttgg gcaacacgcg tggcggatgt    60

<210> SEQ ID NO 1546
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1546
cgcgaatgcc gatgagagcc ttgtgtgcag acgaatacag agcccacgcg tggcggatgt    60

<210> SEQ ID NO 1547
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1547
cgcgaatgcc gtgggcgccg atgctgatgc tgtagctgcg gcagcacgcg tggcggatgt    60

<210> SEQ ID NO 1548
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1548
cgcgaatgcc ctgttaaccc tgctgtccgc taggaggcac ctgggacgcg tggcggatgt    60

<210> SEQ ID NO 1549
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1549
cgcgaatgcc ttctgagcca gcctcccggc tcgagcggca ccaagacgcg tggcggatgt    60

<210> SEQ ID NO 1550
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1550
cgcgaatgcc ggtcccgctt tgagcagttt tgccacctca gggccacgcg tggcggatgt    60

<210> SEQ ID NO 1551
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1551
cgcgaatgcc ctggtgaaaa gcatctcgtc ttccccgtcg ccgatacgcg tggcggatgt    60

<210> SEQ ID NO 1552
<211> LENGTH: 60
```

```
<212> TYPE: DNA
<213> ORGANISM: Artificial Sequence
<220> FEATURE:
<223> OTHER INFORMATION: Synthetic oligonucleotide

<400> SEQUENCE: 1552
cgcgaatgcc gcgcttcgta acacccagcg agcctgtggc ccactacgcg tggcggatgt    60

<210> SEQ ID NO 1553
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1553
cgcgaatgcc gcgccctctg ggcaggtgca gtcttcctcg cctggacgcg tggcggatgt    60

<210> SEQ ID NO 1554
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1554
cgcgaatgcc aggtcaagga gagcggtttc agtgccggcc agcttacgcg tggcggatgt    60

<210> SEQ ID NO 1555
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1555
cgcgaatgcc ggggacgtgc tgggctgggt gctaagcggc gaaaaacgcg tggcggatgt    60

<210> SEQ ID NO 1556
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1556
cgcgaatgcc ggcaccctgc agaagccccg aacaatggag ctcgcacgcg tggcggatgt    60

<210> SEQ ID NO 1557
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1557
cgcgaatgcc ttgccagagc cagaaccaga cacttcagaa gacagacgcg tggcggatgt    60

<210> SEQ ID NO 1558
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1558
```
cgcgaatgcc ctttggggag gaaggcaatc cccagggcaa agaagacgcg tggcggatgt        60

<210> SEQ ID NO 1559
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1559
cgcgaatgcc cataggcatg tagtcacctc cgcttccttc ctgatacgcg tggcggatgt        60

<210> SEQ ID NO 1560
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1560
cgcgaatgcc aacaattggg gctcaggaaa tggccggggc tcaggacgcg tggcggatgt        60

<210> SEQ ID NO 1561
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1561
cgcgaatgcc tactggagcc ttggccattt gagccctggc cacctacgcg tggcggatgt        60

<210> SEQ ID NO 1562
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1562
cgcgaatgcc gccatagctc gggaggaaac cagtgttcag gcgagacgcg tggcggatgt        60

<210> SEQ ID NO 1563
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1563
cgcgaatgcc ccatttgagc cctgaccacc tcgggatccc tgtccacgcg tggcggatgt        60

<210> SEQ ID NO 1564
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1564
cgcgaatgcc ccagggctca ggaggaaacc agtgctctag agatgacgcg tggcggatgt        60

<210> SEQ ID NO 1565
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 1565
cgcgaatgcc accacctgaa ccgtgcccac ctgcggtgcc ctggcacgcg tggcggatgt    60

<210> SEQ ID NO 1566
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1566
cgcgaatgcc ggccagagac ctggaggtgg gcatggctca ggtggacgcg tggcggatgt    60

<210> SEQ ID NO 1567
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1567
cgcgaatgcc cacctgagcc atggccatct ccaggtccct ggccaacgcg tggcggatgt    60

<210> SEQ ID NO 1568
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1568
cgcgaatgcc gtggcaagaa ctctgggggg ggcaaaggct caggaacgcg tggcggatgt    60

<210> SEQ ID NO 1569
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1569
cgcgaatgcc ccacgttcac catcaccatc ggatcctttc ccactacgcg tggcggatgt    60

<210> SEQ ID NO 1570
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1570
cgcgaatgcc aaaatctctg aagaaaagat cctattttgg caaatacgcg tggcggatgt    60

<210> SEQ ID NO 1571
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1571
cgcgaatgcc aggtggtggc atttgctgtt gcttgctttg agttaacgcg tggcggatgt    60
```

<210> SEQ ID NO 1572
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1572
cgcgaatgcc ccaccacctc ctcctccacc cccaccagct ggaggacgcg tggcggatgt    60

<210> SEQ ID NO 1573
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1573
cgcgaatgcc tgaatcttcc cccagacttc ccttttccac cagttacgcg tggcggatgt    60

<210> SEQ ID NO 1574
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1574
cgcgaatgcc gactttattt ttgtgttgac agaggagcca cgaaaacgcg tggcggatgt    60

<210> SEQ ID NO 1575
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1575
cgcgaatgcc tctgcatctt tcacttcttt ggcttctttg cattcacgcg tggcggatgt    60

<210> SEQ ID NO 1576
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1576
cgcgaatgcc gatcccagaa ggtgcagctc gaggtcccca cagagacgcg tggcggatgt    60

<210> SEQ ID NO 1577
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1577
cgcgaatgcc gtatgggtca tcctcatctt catcaaaagc tctggacgcg tggcggatgt    60

<210> SEQ ID NO 1578
<211> LENGTH: 60
<212> TYPE: DNA
<213> ORGANISM: Artificial Sequence
<220> FEATURE:
<223> OTHER INFORMATION: Synthetic oligonucleotide -continued

<400> SEQUENCE: 1578
cgcgaatgcc gtgccaatga ggccaggggt ggccacccct cttgtacgcg tggcggatgt    60

<210> SEQ ID NO 1579
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1579
cgcgaatgcc tttgaggagc cattggcata taatcactgg agcttacgcg tggcggatgt    60

<210> SEQ ID NO 1580
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1580
cgcgaatgcc atgtctctgc ttcaaaaaag cgccactctc gatccacgcg tggcggatgt    60

<210> SEQ ID NO 1581
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1581
cgcgaatgcc aacatcatca tgtaccctct tgaatcttca aaaggacgcg tggcggatgt    60

<210> SEQ ID NO 1582
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1582
cgcgaatgcc tcccagagtg agcccaccac ctgctccgag tcctcacgcg tggcggatgt    60

<210> SEQ ID NO 1583
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1583
cgcgaatgcc tgagtcatcc tctttattag tatcaggtgc ttttgacgcg tggcggatgt    60

<210> SEQ ID NO 1584
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1584
cgcgaatgcc aaggacaatg acagtgagag tgactacatg tttatacgcg tggcggatgt    60

<210> SEQ ID NO 1585

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1585
cgcgaatgcc tggggttttt tggaattgca ccggctccag gagccacgcg tggcggatgt    60

<210> SEQ ID NO 1586
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1586
cgcgaatgcc gaaatcctca gggtggctct tcctccaaaa gttggacgcg tggcggatgt    60

<210> SEQ ID NO 1587
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1587
cgcgaatgcc ctccgaaaag ggtttggtag agagaagtag gagctacgcg tggcggatgt    60

<210> SEQ ID NO 1588
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1588
cgcgaatgcc ctcacctttg ggacagaatg acaacagtga gtatgacgcg tggcggatgt    60

<210> SEQ ID NO 1589
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1589
cgcgaatgcc gcccctcccc aggaactttc caggtaacat tggcaacgcg tggcggatgt    60

<210> SEQ ID NO 1590
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1590
cgcgaatgcc ctagacaaag aagtctccta taactgggac cccaaacgcg tggcggatgt    60

<210> SEQ ID NO 1591
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1591
```
cgcgaatgcc atgatccctc acctgaaggc tttgaagctg catctacgcg tggcggatgt    60

<210> SEQ ID NO 1592
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1592
cgcgaatgcc tctcaaagcc tggagatggg ggatcacctt caaagacgcg tggcggatgt    60

<210> SEQ ID NO 1593
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1593
cgcgaatgcc ttagctttat tctttggggg ctcatgatct gaaggacgcg tggcggatgt    60

<210> SEQ ID NO 1594
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1594
cgcgaatgcc gagacctaac cgactttctt ttattacaaa aggatacgcg tggcggatgt    60

<210> SEQ ID NO 1595
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1595
cgcgaatgcc atgtgtgggc ttttgtggtt ttggcttgat tttatacgcg tggcggatgt    60

<210> SEQ ID NO 1596
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1596
cgcgaatgcc gagcagagag aagctgacag ctctagtgac tacgtacgcg tggcggatgt    60

<210> SEQ ID NO 1597
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1597
cgcgaatgcc gtgtattgct ctctctttta gtgaagtcca tgttgacgcg tggcggatgt    60

<210> SEQ ID NO 1598
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 1598
cgcgaatgcc cagctccctc tactcaagga ctaccagatt cgtggacgcg tggcggatgt    60

<210> SEQ ID NO 1599
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1599
cgcgaatgcc gaaaaggctg actgtctggg ttcagcaatt atgccacgcg tggcggatgt    60

<210> SEQ ID NO 1600
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1600
cgcgaatgcc taattatgtg aatgttgagt ttggagtgcc atttcacgcg tggcggatgt    60

<210> SEQ ID NO 1601
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1601
cgcgaatgcc tcttaaaaga tctgagaggt cgtttgctgg atttgacgcg tggcggatgt    60

<210> SEQ ID NO 1602
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1602
cgcgaatgcc gctataccac gtgccaaccc cttatctctg gacagacgcg tggcggatgt    60

<210> SEQ ID NO 1603
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1603
cgcgaatgcc cactgagggg aagggagga agtggccacc tagcaacgcg tggcggatgt    60

<210> SEQ ID NO 1604
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1604
cgcgaatgcc ctacaggtag caatgctatt gaggaagagg gtgacacgcg tggcggatgt    60
```

<210> SEQ ID NO 1605
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1605
cgcgaatgcc ggtgtcattg ctgagttgaa aattacttca atgtaacgcg tggcggatgt    60

<210> SEQ ID NO 1606
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1606
cgcgaatgcc agccatggct cttgctgaca gtgccattcg ctatgacgcg tggcggatgt    60

<210> SEQ ID NO 1607
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1607
cgcgaatgcc tgggtcgacc acatagattc gacctgtttc agcatacgcg tggcggatgt    60

<210> SEQ ID NO 1608
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1608
cgcgaatgcc ttttctgagt gctgtatgga tatttctctc tccccacgcg tggcggatgt    60

<210> SEQ ID NO 1609
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1609
cgcgaatgcc gcctagctac aggtggtggt tcagaacatc ggctgacgcg tggcggatgt    60

<210> SEQ ID NO 1610
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1610
cgcgaatgcc tgctgcagga agaagagcag gagagaagac gcccaacgcg tggcggatgt    60

<210> SEQ ID NO 1611
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 1611
cgcgaatgcc ctggctgctg caaagaaact tgagaacgg ctttgacgcg tggcggatgt      60

<210> SEQ ID NO 1612
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1612
cgcgaatgcc agccgctgtc tctgcttttc aacagacag cctcgacgcg tggcggatgt      60

<210> SEQ ID NO 1613
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1613
cgcgaatgcc gacagccggg gctgaggatg gggaaaggtc tctctacgcg tggcggatgt      60

<210> SEQ ID NO 1614
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1614
cgcgaatgcc gcttcggctg cagagccgac tttagccctc agccaacgcg tggcggatgt      60

<210> SEQ ID NO 1615
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1615
cgcgaatgcc gggctgcggc gagcgcggag gccgcagcta caactacgcg tggcggatgt      60

<210> SEQ ID NO 1616
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1616
cgcgaatgcc cgggcatcgg cgcagcagcc gcagctgctg gatttacgcg tggcggatgt      60

<210> SEQ ID NO 1617
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1617
cgcgaatgcc gcaacaggtt gaaaccagcg ggcagaggcg gagtcacgcg tggcggatgt      60

```
<210> SEQ ID NO 1618
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1618
cgcgaatgcc taatgctgct gatgccgaag cagtaagggg agcccacgcg tggcggatgt     60

<210> SEQ ID NO 1619
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1619
cgcgaatgcc gtgggctcca gggttcgagc caccggcaac gtcttacgcg tggcggatgt     60

<210> SEQ ID NO 1620
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1620
cgcgaatgcc aacccatctg caaaccttgc cagaggtgat aaccaacgcg tggcggatgt     60

<210> SEQ ID NO 1621
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1621
cgcgaatgcc ccggagcggc agctgcagcg gcagccccgc cagccacgcg tggcggatgt     60

<210> SEQ ID NO 1622
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1622
cgcgaatgcc aaccaccacc tcgcagtcgc cgggtgccaa gacccacgcg tggcggatgt     60

<210> SEQ ID NO 1623
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1623
cgcgaatgcc gtgtcgtcgt cgttgtcaga atcttctctc tccggacgcg tggcggatgt     60

<210> SEQ ID NO 1624
<211> LENGTH: 60
<212> TYPE: DNA
<213> ORGANISM: Artificial Sequence
<220> FEATURE:
<223> OTHER INFORMATION: Synthetic oligonucleotide
```

```
<400> SEQUENCE: 1624
cgcgaatgcc tcacgtgaga atggattttg ccagacgtga taatcacgcg tggcggatgt    60

<210> SEQ ID NO 1625
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1625
cgcgaatgcc ctaaaattac cgacctcttt tgggagagtc gaactacgcg tggcggatgt    60

<210> SEQ ID NO 1626
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1626
cgcgaatgcc gtccctccag ccgtggcccc agcgcgcacg ggcgaacgcg tggcggatgt    60

<210> SEQ ID NO 1627
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1627
cgcgaatgcc acgcagcccc gcggcaccgg acgtcgcctt cgccaacgcg tggcggatgt    60

<210> SEQ ID NO 1628
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1628
cgcgaatgcc tgttgctgct gctgctgccg ctgctaggca aaggtacgcg tggcggatgt    60

<210> SEQ ID NO 1629
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1629
cgcgaatgcc ccctgcggg agccggcggc cggcagaact cacctacgcg tggcggatgt    60

<210> SEQ ID NO 1630
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1630
cgcgaatgcc ggagggaaga tcccaatcag gtggacatca ccagaacgcg tggcggatgt    60

<210> SEQ ID NO 1631
<211> LENGTH: 60
```

<212> TYPE: DNA
<213> ORGANISM: Artificial Sequence
<220> FEATURE:
<223> OTHER INFORMATION: Synthetic oligonucleotide

<400> SEQUENCE: 1631
cgcgaatgcc cgctggctga cgtgaacttg cggtaggcta tagctacgcg tggcggatgt    60

<210> SEQ ID NO 1632
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1632
cgcgaatgcc atgtatggag ttatgggatt gttctctggg aggtgacgcg tggcggatgt    60

<210> SEQ ID NO 1633
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1633
cgcgaatgcc gacatctccc agtatggtct ctctccataa gacatacgcg tggcggatgt    60

<210> SEQ ID NO 1634
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1634
cgcgaatgcc caatcaggat gtaagtattt gtggtctatg agttaacgcg tggcggatgt    60

<210> SEQ ID NO 1635
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1635
cgcgaatgcc tggtaggctt gagtttgaag aaacagaaga acctgacgcg tggcggatgt    60

<210> SEQ ID NO 1636
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1636
cgcgaatgcc tggtatcttt aatttctgac ataatgcagt aaaatacgcg tggcggatgt    60

<210> SEQ ID NO 1637
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1637

```
cgcgaatgcc gatcatgtca gagagagagc ttggttaact tgggaacgcg tggcggatgt      60

<210> SEQ ID NO 1638
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1638
cgcgaatgcc tccttaccaa tactccatcc acagatgaaa ctttcacgcg tggcggatgt      60

<210> SEQ ID NO 1639
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1639
cgcgaatgcc catttttttt tcagggaag tattacaaat ggaagacgcg tggcggatgt       60

<210> SEQ ID NO 1640
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1640
cgcgaatgcc acatagcatt aactgaaatg aaatcaccag atcatacgcg tggcggatgt      60

<210> SEQ ID NO 1641
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1641
cgcgaatgcc gtccttgact attttattaa actctcacct cccatacgcg tggcggatgt      60

<210> SEQ ID NO 1642
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1642
cgcgaatgcc aaattaaata cttactatat ggttctttga gcaacacgcg tggcggatgt      60

<210> SEQ ID NO 1643
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1643
cgcgaatgcc gtttcaccgt tgtttggaac catctacaat tcaatacgcg tggcggatgt      60

<210> SEQ ID NO 1644
<211> LENGTH: 60
<212> TYPE: DNA
<213> ORGANISM: Artificial Sequence
```

<220> FEATURE:
<223> OTHER INFORMATION: Synthetic oligonucleotide

<400> SEQUENCE: 1644
cgcgaatgcc tcatagcatt attcatggct tgtgcgataa agtaaacgcg tggcggatgt    60

<210> SEQ ID NO 1645
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1645
cgcgaatgcc aagaaaatgg acaggctggt gctgccagcc tggttacgcg tggcggatgt    60

<210> SEQ ID NO 1646
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1646
cgcgaatgcc ttgaatccat ggaactgcat gtttctggaa tgctgacgcg tggcggatgt    60

<210> SEQ ID NO 1647
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1647
cgcgaatgcc ccagttgatg aggacagatt caaatggaaa tggaaacgcg tggcggatgt    60

<210> SEQ ID NO 1648
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1648
cgcgaatgcc tttcaagttg gtgtccagga ttacatattc tgaaaacgcg tggcggatgt    60

<210> SEQ ID NO 1649
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1649
cgcgaatgcc gaatgggaac tccatagcac ctacactgtg gacatacgcg tggcggatgt    60

<210> SEQ ID NO 1650
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1650
cgcgaatgcc tagggtccc tccgaaacgt agcagctcca tttccacgcg tggcggatgt    60

<210> SEQ ID NO 1651
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1651
cgcgaatgcc ttcacttccc tggtggcagg cccctagag cagatacgcg tggcggatgt    60

<210> SEQ ID NO 1652
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1652
cgcgaatgcc tggcagatct tcccttctgc aaaccagcat tttgcacgcg tggcggatgt    60

<210> SEQ ID NO 1653
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1653
cgcgaatgcc tggaggtaag gaatgcaaaa tcactagtag tcaatacgcg tggcggatgt    60

<210> SEQ ID NO 1654
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1654
cgcgaatgcc tctaacagca ccatcatcca ttgctttggt ccaggacgcg tggcggatgt    60

<210> SEQ ID NO 1655
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1655
cgcgaatgcc agccagtgcc acactgtatc ttgtgacttc tttagacgcg tggcggatgt    60

<210> SEQ ID NO 1656
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1656
cgcgaatgcc tggctggaac cagatcggcc caatggggta atcctacgcg tggcggatgt    60

<210> SEQ ID NO 1657
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1657
cgcgaatgcc gtaatacctt ctcataatac ttgacttcat attccacgcg tggcggatgt    60

<210> SEQ ID NO 1658
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1658
cgcgaatgcc tctgatttca tgtttgtttt aggcgtcgta taaatacgcg tggcggatgt    60

<210> SEQ ID NO 1659
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1659
cgcgaatgcc agaattctat tgggtccttt gatcaactgg attttacgcg tggcggatgt    60

<210> SEQ ID NO 1660
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1660
cgcgaatgcc actgactttg gaggatgtaa cgtttatcaa tccccacgcg tggcggatgt    60

<210> SEQ ID NO 1661
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1661
cgcgaatgcc aaagaagagg atactcctta ccttactgcc aaagtacgcg tggcggatgt    60

<210> SEQ ID NO 1662
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1662
cgcgaatgcc atgaaggact tgcgtcatga gaatattaac cctttacgcg tggcggatgt    60

<210> SEQ ID NO 1663
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1663
cgcgaatgcc tggcaaacat ccccgaatca tagaagaaac ccaatacgcg tggcggatgt    60

<210> SEQ ID NO 1664

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1664
cgcgaatgcc ttgtgacaga attctgttcc cgagggagcc tagaaacgcg tggcggatgt    60

<210> SEQ ID NO 1665
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1665
cgcgaatgcc cagtcaagtt tcacatcttg atttgtcagt atgtcacgcg tggcggatgt    60

<210> SEQ ID NO 1666
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1666
cgcgaatgcc gatgtttaaa tcatcactct tgctggatct cataaacgcg tggcggatgt    60

<210> SEQ ID NO 1667
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1667
cgcgaatgcc aaaatccaag atttcctcag tcttcccatt aacctacgcg tggcggatgt    60

<210> SEQ ID NO 1668
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1668
cgcgaatgcc tttttttct gagtgttcaa tctctggttt tcagaacgcg tggcggatgt    60

<210> SEQ ID NO 1669
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1669
cgcgaatgcc gcgcccgggt cggcgtctcc ggcaccggca ccacaacgcg tggcggatgt    60

<210> SEQ ID NO 1670
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1670
```
cgcgaatgcc cccaggtcat cctgcatccg gtgacctcga atccaacgcg tggcggatgt    60

<210> SEQ ID NO 1671
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1671
cgcgaatgcc gggaaagggg gaagatgtct ctgtctcact tacatacgcg tggcggatgt    60

<210> SEQ ID NO 1672
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1672
cgcgaatgcc acatttagtt tgtaatgtgc atgttttatt tatagacgcg tggcggatgt    60

<210> SEQ ID NO 1673
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1673
cgcgaatgcc tttctgcttg actttgtctt gtttatcacc atgagacgcg tggcggatgt    60

<210> SEQ ID NO 1674
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1674
cgcgaatgcc gcgtttgtgg agccgtattt taaaggtgat gaaagacgcg tggcggatgt    60

<210> SEQ ID NO 1675
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1675
cgcgaatgcc agtcacattg ctggtataaa taaaaaccaa cttacacgcg tggcggatgt    60

<210> SEQ ID NO 1676
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1676
cgcgaatgcc ccatgcagtg tgtccaccgt gatctggctg ctcgcacgcg tggcggatgt    60

<210> SEQ ID NO 1677
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 1677
cgcgaatgcc atcttcacaa tttttccttg tgccaggagg acgttacgcg tggcggatgt    60

<210> SEQ ID NO 1678
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1678
cgcgaatgcc ctgtgacttt ggcctggcca gagacatcat gcatgacgcg tggcggatgt    60

<210> SEQ ID NO 1679
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1679
cgcgaatgcc aggacgtaca ctgcctttcg acacatagtt cgaatacgcg tggcggatgt    60

<210> SEQ ID NO 1680
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1680
cgcgaatgcc tctttcaggg agccatggct gccacgtact ccgcaacgcg tggcggatgt    60

<210> SEQ ID NO 1681
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1681
cgcgaatgcc ggcttcagct gggggtgggg cttggagctg ttgagacgcg tggcggatgt    60

<210> SEQ ID NO 1682
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1682
cgcgaatgcc catcgagtca tccatcctgg cccagcggcg agtgaacgcg tggcggatgt    60

<210> SEQ ID NO 1683
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1683
cgcgaatgcc cctggtgcct cacagggtgg tggatggcaa cttccacgcg tggcggatgt    60
```

<210> SEQ ID NO 1684
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1684
cgcgaatgcc ctctcactgc cctctgcacc agcaacatgg attgtacgcg tggcggatgt    60

<210> SEQ ID NO 1685
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1685
cgcgaatgcc acagagcagc tgagaaggag gaggatggag agctgacgcg tggcggatgt    60

<210> SEQ ID NO 1686
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1686
cgcgaatgcc tctcgacagc ttcggggaac tgattccgca gccttacgcg tggcggatgt    60

<210> SEQ ID NO 1687
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1687
cgcgaatgcc tccgtgcgtc gcggtacctg gcttaccttc attggacgcg tggcggatgt    60

<210> SEQ ID NO 1688
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1688
cgcgaatgcc attttaaagg cttgaagagt gtcgaattat gtcctacgcg tggcggatgt    60

<210> SEQ ID NO 1689
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1689
cgcgaatgcc gttctcccaa ttcaaccaca gtggcctttt tgcagacgcg tggcggatgt    60

<210> SEQ ID NO 1690
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 1690
cgcgaatgcc ccagacatca tgtcagagtt actgtttcag aacaaacgcg tggcggatgt    60

<210> SEQ ID NO 1691
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1691
cgcgaatgcc cttccttacc atccccattt ttaaagatga tctcaacgcg tggcggatgt    60

<210> SEQ ID NO 1692
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1692
cgcgaatgcc cttgccctgc agggacattc aaggccagcc aggaaacgcg tggcggatgt    60

<210> SEQ ID NO 1693
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1693
cgcgaatgcc cggctgttgg aggggcagtg ggagcagcct tcagcacgcg tggcggatgt    60

<210> SEQ ID NO 1694
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1694
cgcgaatgcc ctcccctgca gaggcgtctc ccatctgcac ctgtcacgcg tggcggatgt    60

<210> SEQ ID NO 1695
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1695
cgcgaatgcc tggagggtca aagtccgctc ggtaataacc ggtccacgcg tggcggatgt    60

<210> SEQ ID NO 1696
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1696
cgcgaatgcc gaagtggcat gcactagtaa gtgtctagta atggcacgcg tggcggatgt    60

```
<210> SEQ ID NO 1697
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1697
cgcgaatgcc taggacattc ttctcttctg ctgggccttt gaacaacgcg tggcggatgt    60

<210> SEQ ID NO 1698
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1698
cgcgaatgcc tgtccatgag cttggtgaag gtaggtctct cttctacgcg tggcggatgt    60

<210> SEQ ID NO 1699
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1699
cgcgaatgcc tgctggagaa actgccaaag cgaaaccgtc gcctgacgcg tggcggatgt    60

<210> SEQ ID NO 1700
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1700
cgcgaatgcc tactctgcag acttccagaa atgtccaggg tgagaacgcg tggcggatgt    60

<210> SEQ ID NO 1701
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1701
cgcgaatgcc gaggcaacct ttccaaacaa gactggacca tccagacgcg tggcggatgt    60

<210> SEQ ID NO 1702
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1702
cgcgaatgcc ggattgttct ccttccccgt ctctgtcgtg ggccaacgcg tggcggatgt    60

<210> SEQ ID NO 1703
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 1703
cgcgaatgcc cgtgtgcccc ccggagccca ccccgtggat ccgcaacgcg tggcggatgt    60

<210> SEQ ID NO 1704
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1704
cgcgaatgcc cttggacggg accctggggc tctgggagag atgggacgcg tggcggatgt    60

<210> SEQ ID NO 1705
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1705
cgcgaatgcc tgcgtccagc actattgtca caccagcccc actccacgcg tggcggatgt    60

<210> SEQ ID NO 1706
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1706
cgcgaatgcc taagcctgtc cacgtgggtg tacacagggg ccccgacgcg tggcggatgt    60

<210> SEQ ID NO 1707
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1707
cgcgaatgcc ccgtggacgc ctacccgggc ttgtgcccgc ccccgacgcg tggcggatgt    60

<210> SEQ ID NO 1708
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1708
cgcgaatgcc gatgggggca gggaacggtg gcccgactcc agtggacgcg tggcggatgt    60

<210> SEQ ID NO 1709
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1709
cgcgaatgcc gccccggcag cggcacgcgg tccgcacccc gccgcacgcg tggcggatgt    60

<210> SEQ ID NO 1710
<211> LENGTH: 60

<212> TYPE: DNA
<213> ORGANISM: Artificial Sequence
<220> FEATURE:
<223> OTHER INFORMATION: Synthetic oligonucleotide

<400> SEQUENCE: 1710
cgcgaatgcc cggcggggtc acggtggtga cgatgttggg ggtgcacgcg tggcggatgt    60

<210> SEQ ID NO 1711
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1711
cgcgaatgcc ggcacgccgc ccatgaggaa gaagaacaag ctgaaacgcg tggcggatgt    60

<210> SEQ ID NO 1712
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1712
cgcgaatgcc gttttcggga ggagggcggt ggggtccccg ggggcacgcg tggcggatgt    60

<210> SEQ ID NO 1713
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1713
cgcgaatgcc tgatacactt gatcccggga ttcaccgcgc tgcatacgcg tggcggatgt    60

<210> SEQ ID NO 1714
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1714
cgcgaatgcc cggtgcccca gctggaactc gtgggatttg ctccgacgcg tggcggatgt    60

<210> SEQ ID NO 1715
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1715
cgcgaatgcc cgtggacgag gcccacacgc ccaagtgagt gcgatacgcg tggcggatgt    60

<210> SEQ ID NO 1716
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1716
cgcgaatgcc cgatgtctcc ctggggacac tcactttgat gttttacgcg tggcggatgt    60

<210> SEQ ID NO 1717
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1717
cgcgaatgcc tgtatttgta gtagtgggat gcttgcaaaa gaaagacgcg tggcggatgt    60

<210> SEQ ID NO 1718
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1718
cgcgaatgcc agcagcagtt catcttccca ggtgagtttc atgtgacgcg tggcggatgt    60

<210> SEQ ID NO 1719
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1719
cgcgaatgcc cagcggggct tgttcagaag gggctgcttc cagctacgcg tggcggatgt    60

<210> SEQ ID NO 1720
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1720
cgcgaatgcc ttctcttcaa cctcacagct ttctccatct ctggtacgcg tggcggatgt    60

<210> SEQ ID NO 1721
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1721
cgcgaatgcc gctgaaatgg cgatcatgac cacttggcta ctttcacgcg tggcggatgt    60

<210> SEQ ID NO 1722
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1722
cgcgaatgcc ggcagtagca attattctcc tcactgttgt catctacgcg tggcggatgt    60

<210> SEQ ID NO 1723
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 1723
cgcgaatgcc aaacagactg tgaactcacc tcccaatcaa aacatacgcg tggcggatgt    60

<210> SEQ ID NO 1724
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1724
cgcgaatgcc agcaagctgg tgaagtactt cagccggcag ctgtcacgcg tggcggatgt    60

<210> SEQ ID NO 1725
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1725
cgcgaatgcc cgttgcgctc ctgcaaggct accttctttt tgcagacgcg tggcggatgt    60

<210> SEQ ID NO 1726
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1726
cgcgaatgcc cggagctgga cggcttcccc cagctacggc actggacgcg tggcggatgt    60

<210> SEQ ID NO 1727
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1727
cgcgaatgcc tccaggacct ccttgcgcac atcgacgatt cggaaacgcg tggcggatgt    60

<210> SEQ ID NO 1728
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1728
cgcgaatgcc ggtgacctgg ggggcccctg tgtcccctgc ccttacgcg tggcggatgt    60

<210> SEQ ID NO 1729
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1729
cgcgaatgcc gtcattgagt gcattaccca aggtcgtgtt ttggaacgcg tggcggatgt    60
```

<210> SEQ ID NO 1730
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1730
cgcgaatgcc catcgtacac ctctttgggg cagactcggg gccgcacgcg tggcggatgt    60

<210> SEQ ID NO 1731
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1731
cgcgaatgcc tcatgctggg gtgctggcag agggaaccac agcagacgcg tggcggatgt    60

<210> SEQ ID NO 1732
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1732
cgcgaatgcc tggaggattt tgtagatctc cttgatgttc aaccgacgcg tggcggatgt    60

<210> SEQ ID NO 1733
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1733
cgcgaatgcc tgctttgggg aaggccaccc caatctacct ggacaacgcg tggcggatgt    60

<210> SEQ ID NO 1734
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1734
cgcgaatgcc tgaattcatg accaccagcc accactagcc aagaaacgcg tggcggatgt    60

<210> SEQ ID NO 1735
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1735
cgcgaatgcc ggtgtgctgg gcgatgccag gagtgggaag tcatcacgcg tggcggatgt    60

<210> SEQ ID NO 1736
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1736
cgcgaatgcc cctggtatga gccagtcagg aatcggtgga tgagcacgcg tggcggatgt    60

<210> SEQ ID NO 1737
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1737
cgcgaatgcc tgctggagaa gacagagagt gagttctgaa gagccacgcg tggcggatgt    60

<210> SEQ ID NO 1738
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1738
cgcgaatgcc tcctggatcc ctgaccccaa tggttagctt actatacgcg tggcggatgt    60

<210> SEQ ID NO 1739
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1739
cgcgaatgcc gtgagatcaa tgattaggca ggtgtggaga ccaggacgcg tggcggatgt    60

<210> SEQ ID NO 1740
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1740
cgcgaatgcc ccagtgcttt tgctattatg gcctcatcct tccccacgcg tggcggatgt    60

<210> SEQ ID NO 1741
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1741
cgcgaatgcc gagcatgggg aggtttggtg acctgtcacc tctgaacgcg tggcggatgt    60

<210> SEQ ID NO 1742
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1742
cgcgaatgcc ctcacctgtc cagaagagtt ggaaggggta acaggacgcg tggcggatgt    60

<210> SEQ ID NO 1743

<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1743
cgcgaatgcc cagtacaaga aagaaatgtt ggtggatgga cagacacgcg tggcggatgt    60

<210> SEQ ID NO 1744
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1744
cgcgaatgcc gtgccccagc ttcctctcgg attagcacca gatgtacgcg tggcggatgt    60

<210> SEQ ID NO 1745
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1745
cgcgaatgcc ctgatgccaa ggtgagggtg gaggtggtgg gggacacgcg tggcggatgt    60

<210> SEQ ID NO 1746
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1746
cgcgaatgcc cctctccttt ggccagtgct gaccccagcc agcctacgcg tggcggatgt    60

<210> SEQ ID NO 1747
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1747
cgcgaatgcc gctctggttt cccaggtctt catctggatt gggtcacgcg tggcggatgt    60

<210> SEQ ID NO 1748
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1748
cgcgaatgcc gagcaaatgg aaagtcagac aggtctactc ctctgacgcg tggcggatgt    60

<210> SEQ ID NO 1749
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1749
cgcgaatgcc cctcactccc cgcaagttct caggctgggc agatgacgcg tggcggatgt    60

<210> SEQ ID NO 1750
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1750
cgcgaatgcc gttctcatcc tccaggctga agacgaagat cacagacgcg tggcggatgt    60

<210> SEQ ID NO 1751
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1751
cgcgaatgcc agtttccagg ctgtgagccg tctccatggg cagctacgcg tggcggatgt    60

<210> SEQ ID NO 1752
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1752
cgcgaatgcc ccaggcctcc tcgtccctcc ccgcgaaggg aactcacgcg tggcggatgt    60

<210> SEQ ID NO 1753
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1753
cgcgaatgcc ccttggcact ggtggggaca caaggtaagg aggggacgcg tggcggatgt    60

<210> SEQ ID NO 1754
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1754
cgcgaatgcc tccctccatc aggatgaggg cgtcctcaag gagatacgcg tggcggatgt    60

<210> SEQ ID NO 1755
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1755
cgcgaatgcc tctcagagcc agccttgacg tggtgcgtga tggagacgcg tggcggatgt    60

<210> SEQ ID NO 1756
<211> LENGTH: 60
<212> TYPE: DNA

<213> ORGANISM: Artificial Sequence
<220> FEATURE:
<223> OTHER INFORMATION: Synthetic oligonucleotide

<400> SEQUENCE: 1756
cgcgaatgcc aggctgatcc atcccatttc gagctcctca aggttacgcg tggcggatgt    60

<210> SEQ ID NO 1757
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1757
cgcgaatgcc tcatgactca ctttgccaaa ggatccctgg cccagacgcg tggcggatgt    60

<210> SEQ ID NO 1758
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1758
cgcgaatgcc atctgagatg cacaataaaa cagttagcca gaggtacgcg tggcggatgt    60

<210> SEQ ID NO 1759
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1759
cgcgaatgcc acatgcacga caataggact ccaaaagcag gccaaacgcg tggcggatgt    60

<210> SEQ ID NO 1760
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1760
cgcgaatgcc gggatgtatt tgaagcacct gaataggcaa gtcgaacgcg tggcggatgt    60

<210> SEQ ID NO 1761
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1761
cgcgaatgcc gaatgtcagt taagttaatg agcttttcca ttgccacgcg tggcggatgt    60

<210> SEQ ID NO 1762
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1762
cgcgaatgcc ctcaaacagg agaagaagga tgaaacacaa aaggtacgcg tggcggatgt    60

<210> SEQ ID NO 1763
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1763
cgcgaatgcc gagaattcgg tgaagtctgc agtggccgtt tgaaaacgcg tggcggatgt      60

<210> SEQ ID NO 1764
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1764
cgcgaatgcc tttatggcta ctgcaacatc tcttttccct ggaagacgcg tggcggatgt      60

<210> SEQ ID NO 1765
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1765
cgcgaatgcc aaccctgaaa gttggttaca cagaaaaaca aaggaacgcg tggcggatgt      60

<210> SEQ ID NO 1766
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1766
cgcgaatgcc ctgccccatg atgcttgctt cacacaaaaa gtctcacgcg tggcggatgt      60

<210> SEQ ID NO 1767
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1767
cgcgaatgcc tttgaccacc cgaatgttgt ccatttggaa ggggtacgcg tggcggatgt      60

<210> SEQ ID NO 1768
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1768
cgcgaatgcc aataaagata taaccaatat ctacctcttg taacaacgcg tggcggatgt      60

<210> SEQ ID NO 1769
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 1769
cgcgaatgcc atgcatgccc agaggcagtt cgttgtagct gcagtacgcg tggcggatgt    60

<210> SEQ ID NO 1770
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1770
cgcgaatgcc gcttggccac ctcatgtcgt ctgacttctg ctctcacgcg tggcggatgt    60

<210> SEQ ID NO 1771
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1771
cgcgaatgcc aggctctaaa ccgcctcagg aagctggcag agaggacgcg tggcggatgt    60

<210> SEQ ID NO 1772
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1772
cgcgaatgcc gcctggatgc tgtcctggag ttcggggtcg tccacacgcg tggcggatgt    60

<210> SEQ ID NO 1773
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1773
cgcgaatgcc ctcattggac agcattcgag gtaagagaaa ggtcaacgcg tggcggatgt    60

<210> SEQ ID NO 1774
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1774
cgcgaatgcc atggcgagcc ctccggagag cgatggcttc tcggaacgcg tggcggatgt    60

<210> SEQ ID NO 1775
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1775
cgcgaatgcc tcttgggttt gcgcaggtag cccaccttgc gcacgacgcg tggcggatgt    60

```
<210> SEQ ID NO 1776
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1776
cgcgaatgcc gcatgcacaa acgcttcttc gtactgcgcg cggccacgcg tggcggatgt      60

<210> SEQ ID NO 1777
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1777
cgcgaatgcc tagtactcga ggcgcgccgg gcccccagcc tcgctacgcg tggcggatgt      60

<210> SEQ ID NO 1778
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1778
cgcgaatgcc cgagaacgag aagaagtggc ggcacaagtc gagcgacgcg tggcggatgt      60

<210> SEQ ID NO 1779
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1779
cgcgaatgcc gaagcagctc tcaaggggga tcgagcgttt ggggacgcg tggcggatgt       60

<210> SEQ ID NO 1780
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1780
cgcgaatgcc aacatcaaca agcgggctga ctccaagaac aagcaacgcg tggcggatgt      60

<210> SEQ ID NO 1781
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1781
cgcgaatgcc caaagtgctc gtcccgggtg tagagagcca ccaggacgcg tggcggatgt      60

<210> SEQ ID NO 1782
<211> LENGTH: 60
<212> TYPE: DNA
<213> ORGANISM: Artificial Sequence
<220> FEATURE:
<223> OTHER INFORMATION: Synthetic oligonucleotide
```

```
<400> SEQUENCE: 1782
cgcgaatgcc ccatcgcggc ggacagcgag gccgagcaag acagcacgcg tggcggatgt    60

<210> SEQ ID NO 1783
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1783
cgcgaatgcc gcacggttgt gcagctgtag gagagcctgg taccaacgcg tggcggatgt    60

<210> SEQ ID NO 1784
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1784
cgcgaatgcc taagggccac cacgacggag ctgcggccct cggggacgcg tggcggatgt    60

<210> SEQ ID NO 1785
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1785
cgcgaatgcc ggagctgccg ctgcagctgc ccccaccacc tcccgacgcg tggcggatgt    60

<210> SEQ ID NO 1786
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1786
cgcgaatgcc ggccttggtg aggctgggga ggacttgagc tacggacgcg tggcggatgt    60

<210> SEQ ID NO 1787
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1787
cgcgaatgcc agacctcttt gaatgcgggt cctgggggca cgtcaacgcg tggcggatgt    60

<210> SEQ ID NO 1788
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1788
cgcgaatgcc ggcaagtgat cctgaagccc aagggcctgg gtcagacgcg tggcggatgt    60

<210> SEQ ID NO 1789
<211> LENGTH: 60
```

<212> TYPE: DNA
<213> ORGANISM: Artificial Sequence
<220> FEATURE:
<223> OTHER INFORMATION: Synthetic oligonucleotide

<400> SEQUENCE: 1789
cgcgaatgcc aggcaaaggc ggtagatacc aatcaggttc tttgtacgcg tggcggatgt    60

<210> SEQ ID NO 1790
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1790
cgcgaatgcc gaccagcaag accatcagct tcgtgaagct gaactacgcg tggcggatgt    60

<210> SEQ ID NO 1791
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1791
cgcgaatgcc gttcatcagc tgcagcacca cggccgctgc ctccgacgcg tggcggatgt    60

<210> SEQ ID NO 1792
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1792
cgcgaatgcc atcaggcgct gtggccactc ggaaaacttc ttcttacgcg tggcggatgt    60

<210> SEQ ID NO 1793
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1793
cgcgaatgcc cgggccccgt cacggcagaa cggcccacct cgatgacgcg tggcggatgt    60

<210> SEQ ID NO 1794
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1794
cgcgaatgcc gggagttctg gatgcaggtg gatgactctg tggtgacgcg tggcggatgt    60

<210> SEQ ID NO 1795
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1795
cgcgaatgcc atggcctcca ggatggtctc gtgcatgttc tgggcacgcg tggcggatgt    60

<210> SEQ ID NO 1796
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1796
cgcgaatgcc gcgggccatg agtgatgagt tccgccctcg cagcaacgcg tggcggatgt    60

<210> SEQ ID NO 1797
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1797
cgcgaatgcc gatggggtta gagcagttgg acgaggactg gctctacgcg tggcggatgt    60

<210> SEQ ID NO 1798
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1798
cgcgaatgcc agcgtccccc tgcgccggca ccatctcaac aatccacgcg tggcggatgt    60

<210> SEQ ID NO 1799
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1799
cgcgaatgcc gtgatcggcg ggtcagcccc acctggctgg gcgggacgcg tggcggatgt    60

<210> SEQ ID NO 1800
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1800
cgcgaatgcc gcactgagag catcaccgcc acctccccgg ccagcacgcg tggcggatgt    60

<210> SEQ ID NO 1801
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1801
cgcgaatgcc cggacacgga aggagcctgg cttcccgccc accatacgcg tggcggatgt    60

<210> SEQ ID NO 1802
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1802
cgcgaatgcc cgcctccagt gacggcgaag gcaccatgtc ccgccacgcg tggcggatgt    60

<210> SEQ ID NO 1803
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1803
cgcgaatgcc gctgggactc acagggctgc cgtccaccga ggctgacgcg tggcggatgt    60

<210> SEQ ID NO 1804
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1804
cgcgaatgcc accaacagaa cccacgccca ccggcatcgg ggcagacgcg tggcggatgt    60

<210> SEQ ID NO 1805
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1805
cgcgaatgcc agcggctgtg gttgagcggg gggtgcagcc gggcgacgcg tggcggatgt    60

<210> SEQ ID NO 1806
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1806
cgcgaatgcc ccatccccat gccggcttcc cgctgctcgc cttcgacgcg tggcggatgt    60

<210> SEQ ID NO 1807
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1807
cgcgaatgcc gtgctactgg acgacagact gaccgggctg gtggcacgcg tggcggatgt    60

<210> SEQ ID NO 1808
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1808
cgcgaatgcc cagtggccat ggctccacct cggattgtct cttccacgcg tggcggatgt    60

<210> SEQ ID NO 1809
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1809
cgcgaatgcc ggggaacca gacaccgaag cactagatcg ccgtgacgcg tggcggatgt    60

<210> SEQ ID NO 1810
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1810
cgcgaatgcc agcgatggcg gtttcatctc ctcggatgag tatggacgcg tggcggatgt    60

<210> SEQ ID NO 1811
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1811
cgcgaatgcc tgcggaagga actccggaaa tcgcagggac tggagacgcg tggcggatgt    60

<210> SEQ ID NO 1812
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1812
cgcgaatgcc gtgtcactcc ggattccctg ggccacaccc caccaacgcg tggcggatgt    60

<210> SEQ ID NO 1813
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1813
cgcgaatgcc cagatatagt tgcttagctc ctcctcaccg cgggcacgcg tggcggatgt    60

<210> SEQ ID NO 1814
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1814
cgcgaatgcc catgggtggc aaggggccct ccaccctgac cgcccacgcg tggcggatgt    60

<210> SEQ ID NO 1815
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1815
cgcgaatgcc attgccaccc cgagacaaaa tgtagtgacc gttggacgcg tggcggatgt    60

<210> SEQ ID NO 1816
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1816
cgcgaatgcc ggccaccgct gcacccagg aacaggcttg ggcacacgcg tggcggatgt    60

<210> SEQ ID NO 1817
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1817
cgcgaatgcc cactggctgc ttcatcccca gccaaggctg gactcacgcg tggcggatgt    60

<210> SEQ ID NO 1818
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1818
cgcgaatgcc ctgcagatct ggataatcgg ttccgaaaga gaactacgcg tggcggatgt    60

<210> SEQ ID NO 1819
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1819
cgcgaatgcc tggtgggtaa tggtagggga tgtgcctgcc gagtgacgcg tggcggatgt    60

<210> SEQ ID NO 1820
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1820
cgcgaatgcc gaagaccccg tcccagtcct cagtggcttc cattgacgcg tggcggatgt    60

<210> SEQ ID NO 1821
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1821
cgcgaatgcc tggtgggtag gcaggcatca tctctgtgta ctcctacgcg tggcggatgt    60

<210> SEQ ID NO 1822

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1822
cgcgaatgcc ggaggtggca gtggaggccg actgccggga cacagacgcg tggcggatgt    60

<210> SEQ ID NO 1823
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1823
cgcgaatgcc ctgggtagga gcgggtgggc acgaaggcgg agtgcacgcg tggcggatgt    60

<210> SEQ ID NO 1824
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1824
cgcgaatgcc aggagggtct ggaaatgcac cccttggagc gtcggacgcg tggcggatgt    60

<210> SEQ ID NO 1825
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1825
cgcgaatgcc tggagggtgg agctgtctgg gcggtggtgc cccccacgcg tggcggatgt    60

<210> SEQ ID NO 1826
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1826
cgcgaatgcc cacggatgat ggctacatgc ccatgtcccc aggggacgcg tggcggatgt    60

<210> SEQ ID NO 1827
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1827
cgcgaatgcc tccactgccc tttcggccac tgggcactgg ggccaacgcg tggcggatgt    60

<210> SEQ ID NO 1828
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1828
```

```
cgcgaatgcc gactatatgc ccatgagccc aagagcgta tctgcacgcg tggcggatgt    60
```

<210> SEQ ID NO 1829
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1829

```
cgcgaatgcc gatggcgtct gatgggattg atgatctgct gtgggacgcg tggcggatgt    60
```

<210> SEQ ID NO 1830
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1830

```
cgcgaatgcc cccagagagt ggaccccaat ggctacatga tgatgacgcg tggcggatgt    60
```

<210> SEQ ID NO 1831
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1831

```
cgcgaatgcc cctccaatgt caggagagca gccaccgctg ggggaacgcg tggcggatgt    60
```

<210> SEQ ID NO 1832
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1832

```
cgcgaatgcc tggccccagc agcagcagca gcagcagcaa cgccgacgcg tggcggatgt    60
```

<210> SEQ ID NO 1833
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1833

```
cgcgaatgcc tgtccacagc tttccatagc tggtcccgga agggaacgcg tggcggatgt    60
```

<210> SEQ ID NO 1834
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1834

```
cgcgaatgcc aacggggtag ggggccacca ctctcatgtc ttgccacgcg tggcggatgt    60
```

<210> SEQ ID NO 1835
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 1835
cgcgaatgcc taccaccgct gctctccact gggggtttgg ggtgaacgcg tggcggatgt    60

<210> SEQ ID NO 1836
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1836
cgcgaatgcc agctcttacc ttgcacaggt gactacatga acatgacgcg tggcggatgt    60

<210> SEQ ID NO 1837
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1837
cgcgaatgcc gagggctgc tggtgttgga gtcccccact ggtgaacgcg tggcggatgt    60

<210> SEQ ID NO 1838
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1838
cgcgaatgcc cgactgctac tacggccctg aggaccccca gcacaacgcg tggcggatgt    60

<210> SEQ ID NO 1839
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1839
cgcgaatgcc ggatcttggc aatgagtagt aggagaggac tggctacgcg tggcggatgt    60

<210> SEQ ID NO 1840
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1840
cgcgaatgcc tttaagcaca cccagcgccc cggggagccg gaggaacgcg tggcggatgt    60

<210> SEQ ID NO 1841
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1841
cgcgaatgcc tagtggaaag gcggaggtgc tgatgccggg cacccacgcg tggcggatgt    60
```

<210> SEQ ID NO 1842
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1842
cgcgaatgcc gctctggtcg ccttctctat gctgcaacag cagatacgcg tggcggatgt    60

<210> SEQ ID NO 1843
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1843
cgcgaatgcc cccaggctgt cgctgctggt ggaagaggaa gaatcacgcg tggcggatgt    60

<210> SEQ ID NO 1844
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1844
cgcgaatgcc tgggggatac tgcggggcta ggctggagcc cagccacgcg tggcggatgt    60

<210> SEQ ID NO 1845
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1845
cgcgaatgcc atggggctgc agaacctgat ggtgggatg tggaaacgcg tggcggatgt    60

<210> SEQ ID NO 1846
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1846
cgcgaatgcc ctgcctcgaa aggtggacac agctgctcag accaaacgcg tggcggatgt    60

<210> SEQ ID NO 1847
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1847
cgcgaatgcc ccagggacag cctcgtgggc cgggccaggc ggctaacgcg tggcggatgt    60

<210> SEQ ID NO 1848
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 1848
cgcgaatgcc gggatcccaa ggccagcacc ttacctcggg cccgaacgcg tggcggatgt    60

<210> SEQ ID NO 1849
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1849
cgcgaatgcc tggagggtgc agcaagggct gctgctgctg ctgctacgcg tggcggatgt    60

<210> SEQ ID NO 1850
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1850
cgcgaatgcc tccagagccc aagagcccgg gggaatatgt caataacgcg tggcggatgt    60

<210> SEQ ID NO 1851
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1851
cgcgaatgcc agacaagtag ccagactgat cactcccaaa ttcaaacgcg tggcggatgt    60

<210> SEQ ID NO 1852
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1852
cgcgaatgcc ggcccggtgg ctttccacag ctcaccttct gtcagacgcg tggcggatgt    60

<210> SEQ ID NO 1853
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1853
cgcgaatgcc cctctctggg agctggctgg agctgggatg gacacacgcg tggcggatgt    60

<210> SEQ ID NO 1854
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1854
cgcgaatgcc aagagactgg cactgaggag tacatgaaga tggacacgcg tggcggatgt    60

```
<210> SEQ ID NO 1855
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1855
cgcgaatgcc ctctcctgcc aggctgccct ccggcccggc cccagacgcg tggcggatgt      60

<210> SEQ ID NO 1856
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1856
cgcgaatgcc cactggggtc gagatgggca gactgggccc tgcacacgcg tggcggatgt      60

<210> SEQ ID NO 1857
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1857
cgcgaatgcc ccgggtaggc ctgcaaatgc tagcagcccc gggagacgcg tggcggatgt      60

<210> SEQ ID NO 1858
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1858
cgcgaatgcc gcagtgccca gcagccgggg tgactacatg accatacgcg tggcggatgt      60

<210> SEQ ID NO 1859
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1859
cgcgaatgcc tgtccacgta gctctgacgg ggacaactca tctgcacgcg tggcggatgt      60

<210> SEQ ID NO 1860
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1860
cgcgaatgcc cctcgccagc tgcccctgta agctatgctg acatgacgcg tggcggatgt      60

<210> SEQ ID NO 1861
<211> LENGTH: 60
<212> TYPE: DNA
<213> ORGANISM: Artificial Sequence
<220> FEATURE:
<223> OTHER INFORMATION: Synthetic oligonucleotide
```

```
<400> SEQUENCE: 1861
cgcgaatgcc ggcaggctca cctcctctgc agcaatgcct gttcgacgcg tggcggatgt    60

<210> SEQ ID NO 1862
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1862
cgcgaatgcc cagggccacc atggctgctg cctcctcatc ctcagacgcg tggcggatgt    60

<210> SEQ ID NO 1863
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1863
cgcgaatgcc tgccccttga ggcccagtcg gggaagcaga ggctgacgcg tggcggatgt    60

<210> SEQ ID NO 1864
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1864
cgcgaatgcc gcagagctgg ctgcccactc gtccctgctg ggggacgcg tggcggatgt     60

<210> SEQ ID NO 1865
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1865
cgcgaatgcc gggtgaaggc gctcatgccc ccaggtcctt gtgggacgcg tggcggatgt    60

<210> SEQ ID NO 1866
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1866
cgcgaatgcc gggtgaacct cagtcctaac cgcaaccaga gtgccacgcg tggcggatgt    60

<210> SEQ ID NO 1867
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1867
cgcgaatgcc cgccggcacc cttgtgggtc tgcacggatc actttacgcg tggcggatgt    60

<210> SEQ ID NO 1868
<211> LENGTH: 60
```

```
<212> TYPE: DNA
<213> ORGANISM: Artificial Sequence
<220> FEATURE:
<223> OTHER INFORMATION: Synthetic oligonucleotide

<400> SEQUENCE: 1868
cgcgaatgcc gaggcatagc tccgagactt tctcctcaac acccaacgcg tggcggatgt    60

<210> SEQ ID NO 1869
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1869
cgcgaatgcc tccaaagggc actgtgttgc ccacccgggt ggcacacgcg tggcggatgt    60

<210> SEQ ID NO 1870
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1870
cgcgaatgcc gcggggcag cagtaggggg cggtggcggt agcagacgcg tggcggatgt    60

<210> SEQ ID NO 1871
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1871
cgcgaatgcc cagagctgtg gcgtttcaca tcctcgctgc tgctgacgcg tggcggatgt    60

<210> SEQ ID NO 1872
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1872
cgcgaatgcc cttcctttga gaatgtgtgg ctgaggcctg gggagacgcg tggcggatgt    60

<210> SEQ ID NO 1873
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1873
cgcgaatgcc cacagtttgg ctggctcctt gggggctccc ccaagacgcg tggcggatgt    60

<210> SEQ ID NO 1874
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1874
```
cgcgaatgcc tggggctgct gggggtttgg agaatggtct taactacgcg tggcggatgt     60

<210> SEQ ID NO 1875
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1875
cgcgaatgcc ctgtttgaag tccttgacca aatccaggtc tatgtacgcg tggcggatgt     60

<210> SEQ ID NO 1876
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1876
cgcgaatgcc tgccctcagg agtgcacccc tgaaccgcag cctccacgcg tggcggatgt     60

<210> SEQ ID NO 1877
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1877
cgcgaatgcc cgctgcccag gggttgatga gggggtgggg gtgggacgcg tggcggatgt     60

<210> SEQ ID NO 1878
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1878
cgcgaatgcc gtgagagcag ctccacccgc cgctcaagtg aggatacgcg tggcggatgt     60

<210> SEQ ID NO 1879
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1879
cgcgaatgcc tgcttctgga aactgatgct ggcataggcg cttaaacgcg tggcggatgt     60

<210> SEQ ID NO 1880
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1880
cgcgaatgcc gccagaggac cgtcagtagc tcaactggac atcacacgcg tggcggatgt     60

<210> SEQ ID NO 1881
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 1881
cgcgaatgcc cataaaggaa ctgttgtaga agtaatacct tttctacgcg tggcggatgt    60

<210> SEQ ID NO 1882
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1882
cgcgaatgcc ttggttactt ttacttgtaa acctgaaaag taaaaacgcg tggcggatgt    60

<210> SEQ ID NO 1883
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1883
cgcgaatgcc gctaaaacag gaacgaatct tgtaagtatc agtatacgcg tggcggatgt    60

<210> SEQ ID NO 1884
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1884
cgcgaatgcc tatcaactac tctataaata acacatgagt attacacgcg tggcggatgt    60

<210> SEQ ID NO 1885
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1885
cgcgaatgcc atcccccacg tgtggtgagc ctggaggagc ctgagacgcg tggcggatgt    60

<210> SEQ ID NO 1886
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1886
cgcgaatgcc cgcaccacaa actcgatgca gtgctccagg cgcagacgcg tggcggatgt    60

<210> SEQ ID NO 1887
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1887
cgcgaatgcc tggcaacccc ccaccaacgc tgcactggct gcacaacgcg tggcggatgt    60
```

<210> SEQ ID NO 1888
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1888
cgcgaatgcc atggatgatc ttggactccc gcagaggctg cccatacgcg tggcggatgt    60

<210> SEQ ID NO 1889
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1889
cgcgaatgcc gtggaatact accaagaggg agagatttcc gagggacgcg tggcggatgt    60

<210> SEQ ID NO 1890
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1890
cgcgaatgcc tgttgtagtg ggtgggcttg ttgaagagca ggcagacgcg tggcggatgt    60

<210> SEQ ID NO 1891
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1891
cgcgaatgcc atggcaacta taccctcatt gccaaaaacc cactgacgcg tggcggatgt    60

<210> SEQ ID NO 1892
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1892
cgcgaatgcc aggaagtggc cattgatggt ctggttggct gtgccacgcg tggcggatgt    60

<210> SEQ ID NO 1893
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1893
cgcgaatgcc caaggagccc tttccaggtg agggcagcgt agctgacgcg tggcggatgt    60

<210> SEQ ID NO 1894
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1894
cgcgaatgcc gtggcacccc ttaccccggc atgatggtgg attctacgcg tggcggatgt    60

<210> SEQ ID NO 1895
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1895
cgcgaatgcc atccggtacc cactcttgat cttattgtag aaagtacgcg tggcggatgt    60

<210> SEQ ID NO 1896
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1896
cgcgaatgcc ggccaagcct gaccacgcta ccagtgaagt gtgagacgcg tggcggatgt    60

<210> SEQ ID NO 1897
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1897
cgcgaatgcc gactgtgaac acaggccccc gggatgggga aggagacgcg tggcggatgt    60

<210> SEQ ID NO 1898
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1898
cgcgaatgcc tgtgggtcta gggggaggga ggggccctga gacttacgcg tggcggatgt    60

<210> SEQ ID NO 1899
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1899
cgcgaatgcc ctgtggggac agaactcaag agtgggcaca ggggacgcg tggcggatgt    60

<210> SEQ ID NO 1900
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1900
cgcgaatgcc ctacgagatc atggtgaaat gctggaacag tgagcacgcg tggcggatgt    60

<210> SEQ ID NO 1901

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1901
cgcgaatgcc ctcactcagg tggtaaaagg agggtctctt ctccgacgcg tggcggatgt      60

<210> SEQ ID NO 1902
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1902
cgcgaatgcc attgtggaga atctgctgcc tggacaatat aaaaaacgcg tggcggatgt      60

<210> SEQ ID NO 1903
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1903
cgcgaatgcc atccagacct ttccacccac agatccaaac acaccacgcg tggcggatgt      60

<210> SEQ ID NO 1904
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1904
cgcgaatgcc ttgcagttcc ttcatccatt ctggacttgg tcgatacgcg tggcggatgt      60

<210> SEQ ID NO 1905
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1905
cgcgaatgcc ctcaccgtct gtcccccagt tgagccatgg tgatcacgcg tggcggatgt      60

<210> SEQ ID NO 1906
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1906
cgcgaatgcc gtgcacagct gaaggcacgc cgcttcctga tattgacgcg tggcggatgt      60

<210> SEQ ID NO 1907
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1907
```
cgcgaatgcc tccatacttc ttaatatctt tgcatatcat ccactacgcg tggcggatgt    60

<210> SEQ ID NO 1908
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1908
cgcgaatgcc gattctgcct gcccacaggt cgggtcttgg ggtctacgcg tggcggatgt    60

<210> SEQ ID NO 1909
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1909
cgcgaatgcc taggctgttc cttcaaccac cttcccaaac gctccacgcg tggcggatgt    60

<210> SEQ ID NO 1910
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1910
cgcgaatgcc tggattaagc cggtcccaac ctgtcatgaa agttgacgcg tggcggatgt    60

<210> SEQ ID NO 1911
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1911
cgcgaatgcc caggaaggag cacttacgtt ttagcatctt cactgacgcg tggcggatgt    60

<210> SEQ ID NO 1912
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1912
cgcgaatgcc ttcattctcc tcctttctt tctagggtga ttgggacgcg tggcggatgt    60

<210> SEQ ID NO 1913
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1913
cgcgaatgcc tccaaaatct ccaagggaga acttttcag ccacaacgcg tggcggatgt    60

<210> SEQ ID NO 1914
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 1914
cgcgaatgcc gaccttaagt ccatcaaatc aagagcaagt gatgtacgcg tggcggatgt    60

<210> SEQ ID NO 1915
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1915
cgcgaatgcc ttacataaac gaagatttct cataccattt cgaacacgcg tggcggatgt    60

<210> SEQ ID NO 1916
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1916
cgcgaatgcc ggctgaccgt tacctttcct cctcccctgc agacaacgcg tggcggatgt    60

<210> SEQ ID NO 1917
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1917
cgcgaatgcc cgttgagcgt gtgaagactg cgccagttct ctatgacgcg tggcggatgt    60

<210> SEQ ID NO 1918
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1918
cgcgaatgcc ccgtggacat ggagctctac accggacttc aaaagacgcg tggcggatgt    60

<210> SEQ ID NO 1919
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1919
cgcgaatgcc gggaaaggcc tctctgtggc cgggtgtact cacagacgcg tggcggatgt    60

<210> SEQ ID NO 1920
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1920
cgcgaatgcc tttgcagaat ttaacagttt acccctttgac actttacgcg tggcggatgt    60
```

<210> SEQ ID NO 1921
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1921
cgcgaatgcc agctggtcta tctttgcaat ccatggctgc aaataacgcg tggcggatgt    60

<210> SEQ ID NO 1922
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1922
cgcgaatgcc tttccagtta agaagttaat acaaggtaat tatttacgcg tggcggatgt    60

<210> SEQ ID NO 1923
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1923
cgcgaatgcc actataaact acgaacaact ctttaaccca tttccacgcg tggcggatgt    60

<210> SEQ ID NO 1924
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1924
cgcgaatgcc ggagtcctga cctgggggct gtggagctgc gcatcacgcg tggcggatgt    60

<210> SEQ ID NO 1925
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1925
cgcgaatgcc gcgtgctcca ctcggaagtg gtgccgcagc tcttcacgcg tggcggatgt    60

<210> SEQ ID NO 1926
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1926
cgcgaatgcc ggtggccgag ggtgccaaga acgtactgcg cctgcacgcg tggcggatgt    60

<210> SEQ ID NO 1927
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 1927
cgcgaatgcc gactgccttg cggtccgggg ccttggcagc gctgaacgcg tggcggatgt    60

<210> SEQ ID NO 1928
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1928
cgcgaatgcc agcgaggtga ggggcggagc tttcattaga ggcggacgcg tggcggatgt    60

<210> SEQ ID NO 1929
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1929
cgcgaatgcc cagcagtgcg aactggtcca aaacatgata gacttacgcg tggcggatgt    60

<210> SEQ ID NO 1930
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1930
cgcgaatgcc atttggtcct aagcccttcc aggttggaga tgctcacgcg tggcggatgt    60

<210> SEQ ID NO 1931
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1931
cgcgaatgcc gtgctacctc caacgacctc acacaaaaag aaatcacgcg tggcggatgt    60

<210> SEQ ID NO 1932
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1932
cgcgaatgcc tcccgtaggc aacacctacc tccagggtcc ggattacgcg tggcggatgt    60

<210> SEQ ID NO 1933
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1933
cgcgaatgcc aaataaaacc tgctcatgca ccatggtttt tcaaaacgcg tggcggatgt    60

<210> SEQ ID NO 1934
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1934
cgcgaatgcc gatgtagcat aaaataatcc atgaagggta ccgagacgcg tggcggatgt    60

<210> SEQ ID NO 1935
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1935
cgcgaatgcc tggctgctcc gctttgcaca cacaggggag gcgcaacgcg tggcggatgt    60

<210> SEQ ID NO 1936
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1936
cgcgaatgcc tttgctttcc catcacctta ccttccttcg cagccacgcg tggcggatgt    60

<210> SEQ ID NO 1937
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1937
cgcgaatgcc ttttcattcc agtgtcttac acttagcaat catccacgcg tggcggatgt    60

<210> SEQ ID NO 1938
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1938
cgcgaatgcc ttctagtaga tccctcacaa gttgagaatg aaggtacgcg tggcggatgt    60

<210> SEQ ID NO 1939
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1939
cgcgaatgcc gtcacatctg gtttgatttc tgatgacatt atcaaacgcg tggcggatgt    60

<210> SEQ ID NO 1940
<211> LENGTH: 60
<212> TYPE: DNA
<213> ORGANISM: Artificial Sequence
<220> FEATURE:
<223> OTHER INFORMATION: Synthetic oligonucleotide

```
<400> SEQUENCE: 1940
cgcgaatgcc gatttctgct tacctggtac agatcatttc tcatgacgcg tggcggatgt    60

<210> SEQ ID NO 1941
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1941
cgcgaatgcc cttgcaaaat tggatattac aaggctctct ccacgacgcg tggcggatgt    60

<210> SEQ ID NO 1942
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1942
cgcgaatgcc tagctgtggg gtgggcactt ggcacaggtg gcatcacgcg tggcggatgt    60

<210> SEQ ID NO 1943
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1943
cgcgaatgcc ctctgtctgg gaaggagcca cctcgtgcac ctgtgacgcg tggcggatgt    60

<210> SEQ ID NO 1944
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1944
cgcgaatgcc ggcagcatcg ttgtcagctc tgaaaaagcc tcggtacgcg tggcggatgt    60

<210> SEQ ID NO 1945
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1945
cgcgaatgcc tctatgccct gcacccgtaa gttgtatgct tgtctacgcg tggcggatgt    60

<210> SEQ ID NO 1946
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1946
cgcgaatgcc tatgtgaatg acttcactta ttgttattta gttttacgcg tggcggatgt    60

<210> SEQ ID NO 1947
<211> LENGTH: 60
```

-continued

<212> TYPE: DNA
<213> ORGANISM: Artificial Sequence
<220> FEATURE:
<223> OTHER INFORMATION: Synthetic oligonucleotide

<400> SEQUENCE: 1947
cgcgaatgcc tcaaggttac tttttcgtgg tgttctctgt gtttcacgcg tggcggatgt    60

<210> SEQ ID NO 1948
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1948
cgcgaatgcc tgaagaggtg aatgtaattc ctccacacac tccagacgcg tggcggatgt    60

<210> SEQ ID NO 1949
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1949
cgcgaatgcc tataattaaa agtaggaaaa ttcataccta actggacgcg tggcggatgt    60

<210> SEQ ID NO 1950
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1950
cgcgaatgcc gtgaatttgg tgaggtatgc agtgggcgtc tcaaaacgcg tggcggatgt    60

<210> SEQ ID NO 1951
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1951
cgcgaatgcc ttgatagcca cacagatctc tctcttgcca ggcacacgcg tggcggatgt    60

<210> SEQ ID NO 1952
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1952
cgcgaatgcc gactctgaaa gctggttata cagacaaaca gaggaacgcg tggcggatgt    60

<210> SEQ ID NO 1953
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1953
cgcgaatgcc ctgtcccatg atgctggcct cactcaggaa gtctcacgcg tggcggatgt    60

<210> SEQ ID NO 1954
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1954
cgcgaatgcc tttgaccatc cgaacatcat tcacttggaa ggcgtacgcg tggcggatgt    60

<210> SEQ ID NO 1955
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1955
cgcgaatgcc ttgtaaaggg ggtgacccac gtacatttag tgaccacgcg tggcggatgt    60

<210> SEQ ID NO 1956
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1956
cgcgaatgcc ctaaaatagc aggctcttat ttttctttt gtttgacgcg tggcggatgt    60

<210> SEQ ID NO 1957
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1957
cgcgaatgcc aatacaagcg aactccaagt ttgtatcgct acaaaacgcg tggcggatgt    60

<210> SEQ ID NO 1958
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1958
cgcgaatgcc accgagtaat ggaatccatg cttaaatcag taagtacgcg tggcggatgt    60

<210> SEQ ID NO 1959
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1959
cgcgaatgcc gcccggctga aatttttta tattgttttt aacttacgcg tggcggatgt    60

<210> SEQ ID NO 1960
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 1960
cgcgaatgcc gcctggggtc ggcgacggct gctcttttcg ttctgacgcg tggcggatgt    60

<210> SEQ ID NO 1961
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1961
cgcgaatgcc gggcttcccg ggaggctcgt ccatcgggca ggcgaacgcg tggcggatgt    60

<210> SEQ ID NO 1962
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1962
cgcgaatgcc ctcagctgtg aggagaagga aaaggtgccg ggggtacgcg tggcggatgt    60

<210> SEQ ID NO 1963
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1963
cgcgaatgcc aagcggggtc agagtcctgc gtccgccctt cccgcacgcg tggcggatgt    60

<210> SEQ ID NO 1964
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1964
cgcgaatgcc actgtactga ttattattta ttatttactg tatatacgcg tggcggatgt    60

<210> SEQ ID NO 1965
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1965
cgcgaatgcc atgtattctg tgacaatcat aactggctta cctagacgcg tggcggatgt    60

<210> SEQ ID NO 1966
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1966
cgcgaatgcc ggagaatggt tccttggata gtttcctacg tgtaaacgcg tggcggatgt    60
```

<210> SEQ ID NO 1967
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1967
cgcgaatgcc atttattcat atatatgtat gtgtgtgcat cttacacgcg tggcggatgt    60

<210> SEQ ID NO 1968
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1968
cgcgaatgcc tacctcctaa agaactgcac agtgaatcca aagaacgcg tggcggatgt    60

<210> SEQ ID NO 1969
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1969
cgcgaatgcc tgtatcctat atccttcact cttttcagta tacttacgcg tggcggatgt    60

<210> SEQ ID NO 1970
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1970
cgcgaatgcc tctttaaaga gaaatttgct aaagctgtgg dacagacgcg tggcggatgt    60

<210> SEQ ID NO 1971
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1971
cgcgaatgcc attcaagtta cctgtgatcc aatttcgaca caaccacgcg tggcggatgt    60

<210> SEQ ID NO 1972
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1972
cgcgaatgcc gcgtgtaagt tctgacagtg ctcccccaat ctcctacgcg tggcggatgt    60

<210> SEQ ID NO 1973
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1973
cgcgaatgcc ttcccctga ggtctgtcca ttctggaaaa gagaaacgcg tggcggatgt    60

<210> SEQ ID NO 1974
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1974
cgcgaatgcc aagctggact tcagccgtcc aaggtgagga ccatgacgcg tggcggatgt    60

<210> SEQ ID NO 1975
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1975
cgcgaatgcc aggatccccc acagcccctc gctcagggtg ctggcacgcg tggcggatgt    60

<210> SEQ ID NO 1976
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1976
cgcgaatgcc ttcctgtttt ttttctgctt tctatttgtt taataacgcg tggcggatgt    60

<210> SEQ ID NO 1977
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1977
cgcgaatgcc tagcaccaat gcagaattta tttcagtaga tatccacgcg tggcggatgt    60

<210> SEQ ID NO 1978
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1978
cgcgaatgcc aaagtttctt ggatcacatt tttattagct aaaggacgcg tggcggatgt    60

<210> SEQ ID NO 1979
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1979
cgcgaatgcc tgaaatatta gcatttaata aatataatga acttaacgcg tggcggatgt    60

<210> SEQ ID NO 1980

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1980
cgcgaatgcc ctccctctct tgccctgcag aggtccaagc cccgtacgcg tggcggatgt     60

<210> SEQ ID NO 1981
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1981
cgcgaatgcc ccccacacca cccccagctc cggaagcggc tccacacgcg tggcggatgt     60

<210> SEQ ID NO 1982
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1982
cgcgaatgcc gtggacaccg gcaaggccac cctgacctcg agcccacgcg tggcggatgt     60

<210> SEQ ID NO 1983
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1983
cgcgaatgcc acatacgtca cccctgctct caggatgcac ccagtacgcg tggcggatgt     60

<210> SEQ ID NO 1984
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1984
cgcgaatgcc ctgtctgctc ttcccaccag gtaccgcctg atgctacgcg tggcggatgt     60

<210> SEQ ID NO 1985
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1985
cgcgaatgcc ccggccttttt gtccggctcc tgcttccagc attgcacgcg tggcggatgt    60

<210> SEQ ID NO 1986
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1986
```
cgcgaatgcc tgtttgcgga catcagcaaa gacctggaga agatgacgcg tggcggatgt    60

<210> SEQ ID NO 1987
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1987
cgcgaatgcc aattggaccc aggcactcac tctcctctta accatacgcg tggcggatgt    60

<210> SEQ ID NO 1988
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1988
cgcgaatgcc acgcccttgc acttggcagt gatcactaag caggaacgcg tggcggatgt    60

<210> SEQ ID NO 1989
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1989
cgcgaatgcc cggccccagc cctcagcaaa tcctccacca catctacgcg tggcggatgt    60

<210> SEQ ID NO 1990
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1990
cgcgaatgcc acctgagcct tctggaccgc ttgggtaact ctgttacgcg tggcggatgt    60

<210> SEQ ID NO 1991
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1991
cgcgaatgcc actttatcat gtccttcttt ggcagctagg tgcaaacgcg tggcggatgt    60

<210> SEQ ID NO 1992
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1992
cgcgaatgcc tctcagtatc ttactcaagc acaaaaaggc agcacacgcg tggcggatgt    60

<210> SEQ ID NO 1993
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 1993
cgcgaatgcc tctcttaccg tccccgttgg ggtggtcaag aagtaacgcg tggcggatgt    60

<210> SEQ ID NO 1994
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1994
cgcgaatgcc cttaacgttc acctttgcag agaggatttc gtttcacgcg tggcggatgt    60

<210> SEQ ID NO 1995
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1995
cgcgaatgcc agtccaccat gggatgggcc ttcacataca taacgacgcg tggcggatgt    60

<210> SEQ ID NO 1996
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1996
cgcgaatgcc acctggtgcc tctagtgaaa agaacaagaa gtcttacgcg tggcggatgt    60

<210> SEQ ID NO 1997
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1997
cgcgaatgcc ggagagctac cacaaactta ctttgacctg agggtacgcg tggcggatgt    60

<210> SEQ ID NO 1998
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1998
cgcgaatgcc gggagtttgg agaagtgtac aagggcgtt tgaaaacgcg tggcggatgt     60

<210> SEQ ID NO 1999
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 1999
cgcgaatgcc ttgatggcca cgtagatttc cctcttgcct ggcagacgcg tggcggatgt    60
```

<210> SEQ ID NO 2000
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2000
cgcgaatgcc gaccctgaag gcagggtact cggagaagca gcgtcacgcg tggcggatgt    60

<210> SEQ ID NO 2001
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2001
cgcgaatgcc ctggcccatg atgctcgcct cactcagaaa gtcccacgcg tggcggatgt    60

<210> SEQ ID NO 2002
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2002
cgcgaatgcc ttcgaccatc ctaacatcat tcgcctggag ggtgtacgcg tggcggatgt    60

<210> SEQ ID NO 2003
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2003
cgcgaatgcc ctgtgatgat catgacaggc cgactcttgg tgaccacgcg tggcggatgt    60

<210> SEQ ID NO 2004
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2004
cgcgaatgcc agttcatgga gaatggtgca ttggattctt tcctcacgcg tggcggatgt    60

<210> SEQ ID NO 2005
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2005
cgcgaatgcc agtgcatcat caaacccctg agttgctctt accctacgcg tggcggatgt    60

<210> SEQ ID NO 2006
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 2006
cgcgaatgcc gccttcccag cccctgctcg accgctccat cccagacgcg tggcggatgt    60

<210> SEQ ID NO 2007
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2007
cgcgaatgcc gagccagtca tccacggtgg taaaggccgt gaagtacgcg tggcggatgt    60

<210> SEQ ID NO 2008
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2008
cgcgaatgcc agcgccatca aaatggtcca gtacagggac agcttacgcg tggcggatgt    60

<210> SEQ ID NO 2009
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2009
cgcgaatgcc tgaccagctg gagggaggtg aagccagcag tgaggacgcg tggcggatgt    60

<210> SEQ ID NO 2010
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2010
cgcgaatgcc cccagatgac atcagagtaa gtgatgagaa tctctacgcg tggcggatgt    60

<210> SEQ ID NO 2011
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2011
cgcgaatgcc tagtatatac ctactttttt cttttagatc tatgtacgcg tggcggatgt    60

<210> SEQ ID NO 2012
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2012
cgcgaatgcc ataagggttc tcctccatgg tagatacctg ttcgaacgcg tggcggatgt    60

<210> SEQ ID NO 2013
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2013
cgcgaatgcc gtgacaatgt gaacactcaa agagtacctt gttccacgcg tggcggatgt    60

<210> SEQ ID NO 2014
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2014
cgcgaatgcc gaaatataaa tctatatact tccttacctg ggattacgcg tggcggatgt    60

<210> SEQ ID NO 2015
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2015
cgcgaatgcc acagatgtgc agcacattaa gaggagagac atcgtacgcg tggcggatgt    60

<210> SEQ ID NO 2016
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2016
cgcgaatgcc ttccaaaggc tccctcaccc agttctcgct tcagcacgcg tggcggatgt    60

<210> SEQ ID NO 2017
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2017
cgcgaatgcc aggtcttcct ggccgagtgc tacaacctca gcccgacgcg tggcggatgt    60

<210> SEQ ID NO 2018
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2018
cgcgaatgcc tttaccttca cagccacaag catcttgtcc ttggtacgcg tggcggatgt    60

<210> SEQ ID NO 2019
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2019
cgcgaatgcc gccgtgtacc ctgtctgtcc agattggtgc tgaagacgcg tggcggatgt    60

<210> SEQ ID NO 2020
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2020
cgcgaatgcc tcctccgtgt ctgcctggaa gccgtccatg tcttcacgcg tggcggatgt    60

<210> SEQ ID NO 2021
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2021
cgcgaatgcc aggaggaggg cgactgtatg atcgtggatg tcccgacgcg tggcggatgt    60

<210> SEQ ID NO 2022
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2022
cgcgaatgcc gctatctaca gcccttctca cccgcagcat ccgggacgcg tggcggatgt    60

<210> SEQ ID NO 2023
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2023
cgcgaatgcc atcgggaaaa agagctaatc cgccaagcag ctctgacgcg tggcggatgt    60

<210> SEQ ID NO 2024
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2024
cgcgaatgcc cgcaccacgc tgaggtccat ctccttggtc tgctgacgcg tggcggatgt    60

<210> SEQ ID NO 2025
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2025
cgcgaatgcc gctcatgttt acagcttttc ttccggatag cactgacgcg tggcggatgt    60

<210> SEQ ID NO 2026
<211> LENGTH: 60

```
<212> TYPE: DNA
<213> ORGANISM: Artificial Sequence
<220> FEATURE:
<223> OTHER INFORMATION: Synthetic oligonucleotide

<400> SEQUENCE: 2026
cgcgaatgcc tgataccacg ggttccaggc gccttgtgaa gctgcacgcg tggcggatgt      60

<210> SEQ ID NO 2027
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2027
cgcgaatgcc gacgccatct atgacagtag tgagtacttc acttcacgcg tggcggatgt      60

<210> SEQ ID NO 2028
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2028
cgcgaatgcc gcccacccca ctgtgcagaa gctataccgt cgtgaacgcg tggcggatgt      60

<210> SEQ ID NO 2029
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2029
cgcgaatgcc gctgagccac tgctggcttg aagggtggct tgatcacgcg tggcggatgt      60

<210> SEQ ID NO 2030
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2030
cgcgaatgcc ctgatgacac cttctacttt gacaccgagt tcacgacgcg tggcggatgt      60

<210> SEQ ID NO 2031
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2031
cgcgaatgcc aaacagataa gggacgcacc cttgggtgtg cgggaacgcg tggcggatgt      60

<210> SEQ ID NO 2032
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2032
```
cgcgaatgcc gtcatcaatg ccatcgagca ggactaccgg ctgccacgcg tggcggatgt                60

<210> SEQ ID NO 2033
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2033
cgcgaatgcc gctggtgtag agcagctgga cagtccatgg gtgggacgcg tggcggatgt                60

<210> SEQ ID NO 2034
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2034
cgcgaatgcc tcatgctgga ctgttggcag aaggaccgga acagcacgcg tggcggatgt                60

<210> SEQ ID NO 2035
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2035
cgcgaatgcc tctagggtgt tgacaatctc cgcaaaccgg ggccgacgcg tggcggatgt                60

<210> SEQ ID NO 2036
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2036
cgcgaatgcc taagatgatc cggaacccgg caagtctcaa gactgacgcg tggcggatgt                60

<210> SEQ ID NO 2037
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2037
cgcgaatgcc gtttcactag actcacacgg cggtgatggt tgccaacgcg tggcggatgt                60

<210> SEQ ID NO 2038
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2038
cgcgaatgcc accaatctga actggaccaa tgttcatgcc atcaaacgcg tggcggatgt                60

<210> SEQ ID NO 2039
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 2039
cgcgaatgcc cattgtcctc actcgtcaca ttcaccagcg tcaagacgcg tggcggatgt    60

<210> SEQ ID NO 2040
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2040
cgcgaatgcc gcttcaccct gacgtgcatt gcagagaacg tggtgacgcg tggcggatgt    60

<210> SEQ ID NO 2041
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2041
cgcgaatgcc tagacagtga gggcaacact ggcattgctc atgccacgcg tggcggatgt    60

<210> SEQ ID NO 2042
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2042
cgcgaatgcc ctgtaagtgc atgttattgt gggggatggc tgtgtacgcg tggcggatgt    60

<210> SEQ ID NO 2043
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2043
cgcgaatgcc ggtggaaaaa ttccagtaag gtggacagca cccgaacgcg tggcggatgt    60

<210> SEQ ID NO 2044
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2044
cgcgaatgcc cactggctga tgtgaatttc cggtactgga tggctacgcg tggcggatgt    60

<210> SEQ ID NO 2045
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2045
cgcgaatgcc atgtatggag ctatggaata gtcatgtggg aagttacgcg tggcggatgt    60
```

<210> SEQ ID NO 2046
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2046
cgcgaatgcc gacatgtccc aataaggtct ttctccataa gacatacgcg tggcggatgt       60

<210> SEQ ID NO 2047
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2047
cgcgaatgcc aaatcaagat gtaggtgtta cattcattta acaaacgcg tggcggatgt       60

<210> SEQ ID NO 2048
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2048
cgcgaatgcc cctgtggccg tgggttctac aagtcttcct ctcaaacgcg tggcggatgt       60

<210> SEQ ID NO 2049
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2049
cgcgaatgcc aaactgtgag ttggacaacg agagcactga agatcacgcg tggcggatgt       60

<210> SEQ ID NO 2050
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2050
cgcgaatgcc ttctgataaa gaaggctcct ccagatgtga atgtgacgcg tggcggatgt       60

<210> SEQ ID NO 2051
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2051
cgcgaatgcc tggtgggtca gatggagccc tgtaataccc atcttacgcg tggcggatgt       60

<210> SEQ ID NO 2052
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2052
cgcgaatgcc tacgttgcgt gcacaagtga gttgtattat gaaagacgcg tggcggatgt    60

<210> SEQ ID NO 2053
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2053
cgcgaatgcc ataaagaaga agtgcagagg aaacgtcaga agctcacgcg tggcggatgt    60

<210> SEQ ID NO 2054
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2054
cgcgaatgcc ctaccaccgc cgaaactatc cgaaaaattg ggcatacgcg tggcggatgt    60

<210> SEQ ID NO 2055
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2055
cgcgaatgcc tggtgctgga gctggaggcg gaggcatgtt tggtaacgcg tggcggatgt    60

<210> SEQ ID NO 2056
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2056
cgcgaatgcc acctgtactt ccagtgcccc ctcctccacc gccacacgcg tggcggatgt    60

<210> SEQ ID NO 2057
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2057
cgcgaatgcc ccaggtacaa aaatacttat tcttcctaaa actttacgcg tggcggatgt    60

<210> SEQ ID NO 2058
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2058
cgcgaatgcc atgtataacg atttctggtg tttttctttc caacaacgcg tggcggatgt    60

<210> SEQ ID NO 2059

```
<210> SEQ ID NO 2059
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2059
cgcgaatgcc gctcatatgg tttcccattt aatatgtcaa ataccacgcg tggcggatgt      60

<210> SEQ ID NO 2060
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2060
cgcgaatgcc cagagtttac atctgatgat ttactagcac aaggtacgcg tggcggatgt      60

<210> SEQ ID NO 2061
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2061
cgcgaatgcc ataatggtta agagaatctg gttttatcac aacccacgcg tggcggatgt      60

<210> SEQ ID NO 2062
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2062
cgcgaatgcc ctcatcaaag gtttgtgttt ttctttctga aaactacgcg tggcggatgt      60

<210> SEQ ID NO 2063
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2063
cgcgaatgcc atgtactctg ttatgatcat tactggttta cctagacgcg tggcggatgt      60

<210> SEQ ID NO 2064
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2064
cgcgaatgcc ggagaatggc tccttggatg cattcctcag ggtatacgcg tggcggatgt      60

<210> SEQ ID NO 2065
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2065
```
cgcgaatgcc taccaacatt cttgggttta atataaagta gtcacacgcg tggcggatgt    60

<210> SEQ ID NO 2066
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2066
cgcgaatgcc gatggtcttt tggtgtcctg ctgtgggaga tcgtgacgcg tggcggatgt    60

<210> SEQ ID NO 2067
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2067
cgcgaatgcc ggaggaatcc caggataggg gtttccccct agggtacgcg tggcggatgt    60

<210> SEQ ID NO 2068
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2068
cgcgaatgcc tgagcggctc ttcaaccttc tgaagaccgg ccaccacgcg tggcggatgt    60

<210> SEQ ID NO 2069
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2069
cgcgaatgcc catctcctcg ctgcagttgt ctggcctctc catccacgcg tggcggatgt    60

<210> SEQ ID NO 2070
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2070
cgcgaatgcc gatcagaatg agcgaagcta tcgtatagtt cggacacgcg tggcggatgt    60

<210> SEQ ID NO 2071
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2071
cgcgaatgcc ggttcaggcc tttgatatct gtgttcctgg cagctacgcg tggcggatgt    60

<210> SEQ ID NO 2072
<211> LENGTH: 60
<212> TYPE: DNA

<210> SEQ ID NO 2073
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2072
cgcgaatgcc ctctcacttc ctatgttttc cacgtgcgag ccaggacgcg tggcggatgt    60

<210> SEQ ID NO 2073
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2073
cgcgaatgcc aagggctcac tgaagtctcc atagccagct gctgtacgcg tggcggatgt    60

<210> SEQ ID NO 2074
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2074
cgcgaatgcc ggaggttaca accaacacag gtaacaagga ccaccacgcg tggcggatgt    60

<210> SEQ ID NO 2075
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2075
cgcgaatgcc acaacggatg acatcatcat gtccttgtga cctctacgcg tggcggatgt    60

<210> SEQ ID NO 2076
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2076
cgcgaatgcc cagcctggag tggggagaga agggagagag tggtgacgcg tggcggatgt    60

<210> SEQ ID NO 2077
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2077
cgcgaatgcc tgacctttgg acatcgggac ggcgcccagc tgcctacgcg tggcggatgt    60

<210> SEQ ID NO 2078
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2078
cgcgaatgcc aggacagagt agggagggag aggtgacggg agcccacgcg tggcggatgt    60

<210> SEQ ID NO 2079
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2079
cgcgaatgcc aatccttcag gttcctgttc cgtagatgtg agtgcacgcg tggcggatgt    60

<210> SEQ ID NO 2080
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2080
cgcgaatgcc atggctcttt acaaccggct ctttcccaaa acatgacgcg tggcggatgt    60

<210> SEQ ID NO 2081
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2081
cgcgaatgcc gtatcataac tgcttgcgaa gatgtagttt ctcttacgcg tggcggatgt    60

<210> SEQ ID NO 2082
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2082
cgcgaatgcc agttttccc actgccaagc atccagagct ttccaacgcg tggcggatgt    60

<210> SEQ ID NO 2083
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2083
cgcgaatgcc ttatacctgg cacttcgcag aggtaagtgg gaatcacgcg tggcggatgt    60

<210> SEQ ID NO 2084
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2084
cgcgaatgcc aatgttacct tatggttgtc tgtcaatcgg tgactacgcg tggcggatgt    60

<210> SEQ ID NO 2085
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 2085
cgcgaatgcc gtgagaattt cgcaccacct caataagtcc cacacacgcg tggcggatgt      60

<210> SEQ ID NO 2086
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2086
cgcgaatgcc actattatgc aaattcagtg caaaggcggc ttgaaacgcg tggcggatgt      60

<210> SEQ ID NO 2087
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2087
cgcgaatgcc gatgtagtgt gtggctgttg aactgcagtg cacctacgcg tggcggatgt      60

<210> SEQ ID NO 2088
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2088
cgcgaatgcc agtggctcaa agacaagaac aaaggagaaa tgtgaacgcg tggcggatgt      60

<210> SEQ ID NO 2089
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2089
cgcgaatgcc cattctatct ctatctcctt cgcttcggga aaccaacgcg tggcggatgt      60

<210> SEQ ID NO 2090
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2090
cgcgaatgcc aggattttag tttccacatt ttgcgcttgg ctggtacgcg tggcggatgt      60

<210> SEQ ID NO 2091
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2091
cgcgaatgcc ttggtagttt aagaaatatt tataaagcag gtaacacgcg tggcggatgt      60

```
<210> SEQ ID NO 2092
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2092
cgcgaatgcc cacccagct gagcgcccct cccggctccc cacttacgcg tggcggatgt    60

<210> SEQ ID NO 2093
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2093
cgcgaatgcc ccaaacagct ccctcgcaag tgagtggagt aatgaacgcg tggcggatgt    60

<210> SEQ ID NO 2094
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2094
cgcgaatgcc ggaaagctcg acactccgct gcagtactct ctcctacgcg tggcggatgt    60

<210> SEQ ID NO 2095
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2095
cgcgaatgcc tggcaggaac cagagcatcc caatggagtc atcacacgcg tggcggatgt    60

<210> SEQ ID NO 2096
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2096
cgcgaatgcc cacttacttt ctcgtaatac ttgatttcat attctacgcg tggcggatgt    60

<210> SEQ ID NO 2097
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2097
cgcgaatgcc gccccattta catcatcaca gagtattgct tctatacgcg tggcggatgt    60

<210> SEQ ID NO 2098
<211> LENGTH: 60
<212> TYPE: DNA
<213> ORGANISM: Artificial Sequence
<220> FEATURE:
<223> OTHER INFORMATION: Synthetic oligonucleotide
```

<400> SEQUENCE: 2098
cgcgaatgcc tccctattct tatgcaaata gttgaccaaa tctccacgcg tggcggatgt    60

<210> SEQ ID NO 2099
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2099
cgcgaatgcc tagcttcctg agccaccacc cagagaagcc aaagaacgcg tggcggatgt    60

<210> SEQ ID NO 2100
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2100
cgcgaatgcc atcagcaggg ttcaatccaa agatatccag ctcttacgcg tggcggatgt    60

<210> SEQ ID NO 2101
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2101
cgcgaatgcc gaaagcacac ggaggtgggt gcaaagagag atgttacgcg tggcggatgt    60

<210> SEQ ID NO 2102
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2102
cgcgaatgcc cctgcagatg tggccgagga ggcgggctgc ccctacgcg tggcggatgt    60

<210> SEQ ID NO 2103
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2103
cgcgaatgcc cacactccag ccgtctcttg ctgactgcac aggacacgcg tggcggatgt    60

<210> SEQ ID NO 2104
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2104
cgcgaatgcc aggagtgtgg cggcctgggc tccccaacag gcaggacgcg tggcggatgt    60

<210> SEQ ID NO 2105
<211> LENGTH: 60

```
<212> TYPE: DNA
<213> ORGANISM: Artificial Sequence
<220> FEATURE:
<223> OTHER INFORMATION: Synthetic oligonucleotide

<400> SEQUENCE: 2105
cgcgaatgcc ggcttacctt tgccatctcc ttgcctccac tcacaacgcg tggcggatgt    60

<210> SEQ ID NO 2106
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2106
cgcgaatgcc acccagatgt agcctttgta cctctaggaa tgacgacgcg tggcggatgt    60

<210> SEQ ID NO 2107
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2107
cgcgaatgcc gcagaatcat catcctccac gatgactaaa taatcacgcg tggcggatgt    60

<210> SEQ ID NO 2108
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2108
cgcgaatgcc cattatacct tgtcgcacaa ctgatcccga gactcacgcg tggcggatgt    60

<210> SEQ ID NO 2109
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2109
cgcgaatgcc aggtaccacc ccctcactgt tgtgtaaggt tacagacgcg tggcggatgt    60

<210> SEQ ID NO 2110
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2110
cgcgaatgcc gcctcctacg acagcagaca gggctttaat gggacacgcg tggcggatgt    60

<210> SEQ ID NO 2111
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2111
```
cgcgaatgcc cggtggcctc acagatatag ggccctacag tgaagacgcg tggcggatgt    60

<210> SEQ ID NO 2112
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2112
cgcgaatgcc tcaaaggaaa gaagttccag accatcccat ttaatacgcg tggcggatgt    60

<210> SEQ ID NO 2113
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2113
cgcgaatgcc aaggagatga tacaagtacc ttttaaagca taaacacgcg tggcggatgt    60

<210> SEQ ID NO 2114
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2114
cgcgaatgcc cctcacagct cgttcatcgg gacttggcag ccagaacgcg tggcggatgt    60

<210> SEQ ID NO 2115
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2115
cgcgaatgcc atcttcatct tccgcccctc agctaccagg atgttacgcg tggcggatgt    60

<210> SEQ ID NO 2116
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2116
cgcgaatgcc ttcggatttc ggcttgtccc gagatgttta tgaagacgcg tggcggatgt    60

<210> SEQ ID NO 2117
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2117
cgcgaatgcc actgggcacc tggctcctct tcacgtagga atcctacgcg tggcggatgt    60

<210> SEQ ID NO 2118
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 2118
cgcgaatgcc cagactgacc acctcccctg ccctgttgcc aggtgacgcg tggcggatgt    60

<210> SEQ ID NO 2119
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2119
cgcgaatgcc atgtcgcagc cttcatcgta gccctggcgc ttcagacgcg tggcggatgt    60

<210> SEQ ID NO 2120
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2120
cgcgaatgcc ctggagcctg ggcattctgc tgtacaccat gctggacgcg tggcggatgt    60

<210> SEQ ID NO 2121
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2121
cgcgaatgcc gtggggaagg gtccaggcca ggggcactca ccctgacgcg tggcggatgt    60

<210> SEQ ID NO 2122
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2122
cgcgaatgcc aggaagaaga acgattatcc attcaaaatt ttaggacgcg tggcggatgt    60

<210> SEQ ID NO 2123
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2123
cgcgaatgcc gaaaaaaatt ttttactaaa agtaaaaaat ttaccacgcg tggcggatgt    60

<210> SEQ ID NO 2124
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2124
cgcgaatgcc gaagtaagta ttttataatc ttttttttt tccttacgcg tggcggatgt    60
```

<210> SEQ ID NO 2125
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2125
cgcgaatgcc atgaaaaatg ttgtcattca gaagtttgct aaaggacgcg tggcggatgt    60

<210> SEQ ID NO 2126
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2126
cgcgaatgcc atgtctttat tggcgtgcgc tcttgaggtt gtaatacgcg tggcggatgt    60

<210> SEQ ID NO 2127
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2127
cgcgaatgcc atttatgaaa atttaactta ctgctatatg tggccacgcg tggcggatgt    60

<210> SEQ ID NO 2128
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2128
cgcgaatgcc ctcctgtctt ttgcaggtga tgttcacgga ggaggacgcg tggcggatgt    60

<210> SEQ ID NO 2129
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2129
cgcgaatgcc gcccagagcc agctcagcca ggtaaaactt cacatacgcg tggcggatgt    60

<210> SEQ ID NO 2130
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2130
cgcgaatgcc ctggatcacc tgcacagcct gggtatcatt tacagacgcg tggcggatgt    60

<210> SEQ ID NO 2131
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2131
cgcgaatgcc ctggaggctt cactcacttc tcaggcttga ggtctacgcg tggcggatgt    60

<210> SEQ ID NO 2132
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2132
cgcgaatgcc atggccccca gtccctggt gcgggtggcc ccaccacgcg tggcggatgt    60

<210> SEQ ID NO 2133
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2133
cgcgaatgcc aggcccgcca cgcggctcag gttggtggcc gagcaacgcg tggcggatgt    60

<210> SEQ ID NO 2134
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2134
cgcgaatgcc ggagaagcag ttggccattg agctgaaggt gaagcacgcg tggcggatgt    60

<210> SEQ ID NO 2135
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2135
cgcgaatgcc attgctgtag gtctggatca tgttctccgc ccctacgcg tggcggatgt    60

<210> SEQ ID NO 2136
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2136
cgcgaatgcc ggcagcacca aggtgaggca gcacgtgcac acacaacgcg tggcggatgt    60

<210> SEQ ID NO 2137
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2137
cgcgaatgcc ctatgttatt ttatcttttg aaaacaatgg tgactacgcg tggcggatgt    60

<210> SEQ ID NO 2138

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2138
cgcgaatgcc atactgtgta gtatcagcct gcttcatgtc catgtacgcg tggcggatgt     60

<210> SEQ ID NO 2139
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2139
cgcgaatgcc gtccccatgc tagaaaggaa agaggtttct aaataacgcg tggcggatgt     60

<210> SEQ ID NO 2140
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2140
cgcgaatgcc ctggacgatc atagagtgat ctctggatgt cggaaacgcg tggcggatgt     60

<210> SEQ ID NO 2141
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2141
cgcgaatgcc cctcatataa gaagaaatct atgttaggta aaagtacgcg tggcggatgt     60

<210> SEQ ID NO 2142
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2142
cgcgaatgcc acttctgaga agttccagaa aataaatcag atggtacgcg tggcggatgt     60

<210> SEQ ID NO 2143
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2143
cgcgaatgcc cagcacttct tttgagcaca cggtcgctgt tacatacgcg tggcggatgt     60

<210> SEQ ID NO 2144
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2144
```

```
cgcgaatgcc aaggaagcaa ccctcctaaa ccactgaaaa aactaacgcg tggcggatgt    60

<210> SEQ ID NO 2145
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2145
cgcgaatgcc ccatctgctt catctgatcc ttcaatatca aagcgacgcg tggcggatgt    60

<210> SEQ ID NO 2146
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2146
cgcgaatgcc aaggtaggaa ccagttttga atgttttcca gtagcacgcg tggcggatgt    60

<210> SEQ ID NO 2147
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2147
cgcgaatgcc ggtggggctg aggttcagga agagggcggg gccctacgcg tggcggatgt    60

<210> SEQ ID NO 2148
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2148
cgcgaatgcc gggttattgg cctccgccat cctgggtccg ggctgacgcg tggcggatgt    60

<210> SEQ ID NO 2149
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2149
cgcgaatgcc ctcggagcag gagctggagg tggggtccag ggtccacgcg tggcggatgt    60

<210> SEQ ID NO 2150
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2150
cgcgaatgcc tgccacttgg ggccccttc tgcctgcccc cacagacgcg tggcggatgt    60

<210> SEQ ID NO 2151
<211> LENGTH: 60
<212> TYPE: DNA
```

```
<213> ORGANISM: Artificial Sequence
<220> FEATURE:
<223> OTHER INFORMATION: Synthetic oligonucleotide

<400> SEQUENCE: 2151
cgcgaatgcc atgtaataat gaaacttcct ggactatttt ggccaacgcg tggcggatgt    60

<210> SEQ ID NO 2152
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2152
cgcgaatgcc ggagtggatc tccgtgatga tgtttgagac attgtacgcg tggcggatgt    60

<210> SEQ ID NO 2153
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2153
cgcgaatgcc cgagacagga gtaccgtgga gggccgtgtg actttacgcg tggcggatgt    60

<210> SEQ ID NO 2154
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2154
cgcgaatgcc ggcatcgcac ggcgatggtc tcctccactt tggcgacgcg tggcggatgt    60

<210> SEQ ID NO 2155
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2155
cgcgaatgcc tggctaagaa tctccttgga gctgagaacc gagagacgcg tggcggatgt    60

<210> SEQ ID NO 2156
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2156
cgcgaatgcc ctgttgagga actcactggg agccaccagc ttcagacgcg tggcggatgt    60

<210> SEQ ID NO 2157
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2157
cgcgaatgcc gcagttggag cagaactttt tcaactgcag ctgtgacgcg tggcggatgt    60
```

<210> SEQ ID NO 2158
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2158
cgcgaatgcc cccctgctcc tgccagagct gcatccagcg gatgtacgcg tggcggatgt    60

<210> SEQ ID NO 2159
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2159
cgcgaatgcc gaggccaagc tcaacagcca gaacctctac tgcatacgcg tggcggatgt    60

<210> SEQ ID NO 2160
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2160
cgcgaatgcc tgcggaagag aggaagctgg gagccatcag cgttgacgcg tggcggatgt    60

<210> SEQ ID NO 2161
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2161
cgcgaatgcc tgaacatcag tcagtgtggt gagtgagtgg ccgccacgcg tggcggatgt    60

<210> SEQ ID NO 2162
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2162
cgcgaatgcc cccgtctgcc gtttaagcgc ctgaatcttg tcccaacgcg tggcggatgt    60

<210> SEQ ID NO 2163
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2163
cgcgaatgcc ccctgatcgt ctgacatgtc atcggctttc cccttacgcg tggcggatgt    60

<210> SEQ ID NO 2164
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 2164
cgcgaatgcc tacttctgtg caaagtaaaa gccccgattt agaggacgcg tggcggatgt    60

<210> SEQ ID NO 2165
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2165
cgcgaatgcc cacatgacag ttgttttcca aggtgtccaa agaggacgcg tggcggatgt    60

<210> SEQ ID NO 2166
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2166
cgcgaatgcc ggttctgaca tagactttag accgaaactt gtcaaacgcg tggcggatgt    60

<210> SEQ ID NO 2167
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2167
cgcgaatgcc tatttcttaa aaagttatct aagggaccct tcccgacgcg tggcggatgt    60

<210> SEQ ID NO 2168
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2168
cgcgaatgcc gaatcgaaac cagtattggc cagagcacag tcatcacgcg tggcggatgt    60

<210> SEQ ID NO 2169
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2169
cgcgaatgcc tctggctgct cattcgagtc ctctgtcaaa tcaatacgcg tggcggatgt    60

<210> SEQ ID NO 2170
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2170
cgcgaatgcc cagtcttgtg gaccacaata aactaaattc tgaagacgcg tggcggatgt    60

```
<210> SEQ ID NO 2171
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2171
cgcgaatgcc tcgctggcca tttattgcct ccctggaggg agaggacgcg tggcggatgt      60

<210> SEQ ID NO 2172
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2172
cgcgaatgcc gaagacactg gggatcagca ggggttgttg aaggcacgcg tggcggatgt      60

<210> SEQ ID NO 2173
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2173
cgcgaatgcc tctctccagg aaatgccaac ttgtcgttct gaatgacgcg tggcggatgt      60

<210> SEQ ID NO 2174
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2174
cgcgaatgcc ccctttcaga cattccttgc aaaacagagg aggagacgcg tggcggatgt      60

<210> SEQ ID NO 2175
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2175
cgcgaatgcc tcgcctctcc tccctgcacc tccacagcca acaccacgcg tggcggatgt      60

<210> SEQ ID NO 2176
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2176
cgcgaatgcc ctcccaggaa tgttcgccac ggagctgccc ggagcacgcg tggcggatgt      60

<210> SEQ ID NO 2177
<211> LENGTH: 60
<212> TYPE: DNA
<213> ORGANISM: Artificial Sequence
<220> FEATURE:
<223> OTHER INFORMATION: Synthetic oligonucleotide
```

```
<400> SEQUENCE: 2177
cgcgaatgcc ctcctttctg gggcacattc tcgggccact cgtcaacgcg tggcggatgt    60

<210> SEQ ID NO 2178
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2178
cgcgaatgcc caggacagtt ggagtgaagc tgggggcatc ctgttacgcg tggcggatgt    60

<210> SEQ ID NO 2179
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2179
cgcgaatgcc tgtcctgcaa gaccaccata ggcaccttcc ctttgacgcg tggcggatgt    60

<210> SEQ ID NO 2180
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2180
cgcgaatgcc tcttggctgt gagaccaccg caaatcaagt cccttacgcg tggcggatgt    60

<210> SEQ ID NO 2181
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2181
cgcgaatgcc tcagggtca tgttcttgcc ttggggtgtg gctggacgcg tggcggatgt     60

<210> SEQ ID NO 2182
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2182
cgcgaatgcc gagtgaggtg ctggaatctt tccccgaaga agactacgcg tggcggatgt    60

<210> SEQ ID NO 2183
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2183
cgcgaatgcc agagggagag ctcagggacg aatggctgag tacagacgcg tggcggatgt    60

<210> SEQ ID NO 2184
<211> LENGTH: 60
```

<212> TYPE: DNA
<213> ORGANISM: Artificial Sequence
<220> FEATURE:
<223> OTHER INFORMATION: Synthetic oligonucleotide

<400> SEQUENCE: 2184
cgcgaatgcc tccaccagct cgcccgaggg gccgcctgct cccccacgcg tggcggatgt    60

<210> SEQ ID NO 2185
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2185
cgcgaatgcc aggtggggaa gggactggta ctgctgtgct gctttacgcg tggcggatgt    60

<210> SEQ ID NO 2186
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2186
cgcgaatgcc ccacgcccct ccgcagagtg agtatctccc atggaacgcg tggcggatgt    60

<210> SEQ ID NO 2187
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2187
cgcgaatgcc gagcagcgtt ggcaccggcg aaccatggct gggatacgcg tggcggatgt    60

<210> SEQ ID NO 2188
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2188
cgcgaatgcc tcccgaagag acacgaaaat agggcgaaat agaaaacgcg tggcggatgt    60

<210> SEQ ID NO 2189
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2189
cgcgaatgcc tttgcgacgc tgtcacaggt tccagggtat accccacgcg tggcggatgt    60

<210> SEQ ID NO 2190
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2190
cgcgaatgcc cacagaaagg ccgtcccgct cttaccttca ttcgcacgcg tggcggatgt    60

<210> SEQ ID NO 2191
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2191
cgcgaatgcc taatcatcat gtgtatgcat tcagctttga ttgggacgcg tggcggatgt    60

<210> SEQ ID NO 2192
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2192
cgcgaatgcc tgagcacatt ccaagagatg catctgagtc tctccacgcg tggcggatgt    60

<210> SEQ ID NO 2193
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2193
cgcgaatgcc tgatctgaaa atgactgatg gaacctacgt ctttgacgcg tggcggatgt    60

<210> SEQ ID NO 2194
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2194
cgcgaatgcc ataaggtaaa ctgtagagca gggcatcata aggaaacgcg tggcggatgt    60

<210> SEQ ID NO 2195
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2195
cgcgaatgcc aagcacaccc cctaccgggt cctaaggaac aacccacgcg tggcggatgt    60

<210> SEQ ID NO 2196
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2196
cgcgaatgcc tggtcaacac tgcatcatag gcttcccgga gctttacgcg tggcggatgt    60

<210> SEQ ID NO 2197
<211> LENGTH: 60
<212> TYPE: DNA
<213> ORGANISM: Artificial Sequence

```
<220> FEATURE:
<223> OTHER INFORMATION: Synthetic oligonucleotide

<400> SEQUENCE: 2197
cgcgaatgcc ttacagtgga gtcccaagaa aagaccttct atcaaacgcg tggcggatgt      60

<210> SEQ ID NO 2198
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2198
cgcgaatgcc ggaatttcac ctcttgctgc tgcctctgtg aaggcacgcg tggcggatgt      60

<210> SEQ ID NO 2199
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2199
cgcgaatgcc tgagaagctg gagttcgatc aagtaagtac acattacgcg tggcggatgt      60

<210> SEQ ID NO 2200
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2200
cgcgaatgcc ctcttttttt tttctccttt tgaggatgat gatgaacgcg tggcggatgt      60

<210> SEQ ID NO 2201
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2201
cgcgaatgcc aaccatcgtc ctcatcttca tcctctccca tgtcgacgcg tggcggatgt      60

<210> SEQ ID NO 2202
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2202
cgcgaatgcc tctttgtgcc ccatgggtac ctgtctgagg acgaaacgcg tggcggatgt      60

<210> SEQ ID NO 2203
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2203
cgcgaatgcc gacctccccc ttcactccct cacctctgtc acaccacgcg tggcggatgt      60
```

<210> SEQ ID NO 2204
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2204
cgcgaatgcc ggctggttct caaccggaac ctctccatct cggagacgcg tggcggatgt    60

<210> SEQ ID NO 2205
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2205
cgcgaatgcc tcattgacca gcaccgccag ctgcatggtg cggttacgcg tggcggatgt    60

<210> SEQ ID NO 2206
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2206
cgcgaatgcc ctcagacttc cagggcccag gagcgggcgt cctctacgcg tggcggatgt    60

<210> SEQ ID NO 2207
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2207
cgcgaatgcc gctgaccggc agcaccgaca cgttgaagtg gagcaacgcg tggcggatgt    60

<210> SEQ ID NO 2208
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2208
cgcgaatgcc ctgcacctgc ccagtaccta ctccctctcc gtgagacgcg tggcggatgt    60

<210> SEQ ID NO 2209
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2209
cgcgaatgcc atgggctcac ctgggcaaat cggcgagccc tcctgacgcg tggcggatgt    60

<210> SEQ ID NO 2210
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2210
cgcgaatgcc agctaactgt cctcctcctt tttgtgtttg gttttacgcg tggcggatgt    60

<210> SEQ ID NO 2211
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2211
cgcgaatgcc agtgatagga ggtgtgggac tcacttcgtc aactgacgcg tggcggatgt    60

<210> SEQ ID NO 2212
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2212
cgcgaatgcc gtgacccaca aaccagaaga agacactttt ggggtacgcg tggcggatgt    60

<210> SEQ ID NO 2213
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2213
cgcgaatgcc cagtcaacac actcctcttg accaagaagt gactcacgcg tggcggatgt    60

<210> SEQ ID NO 2214
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2214
cgcgaatgcc atagcaacat cagagctgga tctagaaatg gaagcacgcg tggcggatgt    60

<210> SEQ ID NO 2215
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2215
cgcgaatgcc caatcgtttc ccctgactta tacacggttt taagaacgcg tggcggatgt    60

<210> SEQ ID NO 2216
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2216
cgcgaatgcc tggtcacctg tgctgttttt aacaatgagg tggttacgcg tggcggatgt    60

<210> SEQ ID NO 2217

```
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2217
cgcgaatgcc cctaccactt ctccagggta agtccattga aggtcacgcg tggcggatgt    60

<210> SEQ ID NO 2218
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2218
cgcgaatgcc ctgtgctgca tttcagagaa cgcctccccg agtgaacgcg tggcggatgt    60

<210> SEQ ID NO 2219
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2219
cgcgaatgcc tcaggacgtt gaactctgac agcaggtctc gcagcacgcg tggcggatgt    60

<210> SEQ ID NO 2220
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2220
cgcgaatgcc agcaggtcaa ccacccacat gtcatcaaat tgtatacgcg tggcggatgt    60

<210> SEQ ID NO 2221
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2221
cgcgaatgcc ctgcagctgg ccttaccatc ctggctgcag gccccacgcg tggcggatgt    60

<210> SEQ ID NO 2222
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2222
cgcgaatgcc cagcttattt attttgtta tctaaggaat ttaaaacgcg tggcggatgt    60

<210> SEQ ID NO 2223
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2223
```
cgcgaatgcc catcaatgtg catcttttc aggagttgac cagttacgcg tggcggatgt    60

<210> SEQ ID NO 2224
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2224
cgcgaatgcc attcttacca agcttcagtc tgtcacaaag cctatacgcg tggcggatgt    60

<210> SEQ ID NO 2225
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2225
cgcgaatgcc agtggtccca gccagtcatt acttaccatt tcagaacgcg tggcggatgt    60

<210> SEQ ID NO 2226
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2226
cgcgaatgcc ggtggcaaga ttcctatccg gtggactgcg ccagaacgcg tggcggatgt    60

<210> SEQ ID NO 2227
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2227
cgcgaatgcc cacttgctga tgtgaattta cgataggcaa ttgctacgcg tggcggatgt    60

<210> SEQ ID NO 2228
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2228
cgcgaatgcc atgtatggag ctatggaatc gttatgtggg aagtgacgcg tggcggatgt    60

<210> SEQ ID NO 2229
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2229
cgcgaatgcc gacatatccc aatagggcct ctccccgtac gacatacgcg tggcggatgt    60

<210> SEQ ID NO 2230
<211> LENGTH: 60
<212> TYPE: DNA

```
<213> ORGANISM: Artificial Sequence
<220> FEATURE:
<223> OTHER INFORMATION: Synthetic oligonucleotide

<400> SEQUENCE: 2230
cgcgaatgcc caatcaagat gtaagtctct atgttctgaa atataacgcg tggcggatgt    60

<210> SEQ ID NO 2231
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2231
cgcgaatgcc accttcctga gatcagcgtg agccacgtca acctgacgcg tggcggatgt    60

<210> SEQ ID NO 2232
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2232
cgcgaatgcc caagtgataa cagcgttgtc accctctcgt acggtacgcg tggcggatgt    60

<210> SEQ ID NO 2233
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2233
cgcgaatgcc caatggctct ggatcacccc ttcctgatgt ggactacgcg tggcggatgt    60

<210> SEQ ID NO 2234
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2234
cgcgaatgcc gtgagtgttg atggactgca gcccagtgac tatccacgcg tggcggatgt    60

<210> SEQ ID NO 2235
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2235
cgcgaatgcc caggtaggca tcctgggctt cagccccatc aggagacgcg tggcggatgt    60

<210> SEQ ID NO 2236
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2236
cgcgaatgcc gtgagggtct gcccttccgc tgcgccccgg acagcacgcg tggcggatgt    60
```

<210> SEQ ID NO 2237
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2237
cgcgaatgcc tcgcggtcca gggcccagcg cgtgctcacc tccagacgcg tggcggatgt    60

<210> SEQ ID NO 2238
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2238
cgcgaatgcc gcagcgggag aagtacgagc tggtggccgt gtgcaacgcg tggcggatgt    60

<210> SEQ ID NO 2239
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2239
cgcgaatgcc catcaccacc tcctcgcgcg cgccggcgtg cacggacgcg tggcggatgt    60

<210> SEQ ID NO 2240
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2240
cgcgaatgcc gtgcccttcc cggtgaccgt gtacgacgag gacgaacgcg tggcggatgt    60

<210> SEQ ID NO 2241
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2241
cgcgaatgcc cggtgtcgac gcccgcgggg aaggtgggcg ccgagacgcg tggcggatgt    60

<210> SEQ ID NO 2242
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2242
cgcgaatgcc ccagcgccgt ggtggagttc aagcggaagg aggtgacgcg tggcggatgt    60

<210> SEQ ID NO 2243
<211> LENGTH: 60
<212> TYPE: DNA
<213> ORGANISM: Artificial Sequence
<220> FEATURE:

<223> OTHER INFORMATION: Synthetic oligonucleotide

<400> SEQUENCE: 2243
cgcgaatgcc atcagttgct gaatctctca aaaagggctg cacagacgcg tggcggatgt    60

<210> SEQ ID NO 2244
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2244
cgcgaatgcc gtacaaggtg accaagtcaa agccctcagg ttcaaacgcg tggcggatgt    60

<210> SEQ ID NO 2245
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2245
cgcgaatgcc ttcagcgaca ttgtgggctt cacaaccatt tcagcacgcg tggcggatgt    60

<210> SEQ ID NO 2246
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2246
cgcgaatgcc tcagaagatc cacgacctca atgggctcac tcatgacgcg tggcggatgt    60

<210> SEQ ID NO 2247
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2247
cgcgaatgcc atgacctgta cacactcttt gatgcaataa ttggcacgcg tggcggatgt    60

<210> SEQ ID NO 2248
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2248
cgcgaatgcc cctgctaatt aacctacctt gtagacatca tgactacgcg tggcggatgt    60

<210> SEQ ID NO 2249
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2249
cgcgaatgcc gccctgaagg atcccaccct ggctgcccgg aaggaacgcg tggcggatgt    60

```
<210> SEQ ID NO 2250
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2250
cgcgaatgcc gcaggttggt gagcagctcg gcctccctct ggaaaacgcg tggcggatgt      60

<210> SEQ ID NO 2251
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2251
cgcgaatgcc agcatgagca cattgtcaag ttctatggag tgtgcacgcg tggcggatgt      60

<210> SEQ ID NO 2252
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2252
cgcgaatgcc tattcaaaga ccatgatgag ggggtcccca tcgccacgcg tggcggatgt      60

<210> SEQ ID NO 2253
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 2253
cgcgaatgcc catgaagcat ggagacctga ataagttcct caggtacgcg tggcggatgt      60
```